(12) United States Patent
Gudkov et al.

(10) Patent No.: US 8,007,812 B2
(45) Date of Patent: Aug. 30, 2011

(54) FLAGELLIN RELATED POLYPEPTIDES AND USES THEREOF

(75) Inventors: Andrei V. Gudkov, East Aurora, NY (US); Joseph A. DiDonato, Westlake, OH (US); Vadim Krivokrysenko, Orchard Park, NY (US)

(73) Assignee: Cleveland Clinic Foundation, Cleveland, OH (US)

( * ) Notice: Subject to any disclaimer, the term of this patent is extended or adjusted under 35 U.S.C. 154(b) by 158 days.

(21) Appl. No.: 11/722,682

(22) PCT Filed: Dec. 22, 2005

(86) PCT No.: PCT/US2005/046485
§ 371 (c)(1),
(2), (4) Date: May 2, 2008

(87) PCT Pub. No.: WO2006/069198
PCT Pub. Date: Jun. 29, 2006

(65) Prior Publication Data
US 2009/0011982 A1    Jan. 8, 2009

Related U.S. Application Data

(60) Provisional application No. 60/639,826, filed on Dec. 22, 2004.

(51) Int. Cl.
*A61K 39/02* (2006.01)
*C07K 1/00* (2006.01)

(52) U.S. Cl. .................. 424/190.1; 424/234.1; 530/350; 530/825

(58) Field of Classification Search .................. None
See application file for complete search history.

(56) References Cited

U.S. PATENT DOCUMENTS 5,399,494 A    3/1995   Kaper et al.
6,130,082 A    10/2000  Majarian et al.

FOREIGN PATENT DOCUMENTS

WO    WO 93/18150    *   9/1993
WO    9929312 A1         6/1999

OTHER PUBLICATIONS

Ben-Yedidia et al. International immunology 11: 1043-1051, 1998.*
Andreassen CN, et al., Chemical radioprotection: a critical review of amifostine as a cytoprotector in radiotherapy. 2003, Semin. Radiat. Oncol., vol. 13(1):62-72.
Bachmann, M.F., Wolint,P., Schwarz, K., and Oxenius, A. Recall proliferation potential of memory CD8+ T cells and antiviral protection. 2005, J. Immunol., vol. 175:4677-4685.
Carnes et al., Radiation Research. 2003, vol. 160(2):159-167 (Abstract Only).
Das, U.N., A Radical Approach to Cancer. 2002, Medical Science Monitor, vol. 8(4):RA79-RA92.
Eaves-Pyle TD, et al., *Salmonella* flagellin-dependent proinflammatory responses are localized to the conserved amino and carboxyl regions of the protein. 2001, J. Immunol. vol. 12:7009-1016.
Efferson, C.L. et al., Stimulation of human T cells by an influenza A vector expressing a CTL epitope from the HER-2/neu protooncogene results in higher numbers of antigen-specific TCRhi cells than stimulation with peptide. 2005 Anticancer Res. vol. 25:715-724.
Mutlu-Turkoglu U., et al., The effect of selenium and/or vitamin E treatments on radiation-induced intestinal injury in rats. 2000, Life Sci., vol. 66(20):1905-1913.
Patchen M.L., Amifostine plus granulocyte colony-stimulating factor therapy enhances recovery from supralethal radiation exposures: preclinical experience in animals models. 1995, Eur. J. Cancer., 31A Suppl. 1: S17-21.
Satyamitra M., et al., In vivo postirradiation protection by a vitamin E analog, alpha-TMG. 2003, Radiat. Res. vol. 160(6):655-661.
Seed, T., et al., New strategies for the prevention of radiation injury: possible implications for countering radiation hazards of long-term space travel. 2002, J. Radiat. Res., vol. 43 Suppl:S239-244.
Spadaro, J.A., et al., Radioprotectant combinations spare radiation-induced damage to the physis more than fractionation alone. 2005, Int. J. Radiat. Biol., vol. 10:759-765. (Abstract Only).
Sredini, B., et al., The immunomodulator AS101 administered orally as a chemoprotective and radioprotective agent. 1992, Int. J. Immunopharmacol., vol. 14(4):613-619.
Streeter, P.R., et al., Activation of the G-CSF and Flt-3 receptors protects hematopoietic stem cells from lethal irradiation. 2003, Exp. Hematol., vol. 31(11):1119-1125.
Symon, Z., et al., Selective radioprotection of hepatocytes by systemic and portal vein infusions of amifostine in a rat liver tumor model. 2001, Int. J. Radiat. Oncol. Biol. Phys., vol. 50(2):473-478.
Waddick, K.G., et al., In vitro and in vivo antileukemic activity of B43-pokeweed antiviral protein against radiation-resistant human B-cell precursor leukemia cells. 1995, Blood, vol. 86(11):4228-4233.
Wheeler, C.M., Preventative vaccines for cervical cancer. 1997, Salud Publica de Mexico, vol. 39 No. 4.
Whitnall, M.H., et al., In vivo radioprotection by 5-androstenediol: stimulation of the innate immune system. 2001, Radiat. Res., vol. 156(3):283-293.
Wong, G.H., Protective roles of cytokines against radiation: induction of mitochondrial MnSOD. 1995, Biochim. Biophys. Acta., vol. 1271(1):205-209.
Androstenediol and Androstenedione. Wikipedia. http://enwikipedia.org/wiki.
Grdina, D.J., Relationships between cytoprotection and mutation prevention by WR-1065. Feb. 2002, Military Medicine, vol. 167(2):51-53.
Murley, J.S. et al., Delayed cytoprotection after enhancement of Sod2 (MnSOD) gene expression in SA-NH mouse sarcoma cells exposed to WR-1065, the active metabolite of amifostine. 2002, Radiation Res., vol. 158 (1):101-109.

(Continued)

*Primary Examiner* — S. Devi
(74) *Attorney, Agent, or Firm* — Polsinelli Shughart PC; Teddy C. Scott, Jr.; Ron A. Galant

(57) ABSTRACT

The use of flagellin and flagellin related polypeptides for the protection of mammals from the effects of apoptosis is described.

3 Claims, 101 Drawing Sheets

OTHER PUBLICATIONS

Eaves-Pyles, T. et al., Flagellin, a novel mediator of *Salmonella*-induced epithelial activation andsystemic inflammation: I kappa B alpha degradation, induction of nitric oxide synthase, induction of proinflammatory mediators, and cardiovascular dysfunction. 2001, J. Immunol. vol. 166(2):1248-1260.

Kemp, G et al. Journal of Clinical Onocology (1996); 14(7): 2101-2112. Amifostine pretreatment for protection against cyclophosphamide-induced and cisplatin-induced toxicities; results of a randomized control in patients with advanced ovarian cancer.

Burdelya et al., "An Agonist of Toll-Like Receptor 5 Has Radioprotective Activity in Mouse and Primate Models," Science Apr. 11, 2008, (320) pp. 226-230.

Hall, "Physics and Chemistry of Radiation Absorption," Radiobiology for the Radiobiologist, pp. 5-15, 5th ed., Lippincott Williams and Wilkins, Phila., PA, 2000.

Carnes et al., Radiation Research 160(2): 159-167 (2003) (abstract only).

Bachmann, M.F., Wolint, P., Schwarz, K., and Oxenius, A. Recall proliferation potential of memory CD8+ T cells and antiviral protection. 2005 Journal of Immunology, vol. 175, pp. 4677-4685.

Das, U.N. A radical approach to cancer. 2002 Medical Science Monitor, vol. 8 No. 4, pp. RA79-RA92.

Efferson, C.L., Kawano, K., Tsuda, N., Palese, P., Garcia-Sastre, A., and Ioannides, C.G. Stimulation of human T cells by an influenza A vector expressing a CTL epitope from HER-2/neu protooncogene results in higher numbers of antigen-specific TCRhi cells than stimulation with peptide. 2005 Anticancer Research vol. 25, pp. 715-724.

Wheeler, C.M. Preventative vaccines for cervical cancer. 1997, Salud Publica de Mexico, vol. 39. No. 4.

Androstenediol and Androstenedione. Wikipedia. http://en.wikipedia.org/wiki, Sep. 28, 2006.

Amendment after Final for U.S. Appl. No. 11/421,918 dated Mar. 16, 2009.

Final Rejection for U.S. Appl. No. 11/421,918 dated Mar. 10, 2009.

Supplemental Amendment for U.S. Appl. No. 11/421,918 dated Feb. 20, 2009.

Amendment After Non Final Rejection for U.S. Appl. No. 11/421,918 dated Jan. 23, 2009.

Non-Final Rejection for U.S. Appl. No. 11/421,918 dated Dec. 23, 2008.

Advisory Action for U.S. Appl. No. 11/421,918 dated Oct. 31, 2008.

Request for Continued Examination for U.S. Appl. No. 11/421,918 dated Oct. 10, 2008.

Final Rejection for U.S. Appl. No. 11/421,918 dated Apr. 11, 2008.

Amendment After Non Final Rejection for U.S. Appl. No. 11/421,918 dated Jan. 31, 2008.

Non Final Rejection for U.S. Appl. No. 11/421,918 dated Jan. 22, 2008.

Request for Continued Examination for U.S. Appl. No. 11/421,918 dated Nov. 12, 2007.

Final Rejection for U.S. Appl. No. 11/421,918 dated Aug. 13, 2007.

Amendment After Non Final Rejection for U.S. Appl. No. 11/421,918 dated Jun. 21, 2007.

Non Final Rejection for U.S. Appl. No. 11/421,918 dated Dec. 21, 2006.

* cited by examiner

Fig. 5
Small intestine, day 7
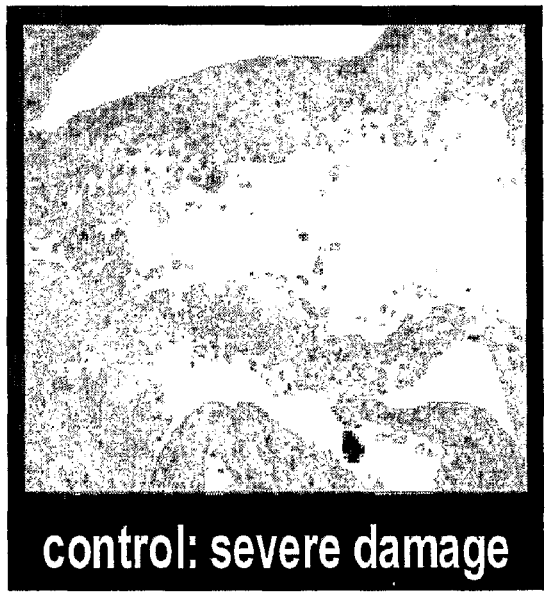 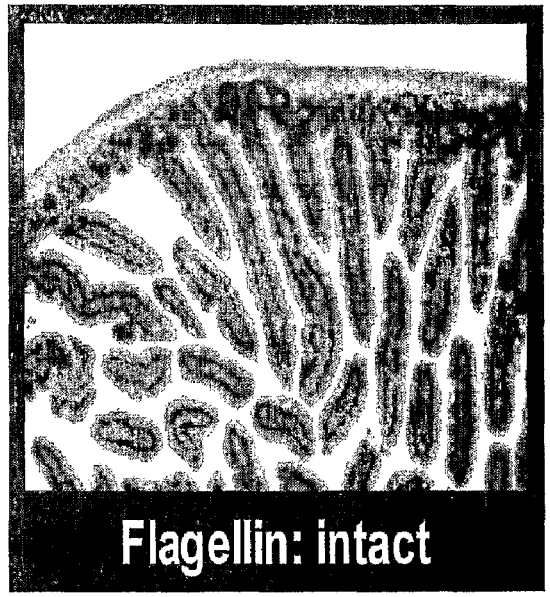

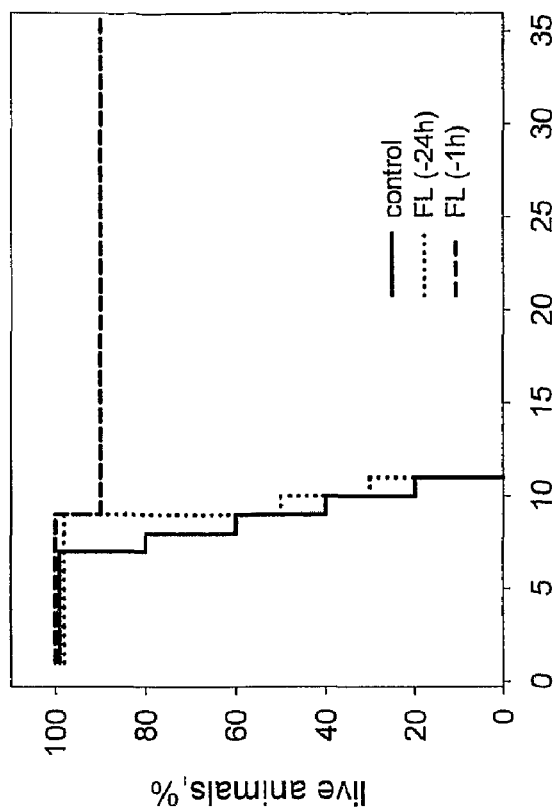
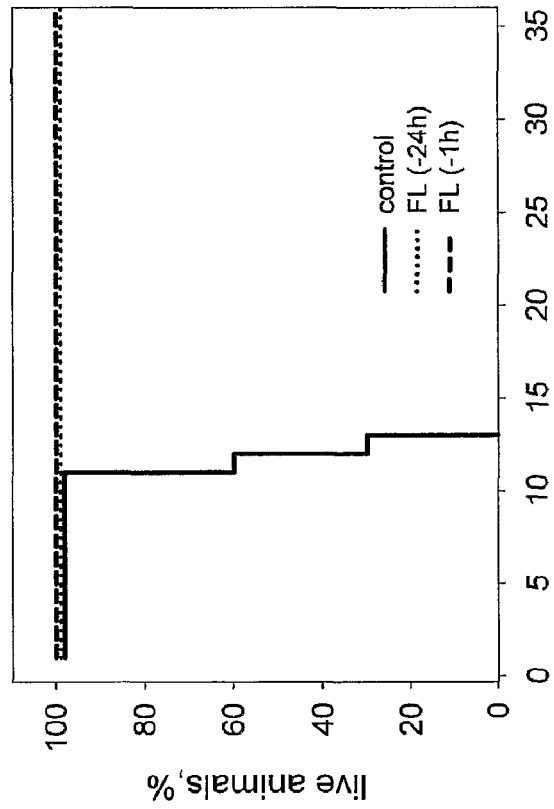
Fig. 7

Fig. 24(A)

```
Q53970   1 MAQVINTNSLSLLTQNNLNKSQSSLSSAIERLSSGLRINSAKDDAAGQAIANRFTSNIKGLTQASRNAND
P72151   1 MALTVNTNIASLNTQRNLNASSNDLNTSLQRLTTGYRINSAKDDAAGLQISNRLSNQISGLNVATRNAND
Q5X5M6   1 MAQVINTNVASLTAQRNLGVSGNMMQTSIQRLSSGLRINSAKDDAAGLAISQRMTAQIRGMNQAVRNAND
Q6VMV6   1 MAQVINTNSLSLLTQNNLNKSQSSLSSAIERLSSGLRINSAKDDAAGQAIANRFTANIKGLTQASRNAND
P13713   1 MAQVINTNSLSLMAQNNLNKSQSSLGTAIERLSSGLRINSAKDDAAGQAISNRFTANIKGLTQASRNAND
Q93RK8   1 --MRINHNIAALNTSRQLNAGSNSAAKNMEKLSSGLRINRAGDDAAGLAISEKMRSQIRGLDMASKNAQD
Q02551   1 --MKVNTNIISLKTQEYLRKNNEGMTQAQERLASGKRINSSLDDAAGLAVVTRMNVKSTGLDAASKNSSM
Q09012   1 MAQVINTNSLSLLTQNNLNKSQSSLSSAIERLSSGLRINSAKDDAAGQAIANRFTANIKGLTQASRNAND
Q8GNT8   1 MAQVINTNSLSLMAQNNLNKSQSALGTAIERLSSGLRINSAKDDAAGQAISNRFTANINGLTQASRNAND
Q9FAE7   1 MASTINTNVSSLTAQRNLSLSQSSLNTSIQRLSSGLRINSAKDDAAGLAISERFTSQIRGLNQAVRNAND
Q8ZF76   1 MA-VINTNSLSLLTQNNLNKSQSSLGTAIERLSSGLRINSAKDDAAGQAIANRFTSNIKGLTQAARNAND
Q7N5J4   1 MAQVINTNSLSLLTQNNLNRSQGTLGSAIERLSSGLRINSAKDDAAGQAIANRFTANVRGLTQAARNAND
O33578   1 -MTTINTNIGAIAAQANMTKVNDQFNTAMTRLSTGLRINAAKDDAAGMAIGEKMTAQVMGLNQAIRNAQD
Q56826   1 MASVINTNDSALLAQNNLTKSKGILGSAIERLSSGLRINSAKDDAAGQAIANRFTANVKGLTQAARNAND
P42273   1 MAQVINTNYLSLVTQNNLNRSQSALGNAIERLSSGMRINSAKDDAAGQAIANRFTSNINGLTQASRNAND
O31059   1 --MVVQHNMQAANASRMLGITTGDQSKSTEKLSSGFKINRAADDAAGLSISEKMRKQIRGLDQASTNASD
Q7VZC2   1 MAAVINTNYLSLVAQNNLNKSQSALGSAIERLSSGLRINSAKDDAAGQAIANRFTANVKGLTQAARNAND
Q9F4A4   1 --MIINHNMNALNAHRNMMGNIATAGKSMEKLSSGLRINRAGDDAAGLAISEKMRGQIRGLDQASRNAQD
Q8P9C4   1 MAQVINTNVMSLNAQRNLNTNSSSMALSIQQLSSGKRITSASVDAAGLAISERFTTQIRGLDVASRNAND
Q82UA3   1 MPQVINTNIASLNAQRNLNVSQNSLSTALQRLSSGLRINSAKDDAAGLAISERMTSQIRGMNQAARNAND
Q84IC5   1 -GFRINTNGASLNAQVNAGLNSRNLDSSLARLSSGLRINSAADDASGLAIADSLKTQANSLGQAINNAND
              ::  *    :   :                 :*::*  :*. :   **:*    :     :  .:  *   *:.

Q53970  71 GISIAQTTEGALNEINNNLQRVRELSVQATNGTNSDSDLKSIQDEIQQRLEEIDRVSNQTQFNGVKVLSQ
P72151  71 GISLAQTAEGALQQSTNILQRIRDLALQSANGSNSDADRAALQKEVAAQQAELTRISDTTTFGGRKLLDG
Q5X5M6  71 GISLAQVAEGAMQETTNILQRMRELSVQAANSTNNSSDRASIQSEISQLKSELERIAQNTEFNGQRILDG
Q6VMV6  71 GISVAQTTEGALNEINNNLQRVRELTVQATNGTNSDSDLSSIQAEITQRLEEIDRVSEQTQFNGVKVLAE
P13713  71 GISLAQTTEGALNEVDNLQNIRRLTVQAQNGSNSTSDLKSIQDEITQRLSEINRISEQTDFNGVKVLSS
Q93RK8  69 GISLIQTSEGALNETHSILQRMSELATQAANDTNTDSDRSELQKEMDQLASEVTRISTDTEFNTKKLLDG
Q02551  71 GIDLLQTADSALSSMSSILQRMRQLAVQSSNGSFSDEDRKQYTAEFGSLIKELDHVADTTNYNNIKLLDQ
Q09012  69 GISVAQTTEGALSEINNNLQRIRELSVQATNGTNSDSDLNSIQDEITQRLSEIDRVSNQTQFNGVKVLAS
Q8GNT8  71 GISLAQTTEGALNEVDNLQNIRRLTVQAQNGSNSSSDLQSIQDEITQRLSEIDRISQQTDFNGVKVLSK
Q9FAE7  71 GISLAQTAEGALKSTGDILQRVRELAVQSANATNSSGDRKAIQAEVGQLLSEMDRIAGNTEFNGQKLLDG
Q8ZF76  70 GISIAQTTEGSLNEINNNLQRVRELTVQAQNGSNSSSDLDSIQDEISLRLAEIDRVSDQTQFNGKKVLAE
Q7N5J4  71 GISIAQTTEGALNEINNNLQRIRELTVQSNGTNSASDIKSIQEEVTQRLKEIDRISEQTQFNGVRVLRE
O33578  70 GKNLVDTTEGAHVEVSSMLQRLRELAVQSSNDTNTAADRGSLAAEGKQLIAEINRVAESTTFNGMKVLDG
Q56826  71 GISIAQTTEGALNEINNNLQRIRELTVQSENGSNSKSDLDSIQKEVTQRLEEIDRISTQTQFNGIKVLNG
P42273  71 GISVSQTTEGALNEINNNLQRIRELTVQAKNGTNSNSDINSIQNEVNQRLDEINRVSEQTQFNGVKVLSG
O31059  69 GISAVQTAEGALTEVHSMLQRMNELAVQAANGTNSESDRSSIQDEINQLTTEIDRVAETTKFNETYLLKG
Q7VZC2  71 GISIAQTTEGALNEINNNLQRIRELTVQASNGTNSASDIDSIQQEVNQRLEEINRIAEQTDFNGIKVLKS
Q9F4A4  69 GISLIQTAEGALAETHSILQRMRELSVQSANDTNVAVDRTAIQDEINSLTEEINRISGDTEFNTQKLLDG
Q8P9C4  71 GISLAQTAEGAMVEIGNNLQRIRELSVQSANATNSATDREALNSEVKQLTSEIDRVANQTSFNGTKLLNG
Q82UA3  71 GISLAQTAEGALVEIGNNLQRIRELAVQSANATNSEDDREALQKEVTQLIDEIQRVGEQTSFNGTKLLDG
Q84IC5  70 ANSMLQIADKAMDEQLKILDTIKVKATQAAQDGQTAKTRAMIQGEINKLMEELDNIANTTTYNGKQLLSG
                . . ::: :   .     *: :     : *: :               *        *: ..   *  :.     :*
```

Fig. 24 (A) Continued

```
Q53970  141 DNQ-MK--IQVGANDG---------------ETITIDLQ----------KID-VKSLG----LDGFN
P72151  141 SFGTTS--FQVGSNAY---------------ETIDISLQNASASAIGSYQVG-SNGAGTVASVAGTA
Q5X5M6  141 SFSGAS--FQVGANSN---------------QTINFSIG----------SIK-ASSIGGIATATGTE
Q6VMV6  141 NNE-MK--IQVGANDG---------------ETITINLA----------KID-AKTLG----LDGFN
P13713  141 DQK-LT--IQVGANDG---------------ETTDIDLK----------KID-AKQLG----MDTF-
Q93RK8  139 TAQNLT--FQIGANEG---------------QTMSLSIN----------KMD-SE--------SLK
Q02551  139 TATGAATQVSIQASDKAN-------------DLINIDLFNAKGLSAGTITLGSGSTVAGYSALSVAD
Q09012  141 DQT-MK--IQVGANDG---------------ETIEIALD----------KID-AKTLG----LDNFS
Q8GNT8  141 DQK-LT--IQVGANDG---------------ETIDIDLK----------NIN-AQSLG----LDKFN
Q9FAE7  141 SFGSAT--FQVGANAN---------------QTITATTGNFRTNNY-GAQLT-ASASG--AATSGAS
Q8ZF76  140 NTT-MS--IQVGANDG---------------ETIDINLQ----------KID-SKSLG----LGSYS
Q7N5J4  141 DSK-MT--IQVGANDN---------------EVIDIDLK----------KID-KEALN----LGKFT
O33578  140 SFTGKQ--LQIGADSG---------------QTMAINVDSAAATDIGAHKISSASTVVADAALTDTT
Q56826  141 DVTEMK--IQVGANDN---------------ETIGIKLG----------KIN-SEKLN----LKEFS
P42273  141 EKSKMT--IQVGTNDN---------------EVIEFNLD----------KID-NDTLG----VASDK
O31059  139 GNGDRT--VRVYAHDAGLVGSLSQNTTKATFQMRKLEIGDSYTIGGTTYKIG-AETVK--EAMTALK
Q7VZC2  141 NATDMTLSIQVGAKDN---------------ETIDIKID----------RNS-NWNLY----DAVGT
Q9F4A4  139 GFKG-E--FQIGANSN---------------QTVKLDIG----------NMS-AA--------SLG
Q8P9C4  141 DFSGAL--FQVGADAG---------------QTIGINS----------IVDAN-VDSLG--KANFAAS
Q82UA3  141 SFASQI--FQVGANEG---------------ETIDFTD-----------------------
Q84IC5  140 SFSNAQ--FQIGDKAN---------------QTVNATIG----------STN-SAKVGQTRFETGAV
```

Fig. 24 (B)

```
Q53970  418  PLASIDSALSKVDAVRSSLGAIQNRFDSAITNLGNTVTNLNSARSRIEDADYATEVSNMSKAQILQQAGTSVLAQANQVPQNVLSLLR--
P72151  401  AIAVVDNALAAIDAQRADLGAVQNRFKNTIDNLTNISENATNARSRIKDTDFAAETAALSKNQVLQQAGTAILAQANQLPQAVLSLLR--
Q5X5M6  387  AIKRIDAAINSVNSNRANMGAIQNRFESTIANLQNVSDNLSAARSRIQDADYAAEMASLTKNQILQQAGTAMLAQANSLPQSVLSLLGR-
Q6VMV6  400  PLFTIDKALAKVDNLRSDLGAVQNRFDSAITNLGNTVNNLSSARSRIEDADYATEVSNMSRAQILQQAGTSVLAQANQTTQNVLSLLQG-
P13713  264  PLATLDKALAQVDGLRSSLGAVQNRFDSVINNLNNLSASQSRIQDADYATEVSNMSRANILQQAGTSVLAQANQSTQNVLSLLR--
Q93RK8  245  ALTTIKTAIDTVSSERAKLGAVQNRLEHTINNLLGTSSENLTSAESRIRDVDMASEMMEYTKNNILTQASQAMLAQANQPQQVLQLLKG-
Q02551  481  VIGLADAALTKIMKQRADMGAYYNRLEYTAKGLMGAYENMQASESRIRDADMAEEVVSLTTKQILVQSGTAMLAQANMKPNSVLKLLQQI
Q09012  437  PLSKLDEALAKVDKLRSSLGAVQNRFDSAITNLGNTVNDLSSARSRIEDADYATEVSNMSRAQILQQAGTSVLAQANQTTQNVLSLLR--
Q8GNT8  329  PLATLDKALSQVDDLRSGLGAVQNRFDSVINNLNSTVNNLQSTSENMSASRSRIQDADFAAETANLSRSQILQQAGTSVLAQAMVAQANQLPQGVLSLLK-
Q9FAE7  405  ALKIIDDAALAAVNGQRASFGALQSRFETTVNNLQSTSENMSASRSRIQDADFAAETANLSRSQILQQAGTSVLAQAMVAQANQLPQGVLSLLK-
Q8ZF76  282  PLFTIDDAIKQVDGLRSSLGAVQNRFESAVTNLNNTVTNLTSENLTVNNLSAARSRIEDADYATEVSNMSRAQILQQAGTSVLSQANQVPQTVLSLLN-
Q7N5J4  268  PLFTIDSALAQVDSLRSSLGAIQNRFDSAITNLGNTVNNLNNTVNNLSAARSRIEDADYATEVSNMSRGQILQQAGTAVLAQANQVPQNVMSLLR-
O33578  405  AIGVIDVALSKISQSRSELGAVSNRLDSTISNLTNISTSVQAAKSQVMDADFAAESTNLARSQILSQASTAMLAQANSSKQNVLSLLRG-
Q56826  226  PLDTIDKALAQVDDMRSSLGAIQNRFQSTINNLNNTVNNLSAARSRIEDADYAVEVSNMSRGQILQQAGTSVLAQANQVPQTVLSLLR--
P42273  280  ALATLDNALSKVDESRSKLGAIQNRFQSTINNLNNTVNNLSASRSRILDADYATEVSNMSKNQILQQAGTAVLAQANQVPQTVLSLLR--
O31059  385  AIDAISDALAKVSAQRSALGSIQNRLEHSIANLDNVENTNAAESRIRDTDMADEMVTYSKNNILMQAGQSMLAQANQATQGVLSILQ--
Q7VZC2  304  ALSKLDDAMKAVDEQRSSLGAIQNRFESTVANLANTITTNLSAARSRIEDSDYATEVSNMTKNQILQQAGTSVLSQAAQAMLGQANQPQGVLQLLR--
Q9F4A4  326  SIKTINSATEQVSTQRSKIGAVQNRLEHTINNLNTSSENLTAAESRVRDVDMAKEMMAFSKNNILSQAAQAMLGQANQPQGVLQLLR--
Q8P9C4  312  ALEIVDKALTSVNSSRADWGAVQNRFTSTIANLAATSENLTASRSRIADTDYAKTTAELTRTQILQQAGTAMLAQAKSVPQNVLSLLQ-
Q82UA3  192  ----IDDAIKIVNSTRADLGAIQNRFSSAIANLQTSAENLSASRSRIQDADFAAETAALTRAQILQQAGVAMLSQANALPNNVLSLLR--
Q84IC5  403  VMDIADTAIANLDTIRANLGATQNQITSTINNLSVTQVNVKAAESQIRDVDFASESANYSKANILAQSGSYAMAQANAASQNVLRLLQ--
                    *   *       *     *  :        ::  :  :  *    *  *    **   ::  * :       *  :  **  ::  : *   *
```

Fig. 25A

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AJ605765 | 1050 | 386 | 1.00E-107 | 348 | 215 | 61 | AY353403 | 1518 | 196 | 2.00E-49 | 227 | 126 | 55 |
| AJ536600 | 1050 | 385 | 1.00E-106 | 348 | 214 | 61 | AY353402 | 1518 | 336 | 1.00E-91 | 178 | 177 | 99 |
| AY249989 | 1050 | 384 | 1.00E-106 | 348 | 213 | 61 | AY353402 | 1518 | 194 | 5.00E-49 | 106 | 104 | 98 |
| AJ605764 | 1050 | 384 | 1.00E-106 | 348 | 213 | 61 | AY353401 | 1518 | 336 | 1.00E-91 | 178 | 177 | 99 |
| AB028472 | 1433 | 384 | 1.00E-106 | 348 | 213 | 61 | AY353401 | 1518 | 194 | 5.00E-49 | 106 | 104 | 98 |
| AJ605766 | 1050 | 383 | 1.00E-106 | 348 | 214 | 61 | AY353400 | 1518 | 336 | 1.00E-91 | 178 | 177 | 99 |
| AJ515904 | 1243 | 382 | 1.00E-105 | 348 | 213 | 61 | AY353400 | 1518 | 194 | 5.00E-49 | 106 | 104 | 98 |
| AY743588 | 829 | 378 | 1.00E-104 | 284 | 201 | 70 | AY353399 | 1518 | 336 | 1.00E-91 | 178 | 177 | 99 |
| X91047 | 2820 | 369 | 1.00E-101 | 313 | 206 | 65 | AY353399 | 1518 | 194 | 5.00E-49 | 106 | 104 | 98 |
| D32256 | 1240 | 367 | 1.00E-101 | 356 | 214 | 60 | AY353398 | 1518 | 336 | 1.00E-91 | 178 | 177 | 99 |
| BX571865 | 348813 | 364 | 1.00E-100 | 355 | 207 | 58 | AY353398 | 1518 | 194 | 5.00E-49 | 106 | 104 | 98 |
| AF221596 | 7867 | 356 | 8.00E-98 | 367 | 213 | 58 | AY353397 | 1515 | 336 | 1.00E-91 | 178 | 177 | 99 |
| AF221596 | 7867 | 355 | 1.00E-97 | 365 | 211 | 57 | AY353397 | 1515 | 193 | 1.00E-48 | 106 | 103 | 97 |
| AY649742 | 1518 | 336 | 1.00E-91 | 178 | 177 | 99 | AY353396 | 1515 | 336 | 1.00E-91 | 178 | 177 | 99 |
| AY649742 | 1518 | 194 | 5.00E-49 | 106 | 104 | 98 | AY353396 | 1515 | 193 | 1.00E-48 | 106 | 103 | 97 |
| AY649741 | 1518 | 336 | 1.00E-91 | 178 | 177 | 99 | AY353395 | 1518 | 336 | 1.00E-91 | 178 | 177 | 99 |
| AY649741 | 1518 | 194 | 5.00E-49 | 106 | 104 | 98 | AY353395 | 1518 | 194 | 5.00E-49 | 106 | 104 | 98 |
| AY649715 | 1518 | 336 | 1.00E-91 | 178 | 177 | 99 | AY353394 | 1518 | 336 | 1.00E-91 | 178 | 177 | 99 |
| AY649715 | 1518 | 197 | 5.00E-50 | 227 | 126 | 55 | AY353394 | 1518 | 194 | 5.00E-49 | 106 | 104 | 98 |
| AY649714 | 1518 | 336 | 1.00E-91 | 178 | 177 | 99 | AY353393 | 1518 | 336 | 1.00E-91 | 178 | 177 | 99 |
| AY649714 | 1518 | 195 | 2.00E-49 | 227 | 125 | 55 | AY353393 | 1518 | 194 | 5.00E-49 | 106 | 104 | 98 |
| AY649713 | 1518 | 336 | 1.00E-91 | 178 | 177 | 99 | AY353392 | 1518 | 336 | 1.00E-91 | 178 | 177 | 99 |
| AY649713 | 1518 | 196 | 2.00E-49 | 227 | 126 | 55 | AY353392 | 1518 | 194 | 5.00E-49 | 106 | 104 | 98 |
| AY649712 | 1518 | 336 | 1.00E-91 | 178 | 177 | 99 | AY353391 | 1518 | 336 | 1.00E-91 | 178 | 177 | 99 |
| AY649712 | 1518 | 194 | 5.00E-49 | 106 | 104 | 98 | AY353391 | 1518 | 194 | 5.00E-49 | 106 | 104 | 98 |
| AY649711 | 1518 | 336 | 1.00E-91 | 178 | 177 | 99 | AY353389 | 1518 | 336 | 1.00E-91 | 178 | 177 | 99 |
| AY649711 | 1518 | 194 | 5.00E-49 | 106 | 104 | 98 | AY353389 | 1518 | 194 | 5.00E-49 | 106 | 104 | 98 |
| AY649710 | 1518 | 336 | 1.00E-91 | 178 | 177 | 99 | AY353388 | 1518 | 336 | 1.00E-91 | 178 | 177 | 99 |
| AY649710 | 1518 | 194 | 5.00E-49 | 106 | 104 | 98 | AY353388 | 1518 | 194 | 5.00E-49 | 106 | 104 | 98 |
| AY649709 | 1518 | 336 | 1.00E-91 | 178 | 177 | 99 | AY353387 | 1518 | 336 | 1.00E-91 | 178 | 177 | 99 |
| AY649709 | 1518 | 194 | 5.00E-49 | 106 | 104 | 98 | AY353387 | 1518 | 194 | 5.00E-49 | 106 | 104 | 98 |
| AY649708 | 1518 | 336 | 1.00E-91 | 178 | 177 | 99 | AY353386 | 1518 | 336 | 1.00E-91 | 178 | 177 | 99 |
| AY649708 | 1518 | 194 | 5.00E-49 | 106 | 104 | 98 | AY353386 | 1518 | 194 | 5.00E-49 | 106 | 104 | 98 |
| AY649707 | 1518 | 336 | 1.00E-91 | 178 | 177 | 99 | AY353385 | 1518 | 336 | 1.00E-91 | 178 | 177 | 99 |
| AY649707 | 1518 | 197 | 8.00E-50 | 227 | 126 | 55 | AY353385 | 1518 | 197 | 8.00E-50 | 227 | 126 | 55 |
| AY649706 | 1518 | 336 | 1.00E-91 | 178 | 177 | 99 | AY353384 | 1518 | 336 | 1.00E-91 | 178 | 177 | 99 |
| AY649706 | 1518 | 194 | 4.00E-49 | 227 | 125 | 55 | AY353384 | 1518 | 197 | 8.00E-50 | 227 | 126 | 55 |
| AY649705 | 1518 | 336 | 1.00E-91 | 178 | 177 | 99 | AY353383 | 1518 | 336 | 1.00E-91 | 178 | 177 | 99 |
| AY649705 | 1518 | 197 | 8.00E-50 | 227 | 126 | 55 | AY353383 | 1518 | 197 | 8.00E-50 | 227 | 126 | 55 |
| AY353534 | 1518 | 336 | 1.00E-91 | 178 | 177 | 99 | AY353381 | 1518 | 336 | 1.00E-91 | 178 | 177 | 99 |
| AY353534 | 1518 | 194 | 4.00E-49 | 227 | 125 | 55 | AY353381 | 1518 | 197 | 8.00E-50 | 227 | 126 | 55 |
| AY353533 | 1527 | 336 | 1.00E-91 | 178 | 177 | 99 | AY353380 | 1518 | 336 | 1.00E-91 | 178 | 177 | 99 |
| AY353533 | 1527 | 197 | 5.00E-50 | 324 | 142 | 43 | AY353380 | 1518 | 197 | 8.00E-50 | 227 | 126 | 55 |
| AY353532 | 1527 | 336 | 1.00E-91 | 178 | 177 | 99 | D78639 | 1530 | 336 | 1.00E-91 | 178 | 177 | 99 |
| AY353532 | 1527 | 197 | 5.00E-50 | 324 | 142 | 43 | D78639 | 1530 | 194 | 5.00E-49 | 106 | 104 | 98 |
| AY353416 | 1515 | 336 | 1.00E-91 | 178 | 177 | 99 | M84980 | 1518 | 336 | 1.00E-91 | 178 | 177 | 99 |
| AY353416 | 1515 | 194 | 4.00E-49 | 309 | 141 | 45 | M84980 | 1518 | 194 | 5.00E-49 | 106 | 104 | 98 |
| AY353415 | 1515 | 336 | 1.00E-91 | 178 | 177 | 99 | M84979 | 1518 | 336 | 1.00E-91 | 178 | 177 | 99 |
| AY353415 | 1515 | 194 | 4.00E-49 | 309 | 141 | 45 | M84979 | 1518 | 194 | 5.00E-49 | 106 | 104 | 98 |
| AY353412 | 1527 | 336 | 1.00E-91 | 178 | 177 | 99 | M84972 | 1518 | 336 | 1.00E-91 | 178 | 177 | 99 |
| AY353412 | 1527 | 194 | 5.00E-49 | 106 | 104 | 98 | M84972 | 1518 | 194 | 5.00E-49 | 106 | 104 | 98 |
| AY353411 | 1527 | 336 | 1.00E-91 | 178 | 177 | 99 | M84976 | 1518 | 336 | 1.00E-91 | 178 | 177 | 99 |
| AY353411 | 1527 | 194 | 5.00E-49 | 106 | 104 | 98 | M84976 | 1518 | 194 | 5.00E-49 | 106 | 104 | 98 |
| AY353410 | 1527 | 336 | 1.00E-91 | 178 | 177 | 99 | M84975 | 1518 | 336 | 1.00E-91 | 178 | 177 | 99 |
| AY353410 | 1527 | 194 | 5.00E-49 | 106 | 104 | 98 | M84975 | 1518 | 191 | 6.00E-48 | 106 | 103 | 97 |
| AY353409 | 1527 | 336 | 1.00E-91 | 178 | 177 | 99 | M84973 | 1518 | 336 | 1.00E-91 | 178 | 177 | 99 |
| AY353409 | 1527 | 194 | 5.00E-49 | 106 | 104 | 98 | M84973 | 1518 | 194 | 5.00E-49 | 106 | 104 | 98 |
| AY353408 | 1518 | 336 | 1.00E-91 | 178 | 177 | 99 | U06455 | 1867 | 336 | 1.00E-91 | 178 | 177 | 99 |
| AY353408 | 1518 | 194 | 4.00E-49 | 227 | 125 | 55 | U06455 | 1867 | 194 | 5.00E-49 | 106 | 104 | 98 |
| AY353407 | 1518 | 336 | 1.00E-91 | 178 | 177 | 99 | U06227 | 1876 | 336 | 1.00E-91 | 178 | 177 | 99 |
| AY353407 | 1518 | 197 | 5.00E-50 | 227 | 126 | 55 | U06227 | 1876 | 197 | 5.00E-50 | 324 | 142 | 43 |
| AY353406 | 1518 | 336 | 1.00E-91 | 178 | 177 | 99 | U06225 | 1867 | 336 | 1.00E-91 | 178 | 177 | 99 |
| AY353406 | 1518 | 197 | 5.00E-50 | 227 | 126 | 55 | U06225 | 1867 | 197 | 8.00E-50 | 227 | 126 | 55 |
| AY353405 | 1518 | 336 | 1.00E-91 | 178 | 177 | 99 | U06205 | 1864 | 336 | 1.00E-91 | 178 | 177 | 99 |
| AY353405 | 1518 | 197 | 5.00E-50 | 227 | 126 | 55 | U06205 | 1864 | 193 | 1.00E-48 | 106 | 103 | 97 |
| AY353404 | 1518 | 336 | 1.00E-91 | 178 | 177 | 99 | U06204 | 1876 | 336 | 1.00E-91 | 178 | 177 | 99 |
| AY353404 | 1518 | 194 | 5.00E-49 | 106 | 104 | 98 | U06204 | 1876 | 194 | 4.00E-49 | 227 | 125 | 55 |
| AY353403 | 1518 | 336 | 1.00E-91 | 178 | 177 | 99 | U06203 | 1867 | 336 | 1.00E-91 | 178 | 177 | 99 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| U06203 | 1867 | 197 | 5.00E-50 | 227 | 126 | 55 | M84978 | 1518 | 192 | 1.00E-48 | 106 | 103 | 97 |
| U06202 | 1876 | 336 | 1.00E-91 | 178 | 177 | 99 | M84977 | 1518 | 333 | 5.00E-91 | 178 | 176 | 98 |
| U06202 | 1876 | 194 | 5.00E-49 | 106 | 104 | 98 | M84977 | 1518 | 194 | 5.00E-49 | 106 | 104 | 98 |
| U06201 | 1876 | 336 | 1.00E-91 | 178 | 177 | 99 | M27219 | 1544 | 333 | 7.00E-91 | 354 | 196 | 55 |
| U06201 | 1876 | 194 | 5.00E-49 | 106 | 104 | 98 | U05298 | 1398 | 330 | 5.00E-90 | 177 | 175 | 98 |
| U06200 | 1876 | 336 | 1.00E-91 | 178 | 177 | 99 | U05298 | 1398 | 171 | 6.00E-42 | 91 | 91 | 100 |
| U06200 | 1876 | 197 | 8.00E-50 | 305 | 140 | 45 | AY353413 | 1515 | 330 | 6.00E-90 | 178 | 173 | 97 |
| U06197 | 1867 | 336 | 1.00E-91 | 178 | 177 | 99 | AY353413 | 1515 | 187 | 6.00E-47 | 227 | 120 | 52 |
| U06197 | 1867 | 194 | 4.00E-49 | 227 | 125 | 55 | U06199 | 1864 | 330 | 6.00E-90 | 178 | 173 | 97 |
| M84974 | 1867 | 336 | 1.00E-91 | 178 | 177 | 99 | U06199 | 1864 | 187 | 6.00E-47 | 227 | 120 | 52 |
| M84974 | 1867 | 194 | 5.00E-49 | 106 | 104 | 98 | U05301 | 1512 | 328 | 2.00E-89 | 177 | 172 | 97 |
| AY353535 | 1518 | 335 | 2.00E-91 | 178 | 176 | 98 | U05301 | 1512 | 187 | 6.00E-47 | 227 | 120 | 52 |
| AY353535 | 1518 | 194 | 4.00E-49 | 227 | 125 | 55 | BX950851 | 5064019 | 327 | 5.00E-89 | 302 | 187 | 61 |
| U06206 | 1876 | 335 | 2.00E-91 | 178 | 176 | 98 | BX950851 | 5064019 | 131 | 4.00E-30 | 126 | 71 | 56 |
| U06206 | 1876 | 193 | 1.00E-48 | 106 | 103 | 97 | BX950851 | 5064019 | 88.6 | 4.00E-17 | 152 | 63 | 41 |
| AY353537 | 1515 | 334 | 3.00E-91 | 178 | 176 | 98 | L33468 | 1282 | 319 | 1.00E-86 | 365 | 203 | 55 |
| AY353537 | 1515 | 189 | 2.00E-47 | 106 | 101 | 95 | AE017132 | 290155 | 318 | 3.00E-86 | 368 | 202 | 54 |
| AY353536 | 1515 | 334 | 3.00E-91 | 178 | 176 | 98 | AJ414150 | 335050 | 318 | 3.00E-86 | 368 | 202 | 54 |
| AY353536 | 1515 | 190 | 7.00E-48 | 280 | 139 | 49 | AE013850 | 10283 | 318 | 3.00E-86 | 368 | 202 | 54 |
| AY353382 | 1518 | 334 | 3.00E-91 | 178 | 176 | 98 | BX936398 | 4744671 | 318 | 3.00E-86 | 368 | 202 | 54 |
| AY353382 | 1518 | 194 | 4.00E-49 | 227 | 125 | 55 | BX936398 | 4744671 | 98.2 | 5.00E-20 | 207 | 61 | 29 |
| AY649717 | 1515 | 334 | 4.00E-91 | 178 | 176 | 98 | BX936398 | 4744671 | 60.1 | 2.00E-08 | 115 | 37 | 32 |
| AY649717 | 1515 | 191 | 6.00E-48 | 301 | 136 | 45 | AY244555 | 1515 | 315 | 2.00E-85 | 368 | 201 | 54 |
| AY649716 | 1515 | 334 | 4.00E-91 | 178 | 176 | 98 | U12963 | 1484 | 315 | 3.00E-85 | 166 | 165 | 99 |
| AY649716 | 1515 | 191 | 6.00E-48 | 301 | 136 | 45 | U12963 | 1484 | 194 | 5.00E-49 | 106 | 104 | 98 |
| Z15086 | 1515 | 334 | 4.00E-91 | 177 | 176 | 99 | AY337465 | 1467 | 311 | 2.00E-84 | 263 | 178 | 67 |
| Z15086 | 1515 | 196 | 2.00E-49 | 227 | 126 | 55 | AY337465 | 1467 | 160 | 8.00E-39 | 103 | 83 | 80 |
| Z15072 | 1515 | 334 | 4.00E-91 | 177 | 176 | 99 | AY353477 | 1518 | 311 | 2.00E-84 | 244 | 175 | 71 |
| Z15072 | 1515 | 197 | 5.00E-50 | 227 | 126 | 55 | AY353477 | 1518 | 175 | 3.00E-43 | 140 | 96 | 68 |
| Z15071 | 1515 | 334 | 4.00E-91 | 177 | 176 | 99 | AY353476 | 1518 | 311 | 2.00E-84 | 244 | 175 | 71 |
| Z15071 | 1515 | 194 | 5.00E-49 | 106 | 104 | 98 | AY353476 | 1518 | 175 | 3.00E-43 | 140 | 96 | 68 |
| Z15070 | 1524 | 334 | 4.00E-91 | 177 | 176 | 99 | AY353475 | 1518 | 311 | 2.00E-84 | 244 | 175 | 71 |
| Z15070 | 1524 | 194 | 5.00E-49 | 106 | 104 | 98 | AY353475 | 1518 | 175 | 3.00E-43 | 140 | 96 | 68 |
| Z15069 | 1515 | 334 | 4.00E-91 | 177 | 176 | 99 | AY353474 | 1518 | 311 | 2.00E-84 | 244 | 175 | 71 |
| Z15069 | 1515 | 194 | 5.00E-49 | 106 | 104 | 98 | AY353474 | 1518 | 175 | 3.00E-43 | 140 | 96 | 68 |
| Z15068 | 1515 | 334 | 4.00E-91 | 177 | 176 | 99 | AB108532 | 3325 | 310 | 5.00E-84 | 273 | 180 | 65 |
| Z15068 | 1515 | 194 | 5.00E-49 | 106 | 104 | 98 | AB108532 | 3325 | 166 | 2.00E-40 | 280 | 121 | 43 |
| Z15067 | 1515 | 334 | 4.00E-91 | 177 | 176 | 99 | L33467 | 1300 | 310 | 8.00E-84 | 359 | 194 | 54 |
| Z15067 | 1515 | 194 | 5.00E-49 | 106 | 104 | 98 | AY337472 | 1467 | 309 | 1.00E-83 | 263 | 177 | 67 |
| Z15066 | 1515 | 334 | 4.00E-91 | 177 | 176 | 99 | AY337472 | 1467 | 160 | 8.00E-39 | 103 | 83 | 80 |
| Z15066 | 1515 | 197 | 8.00E-50 | 227 | 126 | 55 | AF345848 | 1464 | 308 | 2.00E-83 | 256 | 177 | 69 |
| Z15065 | 1515 | 334 | 4.00E-91 | 177 | 176 | 99 | AF345848 | 1464 | 158 | 4.00E-38 | 103 | 82 | 79 |
| Z15065 | 1515 | 197 | 5.00E-50 | 227 | 126 | 55 | AJ567919 | 1392 | 308 | 3.00E-83 | 262 | 173 | 66 |
| Z15064 | 1524 | 334 | 4.00E-91 | 177 | 176 | 99 | AJ567919 | 1392 | 117 | 6.00E-26 | 75 | 59 | 78 |
| Z15064 | 1524 | 197 | 5.00E-50 | 324 | 142 | 43 | AY353479 | 1518 | 308 | 3.00E-83 | 244 | 172 | 70 |
| AY353414 | 1515 | 334 | 4.00E-91 | 178 | 176 | 98 | AY353479 | 1518 | 171 | 5.00E-42 | 140 | 94 | 67 |
| AY353414 | 1515 | 191 | 6.00E-48 | 301 | 136 | 45 | AY353478 | 1518 | 308 | 3.00E-83 | 244 | 172 | 70 |
| U05303 | 1515 | 334 | 4.00E-91 | 177 | 176 | 99 | AY353478 | 1518 | 173 | 9.00E-43 | 140 | 95 | 67 |
| U05303 | 1515 | 197 | 5.00E-50 | 227 | 126 | 55 | AY337475 | 1578 | 306 | 9.00E-83 | 299 | 184 | 61 |
| U05302 | 1524 | 334 | 4.00E-91 | 177 | 176 | 99 | AY337475 | 1578 | 149 | 2.00E-35 | 92 | 76 | 82 |
| U05302 | 1524 | 194 | 5.00E-49 | 106 | 104 | 98 | AB128919 | 1996 | 306 | 9.00E-83 | 299 | 184 | 61 |
| U05300 | 1515 | 334 | 4.00E-91 | 177 | 176 | 99 | AB128919 | 1996 | 150 | 7.00E-36 | 92 | 77 | 83 |
| U05300 | 1515 | 194 | 5.00E-49 | 106 | 104 | 98 | AY337476 | 1578 | 305 | 2.00E-82 | 299 | 184 | 61 |
| U05299 | 1515 | 334 | 4.00E-91 | 177 | 176 | 99 | AY337476 | 1578 | 149 | 2.00E-35 | 92 | 76 | 82 |
| U05299 | 1515 | 194 | 5.00E-49 | 106 | 104 | 98 | U47614 | 1762 | 305 | 2.00E-82 | 274 | 170 | 62 |
| U05297 | 1515 | 334 | 4.00E-91 | 177 | 176 | 99 | U47614 | 1762 | 142 | 3.00E-33 | 115 | 74 | 64 |
| U05297 | 1515 | 194 | 5.00E-49 | 106 | 104 | 98 | AE005174 | 5528445 | 305 | 3.00E-82 | 274 | 169 | 61 |
| U05296 | 1524 | 334 | 4.00E-91 | 177 | 176 | 99 | AE005174 | 5528445 | 142 | 3.00E-33 | 115 | 74 | 64 |
| U05296 | 1524 | 194 | 5.00E-49 | 106 | 104 | 98 | AE005174 | 5528445 | 51.6 | 5.00E-06 | 299 | 66 | 22 |
| U05295 | 1515 | 334 | 4.00E-91 | 177 | 176 | 99 | AE005174 | 5528445 | 33.5 | 1.5 | 185 | 42 | 22 |
| U05295 | 1515 | 196 | 1.00E-49 | 227 | 126 | 55 | AY337468 | 1758 | 305 | 3.00E-82 | 274 | 169 | 61 |
| U06226 | 1864 | 334 | 4.00E-91 | 178 | 176 | 98 | AY337468 | 1758 | 142 | 3.00E-33 | 115 | 74 | 64 |
| U06226 | 1864 | 191 | 6.00E-48 | 301 | 136 | 45 | AY249992 | 1758 | 305 | 3.00E-82 | 267 | 168 | 62 |
| U06198 | 1864 | 334 | 4.00E-91 | 178 | 176 | 98 | AY249992 | 1758 | 142 | 3.00E-33 | 115 | 74 | 64 |
| U06198 | 1864 | 191 | 6.00E-48 | 301 | 136 | 45 | BA000007 | 5498450 | 305 | 3.00E-82 | 274 | 169 | 61 |
| AY649696 | 1518 | 333 | 5.00E-91 | 178 | 176 | 98 | BA000007 | 5498450 | 142 | 3.00E-33 | 115 | 74 | 64 |
| AY649696 | 1518 | 194 | 5.00E-49 | 106 | 104 | 98 | BA000007 | 5498450 | 51.6 | 5.00E-06 | 299 | 66 | 22 |
| M84978 | 1518 | 333 | 5.00E-91 | 178 | 176 | 98 | BA000007 | 5498450 | 33.5 | 1.5 | 185 | 42 | 22 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AF228496 | 1758 | 305 | 3.00E-82 | 274 | 169 | 61 | AY250027 | 1818 | 296 | 7.00E-80 | 222 | 157 | 70 |
| AF228496 | 1758 | 142 | 3.00E-33 | 115 | 74 | 64 | AY250027 | 1818 | 139 | 2.00E-32 | 163 | 81 | 49 |
| AF228494 | 1758 | 305 | 3.00E-82 | 267 | 168 | 62 | AB028481 | 2168 | 296 | 7.00E-80 | 222 | 157 | 70 |
| AF228494 | 1758 | 142 | 3.00E-33 | 115 | 74 | 64 | AB028481 | 2168 | 139 | 2.00E-32 | 163 | 81 | 49 |
| AF228493 | 1758 | 305 | 3.00E-82 | 267 | 168 | 62 | AY250029 | 1311 | 296 | 1.00E-79 | 300 | 175 | 58 |
| AF228493 | 1758 | 142 | 3.00E-33 | 115 | 74 | 64 | AY250029 | 1311 | 135 | 4.00E-31 | 92 | 67 | 72 |
| AF228492 | 1758 | 305 | 3.00E-82 | 267 | 168 | 62 | AF345847 | 1497 | 296 | 1.00E-79 | 178 | 155 | 87 |
| AF228492 | 1758 | 142 | 3.00E-33 | 115 | 74 | 64 | AF345847 | 1497 | 155 | 2.00E-37 | 174 | 94 | 54 |
| AF228491 | 1758 | 305 | 3.00E-82 | 267 | 168 | 62 | AY380836 | 1714 | 296 | 1.00E-79 | 223 | 159 | 71 |
| AF228491 | 1758 | 142 | 3.00E-33 | 115 | 74 | 64 | AY380836 | 1714 | 140 | 7.00E-33 | 114 | 74 | 64 |
| AF228490 | 1758 | 305 | 3.00E-82 | 267 | 168 | 62 | AB028480 | 2269 | 296 | 1.00E-79 | 302 | 176 | 58 |
| AF228490 | 1758 | 142 | 3.00E-33 | 115 | 74 | 64 | AB028480 | 2269 | 133 | 1.00E-30 | 102 | 66 | 64 |
| AF228489 | 1758 | 305 | 3.00E-82 | 274 | 169 | 61 | L07389 | 1788 | 296 | 1.00E-79 | 223 | 156 | 69 |
| AF228489 | 1758 | 142 | 3.00E-33 | 115 | 74 | 64 | L07389 | 1788 | 135 | 3.00E-31 | 113 | 70 | 61 |
| AF228488 | 1758 | 305 | 3.00E-82 | 274 | 169 | 61 | AY250001 | 1665 | 296 | 1.00E-79 | 237 | 161 | 67 |
| AF228488 | 1758 | 142 | 3.00E-33 | 115 | 74 | 64 | AY250001 | 1665 | 141 | 5.00E-33 | 295 | 105 | 35 |
| AF228487 | 1758 | 305 | 3.00E-82 | 274 | 169 | 61 | AF194946 | 1664 | 296 | 1.00E-79 | 237 | 161 | 67 |
| AF228487 | 1758 | 142 | 3.00E-33 | 115 | 74 | 64 | AF194946 | 1664 | 139 | 2.00E-32 | 293 | 104 | 35 |
| D16821 | 2006 | 305 | 3.00E-82 | 299 | 183 | 61 | AY337480 | 1512 | 295 | 2.00E-79 | 178 | 155 | 87 |
| D16821 | 2006 | 148 | 3.00E-35 | 92 | 76 | 82 | AY337480 | 1512 | 158 | 4.00E-38 | 265 | 111 | 41 |
| D16820 | 1851 | 305 | 3.00E-82 | 299 | 183 | 61 | AY250016 | 1638 | 295 | 2.00E-79 | 218 | 157 | 72 |
| D16820 | 1851 | 148 | 3.00E-35 | 92 | 76 | 82 | AY250016 | 1638 | 140 | 7.00E-33 | 172 | 85 | 49 |
| AB028474 | 2329 | 305 | 3.00E-82 | 267 | 168 | 62 | Z36877 | 1925 | 295 | 2.00E-79 | 222 | 156 | 70 |
| AB028474 | 2329 | 142 | 3.00E-33 | 115 | 74 | 64 | Z36877 | 1925 | 133 | 1.00E-30 | 102 | 66 | 64 |
| AY337477 | 1578 | 304 | 4.00E-82 | 299 | 183 | 61 | AY337483 | 1674 | 295 | 2.00E-79 | 284 | 169 | 59 |
| AY337477 | 1578 | 149 | 2.00E-35 | 92 | 76 | 82 | AY337483 | 1674 | 141 | 5.00E-33 | 115 | 71 | 61 |
| AF228495 | 1758 | 304 | 5.00E-82 | 274 | 169 | 61 | AY250028 | 1344 | 295 | 2.00E-79 | 274 | 171 | 62 |
| AF228495 | 1758 | 142 | 3.00E-33 | 115 | 74 | 64 | AY250028 | 1344 | 134 | 6.00E-31 | 92 | 67 | 72 |
| AY337478 | 1578 | 303 | 1.00E-81 | 299 | 183 | 61 | AY250010 | 1740 | 295 | 2.00E-79 | 236 | 161 | 68 |
| AY337478 | 1578 | 145 | 4.00E-34 | 92 | 74 | 80 | AY250010 | 1740 | 140 | 9.00E-33 | 116 | 72 | 62 |
| L07388 | 1755 | 303 | 1.00E-81 | 267 | 169 | 63 | AY250008 | 1674 | 295 | 2.00E-79 | 284 | 169 | 59 |
| L07388 | 1755 | 141 | 5.00E-33 | 115 | 73 | 63 | AY250008 | 1674 | 142 | 3.00E-33 | 115 | 71 | 61 |
| AB128917 | 8242 | 301 | 4.00E-81 | 296 | 186 | 62 | AY249999 | 1689 | 295 | 2.00E-79 | 257 | 168 | 65 |
| AB128917 | 8242 | 141 | 5.00E-33 | 87 | 75 | 86 | AY249999 | 1689 | 142 | 2.00E-33 | 273 | 102 | 37 |
| AY337481 | 1604 | 300 | 9.00E-81 | 177 | 157 | 89 | AY249990 | 1311 | 295 | 3.00E-79 | 291 | 174 | 59 |
| AY337481 | 1604 | 147 | 7.00E-35 | 92 | 75 | 81 | AY249990 | 1311 | 135 | 4.00E-31 | 92 | 67 | 72 |
| AY249991 | 1647 | 300 | 9.00E-81 | 266 | 171 | 64 | AF345850 | 1638 | 295 | 3.00E-79 | 218 | 157 | 72 |
| AY249991 | 1647 | 140 | 7.00E-33 | 102 | 69 | 67 | AF345850 | 1638 | 140 | 7.00E-33 | 172 | 85 | 49 |
| AY250013 | 1668 | 299 | 1.00E-80 | 295 | 171 | 57 | AB028473 | 1867 | 295 | 3.00E-79 | 291 | 174 | 59 |
| AY250013 | 1668 | 140 | 7.00E-33 | 116 | 71 | 61 | AB028473 | 1867 | 135 | 4.00E-31 | 92 | 67 | 72 |
| AY337474 | 1788 | 298 | 2.00E-80 | 223 | 157 | 70 | AY337473 | 1344 | 294 | 4.00E-79 | 290 | 171 | 58 |
| AY337474 | 1788 | 137 | 7.00E-32 | 113 | 71 | 62 | AY337473 | 1344 | 137 | 7.00E-32 | 314 | 115 | 36 |
| AY337471 | 1788 | 298 | 2.00E-80 | 223 | 157 | 70 | AY250018 | 1344 | 294 | 4.00E-79 | 290 | 171 | 58 |
| AY337471 | 1788 | 137 | 7.00E-32 | 113 | 71 | 62 | AY250018 | 1344 | 137 | 1.00E-31 | 314 | 114 | 36 |
| AY250023 | 1707 | 298 | 2.00E-80 | 223 | 160 | 71 | AY249994 | 2013 | 294 | 4.00E-79 | 247 | 162 | 65 |
| AY250023 | 1707 | 140 | 7.00E-33 | 114 | 74 | 64 | AY249994 | 2013 | 147 | 9.00E-35 | 312 | 104 | 33 |
| AY249997 | 1788 | 298 | 2.00E-80 | 223 | 157 | 70 | AF079163 | 2078 | 294 | 4.00E-79 | 247 | 162 | 65 |
| AY249997 | 1788 | 137 | 7.00E-32 | 113 | 71 | 62 | AF079163 | 2078 | 147 | 9.00E-35 | 312 | 104 | 33 |
| AE016762 | 311143 | 298 | 2.00E-80 | 223 | 157 | 70 | AY250026 | 1695 | 294 | 5.00E-79 | 222 | 156 | 70 |
| AE016762 | 311143 | 138 | 3.00E-32 | 255 | 106 | 41 | AY250026 | 1695 | 133 | 1.00E-30 | 102 | 66 | 64 |
| AB028477 | 2277 | 298 | 2.00E-80 | 223 | 160 | 71 | AF345851 | 1695 | 294 | 5.00E-79 | 222 | 156 | 70 |
| AB028477 | 2277 | 141 | 4.00E-33 | 270 | 104 | 38 | AF345851 | 1695 | 132 | 2.00E-30 | 102 | 66 | 64 |
| AB028475 | 2359 | 298 | 2.00E-80 | 223 | 157 | 70 | AE005674 | 4607203 | 293 | 6.00E-79 | 202 | 154 | 76 |
| AB028475 | 2359 | 137 | 7.00E-32 | 113 | 71 | 62 | AE005674 | 4607203 | 140 | 7.00E-33 | 116 | 71 | 61 |
| AB028471 | 2351 | 298 | 2.00E-80 | 223 | 157 | 70 | AY337485 | 1323 | 293 | 6.00E-79 | 288 | 177 | 61 |
| AB028471 | 2351 | 138 | 3.00E-32 | 255 | 106 | 41 | AY337485 | 1323 | 137 | 1.00E-31 | 312 | 109 | 34 |
| L07387 | 1788 | 298 | 2.00E-80 | 223 | 157 | 70 | AF543692 | 1497 | 293 | 6.00E-79 | 178 | 153 | 85 |
| L07387 | 1788 | 139 | 2.00E-32 | 255 | 106 | 41 | AF543692 | 1497 | 155 | 2.00E-37 | 174 | 94 | 54 |
| AJ566339 | 1634 | 298 | 3.00E-80 | 246 | 163 | 66 | AE016984 | 290582 | 293 | 6.00E-79 | 202 | 154 | 76 |
| AJ566339 | 1634 | 89.7 | 2.00E-17 | 83 | 44 | 53 | AE016984 | 290582 | 140 | 7.00E-33 | 116 | 71 | 61 |
| AJ566338 | 1634 | 298 | 3.00E-80 | 246 | 163 | 66 | AY250003 | 1731 | 293 | 6.00E-79 | 299 | 171 | 57 |
| AJ566338 | 1634 | 89.7 | 2.00E-17 | 83 | 44 | 53 | AY250003 | 1731 | 142 | 2.00E-33 | 287 | 111 | 38 |
| AY250005 | 1767 | 297 | 6.00E-80 | 219 | 162 | 73 | D16819 | 1966 | 293 | 6.00E-79 | 202 | 154 | 76 |
| AY250005 | 1767 | 142 | 2.00E-33 | 149 | 83 | 55 | D16819 | 1966 | 140 | 7.00E-33 | 116 | 71 | 61 |
| AB028476 | 2338 | 297 | 6.00E-80 | 219 | 162 | 73 | AY250024 | 1719 | 293 | 8.00E-79 | 229 | 160 | 69 |
| AB028476 | 2338 | 142 | 2.00E-33 | 149 | 83 | 55 | AY250024 | 1719 | 144 | 8.00E-34 | 116 | 73 | 62 |
| AY337466 | 1344 | 296 | 7.00E-80 | 290 | 172 | 59 | AY249998 | 1653 | 293 | 8.00E-79 | 202 | 154 | 76 |
| AY337466 | 1344 | 135 | 2.00E-31 | 181 | 87 | 48 | AY249998 | 1653 | 140 | 7.00E-33 | 116 | 71 | 61 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AF169321 | 1653 | 293 | 8.00E-79 | 202 | 154 | 76 | AY649737 | 1281 | 288 | 3.00E-77 | 214 | 161 | 75 |
| AF169321 | 1653 | 138 | 4.00E-32 | 276 | 102 | 36 | AY649737 | 1281 | 150 | 7.00E-36 | 100 | 79 | 79 |
| AY337469 | 1311 | 293 | 1.00E-78 | 291 | 169 | 58 | AY649736 | 1269 | 288 | 3.00E-77 | 214 | 161 | 75 |
| AY337469 | 1311 | 134 | 5.00E-31 | 92 | 67 | 72 | AY649736 | 1269 | 148 | 3.00E-35 | 100 | 78 | 78 |
| AY250020 | 1680 | 292 | 1.00E-78 | 179 | 149 | 83 | AY649735 | 1275 | 288 | 3.00E-77 | 214 | 161 | 75 |
| AY250020 | 1680 | 139 | 3.00E-32 | 113 | 69 | 61 | AY649735 | 1275 | 150 | 7.00E-36 | 100 | 79 | 79 |
| AY250012 | 1332 | 291 | 2.00E-78 | 288 | 176 | 61 | AY649704 | 1509 | 288 | 3.00E-77 | 220 | 160 | 72 |
| AY250012 | 1332 | 135 | 3.00E-31 | 315 | 107 | 33 | AY649704 | 1509 | 157 | 7.00E-38 | 100 | 82 | 82 |
| D26166 | 3294 | 291 | 2.00E-78 | 234 | 159 | 67 | AY649703 | 1509 | 288 | 3.00E-77 | 220 | 160 | 72 |
| D26166 | 3294 | 134 | 6.00E-31 | 100 | 66 | 66 | AY649703 | 1509 | 157 | 7.00E-38 | 100 | 82 | 82 |
| AF543693 | 1497 | 291 | 3.00E-78 | 178 | 152 | 85 | AY250022 | 1506 | 288 | 3.00E-77 | 220 | 156 | 70 |
| AF543693 | 1497 | 155 | 2.00E-37 | 174 | 94 | 54 | AY250022 | 1506 | 134 | 8.00E-31 | 151 | 77 | 50 |
| AY353496 | 1242 | 291 | 3.00E-78 | 275 | 175 | 63 | AF169323 | 1506 | 288 | 3.00E-77 | 220 | 156 | 70 |
| AY353496 | 1242 | 150 | 9.00E-36 | 100 | 79 | 79 | AF169323 | 1506 | 134 | 8.00E-31 | 151 | 77 | 50 |
| AY353486 | 1266 | 291 | 3.00E-78 | 276 | 170 | 61 | AY353549 | 1269 | 288 | 3.00E-77 | 214 | 161 | 75 |
| AY353486 | 1266 | 152 | 3.00E-36 | 102 | 79 | 77 | AY353549 | 1269 | 148 | 3.00E-35 | 100 | 78 | 78 |
| AY353485 | 1266 | 291 | 3.00E-78 | 276 | 170 | 61 | AY353548 | 1269 | 288 | 3.00E-77 | 214 | 161 | 75 |
| AY353485 | 1266 | 152 | 3.00E-36 | 102 | 79 | 77 | AY353548 | 1269 | 150 | 7.00E-36 | 100 | 79 | 79 |
| D26165 | 2520 | 291 | 3.00E-78 | 263 | 159 | 60 | AY353544 | 1269 | 288 | 3.00E-77 | 214 | 161 | 75 |
| D26165 | 2520 | 140 | 7.00E-33 | 114 | 74 | 64 | AY353544 | 1269 | 148 | 3.00E-35 | 100 | 78 | 78 |
| AY337479 | 1851 | 291 | 4.00E-78 | 191 | 151 | 79 | AY353507 | 1269 | 288 | 3.00E-77 | 214 | 161 | 75 |
| AY337479 | 1851 | 145 | 3.00E-34 | 287 | 109 | 37 | AY353507 | 1269 | 150 | 7.00E-36 | 100 | 79 | 79 |
| AY250014 | 1713 | 291 | 4.00E-78 | 179 | 150 | 83 | AY353506 | 1269 | 288 | 3.00E-77 | 214 | 161 | 75 |
| AY250014 | 1713 | 139 | 2.00E-32 | 234 | 88 | 37 | AY353506 | 1269 | 150 | 7.00E-36 | 100 | 79 | 79 |
| AY250002 | 1842 | 291 | 4.00E-78 | 191 | 151 | 79 | AY353505 | 1281 | 288 | 3.00E-77 | 214 | 161 | 75 |
| AY250002 | 1842 | 146 | 2.00E-34 | 285 | 109 | 38 | AY353505 | 1281 | 151 | 5.00E-36 | 174 | 92 | 52 |
| AJ567918 | 1359 | 291 | 4.00E-78 | 251 | 164 | 65 | AY353503 | 1281 | 288 | 3.00E-77 | 214 | 161 | 75 |
| AJ567918 | 1359 | 117 | 6.00E-26 | 75 | 59 | 78 | AY353503 | 1281 | 149 | 1.00E-35 | 174 | 91 | 52 |
| AJ271930 | 1713 | 291 | 4.00E-78 | 179 | 150 | 83 | AY353499 | 1269 | 288 | 3.00E-77 | 214 | 161 | 75 |
| AJ271930 | 1713 | 139 | 2.00E-32 | 234 | 88 | 37 | AY353499 | 1269 | 150 | 7.00E-36 | 100 | 79 | 79 |
| AB028478 | 2284 | 290 | 7.00E-78 | 229 | 159 | 69 | AY353497 | 1275 | 288 | 3.00E-77 | 214 | 161 | 75 |
| AB028478 | 2284 | 144 | 8.00E-34 | 116 | 73 | 62 | AY353497 | 1275 | 150 | 7.00E-36 | 100 | 79 | 79 |
| AB128916 | 11067 | 290 | 7.00E-78 | 296 | 177 | 59 | AY353495 | 1269 | 288 | 3.00E-77 | 214 | 161 | 75 |
| AB128916 | 11067 | 151 | 5.00E-36 | 293 | 112 | 38 | AY353495 | 1269 | 150 | 7.00E-36 | 100 | 79 | 79 |
| AY250019 | 1299 | 290 | 9.00E-78 | 286 | 169 | 59 | AY353494 | 1269 | 288 | 3.00E-77 | 214 | 161 | 75 |
| AY250019 | 1299 | 136 | 1.00E-31 | 253 | 102 | 40 | AY353494 | 1269 | 150 | 7.00E-36 | 100 | 79 | 79 |
| AY250015 | 1287 | 290 | 9.00E-78 | 267 | 166 | 62 | AY353492 | 1269 | 288 | 3.00E-77 | 214 | 161 | 75 |
| AY250015 | 1287 | 134 | 6.00E-31 | 127 | 74 | 58 | AY353492 | 1269 | 150 | 7.00E-36 | 100 | 79 | 79 |
| AF345849 | 1287 | 290 | 9.00E-78 | 267 | 166 | 62 | AY353454 | 1506 | 288 | 3.00E-77 | 216 | 158 | 73 |
| AF345849 | 1287 | 131 | 4.00E-30 | 127 | 73 | 57 | AY353454 | 1506 | 156 | 1.00E-37 | 100 | 82 | 82 |
| AY353488 | 1266 | 290 | 9.00E-78 | 271 | 170 | 62 | AY353447 | 1503 | 288 | 3.00E-77 | 208 | 157 | 75 |
| AY353488 | 1266 | 152 | 3.00E-36 | 102 | 79 | 77 | AY353447 | 1503 | 156 | 1.00E-37 | 100 | 82 | 82 |
| AY353487 | 1266 | 290 | 9.00E-78 | 271 | 170 | 62 | AY353446 | 1503 | 288 | 3.00E-77 | 208 | 157 | 75 |
| AY353487 | 1266 | 152 | 3.00E-36 | 102 | 79 | 77 | AY353446 | 1503 | 156 | 1.00E-37 | 100 | 82 | 82 |
| AY353483 | 1266 | 290 | 9.00E-78 | 175 | 153 | 87 | AY353379 | 1509 | 288 | 3.00E-77 | 220 | 160 | 72 |
| AY353484 | 1266 | 289 | 1.00E-77 | 175 | 153 | 87 | AY353379 | 1509 | 157 | 7.00E-38 | 100 | 82 | 82 |
| AY353484 | 1266 | 152 | 3.00E-36 | 102 | 79 | 77 | AY353377 | 1509 | 288 | 3.00E-77 | 220 | 160 | 72 |
| AY353482 | 1266 | 289 | 1.00E-77 | 175 | 153 | 87 | AY353377 | 1509 | 157 | 7.00E-38 | 100 | 82 | 82 |
| AY250017 | 1686 | 289 | 2.00E-77 | 233 | 162 | 69 | AY353331 | 1503 | 288 | 3.00E-77 | 208 | 157 | 75 |
| AY250017 | 1686 | 150 | 9.00E-36 | 279 | 102 | 36 | AY353331 | 1503 | 154 | 5.00E-37 | 100 | 81 | 81 |
| AY353547 | 1269 | 289 | 2.00E-77 | 284 | 175 | 61 | AY353455 | 1506 | 287 | 4.00E-77 | 216 | 158 | 73 |
| AY353547 | 1269 | 150 | 7.00E-36 | 100 | 79 | 79 | AY353455 | 1506 | 156 | 1.00E-37 | 100 | 82 | 82 |
| AY353546 | 1269 | 289 | 2.00E-77 | 284 | 175 | 61 | AY337470 | 1281 | 287 | 6.00E-77 | 258 | 163 | 63 |
| AY353546 | 1269 | 150 | 7.00E-36 | 100 | 79 | 79 | AY337470 | 1281 | 138 | 4.00E-32 | 232 | 93 | 40 |
| AY353545 | 1269 | 289 | 2.00E-77 | 284 | 175 | 61 | AY649725 | 1503 | 287 | 6.00E-77 | 206 | 157 | 76 |
| AY353545 | 1269 | 150 | 7.00E-36 | 100 | 79 | 79 | AY649725 | 1503 | 152 | 2.00E-36 | 98 | 79 | 80 |
| AY353332 | 1503 | 288 | 2.00E-77 | 208 | 157 | 75 | AY649724 | 1503 | 287 | 6.00E-77 | 198 | 154 | 77 |
| AY353332 | 1503 | 155 | 3.00E-37 | 100 | 81 | 81 | AY649724 | 1503 | 156 | 1.00E-37 | 100 | 82 | 82 |
| AY250021 | 1281 | 288 | 3.00E-77 | 258 | 164 | 63 | AY649723 | 1503 | 287 | 6.00E-77 | 198 | 154 | 77 |
| AY250021 | 1281 | 138 | 4.00E-32 | 232 | 93 | 40 | AY649723 | 1503 | 156 | 1.00E-37 | 100 | 82 | 82 |
| AY250011 | 1713 | 288 | 3.00E-77 | 179 | 149 | 83 | AY250025 | 1497 | 287 | 6.00E-77 | 177 | 146 | 82 |
| AY250011 | 1713 | 139 | 3.00E-32 | 237 | 91 | 38 | AY250025 | 1497 | 149 | 2.00E-35 | 151 | 80 | 52 |
| AF169322 | 1281 | 288 | 3.00E-77 | 258 | 164 | 63 | X17440 | 2526 | 287 | 6.00E-77 | 177 | 146 | 82 |
| AF169322 | 1281 | 136 | 2.00E-31 | 92 | 69 | 75 | X17440 | 2526 | 151 | 4.00E-36 | 244 | 101 | 41 |
| AY353498 | 1269 | 288 | 3.00E-77 | 237 | 164 | 69 | U00096 | 4639675 | 287 | 6.00E-77 | 177 | 146 | 82 |
| AY353498 | 1269 | 148 | 3.00E-35 | 100 | 78 | 78 | U00096 | 4639675 | 149 | 2.00E-35 | 151 | 80 | 52 |
| AY353493 | 1269 | 288 | 3.00E-77 | 237 | 164 | 69 | U00096 | 4639675 | 33.1 | 2 | 147 | 37 | 25 |
| AY353493 | 1269 | 148 | 3.00E-35 | 100 | 78 | 78 | AY353543 | 1269 | 287 | 6.00E-77 | 211 | 159 | 75 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AY353543 | 1269 | 150 | 7.00E-36 | 100 | 79 | 79 | AJ566340 | 1223 | 85.1 | 4.00E-16 | 284 | 81 | 28 |
| AY353457 | 1482 | 287 | 6.00E-77 | 198 | 154 | 77 | AY649698 | 1488 | 285 | 3.00E-76 | 306 | 176 | 57 |
| AY353457 | 1482 | 156 | 1.00E-37 | 100 | 82 | 82 | AY649698 | 1488 | 151 | 4.00E-36 | 96 | 78 | 81 |
| AY353456 | 1446 | 287 | 6.00E-77 | 245 | 162 | 66 | AY249995 | 1263 | 285 | 3.00E-76 | 189 | 147 | 77 |
| AY353456 | 1446 | 156 | 1.00E-37 | 100 | 82 | 82 | AY249995 | 1263 | 137 | 1.00E-31 | 138 | 78 | 56 |
| AY353453 | 1506 | 287 | 6.00E-77 | 206 | 157 | 76 | AY657001 | 1488 | 285 | 3.00E-76 | 306 | 176 | 57 |
| AY353453 | 1506 | 156 | 1.00E-37 | 100 | 82 | 82 | AY657001 | 1488 | 151 | 4.00E-36 | 96 | 78 | 81 |
| AY353452 | 1506 | 287 | 6.00E-77 | 206 | 157 | 76 | BX321861 | 298050 | 285 | 3.00E-76 | 297 | 159 | 53 |
| AY353452 | 1506 | 154 | 5.00E-37 | 100 | 81 | 81 | AY353508 | 1269 | 285 | 3.00E-76 | 211 | 158 | 74 |
| AY353451 | 1503 | 287 | 6.00E-77 | 198 | 154 | 77 | AY353508 | 1269 | 150 | 7.00E-36 | 100 | 79 | 79 |
| AY353451 | 1503 | 156 | 1.00E-37 | 100 | 82 | 82 | AY353363 | 1488 | 285 | 3.00E-76 | 306 | 175 | 57 |
| AY353450 | 1503 | 287 | 6.00E-77 | 206 | 157 | 76 | AY353363 | 1488 | 151 | 4.00E-36 | 96 | 78 | 81 |
| AY353450 | 1503 | 156 | 1.00E-37 | 100 | 82 | 82 | AY353362 | 1488 | 285 | 3.00E-76 | 306 | 176 | 57 |
| AY353449 | 1503 | 287 | 6.00E-77 | 206 | 157 | 76 | AY353362 | 1488 | 151 | 4.00E-36 | 96 | 78 | 81 |
| AY353449 | 1503 | 152 | 2.00E-36 | 98 | 79 | 80 | AY353361 | 1488 | 285 | 3.00E-76 | 306 | 176 | 57 |
| AY353448 | 1503 | 287 | 6.00E-77 | 198 | 154 | 77 | AY353361 | 1488 | 151 | 4.00E-36 | 96 | 78 | 81 |
| AY353448 | 1503 | 156 | 1.00E-37 | 100 | 82 | 82 | AY353359 | 1488 | 285 | 3.00E-76 | 306 | 176 | 57 |
| AY353444 | 1503 | 287 | 6.00E-77 | 198 | 154 | 77 | AY353359 | 1488 | 151 | 4.00E-36 | 96 | 78 | 81 |
| AY353444 | 1503 | 156 | 1.00E-37 | 100 | 82 | 82 | AY353358 | 1488 | 285 | 3.00E-76 | 306 | 176 | 57 |
| AY353443 | 1503 | 287 | 6.00E-77 | 198 | 154 | 77 | AY353358 | 1488 | 151 | 4.00E-36 | 96 | 78 | 81 |
| AY353443 | 1503 | 156 | 1.00E-37 | 100 | 82 | 82 | AY353303 | 1506 | 285 | 3.00E-76 | 175 | 150 | 85 |
| AY353378 | 1509 | 287 | 6.00E-77 | 220 | 160 | 72 | AY353303 | 1506 | 155 | 3.00E-37 | 100 | 81 | 81 |
| AY353378 | 1509 | 157 | 7.00E-38 | 100 | 82 | 82 | AY353517 | 1506 | 284 | 4.00E-76 | 215 | 157 | 73 |
| D90833 | 15605 | 287 | 6.00E-77 | 177 | 146 | 82 | AY353517 | 1506 | 152 | 2.00E-36 | 98 | 79 | 80 |
| D90833 | 15605 | 149 | 2.00E-35 | 151 | 80 | 52 | AY353516 | 1506 | 284 | 4.00E-76 | 215 | 157 | 73 |
| AB028479 | 2060 | 287 | 6.00E-77 | 177 | 146 | 82 | AY353516 | 1506 | 152 | 2.00E-36 | 98 | 79 | 80 |
| AB028479 | 2060 | 149 | 2.00E-35 | 151 | 80 | 52 | AY353504 | 1281 | 284 | 4.00E-76 | 214 | 160 | 74 |
| M14358 | 1667 | 287 | 6.00E-77 | 177 | 146 | 82 | AY353504 | 1281 | 149 | 1.00E-35 | 174 | 91 | 52 |
| M14358 | 1667 | 149 | 2.00E-35 | 151 | 80 | 52 | AY353490 | 1500 | 284 | 4.00E-76 | 192 | 152 | 79 |
| AY353509 | 1266 | 286 | 8.00E-77 | 175 | 152 | 86 | AY353490 | 1500 | 153 | 1.00E-36 | 100 | 80 | 80 |
| AY353509 | 1266 | 150 | 9.00E-36 | 100 | 79 | 79 | AY353489 | 1500 | 284 | 4.00E-76 | 192 | 152 | 79 |
| AY353501 | 1266 | 286 | 8.00E-77 | 175 | 152 | 86 | AY353489 | 1500 | 153 | 1.00E-36 | 100 | 80 | 80 |
| AY353501 | 1266 | 150 | 9.00E-36 | 100 | 79 | 79 | AY337482 | 1263 | 284 | 5.00E-76 | 189 | 147 | 77 |
| AY353500 | 1266 | 286 | 8.00E-77 | 175 | 152 | 86 | AY337482 | 1263 | 135 | 4.00E-31 | 138 | 77 | 55 |
| AY353500 | 1266 | 150 | 9.00E-36 | 100 | 79 | 79 | AY649732 | 1521 | 284 | 5.00E-76 | 175 | 150 | 85 |
| AY353445 | 1503 | 286 | 8.00E-77 | 198 | 154 | 77 | AY649732 | 1521 | 149 | 2.00E-35 | 91 | 76 | 83 |
| AY353445 | 1503 | 152 | 2.00E-36 | 98 | 79 | 80 | AY649701 | 1521 | 284 | 5.00E-76 | 175 | 150 | 85 |
| AY337467 | 1281 | 286 | 1.00E-76 | 258 | 163 | 63 | AY649701 | 1521 | 149 | 2.00E-35 | 91 | 76 | 83 |
| AY337467 | 1281 | 136 | 1.00E-31 | 232 | 92 | 39 | AY649700 | 1521 | 284 | 5.00E-76 | 175 | 150 | 85 |
| AY353334 | 1506 | 286 | 1.00E-76 | 206 | 157 | 76 | AY649700 | 1521 | 150 | 9.00E-36 | 91 | 77 | 84 |
| AY353334 | 1506 | 156 | 1.00E-37 | 100 | 82 | 82 | AE016837 | 300247 | 284 | 5.00E-76 | 175 | 150 | 85 |
| AY353333 | 1506 | 286 | 1.00E-76 | 206 | 157 | 76 | AE016837 | 300247 | 149 | 2.00E-35 | 91 | 76 | 83 |
| AY353333 | 1506 | 156 | 1.00E-37 | 100 | 82 | 82 | X03395 | 1530 | 284 | 5.00E-76 | 175 | 150 | 85 |
| AB128918 | 12979 | 286 | 1.00E-76 | 291 | 170 | 58 | X03395 | 1530 | 149 | 2.00E-35 | 91 | 76 | 83 |
| AB128918 | 12979 | 146 | 2.00E-34 | 95 | 75 | 78 | AL627272 | 245050 | 284 | 5.00E-76 | 175 | 150 | 85 |
| AY649702 | 1509 | 286 | 1.00E-76 | 220 | 159 | 72 | AL627272 | 245050 | 149 | 2.00E-35 | 91 | 76 | 83 |
| AY649702 | 1509 | 157 | 7.00E-38 | 100 | 82 | 82 | AY353434 | 1260 | 284 | 5.00E-76 | 175 | 150 | 85 |
| AY353350 | 1500 | 286 | 1.00E-76 | 209 | 158 | 75 | AY353434 | 1260 | 149 | 2.00E-35 | 91 | 76 | 83 |
| AY353350 | 1500 | 158 | 3.00E-38 | 338 | 127 | 37 | AY353433 | 1260 | 284 | 5.00E-76 | 175 | 150 | 85 |
| AY353349 | 1500 | 286 | 1.00E-76 | 209 | 158 | 75 | AY353433 | 1260 | 149 | 2.00E-35 | 91 | 76 | 83 |
| AY353349 | 1500 | 158 | 4.00E-38 | 338 | 127 | 37 | AY353376 | 1521 | 284 | 5.00E-76 | 175 | 150 | 85 |
| AY353348 | 1500 | 286 | 1.00E-76 | 209 | 158 | 75 | AY353376 | 1521 | 150 | 9.00E-36 | 91 | 77 | 84 |
| AY353348 | 1500 | 158 | 3.00E-38 | 338 | 127 | 37 | AY353375 | 1521 | 284 | 5.00E-76 | 175 | 150 | 85 |
| AY353347 | 1500 | 286 | 1.00E-76 | 209 | 158 | 75 | AY353375 | 1521 | 149 | 2.00E-35 | 91 | 76 | 83 |
| AY353347 | 1500 | 158 | 4.00E-38 | 338 | 127 | 37 | AY353374 | 1521 | 284 | 5.00E-76 | 175 | 150 | 85 |
| AY353346 | 1500 | 286 | 1.00E-76 | 209 | 158 | 75 | AY353374 | 1521 | 149 | 2.00E-35 | 91 | 76 | 83 |
| AY353346 | 1500 | 157 | 5.00E-38 | 338 | 127 | 37 | AY353373 | 1521 | 284 | 5.00E-76 | 175 | 150 | 85 |
| AY353345 | 1500 | 286 | 1.00E-76 | 209 | 158 | 75 | AY353373 | 1521 | 149 | 2.00E-35 | 91 | 76 | 83 |
| AY353345 | 1500 | 158 | 4.00E-38 | 338 | 127 | 37 | AY353372 | 1521 | 284 | 5.00E-76 | 175 | 150 | 85 |
| AF169320 | 1263 | 285 | 2.00E-76 | 269 | 160 | 59 | AY353372 | 1521 | 149 | 2.00E-35 | 91 | 76 | 83 |
| AF169320 | 1263 | 135 | 4.00E-31 | 138 | 77 | 55 | AY353371 | 1521 | 284 | 5.00E-76 | 175 | 150 | 85 |
| AY353502 | 1266 | 285 | 2.00E-76 | 175 | 151 | 86 | AY353371 | 1521 | 149 | 2.00E-35 | 91 | 76 | 83 |
| AY353502 | 1266 | 150 | 9.00E-36 | 100 | 79 | 79 | AY353302 | 1521 | 284 | 5.00E-76 | 175 | 150 | 85 |
| AY353360 | 1488 | 285 | 2.00E-76 | 306 | 176 | 57 | AY353302 | 1521 | 150 | 9.00E-36 | 91 | 77 | 84 |
| AY353360 | 1488 | 149 | 2.00E-35 | 89 | 76 | 85 | L21912 | 2001 | 284 | 5.00E-76 | 175 | 150 | 85 |
| AJ566341 | 1223 | 285 | 3.00E-76 | 179 | 145 | 81 | L21912 | 2001 | 149 | 2.00E-35 | 91 | 76 | 83 |
| AJ566341 | 1223 | 85.1 | 4.00E-16 | 284 | 81 | 28 | CP000026 | 4585229 | 283 | 6.00E-76 | 279 | 165 | 59 |
| AJ566340 | 1223 | 285 | 3.00E-76 | 179 | 145 | 81 | CP000026 | 4585229 | 278 | 2.00E-74 | 175 | 147 | 84 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| CP0000264585229 | 156 | 1.00E-37 | 100 | 82 | 82 | | AY353275 | 1521 | 155 | 3.00E-37 | 100 | 81 | 81 |
| CP0000264585229 | 155 | 3.00E-37 | 100 | 81 | 81 | | U17172 | 1521 | 282 | 2.00E-75 | 232 | 159 | 68 |
| AE008826 | 20513 | 283 | 6.00E-76 | 232 | 160 | 68 | U17172 | 1521 | 155 | 3.00E-37 | 100 | 81 | 81 |
| AE008826 | 20513 | 155 | 3.00E-37 | 100 | 81 | 81 | AY353292 | 1521 | 281 | 2.00E-75 | 268 | 163 | 60 |
| AY353521 | 1521 | 283 | 6.00E-76 | 232 | 160 | 68 | AY353292 | 1521 | 155 | 3.00E-37 | 100 | 81 | 81 |
| AY353521 | 1521 | 155 | 3.00E-37 | 100 | 81 | 81 | AY353283 | 1521 | 281 | 2.00E-75 | 268 | 162 | 60 |
| AY353271 | 1521 | 283 | 6.00E-76 | 232 | 160 | 68 | AY353283 | 1521 | 155 | 3.00E-37 | 100 | 81 | 81 |
| AY353271 | 1521 | 155 | 3.00E-37 | 100 | 81 | 81 | AY353263 | 1521 | 281 | 2.00E-75 | 268 | 163 | 60 |
| AY353269 | 1521 | 283 | 6.00E-76 | 232 | 160 | 68 | AY353263 | 1521 | 155 | 3.00E-37 | 100 | 81 | 81 |
| AY353269 | 1521 | 155 | 3.00E-37 | 100 | 81 | 81 | U17175 | 1521 | 281 | 2.00E-75 | 228 | 156 | 68 |
| AY353268 | 1521 | 283 | 6.00E-76 | 232 | 160 | 68 | U17175 | 1521 | 155 | 3.00E-37 | 100 | 81 | 81 |
| AY353268 | 1521 | 155 | 3.00E-37 | 100 | 81 | 81 | AY353542 | 1485 | 281 | 3.00E-75 | 175 | 148 | 84 |
| AY353267 | 1521 | 283 | 6.00E-76 | 232 | 160 | 68 | AY353542 | 1485 | 152 | 2.00E-36 | 98 | 79 | 80 |
| AY353267 | 1521 | 155 | 3.00E-37 | 100 | 81 | 81 | AY353541 | 1485 | 281 | 3.00E-75 | 175 | 148 | 84 |
| AY353266 | 1521 | 283 | 6.00E-76 | 232 | 160 | 68 | AY353541 | 1485 | 152 | 2.00E-36 | 98 | 79 | 80 |
| AY353266 | 1521 | 155 | 3.00E-37 | 100 | 81 | 81 | AY353540 | 1485 | 281 | 3.00E-75 | 175 | 148 | 84 |
| AY353264 | 1521 | 283 | 6.00E-76 | 232 | 160 | 68 | AY353540 | 1485 | 152 | 2.00E-36 | 98 | 79 | 80 |
| AY353264 | 1521 | 155 | 3.00E-37 | 100 | 81 | 81 | AY353539 | 1488 | 281 | 3.00E-75 | 175 | 148 | 84 |
| AY353259 | 1506 | 283 | 6.00E-76 | 295 | 169 | 57 | AY353539 | 1488 | 148 | 4.00E-35 | 98 | 77 | 78 |
| AY353259 | 1506 | 151 | 4.00E-36 | 98 | 78 | 79 | AY353538 | 1488 | 281 | 3.00E-75 | 175 | 148 | 84 |
| AF045151 | 1521 | 283 | 6.00E-76 | 232 | 160 | 68 | AY353538 | 1488 | 152 | 2.00E-36 | 98 | 79 | 80 |
| AF045151 | 1521 | 155 | 3.00E-37 | 100 | 81 | 81 | AY353531 | 1521 | 281 | 3.00E-75 | 175 | 148 | 84 |
| U17177 | 1521 | 283 | 6.00E-76 | 232 | 160 | 68 | AY353531 | 1521 | 155 | 3.00E-37 | 100 | 81 | 81 |
| U17177 | 1521 | 155 | 3.00E-37 | 100 | 81 | 81 | AY353530 | 1521 | 281 | 3.00E-75 | 175 | 148 | 84 |
| U17176 | 1521 | 283 | 6.00E-76 | 232 | 160 | 68 | AY353530 | 1521 | 155 | 3.00E-37 | 100 | 81 | 81 |
| U17176 | 1521 | 155 | 3.00E-37 | 100 | 81 | 81 | AY353529 | 1521 | 281 | 3.00E-75 | 175 | 148 | 84 |
| U17173 | 1521 | 283 | 6.00E-76 | 232 | 160 | 68 | AY353529 | 1521 | 154 | 8.00E-37 | 100 | 80 | 80 |
| U17173 | 1521 | 155 | 3.00E-37 | 100 | 81 | 81 | AY353528 | 1521 | 281 | 3.00E-75 | 175 | 148 | 84 |
| AY353272 | 1521 | 283 | 8.00E-76 | 232 | 160 | 68 | AY353528 | 1521 | 155 | 3.00E-37 | 100 | 81 | 81 |
| AY353272 | 1521 | 155 | 3.00E-37 | 100 | 81 | 81 | AY353518 | 1488 | 281 | 3.00E-75 | 175 | 148 | 84 |
| AJ243796 | 1368 | 283 | 1.00E-75 | 247 | 162 | 65 | AY353518 | 1488 | 155 | 3.00E-37 | 245 | 105 | 42 |
| AJ243796 | 1368 | 137 | 6.00E-32 | 87 | 70 | 80 | AY353512 | 1485 | 281 | 3.00E-75 | 175 | 148 | 84 |
| AJ243795 | 1368 | 283 | 1.00E-75 | 247 | 162 | 65 | AY353512 | 1485 | 158 | 3.00E-38 | 272 | 108 | 39 |
| AJ243795 | 1368 | 137 | 6.00E-32 | 87 | 70 | 80 | AY353470 | 1500 | 281 | 3.00E-75 | 175 | 148 | 84 |
| AY353525 | 1521 | 283 | 1.00E-75 | 229 | 160 | 69 | AY353470 | 1500 | 154 | 8.00E-37 | 100 | 80 | 80 |
| AY353525 | 1521 | 154 | 6.00E-37 | 150 | 87 | 58 | AY353469 | 1500 | 281 | 3.00E-75 | 175 | 148 | 84 |
| AY353524 | 1521 | 283 | 1.00E-75 | 229 | 160 | 69 | AY353469 | 1500 | 154 | 8.00E-37 | 100 | 80 | 80 |
| AY353524 | 1521 | 154 | 6.00E-37 | 150 | 87 | 58 | AY353439 | 1485 | 281 | 3.00E-75 | 175 | 148 | 84 |
| AY353523 | 1521 | 283 | 1.00E-75 | 229 | 160 | 69 | AY353439 | 1485 | 152 | 2.00E-36 | 98 | 79 | 80 |
| AY353523 | 1521 | 154 | 8.00E-37 | 100 | 80 | 80 | AY353438 | 1485 | 281 | 3.00E-75 | 175 | 148 | 84 |
| AY353522 | 1521 | 283 | 1.00E-75 | 229 | 160 | 69 | AY353438 | 1485 | 152 | 2.00E-36 | 98 | 79 | 80 |
| AY353522 | 1521 | 154 | 8.00E-37 | 100 | 80 | 80 | AY353436 | 1488 | 281 | 3.00E-75 | 175 | 148 | 84 |
| AY353491 | 1500 | 282 | 1.00E-75 | 199 | 154 | 77 | AY353436 | 1488 | 152 | 2.00E-36 | 98 | 79 | 80 |
| AY353491 | 1500 | 151 | 5.00E-36 | 98 | 78 | 79 | AY353355 | 1521 | 281 | 3.00E-75 | 175 | 148 | 84 |
| AY353287 | 1521 | 282 | 1.00E-75 | 275 | 164 | 59 | AY353355 | 1521 | 155 | 3.00E-37 | 100 | 81 | 81 |
| AY353287 | 1521 | 155 | 3.00E-37 | 100 | 81 | 81 | AY353354 | 1503 | 281 | 3.00E-75 | 175 | 148 | 84 |
| AY353286 | 1521 | 282 | 1.00E-75 | 275 | 164 | 59 | AY353354 | 1503 | 157 | 9.00E-38 | 100 | 82 | 82 |
| AY353286 | 1521 | 155 | 3.00E-37 | 100 | 81 | 81 | AY353353 | 1503 | 281 | 3.00E-75 | 175 | 148 | 84 |
| AY353285 | 1521 | 282 | 1.00E-75 | 275 | 164 | 59 | AY353353 | 1503 | 157 | 9.00E-38 | 100 | 82 | 82 |
| AY353285 | 1521 | 155 | 3.00E-37 | 100 | 81 | 81 | AY353352 | 1503 | 281 | 3.00E-75 | 175 | 148 | 84 |
| AJ430202 | 8179 | 282 | 2.00E-75 | 296 | 167 | 56 | AY353352 | 1503 | 155 | 3.00E-37 | 100 | 81 | 81 |
| AY353527 | 1521 | 282 | 2.00E-75 | 217 | 156 | 71 | AY353330 | 1488 | 281 | 3.00E-75 | 175 | 148 | 84 |
| AY353527 | 1521 | 154 | 5.00E-37 | 100 | 80 | 80 | AY353330 | 1488 | 155 | 3.00E-37 | 100 | 81 | 81 |
| AY353300 | 1521 | 282 | 2.00E-75 | 232 | 159 | 68 | AY353329 | 1488 | 281 | 3.00E-75 | 175 | 148 | 84 |
| AY353300 | 1521 | 155 | 3.00E-37 | 100 | 81 | 81 | AY353329 | 1488 | 155 | 3.00E-37 | 100 | 81 | 81 |
| AY353299 | 1521 | 282 | 2.00E-75 | 232 | 159 | 68 | AY353328 | 1488 | 281 | 3.00E-75 | 175 | 148 | 84 |
| AY353299 | 1521 | 155 | 3.00E-37 | 100 | 81 | 81 | AY353328 | 1488 | 155 | 3.00E-37 | 100 | 81 | 81 |
| AY353298 | 1521 | 282 | 2.00E-75 | 232 | 159 | 68 | AY353327 | 1506 | 281 | 3.00E-75 | 175 | 148 | 84 |
| AY353298 | 1521 | 155 | 3.00E-37 | 100 | 81 | 81 | AY353327 | 1506 | 155 | 3.00E-37 | 100 | 81 | 81 |
| AY353297 | 1521 | 282 | 2.00E-75 | 232 | 159 | 68 | AY353326 | 1506 | 281 | 3.00E-75 | 175 | 148 | 84 |
| AY353297 | 1521 | 155 | 3.00E-37 | 100 | 81 | 81 | AY353326 | 1506 | 155 | 3.00E-37 | 100 | 81 | 81 |
| AY353296 | 1521 | 282 | 2.00E-75 | 232 | 159 | 68 | AY353325 | 1506 | 281 | 3.00E-75 | 175 | 148 | 84 |
| AY353296 | 1521 | 155 | 3.00E-37 | 100 | 81 | 81 | AY353325 | 1506 | 155 | 3.00E-37 | 100 | 81 | 81 |
| AY353277 | 1521 | 282 | 2.00E-75 | 232 | 159 | 68 | AY353324 | 1506 | 281 | 3.00E-75 | 175 | 148 | 84 |
| AY353277 | 1521 | 155 | 3.00E-37 | 100 | 81 | 81 | AY353324 | 1506 | 155 | 3.00E-37 | 100 | 81 | 81 |
| AY353276 | 1521 | 282 | 2.00E-75 | 232 | 159 | 68 | AY353323 | 1506 | 281 | 3.00E-75 | 175 | 148 | 84 |
| AY353276 | 1521 | 155 | 3.00E-37 | 100 | 81 | 81 | AY353323 | 1506 | 155 | 3.00E-37 | 100 | 81 | 81 |
| AY353275 | 1521 | 282 | 2.00E-75 | 232 | 159 | 68 | AY353320 | 1506 | 281 | 3.00E-75 | 175 | 148 | 84 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AY353320 | 1506 | 155 | 3.00E-37 | 100 | 81 | 81 | AY649730 | 1482 | 152 | 2.00E-36 | 98 | 79 | 80 |
| AY353319 | 1506 | 281 | 3.00E-75 | 175 | 148 | 84 | AY649729 | 1482 | 280 | 5.00E-75 | 175 | 148 | 84 |
| AY353319 | 1506 | 155 | 3.00E-37 | 100 | 81 | 81 | AY649729 | 1482 | 152 | 2.00E-36 | 98 | 79 | 80 |
| AY353318 | 1506 | 281 | 3.00E-75 | 175 | 148 | 84 | AY649728 | 1482 | 280 | 5.00E-75 | 175 | 148 | 84 |
| AY353318 | 1506 | 155 | 3.00E-37 | 100 | 81 | 81 | AY649728 | 1482 | 152 | 2.00E-36 | 98 | 79 | 80 |
| AY353317 | 1506 | 281 | 3.00E-75 | 175 | 148 | 84 | AY649727 | 1482 | 280 | 5.00E-75 | 175 | 148 | 84 |
| AY353317 | 1506 | 155 | 3.00E-37 | 100 | 81 | 81 | AY649727 | 1482 | 152 | 2.00E-36 | 98 | 79 | 80 |
| AY353316 | 1506 | 281 | 3.00E-75 | 175 | 148 | 84 | AY649726 | 1482 | 280 | 5.00E-75 | 175 | 148 | 84 |
| AY353316 | 1506 | 155 | 3.00E-37 | 100 | 81 | 81 | AY649726 | 1482 | 152 | 2.00E-36 | 98 | 79 | 80 |
| AY353315 | 1506 | 281 | 3.00E-75 | 175 | 148 | 84 | AY649722 | 1488 | 280 | 5.00E-75 | 175 | 148 | 84 |
| AY353315 | 1506 | 155 | 3.00E-37 | 100 | 81 | 81 | AY649722 | 1488 | 156 | 1.00E-37 | 245 | 106 | 43 |
| AY353314 | 1506 | 281 | 3.00E-75 | 175 | 148 | 84 | AY649721 | 1488 | 280 | 5.00E-75 | 175 | 148 | 84 |
| AY353314 | 1506 | 155 | 3.00E-37 | 100 | 81 | 81 | AY649721 | 1488 | 152 | 2.00E-36 | 98 | 79 | 80 |
| AY353311 | 1506 | 281 | 3.00E-75 | 175 | 148 | 84 | AY649720 | 1488 | 280 | 5.00E-75 | 175 | 148 | 84 |
| AY353311 | 1506 | 155 | 3.00E-37 | 100 | 81 | 81 | AY649720 | 1488 | 152 | 2.00E-36 | 98 | 79 | 80 |
| AY353309 | 1506 | 281 | 3.00E-75 | 175 | 148 | 84 | AY649719 | 1488 | 280 | 5.00E-75 | 175 | 148 | 84 |
| AY353309 | 1506 | 155 | 3.00E-37 | 100 | 81 | 81 | AY649719 | 1488 | 152 | 2.00E-36 | 98 | 79 | 80 |
| AY353308 | 1506 | 281 | 3.00E-75 | 175 | 148 | 84 | AY649718 | 1488 | 280 | 5.00E-75 | 175 | 148 | 84 |
| AY353308 | 1506 | 155 | 3.00E-37 | 100 | 81 | 81 | AY649718 | 1488 | 152 | 2.00E-36 | 98 | 79 | 80 |
| AY353306 | 1506 | 281 | 3.00E-75 | 175 | 148 | 84 | AY649699 | 1506 | 280 | 5.00E-75 | 175 | 148 | 84 |
| AY353306 | 1506 | 155 | 3.00E-37 | 100 | 81 | 81 | AY649699 | 1506 | 154 | 5.00E-37 | 100 | 81 | 81 |
| AY353305 | 1506 | 281 | 3.00E-75 | 175 | 148 | 84 | AY649697 | 1488 | 280 | 5.00E-75 | 175 | 148 | 84 |
| AY353305 | 1506 | 155 | 3.00E-37 | 100 | 81 | 81 | AY649697 | 1488 | 156 | 1.00E-37 | 100 | 82 | 82 |
| AY353295 | 1521 | 281 | 3.00E-75 | 175 | 148 | 84 | AE008787 | 24186 | 280 | 5.00E-75 | 175 | 148 | 84 |
| AY353295 | 1521 | 155 | 3.00E-37 | 100 | 81 | 81 | AE008787 | 24186 | 152 | 2.00E-36 | 98 | 79 | 80 |
| AY353294 | 1521 | 281 | 3.00E-75 | 175 | 148 | 84 | X03394 | 1482 | 280 | 5.00E-75 | 175 | 148 | 84 |
| AY353294 | 1521 | 155 | 3.00E-37 | 100 | 81 | 81 | X03394 | 1482 | 154 | 8.00E-37 | 329 | 126 | 38 |
| AY353293 | 1398 | 281 | 3.00E-75 | 175 | 148 | 84 | X03393 | 1497 | 280 | 5.00E-75 | 175 | 148 | 84 |
| AY353293 | 1398 | 155 | 3.00E-37 | 100 | 81 | 81 | X03393 | 1497 | 157 | 5.00E-38 | 100 | 83 | 83 |
| AY353289 | 1521 | 281 | 3.00E-75 | 175 | 148 | 84 | AY657000 | 1474 | 280 | 5.00E-75 | 175 | 148 | 84 |
| AY353289 | 1521 | 155 | 3.00E-37 | 100 | 81 | 81 | AY657000 | 1474 | 136 | 1.00E-31 | 90 | 71 | 78 |
| AY353284 | 1521 | 281 | 3.00E-75 | 175 | 148 | 84 | X04505 | 1479 | 280 | 5.00E-75 | 175 | 148 | 84 |
| AY353284 | 1521 | 155 | 3.00E-37 | 100 | 81 | 81 | X04505 | 1479 | 152 | 2.00E-36 | 98 | 79 | 80 |
| AY353282 | 1521 | 281 | 3.00E-75 | 175 | 148 | 84 | AF336929 | 1506 | 280 | 5.00E-75 | 175 | 148 | 84 |
| AY353282 | 1521 | 155 | 3.00E-37 | 100 | 81 | 81 | AF336929 | 1506 | 154 | 8.00E-37 | 100 | 80 | 80 |
| AY353280 | 1521 | 281 | 3.00E-75 | 175 | 148 | 84 | AF420425 | 1460 | 280 | 5.00E-75 | 175 | 148 | 84 |
| AY353280 | 1521 | 155 | 3.00E-37 | 100 | 81 | 81 | AF420425 | 1460 | 129 | 3.00E-29 | 85 | 66 | 77 |
| U17174 | 1521 | 281 | 3.00E-75 | 175 | 148 | 84 | AY353526 | 1521 | 280 | 5.00E-75 | 175 | 148 | 84 |
| U17174 | 1521 | 155 | 3.00E-37 | 100 | 81 | 81 | AY353526 | 1521 | 155 | 3.00E-37 | 100 | 81 | 81 |
| U17171 | 1521 | 281 | 3.00E-75 | 175 | 148 | 84 | AY353519 | 1503 | 280 | 5.00E-75 | 175 | 148 | 84 |
| U17171 | 1521 | 154 | 5.00E-37 | 100 | 81 | 81 | AY353519 | 1503 | 152 | 2.00E-36 | 98 | 79 | 80 |
| AY353462 | 1482 | 281 | 4.00E-75 | 229 | 160 | 69 | AY353515 | 1488 | 280 | 5.00E-75 | 175 | 148 | 84 |
| AY353462 | 1482 | 147 | 7.00E-35 | 98 | 77 | 78 | AY353515 | 1488 | 156 | 1.00E-37 | 245 | 106 | 43 |
| AY353461 | 1482 | 281 | 4.00E-75 | 229 | 160 | 69 | AY353513 | 1491 | 280 | 5.00E-75 | 175 | 148 | 84 |
| AY353461 | 1482 | 152 | 2.00E-36 | 98 | 79 | 80 | AY353513 | 1491 | 155 | 3.00E-37 | 100 | 81 | 81 |
| AY353460 | 1482 | 281 | 4.00E-75 | 229 | 160 | 69 | AY353511 | 1491 | 280 | 5.00E-75 | 175 | 148 | 84 |
| AY353460 | 1482 | 152 | 2.00E-36 | 98 | 79 | 80 | AY353511 | 1491 | 153 | 1.00E-36 | 100 | 80 | 80 |
| AY353339 | 1500 | 281 | 4.00E-75 | 217 | 157 | 72 | AY353510 | 1491 | 280 | 5.00E-75 | 175 | 148 | 84 |
| AY353339 | 1500 | 155 | 3.00E-37 | 100 | 81 | 81 | AY353510 | 1491 | 152 | 2.00E-36 | 98 | 79 | 80 |
| AY353338 | 1500 | 281 | 4.00E-75 | 217 | 157 | 72 | AY353481 | 1488 | 280 | 5.00E-75 | 175 | 148 | 84 |
| AY353338 | 1500 | 155 | 3.00E-37 | 100 | 81 | 81 | AY353481 | 1488 | 154 | 5.00E-37 | 100 | 81 | 81 |
| AY353337 | 1500 | 281 | 4.00E-75 | 217 | 157 | 72 | AY353480 | 1488 | 280 | 5.00E-75 | 175 | 148 | 84 |
| AY353337 | 1500 | 155 | 3.00E-37 | 100 | 81 | 81 | AY353480 | 1488 | 152 | 2.00E-36 | 98 | 79 | 80 |
| AY353336 | 1500 | 281 | 4.00E-75 | 217 | 157 | 72 | AY353472 | 1500 | 280 | 5.00E-75 | 175 | 148 | 84 |
| AY353336 | 1500 | 155 | 3.00E-37 | 100 | 81 | 81 | AY353472 | 1500 | 154 | 6.00E-37 | 98 | 80 | 81 |
| AY353335 | 1500 | 281 | 4.00E-75 | 217 | 157 | 72 | AY353471 | 1500 | 280 | 5.00E-75 | 175 | 148 | 84 |
| AY353335 | 1500 | 155 | 3.00E-37 | 100 | 81 | 81 | AY353471 | 1500 | 154 | 6.00E-37 | 98 | 80 | 81 |
| AY649740 | 1506 | 280 | 5.00E-75 | 175 | 148 | 84 | AY353468 | 1500 | 280 | 5.00E-75 | 175 | 148 | 84 |
| AY649740 | 1506 | 154 | 5.00E-37 | 100 | 81 | 81 | AY353468 | 1500 | 155 | 3.00E-37 | 100 | 81 | 81 |
| AY649739 | 1500 | 280 | 5.00E-75 | 175 | 148 | 84 | AY353467 | 1500 | 280 | 5.00E-75 | 175 | 148 | 84 |
| AY649739 | 1500 | 155 | 3.00E-37 | 100 | 81 | 81 | AY353467 | 1500 | 155 | 3.00E-37 | 100 | 81 | 81 |
| AY649734 | 1500 | 280 | 5.00E-75 | 175 | 148 | 84 | AY353466 | 1521 | 280 | 5.00E-75 | 175 | 148 | 84 |
| AY649734 | 1500 | 154 | 6.00E-37 | 98 | 80 | 81 | AY353466 | 1521 | 159 | 2.00E-38 | 100 | 83 | 83 |
| AY649733 | 1488 | 280 | 5.00E-75 | 175 | 148 | 84 | AY353465 | 1521 | 280 | 5.00E-75 | 175 | 148 | 84 |
| AY649733 | 1488 | 152 | 2.00E-36 | 98 | 79 | 80 | AY353465 | 1521 | 158 | 3.00E-38 | 98 | 82 | 83 |
| AY649731 | 1482 | 280 | 5.00E-75 | 175 | 148 | 84 | AY353464 | 1476 | 280 | 5.00E-75 | 175 | 148 | 84 |
| AY649731 | 1482 | 152 | 2.00E-36 | 98 | 79 | 80 | AY353464 | 1476 | 152 | 2.00E-36 | 98 | 79 | 80 |
| AY649730 | 1482 | 280 | 5.00E-75 | 175 | 148 | 84 | AY353463 | 1476 | 280 | 5.00E-75 | 175 | 148 | 84 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AY353463 | 1476 | 152 | 2.00E-36 | 98 | 79 | 80 | AY353322 | 1506 | 155 | 3.00E-37 | 100 | 81 | 81 |
| AY353459 | 1482 | 280 | 5.00E-75 | 175 | 148 | 84 | AY353321 | 1506 | 280 | 5.00E-75 | 175 | 148 | 84 |
| AY353459 | 1482 | 152 | 2.00E-36 | 98 | 79 | 80 | AY353321 | 1506 | 155 | 3.00E-37 | 100 | 81 | 81 |
| AY353458 | 1482 | 280 | 5.00E-75 | 175 | 148 | 84 | AY353313 | 1506 | 280 | 5.00E-75 | 175 | 148 | 84 |
| AY353458 | 1482 | 152 | 2.00E-36 | 98 | 79 | 80 | AY353313 | 1506 | 155 | 3.00E-37 | 100 | 81 | 81 |
| AY353442 | 1488 | 280 | 5.00E-75 | 175 | 148 | 84 | AY353312 | 1506 | 280 | 5.00E-75 | 175 | 148 | 84 |
| AY353442 | 1488 | 156 | 1.00E-37 | 245 | 106 | 43 | AY353312 | 1506 | 155 | 3.00E-37 | 100 | 81 | 81 |
| AY353441 | 1488 | 280 | 5.00E-75 | 175 | 148 | 84 | AY353307 | 1506 | 280 | 5.00E-75 | 175 | 148 | 84 |
| AY353441 | 1488 | 157 | 9.00E-38 | 245 | 106 | 43 | AY353307 | 1506 | 155 | 3.00E-37 | 100 | 81 | 81 |
| AY353432 | 1488 | 280 | 5.00E-75 | 175 | 148 | 84 | AY353301 | 1488 | 280 | 5.00E-75 | 175 | 148 | 84 |
| AY353432 | 1488 | 152 | 2.00E-36 | 98 | 79 | 80 | AY353301 | 1488 | 155 | 3.00E-37 | 100 | 81 | 81 |
| AY353431 | 1488 | 280 | 5.00E-75 | 175 | 148 | 84 | AY353291 | 1521 | 280 | 5.00E-75 | 175 | 148 | 84 |
| AY353431 | 1488 | 152 | 2.00E-36 | 98 | 79 | 80 | AY353291 | 1521 | 154 | 5.00E-37 | 98 | 80 | 81 |
| AY353430 | 1488 | 280 | 5.00E-75 | 175 | 148 | 84 | AY353290 | 1521 | 280 | 5.00E-75 | 175 | 148 | 84 |
| AY353430 | 1488 | 152 | 2.00E-36 | 98 | 79 | 80 | AY353290 | 1521 | 154 | 5.00E-37 | 98 | 80 | 81 |
| AY353429 | 1488 | 280 | 5.00E-75 | 175 | 148 | 84 | AY353281 | 1521 | 280 | 5.00E-75 | 175 | 148 | 84 |
| AY353429 | 1488 | 152 | 2.00E-36 | 98 | 79 | 80 | AY353281 | 1521 | 154 | 5.00E-37 | 98 | 80 | 81 |
| AY353428 | 1488 | 280 | 5.00E-75 | 175 | 148 | 84 | AY353279 | 1521 | 280 | 5.00E-75 | 175 | 148 | 84 |
| AY353428 | 1488 | 152 | 2.00E-36 | 98 | 79 | 80 | AY353279 | 1521 | 154 | 5.00E-37 | 98 | 80 | 81 |
| AY353427 | 1488 | 280 | 5.00E-75 | 175 | 148 | 84 | AY353278 | 1521 | 280 | 5.00E-75 | 175 | 148 | 84 |
| AY353427 | 1488 | 152 | 2.00E-36 | 98 | 79 | 80 | AY353278 | 1521 | 154 | 5.00E-37 | 98 | 80 | 81 |
| AY353426 | 1488 | 280 | 5.00E-75 | 175 | 148 | 84 | AY353274 | 1521 | 280 | 5.00E-75 | 175 | 148 | 84 |
| AY353426 | 1488 | 152 | 2.00E-36 | 98 | 79 | 80 | AY353274 | 1521 | 154 | 5.00E-37 | 98 | 80 | 81 |
| AY353425 | 1488 | 280 | 5.00E-75 | 175 | 148 | 84 | AY353273 | 1521 | 280 | 5.00E-75 | 175 | 148 | 84 |
| AY353425 | 1488 | 152 | 2.00E-36 | 98 | 79 | 80 | AY353273 | 1521 | 154 | 5.00E-37 | 98 | 80 | 81 |
| AY353424 | 1488 | 280 | 5.00E-75 | 175 | 148 | 84 | AY353262 | 1488 | 280 | 5.00E-75 | 175 | 148 | 84 |
| AY353424 | 1488 | 152 | 2.00E-36 | 98 | 79 | 80 | AY353262 | 1488 | 155 | 3.00E-37 | 100 | 81 | 81 |
| AY353423 | 1488 | 280 | 5.00E-75 | 175 | 148 | 84 | AF332601 | 1515 | 280 | 5.00E-75 | 173 | 148 | 85 |
| AY353423 | 1488 | 152 | 2.00E-36 | 98 | 79 | 80 | AF332601 | 1515 | 149 | 2.00E-35 | 91 | 76 | 83 |
| AY353422 | 1488 | 280 | 5.00E-75 | 175 | 148 | 84 | D13689 | 1826 | 280 | 5.00E-75 | 175 | 148 | 84 |
| AY353422 | 1488 | 152 | 2.00E-36 | 98 | 79 | 80 | D13689 | 1826 | 152 | 2.00E-36 | 98 | 79 | 80 |
| AY353421 | 1488 | 280 | 5.00E-75 | 175 | 148 | 84 | AF159459 | 1602 | 280 | 7.00E-75 | 175 | 148 | 84 |
| AY353421 | 1488 | 152 | 2.00E-36 | 98 | 79 | 80 | AF159459 | 1602 | 154 | 5.00E-37 | 100 | 81 | 81 |
| AY353420 | 1488 | 280 | 5.00E-75 | 175 | 148 | 84 | AY353440 | 1488 | 280 | 9.00E-75 | 175 | 147 | 84 |
| AY353420 | 1488 | 152 | 2.00E-36 | 98 | 79 | 80 | AY353440 | 1488 | 152 | 2.00E-36 | 98 | 79 | 80 |
| AY353419 | 1488 | 280 | 5.00E-75 | 175 | 148 | 84 | AY353261 | 1485 | 280 | 9.00E-75 | 175 | 147 | 84 |
| AY353419 | 1488 | 152 | 2.00E-36 | 98 | 79 | 80 | AY353261 | 1485 | 153 | 1.00E-36 | 100 | 80 | 80 |
| AY353418 | 1488 | 280 | 5.00E-75 | 175 | 148 | 84 | AY353260 | 1485 | 280 | 9.00E-75 | 175 | 147 | 84 |
| AY353418 | 1488 | 152 | 2.00E-36 | 98 | 79 | 80 | AY353260 | 1485 | 152 | 2.00E-36 | 98 | 79 | 80 |
| AY353417 | 1488 | 280 | 5.00E-75 | 175 | 148 | 84 | AY337484 | 1472 | 194 | 9.00E-75 | 114 | 97 | 85 |
| AY353417 | 1488 | 152 | 2.00E-36 | 98 | 79 | 80 | AY337484 | 1472 | 163 | 1.00E-39 | 258 | 114 | 44 |
| AY353369 | 1506 | 280 | 5.00E-75 | 175 | 148 | 84 | AY337484 | 1472 | 113 | 9.00E-75 | 66 | 60 | 90 |
| AY353369 | 1506 | 152 | 2.00E-36 | 98 | 79 | 80 | D13690 | 3471 | 279 | 1.00E-74 | 175 | 147 | 84 |
| AY353368 | 1506 | 280 | 5.00E-75 | 175 | 148 | 84 | D13690 | 3471 | 155 | 3.00E-37 | 100 | 81 | 81 |
| AY353368 | 1506 | 154 | 5.00E-37 | 100 | 81 | 81 | AY649738 | 1491 | 279 | 2.00E-74 | 175 | 147 | 84 |
| AY353367 | 1506 | 280 | 5.00E-75 | 175 | 148 | 84 | AY649738 | 1491 | 153 | 1.00E-36 | 100 | 80 | 80 |
| AY353367 | 1506 | 154 | 5.00E-37 | 100 | 81 | 81 | AY249996 | 1368 | 279 | 2.00E-74 | 245 | 160 | 65 |
| AY353366 | 1506 | 280 | 5.00E-75 | 175 | 148 | 84 | AY249996 | 1368 | 142 | 2.00E-33 | 90 | 73 | 81 |
| AY353366 | 1506 | 152 | 2.00E-36 | 98 | 79 | 80 | AY353520 | 1503 | 279 | 2.00E-74 | 175 | 147 | 84 |
| AY353365 | 1506 | 280 | 5.00E-75 | 175 | 148 | 84 | AY353520 | 1503 | 153 | 1.00E-36 | 100 | 80 | 80 |
| AY353365 | 1506 | 154 | 5.00E-37 | 100 | 81 | 81 | AY353473 | 1500 | 279 | 2.00E-74 | 175 | 147 | 84 |
| AY353364 | 1506 | 280 | 5.00E-75 | 175 | 148 | 84 | AY353473 | 1500 | 152 | 2.00E-36 | 98 | 79 | 80 |
| AY353364 | 1506 | 154 | 5.00E-37 | 100 | 81 | 81 | AY353265 | 1521 | 279 | 2.00E-74 | 232 | 158 | 68 |
| AY353357 | 1488 | 280 | 5.00E-75 | 175 | 148 | 84 | AY353265 | 1521 | 155 | 3.00E-37 | 100 | 81 | 81 |
| AY353357 | 1488 | 156 | 1.00E-37 | 100 | 82 | 82 | AY353258 | 1494 | 279 | 2.00E-74 | 175 | 147 | 84 |
| AY353356 | 1488 | 280 | 5.00E-75 | 175 | 148 | 84 | AY353258 | 1494 | 155 | 2.00E-37 | 273 | 112 | 41 |
| AY353356 | 1488 | 156 | 1.00E-37 | 100 | 82 | 82 | AY353370 | 1506 | 278 | 2.00E-74 | 175 | 147 | 84 |
| AY353351 | 1497 | 280 | 5.00E-75 | 175 | 148 | 84 | AY353370 | 1506 | 152 | 2.00E-36 | 98 | 79 | 80 |
| AY353351 | 1497 | 155 | 3.00E-37 | 100 | 81 | 81 | AY353344 | 1488 | 278 | 2.00E-74 | 175 | 147 | 84 |
| AY353343 | 1488 | 280 | 5.00E-75 | 175 | 148 | 84 | AY353344 | 1488 | 155 | 3.00E-37 | 100 | 81 | 81 |
| AY353343 | 1488 | 155 | 3.00E-37 | 100 | 81 | 81 | AB128921 | 2358 | 278 | 3.00E-74 | 158 | 145 | 91 |
| AY353342 | 1488 | 280 | 5.00E-75 | 175 | 148 | 84 | AB128921 | 2358 | 136 | 1.00E-31 | 85 | 72 | 84 |
| AY353342 | 1488 | 155 | 3.00E-37 | 100 | 81 | 81 | AY249993 | 1383 | 278 | 4.00E-74 | 244 | 157 | 64 |
| AY353341 | 1488 | 280 | 5.00E-75 | 175 | 148 | 84 | AY249993 | 1383 | 142 | 2.00E-33 | 90 | 73 | 81 |
| AY353341 | 1488 | 155 | 3.00E-37 | 100 | 81 | 81 | AY353437 | 1488 | 278 | 4.00E-74 | 175 | 147 | 84 |
| AY353340 | 1488 | 280 | 5.00E-75 | 175 | 148 | 84 | AY353437 | 1488 | 152 | 2.00E-36 | 98 | 79 | 80 |
| AY353340 | 1488 | 155 | 3.00E-37 | 100 | 81 | 81 | M11332 | 1485 | 277 | 5.00E-74 | 175 | 146 | 83 |
| AY353322 | 1506 | 280 | 5.00E-75 | 175 | 148 | 84 | M11332 | 1485 | 153 | 1.00E-36 | 100 | 80 | 80 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AF128953 | 1668 | 276 | 1.00E-73 | 258 | 154 | 59 | AF077601 | 831 | 243 | 1.00E-63 | 292 | 136 | 46 |
| AF128953 | 1668 | 123 | 1.00E-27 | 103 | 64 | 62 | AF198617 | 6830 | 242 | 2.00E-63 | 304 | 141 | 46 |
| AF128950 | 1681 | 276 | 1.00E-73 | 258 | 154 | 59 | AF198617 | 6830 | 238 | 4.00E-62 | 305 | 142 | 46 |
| AF128950 | 1681 | 132 | 3.00E-30 | 107 | 68 | 63 | AF105060 | 3785 | 236 | 1.00E-61 | 296 | 129 | 43 |
| AF487406 | 1656 | 275 | 2.00E-73 | 222 | 151 | 68 | AE015761 | 14255 | 236 | 2.00E-61 | 297 | 140 | 47 |
| AF487406 | 1656 | 143 | 1.00E-33 | 335 | 118 | 35 | AE015761 | 14255 | 233 | 1.00E-60 | 297 | 138 | 46 |
| AY250009 | 1365 | 275 | 2.00E-73 | 238 | 159 | 66 | AE015761 | 14255 | 55.1 | 5.00E-07 | 136 | 36 | 26 |
| AY250009 | 1365 | 140 | 9.00E-33 | 90 | 72 | 80 | AE015761 | 14255 | 34.3 | 0.89 | 89 | 26 | 29 |
| AF517662 | 1348 | 275 | 3.00E-73 | 243 | 158 | 65 | BA000043 3544776 | | 234 | 4.00E-61 | 307 | 134 | 43 |
| AF517662 | 1348 | 126 | 2.00E-28 | 85 | 65 | 76 | BA000043 3544776 | | 142 | 2.00E-33 | 269 | 96 | 35 |
| AY250004 | 1380 | 274 | 4.00E-73 | 158 | 141 | 89 | BA000043 3544776 | | 103 | 2.00E-21 | 179 | 62 | 34 |
| AY250004 | 1380 | 142 | 2.00E-33 | 90 | 73 | 81 | BA000043 3544776 | | 80.5 | 1.00E-14 | 288 | 69 | 23 |
| AF517661 | 1361 | 274 | 4.00E-73 | 242 | 155 | 64 | AB061233 | 849 | 233 | 1.00E-60 | 299 | 137 | 45 |
| AF517661 | 1361 | 124 | 7.00E-28 | 84 | 64 | 76 | AF077600 | 834 | 232 | 2.00E-60 | 296 | 137 | 46 |
| AY250000 | 1506 | 273 | 7.00E-73 | 281 | 166 | 59 | AF399739 | 6492 | 231 | 5.00E-60 | 300 | 138 | 46 |
| AY250000 | 1506 | 144 | 8.00E-34 | 88 | 73 | 82 | AF232939 | 1045 | 230 | 6.00E-60 | 348 | 157 | 45 |
| AF128952 | 1695 | 273 | 1.00E-72 | 208 | 143 | 68 | AF232941 | 1051 | 230 | 8.00E-60 | 350 | 154 | 44 |
| AF128952 | 1695 | 117 | 1.00E-25 | 99 | 60 | 60 | AY590686 | 874 | 229 | 1.00E-59 | 289 | 127 | 43 |
| AF517665 | 1365 | 272 | 1.00E-72 | 158 | 140 | 88 | AY590679 | 873 | 229 | 1.00E-59 | 289 | 127 | 43 |
| AF517665 | 1365 | 130 | 9.00E-30 | 294 | 104 | 35 | AY590678 | 873 | 229 | 1.00E-59 | 289 | 127 | 43 |
| AY353514 | 1500 | 272 | 1.00E-72 | 197 | 149 | 75 | AY590677 | 873 | 229 | 1.00E-59 | 289 | 127 | 43 |
| AY353514 | 1500 | 152 | 2.00E-36 | 98 | 79 | 80 | AY590676 | 873 | 229 | 1.00E-59 | 289 | 127 | 43 |
| BX640427 | 348997 | 272 | 1.00E-72 | 392 | 180 | 45 | AY590675 | 873 | 229 | 1.00E-59 | 289 | 127 | 43 |
| BX640427 | 348997 | 54.3 | 8.00E-07 | 136 | 42 | 30 | AY590674 | 864 | 229 | 1.00E-59 | 289 | 127 | 43 |
| AF128948 | 1569 | 272 | 2.00E-72 | 251 | 156 | 62 | AY590673 | 873 | 229 | 1.00E-59 | 289 | 127 | 43 |
| AF128948 | 1569 | 128 | 5.00E-29 | 93 | 62 | 66 | AY590672 | 873 | 229 | 1.00E-59 | 289 | 127 | 43 |
| AF517664 | 1343 | 271 | 3.00E-72 | 236 | 157 | 66 | AY590671 | 873 | 229 | 1.00E-59 | 289 | 127 | 43 |
| AF517664 | 1343 | 119 | 2.00E-26 | 84 | 61 | 72 | AY590670 | 873 | 229 | 1.00E-59 | 289 | 127 | 43 |
| AF517663 | 1356 | 270 | 7.00E-72 | 156 | 139 | 89 | AY590669 | 873 | 229 | 1.00E-59 | 289 | 127 | 43 |
| AF517663 | 1356 | 124 | 7.00E-28 | 84 | 64 | 76 | AE017180 3814139 | | 228 | 3.00E-59 | 298 | 133 | 44 |
| AF128958 | 1665 | 268 | 3.00E-71 | 253 | 151 | 59 | AE017180 3814139 | | 90.1 | 1.00E-17 | 293 | 76 | 25 |
| AF128958 | 1665 | 132 | 3.00E-30 | 107 | 68 | 63 | AB128920 | 2676 | 228 | 3.00E-59 | 127 | 121 | 95 |
| AF128951 | 1665 | 268 | 3.00E-71 | 253 | 151 | 59 | AB128920 | 2676 | 167 | 7.00E-41 | 313 | 124 | 39 |
| AF128951 | 1665 | 132 | 3.00E-30 | 107 | 68 | 63 | AB128920 | 2676 | 85.9 | 3.00E-16 | 51 | 40 | 78 |
| BX640413 | 349028 | 268 | 4.00E-71 | 391 | 182 | 46 | AB061232 | 849 | 227 | 5.00E-59 | 299 | 131 | 43 |
| BX640444 | 349008 | 266 | 1.00E-70 | 391 | 183 | 46 | AB106910 | 15284 | 226 | 1.00E-58 | 299 | 131 | 43 |
| BX640444 | 349008 | 54.3 | 8.00E-07 | 136 | 42 | 30 | AB061230 | 19187 | 226 | 1.00E-58 | 299 | 131 | 43 |
| L13034 | 1572 | 266 | 1.00E-70 | 391 | 183 | 46 | AB061230 | 19187 | 59.3 | 3.00E-08 | 130 | 38 | 29 |
| AF128954 | 1680 | 265 | 2.00E-70 | 204 | 140 | 68 | AE016862 | 310266 | 223 | 8.00E-58 | 297 | 129 | 43 |
| AF128954 | 1680 | 114 | 9.00E-25 | 97 | 58 | 59 | AF095238 | 846 | 222 | 2.00E-57 | 291 | 129 | 44 |
| AF128947 | 1649 | 265 | 2.00E-70 | 254 | 149 | 58 | AB061231 | 849 | 222 | 2.00E-57 | 297 | 129 | 43 |
| AF128947 | 1649 | 117 | 6.00E-26 | 100 | 62 | 62 | AE013021 | 10029 | 220 | 7.00E-57 | 298 | 134 | 44 |
| AF128955 | 1524 | 265 | 3.00E-70 | 247 | 153 | 61 | BA000021 | 697724 | 219 | 1.00E-56 | 181 | 109 | 60 |
| AF128955 | 1524 | 112 | 3.00E-24 | 82 | 53 | 64 | BA000021 | 697724 | 120 | 9.00E-27 | 345 | 109 | 31 |
| AY249138 | 1398 | 263 | 7.00E-70 | 160 | 137 | 85 | AF077341 | 874 | 219 | 1.00E-56 | 292 | 124 | 42 |
| AY249138 | 1398 | 138 | 4.00E-32 | 161 | 84 | 52 | AF095237 | 873 | 219 | 2.00E-56 | 292 | 123 | 42 |
| AF128956 | 1551 | 262 | 2.00E-69 | 245 | 152 | 62 | AB080999 | 348 | 218 | 3.00E-56 | 115 | 115 | 100 |
| AF128956 | 1551 | 126 | 1.00E-28 | 93 | 62 | 66 | AB033501 | 1210 | 217 | 6.00E-56 | 330 | 134 | 40 |
| AF128949 | 1563 | 259 | 2.00E-68 | 246 | 151 | 61 | CP000002 4222334 | | 215 | 3.00E-55 | 313 | 135 | 43 |
| AF128949 | 1563 | 121 | 6.00E-27 | 90 | 58 | 64 | CP000002 4222334 | | 33.9 | 1.2 | 87 | 22 | 25 |
| AF425736 | 1351 | 254 | 3.00E-67 | 160 | 133 | 83 | AE017333 4222645 | | 215 | 3.00E-55 | 313 | 135 | 43 |
| AF425736 | 1351 | 92.4 | 3.00E-18 | 64 | 46 | 71 | AE017333 4222645 | | 33.9 | 1.2 | 87 | 22 | 25 |
| AF128957 | 1668 | 254 | 3.00E-67 | 248 | 143 | 57 | BA000004 4202352 | | 214 | 6.00E-55 | 294 | 124 | 42 |
| AF128957 | 1668 | 129 | 2.00E-29 | 106 | 67 | 63 | BA000004 4202352 | | 130 | 1.00E-29 | 135 | 70 | 51 |
| AY534751 | 1404 | 253 | 7.00E-67 | 158 | 135 | 85 | BA000004 4202352 | | 95.9 | 2.00E-19 | 169 | 57 | 33 |
| AY534751 | 1404 | 123 | 1.00E-27 | 117 | 70 | 59 | D10063 | 1064 | 214 | 6.00E-55 | 294 | 124 | 42 |
| AY250006 | 1383 | 251 | 4.00E-66 | 177 | 133 | 75 | AF232940 | 1045 | 213 | 1.00E-54 | 273 | 137 | 50 |
| AY250006 | 1383 | 118 | 5.00E-26 | 280 | 93 | 33 | AF065259 | 1631 | 211 | 3.00E-54 | 300 | 125 | 41 |
| AY534750 | 1380 | 250 | 8.00E-66 | 158 | 133 | 84 | AF095236 | 873 | 211 | 3.00E-54 | 300 | 125 | 41 |
| AY534750 | 1380 | 123 | 1.00E-27 | 189 | 82 | 43 | AF011370 | 1300 | 211 | 5.00E-54 | 381 | 141 | 37 |
| AF002709 | 3434 | 250 | 8.00E-66 | 303 | 140 | 46 | AE015942 | 300171 | 209 | 1.00E-53 | 296 | 125 | 42 |
| AF002709 | 3434 | 239 | 2.00E-62 | 304 | 139 | 45 | AE015942 | 300171 | 68.2 | 6.00E-11 | 284 | 68 | 23 |
| AY250007 | 1197 | 249 | 2.00E-65 | 158 | 127 | 80 | BA000028 3630528 | | 209 | 1.00E-53 | 338 | 131 | 38 |
| AY250007 | 1197 | 107 | 6.00E-23 | 304 | 93 | 30 | BA000028 3630528 | | 91.3 | 6.00E-18 | 293 | 75 | 25 |
| AE016923 | 303642 | 248 | 4.00E-65 | 297 | 137 | 46 | AF080260 | 1149 | 209 | 2.00E-53 | 380 | 141 | 37 |
| AE016923 | 303642 | 246 | 1.00E-64 | 297 | 137 | 46 | AF080259 | 1149 | 209 | 2.00E-53 | 380 | 141 | 37 |
| AF420426 | 1364 | 248 | 4.00E-65 | 157 | 130 | 82 | Z99122 | 200690 | 208 | 3.00E-53 | 306 | 130 | 42 |
| AF420426 | 1364 | 114 | 5.00E-25 | 77 | 58 | 75 | U56901 | 20320 | 208 | 3.00E-53 | 306 | 130 | 42 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| M26948 | 2360 | 208 | 3.00E-53 | 306 | 130 | 42 | AF084813 | 1952 | 189 | 1.00E-47 | 385 | 136 | 35 |
| M26947 | 1474 | 208 | 3.00E-53 | 306 | 130 | 42 | AF084812 | 1952 | 189 | 1.00E-47 | 385 | 136 | 35 |
| AB058936 | 884 | 207 | 4.00E-53 | 294 | 123 | 41 | AF019213 | 7256 | 189 | 1.00E-47 | 375 | 130 | 34 |
| BA000032 | 1877212 | 207 | 6.00E-53 | 301 | 119 | 39 | AF030239 | 1167 | 189 | 1.00E-47 | 385 | 136 | 35 |
| BA000032 | 1877212 | 36.6 | 0.18 | 116 | 29 | 25 | U82287 | 1199 | 189 | 1.00E-47 | 385 | 136 | 35 |
| AF124349 | 42050 | 207 | 6.00E-53 | 299 | 120 | 40 | U82286 | 1199 | 189 | 1.00E-47 | 385 | 136 | 35 |
| AE007720 | 7354 | 207 | 8.00E-53 | 295 | 122 | 41 | AE017003 | 347456 | 189 | 2.00E-47 | 296 | 114 | 38 |
| AF064086 | 1020 | 207 | 8.00E-53 | 295 | 122 | 41 | AE017003 | 347456 | 180 | 1.00E-44 | 298 | 115 | 38 |
| AE008692 | 2056416 | 206 | 1.00E-52 | 296 | 119 | 40 | AE017003 | 347456 | 165 | 3.00E-40 | 271 | 98 | 36 |
| U52957 | 9544 | 206 | 2.00E-52 | 301 | 119 | 39 | AE017003 | 347456 | 140 | 9.00E-33 | 291 | 95 | 32 |
| L06176 | 3724 | 206 | 2.00E-52 | 301 | 119 | 39 | AE017003 | 347456 | 56.6 | 2.00E-07 | 243 | 57 | 23 |
| BA000031 | 3288558 | 201 | 3.00E-51 | 376 | 131 | 34 | AF111790 | 1161 | 189 | 2.00E-47 | 384 | 136 | 35 |
| BA000031 | 3288558 | 173 | 9.00E-43 | 384 | 125 | 32 | AF098793 | 1167 | 189 | 2.00E-47 | 385 | 134 | 34 |
| BA000031 | 3288558 | 167 | 9.00E-41 | 377 | 125 | 33 | AF078151 | 1161 | 189 | 2.00E-47 | 384 | 136 | 35 |
| BA000031 | 3288558 | 167 | 9.00E-41 | 377 | 126 | 33 | AP006840 | 3566135 | 189 | 2.00E-47 | 296 | 114 | 38 |
| BA000031 | 3288558 | 167 | 9.00E-41 | 377 | 126 | 33 | AF078152 | 1161 | 188 | 3.00E-47 | 384 | 136 | 35 |
| BA000031 | 3288558 | 109 | 2.00E-23 | 148 | 60 | 40 | AJ748315 | 3011 | 188 | 3.00E-47 | 301 | 117 | 38 |
| BA000031 | 3288558 | 74.3 | 8.00E-13 | 217 | 61 | 28 | AE017029 | 290525 | 188 | 4.00E-47 | 292 | 112 | 38 |
| AB058937 | 820 | 199 | 1.00E-50 | 287 | 118 | 41 | AE017334 | 5227419 | 188 | 4.00E-47 | 292 | 112 | 38 |
| AJ748317 | 3009 | 199 | 2.00E-50 | 295 | 124 | 42 | AE017225 | 5228663 | 188 | 4.00E-47 | 292 | 112 | 38 |
| BX842647 | 346357 | 199 | 2.00E-50 | 295 | 124 | 42 | Y18889 | 5040 | 187 | 5.00E-47 | 300 | 111 | 37 |
| BX842647 | 346357 | 196 | 2.00E-49 | 292 | 120 | 41 | Y18889 | 5040 | 174 | 7.00E-43 | 304 | 103 | 33 |
| BX842647 | 346357 | 188 | 3.00E-47 | 301 | 117 | 38 | AF078154 | 1161 | 187 | 5.00E-47 | 384 | 135 | 35 |
| BX842647 | 346357 | 186 | 2.00E-46 | 292 | 115 | 39 | AF007121 | 4400 | 187 | 5.00E-47 | 375 | 129 | 34 |
| AE011832 | 13074 | 196 | 2.00E-49 | 212 | 113 | 53 | AF007121 | 4400 | 175 | 2.00E-43 | 377 | 129 | 34 |
| AE011832 | 13074 | 103 | 9.00E-22 | 307 | 87 | 28 | AE017251 | 301045 | 187 | 6.00E-47 | 300 | 113 | 37 |
| AE011832 | 13074 | 62.4 | 3.00E-09 | 134 | 40 | 29 | AE017251 | 301045 | 172 | 3.00E-42 | 304 | 106 | 34 |
| AB039913 | 921 | 195 | 3.00E-49 | 302 | 118 | 39 | AB110834 | 1155 | 187 | 8.00E-47 | 382 | 131 | 34 |
| AF081500 | 1152 | 194 | 4.00E-49 | 380 | 136 | 35 | AJ851165 | 2169 | 186 | 2.00E-46 | 292 | 115 | 39 |
| AF078155 | 1146 | 194 | 5.00E-49 | 379 | 136 | 35 | X67138 | 5206 | 185 | 3.00E-46 | 292 | 107 | 36 |
| AF078153 | 1146 | 194 | 5.00E-49 | 379 | 136 | 35 | X67138 | 5206 | 182 | 3.00E-45 | 292 | 107 | 36 |
| AJ748319 | 3196 | 194 | 5.00E-49 | 291 | 119 | 40 | X67138 | 5206 | 180 | 1.00E-44 | 296 | 107 | 36 |
| AJ748319 | 3196 | 90.1 | 1.00E-17 | 101 | 49 | 48 | AB039909 | 750 | 185 | 3.00E-46 | 269 | 114 | 42 |
| AE012298 | 12693 | 193 | 9.00E-49 | 241 | 119 | 49 | U52198 | 5354 | 184 | 5.00E-46 | 375 | 128 | 34 |
| AE012298 | 12693 | 104 | 7.00E-22 | 319 | 93 | 29 | U52198 | 5354 | 155 | 3.00E-37 | 182 | 80 | 43 |
| AE012298 | 12693 | 58.2 | 6.00E-08 | 134 | 38 | 28 | U52198 | 5354 | 150 | 9.00E-36 | 376 | 119 | 31 |
| AY514454 | 9258 | 193 | 9.00E-49 | 379 | 140 | 36 | AB040140 | 1479 | 184 | 5.00E-46 | 235 | 116 | 49 |
| AY514454 | 9258 | 174 | 4.00E-43 | 370 | 126 | 34 | AB040140 | 1479 | 114 | 9.00E-25 | 251 | 80 | 31 |
| AY514454 | 9258 | 174 | 4.00E-43 | 377 | 126 | 33 | AB039906 | 756 | 184 | 5.00E-46 | 270 | 111 | 41 |
| AY514454 | 9258 | 153 | 1.00E-36 | 218 | 89 | 40 | CR378665 | 347213 | 184 | 5.00E-46 | 382 | 130 | 34 |
| AY514454 | 9258 | 57 | 1.00E-07 | 60 | 27 | 45 | CR378665 | 347213 | 145 | 3.00E-34 | 213 | 82 | 38 |
| AB039905 | 921 | 193 | 9.00E-49 | 302 | 117 | 38 | CR378665 | 347213 | 90.5 | 1.00E-17 | 203 | 63 | 31 |
| AB058938 | 817 | 192 | 1.00E-48 | 287 | 119 | 41 | AE001250 | 14793 | 183 | 1.00E-45 | 298 | 114 | 38 |
| CR522870 | 3523383 | 192 | 2.00E-48 | 252 | 120 | 47 | AY331139 | 686 | 182 | 2.00E-45 | 251 | 102 | 40 |
| CR522870 | 3523383 | 177 | 8.00E-44 | 231 | 108 | 46 | AB110832 | 1155 | 182 | 2.00E-45 | 381 | 132 | 34 |
| CR522870 | 3523383 | 115 | 3.00E-25 | 227 | 81 | 35 | AE007665 | 12205 | 182 | 2.00E-45 | 292 | 115 | 39 |
| CR522870 | 3523383 | 107 | 1.00E-22 | 254 | 79 | 31 | AE017314 | 300029 | 182 | 2.00E-45 | 311 | 119 | 38 |
| CR522870 | 3523383 | 51.6 | 5.00E-06 | 130 | 40 | 30 | AE004287 | 14585 | 182 | 3.00E-45 | 375 | 133 | 35 |
| CR522870 | 3523383 | 34.3 | 0.89 | 148 | 33 | 22 | AE004287 | 14585 | 176 | 1.00E-43 | 377 | 134 | 35 |
| AB039911 | 927 | 191 | 3.00E-48 | 304 | 119 | 39 | AE004287 | 14585 | 169 | 1.00E-41 | 379 | 127 | 33 |
| AB039907 | 927 | 191 | 4.00E-48 | 304 | 119 | 39 | AF069392 | 39101 | 182 | 3.00E-45 | 376 | 124 | 32 |
| AE011409 | 10859 | 190 | 7.00E-48 | 302 | 111 | 36 | AF069392 | 39101 | 167 | 9.00E-41 | 377 | 125 | 33 |
| AE011409 | 10859 | 176 | 2.00E-43 | 300 | 107 | 35 | AF069392 | 39101 | 167 | 9.00E-41 | 377 | 126 | 33 |
| AE017293 | 301124 | 190 | 7.00E-48 | 302 | 111 | 36 | AF007122 | 4700 | 182 | 3.00E-45 | 375 | 133 | 35 |
| AE017293 | 301124 | 176 | 1.00E-43 | 300 | 107 | 35 | AF007122 | 4700 | 176 | 1.00E-43 | 377 | 134 | 35 |
| AE017293 | 301124 | 33.9 | 1.2 | 59 | 18 | 30 | AF007122 | 4700 | 171 | 6.00E-42 | 379 | 127 | 33 |
| AB039910 | 927 | 190 | 1.00E-47 | 304 | 119 | 39 | X63965 | 2072 | 181 | 3.00E-45 | 301 | 112 | 37 |
| M20983 | 1031 | 190 | 1.00E-47 | 304 | 121 | 39 | X63965 | 2072 | 181 | 6.00E-45 | 304 | 107 | 35 |
| AE004290 | 10581 | 189 | 1.00E-47 | 375 | 130 | 34 | AB040139 | 1479 | 181 | 3.00E-45 | 236 | 111 | 47 |
| AE004290 | 10581 | 175 | 2.00E-43 | 377 | 129 | 34 | AB040139 | 1479 | 115 | 3.00E-25 | 284 | 83 | 29 |
| CP000010 | 3510148 | 189 | 1.00E-47 | 385 | 136 | 35 | AY331140 | 686 | 181 | 6.00E-45 | 251 | 105 | 41 |
| CP000010 | 3510148 | 34.3 | 0.89 | 76 | 24 | 31 | AE001257 | 13979 | 181 | 6.00E-45 | 301 | 111 | 36 |
| BX571965 | 4074542 | 189 | 1.00E-47 | 385 | 136 | 35 | AE001257 | 13979 | 181 | 6.00E-45 | 304 | 107 | 35 |
| BX571965 | 4074542 | 40 | 0.016 | 335 | 74 | 22 | AY331141 | 686 | 180 | 8.00E-45 | 251 | 105 | 41 |
| BX571965 | 4074542 | 34.3 | 0.89 | 76 | 24 | 31 | M94015 | 1198 | 180 | 8.00E-45 | 304 | 113 | 37 |
| U73848 | 2046 | 189 | 1.00E-47 | 385 | 136 | 35 | AB110833 | 1155 | 180 | 1.00E-44 | 381 | 131 | 34 |
| AF084815 | 1951 | 189 | 1.00E-47 | 385 | 136 | 35 | AB110831 | 1155 | 179 | 1.00E-44 | 381 | 131 | 34 |
| AF084814 | 1951 | 189 | 1.00E-47 | 385 | 136 | 35 | CR628336 | 3503610 | 179 | 1.00E-44 | 309 | 124 | 40 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| CR628336 3503610 | 110 | 7.00E-24 | 200 | 77 | 38 | | AF320637 | 1685 | 174 | 5.00E-43 | 300 | 107 | 35 |
| L47122 | 2101 | 179 | 1.00E-44 | 379 | 129 | 34 | L42885 | 1011 | 174 | 5.00E-43 | 342 | 113 | 33 |
| L34686 | 2350 | 179 | 1.00E-44 | 304 | 116 | 38 | X69614 | 1011 | 174 | 7.00E-43 | 342 | 112 | 32 |
| AE017355 5237682 | 179 | 2.00E-44 | 365 | 125 | 34 | | X69610 | 1011 | 174 | 7.00E-43 | 342 | 113 | 33 |
| AE017355 5237682 | 142 | 3.00E-33 | 292 | 97 | 33 | | AB022138 | 974 | 174 | 7.00E-43 | 329 | 114 | 34 |
| AY166716 | 1608 | 179 | 2.00E-44 | 335 | 120 | 35 | AE016803 300045 | | 173 | 9.00E-43 | 375 | 121 | 32 |
| AY028400 | 8125 | 179 | 2.00E-44 | 296 | 109 | 36 | AE016803 300045 | | 169 | 1.00E-41 | 376 | 122 | 32 |
| AF348135 | 3834 | 179 | 2.00E-44 | 301 | 109 | 36 | AE016803 300045 | | 151 | 5.00E-36 | 376 | 119 | 31 |
| AF348135 | 3834 | 172 | 2.00E-42 | 301 | 109 | 36 | AY660550 | 864 | 173 | 9.00E-43 | 296 | 107 | 36 |
| AE017354 3397754 | 178 | 3.00E-44 | 309 | 125 | 40 | | AY660549 | 864 | 173 | 9.00E-43 | 296 | 107 | 36 |
| AE017354 3397754 | 109 | 2.00E-23 | 198 | 78 | 39 | | X63413 | 1011 | 173 | 9.00E-43 | 342 | 113 | 33 |
| AJ496278 | 1490 | 178 | 3.00E-44 | 309 | 123 | 39 | X65624 | 1498 | 173 | 9.00E-43 | 296 | 107 | 36 |
| AJ496278 | 1490 | 109 | 2.00E-23 | 198 | 78 | 39 | X16833 | 1435 | 173 | 9.00E-43 | 342 | 112 | 32 |
| AB022132 | 1011 | 178 | 3.00E-44 | 342 | 116 | 33 | X15661 | 1011 | 173 | 9.00E-43 | 342 | 112 | 32 |
| AE011374 | 11076 | 177 | 6.00E-44 | 300 | 107 | 35 | BA000037 3354505 | | 173 | 9.00E-43 | 375 | 121 | 32 |
| AE011374 | 11076 | 162 | 3.00E-39 | 301 | 100 | 33 | BA000037 3354505 | | 153 | 1.00E-36 | 376 | 118 | 31 |
| AE017249 301384 | 177 | 6.00E-44 | 304 | 109 | 35 | | BA000037 3354505 | | 151 | 5.00E-36 | 376 | 119 | 31 |
| AE017294 300207 | 177 | 6.00E-44 | 300 | 107 | 35 | | BA000037 3354505 | | 149 | 2.00E-35 | 178 | 80 | 44 |
| AE017294 300207 | 161 | 4.00E-39 | 301 | 99 | 32 | | BA000037 3354505 | | 148 | 4.00E-35 | 376 | 111 | 29 |
| gi|94646 | 107 | 2.00E-22 | 181 | 65 | 35 | | BA000037 3354505 | | 121 | 4.00E-27 | 374 | 108 | 28 |
| AB022136 | 1011 | 177 | 6.00E-44 | 342 | 115 | 33 | BA000037 3354505 | | 102 | 3.00E-21 | 301 | 92 | 30 |
| AE016918 302178 | 177 | 8.00E-44 | 299 | 104 | 34 | | AL591976 250050 | | 173 | 9.00E-43 | 296 | 107 | 36 |
| AE016918 302178 | 35.4 | 0.4 | 266 | 61 | 22 | | AL596166 260050 | | 173 | 9.00E-43 | 296 | 107 | 36 |
| X69609 | 1011 | 177 | 8.00E-44 | 342 | 114 | 33 | X69612 | 1011 | 173 | 9.00E-43 | 342 | 113 | 33 |
| AE017317 302040 | 177 | 8.00E-44 | 310 | 113 | 36 | | X69613 | 1008 | 173 | 9.00E-43 | 342 | 113 | 33 |
| AJ496382 | 1548 | 176 | 1.00E-43 | 309 | 122 | 39 | AE017324 290242 | | 173 | 9.00E-43 | 296 | 107 | 36 |
| AJ496382 | 1548 | 110 | 1.00E-23 | 251 | 88 | 35 | AY275679 | 1223 | 173 | 1.00E-42 | 314 | 118 | 37 |
| AJ496283 | 1468 | 176 | 1.00E-43 | 309 | 122 | 39 | AY275679 | 1223 | 122 | 3.00E-27 | 182 | 73 | 40 |
| AJ496283 | 1468 | 110 | 1.00E-23 | 251 | 88 | 35 | AB022137 | 960 | 173 | 1.00E-42 | 323 | 113 | 34 |
| AJ496281 | 1472 | 176 | 1.00E-43 | 309 | 122 | 39 | AE016822 2584158 | | 172 | 2.00E-42 | 299 | 105 | 35 |
| AJ496281 | 1472 | 95.9 | 2.00E-19 | 84 | 46 | 54 | AE016822 2584158 | | 99.8 | 2.00E-20 | 308 | 85 | 27 |
| AJ496276 | 1493 | 176 | 1.00E-43 | 309 | 122 | 39 | AJ496277 | 1486 | 172 | 2.00E-42 | 166 | 92 | 55 |
| AJ496276 | 1493 | 92.8 | 2.00E-18 | 138 | 61 | 44 | AJ496277 | 1486 | 109 | 2.00E-23 | 198 | 78 | 39 |
| X83232 | 1755 | 176 | 1.00E-43 | 309 | 122 | 39 | AJ748318 | 3949 | 172 | 2.00E-42 | 295 | 109 | 36 |
| X83232 | 1755 | 109 | 2.00E-23 | 251 | 87 | 34 | BX842654 | 344249 | 172 | 2.00E-42 | 295 | 109 | 36 |
| AJ496282 | 1482 | 176 | 1.00E-43 | 309 | 122 | 39 | CR555306 4296230 | | 171 | 4.00E-42 | 151 | 89 | 58 |
| AJ496282 | 1482 | 110 | 1.00E-23 | 251 | 88 | 35 | AB039912 | 843 | 171 | 4.00E-42 | 280 | 110 | 39 |
| CR628337 3345687 | 176 | 1.00E-43 | 309 | 122 | 39 | | AY445112 | 990 | 171 | 5.00E-42 | 314 | 117 | 37 |
| CR628337 3345687 | 110 | 1.00E-23 | 251 | 88 | 35 | | L81147 | 1272 | 171 | 5.00E-42 | 314 | 117 | 37 |
| AB022133 | 1011 | 176 | 1.00E-43 | 342 | 115 | 33 | D82864 | 978 | 171 | 5.00E-42 | 325 | 109 | 33 |
| AJ748316 | 3730 | 176 | 1.00E-43 | 295 | 110 | 37 | AB014678 | 963 | 171 | 5.00E-42 | 323 | 111 | 34 |
| BX842655 | 349965 | 176 | 1.00E-43 | 295 | 110 | 37 | AY660548 | 864 | 171 | 6.00E-42 | 296 | 106 | 35 |
| CP000013 | 904246 | 176 | 2.00E-43 | 342 | 113 | 33 | AE007717 | 14157 | 171 | 6.00E-42 | 290 | 104 | 35 |
| CP000013 | 904246 | 35 | 0.52 | 77 | 18 | 23 | AY275678 | 1223 | 171 | 6.00E-42 | 314 | 117 | 37 |
| AE001126 | 11037 | 176 | 2.00E-43 | 342 | 113 | 33 | AY275678 | 1223 | 122 | 3.00E-27 | 182 | 73 | 40 |
| X69597 | 1011 | 176 | 2.00E-43 | 342 | 114 | 33 | AY275677 | 1222 | 171 | 6.00E-42 | 314 | 117 | 37 |
| X69611 | 1008 | 176 | 2.00E-43 | 342 | 113 | 33 | AY275677 | 1222 | 122 | 3.00E-27 | 182 | 73 | 40 |
| X69607 | 1008 | 176 | 2.00E-43 | 342 | 114 | 33 | AB014677 | 973 | 171 | 6.00E-42 | 323 | 111 | 34 |
| AB039908 | 843 | 176 | 2.00E-43 | 285 | 113 | 39 | AE015941 299511 | | 170 | 8.00E-42 | 294 | 105 | 35 |
| X84699 | 2178 | 175 | 2.00E-43 | 228 | 105 | 46 | AE015941 299511 | | 142 | 2.00E-33 | 270 | 80 | 29 |
| X84699 | 2178 | 107 | 8.00E-23 | 214 | 79 | 36 | X75200 | 1117 | 170 | 8.00E-42 | 342 | 111 | 32 |
| X53940 | 1005 | 175 | 2.00E-43 | 340 | 116 | 34 | D82853 | 987 | 170 | 8.00E-42 | 335 | 111 | 33 |
| X75202 | 1123 | 175 | 2.00E-43 | 342 | 114 | 33 | D82852 | 987 | 170 | 8.00E-42 | 335 | 111 | 33 |
| X15660 | 1011 | 175 | 2.00E-43 | 342 | 113 | 33 | AE017316 300704 | | 169 | 1.00E-41 | 295 | 101 | 34 |
| X56334 | 1426 | 175 | 2.00E-43 | 342 | 113 | 33 | D82856 | 987 | 169 | 1.00E-41 | 335 | 110 | 32 |
| AL646078 203050 | 175 | 2.00E-43 | 297 | 109 | 36 | | AJ496279 | 1495 | 169 | 2.00E-41 | 314 | 122 | 38 |
| AF241832 | 1300 | 175 | 2.00E-43 | 296 | 107 | 36 | AJ496279 | 1495 | 109 | 2.00E-23 | 198 | 78 | 39 |
| L42881 | 1011 | 175 | 2.00E-43 | 342 | 113 | 33 | X75204 | 1121 | 169 | 2.00E-41 | 334 | 112 | 33 |
| L42876 | 1011 | 175 | 2.00E-43 | 342 | 113 | 33 | L81146 | 1272 | 169 | 2.00E-41 | 300 | 114 | 38 |
| D43777 | 1398 | 175 | 2.00E-43 | 337 | 115 | 34 | U54775 | 2745 | 168 | 3.00E-41 | 242 | 104 | 42 |
| M86838 | 1736 | 175 | 2.00E-43 | 340 | 116 | 34 | U54775 | 2745 | 113 | 1.00E-24 | 335 | 100 | 29 |
| X69608 | 1008 | 175 | 3.00E-43 | 342 | 113 | 33 | AY380808 | 1011 | 168 | 4.00E-41 | 342 | 110 | 32 |
| AF283285 | 1371 | 175 | 3.00E-43 | 300 | 111 | 37 | D82855 | 987 | 168 | 4.00E-41 | 335 | 108 | 32 |
| AJ496275 | 1487 | 174 | 4.00E-43 | 310 | 122 | 39 | AE016920 305584 | | 167 | 5.00E-41 | 369 | 122 | 33 |
| AJ496275 | 1487 | 99.8 | 2.00E-20 | 191 | 72 | 37 | AE016920 305584 | | 58.9 | 3.00E-08 | 299 | 62 | 20 |
| X75201 | 1112 | 174 | 4.00E-43 | 333 | 113 | 33 | D82854 | 987 | 167 | 5.00E-41 | 335 | 108 | 32 |
| X69598 | 1011 | 174 | 4.00E-43 | 342 | 113 | 33 | D82848 | 987 | 167 | 5.00E-41 | 335 | 109 | 32 |
| X75203 | 1087 | 174 | 5.00E-43 | 342 | 113 | 33 | D82847 | 987 | 167 | 5.00E-41 | 335 | 109 | 32 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AB022134 | 987 | 167 | 5.00E-41 | 335 | 109 | 32 | BA000040 | 9105828 | 36.2 | 0.23 | 109 | 29 | 26 |
| AE004540 | 15833 | 167 | 7.00E-41 | 242 | 103 | 42 | BA000040 | 9105828 | 35.4 | 0.4 | 121 | 28 | 23 |
| AE004540 | 15833 | 113 | 2.00E-24 | 335 | 100 | 29 | BA000040 | 9105828 | 34.7 | 0.68 | 109 | 29 | 26 |
| AF034764 | 1170 | 167 | 7.00E-41 | 271 | 105 | 38 | BA000040 | 9105828 | 34.3 | 0.89 | 109 | 29 | 26 |
| AY275676 | 1229 | 167 | 7.00E-41 | 271 | 105 | 38 | BA000040 | 9105828 | 33.9 | 1.2 | 109 | 29 | 26 |
| AY275675 | 1228 | 167 | 7.00E-41 | 271 | 105 | 38 | BA000040 | 9105828 | 33.1 | 2 | 62 | 19 | 30 |
| AY275674 | 1243 | 167 | 7.00E-41 | 271 | 105 | 38 | AF014114 | 852 | 160 | 1.00E-38 | 301 | 98 | 32 |
| D82862 | 981 | 167 | 7.00E-41 | 333 | 109 | 32 | AF034766 | 1458 | 160 | 1.00E-38 | 232 | 99 | 42 |
| D82858 | 987 | 167 | 7.00E-41 | 335 | 108 | 32 | AF034766 | 1458 | 100 | 8.00E-21 | 346 | 89 | 25 |
| D82857 | 987 | 167 | 7.00E-41 | 335 | 108 | 32 | AJ277361 | 822 | 159 | 2.00E-38 | 273 | 94 | 34 |
| AF034768 | 1434 | 167 | 9.00E-41 | 225 | 101 | 44 | D86618 | 984 | 159 | 2.00E-38 | 327 | 106 | 32 |
| AF034768 | 1434 | 111 | 4.00E-24 | 278 | 83 | 29 | D89073 | 1560 | 159 | 2.00E-38 | 256 | 101 | 39 |
| D63372 | 987 | 167 | 9.00E-41 | 335 | 107 | 31 | D89073 | 1560 | 89.7 | 2.00E-17 | 173 | 60 | 34 |
| D63366 | 987 | 167 | 9.00E-41 | 335 | 108 | 32 | D82859 | 984 | 159 | 2.00E-38 | 327 | 106 | 32 |
| D63365 | 987 | 167 | 9.00E-41 | 335 | 108 | 32 | AB058931 | 1313 | 159 | 2.00E-38 | 256 | 101 | 39 |
| D63364 | 987 | 167 | 9.00E-41 | 335 | 107 | 31 | AB058931 | 1313 | 89.7 | 2.00E-17 | 173 | 60 | 34 |
| D82851 | 987 | 167 | 9.00E-41 | 335 | 107 | 31 | AF034767 | 2007 | 159 | 2.00E-38 | 260 | 105 | 40 |
| D82850 | 987 | 167 | 9.00E-41 | 335 | 107 | 31 | AF034767 | 2007 | 108 | 3.00E-23 | 273 | 74 | 27 |
| D82849 | 987 | 167 | 9.00E-41 | 335 | 107 | 31 | AY424358 | 705 | 158 | 3.00E-38 | 217 | 92 | 42 |
| AB022139 | 976 | 167 | 9.00E-41 | 323 | 109 | 33 | AJ277358 | 822 | 158 | 3.00E-38 | 273 | 95 | 34 |
| D63374 | 987 | 166 | 1.00E-40 | 335 | 107 | 31 | AF064055 | 852 | 158 | 3.00E-38 | 301 | 98 | 32 |
| D63373 | 987 | 166 | 1.00E-40 | 335 | 107 | 31 | AY744156 | 858 | 158 | 4.00E-38 | 304 | 106 | 34 |
| D63371 | 987 | 166 | 1.00E-40 | 335 | 107 | 31 | AB022135 | 934 | 158 | 4.00E-38 | 313 | 103 | 32 |
| D63370 | 987 | 166 | 1.00E-40 | 335 | 107 | 31 | AB058932 | 1313 | 156 | 1.00E-37 | 278 | 102 | 36 |
| D63369 | 987 | 166 | 1.00E-40 | 335 | 107 | 31 | AB058932 | 1313 | 85.1 | 4.00E-16 | 108 | 45 | 41 |
| D63368 | 987 | 166 | 1.00E-40 | 335 | 107 | 31 | AJ277360 | 822 | 156 | 2.00E-37 | 273 | 93 | 34 |
| D63367 | 987 | 166 | 1.00E-40 | 335 | 107 | 31 | AF011371 | 1515 | 156 | 2.00E-37 | 246 | 97 | 39 |
| D63363 | 987 | 166 | 1.00E-40 | 335 | 107 | 31 | AF011371 | 1515 | 92 | 4.00E-18 | 87 | 46 | 52 |
| D82846 | 987 | 166 | 1.00E-40 | 335 | 107 | 31 | AB058934 | 1150 | 155 | 2.00E-37 | 374 | 115 | 30 |
| D82861 | 981 | 166 | 1.00E-40 | 333 | 110 | 33 | AJ277359 | 813 | 152 | 2.00E-36 | 268 | 91 | 33 |
| M57501 | 1596 | 166 | 2.00E-40 | 271 | 105 | 38 | BX572595 | 349260 | 152 | 2.00E-36 | 295 | 92 | 31 |
| M57501 | 1596 | 107 | 1.00E-22 | 197 | 73 | 37 | BX572595 | 349260 | 35 | 0.52 | 261 | 58 | 22 |
| AF307102 | 981 | 165 | 3.00E-40 | 333 | 108 | 32 | AE016797 | 301380 | 151 | 4.00E-36 | 376 | 120 | 31 |
| AF307101 | 981 | 165 | 3.00E-40 | 333 | 108 | 32 | AE016797 | 301380 | 149 | 2.00E-35 | 178 | 80 | 44 |
| U12817 | 19811 | 165 | 3.00E-40 | 377 | 125 | 33 | AE016797 | 301380 | 121 | 4.00E-27 | 374 | 108 | 28 |
| U12817 | 19811 | 147 | 6.00E-35 | 188 | 78 | 41 | AE016797 | 301380 | 102 | 3.00E-21 | 301 | 92 | 30 |
| U12817 | 19811 | 107 | 6.00E-23 | 160 | 61 | 38 | AB058933 | 1217 | 151 | 4.00E-36 | 169 | 82 | 48 |
| U12817 | 19811 | 75.9 | 3.00E-13 | 217 | 59 | 27 | AY192720 | 724 | 151 | 5.00E-36 | 263 | 96 | 36 |
| U28496 | 1085 | 165 | 3.00E-40 | 334 | 111 | 33 | AB058935 | 1156 | 151 | 5.00E-36 | 169 | 82 | 48 |
| D82863 | 981 | 165 | 3.00E-40 | 333 | 108 | 32 | AB058935 | 1156 | 79.7 | 2.00E-14 | 291 | 83 | 28 |
| AE016790 | 300242 | 164 | 6.00E-40 | 252 | 103 | 40 | CR378663 | 348044 | 151 | 5.00E-36 | 251 | 106 | 42 |
| AE016790 | 300242 | 96.3 | 2.00E-19 | 129 | 53 | 41 | CR378663 | 348044 | 89.4 | 2.00E-17 | 149 | 55 | 36 |
| AE016790 | 300242 | 56.2 | 2.00E-07 | 130 | 41 | 31 | U28499 | 1093 | 150 | 9.00E-36 | 335 | 102 | 30 |
| L15366 | 2531 | 164 | 6.00E-40 | 252 | 103 | 40 | AF011372 | 1620 | 150 | 1.00E-35 | 266 | 100 | 37 |
| L15366 | 2531 | 95.9 | 2.00E-19 | 92 | 46 | 50 | AF011372 | 1620 | 51.2 | 7.00E-06 | 147 | 43 | 29 |
| AB017479 | 952 | 164 | 7.00E-40 | 323 | 108 | 33 | U52199 | 2471 | 149 | 1.00E-35 | 376 | 116 | 30 |
| AF064056 | 852 | 163 | 1.00E-39 | 301 | 100 | 33 | AY192721 | 724 | 149 | 2.00E-35 | 263 | 95 | 36 |
| AJ537492 | 1203 | 162 | 3.00E-39 | 103 | 84 | 81 | AJ277355 | 661 | 149 | 2.00E-35 | 238 | 90 | 37 |
| AJ537491 | 1202 | 162 | 3.00E-39 | 103 | 84 | 81 | D90832 | 19662 | 149 | 2.00E-35 | 151 | 80 | 52 |
| AJ537490 | 1203 | 162 | 3.00E-39 | 103 | 84 | 81 | AB018734 | 603 | 149 | 2.00E-35 | 214 | 90 | 42 |
| AJ537489 | 1204 | 162 | 3.00E-39 | 103 | 84 | 81 | AE017340 | 2839318 | 148 | 3.00E-35 | 170 | 82 | 48 |
| AJ537488 | 1203 | 162 | 3.00E-39 | 103 | 84 | 81 | AE017340 | 2839318 | 99.4 | 2.00E-20 | 267 | 77 | 28 |
| AJ537487 | 1202 | 162 | 3.00E-39 | 103 | 84 | 81 | AE017340 | 2839318 | 44.7 | 7.00E-04 | 130 | 35 | 26 |
| AJ537486 | 1201 | 162 | 3.00E-39 | 103 | 84 | 81 | AJ277351 | 667 | 147 | 7.00E-35 | 237 | 85 | 35 |
| AJ537485 | 1204 | 162 | 3.00E-39 | 103 | 84 | 81 | AY192718 | 724 | 147 | 9.00E-35 | 267 | 96 | 35 |
| X63513 | 1035 | 161 | 4.00E-39 | 307 | 109 | 35 | AE017269 | 294300 | 145 | 3.00E-34 | 292 | 96 | 32 |
| AF064057 | 852 | 161 | 5.00E-39 | 301 | 99 | 32 | AE017269 | 294300 | 126 | 1.00E-28 | 221 | 77 | 34 |
| M81344 | 1207 | 161 | 5.00E-39 | 301 | 99 | 32 | AE017269 | 294300 | 75.1 | 5.00E-13 | 84 | 41 | 48 |
| AF034765 | 1179 | 160 | 6.00E-39 | 300 | 108 | 36 | AY192722 | 724 | 145 | 4.00E-34 | 263 | 91 | 34 |
| BA000040 | 9105828 | 160 | 8.00E-39 | 295 | 95 | 32 | AJ277350 | 667 | 145 | 4.00E-34 | 237 | 84 | 35 |
| BA000040 | 9105828 | 85.1 | 4.00E-16 | 311 | 73 | 23 | U28498 | 1089 | 145 | 4.00E-34 | 330 | 102 | 30 |
| BA000040 | 9105828 | 80.9 | 8.00E-15 | 317 | 74 | 23 | AB018732 | 606 | 145 | 4.00E-34 | 217 | 91 | 41 |
| BA000040 | 9105828 | 58.5 | 4.00E-08 | 273 | 72 | 26 | AY192719 | 724 | 144 | 5.00E-34 | 264 | 93 | 35 |
| BA000040 | 9105828 | 57.4 | 1.00E-07 | 255 | 72 | 28 | AJ242662 | 1131 | 144 | 5.00E-34 | 377 | 112 | 29 |
| BA000040 | 9105828 | 55.1 | 5.00E-07 | 250 | 63 | 25 | AJ277356 | 660 | 144 | 6.00E-34 | 238 | 89 | 37 |
| BA000040 | 9105828 | 53.9 | 1.00E-06 | 186 | 47 | 25 | AY331135 | 1880 | 143 | 1.00E-33 | 263 | 99 | 37 |
| BA000040 | 9105828 | 38.5 | 0.047 | 233 | 50 | 21 | AY331135 | 1880 | 70.9 | 9.00E-12 | 68 | 35 | 51 |
| BA000040 | 9105828 | 37.7 | 0.08 | 134 | 39 | 29 | D85070 | 876 | 143 | 1.00E-33 | 291 | 94 | 32 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| D85069 | 876 | 143 | 1.00E-33 | 291 | 94 | 32 | AB027159 | 746 | 141 | 5.00E-33 | 267 | 87 | 32 |
| AY192716 | 724 | 143 | 1.00E-33 | 264 | 92 | 34 | AB027158 | 746 | 141 | 5.00E-33 | 267 | 87 | 32 |
| AY192717 | 724 | 142 | 2.00E-33 | 264 | 89 | 33 | AB027157 | 746 | 141 | 5.00E-33 | 267 | 87 | 32 |
| D83764 | 876 | 142 | 2.00E-33 | 291 | 94 | 32 | AY192726 | 724 | 140 | 7.00E-33 | 267 | 92 | 34 |
| D83763 | 876 | 142 | 2.00E-33 | 291 | 94 | 32 | AY192725 | 724 | 140 | 7.00E-33 | 267 | 92 | 34 |
| D83762 | 876 | 142 | 2.00E-33 | 291 | 94 | 32 | CP000001 5300915 | | 140 | 7.00E-33 | 292 | 95 | 32 |
| D88295 | 876 | 142 | 2.00E-33 | 291 | 93 | 31 | CP000001 5300915 | | 137 | 6.00E-32 | 289 | 96 | 33 |
| AJ277352 | 667 | 142 | 2.00E-33 | 237 | 86 | 36 | CP000001 5300915 | | 80.9 | 8.00E-15 | 111 | 46 | 41 |
| AF515472 | 674 | 142 | 2.00E-33 | 125 | 80 | 64 | CP000001 5300915 | | 57.8 | 8.00E-08 | 242 | 57 | 23 |
| AF515472 | 674 | 57.8 | 8.00E-08 | 58 | 33 | 56 | Y14687 | 2026 | 140 | 7.00E-33 | 166 | 74 | 44 |
| D85071 | 876 | 142 | 3.00E-33 | 291 | 92 | 31 | Y14687 | 2026 | 97.1 | 1.00E-19 | 176 | 63 | 35 |
| D88291 | 866 | 142 | 3.00E-33 | 291 | 92 | 31 | AF274346 | 699 | 140 | 7.00E-33 | 166 | 74 | 44 |
| AB001704 | 876 | 142 | 3.00E-33 | 291 | 92 | 31 | D85073 | 876 | 140 | 7.00E-33 | 291 | 92 | 31 |
| AB167766 | 746 | 141 | 4.00E-33 | 267 | 88 | 32 | AB174780 | 746 | 140 | 9.00E-33 | 267 | 87 | 32 |
| X98463 | 998 | 141 | 4.00E-33 | 332 | 107 | 32 | AB174779 | 746 | 140 | 9.00E-33 | 267 | 87 | 32 |
| D85076 | 876 | 141 | 4.00E-33 | 291 | 92 | 31 | AB174778 | 746 | 140 | 9.00E-33 | 267 | 87 | 32 |
| D85075 | 876 | 141 | 4.00E-33 | 291 | 92 | 31 | AB174777 | 746 | 140 | 9.00E-33 | 267 | 87 | 32 |
| D85074 | 876 | 141 | 4.00E-33 | 291 | 92 | 31 | AB174776 | 746 | 140 | 9.00E-33 | 267 | 87 | 32 |
| D85072 | 876 | 141 | 4.00E-33 | 291 | 92 | 31 | AB174775 | 746 | 140 | 9.00E-33 | 267 | 87 | 32 |
| D88293 | 876 | 141 | 4.00E-33 | 291 | 92 | 31 | AB174774 | 746 | 140 | 9.00E-33 | 267 | 87 | 32 |
| AB001718 | 876 | 141 | 4.00E-33 | 291 | 92 | 31 | AB031514 | 746 | 140 | 9.00E-33 | 267 | 87 | 32 |
| AB001717 | 876 | 141 | 4.00E-33 | 291 | 92 | 31 | AB027181 | 746 | 140 | 9.00E-33 | 267 | 87 | 32 |
| AB001716 | 876 | 141 | 4.00E-33 | 291 | 92 | 31 | AB027176 | 746 | 140 | 9.00E-33 | 267 | 87 | 32 |
| AB001715 | 876 | 141 | 4.00E-33 | 291 | 92 | 31 | AB027173 | 746 | 140 | 9.00E-33 | 267 | 87 | 32 |
| AB001714 | 876 | 141 | 4.00E-33 | 291 | 92 | 31 | AB027169 | 746 | 140 | 9.00E-33 | 267 | 87 | 32 |
| AB001713 | 876 | 141 | 4.00E-33 | 291 | 92 | 31 | AB027163 | 746 | 140 | 9.00E-33 | 267 | 87 | 32 |
| AB001712 | 876 | 141 | 4.00E-33 | 291 | 92 | 31 | AY192723 | 724 | 140 | 1.00E-32 | 267 | 92 | 34 |
| AB001711 | 876 | 141 | 4.00E-33 | 291 | 92 | 31 | AE001746 | 18364 | 140 | 1.00E-32 | 392 | 119 | 30 |
| AB001710 | 876 | 141 | 4.00E-33 | 291 | 92 | 31 | AF336830 | 772 | 140 | 1.00E-32 | 273 | 87 | 31 |
| AB001709 | 876 | 141 | 4.00E-33 | 291 | 92 | 31 | AB030272 | 746 | 140 | 1.00E-32 | 267 | 87 | 32 |
| AB001708 | 876 | 141 | 4.00E-33 | 291 | 92 | 31 | AB018737 | 600 | 139 | 2.00E-32 | 218 | 89 | 40 |
| AB001707 | 876 | 141 | 4.00E-33 | 291 | 92 | 31 | AB018736 | 600 | 139 | 2.00E-32 | 218 | 89 | 40 |
| AB001706 | 876 | 141 | 4.00E-33 | 291 | 92 | 31 | AY331136 | 1863 | 139 | 3.00E-32 | 258 | 96 | 37 |
| AB001705 | 876 | 141 | 4.00E-33 | 291 | 92 | 31 | AY331136 | 1863 | 63.2 | 2.00E-09 | 64 | 31 | 48 |
| AB030271 | 746 | 141 | 4.00E-33 | 267 | 87 | 32 | AY192727 | 722 | 139 | 3.00E-32 | 266 | 91 | 34 |
| AB030270 | 746 | 141 | 4.00E-33 | 267 | 88 | 32 | AJ277362 | 703 | 139 | 3.00E-32 | 248 | 85 | 34 |
| AB027180 | 746 | 141 | 4.00E-33 | 267 | 88 | 32 | AB058939 | 1685 | 138 | 4.00E-32 | 136 | 71 | 52 |
| AB027175 | 746 | 141 | 4.00E-33 | 267 | 88 | 32 | AB058939 | 1685 | 99.8 | 2.00E-20 | 291 | 82 | 28 |
| AB027166 | 746 | 141 | 4.00E-33 | 267 | 87 | 32 | AE007672 | 10661 | 137 | 7.00E-32 | 292 | 89 | 30 |
| AB027161 | 746 | 141 | 4.00E-33 | 267 | 88 | 32 | AY192724 | 723 | 135 | 2.00E-31 | 266 | 90 | 33 |
| AB091716 | 746 | 141 | 5.00E-33 | 267 | 87 | 32 | AY331137 | 1411 | 134 | 5.00E-31 | 233 | 86 | 36 |
| AB031516 | 746 | 141 | 5.00E-33 | 267 | 87 | 32 | AY331137 | 1411 | 65.1 | 5.00E-10 | 264 | 68 | 25 |
| AB031515 | 746 | 141 | 5.00E-33 | 267 | 87 | 32 | AF017113 | 47739 | 134 | 6.00E-31 | 206 | 81 | 39 |
| AB031513 | 746 | 141 | 5.00E-33 | 267 | 87 | 32 | Z99121 | 194692 | 134 | 6.00E-31 | 206 | 81 | 39 |
| AB031512 | 746 | 141 | 5.00E-33 | 267 | 87 | 32 | L15367 | 1666 | 130 | 7.00E-31 | 132 | 69 | 52 |
| AB031511 | 746 | 141 | 5.00E-33 | 267 | 87 | 32 | L15367 | 1666 | 97.4 | 9.00E-20 | 280 | 77 | 27 |
| AB031510 | 746 | 141 | 5.00E-33 | 267 | 87 | 32 | L15367 | 1666 | 29.6 | 7.00E-31 | 24 | 13 | 54 |
| AB031509 | 746 | 141 | 5.00E-33 | 267 | 87 | 32 | AB030273 | 746 | 134 | 8.00E-31 | 268 | 84 | 31 |
| AB031508 | 746 | 141 | 5.00E-33 | 267 | 87 | 32 | AJ277353 | 703 | 132 | 3.00E-30 | 248 | 83 | 33 |
| AB018733 | 624 | 141 | 5.00E-33 | 214 | 87 | 40 | AY551006 | 1380 | 132 | 3.00E-30 | 139 | 70 | 50 |
| AB027186 | 746 | 141 | 5.00E-33 | 267 | 87 | 32 | AY551006 | 1380 | 87.4 | 9.00E-17 | 159 | 57 | 35 |
| AB027185 | 746 | 141 | 5.00E-33 | 267 | 87 | 32 | AF026811 | 3031 | 131 | 4.00E-30 | 265 | 93 | 35 |
| AB027184 | 746 | 141 | 5.00E-33 | 267 | 87 | 32 | AF026811 | 3031 | 98.2 | 5.00E-20 | 153 | 63 | 41 |
| AB027183 | 746 | 141 | 5.00E-33 | 267 | 87 | 32 | AJ277363 | 669 | 131 | 5.00E-30 | 241 | 78 | 32 |
| AB027182 | 746 | 141 | 5.00E-33 | 267 | 87 | 32 | AB018735 | 600 | 130 | 9.00E-30 | 216 | 85 | 39 |
| AB027179 | 746 | 141 | 5.00E-33 | 267 | 87 | 32 | AY129557 | 9117 | 129 | 2.00E-29 | 251 | 82 | 32 |
| AB027178 | 746 | 141 | 5.00E-33 | 267 | 87 | 32 | AY129557 | 9117 | 49.3 | 3.00E-05 | 87 | 34 | 39 |
| AB027177 | 746 | 141 | 5.00E-33 | 267 | 87 | 32 | AJ277364 | 669 | 129 | 3.00E-29 | 241 | 79 | 32 |
| AB027174 | 746 | 141 | 5.00E-33 | 267 | 87 | 32 | AY551005 | 1482 | 129 | 3.00E-29 | 140 | 68 | 48 |
| AB027172 | 746 | 141 | 5.00E-33 | 267 | 87 | 32 | AY551005 | 1482 | 94 | 9.00E-19 | 195 | 67 | 34 |
| AB027171 | 746 | 141 | 5.00E-33 | 267 | 87 | 32 | AF026812 | 1863 | 128 | 5.00E-29 | 150 | 68 | 45 |
| AB027170 | 746 | 141 | 5.00E-33 | 267 | 87 | 32 | AF026812 | 1863 | 86.7 | 2.00E-16 | 158 | 58 | 36 |
| AB027168 | 746 | 141 | 5.00E-33 | 267 | 87 | 32 | AF312378 | 687 | 126 | 1.00E-28 | 248 | 79 | 31 |
| AB027167 | 746 | 141 | 5.00E-33 | 267 | 87 | 32 | AY331138 | 1293 | 124 | 7.00E-28 | 165 | 67 | 40 |
| AB027165 | 746 | 141 | 5.00E-33 | 267 | 87 | 32 | AY331138 | 1293 | 60.1 | 2.00E-08 | 92 | 33 | 35 |
| AB027164 | 746 | 141 | 5.00E-33 | 267 | 87 | 32 | AJ131736 | 2833 | 124 | 9.00E-28 | 81 | 63 | 77 |
| AB027162 | 746 | 141 | 5.00E-33 | 267 | 87 | 32 | AJ277357 | 670 | 122 | 3.00E-27 | 240 | 77 | 32 |
| AB027160 | 746 | 141 | 5.00E-33 | 267 | 87 | 32 | AY278534 | 577 | 122 | 3.00E-27 | 182 | 73 | 40 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AY278531 | 566 | 122 | 3.00E-27 | 182 | 73 | 40 | U76543 | 1023 | 113 | 2.00E-24 | 225 | 76 | 33 |
| AF529084 | 780 | 121 | 4.00E-27 | 260 | 83 | 31 | U76543 | 1023 | 107 | 6.00E-23 | 187 | 70 | 37 |
| L81176 | 5735 | 119 | 2.00E-26 | 195 | 77 | 39 | AF003905 | 1023 | 113 | 2.00E-24 | 225 | 76 | 33 |
| AY278546 | 607 | 119 | 2.00E-26 | 195 | 77 | 39 | AF003905 | 1023 | 105 | 3.00E-22 | 187 | 69 | 36 |
| AY278537 | 599 | 119 | 2.00E-26 | 195 | 77 | 39 | AB018711 | 1194 | 113 | 2.00E-24 | 215 | 86 | 40 |
| X98462 | 1301 | 119 | 2.00E-26 | 197 | 78 | 39 | AB018711 | 1194 | 55.8 | 3.00E-07 | 130 | 43 | 33 |
| X98462 | 1301 | 92.4 | 3.00E-18 | 309 | 90 | 29 | X98464 | 1019 | 112 | 2.00E-24 | 225 | 76 | 33 |
| AF416443 | 388 | 118 | 4.00E-26 | 117 | 60 | 51 | X98464 | 1019 | 105 | 4.00E-22 | 186 | 69 | 37 |
| X98280 | 1301 | 118 | 4.00E-26 | 196 | 78 | 39 | AF016232 | 1302 | 112 | 2.00E-24 | 196 | 73 | 37 |
| X98280 | 1301 | 98.6 | 4.00E-20 | 326 | 91 | 27 | AF016232 | 1302 | 102 | 3.00E-21 | 327 | 93 | 28 |
| AF416435 | 381 | 118 | 5.00E-26 | 120 | 59 | 49 | X98461 | 1301 | 112 | 3.00E-24 | 196 | 75 | 38 |
| AB181529 | 1701 | 118 | 5.00E-26 | 180 | 68 | 37 | X98461 | 1301 | 95.5 | 3.00E-19 | 326 | 90 | 27 |
| AB181529 | 1701 | 75.9 | 3.00E-13 | 84 | 34 | 40 | AB018724 | 510 | 111 | 4.00E-24 | 125 | 61 | 48 |
| AB018719 | 1449 | 118 | 5.00E-26 | 254 | 87 | 34 | AB018722 | 450 | 111 | 4.00E-24 | 125 | 61 | 48 |
| AB018719 | 1449 | 58.5 | 4.00E-08 | 221 | 60 | 27 | X98281 | 1301 | 110 | 7.00E-24 | 196 | 74 | 37 |
| AF416449 | 396 | 117 | 8.00E-26 | 117 | 59 | 50 | X98281 | 1301 | 89 | 3.00E-17 | 321 | 85 | 26 |
| AF416448 | 399 | 117 | 8.00E-26 | 117 | 59 | 50 | AB018714 | 528 | 110 | 7.00E-24 | 174 | 74 | 42 |
| AF416447 | 399 | 117 | 8.00E-26 | 117 | 59 | 50 | AB181534 | 1704 | 110 | 1.00E-23 | 180 | 64 | 35 |
| AF416446 | 394 | 117 | 8.00E-26 | 117 | 59 | 50 | AB181534 | 1704 | 75.5 | 3.00E-13 | 83 | 34 | 40 |
| AF416445 | 396 | 117 | 8.00E-26 | 117 | 59 | 50 | BX571662 | 349859 | 109 | 2.00E-23 | 294 | 89 | 30 |
| AF416444 | 399 | 117 | 8.00E-26 | 117 | 59 | 50 | BX571662 | 349859 | 73.2 | 2.00E-12 | 122 | 44 | 36 |
| AF416442 | 389 | 117 | 8.00E-26 | 117 | 59 | 50 | AB181533 | 1704 | 109 | 2.00E-23 | 180 | 64 | 35 |
| AF416441 | 397 | 117 | 8.00E-26 | 117 | 59 | 50 | AB181533 | 1704 | 75.5 | 3.00E-13 | 83 | 34 | 40 |
| AF416440 | 393 | 117 | 8.00E-26 | 117 | 59 | 50 | AB181526 | 1704 | 109 | 2.00E-23 | 180 | 63 | 35 |
| AF416439 | 393 | 117 | 8.00E-26 | 117 | 59 | 50 | AB181526 | 1704 | 74.7 | 6.00E-13 | 83 | 34 | 40 |
| AF416438 | 396 | 117 | 8.00E-26 | 117 | 59 | 50 | AF290503 | 1728 | 109 | 2.00E-23 | 184 | 63 | 34 |
| AF416436 | 399 | 117 | 8.00E-26 | 117 | 59 | 50 | AF290503 | 1728 | 79 | 3.00E-14 | 107 | 43 | 40 |
| AF416434 | 399 | 117 | 8.00E-26 | 117 | 59 | 50 | AF290502 | 1728 | 109 | 2.00E-23 | 184 | 63 | 34 |
| AF416433 | 397 | 117 | 8.00E-26 | 117 | 59 | 50 | AF290502 | 1728 | 79 | 3.00E-14 | 107 | 43 | 40 |
| AB181536 | 1698 | 117 | 1.00E-25 | 180 | 68 | 37 | AF290501 | 1728 | 109 | 2.00E-23 | 184 | 63 | 34 |
| AB181536 | 1698 | 75.5 | 3.00E-13 | 83 | 34 | 40 | AF290501 | 1728 | 79 | 3.00E-14 | 107 | 43 | 40 |
| AB181530 | 1701 | 117 | 1.00E-25 | 180 | 68 | 37 | AF290500 | 1722 | 109 | 2.00E-23 | 184 | 63 | 34 |
| AB181530 | 1701 | 74.7 | 6.00E-13 | 83 | 34 | 40 | AF290500 | 1722 | 79.3 | 2.00E-14 | 124 | 47 | 37 |
| AB181528 | 1701 | 117 | 1.00E-25 | 180 | 68 | 37 | AF290499 | 1722 | 109 | 2.00E-23 | 184 | 63 | 34 |
| AB181528 | 1701 | 74.7 | 6.00E-13 | 83 | 34 | 40 | AF290499 | 1722 | 79.3 | 2.00E-14 | 124 | 47 | 37 |
| AB181524 | 1701 | 117 | 1.00E-25 | 180 | 68 | 37 | AF290498 | 1722 | 109 | 2.00E-23 | 184 | 63 | 34 |
| AB181524 | 1701 | 74.7 | 6.00E-13 | 83 | 34 | 40 | AF290498 | 1722 | 79.3 | 2.00E-14 | 124 | 47 | 37 |
| AB181522 | 1698 | 117 | 1.00E-25 | 180 | 68 | 37 | AF290497 | 1722 | 109 | 2.00E-23 | 184 | 63 | 34 |
| AB181522 | 1698 | 75.5 | 3.00E-13 | 83 | 34 | 40 | AF290497 | 1722 | 79.3 | 2.00E-14 | 124 | 47 | 37 |
| AB181521 | 1698 | 117 | 1.00E-25 | 180 | 68 | 37 | AF290496 | 1722 | 109 | 2.00E-23 | 184 | 63 | 34 |
| AB181521 | 1698 | 75.5 | 3.00E-13 | 83 | 34 | 40 | AF290496 | 1722 | 79.3 | 2.00E-14 | 124 | 47 | 37 |
| AB105426 | 3847 | 116 | 1.00E-25 | 132 | 58 | 43 | AF202168 | 7756 | 109 | 2.00E-23 | 184 | 63 | 34 |
| AB105426 | 3847 | 102 | 2.00E-21 | 297 | 90 | 30 | AF202168 | 7756 | 105 | 3.00E-22 | 184 | 63 | 34 |
| AJ277354 | 663 | 116 | 1.00E-25 | 238 | 74 | 31 | AF202168 | 7756 | 77 | 1.00E-13 | 83 | 37 | 44 |
| AB181523 | 1701 | 116 | 1.00E-25 | 180 | 68 | 37 | AF202168 | 7756 | 77 | 1.00E-13 | 83 | 37 | 44 |
| AB181523 | 1701 | 74.7 | 6.00E-13 | 83 | 34 | 40 | AF202168 | 7756 | 73.6 | 1.00E-12 | 83 | 34 | 40 |
| AB181525 | 1689 | 116 | 2.00E-25 | 180 | 67 | 37 | AF202168 | 7756 | 63.5 | 1.00E-09 | 133 | 36 | 27 |
| AB181525 | 1689 | 76.6 | 2.00E-13 | 173 | 50 | 28 | AF202168 | 7756 | 47 | 1.00E-04 | 52 | 26 | 50 |
| AB181532 | 1695 | 115 | 2.00E-25 | 180 | 67 | 37 | AF050191 | 1731 | 109 | 2.00E-23 | 184 | 62 | 33 |
| AB181532 | 1695 | 78.2 | 5.00E-14 | 127 | 45 | 35 | AF050191 | 1731 | 77.4 | 9.00E-14 | 156 | 52 | 33 |
| AF016231 | 1302 | 115 | 2.00E-25 | 196 | 76 | 38 | AJ297532 | 1370 | 108 | 3.00E-23 | 144 | 65 | 45 |
| AF016231 | 1302 | 103 | 1.00E-21 | 327 | 93 | 28 | AJ297532 | 1370 | 98.6 | 4.00E-20 | 275 | 84 | 30 |
| AF016230 | 1302 | 115 | 2.00E-25 | 196 | 76 | 38 | AB181531 | 1704 | 108 | 4.00E-23 | 180 | 63 | 35 |
| AF016230 | 1302 | 102 | 3.00E-21 | 327 | 93 | 28 | AB181531 | 1704 | 75.5 | 3.00E-13 | 83 | 34 | 40 |
| AF016229 | 1302 | 115 | 2.00E-25 | 196 | 76 | 38 | AB098070 | 1713 | 108 | 4.00E-23 | 181 | 66 | 36 |
| AF016229 | 1302 | 102 | 3.00E-21 | 327 | 93 | 28 | AB098070 | 1713 | 72 | 4.00E-12 | 83 | 34 | 40 |
| AF003906 | 1004 | 115 | 2.00E-25 | 265 | 87 | 32 | AB098067 | 1725 | 108 | 4.00E-23 | 184 | 63 | 34 |
| AF003906 | 1004 | 110 | 1.00E-23 | 174 | 66 | 37 | AB098067 | 1725 | 77.4 | 9.00E-14 | 159 | 55 | 34 |
| AB181527 | 1698 | 115 | 3.00E-25 | 180 | 67 | 37 | AF140252 | 2031 | 108 | 4.00E-23 | 184 | 63 | 34 |
| AB181527 | 1698 | 75.5 | 3.00E-13 | 83 | 34 | 40 | AF140252 | 2031 | 77 | 1.00E-13 | 83 | 37 | 44 |
| AF416437 | 379 | 114 | 5.00E-25 | 127 | 61 | 48 | AF270499 | 1146 | 108 | 4.00E-23 | 215 | 72 | 33 |
| AY024344 | 763 | 114 | 7.00E-25 | 257 | 80 | 31 | AF050195 | 1731 | 108 | 4.00E-23 | 184 | 62 | 33 |
| X98465 | 2099 | 114 | 7.00E-25 | 301 | 93 | 30 | AF050195 | 1731 | 77.4 | 9.00E-14 | 83 | 37 | 44 |
| X98465 | 2099 | 99.8 | 2.00E-20 | 297 | 91 | 30 | AF050190 | 1731 | 108 | 4.00E-23 | 184 | 63 | 34 |
| AJ297533 | 1319 | 113 | 1.00E-24 | 237 | 83 | 35 | AF050190 | 1731 | 77.4 | 9.00E-14 | 124 | 44 | 35 |
| AJ297533 | 1319 | 103 | 1.00E-21 | 254 | 79 | 31 | AF050184 | 1731 | 108 | 4.00E-23 | 184 | 62 | 33 |
| AB181535 | 1713 | 113 | 2.00E-24 | 180 | 66 | 36 | AF050184 | 1731 | 77 | 1.00E-13 | 83 | 37 | 44 |
| AB181535 | 1713 | 74.7 | 6.00E-13 | 83 | 33 | 39 | AB070578 | 1458 | 108 | 4.00E-23 | 183 | 67 | 36 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AB070578 | 1458 | 80.1 | 1.00E-14 | 83 | 38 | 45 | U28497 | 1055 | 105 | 3.00E-22 | 308 | 87 | 28 |
| M64671 | 4200 | 108 | 4.00E-23 | 184 | 63 | 34 | AB018726 | 372 | 105 | 3.00E-22 | 124 | 57 | 45 |
| M64671 | 4200 | 105 | 3.00E-22 | 184 | 64 | 34 | M35141 | 1932 | 105 | 3.00E-22 | 184 | 64 | 34 |
| M64671 | 4200 | 79.7 | 2.00E-14 | 124 | 46 | 37 | M35141 | 1932 | 72.8 | 2.00E-12 | 124 | 43 | 34 |
| M64671 | 4200 | 73.9 | 1.00E-12 | 124 | 43 | 34 | AY102622 | 7647 | 105 | 4.00E-22 | 184 | 62 | 33 |
| J05635 | 3832 | 108 | 4.00E-23 | 184 | 62 | 33 | AY102622 | 7647 | 73.6 | 1.00E-12 | 83 | 34 | 40 |
| J05635 | 3832 | 105 | 3.00E-22 | 184 | 63 | 34 | AY278540 | 550 | 105 | 4.00E-22 | 186 | 69 | 37 |
| J05635 | 3832 | 77 | 1.00E-13 | 83 | 37 | 44 | AE017149 | 266956 | 104 | 5.00E-22 | 188 | 67 | 35 |
| J05635 | 3832 | 71.6 | 5.00E-12 | 83 | 33 | 39 | AE017149 | 266956 | 97.8 | 7.00E-20 | 170 | 60 | 35 |
| M64670 | 4200 | 108 | 4.00E-23 | 184 | 63 | 34 | AE017149 | 266956 | 76.3 | 2.00E-13 | 297 | 74 | 24 |
| M64670 | 4200 | 105 | 3.00E-22 | 184 | 64 | 34 | AE017149 | 266956 | 68.9 | 3.00E-11 | 115 | 40 | 34 |
| M64670 | 4200 | 79.7 | 2.00E-14 | 124 | 46 | 37 | AB103059 | 1461 | 104 | 5.00E-22 | 183 | 65 | 35 |
| M64670 | 4200 | 73.9 | 1.00E-12 | 124 | 43 | 34 | AB103059 | 1461 | 80.1 | 1.00E-14 | 83 | 38 | 45 |
| AE000533 | 11152 | 108 | 5.00E-23 | 187 | 67 | 35 | AB103056 | 1461 | 104 | 5.00E-22 | 183 | 65 | 35 |
| AE000533 | 11152 | 77.4 | 9.00E-14 | 121 | 47 | 38 | AB103056 | 1461 | 79 | 3.00E-14 | 83 | 37 | 44 |
| AB073915 | 1458 | 108 | 5.00E-23 | 183 | 66 | 36 | AB103053 | 1461 | 104 | 5.00E-22 | 183 | 65 | 35 |
| AB073915 | 1458 | 80.1 | 1.00E-14 | 83 | 38 | 45 | AB103053 | 1461 | 79 | 3.00E-14 | 83 | 37 | 44 |
| AY304577 | 1545 | 107 | 6.00E-23 | 166 | 62 | 37 | AB073918 | 1473 | 104 | 5.00E-22 | 180 | 63 | 35 |
| AY304577 | 1545 | 77.4 | 9.00E-14 | 121 | 47 | 38 | AB073918 | 1473 | 81.6 | 5.00E-15 | 174 | 54 | 31 |
| AB098069 | 1722 | 107 | 6.00E-23 | 181 | 65 | 35 | L08908 | 1800 | 104 | 5.00E-22 | 189 | 63 | 33 |
| AB098069 | 1722 | 82 | 4.00E-14 | 162 | 56 | 34 | L08908 | 1800 | 80.5 | 1.00E-14 | 123 | 48 | 39 |
| AB098068 | 1722 | 107 | 6.00E-23 | 181 | 65 | 35 | AE005820 | 14021 | 104 | 7.00E-22 | 297 | 76 | 25 |
| AB098068 | 1722 | 79 | 3.00E-14 | 83 | 37 | 44 | AE005820 | 14021 | 99.4 | 2.00E-20 | 298 | 76 | 25 |
| AF050186 | 1728 | 107 | 6.00E-23 | 181 | 65 | 35 | AE005820 | 14021 | 99 | 3.00E-20 | 292 | 75 | 25 |
| AF050186 | 1728 | 82 | 4.00E-14 | 162 | 56 | 34 | AB084912 | 1461 | 104 | 7.00E-22 | 183 | 64 | 34 |
| AY714226 | 1545 | 107 | 8.00E-23 | 187 | 67 | 35 | AB084912 | 1461 | 82.8 | 2.00E-15 | 170 | 56 | 32 |
| AY714226 | 1545 | 77.4 | 9.00E-14 | 121 | 47 | 38 | AB084911 | 1461 | 104 | 7.00E-22 | 183 | 64 | 34 |
| AY319299 | 1545 | 107 | 8.00E-23 | 187 | 67 | 35 | AB084911 | 1461 | 82.8 | 2.00E-15 | 170 | 56 | 32 |
| AY319299 | 1545 | 77.4 | 9.00E-14 | 121 | 47 | 38 | AF050185 | 1731 | 104 | 7.00E-22 | 181 | 64 | 35 |
| AF479024 | 1545 | 107 | 8.00E-23 | 187 | 67 | 35 | AF050185 | 1731 | 79.3 | 2.00E-14 | 121 | 44 | 36 |
| AF479024 | 1545 | 77.4 | 9.00E-14 | 121 | 47 | 38 | AB080202 | 1473 | 104 | 7.00E-22 | 181 | 63 | 34 |
| Z29327 | 3879 | 107 | 8.00E-23 | 182 | 67 | 36 | AB080202 | 1473 | 83.2 | 2.00E-15 | 174 | 55 | 31 |
| Z29327 | 3879 | 105 | 9.00E-22 | 182 | 69 | 37 | AB103052 | 1473 | 103 | 9.00E-22 | 184 | 63 | 34 |
| Z29327 | 3879 | 79.3 | 2.00E-14 | 107 | 43 | 40 | AB103052 | 1473 | 82.8 | 2.00E-15 | 174 | 59 | 33 |
| Z29327 | 3879 | 73.9 | 1.00E-12 | 107 | 40 | 37 | AF050194 | 1728 | 103 | 9.00E-22 | 171 | 62 | 36 |
| Y11602 | 1900 | 107 | 8.00E-23 | 249 | 79 | 31 | AF050194 | 1728 | 78.6 | 4.00E-14 | 107 | 43 | 40 |
| Y11602 | 1900 | 75.1 | 5.00E-13 | 148 | 50 | 33 | BX571661 | 346613 | 103 | 1.00E-21 | 192 | 63 | 32 |
| AY155232 | 1545 | 107 | 8.00E-23 | 187 | 67 | 35 | BX571661 | 346613 | 94.7 | 6.00E-19 | 333 | 85 | 25 |
| AY155232 | 1545 | 77.4 | 9.00E-14 | 121 | 47 | 38 | Y11762 | 4057 | 103 | 1.00E-21 | 181 | 64 | 35 |
| AB103061 | 1725 | 107 | 8.00E-23 | 171 | 64 | 37 | Y11762 | 4057 | 102 | 3.00E-21 | 183 | 65 | 35 |
| AB103061 | 1725 | 79.7 | 2.00E-14 | 121 | 44 | 36 | Y11762 | 4057 | 79.3 | 2.00E-14 | 148 | 50 | 33 |
| M74578 | 1800 | 107 | 8.00E-23 | 182 | 67 | 36 | Y11762 | 4057 | 71.2 | 7.00E-12 | 105 | 38 | 36 |
| M74578 | 1800 | 73.9 | 1.00E-12 | 107 | 40 | 37 | AF050193 | 1719 | 103 | 1.00E-21 | 181 | 67 | 37 |
| AE001449 | 13631 | 107 | 8.00E-23 | 187 | 67 | 35 | AF050193 | 1719 | 72.8 | 2.00E-12 | 132 | 45 | 34 |
| AE001449 | 13631 | 77.4 | 9.00E-14 | 121 | 47 | 38 | M82917 | 2236 | 103 | 1.00E-21 | 192 | 63 | 32 |
| L08907 | 1800 | 107 | 8.00E-23 | 187 | 67 | 35 | M82917 | 2236 | 94.7 | 6.00E-19 | 333 | 85 | 25 |
| L08907 | 1800 | 77.4 | 9.00E-14 | 121 | 47 | 38 | AB073917 | 1461 | 103 | 1.00E-21 | 183 | 63 | 34 |
| X57173 | 1731 | 107 | 1.00E-22 | 181 | 65 | 35 | AB073917 | 1461 | 80.1 | 1.00E-14 | 83 | 38 | 45 |
| X57173 | 1731 | 82 | 4.00E-15 | 162 | 56 | 34 | AB103055 | 1473 | 103 | 2.00E-21 | 219 | 68 | 31 |
| AF050197 | 1719 | 107 | 1.00E-22 | 171 | 64 | 37 | AB103055 | 1473 | 84 | 1.00E-15 | 171 | 56 | 32 |
| AF050197 | 1719 | 77.8 | 7.00E-14 | 132 | 48 | 36 | AF089835 | 2310 | 103 | 2.00E-21 | 297 | 75 | 25 |
| AF050196 | 1719 | 107 | 1.00E-22 | 181 | 65 | 35 | AF089835 | 2310 | 99 | 3.00E-20 | 292 | 75 | 25 |
| AF050196 | 1719 | 78.2 | 5.00E-14 | 132 | 48 | 36 | AE017138 | 290924 | 102 | 2.00E-21 | 223 | 67 | 30 |
| AF050192 | 1719 | 107 | 1.00E-22 | 181 | 65 | 35 | AE017138 | 290924 | 47.8 | 8.00E-05 | 66 | 22 | 33 |
| AF050192 | 1719 | 79.3 | 2.00E-14 | 132 | 48 | 36 | AE013947 | 10446 | 102 | 2.00E-21 | 223 | 67 | 30 |
| AF050188 | 1719 | 107 | 1.00E-22 | 181 | 65 | 35 | AE013947 | 10446 | 57.4 | 1.00E-07 | 84 | 28 | 33 |
| AF050188 | 1719 | 78.6 | 4.00E-14 | 83 | 37 | 44 | AJ414144 | 208050 | 102 | 2.00E-21 | 223 | 67 | 30 |
| AB103060 | 1716 | 106 | 1.00E-22 | 184 | 61 | 33 | AJ414144 | 208050 | 95.9 | 2.00E-19 | 295 | 76 | 25 |
| AB103060 | 1716 | 79.7 | 2.00E-14 | 124 | 46 | 37 | AJ414144 | 208050 | 92 | 4.00E-18 | 309 | 79 | 25 |
| AL139078 | 263335 | 106 | 2.00E-22 | 171 | 63 | 36 | AY751741 | 1630 | 102 | 3.00E-21 | 169 | 61 | 36 |
| AL139078 | 263335 | 102 | 3.00E-21 | 181 | 66 | 36 | AY751741 | 1630 | 62 | 4.00E-09 | 141 | 42 | 29 |
| AL139078 | 263335 | 79.3 | 2.00E-14 | 132 | 48 | 36 | AB103054 | 1470 | 102 | 3.00E-21 | 219 | 68 | 31 |
| AL139078 | 263335 | 72.8 | 2.00E-12 | 132 | 45 | 34 | AB103054 | 1470 | 83.6 | 1.00E-15 | 171 | 59 | 34 |
| AB018730 | 375 | 106 | 2.00E-22 | 125 | 57 | 45 | AB018720 | 360 | 102 | 3.00E-21 | 119 | 55 | 46 |
| AB018728 | 393 | 106 | 2.00E-22 | 125 | 57 | 45 | AF369587 | 1671 | 101 | 5.00E-21 | 178 | 59 | 33 |
| AB103058 | 1461 | 105 | 2.00E-22 | 183 | 64 | 34 | AF369587 | 1671 | 70.1 | 1.00E-11 | 113 | 41 | 36 |
| AB103058 | 1461 | 80.1 | 1.00E-14 | 83 | 38 | 45 | AF050187 | 1728 | 101 | 5.00E-21 | 181 | 65 | 35 |
| AB018716 | 495 | 105 | 2.00E-22 | 165 | 68 | 41 | AF050187 | 1728 | 77.8 | 7.00E-14 | 296 | 78 | 26 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| Y11601 | 1900 | 101 | 6.00E-21 | 240 | 73 | 30 | AY319298 | 1533 | 82 | 4.00E-15 | 311 | 78 | 25 |
| Y11601 | 1900 | 77.8 | 7.00E-14 | 329 | 89 | 27 | AY278532 | 503 | 94.7 | 6.00E-19 | 164 | 59 | 35 |
| AB103051 | 1476 | 101 | 6.00E-21 | 174 | 61 | 35 | Z25773 | 404 | 93.6 | 1.00E-18 | 154 | 59 | 38 |
| AB103051 | 1476 | 82.8 | 2.00E-15 | 175 | 58 | 33 | BX294145 | 300350 | 92.8 | 2.00E-18 | 169 | 62 | 36 |
| AF369581 | 1671 | 101 | 6.00E-21 | 178 | 59 | 33 | BX294145 | 300350 | 85.5 | 3.00E-16 | 126 | 55 | 43 |
| AF369581 | 1671 | 70.1 | 1.00E-11 | 113 | 41 | 36 | AJ297534 | 1512 | 92.4 | 3.00E-18 | 208 | 66 | 31 |
| AF050189 | 1719 | 101 | 6.00E-21 | 181 | 66 | 36 | AJ297534 | 1512 | 66.2 | 2.00E-10 | 252 | 61 | 24 |
| AF050189 | 1719 | 71.6 | 5.00E-12 | 132 | 45 | 34 | X96435 | 3919 | 91.3 | 6.00E-18 | 313 | 77 | 24 |
| AE000767 | 13413 | 100 | 8.00E-21 | 209 | 62 | 29 | X96435 | 3919 | 79.7 | 2.00E-14 | 313 | 75 | 23 |
| AE000767 | 13413 | 62 | 4.00E-09 | 129 | 39 | 30 | X96435 | 3919 | 71.6 | 5.00E-12 | 324 | 75 | 23 |
| AB103050 | 1500 | 100 | 8.00E-21 | 153 | 61 | 39 | AE009023 | 9808 | 91.3 | 6.00E-18 | 313 | 77 | 24 |
| AB103050 | 1500 | 85.9 | 3.00E-16 | 316 | 82 | 25 | AE009023 | 9808 | 79.7 | 2.00E-14 | 313 | 75 | 23 |
| AF369584 | 1668 | 100 | 1.00E-20 | 175 | 62 | 35 | AE009023 | 9808 | 71.6 | 5.00E-12 | 324 | 75 | 23 |
| AF369584 | 1668 | 71.6 | 5.00E-12 | 287 | 73 | 25 | AE007989 | 10029 | 91.3 | 6.00E-18 | 313 | 77 | 24 |
| AF369583 | 1674 | 100 | 1.00E-20 | 175 | 62 | 35 | AE007989 | 10029 | 79.7 | 2.00E-14 | 313 | 75 | 23 |
| AF369583 | 1674 | 74.7 | 6.00E-13 | 287 | 72 | 25 | AE007989 | 10029 | 71.6 | 5.00E-12 | 324 | 75 | 23 |
| AF369580 | 582 | 100 | 1.00E-20 | 175 | 62 | 35 | U95165 | 21846 | 91.3 | 6.00E-18 | 313 | 77 | 24 |
| AF369586 | 1662 | 100 | 1.00E-20 | 175 | 61 | 34 | U95165 | 21846 | 79.7 | 2.00E-14 | 313 | 75 | 23 |
| AF369586 | 1662 | 68.6 | 4.00E-11 | 74 | 31 | 41 | U95165 | 21846 | 71.6 | 5.00E-12 | 324 | 75 | 23 |
| AF369585 | 1662 | 100 | 1.00E-20 | 175 | 61 | 34 | U95165 | 21846 | 53.5 | 1.00E-06 | 256 | 60 | 23 |
| AF369585 | 1662 | 68.6 | 4.00E-11 | 74 | 31 | 41 | U95165 | 21846 | 46.2 | 2.00E-04 | 140 | 34 | 24 |
| AF369582 | 1662 | 100 | 1.00E-20 | 175 | 61 | 34 | X80701 | 4423 | 91.3 | 6.00E-18 | 313 | 77 | 24 |
| AF369582 | 1662 | 68.6 | 4.00E-11 | 74 | 31 | 41 | X80701 | 4423 | 79.7 | 2.00E-14 | 313 | 75 | 23 |
| AF369579 | 582 | 100 | 1.00E-20 | 175 | 61 | 34 | X80701 | 4423 | 71.6 | 5.00E-12 | 324 | 75 | 23 |
| AF369578 | 582 | 100 | 1.00E-20 | 175 | 61 | 34 | AB110835 | 909 | 90.5 | 1.00E-17 | 301 | 81 | 26 |
| AF369577 | 582 | 100 | 1.00E-20 | 175 | 61 | 34 | L38478 | 1446 | 90.5 | 1.00E-17 | 150 | 51 | 34 |
| AB018712 | 345 | 99.8 | 2.00E-20 | 115 | 58 | 50 | U17575 | 2803 | 90.5 | 1.00E-17 | 200 | 57 | 28 |
| AB073916 | 1476 | 99.8 | 2.00E-20 | 174 | 59 | 33 | U17575 | 2803 | 56.6 | 2.00E-07 | 146 | 47 | 32 |
| AB073916 | 1476 | 85.9 | 3.00E-16 | 172 | 57 | 33 | AE001699 | 13774 | 89.7 | 2.00E-17 | 248 | 63 | 25 |
| AE005755 | 12263 | 99 | 3.00E-20 | 292 | 72 | 24 | AE014292 | 1207381 | 88.6 | 4.00E-17 | 298 | 76 | 25 |
| AE005755 | 12263 | 98.6 | 4.00E-20 | 292 | 72 | 24 | U42432 | 305 | 88.6 | 4.00E-17 | 87 | 45 | 51 |
| AE005755 | 12263 | 97.4 | 9.00E-20 | 292 | 70 | 23 | AF019251 | 3817 | 88.6 | 4.00E-17 | 298 | 76 | 25 |
| M26945 | 1719 | 99 | 3.00E-20 | 171 | 58 | 33 | AY751740 | 1595 | 87.4 | 9.00E-17 | 142 | 52 | 36 |
| M26945 | 1719 | 79.7 | 2.00E-14 | 124 | 46 | 37 | AY751740 | 1595 | 63.9 | 1.00E-09 | 94 | 34 | 36 |
| AF040268 | 3447 | 99 | 3.00E-20 | 292 | 72 | 24 | AE009654 | 10807 | 86.7 | 2.00E-16 | 298 | 75 | 25 |
| AF040268 | 3447 | 98.6 | 4.00E-20 | 292 | 72 | 24 | BA000012 | 7036071 | 84.7 | 6.00E-16 | 329 | 75 | 22 |
| AF040268 | 3447 | 95.5 | 3.00E-19 | 292 | 70 | 23 | BA000012 | 7036071 | 59.7 | 2.00E-08 | 356 | 80 | 22 |
| AE013020 | 10181 | 98.2 | 5.00E-20 | 290 | 83 | 28 | AB110836 | 909 | 84.3 | 7.00E-16 | 92 | 44 | 47 |
| BX294139 | 287650 | 98.2 | 5.00E-20 | 284 | 88 | 30 | U42431 | 305 | 84 | 1.00E-15 | 87 | 43 | 49 |
| BX294139 | 287650 | 81.3 | 6.00E-15 | 143 | 57 | 39 | J01556 | 1193 | 82.4 | 3.00E-15 | 298 | 70 | 23 |
| AB018718 | 1191 | 98 | 5.00E-20 | 188 | 67 | 35 | AJ418317 | 1384 | 79 | 3.00E-14 | 149 | 49 | 32 |
| AB018718 | 1191 | 51.2 | 7.00E-06 | 91 | 27 | 29 | AJ418317 | 1384 | 63.9 | 1.00E-09 | 109 | 39 | 35 |
| AE017148 | 317022 | 97.8 | 7.00E-20 | 170 | 60 | 35 | AJ418316 | 1384 | 79 | 3.00E-14 | 149 | 49 | 32 |
| AE017148 | 317022 | 76.3 | 2.00E-13 | 297 | 74 | 24 | AJ418316 | 1384 | 63.9 | 1.00E-09 | 109 | 39 | 35 |
| BX294140 | 307050 | 97.4 | 9.00E-20 | 257 | 76 | 29 | AJ418322 | 1376 | 77.8 | 7.00E-14 | 136 | 45 | 33 |
| BX294140 | 307050 | 79.3 | 2.00E-14 | 250 | 70 | 28 | AJ418322 | 1376 | 67.8 | 7.00E-11 | 294 | 70 | 23 |
| BX294140 | 307050 | 34.3 | 0.89 | 120 | 34 | 28 | AJ418321 | 1376 | 77.8 | 7.00E-14 | 136 | 45 | 33 |
| BX294140 | 307050 | 33.1 | 2 | 116 | 34 | 29 | AJ418321 | 1376 | 65.9 | 3.00E-10 | 294 | 69 | 23 |
| X60746 | 1800 | 97.1 | 1.00E-19 | 170 | 57 | 33 | AJ418320 | 1377 | 77.8 | 7.00E-14 | 136 | 45 | 33 |
| X60746 | 1800 | 82.4 | 3.00E-15 | 311 | 78 | 25 | AJ418320 | 1377 | 65.9 | 3.00E-10 | 294 | 69 | 23 |
| AB103057 | 1500 | 97.1 | 1.00E-19 | 222 | 73 | 32 | AJ418319 | 1377 | 77.8 | 7.00E-14 | 136 | 45 | 33 |
| AB103057 | 1500 | 82.4 | 3.00E-15 | 174 | 55 | 31 | AJ418319 | 1377 | 65.9 | 3.00E-10 | 294 | 69 | 23 |
| AY304576 | 1533 | 96.3 | 2.00E-19 | 170 | 57 | 33 | AJ418318 | 1377 | 77.8 | 7.00E-14 | 136 | 45 | 33 |
| AY304576 | 1533 | 83.2 | 2.00E-15 | 311 | 79 | 25 | AJ418318 | 1377 | 65.9 | 3.00E-10 | 294 | 69 | 23 |
| AY714225 | 1533 | 96.3 | 2.00E-19 | 170 | 57 | 33 | AY134860 | 420 | 77.4 | 9.00E-14 | 74 | 38 | 51 |
| AY714225 | 1533 | 82 | 4.00E-15 | 311 | 78 | 25 | AJ297531 | 1299 | 77.4 | 9.00E-14 | 315 | 74 | 23 |
| AJ297530 | 1280 | 96.3 | 2.00E-19 | 251 | 76 | 30 | AB035615 | 600 | 77.4 | 9.00E-14 | 134 | 46 | 34 |
| AJ297530 | 1280 | 91.7 | 5.00E-18 | 270 | 73 | 27 | AB035614 | 600 | 77.4 | 9.00E-14 | 134 | 46 | 34 |
| AY155231 | 1533 | 96.3 | 2.00E-19 | 170 | 57 | 33 | AB035613 | 600 | 77.4 | 9.00E-14 | 134 | 46 | 34 |
| AY155231 | 1533 | 82.4 | 3.00E-15 | 311 | 78 | 25 | AF398973 | 437 | 77 | 1.00E-13 | 158 | 53 | 33 |
| AE000574 | 10042 | 96.3 | 2.00E-19 | 170 | 57 | 33 | AB091714 | 600 | 77 | 1.00E-13 | 134 | 46 | 34 |
| AE000574 | 10042 | 82.4 | 3.00E-15 | 311 | 78 | 25 | AB091713 | 600 | 77 | 1.00E-13 | 134 | 46 | 34 |
| AE001487 | 17223 | 96.3 | 2.00E-19 | 170 | 57 | 33 | AB091712 | 600 | 77 | 1.00E-13 | 134 | 46 | 34 |
| AE001487 | 17223 | 82.4 | 3.00E-15 | 311 | 78 | 25 | AB091711 | 600 | 77 | 1.00E-13 | 134 | 46 | 34 |
| L36137 | 1548 | 96.3 | 2.00E-19 | 172 | 69 | 40 | AB091710 | 600 | 77 | 1.00E-13 | 134 | 46 | 34 |
| L36137 | 1548 | 45.8 | 3.00E-04 | 69 | 33 | 47 | AB091709 | 600 | 77 | 1.00E-13 | 134 | 46 | 34 |
| L36137 | 1548 | 45.4 | 4.00E-04 | 60 | 31 | 51 | AB091708 | 600 | 77 | 1.00E-13 | 134 | 46 | 34 |
| AY319298 | 1533 | 95.9 | 2.00E-19 | 170 | 57 | 33 | AB091707 | 600 | 77 | 1.00E-13 | 134 | 46 | 34 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AB091706 | 600 | 77 | 1.00E-13 | 134 | 46 | 34 | AB178325 | 597 | 73.9 | 1.00E-12 | 133 | 44 | 33 |
| AB091705 | 600 | 77 | 1.00E-13 | 134 | 46 | 34 | AY278543 | 479 | 73.2 | 2.00E-12 | 162 | 54 | 33 |
| AB091704 | 600 | 77 | 1.00E-13 | 134 | 46 | 34 | AB189459 | 597 | 72 | 4.00E-12 | 133 | 43 | 32 |
| AB091703 | 600 | 77 | 1.00E-13 | 134 | 46 | 34 | CR354386 | 888 | 71.6 | 5.00E-12 | 294 | 67 | 22 |
| AB091702 | 600 | 77 | 1.00E-13 | 134 | 46 | 34 | AF072133 | 582 | 71.2 | 7.00E-12 | 100 | 41 | 41 |
| AB091701 | 600 | 77 | 1.00E-13 | 134 | 46 | 34 | AY278539 | 474 | 71.2 | 7.00E-12 | 160 | 53 | 33 |
| AB091700 | 600 | 77 | 1.00E-13 | 134 | 46 | 34 | AY278536 | 463 | 71.2 | 7.00E-12 | 160 | 53 | 33 |
| AB037130 | 600 | 77 | 1.00E-13 | 134 | 46 | 34 | AY278544 | 468 | 69.7 | 2.00E-11 | 159 | 52 | 32 |
| AB037129 | 600 | 77 | 1.00E-13 | 134 | 46 | 34 | CR354387 | 852 | 69.7 | 2.00E-11 | 284 | 61 | 21 |
| AB037128 | 600 | 77 | 1.00E-13 | 134 | 46 | 34 | AF030241 | 751 | 68.9 | 3.00E-11 | 186 | 50 | 26 |
| AB037127 | 600 | 77 | 1.00E-13 | 134 | 46 | 34 | AF030241 | 751 | 38.5 | 0.047 | 49 | 20 | 40 |
| AY505350 | 209 | 76.6 | 2.00E-13 | 69 | 39 | 56 | U85622 | 1105 | 68.9 | 3.00E-11 | 288 | 68 | 23 |
| AB052665 | 600 | 75.9 | 3.00E-13 | 134 | 45 | 33 | AL139076 | 317511 | 68.6 | 4.00E-11 | 288 | 66 | 22 |
| AB035621 | 600 | 75.9 | 3.00E-13 | 134 | 45 | 33 | AF461538 | 7599 | 68.2 | 6.00E-11 | 257 | 63 | 24 |
| AB035620 | 600 | 75.9 | 3.00E-13 | 134 | 45 | 33 | AY278541 | 466 | 67.4 | 9.00E-11 | 158 | 52 | 32 |
| AB035619 | 600 | 75.9 | 3.00E-13 | 134 | 45 | 33 | U26705 | 641 | 67.4 | 9.00E-11 | 221 | 58 | 26 |
| AB035618 | 600 | 75.9 | 3.00E-13 | 134 | 45 | 33 | U26704 | 641 | 67.4 | 9.00E-11 | 221 | 58 | 26 |
| AB035617 | 600 | 75.9 | 3.00E-13 | 134 | 45 | 33 | AF398975 | 351 | 67 | 1.00E-10 | 129 | 46 | 35 |
| AB035616 | 600 | 75.9 | 3.00E-13 | 134 | 45 | 33 | AF398974 | 351 | 67 | 1.00E-10 | 129 | 46 | 35 |
| AB035612 | 600 | 75.9 | 3.00E-13 | 134 | 45 | 33 | AE017253 | 302836 | 66.6 | 2.00E-10 | 285 | 65 | 22 |
| AB035611 | 600 | 75.9 | 3.00E-13 | 134 | 45 | 33 | V01370 | 1149 | 66.2 | 2.00E-10 | 37 | 34 | 91 |
| AB035610 | 600 | 75.9 | 3.00E-13 | 134 | 45 | 33 | AF398982 | 378 | 65.1 | 5.00E-10 | 130 | 41 | 31 |
| AB035609 | 600 | 75.9 | 3.00E-13 | 134 | 45 | 33 | AF398981 | 378 | 65.1 | 5.00E-10 | 130 | 41 | 31 |
| AB035608 | 600 | 75.9 | 3.00E-13 | 134 | 45 | 33 | AF398976 | 378 | 65.1 | 5.00E-10 | 130 | 42 | 32 |
| AB035607 | 600 | 75.9 | 3.00E-13 | 134 | 45 | 33 | AE001695 | 13302 | 65.1 | 5.00E-10 | 256 | 62 | 24 |
| AB035606 | 600 | 75.9 | 3.00E-13 | 134 | 45 | 33 | AF030240 | 766 | 63.5 | 1.00E-09 | 202 | 51 | 25 |
| AB035605 | 600 | 75.9 | 3.00E-13 | 134 | 45 | 33 | AF030240 | 766 | 38.5 | 0.047 | 49 | 20 | 40 |
| AB035604 | 600 | 75.9 | 3.00E-13 | 134 | 45 | 33 | AE001240 | 14244 | 63.2 | 2.00E-09 | 268 | 60 | 22 |
| AB035603 | 600 | 75.9 | 3.00E-13 | 134 | 45 | 33 | AY342020 | 584 | 63.2 | 2.00E-09 | 190 | 50 | 26 |
| AB035602 | 600 | 75.9 | 3.00E-13 | 134 | 45 | 33 | AL591784 | 300000 | 62.4 | 3.00E-09 | 321 | 68 | 21 |
| AB035601 | 600 | 75.9 | 3.00E-13 | 134 | 45 | 33 | AL591784 | 300000 | 50.4 | 1.00E-05 | 87 | 29 | 33 |
| AB035600 | 600 | 75.9 | 3.00E-13 | 134 | 45 | 33 | AL591784 | 300000 | 45.8 | 3.00E-04 | 245 | 56 | 22 |
| AB035599 | 600 | 75.9 | 3.00E-13 | 134 | 45 | 33 | AL591784 | 300000 | 40 | 0.016 | 87 | 24 | 27 |
| AB035598 | 600 | 75.9 | 3.00E-13 | 134 | 45 | 33 | AJ297535 | 949 | 62.4 | 3.00E-09 | 141 | 46 | 32 |
| AB035597 | 600 | 75.9 | 3.00E-13 | 134 | 45 | 33 | AJ297535 | 949 | 40.4 | 1.00E-04 | 57 | 26 | 45 |
| AB035596 | 600 | 75.9 | 3.00E-13 | 134 | 45 | 33 | AJ297535 | 949 | 31.2 | 1.00E-04 | 78 | 21 | 26 |
| AB035595 | 600 | 75.9 | 3.00E-13 | 134 | 45 | 33 | L49337 | 19824 | 62 | 4.00E-09 | 321 | 65 | 20 |
| AB091808 | 597 | 75.5 | 3.00E-13 | 133 | 45 | 33 | L49337 | 19824 | 61 | 1.00E-05 | 149 | 43 | 28 |
| AB091806 | 597 | 75.5 | 3.00E-13 | 133 | 45 | 33 | L49337 | 19824 | 45.1 | 5.00E-04 | 146 | 38 | 26 |
| AB178780 | 597 | 75.5 | 3.00E-13 | 133 | 45 | 33 | L49337 | 19824 | 40 | 0.016 | 87 | 24 | 27 |
| AB178779 | 597 | 75.5 | 3.00E-13 | 133 | 45 | 33 | AF264897 | 608 | 61.2 | 7.00E-09 | 208 | 52 | 25 |
| AB178335 | 597 | 75.5 | 3.00E-13 | 133 | 45 | 33 | AF264883 | 608 | 61.2 | 7.00E-09 | 208 | 52 | 25 |
| AB178334 | 597 | 75.5 | 3.00E-13 | 133 | 45 | 33 | AY342021 | 584 | 61.2 | 7.00E-09 | 190 | 49 | 25 |
| AB091812 | 597 | 75.1 | 5.00E-13 | 133 | 45 | 33 | AY342019 | 584 | 61.2 | 7.00E-09 | 190 | 48 | 25 |
| AB091811 | 597 | 75.1 | 5.00E-13 | 133 | 45 | 33 | AF264899 | 608 | 60.8 | 9.00E-09 | 208 | 51 | 24 |
| AB091810 | 597 | 75.1 | 5.00E-13 | 133 | 45 | 33 | AF264898 | 608 | 60.8 | 9.00E-09 | 208 | 51 | 24 |
| AB091809 | 597 | 75.1 | 5.00E-13 | 133 | 45 | 33 | AF264896 | 608 | 60.5 | 1.00E-08 | 208 | 50 | 24 |
| AB091805 | 597 | 75.1 | 5.00E-13 | 133 | 45 | 33 | AF264895 | 608 | 60.5 | 1.00E-08 | 208 | 50 | 24 |
| AB178333 | 597 | 75.1 | 5.00E-13 | 133 | 45 | 33 | AF264894 | 608 | 60.5 | 1.00E-08 | 208 | 50 | 24 |
| AB091715 | 600 | 74.7 | 6.00E-13 | 134 | 45 | 33 | AF264893 | 608 | 60.5 | 1.00E-08 | 208 | 50 | 24 |
| BX571659 | 349970 | 74.3 | 8.00E-13 | 278 | 65 | 23 | AF264892 | 608 | 60.5 | 1.00E-08 | 208 | 50 | 24 |
| AB109246 | 596 | 74.3 | 8.00E-13 | 133 | 44 | 33 | AF264891 | 608 | 60.5 | 1.00E-08 | 208 | 50 | 24 |
| AB109245 | 596 | 74.3 | 8.00E-13 | 133 | 44 | 33 | AF264890 | 608 | 60.5 | 1.00E-08 | 208 | 50 | 24 |
| AB109244 | 596 | 74.3 | 8.00E-13 | 133 | 44 | 33 | AF264888 | 608 | 60.5 | 1.00E-08 | 208 | 50 | 24 |
| AB109243 | 596 | 74.3 | 8.00E-13 | 133 | 44 | 33 | AF264887 | 608 | 60.5 | 1.00E-08 | 208 | 50 | 24 |
| AB109242 | 596 | 74.3 | 8.00E-13 | 133 | 44 | 33 | AY342027 | 584 | 60.5 | 1.00E-08 | 190 | 48 | 25 |
| AB109241 | 596 | 74.3 | 8.00E-13 | 133 | 44 | 33 | AY342026 | 584 | 60.5 | 1.00E-08 | 190 | 48 | 25 |
| AB091814 | 597 | 73.9 | 1.00E-12 | 133 | 44 | 33 | AY342025 | 584 | 60.5 | 1.00E-08 | 190 | 48 | 25 |
| AB091813 | 597 | 73.9 | 1.00E-12 | 133 | 44 | 33 | AY342024 | 584 | 60.5 | 1.00E-08 | 190 | 48 | 25 |
| AB091807 | 597 | 73.9 | 1.00E-12 | 133 | 44 | 33 | AY342023 | 584 | 60.5 | 1.00E-08 | 190 | 48 | 25 |
| AB189460 | 597 | 73.9 | 1.00E-12 | 133 | 44 | 33 | AY342022 | 584 | 60.5 | 1.00E-08 | 190 | 48 | 25 |
| AB178331 | 597 | 73.9 | 1.00E-12 | 133 | 44 | 33 | AY342018 | 584 | 60.5 | 1.00E-08 | 190 | 48 | 25 |
| AB178332 | 597 | 73.9 | 1.00E-12 | 133 | 44 | 33 | AB001703 | 584 | 60.5 | 1.00E-08 | 190 | 48 | 25 |
| AB178330 | 597 | 73.9 | 1.00E-12 | 133 | 44 | 33 | AB001701 | 584 | 60.5 | 1.00E-08 | 190 | 48 | 25 |
| AB178329 | 597 | 73.9 | 1.00E-12 | 133 | 44 | 33 | AB001700 | 584 | 60.5 | 1.00E-08 | 190 | 48 | 25 |
| AB178328 | 597 | 73.9 | 1.00E-12 | 133 | 44 | 33 | AF398984 | 378 | 60.1 | 2.00E-08 | 124 | 41 | 33 |
| AB178327 | 597 | 73.9 | 1.00E-12 | 133 | 44 | 33 | AF398983 | 378 | 60.1 | 2.00E-08 | 124 | 41 | 33 |
| AB178326 | 597 | 73.9 | 1.00E-12 | 133 | 44 | 33 | AF264886 | 608 | 60.1 | 2.00E-08 | 208 | 49 | 23 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AE007721 | 8198 | 60.1 | 2.00E-08 | 289 | 65 | 22 | AY366539 | 426 | 47 | 1.00E-04 | 132 | 36 | 27 |
| AE007721 | 8198 | 42.4 | 0.003 | 310 | 69 | 22 | AE004539 | 25022 | 46.6 | 2.00E-04 | 134 | 34 | 25 |
| AF264889 | 608 | 60.1 | 2.00E-08 | 208 | 49 | 23 | AY007305 | 1233 | 46.6 | 2.00E-04 | 116 | 29 | 25 |
| AF264885 | 608 | 60.1 | 2.00E-08 | 208 | 49 | 23 | AF408410 | 423 | 46.2 | 2.00E-04 | 126 | 35 | 27 |
| AF264882 | 608 | 60.1 | 2.00E-08 | 208 | 49 | 23 | AJ311998 | 235 | 46.2 | 2.00E-04 | 71 | 25 | 35 |
| AF264881 | 608 | 60.1 | 2.00E-08 | 208 | 49 | 23 | AJ311997 | 235 | 46.2 | 2.00E-04 | 71 | 25 | 35 |
| AF264880 | 608 | 60.1 | 2.00E-08 | 208 | 49 | 23 | AJ311996 | 235 | 46.2 | 2.00E-04 | 71 | 25 | 35 |
| AF264879 | 608 | 60.1 | 2.00E-08 | 208 | 49 | 23 | AJ311995 | 235 | 46.2 | 2.00E-04 | 71 | 25 | 35 |
| AF398980 | 378 | 59.7 | 2.00E-08 | 138 | 44 | 31 | AJ311993 | 235 | 46.2 | 2.00E-04 | 71 | 25 | 35 |
| AF398979 | 378 | 59.7 | 2.00E-08 | 138 | 44 | 31 | AE001532 | 11113 | 46.2 | 2.00E-04 | 149 | 40 | 26 |
| AF398978 | 378 | 59.7 | 2.00E-08 | 138 | 44 | 31 | AF015108 | 267 | 46.2 | 2.00E-04 | 77 | 21 | 27 |
| AF398977 | 378 | 59.7 | 2.00E-08 | 138 | 44 | 31 | Y15098 | 477 | 45.8 | 3.00E-04 | 139 | 33 | 23 |
| AB001702 | 584 | 59.7 | 2.00E-08 | 190 | 48 | 25 | Y15095 | 463 | 45.8 | 3.00E-04 | 139 | 33 | 23 |
| AF264884 | 608 | 59.3 | 3.00E-08 | 208 | 49 | 23 | Y15094 | 481 | 45.8 | 3.00E-04 | 139 | 33 | 23 |
| AF264901 | 602 | 58.5 | 4.00E-08 | 206 | 50 | 24 | Y15091 | 463 | 45.8 | 3.00E-04 | 139 | 33 | 23 |
| AB018725 | 537 | 58.5 | 4.00E-08 | 69 | 29 | 42 | AF015109 | 267 | 45.8 | 3.00E-04 | 77 | 21 | 27 |
| AB018723 | 408 | 58.5 | 4.00E-08 | 69 | 29 | 42 | AY365212 | 402 | 45.4 | 4.00E-04 | 132 | 35 | 26 |
| M21445 | 867 | 58.5 | 4.00E-08 | 46 | 28 | 60 | Y15101 | 490 | 45.4 | 4.00E-04 | 139 | 33 | 23 |
| M21445 | 867 | 41.6 | 0.006 | 307 | 79 | 25 | Y15099 | 466 | 45.4 | 4.00E-04 | 139 | 33 | 23 |
| AY083505 | 621 | 58.2 | 6.00E-08 | 161 | 41 | 25 | Y15097 | 479 | 45.4 | 4.00E-04 | 139 | 33 | 23 |
| AY083504 | 621 | 58.2 | 6.00E-08 | 161 | 41 | 25 | Y15092 | 463 | 45.4 | 4.00E-04 | 139 | 33 | 23 |
| AJ297537 | 384 | 57.8 | 8.00E-08 | 64 | 28 | 43 | Y15090 | 473 | 45.4 | 4.00E-04 | 139 | 33 | 23 |
| AF264900 | 608 | 57.8 | 8.00E-08 | 208 | 51 | 24 | Y15089 | 478 | 45.4 | 4.00E-04 | 139 | 33 | 23 |
| AY450560 | 570 | 57.4 | 1.00E-07 | 185 | 47 | 25 | AF116904 | 467 | 45.4 | 4.00E-04 | 143 | 36 | 25 |
| AY278538 | 432 | 57 | 1.00E-07 | 149 | 47 | 31 | Y15100 | 456 | 45.1 | 5.00E-04 | 139 | 33 | 23 |
| AY278533 | 417 | 57 | 1.00E-07 | 135 | 41 | 30 | X89239 | 1310 | 45.1 | 5.00E-04 | 105 | 29 | 27 |
| U62056 | 2236 | 56.2 | 2.00E-07 | 47 | 27 | 57 | AF228032 | 476 | 45.1 | 5.00E-04 | 146 | 37 | 25 |
| AJ297536 | 340 | 52.8 | 2.00E-07 | 43 | 27 | 62 | D12510 | 832 | 45.1 | 5.00E-04 | 24 | 23 | 95 |
| AJ297536 | 340 | 28.5 | 2.00E-07 | 31 | 13 | 41 | AY226590 | 321 | 44.7 | 7.00E-04 | 94 | 24 | 25 |
| AF332547 | 19758 | 55.8 | 3.00E-07 | 132 | 36 | 27 | BX571966 | 3173005 | 44.7 | 7.00E-04 | 292 | 64 | 21 |
| M34710 | 684 | 55.8 | 3.00E-07 | 63 | 27 | 42 | BX571966 | 3173005 | 42.7 | 0.002 | 320 | 69 | 21 |
| AJ251711 | 1260 | 55.1 | 5.00E-07 | 193 | 48 | 24 | BX571966 | 3173005 | 40.4 | 0.012 | 278 | 59 | 21 |
| AJ251711 | 1260 | 39.7 | 0.021 | 72 | 22 | 30 | BX571966 | 3173005 | 40.4 | 0.012 | 291 | 65 | 22 |
| AB018721 | 282 | 55.1 | 5.00E-07 | 49 | 23 | 46 | BX571966 | 3173005 | 39.3 | 0.028 | 302 | 59 | 19 |
| AE011584 | 11491 | 54.7 | 6.00E-07 | 110 | 34 | 30 | AF228034 | 476 | 44.7 | 7.00E-04 | 146 | 37 | 25 |
| AY083503 | 615 | 54.7 | 6.00E-07 | 156 | 41 | 26 | AF228033 | 476 | 44.7 | 7.00E-04 | 146 | 37 | 25 |
| AY083502 | 615 | 54.7 | 6.00E-07 | 156 | 41 | 26 | AF354560 | 321 | 44.7 | 7.00E-04 | 94 | 24 | 25 |
| AE017300 | 358408 | 54.7 | 6.00E-07 | 110 | 34 | 30 | AF354559 | 321 | 44.7 | 7.00E-04 | 94 | 24 | 25 |
| BX640415 | 347071 | 54.7 | 6.00E-07 | 136 | 43 | 31 | AF354558 | 321 | 44.7 | 7.00E-04 | 94 | 24 | 25 |
| Y15093 | 506 | 53.9 | 1.00E-06 | 159 | 39 | 24 | AF355599 | 321 | 44.7 | 7.00E-04 | 94 | 24 | 25 |
| AB018731 | 363 | 53.9 | 1.00E-06 | 92 | 32 | 34 | Y15096 | 480 | 44.3 | 9.00E-04 | 139 | 33 | 23 |
| AB018729 | 363 | 53.9 | 1.00E-06 | 92 | 32 | 34 | AE006319 | 10302 | 44.3 | 9.00E-04 | 287 | 50 | 17 |
| AB018727 | 369 | 53.9 | 1.00E-06 | 92 | 32 | 34 | AF119150 | 18605 | 44.3 | 9.00E-04 | 228 | 52 | 22 |
| AE009025 | 11897 | 53.5 | 1.00E-06 | 256 | 60 | 23 | M33808 | 852 | 44.3 | 9.00E-04 | 30 | 21 | 70 |
| AE009025 | 11897 | 46.2 | 2.00E-04 | 140 | 34 | 24 | M33808 | 852 | 37.4 | 0.1 | 31 | 18 | 58 |
| AE007991 | 9626 | 53.5 | 1.00E-06 | 256 | 60 | 23 | AE004223 | 24353 | 43.9 | 0.001 | 228 | 52 | 22 |
| AE007991 | 9626 | 46.2 | 2.00E-04 | 140 | 34 | 24 | AF354561 | 321 | 43.9 | 0.001 | 94 | 24 | 25 |
| AB018713 | 369 | 53.5 | 1.00E-06 | 108 | 33 | 30 | AF015104 | 267 | 43.9 | 0.001 | 77 | 21 | 27 |
| AF515473 | 528 | 53.1 | 2.00E-06 | 92 | 37 | 40 | AY226588 | 321 | 43.5 | 0.001 | 91 | 28 | 30 |
| AF515473 | 528 | 49.7 | 2.00E-05 | 132 | 41 | 31 | AY226587 | 321 | 43.5 | 0.001 | 91 | 28 | 30 |
| AY357714 | 479 | 52.4 | 3.00E-06 | 150 | 40 | 26 | AF354554 | 321 | 43.5 | 0.001 | 91 | 28 | 30 |
| AY362359 | 436 | 52 | 4.00E-06 | 144 | 38 | 26 | AF354553 | 321 | 43.5 | 0.001 | 91 | 28 | 30 |
| Y15088 | 506 | 52 | 4.00E-06 | 159 | 38 | 23 | AF354548 | 321 | 43.5 | 0.001 | 91 | 28 | 30 |
| U26679 | 1573 | 52 | 4.00E-06 | 108 | 32 | 29 | AF015105 | 267 | 43.5 | 0.001 | 77 | 20 | 25 |
| AF497995 | 544 | 51.6 | 5.00E-06 | 181 | 44 | 24 | AF015101 | 267 | 43.5 | 0.001 | 77 | 20 | 25 |
| AB018715 | 468 | 51.6 | 5.00E-06 | 88 | 27 | 30 | AF015097 | 267 | 43.5 | 0.001 | 77 | 20 | 25 |
| BX572605 | 349746 | 50.8 | 9.00E-06 | 284 | 69 | 24 | AF015089 | 267 | 43.5 | 0.001 | 77 | 20 | 25 |
| BX572605 | 349746 | 44.7 | 7.00E-04 | 194 | 49 | 25 | AY226589 | 321 | 43.1 | 0.002 | 91 | 27 | 29 |
| BX572600 | 349640 | 50.8 | 9.00E-06 | 284 | 70 | 24 | X51740 | 1766 | 43.1 | 0.002 | 21 | 21 | 100 |
| M57565 | 3608 | 50.4 | 1.00E-05 | 87 | 29 | 33 | BA000038 | 1857073 | 43.1 | 0.002 | 289 | 63 | 21 |
| M57565 | 3608 | 45.8 | 3.00E-04 | 245 | 56 | 22 | BA000038 | 1857073 | 33.1 | 2 | 120 | 30 | 25 |
| M24526 | 3530 | 50.4 | 1.00E-05 | 149 | 43 | 28 | AF354555 | 321 | 43.1 | 0.002 | 91 | 27 | 29 |
| M24526 | 3530 | 42 | 0.004 | 87 | 23 | 26 | AF354550 | 321 | 43.1 | 0.002 | 91 | 27 | 29 |
| AY533375 | 7214 | 49.3 | 3.00E-05 | 134 | 34 | 25 | AF354549 | 321 | 43.1 | 0.002 | 91 | 27 | 29 |
| AY533375 | 7214 | 48.5 | 5.00E-05 | 130 | 34 | 26 | AF354547 | 321 | 43.1 | 0.002 | 91 | 27 | 29 |
| AB018717 | 234 | 48.9 | 3.00E-05 | 74 | 28 | 37 | AF354546 | 321 | 43.1 | 0.002 | 91 | 27 | 29 |
| D26168 | 866 | 47.8 | 8.00E-05 | 24 | 24 | 100 | X89238 | 1310 | 42.7 | 0.002 | 99 | 27 | 27 |
| D26167 | 832 | 47.8 | 8.00E-05 | 24 | 24 | 100 | AF354552 | 321 | 42.7 | 0.002 | 81 | 26 | 32 |

Fig. 25A-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AF354551 | 321 | 42.7 | 0.002 | 81 | 26 | 32 | BA000033 | 2820462 | 34.3 | 0.89 | 299 | 60 | 20 |
| AF015106 | 267 | 42.7 | 0.002 | 77 | 20 | 25 | U96234 | 390 | 39.3 | 0.028 | 97 | 26 | 26 |
| BX248358 | 348408 | 42.4 | 0.003 | 169 | 38 | 22 | AL596163 | 231450 | 38.9 | 0.036 | 261 | 57 | 21 |
| BX571658 | 346792 | 42.4 | 0.003 | 168 | 37 | 22 | U25727 | 108 | 38.9 | 0.036 | 34 | 21 | 61 |
| AL591982 | 295050 | 42.4 | 0.003 | 273 | 58 | 21 | AY708387 | 1232 | 38.5 | 0.047 | 260 | 55 | 21 |
| AF354557 | 321 | 42.4 | 0.003 | 81 | 25 | 30 | AY708385 | 1250 | 38.5 | 0.047 | 260 | 55 | 21 |
| AF354556 | 321 | 42.4 | 0.003 | 81 | 25 | 30 | AF386506 | 441 | 38.5 | 0.047 | 95 | 25 | 26 |
| AY007306 | 1236 | 42.4 | 0.003 | 116 | 27 | 23 | AF386505 | 442 | 38.5 | 0.047 | 95 | 25 | 26 |
| AF015103 | 267 | 42.4 | 0.003 | 77 | 20 | 25 | AE016747 | 300892 | 38.5 | 0.047 | 169 | 43 | 25 |
| AL935252 | 343050 | 42 | 0.004 | 285 | 64 | 22 | AE016747 | 300892 | 34.7 | 0.68 | 302 | 60 | 19 |
| AL646086 | 92509 | 42 | 0.004 | 264 | 60 | 22 | U25820 | 108 | 38.5 | 0.047 | 36 | 19 | 52 |
| AL646086 | 92509 | 36.2 | 0.23 | 260 | 56 | 21 | AF015111 | 267 | 38.5 | 0.047 | 74 | 22 | 29 |
| AL646086 | 92509 | 35.8 | 0.31 | 247 | 57 | 23 | AE005766 | 10091 | 38.1 | 0.062 | 73 | 21 | 28 |
| AJ311994 | 206 | 41.6 | 0.006 | 65 | 24 | 36 | Z31376 | 4192 | 38.1 | 0.062 | 29 | 19 | 65 |
| J01801 | 1094 | 41.6 | 0.006 | 20 | 20 | 100 | X86999 | 186 | 37.7 | 0.08 | 43 | 16 | 37 |
| AF015095 | 267 | 41.6 | 0.006 | 74 | 24 | 32 | X86998 | 186 | 37.7 | 0.08 | 43 | 16 | 37 |
| AF015090 | 267 | 41.6 | 0.006 | 74 | 24 | 32 | X86997 | 186 | 37.7 | 0.08 | 43 | 16 | 37 |
| M58145 | 224 | 41.6 | 0.006 | 20 | 20 | 100 | X86996 | 186 | 37.7 | 0.08 | 43 | 16 | 37 |
| J01800 | 349 | 41.6 | 0.006 | 20 | 20 | 100 | X86995 | 186 | 37.7 | 0.08 | 43 | 16 | 37 |
| BA000018 | 2814816 | 41.2 | 0.007 | 332 | 72 | 21 | X86994 | 186 | 37.7 | 0.08 | 43 | 16 | 37 |
| AF015115 | 267 | 41.2 | 0.007 | 74 | 23 | 31 | X86993 | 186 | 37.7 | 0.08 | 43 | 16 | 37 |
| AF015113 | 267 | 41.2 | 0.007 | 74 | 23 | 31 | X86992 | 186 | 37.7 | 0.08 | 43 | 16 | 37 |
| AF015112 | 267 | 41.2 | 0.007 | 74 | 23 | 31 | X86990 | 186 | 37.7 | 0.08 | 43 | 16 | 37 |
| AF015102 | 267 | 41.2 | 0.007 | 74 | 23 | 31 | X86989 | 186 | 37.7 | 0.08 | 43 | 16 | 37 |
| AF015100 | 267 | 41.2 | 0.007 | 74 | 23 | 31 | X86988 | 186 | 37.7 | 0.08 | 43 | 16 | 37 |
| AF015099 | 267 | 41.2 | 0.007 | 74 | 23 | 31 | X86987 | 186 | 37.7 | 0.08 | 43 | 16 | 37 |
| AF015098 | 267 | 41.2 | 0.007 | 74 | 23 | 31 | X86986 | 186 | 37.7 | 0.08 | 43 | 16 | 37 |
| AF015096 | 267 | 41.2 | 0.007 | 74 | 23 | 31 | X86985 | 186 | 37.7 | 0.08 | 43 | 16 | 37 |
| AF015094 | 267 | 41.2 | 0.007 | 74 | 23 | 31 | X86984 | 186 | 37.7 | 0.08 | 43 | 16 | 37 |
| AF015091 | 267 | 41.2 | 0.007 | 74 | 23 | 31 | X86983 | 186 | 37.7 | 0.08 | 43 | 16 | 37 |
| AP003362 | 346300 | 41.2 | 0.007 | 332 | 72 | 21 | X86982 | 186 | 37.7 | 0.08 | 43 | 16 | 37 |
| Z54217 | 2262 | 40.8 | 0.009 | 20 | 20 | 100 | X86981 | 186 | 37.7 | 0.08 | 43 | 16 | 37 |
| AY575004 | 136 | 40.8 | 0.009 | 38 | 18 | 47 | X86980 | 186 | 37.7 | 0.08 | 43 | 16 | 37 |
| AY575002 | 136 | 40.8 | 0.009 | 38 | 18 | 47 | X86979 | 186 | 37.7 | 0.08 | 43 | 16 | 37 |
| AY575001 | 136 | 40.8 | 0.009 | 38 | 18 | 47 | X87005 | 186 | 37.7 | 0.08 | 43 | 16 | 37 |
| AF270112 | 3067 | 40.8 | 0.009 | 262 | 58 | 22 | X87004 | 186 | 37.7 | 0.08 | 43 | 16 | 37 |
| AF269857 | 3319 | 40.8 | 0.009 | 262 | 58 | 22 | X87003 | 186 | 37.7 | 0.08 | 43 | 16 | 37 |
| AF269729 | 3867 | 40.8 | 0.009 | 262 | 58 | 22 | X87002 | 186 | 37.7 | 0.08 | 43 | 16 | 37 |
| S62783 | 193 | 40.4 | 0.012 | 32 | 20 | 62 | X87001 | 186 | 37.7 | 0.08 | 43 | 16 | 37 |
| S62780 | 191 | 40.4 | 0.012 | 32 | 20 | 62 | X87000 | 186 | 37.7 | 0.08 | 43 | 16 | 37 |
| S62779 | 191 | 40.4 | 0.012 | 32 | 20 | 62 | AL596172 | 248050 | 37.7 | 0.08 | 292 | 64 | 21 |
| S62776 | 191 | 40.4 | 0.012 | 32 | 20 | 62 | AE004867 | 15356 | 36.6 | 0.18 | 201 | 49 | 24 |
| S62775 | 192 | 40.4 | 0.012 | 32 | 20 | 62 | X86991 | 186 | 36.6 | 0.18 | 43 | 15 | 34 |
| S62773 | 200 | 40.4 | 0.012 | 32 | 20 | 62 | AY603345 | 483 | 36.6 | 0.18 | 166 | 34 | 20 |
| AF525505 | 11500 | 40.4 | 0.012 | 278 | 64 | 23 | AY603344 | 483 | 36.6 | 0.18 | 166 | 34 | 20 |
| AF525505 | 11500 | 39.3 | 0.028 | 321 | 76 | 23 | AY603342 | 483 | 36.6 | 0.18 | 166 | 34 | 20 |
| AY575003 | 136 | 40.4 | 0.012 | 38 | 18 | 47 | AY278535 | 360 | 36.6 | 0.18 | 115 | 31 | 26 |
| AF015114 | 267 | 40.4 | 0.012 | 64 | 21 | 32 | AE016827 | 2314078 | 36.2 | 0.23 | 273 | 58 | 21 |
| AF015110 | 267 | 40.4 | 0.012 | 64 | 21 | 32 | AE016827 | 2314078 | 36.2 | 0.23 | 273 | 58 | 21 |
| AF015107 | 267 | 40.4 | 0.012 | 64 | 21 | 32 | AE016827 | 2314078 | 35.8 | 0.31 | 274 | 61 | 22 |
| AF015093 | 267 | 40.4 | 0.012 | 64 | 21 | 32 | AY603343 | 483 | 36.2 | 0.23 | 166 | 34 | 20 |
| AF015092 | 267 | 40.4 | 0.012 | 64 | 21 | 32 | AY458638 | 19060 | 36.2 | 0.23 | 146 | 39 | 26 |
| CP000024 | 1796226 | 40 | 0.016 | 302 | 64 | 21 | AE016968 | 302070 | 35.8 | 0.31 | 183 | 40 | 21 |
| CP000023 | 1796846 | 40 | 0.016 | 302 | 64 | 21 | BA000019 | 6413771 | 35.8 | 0.31 | 286 | 59 | 20 |
| J01607 | 351 | 40 | 0.016 | 20 | 18 | 90 | M12293 | 181 | 35.8 | 0.31 | 17 | 17 | 100 |
| U96166 | 19841 | 39.7 | 0.021 | 278 | 48 | 17 | AF459093 | 6852 | 35.4 | 0.4 | 269 | 58 | 21 |
| U96239 | 390 | 39.7 | 0.021 | 97 | 26 | 26 | BX294135 | 340750 | 35.4 | 0.4 | 240 | 52 | 21 |
| U96238 | 390 | 39.7 | 0.021 | 97 | 26 | 26 | AY278547 | 377 | 35.4 | 0.4 | 129 | 35 | 27 |
| U96237 | 390 | 39.7 | 0.021 | 97 | 26 | 26 | AE016940 | 304230 | 35 | 0.52 | 150 | 44 | 29 |
| U96236 | 390 | 39.7 | 0.021 | 97 | 26 | 26 | AE001129 | 10845 | 35 | 0.52 | 77 | 18 | 23 |
| U96235 | 390 | 39.7 | 0.021 | 97 | 26 | 26 | AY275838 | 27297 | 35 | 0.52 | 239 | 49 | 20 |
| AY374137 | 491 | 39.7 | 0.021 | 97 | 26 | 26 | AF045472 | 7263 | 34.7 | 0.68 | 95 | 25 | 26 |
| AY374135 | 485 | 39.7 | 0.021 | 97 | 26 | 26 | AE001578 | 29838 | 34.7 | 0.68 | 114 | 30 | 26 |
| AY374134 | 485 | 39.7 | 0.021 | 97 | 26 | 26 | BA000016 | 3031430 | 34.7 | 0.68 | 232 | 49 | 21 |
| AY374133 | 485 | 39.7 | 0.021 | 97 | 26 | 26 | BA000045 | 4659019 | 34.7 | 0.68 | 73 | 24 | 32 |
| AY374132 | 485 | 39.7 | 0.021 | 97 | 26 | 26 | U40259 | 8013 | 34.7 | 0.68 | 95 | 25 | 26 |
| BX571857 | 2799802 | 39.3 | 0.028 | 283 | 66 | 23 | AE016864 | 310325 | 34.3 | 0.89 | 128 | 31 | 24 |
| BA000033 | 2820462 | 39.3 | 0.028 | 283 | 66 | 23 | AE014627 | 10029 | 34.3 | 0.89 | 271 | 54 | 19 |

Fig. 25A-Continued

| Hit_ID | Length | Bitscore | Expected | Length | #Ident | %S |
|---|---|---|---|---|---|---|
| AE017201 | 300478 | 33.9 | 1.2 | 125 | 28 | 22 |
| AE011395 | 10368 | 33.9 | 1.2 | 59 | 18 | 30 |
| AE015945 | 89370 | 33.9 | 1.2 | 103 | 24 | 23 |
| AL935255 | 269050 | 33.9 | 1.2 | 299 | 58 | 19 |
| CR378673 | 349814 | 33.9 | 1.2 | 73 | 16 | 21 |
| AE017310 | 300343 | 33.9 | 1.2 | 171 | 36 | 21 |
| AB015410 | 3519 | 33.9 | 1.2 | 283 | 55 | 19 |
| AE016858 | 312839 | 33.1 | 2 | 162 | 41 | 25 |
| AE016813 | 336182 | 33.1 | 2 | 120 | 30 | 25 |
| gi|42627766 | 3786 | 33.1 | 2 | 62 | 19 | 30 |
| AE016748 | 300029 | 33.1 | 2 | 148 | 30 | 20 |
| CR378667 | 349080 | 33.1 | 2 | 137 | 31 | 22 |
| AF113610 | 3246 | 33.1 | 2 | 240 | 48 | 20 |
| AF322013 | 230573 | 33.1 | 2 | 62 | 19 | 30 |
| D90775 | 16902 | 33.1 | 2 | 147 | 37 | 25 |
| D90774 | 18700 | 33.1 | 2 | 147 | 37 | 25 |
| CR378676 | 343529 | 33.1 | 2 | 107 | 27 | 25 |
| AE017135 | 291326 | 32.7 | 2.6 | 290 | 61 | 21 |
| AY708386 | 1203 | 32.7 | 2.6 | 254 | 52 | 20 |
| AJ414152 | 313050 | 32.7 | 2.6 | 290 | 61 | 21 |
| AE013773 | 10520 | 32.7 | 2.6 | 290 | 61 | 21 |
| AE005723 | 10573 | 32.7 | 2.6 | 235 | 47 | 20 |
| AE017240 | 299986 | 32.7 | 2.6 | 70 | 21 | 30 |

Fig. 25B

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| CAE53942 | 349 | 386 | 1.00E-106 | 348 | 215 | 61 | AAA17862 | 505 | 336 | 2.00E-91 | 178 | 177 | 99 |
| CAD60547 | 349 | 385 | 1.00E-106 | 348 | 214 | 61 | AAA17862 | 505 | 197 | 7.00E-50 | 227 | 126 | 55 |
| AAP13297 | 349 | 384 | 1.00E-106 | 348 | 213 | 61 | AAA17859 | 508 | 336 | 2.00E-91 | 178 | 177 | 99 |
| CAE53943 | 349 | 383 | 1.00E-105 | 348 | 214 | 61 | AAA17859 | 508 | 197 | 1.00E-49 | 305 | 140 | 45 |
| CAD56695 | 349 | 382 | 1.00E-105 | 348 | 213 | 61 | AAR10747 | 505 | 335 | 4.00E-91 | 178 | 176 | 98 |
| AAU90046 | 271 | 379 | 1.00E-104 | 284 | 202 | 71 | AAR10747 | 505 | 194 | 6.00E-49 | 227 | 125 | 55 |
| CAA62509 | 313 | 369 | 1.00E-101 | 313 | 206 | 65 | AAA17865 | 508 | 335 | 4.00E-91 | 178 | 176 | 98 |
| BAA06987 | 348 | 367 | 1.00E-101 | 356 | 214 | 60 | AAA17865 | 508 | 193 | 2.00E-48 | 106 | 103 | 97 |
| NP_929221 | 355 | 364 | 1.00E-100 | 355 | 207 | 58 | AAR10749 | 504 | 334 | 5.00E-91 | 178 | 176 | 98 |
| AAA62397 | 367 | 356 | 1.00E-97 | 367 | 213 | 58 | AAR10749 | 504 | 189 | 3.00E-47 | 106 | 101 | 95 |
| AAA62396 | 365 | 355 | 2.00E-97 | 365 | 211 | 57 | AAR10748 | 504 | 334 | 5.00E-91 | 178 | 176 | 98 |
| ZP_00169997 | 361 | 343 | 1.00E-93 | 361 | 201 | 55 | AAR10748 | 504 | 190 | 1.00E-47 | 280 | 139 | 49 |
| AAT81649 | 505 | 336 | 2.00E-91 | 178 | 177 | 99 | AAR10594 | 505 | 334 | 5.00E-91 | 178 | 176 | 98 |
| AAT81649 | 505 | 194 | 8.00E-49 | 106 | 104 | 98 | AAR10594 | 505 | 194 | 6.00E-49 | 227 | 125 | 55 |
| AAT81648 | 505 | 336 | 2.00E-91 | 178 | 177 | 99 | AAT81624 | 504 | 334 | 7.00E-91 | 178 | 176 | 98 |
| AAT81648 | 505 | 194 | 8.00E-49 | 106 | 104 | 98 | AAT81624 | 504 | 191 | 9.00E-48 | 301 | 136 | 45 |
| AAT81622 | 505 | 336 | 2.00E-91 | 178 | 177 | 99 | AAT81623 | 504 | 334 | 7.00E-91 | 178 | 176 | 98 |
| AAT81622 | 505 | 197 | 7.00E-50 | 227 | 126 | 55 | AAT81623 | 504 | 191 | 9.00E-48 | 301 | 136 | 45 |
| AAT81621 | 505 | 336 | 2.00E-91 | 178 | 177 | 99 | CAA78794 | 504 | 334 | 7.00E-91 | 177 | 176 | 99 |
| AAT81621 | 505 | 195 | 4.00E-49 | 227 | 125 | 55 | CAA78794 | 504 | 196 | 3.00E-49 | 227 | 126 | 55 |
| AAT81620 | 505 | 336 | 2.00E-91 | 178 | 177 | 99 | CAA78781 | 504 | 334 | 7.00E-91 | 177 | 176 | 99 |
| AAT81620 | 505 | 196 | 3.00E-49 | 227 | 126 | 55 | CAA78781 | 504 | 197 | 7.00E-50 | 227 | 126 | 55 |
| AAT81619 | 505 | 336 | 2.00E-91 | 178 | 177 | 99 | CAA78780 | 504 | 334 | 7.00E-91 | 177 | 176 | 99 |
| AAT81619 | 505 | 194 | 8.00E-49 | 106 | 104 | 98 | CAA78780 | 504 | 194 | 8.00E-49 | 106 | 104 | 98 |
| AAT81618 | 505 | 336 | 2.00E-91 | 178 | 177 | 99 | CAA78779 | 507 | 334 | 7.00E-91 | 177 | 176 | 99 |
| AAT81618 | 505 | 194 | 8.00E-49 | 106 | 104 | 98 | CAA78779 | 507 | 194 | 8.00E-49 | 106 | 104 | 98 |
| AAT81617 | 505 | 336 | 2.00E-91 | 178 | 177 | 99 | CAA78778 | 504 | 334 | 7.00E-91 | 177 | 176 | 99 |
| AAT81617 | 505 | 194 | 8.00E-49 | 106 | 104 | 98 | CAA78778 | 504 | 194 | 8.00E-49 | 106 | 104 | 98 |
| AAT81614 | 505 | 336 | 2.00E-91 | 178 | 177 | 99 | CAA78777 | 504 | 334 | 7.00E-91 | 177 | 176 | 99 |
| AAT81614 | 505 | 197 | 1.00E-49 | 227 | 126 | 55 | CAA78777 | 504 | 194 | 8.00E-49 | 106 | 104 | 98 |
| AAT81613 | 505 | 336 | 2.00E-91 | 178 | 177 | 99 | CAA78776 | 504 | 334 | 7.00E-91 | 177 | 176 | 99 |
| AAT81613 | 505 | 194 | 6.00E-49 | 227 | 125 | 55 | CAA78776 | 504 | 194 | 8.00E-49 | 106 | 104 | 98 |
| AAT81612 | 505 | 336 | 2.00E-91 | 178 | 177 | 99 | CAA78775 | 504 | 334 | 7.00E-91 | 177 | 176 | 99 |
| AAT81612 | 505 | 197 | 1.00E-49 | 227 | 126 | 55 | CAA78775 | 504 | 197 | 1.00E-49 | 227 | 126 | 55 |
| AAR10745 | 508 | 336 | 2.00E-91 | 178 | 177 | 99 | CAA78774 | 504 | 334 | 7.00E-91 | 177 | 176 | 99 |
| AAR10745 | 508 | 197 | 7.00E-50 | 324 | 142 | 43 | CAA78774 | 504 | 197 | 7.00E-50 | 227 | 126 | 55 |
| AAR10628 | 504 | 336 | 2.00E-91 | 178 | 177 | 99 | CAA78773 | 507 | 334 | 7.00E-91 | 177 | 176 | 99 |
| AAR10628 | 504 | 194 | 6.00E-49 | 309 | 141 | 45 | CAA78773 | 507 | 197 | 7.00E-50 | 324 | 142 | 43 |
| AAR10624 | 508 | 336 | 2.00E-91 | 178 | 177 | 99 | S33187 | 504 | 334 | 7.00E-91 | 177 | 176 | 99 |
| AAR10624 | 508 | 194 | 8.00E-49 | 106 | 104 | 98 | S33187 | 504 | 197 | 1.00E-49 | 227 | 126 | 55 |
| AAR10622 | 508 | 336 | 2.00E-91 | 178 | 177 | 99 | AAA53497 | 507 | 334 | 7.00E-91 | 177 | 176 | 99 |
| AAR10622 | 508 | 194 | 8.00E-49 | 106 | 104 | 98 | AAA53497 | 507 | 194 | 8.00E-49 | 106 | 104 | 98 |
| AAR10621 | 508 | 336 | 2.00E-91 | 178 | 177 | 99 | AAA53495 | 504 | 334 | 7.00E-91 | 177 | 176 | 99 |
| AAR10621 | 508 | 194 | 8.00E-49 | 106 | 104 | 98 | AAA53495 | 504 | 194 | 8.00E-49 | 106 | 104 | 98 |
| AAR10619 | 505 | 336 | 2.00E-91 | 178 | 177 | 99 | AAA53491 | 507 | 334 | 7.00E-91 | 177 | 176 | 99 |
| AAR10619 | 505 | 197 | 7.00E-50 | 227 | 126 | 55 | AAA53491 | 507 | 194 | 8.00E-49 | 106 | 104 | 98 |
| AAR10618 | 505 | 336 | 2.00E-91 | 178 | 177 | 99 | AAA53490 | 504 | 334 | 7.00E-91 | 177 | 176 | 99 |
| AAR10618 | 505 | 197 | 7.00E-50 | 227 | 126 | 55 | AAA53490 | 504 | 196 | 2.00E-49 | 227 | 126 | 55 |
| AAR10616 | 505 | 336 | 2.00E-91 | 178 | 177 | 99 | AAT81603 | 505 | 333 | 9.00E-91 | 178 | 176 | 98 |
| AAR10616 | 505 | 194 | 8.00E-49 | 106 | 104 | 98 | AAT81603 | 505 | 194 | 8.00E-49 | 106 | 104 | 98 |
| AAR10610 | 505 | 336 | 2.00E-91 | 178 | 177 | 99 | AAA27088 | 505 | 333 | 9.00E-91 | 178 | 176 | 98 |
| AAR10610 | 505 | 194 | 8.00E-49 | 106 | 104 | 98 | AAA27088 | 505 | 192 | 2.00E-48 | 106 | 103 | 97 |
| AAR10609 | 504 | 336 | 2.00E-91 | 178 | 177 | 99 | JU0056 | 351 | 333 | 1.00E-90 | 354 | 196 | 55 |
| AAR10609 | 504 | 193 | 2.00E-48 | 106 | 103 | 97 | AAA53493 | 465 | 330 | 7.00E-90 | 177 | 175 | 98 |
| AAR10608 | 504 | 336 | 2.00E-91 | 178 | 177 | 99 | AAA53493 | 465 | 171 | 1.00E-41 | 91 | 91 | 100 |
| AAR10608 | 504 | 193 | 2.00E-48 | 106 | 103 | 97 | AAR10625 | 504 | 330 | 1.00E-89 | 178 | 173 | 97 |
| AAR10604 | 505 | 336 | 2.00E-91 | 178 | 177 | 99 | AAR10625 | 504 | 187 | 1.00E-46 | 227 | 120 | 52 |
| AAR10604 | 505 | 194 | 8.00E-49 | 106 | 104 | 98 | AAA53496 | 503 | 328 | 4.00E-89 | 177 | 172 | 97 |
| O52959 | 505 | 336 | 2.00E-91 | 178 | 177 | 99 | AAA53496 | 503 | 187 | 1.00E-46 | 227 | 120 | 52 |
| O52959 | 505 | 194 | 8.00E-49 | 106 | 104 | 98 | YP_049831 | 290 | 327 | 8.00E-89 | 302 | 187 | 61 |
| AAA27092 | 505 | 336 | 2.00E-91 | 178 | 177 | 99 | S78461 | 364 | 319 | 2.00E-86 | 365 | 203 | 55 |
| AAA27092 | 505 | 194 | 8.00E-49 | 106 | 104 | 98 | NP_992909 | 369 | 318 | 5.00E-86 | 368 | 202 | 54 |
| AAA27090 | 505 | 336 | 2.00E-91 | 178 | 177 | 99 | NP_405406 | 369 | 318 | 5.00E-86 | 368 | 202 | 54 |
| AAA27090 | 505 | 194 | 8.00E-49 | 106 | 104 | 98 | AAO85383 | 369 | 315 | 2.00E-85 | 368 | 201 | 54 |
| AAA27085 | 494 | 336 | 2.00E-91 | 178 | 177 | 99 | AAA64387 | 493 | 315 | 4.00E-85 | 166 | 165 | 99 |
| AAA27085 | 494 | 174 | 9.00E-43 | 95 | 93 | 97 | AAA64387 | 493 | 194 | 8.00E-49 | 106 | 104 | 98 |
| AAA17863 | 508 | 336 | 2.00E-91 | 178 | 177 | 99 | AAQ22673 | 488 | 311 | 4.00E-84 | 263 | 178 | 67 |
| AAA17863 | 508 | 194 | 6.00E-49 | 227 | 125 | 55 | AAQ22673 | 488 | 160 | 1.00E-38 | 103 | 83 | 80 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AAR10689 | 505 | 311 | 4.00E-84 | 244 | 175 | 71 | A48658 | 595 | 135 | 5.00E-31 | 113 | 70 | 61 |
| AAR10689 | 505 | 175 | 5.00E-43 | 140 | 96 | 68 | AAP13337 | 436 | 296 | 2.00E-79 | 300 | 175 | 58 |
| BAD16577 | 488 | 310 | 8.00E-84 | 273 | 180 | 65 | AAP13337 | 436 | 135 | 6.00E-31 | 92 | 67 | 72 |
| BAD16577 | 488 | 166 | 3.00E-40 | 280 | 121 | 43 | AAL30164 | 498 | 296 | 2.00E-79 | 178 | 155 | 87 |
| S78460 | 358 | 310 | 1.00E-83 | 359 | 194 | 54 | AAL30164 | 498 | 155 | 3.00E-37 | 174 | 94 | 54 |
| AAQ22680 | 488 | 309 | 2.00E-83 | 263 | 177 | 67 | AAR97969 | 376 | 296 | 2.00E-79 | 223 | 159 | 71 |
| AAQ22680 | 488 | 160 | 1.00E-38 | 103 | 83 | 80 | BAA85089 | 565 | 296 | 2.00E-79 | 302 | 176 | 58 |
| AAL30165 | 487 | 308 | 4.00E-83 | 256 | 177 | 69 | BAA85089 | 565 | 133 | 2.00E-30 | 102 | 66 | 64 |
| AAL30165 | 487 | 158 | 7.00E-38 | 103 | 82 | 79 | AAP13309 | 554 | 296 | 2.00E-79 | 237 | 161 | 67 |
| CAD99230 | 464 | 308 | 5.00E-83 | 262 | 173 | 66 | AAP13309 | 554 | 141 | 8.00E-33 | 295 | 105 | 35 |
| CAD99230 | 464 | 117 | 1.00E-25 | 75 | 59 | 78 | AAF85764 | 554 | 296 | 2.00E-79 | 237 | 161 | 67 |
| AAR10691 | 505 | 308 | 5.00E-83 | 244 | 172 | 70 | AAF85764 | 554 | 139 | 3.00E-32 | 293 | 104 | 35 |
| AAR10691 | 505 | 171 | 7.00E-42 | 140 | 94 | 67 | AAQ22687 | 503 | 295 | 3.00E-79 | 178 | 155 | 87 |
| AAR10690 | 505 | 308 | 5.00E-83 | 244 | 172 | 70 | AAQ22687 | 503 | 158 | 7.00E-38 | 265 | 111 | 41 |
| AAR10690 | 505 | 173 | 2.00E-42 | 140 | 95 | 67 | AAP13324 | 545 | 295 | 3.00E-79 | 218 | 157 | 72 |
| AAQ22683 | 525 | 306 | 1.00E-82 | 299 | 184 | 61 | AAP13324 | 545 | 140 | 1.00E-32 | 172 | 85 | 49 |
| AAQ22683 | 525 | 149 | 4.00E-35 | 92 | 76 | 82 | AAP13324 | 545 | 32 | 7.10E+00 | 219 | 51 | 23 |
| BAD14980 | 524 | 306 | 1.00E-82 | 299 | 184 | 61 | CAA85351 | 565 | 295 | 3.00E-79 | 222 | 156 | 70 |
| BAD14980 | 524 | 150 | 1.00E-35 | 92 | 77 | 83 | CAA85351 | 565 | 133 | 2.00E-30 | 102 | 66 | 64 |
| AAQ22684 | 525 | 305 | 3.00E-82 | 299 | 184 | 61 | AAQ22689 | 557 | 295 | 3.00E-79 | 284 | 169 | 59 |
| AAQ22684 | 525 | 149 | 4.00E-35 | 92 | 76 | 82 | AAQ22689 | 557 | 141 | 8.00E-33 | 115 | 71 | 61 |
| AAB17947 | 585 | 305 | 3.00E-82 | 274 | 170 | 62 | AAP13336 | 447 | 295 | 3.00E-79 | 274 | 171 | 62 |
| AAB17947 | 585 | 142 | 5.00E-33 | 115 | 74 | 64 | AAP13336 | 447 | 134 | 1.00E-30 | 92 | 67 | 72 |
| S44982 | 524 | 305 | 4.00E-82 | 299 | 183 | 61 | AAP13318 | 579 | 295 | 3.00E-79 | 236 | 161 | 68 |
| S44982 | 524 | 148 | 5.00E-35 | 92 | 76 | 82 | AAP13318 | 579 | 140 | 1.00E-32 | 116 | 72 | 62 |
| AAG56938 | 585 | 305 | 4.00E-82 | 274 | 169 | 61 | AAP13316 | 557 | 295 | 3.00E-79 | 284 | 169 | 59 |
| AAG56938 | 585 | 142 | 5.00E-33 | 115 | 74 | 64 | AAP13316 | 557 | 142 | 5.00E-33 | 115 | 71 | 61 |
| AAQ22676 | 585 | 305 | 4.00E-82 | 274 | 169 | 61 | AAP13307 | 562 | 295 | 3.00E-79 | 257 | 168 | 65 |
| AAQ22676 | 585 | 142 | 5.00E-33 | 115 | 74 | 64 | AAP13307 | 562 | 142 | 3.00E-33 | 273 | 102 | 37 |
| AAP13300 | 585 | 305 | 4.00E-82 | 267 | 168 | 62 | AAP13298 | 436 | 295 | 4.00E-79 | 291 | 174 | 59 |
| AAP13300 | 585 | 142 | 5.00E-33 | 115 | 74 | 64 | AAP13298 | 436 | 135 | 6.00E-31 | 92 | 67 | 72 |
| AAF71897 | 585 | 305 | 4.00E-82 | 267 | 168 | 62 | AAL30167 | 545 | 295 | 4.00E-79 | 218 | 157 | 72 |
| AAF71897 | 585 | 142 | 5.00E-33 | 115 | 74 | 64 | AAL30167 | 545 | 140 | 1.00E-32 | 172 | 85 | 49 |
| AAQ22685 | 525 | 304 | 6.00E-82 | 299 | 183 | 61 | AAQ22681 | 447 | 294 | 6.00E-79 | 290 | 171 | 58 |
| AAQ22685 | 525 | 149 | 4.00E-35 | 92 | 76 | 82 | AAQ22681 | 447 | 137 | 1.00E-31 | 314 | 115 | 36 |
| AAF71901 | 585 | 304 | 7.00E-82 | 274 | 169 | 61 | AAP13326 | 447 | 294 | 6.00E-79 | 290 | 171 | 58 |
| AAF71901 | 585 | 142 | 5.00E-33 | 115 | 74 | 64 | AAP13326 | 447 | 137 | 2.00E-31 | 314 | 114 | 36 |
| C48658 | 584 | 303 | 2.00E-81 | 267 | 169 | 63 | AAP13302 | 670 | 294 | 6.00E-79 | 247 | 162 | 65 |
| C48658 | 584 | 141 | 8.00E-33 | 115 | 73 | 63 | AAP13302 | 670 | 147 | 2.00E-34 | 312 | 104 | 33 |
| BAD14967 | 423 | 301 | 6.00E-81 | 296 | 186 | 62 | AAP13334 | 564 | 294 | 8.00E-79 | 222 | 156 | 70 |
| BAD14967 | 423 | 141 | 8.00E-33 | 87 | 75 | 86 | AAP13334 | 564 | 133 | 2.00E-30 | 102 | 66 | 64 |
| AAP13299 | 548 | 300 | 1.00E-80 | 266 | 171 | 64 | AAL30168 | 564 | 294 | 8.00E-79 | 222 | 156 | 70 |
| AAP13299 | 548 | 140 | 1.00E-32 | 102 | 69 | 67 | AAL30168 | 564 | 132 | 4.00E-30 | 102 | 66 | 64 |
| AAP13321 | 555 | 299 | 2.00E-80 | 295 | 171 | 57 | NP_707809 | 550 | 293 | 1.00E-78 | 202 | 154 | 76 |
| AAP13321 | 555 | 140 | 1.00E-32 | 116 | 71 | 61 | NP_707809 | 550 | 140 | 1.00E-32 | 116 | 71 | 61 |
| B48658 | 595 | 298 | 3.00E-80 | 223 | 157 | 70 | AAQ22690 | 440 | 293 | 1.00E-78 | 288 | 177 | 61 |
| B48658 | 595 | 139 | 3.00E-32 | 255 | 106 | 41 | AAQ22690 | 440 | 137 | 2.00E-31 | 312 | 109 | 34 |
| AAQ22682 | 595 | 298 | 3.00E-80 | 223 | 157 | 70 | AAN34779 | 498 | 293 | 1.00E-78 | 178 | 153 | 85 |
| AAQ22682 | 595 | 137 | 1.00E-31 | 113 | 71 | 62 | AAN34779 | 498 | 155 | 3.00E-37 | 174 | 94 | 54 |
| AAQ22679 | 595 | 298 | 3.00E-80 | 223 | 157 | 70 | AAP13311 | 576 | 293 | 1.00E-78 | 299 | 171 | 57 |
| AAQ22679 | 595 | 137 | 1.00E-31 | 113 | 71 | 62 | AAP13311 | 576 | 142 | 4.00E-33 | 287 | 111 | 38 |
| NP_754230 | 595 | 298 | 3.00E-80 | 223 | 157 | 70 | AAP13332 | 572 | 293 | 1.00E-78 | 229 | 160 | 69 |
| NP_754230 | 595 | 138 | 5.00E-32 | 255 | 106 | 41 | AAP13332 | 572 | 144 | 1.00E-33 | 116 | 73 | 62 |
| AAP13331 | 568 | 298 | 3.00E-80 | 223 | 160 | 73 | AAP13332 | 572 | 32 | 7.10E+00 | 221 | 44 | 19 |
| AAP13331 | 568 | 140 | 1.00E-32 | 114 | 74 | 64 | AAP13306 | 550 | 293 | 1.00E-78 | 202 | 154 | 76 |
| AAP13305 | 595 | 298 | 3.00E-80 | 223 | 157 | 70 | AAP13306 | 550 | 140 | 1.00E-32 | 116 | 71 | 61 |
| AAP13305 | 595 | 137 | 1.00E-31 | 113 | 71 | 62 | AAF32260 | 550 | 293 | 1.00E-78 | 202 | 154 | 76 |
| BAA85086 | 568 | 298 | 3.00E-80 | 223 | 160 | 73 | AAF32260 | 550 | 138 | 7.00E-32 | 276 | 102 | 36 |
| BAA85086 | 568 | 141 | 6.00E-33 | 270 | 104 | 38 | AAQ22677 | 436 | 293 | 2.00E-78 | 291 | 169 | 58 |
| CAD97427 | 545 | 298 | 5.00E-80 | 246 | 163 | 66 | AAQ22677 | 436 | 134 | 8E-31 | 92 | 67 | 72 |
| CAD97427 | 545 | 91.3 | 1.00E-17 | 84 | 45 | 53 | AAP13328 | 559 | 292 | 2.00E-78 | 179 | 149 | 83 |
| AAP13313 | 588 | 297 | 9.00E-80 | 219 | 162 | 73 | AAP13328 | 559 | 139 | 4.00E-32 | 113 | 69 | 61 |
| AAP13313 | 588 | 142 | 3.00E-33 | 149 | 83 | 55 | AAP13320 | 443 | 291 | 4.00E-78 | 288 | 176 | 61 |
| AAQ22674 | 447 | 296 | 1.00E-79 | 290 | 172 | 59 | AAP13320 | 443 | 135 | 5.00E-31 | 315 | 107 | 33 |
| AAQ22674 | 447 | 135 | 3.00E-31 | 181 | 87 | 48 | AAN34780 | 498 | 291 | 5.00E-78 | 178 | 152 | 85 |
| AAP13335 | 605 | 296 | 1.00E-79 | 222 | 157 | 70 | AAN34780 | 498 | 155 | 3.00E-37 | 174 | 94 | 54 |
| AAP13335 | 605 | 139 | 3.00E-32 | 163 | 81 | 49 | AAR10708 | 413 | 291 | 5.00E-78 | 275 | 175 | 63 |
| A48658 | 595 | 296 | 2.00E-79 | 223 | 156 | 69 | AAR10708 | 413 | 150 | 1E-35 | 100 | 79 | 79 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AAR10698 | 421 | 291 | 5.00E-78 | 276 | 170 | 61 | AAR10715 | 426 | 149 | 2.00E-35 | 174 | 91 | 52 |
| AAR10698 | 421 | 152 | 5.00E-36 | 102 | 79 | 77 | AAR10711 | 422 | 288 | 5.00E-77 | 214 | 161 | 75 |
| BAA05151 | 568 | 291 | 5.00E-78 | 263 | 159 | 60 | AAR10711 | 422 | 150 | 1.00E-35 | 100 | 79 | 79 |
| BAA05151 | 568 | 140 | 1.00E-32 | 114 | 74 | 64 | AAR10706 | 422 | 288 | 5.00E-77 | 214 | 161 | 75 |
| AAQ22686 | 610 | 291 | 6.00E-78 | 191 | 151 | 79 | AAR10706 | 422 | 150 | 1.00E-35 | 100 | 79 | 79 |
| AAQ22686 | 610 | 145 | 4.00E-34 | 287 | 109 | 37 | AAR10666 | 501 | 288 | 5.00E-77 | 216 | 158 | 73 |
| AAP13322 | 570 | 291 | 6.00E-78 | 179 | 150 | 83 | AAR10666 | 501 | 156 | 2.00E-37 | 100 | 82 | 82 |
| AAP13322 | 570 | 139 | 3.00E-32 | 234 | 88 | 37 | AAR10659 | 500 | 288 | 5.00E-77 | 208 | 157 | 75 |
| AAP13310 | 613 | 291 | 6.00E-78 | 191 | 151 | 79 | AAR10659 | 500 | 156 | 2.00E-37 | 100 | 82 | 82 |
| AAP13310 | 613 | 146 | 3.00E-34 | 285 | 109 | 38 | AAR10658 | 500 | 288 | 5.00E-77 | 208 | 157 | 75 |
| CAD99229 | 453 | 291 | 6.00E-78 | 251 | 164 | 65 | AAR10658 | 500 | 156 | 2.00E-37 | 100 | 82 | 82 |
| CAD99229 | 453 | 117 | 1.00E-25 | 75 | 59 | 78 | AAR10543 | 500 | 288 | 5.00E-77 | 208 | 157 | 75 |
| BAA85087 | 570 | 290 | 1.00E-77 | 229 | 159 | 65 | AAR10543 | 500 | 154 | 7.00E-37 | 100 | 81 | 81 |
| BAA85087 | 570 | 144 | 1.00E-33 | 116 | 73 | 62 | AAR10667 | 501 | 287 | 7.00E-77 | 216 | 158 | 73 |
| BAA85087 | 570 | 32 | 7.10E+00 | 221 | 44 | 19 | AAR10667 | 501 | 156 | 2.00E-37 | 100 | 82 | 82 |
| BAD14961 | 529 | 290 | 1.00E-77 | 296 | 177 | 59 | NP_416433 | 498 | 287 | 9.00E-77 | 177 | 146 | 82 |
| BAD14961 | 529 | 151 | 8.00E-36 | 293 | 112 | 38 | NP_416433 | 498 | 149 | 4.00E-35 | 151 | 80 | 52 |
| AAP13327 | 432 | 290 | 1.00E-77 | 286 | 169 | 59 | AAQ22678 | 426 | 287 | 9.00E-77 | 258 | 163 | 63 |
| AAP13327 | 432 | 136 | 2.00E-31 | 253 | 102 | 40 | AAQ22678 | 426 | 138 | 7.00E-32 | 232 | 93 | 40 |
| AAP13323 | 428 | 290 | 1.00E-77 | 267 | 166 | 62 | AAT81632 | 500 | 287 | 9.00E-77 | 206 | 157 | 76 |
| AAP13323 | 428 | 134 | 1.00E-30 | 127 | 74 | 58 | AAT81632 | 500 | 152 | 4.00E-36 | 98 | 79 | 80 |
| AAL30166 | 428 | 290 | 1.00E-77 | 267 | 166 | 62 | AAT81631 | 500 | 287 | 9.00E-77 | 198 | 154 | 77 |
| AAL30166 | 428 | 131 | 7.00E-30 | 127 | 73 | 57 | AAT81631 | 500 | 156 | 2.00E-37 | 100 | 82 | 82 |
| AAR10700 | 421 | 290 | 1.00E-77 | 271 | 170 | 62 | CAA35488 | 498 | 287 | 9.00E-77 | 177 | 146 | 82 |
| AAR10700 | 421 | 152 | 5.00E-36 | 102 | 79 | 77 | CAA35488 | 498 | 151 | 6.00E-36 | 244 | 101 | 41 |
| AAR10699 | 421 | 290 | 1.00E-77 | 271 | 170 | 62 | AAR10755 | 422 | 287 | 9.00E-77 | 211 | 159 | 75 |
| AAR10699 | 421 | 152 | 5.00E-36 | 102 | 79 | 77 | AAR10755 | 422 | 150 | 1.00E-35 | 100 | 79 | 79 |
| AAR10695 | 421 | 290 | 1.00E-77 | 175 | 153 | 87 | AAR10669 | 493 | 287 | 9.00E-77 | 198 | 154 | 77 |
| AAR10696 | 421 | 289 | 2.00E-77 | 175 | 153 | 87 | AAR10669 | 493 | 156 | 2.00E-37 | 100 | 82 | 82 |
| AAR10696 | 421 | 152 | 5.00E-36 | 102 | 79 | 77 | AAR10668 | 481 | 287 | 9.00E-77 | 245 | 162 | 66 |
| AAR10694 | 421 | 289 | 2.00E-77 | 175 | 153 | 87 | AAR10668 | 481 | 156 | 2.00E-37 | 100 | 82 | 82 |
| AAP13325 | 561 | 289 | 2.00E-77 | 233 | 162 | 69 | AAR10665 | 501 | 287 | 9.00E-77 | 206 | 157 | 76 |
| AAP13325 | 561 | 150 | 1.00E-35 | 279 | 102 | 38 | AAR10665 | 501 | 156 | 2.00E-37 | 100 | 82 | 82 |
| AAR10759 | 422 | 289 | 2.00E-77 | 284 | 175 | 61 | AAR10664 | 501 | 287 | 9.00E-77 | 206 | 157 | 76 |
| AAR10759 | 422 | 150 | 1.00E-35 | 100 | 79 | 79 | AAR10664 | 501 | 154 | 7.00E-37 | 100 | 81 | 81 |
| AAR10544 | 500 | 288 | 3.00E-77 | 208 | 157 | 75 | AAR10662 | 500 | 287 | 9.00E-77 | 206 | 157 | 76 |
| AAR10544 | 500 | 155 | 4.00E-37 | 100 | 81 | 81 | AAR10662 | 500 | 156 | 2.00E-37 | 100 | 82 | 82 |
| BAA05153 | 549 | 288 | 3.00E-77 | 234 | 159 | 67 | AAR10660 | 500 | 287 | 9.00E-77 | 198 | 154 | 77 |
| BAA05153 | 549 | 135 | 6.00E-31 | 240 | 86 | 35 | AAR10660 | 500 | 156 | 2.00E-37 | 100 | 82 | 82 |
| AAP13329 | 426 | 288 | 4.00E-77 | 258 | 164 | 63 | AAR10590 | 502 | 287 | 9.00E-77 | 220 | 160 | 72 |
| AAP13329 | 426 | 138 | 7.00E-32 | 232 | 93 | 40 | AAR10590 | 502 | 157 | 1.00E-37 | 100 | 82 | 82 |
| AAP13319 | 570 | 288 | 4.00E-77 | 179 | 149 | 83 | AAR10721 | 421 | 286 | 1.00E-76 | 175 | 152 | 86 |
| AAP13319 | 570 | 139 | 4.00E-32 | 237 | 91 | 38 | AAR10721 | 421 | 150 | 1.00E-35 | 100 | 79 | 79 |
| AAF32261 | 426 | 288 | 4.00E-77 | 258 | 164 | 63 | AAR10713 | 421 | 286 | 1.00E-76 | 175 | 152 | 86 |
| AAF32261 | 426 | 136 | 3.00E-31 | 92 | 69 | 75 | AAR10713 | 421 | 150 | 1.00E-35 | 100 | 79 | 79 |
| AAR10710 | 422 | 288 | 4.00E-77 | 237 | 164 | 69 | AAR10657 | 500 | 286 | 1.00E-76 | 198 | 154 | 77 |
| AAR10710 | 422 | 148 | 5.00E-35 | 100 | 78 | 78 | AAR10657 | 500 | 152 | 4.00E-36 | 98 | 79 | 80 |
| AAT81644 | 426 | 288 | 5.00E-77 | 214 | 161 | 75 | AAQ22675 | 426 | 286 | 2.00E-76 | 258 | 163 | 63 |
| AAT81644 | 426 | 150 | 1.00E-35 | 100 | 79 | 79 | AAQ22675 | 426 | 136 | 2.00E-31 | 232 | 92 | 39 |
| AAT81643 | 422 | 288 | 5.00E-77 | 214 | 161 | 75 | AAR10546 | 501 | 286 | 2.00E-76 | 206 | 157 | 76 |
| AAT81643 | 422 | 148 | 5.00E-35 | 100 | 78 | 78 | AAR10546 | 501 | 156 | 2.00E-37 | 100 | 82 | 82 |
| AAT81642 | 424 | 288 | 5.00E-77 | 214 | 161 | 75 | BAD14977 | 516 | 286 | 2.00E-76 | 291 | 170 | 58 |
| AAT81642 | 424 | 150 | 1.00E-35 | 100 | 79 | 79 | BAD14977 | 516 | 146 | 3.00E-34 | 95 | 75 | 78 |
| AAT81611 | 502 | 288 | 5.00E-77 | 220 | 160 | 72 | AAT81609 | 502 | 286 | 2.00E-76 | 220 | 159 | 72 |
| AAT81611 | 502 | 157 | 1.00E-37 | 100 | 82 | 82 | AAT81609 | 502 | 157 | 1.00E-37 | 100 | 82 | 82 |
| AAT81610 | 502 | 288 | 5.00E-77 | 220 | 160 | 72 | AAR10562 | 499 | 286 | 2.00E-76 | 209 | 158 | 75 |
| AAT81610 | 502 | 157 | 1.00E-37 | 100 | 82 | 82 | AAR10562 | 499 | 158 | 5.00E-38 | 338 | 127 | 37 |
| AAP13330 | 501 | 288 | 5.00E-77 | 220 | 156 | 70 | AAR10561 | 499 | 286 | 2.00E-76 | 209 | 158 | 75 |
| AAP13330 | 501 | 134 | 1.00E-30 | 151 | 77 | 50 | AAR10561 | 499 | 158 | 7.00E-38 | 338 | 127 | 37 |
| AAR10761 | 422 | 288 | 5.00E-77 | 214 | 161 | 75 | AAR10559 | 499 | 286 | 2.00E-76 | 209 | 158 | 75 |
| AAR10761 | 422 | 148 | 5.00E-35 | 100 | 78 | 78 | AAR10559 | 499 | 158 | 7.00E-38 | 338 | 127 | 37 |
| AAR10760 | 422 | 288 | 5.00E-77 | 214 | 161 | 75 | AAR10558 | 499 | 286 | 2.00E-76 | 209 | 158 | 75 |
| AAR10760 | 422 | 150 | 1.00E-35 | 100 | 79 | 79 | AAR10558 | 499 | 157 | 9.00E-38 | 338 | 127 | 37 |
| AAR10719 | 422 | 288 | 5.00E-77 | 214 | 161 | 75 | AAR10557 | 499 | 286 | 2.00E-76 | 209 | 158 | 75 |
| AAR10719 | 422 | 150 | 1.00E-35 | 100 | 79 | 79 | AAR10557 | 499 | 158 | 7.00E-38 | 338 | 127 | 37 |
| AAR10717 | 426 | 288 | 5.00E-77 | 214 | 161 | 75 | AAF32259 | 420 | 285 | 4.00E-76 | 269 | 160 | 59 |
| AAR10717 | 426 | 151 | 8.00E-36 | 174 | 92 | 52 | AAF32259 | 420 | 135 | 6.00E-31 | 138 | 77 | 55 |
| AAR10715 | 426 | 288 | 5.00E-77 | 214 | 161 | 75 | AAR10714 | 421 | 285 | 4.00E-76 | 175 | 151 | 86 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AAR10714 | 421 | 150 | 1.00E-35 | 100 | 79 | 79 | AAR10739 | 506 | 154 | 7.00E-37 | 100 | 80 | 80 |
| AAR10572 | 495 | 285 | 4.00E-76 | 306 | 176 | 57 | AAR10512 | 506 | 282 | 3.00E-75 | 232 | 159 | 68 |
| AAR10572 | 495 | 149 | 3.00E-35 | 89 | 76 | 85 | AAR10512 | 506 | 155 | 4.00E-37 | 100 | 81 | 81 |
| NP_841632 | 275 | 285 | 5.00E-76 | 297 | 159 | 53 | AAR10511 | 506 | 282 | 3.00E-75 | 232 | 159 | 68 |
| CAD97429 | 408 | 285 | 5.00E-76 | 179 | 145 | 81 | AAR10511 | 506 | 155 | 4.00E-37 | 100 | 81 | 81 |
| CAD97429 | 408 | 86.7 | 2.00E-16 | 285 | 82 | 28 | AAR10489 | 506 | 282 | 3.00E-75 | 232 | 159 | 68 |
| AAT81605 | 495 | 285 | 5.00E-76 | 306 | 176 | 57 | AAR10489 | 506 | 155 | 4.00E-37 | 100 | 81 | 81 |
| AAT81605 | 495 | 151 | 6.00E-36 | 96 | 78 | 81 | AAR10488 | 506 | 282 | 3.00E-75 | 232 | 159 | 68 |
| AAP13303 | 420 | 285 | 5.00E-76 | 189 | 147 | 77 | AAR10488 | 506 | 155 | 4.00E-37 | 100 | 81 | 81 |
| AAP13303 | 420 | 137 | 2.00E-31 | 138 | 78 | 56 | AAC43352 | 506 | 281 | 4.00E-75 | 228 | 156 | 68 |
| AAR10720 | 422 | 285 | 5.00E-76 | 211 | 158 | 74 | AAC43352 | 506 | 155 | 4.00E-37 | 100 | 81 | 81 |
| AAR10720 | 422 | 150 | 1.00E-35 | 100 | 79 | 79 | AAR10504 | 506 | 281 | 4.00E-75 | 268 | 163 | 60 |
| AAR10575 | 495 | 285 | 5.00E-76 | 306 | 175 | 57 | AAR10504 | 506 | 155 | 4.00E-37 | 100 | 81 | 81 |
| AAR10575 | 495 | 151 | 6.00E-36 | 96 | 78 | 81 | AAR10495 | 506 | 281 | 4.00E-75 | 268 | 162 | 60 |
| AAR10574 | 495 | 285 | 5.00E-76 | 306 | 176 | 57 | AAR10495 | 506 | 155 | 4.00E-37 | 100 | 81 | 81 |
| AAR10574 | 495 | 151 | 6.00E-36 | 96 | 78 | 81 | AAR10754 | 494 | 281 | 5.00E-75 | 175 | 148 | 84 |
| AAR10515 | 501 | 285 | 5.00E-76 | 175 | 150 | 85 | AAR10754 | 494 | 152 | 4.00E-36 | 98 | 79 | 80 |
| AAR10515 | 501 | 155 | 4.00E-37 | 100 | 81 | 81 | AAC43351 | 506 | 281 | 5.00E-75 | 175 | 148 | 84 |
| AAR10729 | 501 | 284 | 6.00E-76 | 215 | 157 | 73 | AAC43351 | 506 | 155 | 4.00E-37 | 100 | 81 | 81 |
| AAR10729 | 501 | 152 | 4.00E-36 | 98 | 79 | 80 | AAC43348 | 506 | 281 | 5.00E-75 | 175 | 148 | 84 |
| AAR10728 | 501 | 284 | 6.00E-76 | 215 | 157 | 73 | AAC43348 | 506 | 154 | 7.00E-37 | 100 | 81 | 81 |
| AAR10728 | 501 | 152 | 4.00E-36 | 98 | 79 | 80 | AAR10751 | 495 | 281 | 5.00E-75 | 175 | 148 | 84 |
| AAR10716 | 426 | 284 | 6.00E-76 | 214 | 160 | 74 | AAR10751 | 495 | 148 | 7.00E-35 | 98 | 77 | 78 |
| AAR10716 | 426 | 149 | 2.00E-35 | 174 | 91 | 52 | AAR10750 | 495 | 281 | 5.00E-75 | 175 | 148 | 84 |
| AAR10702 | 499 | 284 | 6.00E-76 | 192 | 152 | 79 | AAR10750 | 495 | 152 | 4.00E-36 | 98 | 79 | 80 |
| AAR10702 | 499 | 153 | 2.00E-36 | 100 | 80 | 80 | AAR10743 | 506 | 281 | 5.00E-75 | 175 | 148 | 84 |
| CAA27130 | 509 | 284 | 8.00E-76 | 175 | 150 | 85 | AAR10743 | 506 | 155 | 4.00E-37 | 100 | 81 | 81 |
| CAA27130 | 509 | 149 | 4.00E-35 | 91 | 76 | 83 | AAR10742 | 506 | 281 | 5.00E-75 | 175 | 148 | 84 |
| NP_456520 | 506 | 284 | 8.00E-76 | 175 | 150 | 85 | AAR10742 | 506 | 155 | 4.00E-37 | 100 | 81 | 81 |
| NP_456520 | 506 | 149 | 4.00E-35 | 91 | 76 | 83 | AAR10741 | 506 | 281 | 5.00E-75 | 175 | 148 | 84 |
| AAQ22688 | 420 | 284 | 8.00E-76 | 189 | 147 | 77 | AAR10741 | 506 | 154 | 1.00E-36 | 100 | 80 | 80 |
| AAQ22688 | 420 | 135 | 6.00E-31 | 138 | 77 | 55 | AAR10740 | 506 | 281 | 5.00E-75 | 175 | 148 | 84 |
| AAT81639 | 506 | 284 | 8.00E-76 | 175 | 150 | 85 | AAR10740 | 506 | 155 | 6.00E-37 | 100 | 81 | 81 |
| AAT81639 | 506 | 149 | 4.00E-35 | 91 | 76 | 83 | AAR10730 | 495 | 281 | 5.00E-75 | 175 | 148 | 84 |
| AAT81608 | 506 | 284 | 8.00E-76 | 175 | 150 | 85 | AAR10730 | 495 | 155 | 6.00E-37 | 245 | 105 | 42 |
| AAT81608 | 506 | 149 | 4.00E-35 | 91 | 76 | 83 | AAR10724 | 494 | 281 | 5.00E-75 | 175 | 148 | 84 |
| AAT81607 | 506 | 284 | 8.00E-76 | 175 | 150 | 85 | AAR10724 | 494 | 158 | 5.00E-38 | 272 | 108 | 39 |
| AAT81607 | 506 | 150 | 1.00E-35 | 91 | 77 | 84 | AAR10682 | 499 | 281 | 5.00E-75 | 175 | 148 | 84 |
| AAR10646 | 419 | 284 | 8.00E-76 | 175 | 150 | 85 | AAR10682 | 499 | 154 | 1.00E-36 | 100 | 80 | 80 |
| AAR10646 | 419 | 149 | 4.00E-35 | 91 | 76 | 83 | AAR10681 | 499 | 281 | 5.00E-75 | 175 | 148 | 84 |
| AAR10588 | 506 | 284 | 8.00E-76 | 175 | 150 | 85 | AAR10681 | 499 | 154 | 1.00E-36 | 100 | 80 | 80 |
| AAR10588 | 506 | 150 | 1.00E-35 | 91 | 77 | 84 | AAR10648 | 495 | 281 | 5.00E-75 | 175 | 148 | 84 |
| AAR10514 | 506 | 284 | 8.00E-76 | 175 | 150 | 85 | AAR10648 | 495 | 152 | 4.00E-36 | 98 | 79 | 80 |
| AAR10514 | 506 | 150 | 1.00E-35 | 91 | 77 | 84 | AAR10567 | 506 | 281 | 5.00E-75 | 175 | 148 | 84 |
| S09638 | 505 | 284 | 8.00E-76 | 175 | 150 | 85 | AAR10567 | 506 | 155 | 4.00E-37 | 100 | 81 | 81 |
| S09638 | 505 | 149 | 4.00E-35 | 91 | 76 | 83 | AAR10566 | 500 | 281 | 5.00E-75 | 175 | 148 | 84 |
| NP_461698 | 506 | 283 | 1.00E-75 | 232 | 160 | 68 | AAR10566 | 500 | 157 | 1.00E-37 | 100 | 82 | 82 |
| NP_461698 | 506 | 155 | 4.00E-37 | 100 | 81 | 81 | AAR10564 | 500 | 281 | 5.00E-75 | 175 | 148 | 84 |
| YP_151805 | 506 | 283 | 1.00E-75 | 279 | 165 | 59 | AAR10564 | 500 | 155 | 4.00E-37 | 100 | 81 | 81 |
| YP_151805 | 506 | 155 | 4.00E-37 | 100 | 81 | 81 | AAR10542 | 495 | 281 | 5.00E-75 | 175 | 148 | 84 |
| AAR10471 | 501 | 283 | 1.00E-75 | 295 | 169 | 57 | AAR10542 | 495 | 155 | 6.00E-37 | 100 | 81 | 81 |
| AAR10471 | 501 | 151 | 6.00E-36 | 98 | 78 | 79 | AAR10539 | 501 | 281 | 5.00E-75 | 175 | 148 | 84 |
| AAR10484 | 506 | 283 | 1.00E-75 | 232 | 160 | 68 | AAR10539 | 501 | 155 | 4.00E-37 | 100 | 81 | 81 |
| AAR10484 | 506 | 155 | 4.00E-37 | 100 | 81 | 81 | AAR10538 | 501 | 281 | 5.00E-75 | 175 | 148 | 84 |
| CAB65960 | 456 | 283 | 2.00E-75 | 247 | 162 | 65 | AAR10538 | 501 | 155 | 4.00E-37 | 100 | 81 | 81 |
| CAB65960 | 456 | 139 | 3.00E-32 | 88 | 71 | 80 | AAR10536 | 501 | 281 | 5.00E-75 | 175 | 148 | 84 |
| AAR10737 | 506 | 283 | 2.00E-75 | 229 | 160 | 69 | AAR10536 | 501 | 155 | 4.00E-37 | 100 | 81 | 81 |
| AAR10737 | 506 | 154 | 9.00E-37 | 150 | 87 | 58 | AAR10532 | 501 | 281 | 5.00E-75 | 175 | 148 | 84 |
| AAR10735 | 506 | 283 | 2.00E-75 | 229 | 160 | 69 | AAR10532 | 501 | 155 | 4.00E-37 | 100 | 81 | 81 |
| AAR10735 | 506 | 154 | 1.00E-36 | 100 | 80 | 80 | AAR10530 | 501 | 281 | 5.00E-75 | 175 | 148 | 84 |
| AAR10703 | 499 | 282 | 2.00E-75 | 199 | 154 | 77 | AAR10530 | 501 | 155 | 4.00E-37 | 100 | 81 | 81 |
| AAR10703 | 499 | 151 | 8.00E-36 | 98 | 78 | 79 | AAR10527 | 501 | 281 | 5.00E-75 | 175 | 148 | 84 |
| AAR10499 | 506 | 282 | 2.00E-75 | 275 | 164 | 59 | AAR10527 | 501 | 155 | 4.00E-37 | 100 | 81 | 81 |
| AAR10499 | 506 | 155 | 4.00E-37 | 100 | 81 | 81 | AAR10523 | 501 | 281 | 5.00E-75 | 175 | 148 | 84 |
| AAR10509 | 506 | 282 | 3.00E-75 | 232 | 159 | 68 | AAR10523 | 501 | 155 | 4.00E-37 | 100 | 81 | 81 |
| AAR10509 | 506 | 155 | 4.00E-37 | 100 | 81 | 81 | AAR10521 | 501 | 281 | 5.00E-75 | 175 | 148 | 84 |
| CAD22870 | 280 | 282 | 3.00E-75 | 296 | 167 | 56 | AAR10521 | 501 | 155 | 6E-37 | 100 | 81 | 81 |
| AAR10739 | 506 | 282 | 3.00E-75 | 217 | 156 | 71 | AAR10518 | 501 | 281 | 5.00E-75 | 175 | 148 | 84 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AAR10518 | 501 | 155 | 6.00E-37 | 100 | 81 | 81 | AAR10684 | 499 | 154 | 9.00E-37 | 98 | 80 | 81 |
| AAR10505 | 465 | 281 | 5.00E-75 | 175 | 148 | 84 | AAR10683 | 499 | 280 | 9.00E-75 | 175 | 148 | 84 |
| AAR10505 | 465 | 155 | 4.00E-37 | 100 | 81 | 81 | AAR10683 | 499 | 154 | 9.00E-37 | 98 | 80 | 81 |
| AAR10501 | 506 | 281 | 5.00E-75 | 175 | 148 | 84 | AAR10679 | 499 | 280 | 9.00E-75 | 175 | 148 | 84 |
| AAR10501 | 506 | 155 | 4.00E-37 | 100 | 81 | 81 | AAR10679 | 499 | 155 | 4.00E-37 | 100 | 81 | 81 |
| AAR10496 | 506 | 281 | 5.00E-75 | 175 | 148 | 84 | AAR10678 | 506 | 280 | 9.00E-75 | 175 | 148 | 84 |
| AAR10496 | 506 | 155 | 4.00E-37 | 100 | 81 | 81 | AAR10678 | 506 | 159 | 4.00E-38 | 100 | 83 | 83 |
| AAR10494 | 506 | 281 | 5.00E-75 | 175 | 148 | 84 | AAR10677 | 506 | 280 | 9.00E-75 | 175 | 148 | 84 |
| AAR10494 | 506 | 155 | 4.00E-37 | 100 | 81 | 81 | AAR10677 | 506 | 158 | 5.00E-38 | 98 | 82 | 83 |
| AAR10674 | 493 | 281 | 7.00E-75 | 229 | 160 | 69 | AAR10676 | 491 | 280 | 9.00E-75 | 175 | 148 | 84 |
| AAR10674 | 493 | 147 | 1.00E-34 | 98 | 77 | 78 | AAR10676 | 491 | 152 | 4.00E-36 | 98 | 79 | 80 |
| AAR10673 | 493 | 281 | 7.00E-75 | 229 | 160 | 69 | AAR10675 | 491 | 280 | 9.00E-75 | 175 | 148 | 84 |
| AAR10673 | 493 | 152 | 4.00E-36 | 98 | 79 | 80 | AAR10675 | 491 | 152 | 4.00E-36 | 98 | 79 | 80 |
| AAR10551 | 499 | 281 | 7.00E-75 | 217 | 157 | 72 | AAR10653 | 495 | 280 | 9.00E-75 | 175 | 148 | 84 |
| AAR10551 | 499 | 155 | 6.00E-37 | 100 | 81 | 81 | AAR10653 | 495 | 157 | 1.00E-37 | 245 | 106 | 43 |
| AAR10548 | 499 | 281 | 7.00E-75 | 217 | 157 | 72 | AAR10644 | 495 | 280 | 9.00E-75 | 175 | 148 | 84 |
| AAR10548 | 499 | 155 | 6.00E-37 | 100 | 81 | 81 | AAR10644 | 495 | 152 | 4.00E-36 | 98 | 79 | 80 |
| CAA27129 | 493 | 280 | 9.00E-75 | 175 | 148 | 84 | AAR10637 | 495 | 280 | 9.00E-75 | 175 | 148 | 84 |
| CAA27129 | 493 | 154 | 1.00E-36 | 329 | 126 | 38 | AAR10637 | 495 | 152 | 4.00E-36 | 98 | 79 | 80 |
| CAA27128 | 498 | 280 | 9.00E-75 | 175 | 148 | 84 | AAR10633 | 495 | 280 | 9.00E-75 | 175 | 148 | 84 |
| CAA27128 | 498 | 157 | 9.00E-38 | 100 | 83 | 83 | AAR10633 | 495 | 152 | 4.00E-36 | 98 | 79 | 80 |
| AAR10534 | 501 | 280 | 9.00E-75 | 175 | 148 | 84 | AAR10581 | 501 | 280 | 9.00E-75 | 175 | 148 | 84 |
| AAR10534 | 501 | 155 | 4.00E-37 | 100 | 81 | 81 | AAR10581 | 501 | 152 | 4.00E-36 | 98 | 79 | 80 |
| AAR10503 | 506 | 280 | 9.00E-75 | 175 | 148 | 84 | AAR10579 | 501 | 280 | 9.00E-75 | 175 | 148 | 84 |
| AAR10503 | 506 | 154 | 7.00E-37 | 98 | 80 | 81 | AAR10579 | 501 | 154 | 7.00E-37 | 100 | 81 | 81 |
| NP_460912 | 495 | 280 | 9.00E-75 | 175 | 148 | 84 | AAR10576 | 501 | 280 | 9.00E-75 | 175 | 148 | 84 |
| NP_460912 | 495 | 152 | 4.00E-36 | 98 | 79 | 80 | AAR10576 | 501 | 154 | 7.00E-37 | 100 | 81 | 81 |
| AAT81647 | 501 | 280 | 9.00E-75 | 175 | 148 | 84 | AAR10569 | 495 | 280 | 9.00E-75 | 175 | 148 | 84 |
| AAT81647 | 501 | 154 | 7.00E-37 | 100 | 81 | 81 | AAR10569 | 495 | 156 | 2.00E-37 | 100 | 82 | 82 |
| AAT81646 | 499 | 280 | 9.00E-75 | 175 | 148 | 84 | AAR10568 | 495 | 280 | 9.00E-75 | 175 | 148 | 84 |
| AAT81646 | 499 | 155 | 4.00E-37 | 100 | 81 | 81 | AAR10568 | 495 | 156 | 2.00E-37 | 100 | 82 | 82 |
| AAT81641 | 499 | 280 | 9.00E-75 | 175 | 148 | 84 | AAR10563 | 498 | 280 | 9.00E-75 | 175 | 148 | 84 |
| AAT81641 | 499 | 154 | 9.00E-37 | 98 | 80 | 81 | AAR10563 | 498 | 155 | 6.00E-37 | 100 | 81 | 81 |
| AAT81640 | 495 | 280 | 9.00E-75 | 175 | 148 | 84 | AAR10555 | 495 | 280 | 9.00E-75 | 175 | 148 | 84 |
| AAT81640 | 495 | 152 | 4.00E-36 | 98 | 79 | 80 | AAR10555 | 495 | 155 | 6.00E-37 | 100 | 81 | 81 |
| AAT81638 | 493 | 280 | 9.00E-75 | 175 | 148 | 84 | AAR10553 | 495 | 280 | 9.00E-75 | 175 | 148 | 84 |
| AAT81638 | 493 | 152 | 4.00E-36 | 98 | 79 | 80 | AAR10553 | 495 | 155 | 4.00E-37 | 100 | 81 | 81 |
| AAT81629 | 495 | 280 | 9.00E-75 | 175 | 148 | 84 | AAR10525 | 501 | 280 | 9.00E-75 | 175 | 148 | 84 |
| AAT81629 | 495 | 156 | 2.00E-37 | 245 | 106 | 43 | AAR10525 | 501 | 155 | 6.00E-37 | 100 | 81 | 81 |
| AAT81627 | 495 | 280 | 9.00E-75 | 175 | 148 | 84 | AAR10524 | 501 | 280 | 9.00E-75 | 175 | 148 | 84 |
| AAT81627 | 495 | 152 | 4.00E-36 | 98 | 79 | 80 | AAR10524 | 501 | 155 | 6.00E-37 | 100 | 81 | 81 |
| AAT81606 | 501 | 280 | 9.00E-75 | 175 | 148 | 84 | AAR10513 | 495 | 280 | 9.00E-75 | 175 | 148 | 84 |
| AAT81606 | 501 | 154 | 7.00E-37 | 100 | 81 | 81 | AAR10513 | 495 | 155 | 6.00E-37 | 100 | 81 | 81 |
| AAT81604 | 495 | 280 | 9.00E-75 | 175 | 148 | 84 | AAK20804 | 504 | 280 | 9.00E-75 | 173 | 148 | 85 |
| AAT81604 | 495 | 156 | 2.00E-37 | 100 | 82 | 82 | AAK20804 | 504 | 149 | 4.00E-35 | 91 | 76 | 83 |
| AAT68767 | 491 | 280 | 9.00E-75 | 175 | 148 | 84 | S07276 | 494 | 280 | 9.00E-75 | 175 | 148 | 84 |
| AAT68767 | 491 | 136 | 2.00E-31 | 90 | 71 | 78 | S07276 | 494 | 157 | 9.00E-38 | 100 | 83 | 83 |
| CAA28190 | 493 | 280 | 9.00E-75 | 175 | 148 | 84 | S09637 | 489 | 280 | 9.00E-75 | 175 | 148 | 84 |
| CAA28190 | 493 | 152 | 4.00E-36 | 98 | 79 | 80 | S09637 | 489 | 154 | 1.00E-36 | 329 | 126 | 38 |
| AAO13791 | 501 | 280 | 9.00E-75 | 175 | 148 | 84 | AAF80752 | 501 | 280 | 1.00E-74 | 175 | 148 | 84 |
| AAO13791 | 501 | 154 | 1.00E-36 | 100 | 80 | 80 | AAF80752 | 501 | 154 | 7.00E-37 | 100 | 81 | 81 |
| AAL16053 | 487 | 280 | 9.00E-75 | 175 | 148 | 84 | AAR10652 | 495 | 280 | 1.00E-74 | 175 | 147 | 84 |
| AAL16053 | 487 | 129 | 4.00E-29 | 85 | 66 | 77 | AAR10652 | 495 | 152 | 4.00E-36 | 98 | 79 | 80 |
| AAR10738 | 506 | 280 | 9.00E-75 | 175 | 148 | 84 | AAR10473 | 494 | 280 | 1.00E-74 | 175 | 147 | 84 |
| AAR10738 | 506 | 155 | 6.00E-37 | 100 | 81 | 81 | AAR10473 | 494 | 153 | 2.00E-36 | 100 | 80 | 80 |
| AAR10731 | 500 | 280 | 9.00E-75 | 175 | 148 | 84 | AAR10472 | 494 | 280 | 1.00E-74 | 175 | 147 | 84 |
| AAR10731 | 500 | 152 | 4.00E-36 | 98 | 79 | 80 | AAR10472 | 494 | 152 | 3.00E-36 | 98 | 79 | 80 |
| AAR10725 | 496 | 280 | 9.00E-75 | 175 | 148 | 84 | AAB33953 | 397 | 280 | 1.00E-74 | 276 | 169 | 61 |
| AAR10725 | 496 | 155 | 4.00E-37 | 100 | 81 | 81 | P52615 | 501 | 279 | 2.00E-74 | 175 | 147 | 84 |
| AAR10723 | 496 | 280 | 9.00E-75 | 175 | 148 | 84 | P52615 | 501 | 155 | 4.00E-37 | 100 | 81 | 81 |
| AAR10723 | 496 | 153 | 2.00E-36 | 100 | 80 | 80 | AAT81645 | 496 | 279 | 3.00E-74 | 175 | 147 | 84 |
| AAR10722 | 496 | 280 | 9.00E-75 | 175 | 148 | 84 | AAT81645 | 496 | 153 | 2.00E-36 | 100 | 80 | 80 |
| AAR10722 | 496 | 152 | 3.00E-36 | 98 | 79 | 80 | AAP13304 | 456 | 279 | 3.00E-74 | 245 | 160 | 65 |
| AAR10693 | 495 | 280 | 9.00E-75 | 175 | 148 | 84 | AAP13304 | 456 | 142 | 3.00E-33 | 90 | 73 | 81 |
| AAR10693 | 495 | 154 | 7.00E-37 | 100 | 81 | 81 | AAR10732 | 500 | 279 | 3.00E-74 | 175 | 147 | 84 |
| AAR10692 | 495 | 280 | 9.00E-75 | 175 | 148 | 84 | AAR10732 | 500 | 153 | 2.00E-36 | 100 | 80 | 80 |
| AAR10692 | 495 | 152 | 4.00E-36 | 98 | 79 | 80 | AAR10685 | 499 | 279 | 3.00E-74 | 175 | 147 | 84 |
| AAR10684 | 499 | 280 | 9.00E-75 | 175 | 148 | 84 | AAR10685 | 499 | 152 | 4.00E-36 | 98 | 79 | 80 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AAR10477 | 506 | 279 | 3.00E-74 | 232 | 158 | 68 | AAD28528 | 555 | 254 | 5.00E-67 | 248 | 143 | 57 |
| AAR10477 | 506 | 155 | 4.00E-37 | 100 | 81 | 81 | AAD28528 | 555 | 129 | 3.00E-29 | 106 | 67 | 63 |
| AAR10470 | 497 | 279 | 3.00E-74 | 175 | 147 | 84 | ZP_00091764573 | 254 | 9.00E-67 | 262 | 144 | 54 |
| AAR10470 | 497 | 155 | 3.00E-37 | 273 | 112 | 41 | ZP_00091764573 | 139 | 4.00E-32 | 90 | 71 | 78 |
| YP_150203 | 495 | 278 | 3.00E-74 | 175 | 147 | 84 | AAT06391 | 468 | 253 | 2.00E-66 | 158 | 134 | 84 |
| YP_150203 | 495 | 156 | 2.00E-37 | 100 | 82 | 82 | AAT06391 | 468 | 123 | 2.00E-27 | 117 | 70 | 59 |
| AAR10582 | 501 | 278 | 3.00E-74 | 175 | 147 | 84 | AAP13314 | 461 | 251 | 6.00E-66 | 177 | 133 | 75 |
| AAR10582 | 501 | 152 | 4.00E-36 | 98 | 79 | 80 | AAP13314 | 461 | 118 | 8.00E-26 | 280 | 93 | 33 |
| AAR10556 | 495 | 278 | 3.00E-74 | 175 | 147 | 84 | AAC45643 | 303 | 250 | 1.00E-65 | 303 | 140 | 46 |
| AAR10556 | 495 | 155 | 6.00E-37 | 100 | 81 | 81 | ZP_00173465285 | 249 | 2.00E-65 | 297 | 145 | 48 |
| 1UCU | 494 | 278 | 3.00E-74 | 174 | 147 | 84 | AAT06390 | 460 | 249 | 2.00E-65 | 158 | 132 | 83 |
| 1UCU | 494 | 150 | 1.00E-35 | 98 | 78 | 79 | AAT06390 | 460 | 123 | 2.00E-27 | 189 | 82 | 43 |
| AAB33952 | 405 | 278 | 3.00E-74 | 174 | 147 | 84 | AAP13315 | 399 | 249 | 3.00E-65 | 158 | 127 | 80 |
| S16121 | 494 | 278 | 3.00E-74 | 174 | 147 | 84 | AAP13315 | 399 | 107 | 1.00E-22 | 304 | 93 | 30 |
| S16121 | 494 | 152 | 4.00E-36 | 98 | 79 | 80 | AAQ61541 | 282 | 248 | 6.00E-65 | 297 | 137 | 46 |
| AAP13301 | 461 | 278 | 6.00E-74 | 244 | 157 | 64 | AAL16054 | 455 | 248 | 6.00E-65 | 157 | 130 | 82 |
| AAP13301 | 461 | 142 | 3.00E-33 | 90 | 73 | 81 | AAL16054 | 455 | 116 | 3.00E-25 | 78 | 59 | 75 |
| AAR10649 | 495 | 278 | 6.00E-74 | 175 | 147 | 84 | ZP_00288126272 | 247 | 8.00E-65 | 296 | 145 | 48 |
| AAR10649 | 495 | 152 | 4.00E-36 | 98 | 79 | 80 | AAQ61540 | 282 | 246 | 2.00E-64 | 297 | 137 | 46 |
| A24262 | 490 | 277 | 7.00E-74 | 175 | 146 | 83 | AAC72199 | 277 | 243 | 2.00E-63 | 292 | 136 | 46 |
| A24262 | 490 | 153 | 2.00E-36 | 100 | 80 | 81 | AAF19180 | 305 | 242 | 3.00E-63 | 304 | 141 | 46 |
| AAD28524 | 556 | 276 | 2.00E-73 | 258 | 154 | 59 | AAC45642 | 305 | 239 | 3.00E-62 | 304 | 139 | 45 |
| AAD28524 | 556 | 123 | 2.00E-27 | 103 | 64 | 62 | ZP_00289013269 | 238 | 5.00E-62 | 292 | 133 | 45 |
| AAD28521 | 560 | 276 | 2.00E-73 | 258 | 154 | 59 | AAF19179 | 306 | 238 | 7.00E-62 | 305 | 142 | 46 |
| AAD28521 | 560 | 132 | 5.00E-30 | 107 | 68 | 63 | ZP_00149772273 | 236 | 1.00E-61 | 296 | 131 | 44 |
| AAN52540 | 416 | 275 | 3.00E-73 | 222 | 151 | 68 | AAC79723 | 281 | 236 | 2.00E-61 | 296 | 129 | 43 |
| AAN52540 | 416 | 143 | 2.00E-33 | 335 | 118 | 35 | ZP_00289014271 | 236 | 2.00E-61 | 296 | 133 | 44 |
| AAP13317 | 455 | 275 | 3.00E-73 | 238 | 159 | 66 | NP_718792 | 272 | 236 | 2.00E-61 | 297 | 140 | 47 |
| AAP13317 | 455 | 140 | 1.00E-32 | 90 | 72 | 80 | ZP_00274388386 | 236 | 2.00E-61 | 167 | 122 | 73 |
| AAN77106 | 449 | 275 | 5.00E-73 | 243 | 158 | 65 | ZP_00274388386 | 135 | 6.00E-31 | 92 | 68 | 73 |
| AAN77106 | 449 | 126 | 3.00E-28 | 85 | 65 | 76 | ZP_00289011271 | 235 | 3.00E-61 | 296 | 133 | 44 |
| AAP13312 | 460 | 274 | 6.00E-73 | 158 | 141 | 89 | ZP_00288132271 | 235 | 4.00E-61 | 295 | 136 | 46 |
| AAP13312 | 460 | 142 | 3.00E-33 | 90 | 73 | 81 | ZP_00288131271 | 234 | 6.00E-61 | 295 | 136 | 46 |
| AAN77105 | 454 | 274 | 6.00E-73 | 242 | 155 | 64 | ZP_00299645314 | 234 | 7.00E-61 | 296 | 137 | 46 |
| AAN77105 | 454 | 126 | 3.00E-28 | 85 | 65 | 76 | ZP_00288133271 | 233 | 1.00E-60 | 295 | 135 | 45 |
| AAP13308 | 502 | 273 | 1.00E-72 | 281 | 166 | 59 | YP_148984 | 297 | 233 | 2.00E-60 | 303 | 133 | 43 |
| AAP13308 | 502 | 144 | 1.00E-33 | 88 | 73 | 82 | NP_718793 | 273 | 233 | 2.00E-60 | 297 | 138 | 46 |
| AAD28523 | 565 | 273 | 2.00E-72 | 208 | 143 | 68 | BAD06421 | 282 | 233 | 2.00E-60 | 299 | 137 | 45 |
| AAD28523 | 565 | 117 | 2.00E-25 | 99 | 60 | 60 | AAC72198 | 278 | 232 | 3.00E-60 | 296 | 137 | 46 |
| NP_883763 | 392 | 272 | 2.00E-72 | 392 | 180 | 45 | AAL57341 | 283 | 231 | 8.00E-60 | 300 | 138 | 46 |
| AAN77109 | 455 | 272 | 2.00E-72 | 158 | 140 | 88 | ZP_00288136271 | 230 | 1.00E-59 | 296 | 132 | 44 |
| AAN77109 | 455 | 130 | 1.00E-29 | 294 | 104 | 35 | AAK14995 | 348 | 230 | 1.00E-59 | 348 | 157 | 45 |
| AAR10726 | 499 | 272 | 2.00E-72 | 197 | 149 | 75 | AAK14997 | 350 | 230 | 1.00E-59 | 350 | 154 | 44 |
| AAR10726 | 499 | 152 | 4.00E-36 | 98 | 79 | 80 | AAT86134 | 274 | 229 | 2.00E-59 | 289 | 127 | 43 |
| AAD28519 | 523 | 272 | 3.00E-72 | 251 | 156 | 62 | ZP_00211492272 | 229 | 2.00E-59 | 291 | 134 | 46 |
| AAD28519 | 523 | 128 | 7.00E-29 | 93 | 62 | 66 | AAT86133 | 274 | 229 | 2.00E-59 | 289 | 127 | 43 |
| AAN77108 | 448 | 271 | 5.00E-72 | 236 | 157 | 66 | ZP_00289022272 | 228 | 4.00E-59 | 296 | 136 | 45 |
| AAN77108 | 448 | 121 | 9.00E-27 | 85 | 62 | 72 | NP_954080 | 276 | 228 | 5.00E-59 | 298 | 133 | 44 |
| AAN77107 | 452 | 270 | 1.00E-71 | 156 | 139 | 89 | BAD06420 | 282 | 227 | 9.00E-59 | 299 | 131 | 43 |
| AAN77107 | 452 | 124 | 1.00E-27 | 84 | 64 | 76 | BAD01155 | 282 | 226 | 2.00E-58 | 299 | 131 | 43 |
| AAD28529 | 555 | 268 | 5.00E-71 | 253 | 151 | 59 | NP_791772 | 282 | 223 | 1.00E-57 | 297 | 129 | 43 |
| AAD28529 | 555 | 132 | 5.00E-30 | 107 | 68 | 63 | AAG15516 | 281 | 222 | 3.00E-57 | 291 | 129 | 44 |
| NP_879790 | 391 | 268 | 6.00E-71 | 391 | 182 | 46 | BAD06419 | 282 | 222 | 4.00E-57 | 297 | 129 | 43 |
| NP_889078 | 391 | 266 | 2.00E-70 | 391 | 183 | 46 | BAC54116 | 116 | 220 | 1.00E-56 | 116 | 116 | 100 |
| AAD28525 | 560 | 265 | 4.00E-70 | 204 | 140 | 68 | NP_622175 | 276 | 220 | 1.00E-56 | 296 | 134 | 45 |
| AAD28525 | 560 | 114 | 1.00E-24 | 97 | 58 | 59 | ZP_00302555327 | 219 | 2.00E-56 | 329 | 133 | 40 |
| AAD28518 | 550 | 265 | 4.00E-70 | 254 | 149 | 58 | NP_871067 | 421 | 219 | 2.00E-56 | 181 | 109 | 60 |
| AAD28518 | 550 | 119 | 3.00E-26 | 101 | 63 | 62 | NP_871067 | 421 | 120 | 2.00E-26 | 345 | 109 | 31 |
| AAD28526 | 508 | 265 | 5.00E-70 | 247 | 153 | 61 | AAD46086 | 291 | 219 | 2.00E-56 | 292 | 124 | 42 |
| AAD28526 | 508 | 112 | 5.00E-24 | 82 | 53 | 64 | AAG15515 | 290 | 219 | 3.00E-56 | 292 | 123 | 42 |
| AAO65441 | 466 | 263 | 1.00E-69 | 160 | 137 | 85 | ZP_00127282271 | 218 | 4.00E-56 | 283 | 128 | 45 |
| AAO65441 | 466 | 138 | 7.00E-32 | 161 | 84 | 52 | BAB58972 | 333 | 217 | 9.00E-56 | 330 | 134 | 40 |
| AAD28527 | 517 | 262 | 3.00E-69 | 245 | 152 | 60 | YP_080862 | 310 | 215 | 5.00E-55 | 313 | 135 | 43 |
| AAD28527 | 517 | 126 | 2.00E-28 | 93 | 62 | 66 | S69767 | 378 | 215 | 5.00E-55 | 307 | 147 | 47 |
| AAD28520 | 521 | 259 | 3.00E-68 | 246 | 151 | 61 | NP_244483 | 272 | 214 | 1.00E-54 | 294 | 124 | 42 |
| AAD28520 | 521 | 121 | 9.00E-27 | 90 | 58 | 64 | AAK14996 | 348 | 213 | 2.00E-54 | 273 | 137 | 50 |
| AAL30512 | 450 | 254 | 5.00E-67 | 160 | 133 | 83 | ZP_00263336255 | 213 | 2.00E-54 | 269 | 125 | 46 |
| AAL30512 | 450 | 92.4 | 4.00E-18 | 64 | 46 | 71 | AAF09167 | 290 | 211 | 5.00E-54 | 300 | 125 | 41 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AAC38199 | 384 | 211 | 9.00E-54 | 381 | 141 | 37 | ZP_00200889 | 296 | 184 | 7.00E-46 | 300 | 110 | 36 |
| ZP_00183380 | 275 | 210 | 1.00E-53 | 299 | 128 | 42 | YP_129125 | 382 | 184 | 9.00E-46 | 382 | 130 | 34 |
| NP_782313 | 275 | 209 | 2.00E-53 | 296 | 125 | 42 | Q56572 | 376 | 184 | 9.00E-46 | 375 | 128 | 34 |
| NP_693649 | 338 | 209 | 2.00E-53 | 338 | 131 | 38 | BAB16757 | 492 | 184 | 9.00E-46 | 235 | 116 | 49 |
| ZP_00289017 | 266 | 209 | 2.00E-53 | 285 | 125 | 43 | BAB16757 | 492 | 114 | 1.00E-24 | 251 | 80 | 31 |
| ZP_00289012 | 373 | 209 | 3.00E-53 | 282 | 117 | 41 | BAB58979 | 251 | 184 | 9.00E-46 | 270 | 111 | 41 |
| AAD12054 | 383 | 209 | 3.00E-53 | 380 | 141 | 37 | AAC65757 | 286 | 183 | 2.00E-45 | 298 | 114 | 38 |
| NP_391416 | 304 | 208 | 6.00E-53 | 306 | 130 | 42 | AAC27808 | 377 | 183 | 2.00E-45 | 376 | 125 | 33 |
| BAB87734 | 270 | 207 | 7.00E-53 | 294 | 123 | 41 | AAQ96738 | 228 | 182 | 3.00E-45 | 251 | 102 | 40 |
| NP_801058 | 284 | 207 | 9.00E-53 | 301 | 119 | 39 | NP_348182 | 278 | 182 | 3.00E-45 | 292 | 115 | 39 |
| AAD19738 | 279 | 207 | 9.00E-53 | 299 | 120 | 40 | YP_010660 | 298 | 182 | 3.00E-45 | 311 | 119 | 38 |
| NP_348820 | 275 | 207 | 1.00E-52 | 295 | 122 | 41 | BAC98369 | 384 | 182 | 3.00E-45 | 381 | 132 | 34 |
| YP_162364 | 284 | 206 | 2.00E-52 | 296 | 119 | 40 | AAF95287 | 376 | 182 | 4.00E-45 | 375 | 133 | 35 |
| AAB07350 | 284 | 206 | 3.00E-52 | 301 | 119 | 39 | CAG25467 | 277 | 182 | 4.00E-45 | 292 | 107 | 36 |
| NP_798640 | 377 | 202 | 2.00E-51 | 376 | 132 | 35 | CAA45382 | 285 | 181 | 6.00E-45 | 301 | 112 | 37 |
| ZP_00313276 | 273 | 201 | 9.00E-51 | 295 | 120 | 40 | ZP_00130180 | 299 | 181 | 6.00E-45 | 295 | 107 | 36 |
| ZP_00236467 | 307 | 200 | 1.00E-50 | 309 | 119 | 38 | BAB16756 | 492 | 181 | 6.00E-45 | 236 | 111 | 47 |
| BAB87735 | 263 | 199 | 2.00E-50 | 287 | 118 | 41 | BAB16756 | 492 | 115 | 5.00E-25 | 284 | 83 | 29 |
| NP_967402 | 282 | 199 | 3.00E-50 | 295 | 124 | 42 | AAC65834 | 286 | 181 | 9.00E-45 | 304 | 107 | 35 |
| NP_967404 | 277 | 196 | 3.00E-49 | 292 | 120 | 41 | AAQ96739 | 228 | 181 | 9.00E-45 | 251 | 105 | 41 |
| NP_642301 | 399 | 196 | 3.00E-49 | 212 | 113 | 53 | AAC65835 | 285 | 181 | 9.00E-45 | 301 | 111 | 36 |
| NP_642301 | 399 | 103 | 1.00E-21 | 307 | 87 | 28 | P21989 | 286 | 180 | 1.00E-44 | 304 | 113 | 37 |
| ZP_00236470 | 278 | 196 | 3.00E-49 | 293 | 117 | 39 | AAQ96740 | 228 | 180 | 1.00E-44 | 251 | 105 | 41 |
| ZP_00236469 | 286 | 195 | 4.00E-49 | 292 | 118 | 40 | AAP08636 | 273 | 180 | 2.00E-44 | 298 | 115 | 38 |
| ZP_00244371 | 402 | 195 | 5.00E-49 | 400 | 144 | 36 | BAC98370 | 384 | 180 | 2.00E-44 | 381 | 131 | 34 |
| BAB58986 | 306 | 195 | 5.00E-49 | 302 | 118 | 39 | CAG25466 | 280 | 180 | 2.00E-44 | 296 | 107 | 36 |
| AAC31966 | 383 | 194 | 6.00E-49 | 380 | 136 | 35 | AAA68044 | 290 | 179 | 2.00E-44 | 304 | 116 | 38 |
| AAD24680 | 382 | 194 | 8.00E-49 | 379 | 136 | 35 | JC6021 | 379 | 179 | 2.00E-44 | 379 | 129 | 34 |
| AAD24678 | 382 | 194 | 8.00E-49 | 379 | 136 | 35 | YP_123618 | 475 | 179 | 2.00E-44 | 309 | 124 | 40 |
| CAG38109 | 277 | 194 | 8.00E-49 | 291 | 119 | 40 | YP_123618 | 475 | 110 | 1.00E-23 | 200 | 77 | 38 |
| ZP_00313275 | 272 | 193 | 1.00E-48 | 292 | 118 | 40 | BAC98368 | 384 | 179 | 2.00E-44 | 381 | 131 | 34 |
| ZP_00335280 | 609 | 193 | 1.00E-48 | 290 | 120 | 41 | S24986 | 280 | 179 | 3.00E-44 | 296 | 107 | 36 |
| ZP_00335280 | 609 | 114 | 1.00E-24 | 159 | 67 | 42 | YP_035879 | 367 | 179 | 3.00E-44 | 365 | 125 | 34 |
| NP_637306 | 399 | 193 | 1.00E-48 | 241 | 119 | 49 | AAN86121 | 328 | 179 | 4.00E-44 | 335 | 120 | 35 |
| NP_637306 | 399 | 104 | 1.00E-21 | 319 | 93 | 29 | AAK20919 | 279 | 179 | 4.00E-44 | 296 | 109 | 36 |
| ZP_00244372 | 404 | 193 | 1.00E-48 | 404 | 150 | 37 | AAK57644 | 281 | 179 | 4.00E-44 | 301 | 109 | 36 |
| AAS91569 | 379 | 193 | 1.00E-48 | 379 | 140 | 36 | YP_095369 | 475 | 178 | 5.00E-44 | 309 | 125 | 40 |
| BAB58978 | 306 | 193 | 1.00E-48 | 302 | 117 | 38 | YP_095369 | 475 | 109 | 3.00E-23 | 198 | 78 | 39 |
| BAB87737 | 265 | 192 | 2.00E-48 | 287 | 119 | 41 | CAD42896 | 475 | 178 | 5.00E-44 | 309 | 123 | 39 |
| YP_065397 | 1128 | 192 | 3.00E-48 | 252 | 120 | 47 | CAD42896 | 475 | 109 | 3.00E-23 | 198 | 78 | 39 |
| YP_065397 | 1128 | 107 | 2.00E-22 | 254 | 79 | 31 | BAA82629 | 336 | 178 | 5.00E-44 | 342 | 116 | 33 |
| YP_001491 | 285 | 192 | 4.00E-48 | 302 | 112 | 37 | YP_001839 | 281 | 177 | 1.00E-43 | 300 | 107 | 35 |
| NP_712598 | 285 | 192 | 4.00E-48 | 302 | 112 | 37 | NP_971613 | 286 | 177 | 1.00E-43 | 304 | 109 | 35 |
| BAB58984 | 308 | 191 | 5.00E-48 | 304 | 119 | 39 | BAA82633 | 336 | 177 | 1.00E-43 | 342 | 115 | 33 |
| BAB58980 | 308 | 191 | 7.00E-48 | 304 | 119 | 39 | AAQ60166 | 285 | 177 | 1.00E-43 | 299 | 104 | 34 |
| B32010 | 293 | 190 | 2.00E-47 | 304 | 121 | 39 | YP_066429 | 857 | 177 | 1.00E-43 | 231 | 108 | 46 |
| BAB58983 | 308 | 190 | 2.00E-47 | 304 | 119 | 39 | YP_066429 | 857 | 115 | 5.00E-25 | 227 | 81 | 35 |
| AAF95333 | 379 | 189 | 2.00E-47 | 375 | 130 | 34 | YP_011656 | 297 | 177 | 1.00E-43 | 310 | 113 | 36 |
| YP_109915 | 388 | 189 | 2.00E-47 | 385 | 136 | 35 | CAA49317 | 336 | 177 | 1.00E-43 | 342 | 114 | 33 |
| AAP08635 | 272 | 189 | 3.00E-47 | 296 | 114 | 38 | YP_126643 | 475 | 176 | 2.00E-43 | 309 | 122 | 39 |
| AAD27808 | 387 | 189 | 3.00E-47 | 384 | 136 | 35 | YP_126643 | 475 | 110 | 2.00E-23 | 251 | 88 | 35 |
| 1I01 | 398 | 189 | 3.00E-47 | 122 | 98 | 80 | YP_001490 | 282 | 176 | 2.00E-43 | 300 | 107 | 35 |
| 1I01 | 398 | 72.4 | 5.00E-12 | 54 | 36 | 66 | CAD43143 | 475 | 176 | 2.00E-43 | 309 | 122 | 39 |
| AAC71051 | 388 | 189 | 3.00E-47 | 385 | 134 | 34 | CAD43143 | 475 | 110 | 2.00E-23 | 251 | 88 | 35 |
| YP_076801 | 275 | 189 | 3.00E-47 | 296 | 114 | 38 | CAD42899 | 327 | 176 | 2.00E-43 | 309 | 122 | 39 |
| NP_967579 | 277 | 188 | 5.00E-47 | 301 | 117 | 38 | CAD42894 | 361 | 176 | 2.00E-43 | 309 | 122 | 39 |
| AAD24677 | 387 | 188 | 5.00E-47 | 384 | 136 | 35 | CAA58234 | 475 | 176 | 2.00E-43 | 309 | 122 | 39 |
| YP_027849 | 287 | 188 | 6.00E-47 | 292 | 112 | 38 | CAA58234 | 475 | 109 | 3.00E-23 | 251 | 87 | 34 |
| CAB67250 | 285 | 187 | 8.00E-47 | 300 | 111 | 37 | CAD42900 | 489 | 176 | 2.00E-43 | 309 | 122 | 39 |
| AAD24679 | 387 | 187 | 8.00E-47 | 384 | 135 | 35 | CAD42900 | 489 | 110 | 2.00E-23 | 251 | 88 | 35 |
| AAC01552 | 379 | 187 | 8.00E-47 | 375 | 129 | 34 | BAA82630 | 336 | 176 | 2.00E-43 | 342 | 115 | 33 |
| NP_972081 | 285 | 187 | 1.00E-46 | 300 | 113 | 37 | NP_970090 | 277 | 176 | 2.00E-43 | 295 | 110 | 37 |
| ZP_00236468 | 284 | 187 | 1.00E-46 | 295 | 111 | 37 | AAF95289 | 378 | 176 | 2.00E-43 | 377 | 134 | 35 |
| BAC98371 | 384 | 187 | 1.00E-46 | 382 | 131 | 34 | AAC01555 | 378 | 176 | 2.00E-43 | 377 | 134 | 35 |
| ZP_00288129 | 272 | 186 | 2.00E-46 | 296 | 112 | 37 | AAU07005 | 336 | 176 | 3.00E-43 | 342 | 113 | 33 |
| NP_967577 | 274 | 186 | 3.00E-46 | 292 | 115 | 39 | NP_212281 | 336 | 176 | 3.00E-43 | 342 | 113 | 33 |
| CAA47619 | 276 | 185 | 5.00E-46 | 292 | 107 | 36 | NP_712599 | 282 | 176 | 3.00E-43 | 300 | 107 | 35 |
| BAB58982 | 249 | 185 | 5.00E-46 | 269 | 114 | 42 | CAA49307 | 336 | 176 | 3.00E-43 | 342 | 114 | 33 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| BAB58981 | 280 | 176 | 3.00E-43 | 285 | 113 | 39 | AAA99807 | 488 | 168 | 5.00E-41 | 242 | 104 | 42 |
| CAA53013 | 336 | 175 | 4.00E-43 | 342 | 114 | 33 | AAA99807 | 488 | 113 | 2.00E-24 | 335 | 100 | 29 |
| BAA07832 | 334 | 175 | 4.00E-43 | 337 | 115 | 34 | AAR00324 | 336 | 168 | 6.00E-41 | 342 | 110 | 32 |
| CAA33695 | 336 | 175 | 4.00E-43 | 342 | 113 | 33 | BAA11604 | 329 | 168 | 6.00E-41 | 335 | 108 | 32 |
| CAA37884 | 334 | 175 | 4.00E-43 | 340 | 116 | 34 | AAQ60680 | 372 | 167 | 8.00E-41 | 369 | 122 | 33 |
| NP_521943 | 273 | 175 | 4.00E-43 | 297 | 109 | 36 | BAA11603 | 329 | 167 | 8.00E-41 | 335 | 108 | 32 |
| AAF95332 | 377 | 175 | 4.00E-43 | 377 | 129 | 34 | BAA11597 | 329 | 167 | 8.00E-41 | 335 | 109 | 32 |
| CAA59172 | 474 | 175 | 4.00E-43 | 228 | 105 | 46 | BAA82631 | 329 | 167 | 8.00E-41 | 335 | 109 | 32 |
| CAA59172 | 474 | 107 | 1.00E-22 | 214 | 79 | 36 | BAA11611 | 327 | 167 | 1.00E-40 | 333 | 109 | 32 |
| AAB37005 | 336 | 175 | 4.00E-43 | 342 | 113 | 33 | NP_249783 | 488 | 167 | 1.00E-40 | 242 | 103 | 42 |
| CAA49316 | 336 | 175 | 5.00E-43 | 342 | 113 | 33 | NP_249783 | 488 | 113 | 2.00E-24 | 335 | 100 | 29 |
| AAF87586 | 273 | 175 | 5.00E-43 | 300 | 111 | 37 | P21184 | 394 | 167 | 1.00E-40 | 271 | 105 | 38 |
| AAG34566 | 280 | 175 | 5.00E-43 | 294 | 107 | 36 | ZP_00138680 | 488 | 167 | 1.00E-40 | 242 | 103 | 42 |
| CAA53012 | 334 | 174 | 7.00E-43 | 333 | 113 | 33 | ZP_00138680 | 488 | 113 | 2.00E-24 | 335 | 100 | 29 |
| CAD42893 | 493 | 174 | 7.00E-43 | 310 | 122 | 39 | ZP_00130923 | 288 | 167 | 1.00E-40 | 284 | 103 | 36 |
| CAD42893 | 493 | 99.8 | 3.00E-20 | 191 | 72 | 37 | AAC63946 | 390 | 167 | 1.00E-40 | 271 | 105 | 38 |
| CAA49308 | 336 | 174 | 7.00E-43 | 342 | 113 | 33 | AAP33170 | 394 | 167 | 1.00E-40 | 271 | 105 | 38 |
| AAS91572 | 375 | 174 | 7.00E-43 | 370 | 126 | 34 | BAA11607 | 329 | 167 | 1.00E-40 | 335 | 108 | 32 |
| AAS91571 | 400 | 174 | 7.00E-43 | 377 | 126 | 33 | AAC27800 | 378 | 167 | 1.00E-40 | 377 | 126 | 33 |
| CAA53014 | 336 | 174 | 9.00E-43 | 342 | 113 | 33 | NP_798637 | 376 | 167 | 1.00E-40 | 377 | 125 | 33 |
| AAK01040 | 282 | 174 | 9.00E-43 | 300 | 107 | 35 | NP_798638 | 378 | 167 | 1.00E-40 | 377 | 126 | 33 |
| CAB67249 | 286 | 174 | 1.00E-42 | 304 | 103 | 33 | AAC63950 | 478 | 167 | 1.00E-40 | 225 | 101 | 44 |
| CAA49322 | 336 | 174 | 1.00E-42 | 342 | 112 | 32 | AAC63950 | 478 | 111 | 7.00E-24 | 278 | 83 | 29 |
| CAA49318 | 336 | 174 | 1.00E-42 | 342 | 113 | 33 | BAA09687 | 329 | 167 | 1.00E-40 | 335 | 107 | 31 |
| BAA82635 | 323 | 174 | 1.00E-42 | 329 | 114 | 34 | BAA09681 | 329 | 167 | 1.00E-40 | 335 | 108 | 32 |
| CAA34735 | 336 | 173 | 2.00E-42 | 342 | 112 | 32 | BAA11600 | 329 | 167 | 1.00E-40 | 335 | 107 | 31 |
| YP_013330 | 287 | 173 | 2.00E-42 | 296 | 107 | 36 | BAA82636 | 324 | 167 | 1.00E-40 | 323 | 109 | 33 |
| CAA45011 | 336 | 173 | 2.00E-42 | 342 | 113 | 33 | BAA09689 | 329 | 166 | 2.00E-40 | 335 | 107 | 31 |
| NP_470041 | 287 | 173 | 2.00E-42 | 296 | 107 | 36 | BAA09688 | 329 | 166 | 2.00E-40 | 335 | 107 | 31 |
| NP_464217 | 287 | 173 | 2.00E-42 | 296 | 107 | 36 | BAA09686 | 329 | 166 | 2.00E-40 | 335 | 107 | 31 |
| NP_797167 | 384 | 173 | 2.00E-42 | 384 | 125 | 32 | BAA09684 | 329 | 166 | 2.00E-40 | 335 | 107 | 31 |
| AAO10326 | 376 | 173 | 2.00E-42 | 375 | 121 | 32 | BAA09678 | 329 | 166 | 2.00E-40 | 335 | 107 | 31 |
| AAU95795 | 287 | 173 | 2.00E-42 | 296 | 107 | 36 | BAA11610 | 327 | 166 | 2.00E-40 | 333 | 110 | 33 |
| CAA49321 | 336 | 173 | 2.00E-42 | 342 | 113 | 33 | A37853 | 394 | 166 | 3.00E-40 | 271 | 105 | 38 |
| AAP33175 | 387 | 173 | 2.00E-42 | 314 | 118 | 37 | A37853 | 394 | 107 | 2.00E-22 | 197 | 73 | 37 |
| AAP33175 | 387 | 122 | 5.00E-27 | 182 | 73 | 40 | AAD10272 | 378 | 165 | 5.00E-40 | 377 | 125 | 33 |
| BAA82634 | 319 | 173 | 2.00E-42 | 323 | 113 | 34 | AAG29830 | 327 | 165 | 5.00E-40 | 333 | 108 | 32 |
| AAK57645 | 286 | 172 | 3.00E-42 | 301 | 109 | 36 | AAP08637 | 249 | 165 | 5.00E-40 | 271 | 98 | 36 |
| NP_969824 | 277 | 172 | 3.00E-42 | 295 | 109 | 36 | AAB03518 | 335 | 165 | 5.00E-40 | 334 | 111 | 33 |
| YP_061686 | 277 | 172 | 3.00E-42 | 299 | 105 | 35 | ZP_00317212 | 580 | 164 | 7.00E-40 | 222 | 101 | 45 |
| CAD42895 | 491 | 172 | 3.00E-42 | 166 | 92 | 55 | ZP_00317212 | 580 | 99.4 | 4.00E-20 | 182 | 66 | 36 |
| CAD42895 | 491 | 109 | 3.00E-23 | 198 | 78 | 39 | AAA62843 | 688 | 164 | 9.00E-40 | 252 | 103 | 40 |
| NP_972083 | 286 | 172 | 4.00E-42 | 304 | 106 | 34 | AAA62843 | 688 | 95.9 | 4.00E-19 | 92 | 46 | 50 |
| YP_159591 | 306 | 171 | 6.00E-42 | 151 | 89 | 58 | NP_746492 | 687 | 164 | 9.00E-40 | 252 | 103 | 40 |
| BAB58985 | 280 | 171 | 6.00E-42 | 280 | 110 | 39 | NP_746492 | 687 | 96.3 | 3.00E-19 | 129 | 53 | 41 |
| AAR16426 | 329 | 171 | 7.00E-42 | 314 | 117 | 37 | BAA33017 | 316 | 164 | 1.00E-39 | 323 | 108 | 33 |
| AAO10324 | 377 | 171 | 7.00E-42 | 376 | 123 | 32 | ZP_00100062 | 385 | 163 | 2.00E-39 | 385 | 128 | 33 |
| ZP_00346385 | 295 | 171 | 7.00E-42 | 292 | 98 | 33 | AAC99335 | 283 | 163 | 2.00E-39 | 301 | 100 | 33 |
| AAC28557 | 387 | 171 | 7.00E-42 | 314 | 117 | 37 | ZP_00317210 | 587 | 162 | 5.00E-39 | 254 | 105 | 41 |
| BAA11613 | 326 | 171 | 7.00E-42 | 325 | 109 | 33 | ZP_00317210 | 587 | 95.9 | 4.00E-19 | 129 | 55 | 42 |
| BAA28607 | 320 | 171 | 7.00E-42 | 323 | 111 | 34 | NP_712200 | 283 | 162 | 5.00E-39 | 301 | 100 | 33 |
| NP_348785 | 283 | 171 | 1.00E-41 | 290 | 104 | 35 | CAD65866 | 268 | 162 | 5.00E-39 | 103 | 84 | 81 |
| AAU95794 | 287 | 171 | 1.00E-41 | 296 | 106 | 35 | YP_001838 | 283 | 161 | 6.00E-39 | 301 | 99 | 32 |
| AAP33174 | 387 | 171 | 1.00E-41 | 314 | 117 | 37 | AAC99336 | 283 | 161 | 8.00E-39 | 301 | 99 | 32 |
| AAP33174 | 387 | 122 | 5.00E-27 | 182 | 73 | 40 | AAC63947 | 393 | 160 | 1.00E-38 | 300 | 108 | 36 |
| AAC01556 | 377 | 171 | 1.00E-41 | 379 | 127 | 33 | NP_770335 | 274 | 160 | 1.00E-38 | 295 | 95 | 32 |
| BAA28606 | 323 | 171 | 1.00E-41 | 323 | 111 | 34 | AAB94024 | 283 | 160 | 2.00E-38 | 301 | 98 | 32 |
| NP_782278 | 280 | 170 | 1.00E-41 | 294 | 105 | 35 | AAC63948 | 486 | 160 | 2.00E-38 | 232 | 99 | 42 |
| ZP_00279040 | 381 | 170 | 1.00E-41 | 378 | 127 | 33 | AAC63948 | 486 | 100 | 1.00E-20 | 346 | 89 | 25 |
| CAA53011 | 336 | 170 | 1.00E-41 | 342 | 111 | 32 | CAA45081 | 285 | 159 | 2.00E-38 | 304 | 108 | 35 |
| BAA11602 | 329 | 170 | 1.00E-41 | 335 | 111 | 33 | BAA23224 | 328 | 159 | 3.00E-38 | 327 | 106 | 32 |
| AAF95288 | 377 | 169 | 2.00E-41 | 379 | 127 | 33 | CAC36206 | 274 | 159 | 3.00E-38 | 273 | 94 | 34 |
| YP_011295 | 297 | 169 | 2.00E-41 | 295 | 101 | 34 | BAB13814 | 413 | 159 | 3.00E-38 | 256 | 101 | 39 |
| BAA11605 | 329 | 169 | 2.00E-41 | 335 | 110 | 32 | BAB13814 | 413 | 89.7 | 3.00E-17 | 173 | 60 | 34 |
| CAA53015 | 335 | 169 | 3.00E-41 | 334 | 112 | 33 | BAA11608 | 328 | 159 | 3.00E-38 | 327 | 106 | 32 |
| CAD42897 | 476 | 169 | 3.00E-41 | 314 | 122 | 38 | AAC63949 | 669 | 159 | 4.00E-38 | 260 | 105 | 40 |
| CAD42897 | 476 | 109 | 3.00E-23 | 198 | 78 | 39 | AAC63949 | 669 | 108 | 5.00E-23 | 273 | 74 | 27 |
| AAC28556 | 387 | 169 | 4.00E-41 | 300 | 114 | 38 | AAR08139 | 235 | 158 | 5.00E-38 | 217 | 92 | 42 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| CAC36204 | 274 | 158 | 5.00E-38 | 273 | 95 | 34 | YP_035878 | 266 | 142 | 5.00E-33 | 292 | 97 | 33 |
| AAC99334 | 283 | 158 | 5.00E-38 | 301 | 98 | 32 | BAA12719 | 292 | 142 | 5.00E-33 | 291 | 92 | 31 |
| AAU93692 | 286 | 158 | 7.00E-38 | 304 | 106 | 34 | BAA20904 | 289 | 142 | 5.00E-33 | 291 | 92 | 31 |
| BAA82632 | 311 | 158 | 7.00E-38 | 313 | 103 | 32 | BAA19430 | 292 | 142 | 5.00E-33 | 291 | 92 | 31 |
| ZP_00218989614 | | 156 | 2.00E-37 | 242 | 97 | 40 | AAO08752 | 374 | 141 | 6.00E-33 | 167 | 76 | 45 |
| ZP_00218989614 | | 90.1 | 2.00E-17 | 86 | 46 | 53 | AAO08752 | 374 | 102 | 6.00E-21 | 301 | 92 | 30 |
| BAB87728 | 413 | 156 | 2.00E-37 | 278 | 102 | 36 | NP_782289 | 268 | 141 | 6.00E-33 | 266 | 79 | 29 |
| BAB87728 | 413 | 85.1 | 7.00E-16 | 108 | 45 | 41 | BAD12778 | 248 | 141 | 6E-33 | 267 | 88 | 32 |
| CAC36205 | 274 | 156 | 2.00E-37 | 273 | 93 | 34 | BAA20481 | 292 | 141 | 6.00E-33 | 291 | 92 | 31 |
| AAC38200 | 504 | 156 | 2.00E-37 | 246 | 97 | 39 | BAA20479 | 292 | 141 | 6.00E-33 | 291 | 92 | 31 |
| AAC38200 | 504 | 92 | 6.00E-18 | 87 | 46 | 52 | BAA20477 | 292 | 141 | 6.00E-33 | 291 | 92 | 31 |
| BAB87730 | 375 | 155 | 3.00E-37 | 374 | 115 | 30 | BAA13582 | 292 | 141 | 6.00E-33 | 291 | 92 | 31 |
| AAB09433 | 377 | 155 | 6.00E-37 | 182 | 80 | 43 | BAA19444 | 292 | 141 | 6.00E-33 | 291 | 92 | 31 |
| ZP_00270146298 | | 154 | 1.00E-36 | 305 | 107 | 35 | BAA19443 | 292 | 141 | 6.00E-33 | 291 | 92 | 31 |
| NP_935285 | 396 | 153 | 2.00E-36 | 376 | 118 | 31 | BAA19439 | 292 | 141 | 6.00E-33 | 291 | 92 | 31 |
| AAS91570 | 377 | 153 | 2.00E-36 | 218 | 89 | 40 | BAA89303 | 248 | 141 | 6.00E-33 | 267 | 87 | 32 |
| CAC36223 | 271 | 152 | 3.00E-36 | 268 | 91 | 33 | BAA89302 | 248 | 141 | 6.00E-33 | 267 | 88 | 32 |
| NP_945993 | 274 | 152 | 4.00E-36 | 295 | 92 | 31 | BAA77944 | 248 | 141 | 6.00E-33 | 267 | 87 | 32 |
| AAO08751 | 377 | 151 | 6.00E-36 | 376 | 120 | 31 | BAC16349 | 248 | 141 | 8.00E-33 | 267 | 87 | 32 |
| BAB87729 | 384 | 151 | 6.00E-36 | 169 | 82 | 48 | BAA77321 | 208 | 141 | 8.00E-33 | 214 | 87 | 40 |
| AAO61408 | 241 | 151 | 8.00E-36 | 263 | 96 | 36 | AAO61414 | 241 | 140 | 1.00E-32 | 267 | 92 | 34 |
| AAO10325 | 377 | 151 | 8.00E-36 | 376 | 119 | 31 | ZP_00004597493 | | 140 | 1.00E-32 | 166 | 74 | 44 |
| YP_128298 | 426 | 151 | 8.00E-36 | 251 | 106 | 42 | ZP_00004597493 | | 97.1 | 2.00E-19 | 176 | 63 | 35 |
| YP_128298 | 426 | 89.4 | 4.00E-17 | 149 | 55 | 36 | YP_083129 | 266 | 140 | 1.00E-32 | 292 | 95 | 32 |
| BAB87732 | 377 | 151 | 8.00E-36 | 169 | 82 | 48 | CAA75001 | 493 | 140 | 1.00E-32 | 166 | 74 | 44 |
| BAB87732 | 377 | 79.7 | 3.00E-14 | 291 | 83 | 28 | CAA75001 | 493 | 97.1 | 2.00E-19 | 176 | 63 | 35 |
| AAB09434 | 377 | 150 | 1.00E-35 | 376 | 119 | 31 | AAG21990 | 170 | 140 | 1.00E-32 | 166 | 74 | 44 |
| AAB03521 | 334 | 150 | 1.00E-35 | 335 | 102 | 30 | BAA20478 | 292 | 140 | 1.00E-32 | 291 | 92 | 31 |
| AAC38201 | 540 | 150 | 2.00E-35 | 266 | 100 | 37 | AAP08634 | 266 | 140 | 1.00E-32 | 291 | 95 | 32 |
| AAC38201 | 540 | 51.2 | 1.00E-05 | 147 | 43 | 29 | BAD13295 | 248 | 140 | 1.00E-32 | 267 | 87 | 32 |
| ZP_00329901380 | | 149 | 2.00E-35 | 382 | 125 | 32 | AAO61411 | 241 | 140 | 2.00E-32 | 267 | 92 | 34 |
| NP_935286 | 377 | 149 | 2.00E-35 | 376 | 112 | 29 | NP_228567 | 387 | 140 | 2.00E-32 | 392 | 119 | 30 |
| Q56574 | 377 | 149 | 2.00E-35 | 376 | 116 | 30 | AAK31137 | 257 | 140 | 2.00E-32 | 273 | 87 | 31 |
| AAO61409 | 241 | 149 | 3.00E-35 | 263 | 95 | 36 | BAA89304 | 248 | 140 | 2.00E-32 | 267 | 87 | 32 |
| NP_933764 | 385 | 149 | 4.00E-35 | 178 | 80 | 44 | BAA77325 | 200 | 139 | 3.00E-32 | 218 | 89 | 40 |
| NP_933764 | 385 | 102 | 6.00E-21 | 301 | 92 | 30 | AAQ96735 | 620 | 139 | 4.00E-32 | 258 | 96 | 37 |
| CAC36218 | 220 | 149 | 4.00E-35 | 238 | 90 | 37 | AAQ96735 | 620 | 63.2 | 3.00E-09 | 64 | 31 | 48 |
| BAA15744 | 340 | 149 | 4.00E-35 | 151 | 80 | 52 | AAO61415 | 240 | 139 | 4.00E-32 | 266 | 91 | 34 |
| BAA77322 | 201 | 149 | 4.00E-35 | 214 | 90 | 42 | CAC36207 | 234 | 139 | 4.00E-32 | 248 | 85 | 34 |
| YP_155525 | 471 | 148 | 5.00E-35 | 170 | 82 | 48 | ZP_00236466266 | | 138 | 5.00E-32 | 292 | 96 | 32 |
| YP_155525 | 471 | 99.4 | 4.00E-20 | 267 | 77 | 28 | BAB87738 | 554 | 138 | 7.00E-32 | 136 | 71 | 52 |
| AAD10271 | 384 | 147 | 9.00E-35 | 188 | 78 | 41 | BAB87738 | 554 | 99.8 | 3.00E-20 | 291 | 82 | 28 |
| CAC36221 | 222 | 147 | 1.00E-34 | 237 | 85 | 35 | YP_083130 | 460 | 137 | 9.00E-32 | 289 | 96 | 33 |
| AAO61406 | 241 | 147 | 2.00E-34 | 267 | 96 | 35 | YP_083130 | 460 | 80.9 | 1.00E-14 | 111 | 46 | 41 |
| CAC36220 | 222 | 147 | 2.00E-34 | 237 | 84 | 35 | NP_348261 | 269 | 137 | 1.00E-31 | 292 | 89 | 30 |
| ZP_00273972629 | | 146 | 3.00E-34 | 199 | 85 | 42 | AAO61412 | 240 | 135 | 3.00E-31 | 266 | 90 | 33 |
| ZP_00273972629 | | 104 | 9.00E-22 | 92 | 57 | 61 | AAQ96736 | 470 | 134 | 8.00E-31 | 233 | 86 | 36 |
| YP_129126 | 393 | 145 | 4.00E-34 | 213 | 82 | 38 | AAQ96736 | 470 | 65.1 | 8.00E-10 | 264 | 68 | 25 |
| YP_129126 | 393 | 90.5 | 2.00E-17 | 203 | 63 | 31 | BAA89305 | 248 | 134 | 1.00E-30 | 268 | 84 | 31 |
| NP_978099 | 266 | 145 | 4.00E-34 | 292 | 96 | 32 | CAC36202 | 234 | 132 | 5E-30 | 248 | 83 | 33 |
| AAO61410 | 241 | 145 | 6.00E-34 | 263 | 91 | 34 | AAT06255 | 459 | 132 | 5.00E-30 | 139 | 70 | 50 |
| AAB03520 | 334 | 145 | 6.00E-34 | 330 | 102 | 30 | AAT06255 | 459 | 87.4 | 1E-16 | 159 | 57 | 35 |
| BAA77320 | 202 | 145 | 6.00E-34 | 217 | 91 | 41 | YP_050963 | 484 | 131 | 7.00E-30 | 126 | 71 | 56 |
| AAO61407 | 241 | 144 | 8.00E-34 | 264 | 93 | 35 | YP_050963 | 484 | 88.6 | 6.00E-17 | 152 | 63 | 41 |
| CAB44444 | 377 | 144 | 8.00E-34 | 377 | 112 | 29 | AAB82610 | 472 | 131 | 7.00E-30 | 265 | 93 | 35 |
| CAA67103 | 333 | 144 | 1.00E-33 | 333 | 108 | 32 | AAB82610 | 472 | 98.2 | 8.00E-20 | 153 | 63 | 41 |
| CAC36219 | 220 | 144 | 1.00E-33 | 238 | 89 | 37 | CAC36217 | 223 | 131 | 9.00E-30 | 241 | 78 | 32 |
| AAQ96734 | 626 | 143 | 2.00E-33 | 263 | 99 | 37 | AAA62844 | 479 | 130 | 1.00E-29 | 132 | 69 | 52 |
| AAQ96734 | 626 | 70.9 | 1.00E-11 | 68 | 35 | 51 | AAA62844 | 479 | 97.4 | 1.00E-19 | 280 | 77 | 27 |
| BAA12718 | 292 | 143 | 2.00E-33 | 291 | 94 | 32 | BAA77323 | 200 | 130 | 1.00E-29 | 216 | 85 | 39 |
| AAO61404 | 241 | 143 | 2.00E-33 | 264 | 92 | 34 | NP_242343 | 464 | 130 | 2.00E-29 | 135 | 70 | 51 |
| AAO61405 | 241 | 142 | 3.00E-33 | 264 | 89 | 33 | NP_242343 | 464 | 95.9 | 4.00E-19 | 169 | 57 | 33 |
| BAA12102 | 292 | 142 | 3.00E-33 | 291 | 94 | 32 | CAC36201 | 223 | 129 | 4.00E-29 | 241 | 79 | 32 |
| BAA13584 | 292 | 142 | 3.00E-33 | 291 | 93 | 31 | AAT06254 | 493 | 129 | 4.00E-29 | 140 | 68 | 48 |
| YP_148995 | 604 | 142 | 4.00E-33 | 269 | 95 | 32 | AAT06254 | 493 | 94 | 2.00E-18 | 195 | 67 | 34 |
| YP_148995 | 604 | 103 | 3.00E-21 | 179 | 62 | 34 | AAB82613 | 508 | 128 | 7.00E-29 | 150 | 68 | 45 |
| CAC36224 | 222 | 142 | 4.00E-33 | 237 | 86 | 36 | AAB82613 | 508 | 86.7 | 2.00E-16 | 158 | 58 | 36 |
| ZP_00287990272 | | 142 | 5.00E-33 | 280 | 85 | 30 | NP_978100 | 465 | 126 | 2.00E-28 | 221 | 77 | 34 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| NP_978100 | 465 | 75.1 | 7.00E-13 | 84 | 41 | 48 | BAA77299 | 398 | 55.8 | 5.00E-07 | 130 | 43 | 33 |
| AAL26808 | 229 | 126 | 2.00E-28 | 248 | 79 | 31 | CAA67104 | 340 | 112 | 3.00E-24 | 225 | 76 | 33 |
| AAQ96737 | 430 | 124 | 1.00E-27 | 165 | 67 | 40 | CAA67104 | 340 | 107 | 1.00E-22 | 187 | 70 | 37 |
| AAQ96737 | 430 | 60.1 | 2.00E-08 | 92 | 33 | 35 | CAA67101 | 434 | 112 | 5.00E-24 | 196 | 75 | 38 |
| CAB46359 | 81 | 124 | 1E-27 | 81 | 63 | 77 | CAA67101 | 434 | 98.2 | 8.00E-20 | 327 | 91 | 27 |
| CAC36222 | 223 | 122 | 5.00E-27 | 240 | 77 | 32 | BAA77312 | 170 | 111 | 7.00E-24 | 125 | 61 | 48 |
| AAP34182 | 184 | 122 | 5.00E-27 | 182 | 73 | 40 | BAA77310 | 150 | 111 | 7.00E-24 | 125 | 61 | 48 |
| AAP34179 | 185 | 122 | 5.00E-27 | 182 | 73 | 40 | CAA66928 | 434 | 110 | 1.00E-23 | 196 | 74 | 37 |
| AAO08750 | 375 | 121 | 7.00E-27 | 374 | 108 | 28 | CAA66928 | 434 | 91.7 | 8.00E-18 | 322 | 86 | 26 |
| AAP44578 | 259 | 121 | 7.00E-27 | 260 | 83 | 31 | BAA77302 | 176 | 110 | 1.00E-23 | 174 | 74 | 42 |
| NP_933768 | 375 | 121 | 7.00E-27 | 374 | 108 | 28 | BAD22847 | 568 | 110 | 2.00E-23 | 180 | 64 | 35 |
| AAC09389 | 259 | 119 | 3.00E-26 | 195 | 77 | 39 | BAD22847 | 568 | 75.5 | 6.00E-13 | 83 | 34 | 40 |
| AAP34194 | 195 | 119 | 3.00E-26 | 195 | 77 | 39 | NP_797170 | 374 | 109 | 3.00E-23 | 148 | 60 | 40 |
| AAP34185 | 194 | 119 | 3.00E-26 | 195 | 77 | 39 | NP_797170 | 374 | 74.3 | 1.00E-12 | 217 | 61 | 28 |
| CAA67102 | 434 | 119 | 3.00E-26 | 197 | 78 | 39 | NP_908288 | 513 | 109 | 3.00E-23 | 294 | 89 | 30 |
| CAA67102 | 434 | 95.1 | 7.00E-19 | 310 | 91 | 29 | NP_908288 | 513 | 73.2 | 3.00E-12 | 122 | 44 | 36 |
| AAQ03611 | 128 | 118 | 6.00E-26 | 117 | 60 | 51 | BAD22846 | 568 | 109 | 3.00E-23 | 180 | 64 | 35 |
| CAA66927 | 434 | 118 | 6.00E-26 | 196 | 78 | 39 | BAD22846 | 568 | 75.5 | 6.00E-13 | 83 | 34 | 40 |
| CAA66927 | 434 | 101 | 1.00E-20 | 327 | 92 | 28 | BAD22839 | 568 | 109 | 3.00E-23 | 180 | 63 | 35 |
| AAQ03603 | 127 | 118 | 8.00E-26 | 120 | 59 | 49 | BAD22839 | 568 | 74.7 | 1.00E-12 | 83 | 34 | 40 |
| BAD22842 | 567 | 118 | 8.00E-26 | 180 | 68 | 37 | AAK12380 | 576 | 109 | 3.00E-23 | 184 | 63 | 34 |
| BAD22842 | 567 | 75.9 | 4.00E-13 | 84 | 34 | 40 | AAK12380 | 576 | 79 | 5.00E-14 | 107 | 43 | 40 |
| BAA77307 | 483 | 118 | 8.00E-26 | 254 | 87 | 34 | AAK12377 | 574 | 109 | 3.00E-23 | 184 | 63 | 34 |
| BAA77307 | 483 | 58.5 | 7.00E-08 | 221 | 60 | 27 | AAK12377 | 574 | 79.3 | 4.00E-14 | 124 | 47 | 37 |
| AAQ03617 | 132 | 117 | 1.00E-25 | 117 | 59 | 50 | AAF25214 | 576 | 109 | 3.00E-23 | 184 | 63 | 34 |
| AAQ03616 | 133 | 117 | 1.00E-25 | 117 | 59 | 50 | AAF25214 | 576 | 77 | 2.00E-13 | 83 | 37 | 44 |
| AAQ03614 | 131 | 117 | 1.00E-25 | 117 | 59 | 50 | AAC25644 | 576 | 109 | 3.00E-23 | 184 | 62 | 33 |
| AAQ03610 | 129 | 117 | 1.00E-25 | 117 | 59 | 50 | AAC25644 | 576 | 77.4 | 1.00E-13 | 156 | 52 | 33 |
| BAD22849 | 566 | 117 | 2.00E-25 | 180 | 68 | 37 | S41310 | 575 | 109 | 3.00E-23 | 182 | 68 | 37 |
| BAD22849 | 566 | 75.5 | 6.00E-13 | 83 | 34 | 40 | S41310 | 575 | 79.3 | 4.00E-14 | 107 | 43 | 40 |
| BAD22843 | 567 | 117 | 2.00E-25 | 180 | 68 | 37 | CAC03725 | 457 | 108 | 5.00E-23 | 144 | 65 | 45 |
| BAD22843 | 567 | 74.7 | 1.00E-12 | 83 | 34 | 40 | CAC03725 | 457 | 101 | 1.00E-20 | 276 | 85 | 30 |
| BAD22841 | 567 | 117 | 2.00E-25 | 180 | 68 | 37 | A42474 | 573 | 108 | 6.00E-23 | 184 | 63 | 34 |
| BAD22841 | 567 | 74.7 | 1.00E-12 | 83 | 34 | 40 | A42474 | 573 | 79.7 | 3.00E-14 | 124 | 46 | 37 |
| BAD22837 | 567 | 117 | 2.00E-25 | 180 | 68 | 37 | A39228 | 576 | 108 | 6.00E-23 | 184 | 62 | 33 |
| BAD22837 | 567 | 74.7 | 1.00E-12 | 83 | 34 | 40 | A39228 | 576 | 77 | 2.00E-13 | 83 | 37 | 44 |
| BAD22835 | 566 | 117 | 2.00E-25 | 180 | 68 | 37 | BAD22844 | 568 | 108 | 6.00E-23 | 180 | 63 | 35 |
| BAD22835 | 566 | 75.5 | 6.00E-13 | 83 | 34 | 40 | BAD22844 | 568 | 75.5 | 6.00E-13 | 83 | 34 | 40 |
| BAD22834 | 566 | 117 | 2.00E-25 | 180 | 68 | 37 | BAC44988 | 571 | 108 | 6.00E-23 | 181 | 66 | 36 |
| BAD22834 | 566 | 75.5 | 6.00E-13 | 83 | 34 | 40 | BAC44988 | 571 | 72 | 6.00E-12 | 83 | 34 | 40 |
| CAC36203 | 221 | 116 | 2.00E-25 | 238 | 74 | 31 | BAC44985 | 575 | 108 | 6.00E-23 | 184 | 63 | 34 |
| BAD22836 | 567 | 116 | 2.00E-25 | 180 | 68 | 37 | BAC44985 | 575 | 77.4 | 1.00E-13 | 159 | 55 | 34 |
| BAD22836 | 567 | 74.7 | 1.00E-12 | 83 | 34 | 40 | AAF05902 | 574 | 108 | 6.00E-23 | 184 | 63 | 34 |
| NP_391395 | 160 | 116 | 3.00E-25 | 179 | 68 | 37 | AAF05902 | 574 | 77 | 2.00E-13 | 83 | 37 | 44 |
| BAD22838 | 563 | 116 | 3.00E-25 | 180 | 67 | 37 | AAN75633 | 196 | 108 | 6.00E-23 | 215 | 72 | 33 |
| BAD22838 | 563 | 76.6 | 3.00E-13 | 173 | 50 | 28 | AAC25648 | 576 | 108 | 6.00E-23 | 184 | 62 | 33 |
| BAD22845 | 565 | 115 | 4.00E-25 | 180 | 67 | 37 | AAC25648 | 576 | 77.4 | 1.00E-13 | 83 | 37 | 44 |
| BAD22845 | 565 | 78.2 | 9.00E-14 | 127 | 45 | 35 | AAC25643 | 576 | 108 | 6.00E-23 | 184 | 63 | 34 |
| AAB69135 | 434 | 115 | 4E-25 | 196 | 76 | 38 | AAC25643 | 576 | 77.4 | 1.00E-13 | 124 | 44 | 35 |
| AAB69135 | 434 | 103 | 2.00E-21 | 327 | 93 | 28 | AAC25637 | 576 | 108 | 6.00E-23 | 184 | 62 | 33 |
| AAB69134 | 434 | 115 | 4.00E-25 | 196 | 76 | 38 | AAC25637 | 576 | 77 | 2.00E-13 | 83 | 37 | 44 |
| AAB69134 | 434 | 102 | 4.00E-21 | 327 | 93 | 28 | P27053 | 573 | 108 | 6.00E-23 | 184 | 63 | 34 |
| I40573 | 195 | 115 | 4.00E-25 | 165 | 65 | 39 | P27053 | 573 | 79.7 | 3.00E-14 | 124 | 46 | 37 |
| BAD22840 | 566 | 115 | 5.00E-25 | 180 | 67 | 37 | BAB63937 | 486 | 108 | 6.00E-23 | 183 | 67 | 36 |
| BAD22840 | 566 | 75.5 | 6.00E-13 | 83 | 34 | 40 | BAB63937 | 486 | 80.1 | 2.00E-14 | 83 | 38 | 45 |
| AAQ03605 | 126 | 114 | 8E-25 | 127 | 61 | 48 | NP_206915 | 514 | 108 | 8.00E-23 | 187 | 67 | 35 |
| AAG61259 | 253 | 114 | 1.00E-24 | 257 | 80 | 31 | NP_206915 | 514 | 77.4 | 1.00E-13 | 121 | 47 | 38 |
| CAA67105 | 700 | 114 | 1.00E-24 | 301 | 93 | 30 | BAB71798 | 486 | 108 | 8.00E-23 | 183 | 66 | 36 |
| CAA67105 | 700 | 102 | 4.00E-21 | 298 | 92 | 30 | BAB71798 | 486 | 80.1 | 2.00E-14 | 83 | 38 | 45 |
| CAC03724 | 440 | 113 | 2.00E-24 | 237 | 83 | 35 | AAP72265 | 514 | 107 | 1.00E-22 | 166 | 62 | 37 |
| CAC03724 | 440 | 106 | 3.00E-22 | 255 | 80 | 31 | AAP72265 | 514 | 77.4 | 1.00E-13 | 121 | 47 | 38 |
| BAD22848 | 571 | 113 | 2E-24 | 180 | 66 | 36 | BAC44987 | 574 | 107 | 1.00E-22 | 181 | 65 | 35 |
| BAD22848 | 571 | 74.7 | 1.00E-12 | 83 | 33 | 39 | BAC44987 | 574 | 82 | 6.00E-15 | 162 | 56 | 34 |
| AAB66595 | 340 | 113 | 2E-24 | 225 | 76 | 33 | BAC44986 | 574 | 107 | 1.00E-22 | 181 | 65 | 35 |
| AAB66595 | 340 | 107 | 1E-22 | 187 | 70 | 37 | BAC44986 | 574 | 79 | 5.00E-14 | 83 | 37 | 44 |
| AAB66597 | 340 | 113 | 2.00E-24 | 225 | 76 | 33 | AAD10273 | 374 | 107 | 1.00E-22 | 160 | 61 | 38 |
| AAB66597 | 340 | 105 | 5.00E-22 | 187 | 69 | 36 | AAD10273 | 374 | 75.9 | 4.00E-13 | 217 | 59 | 27 |
| BAA77299 | 398 | 113 | 2.00E-24 | 215 | 86 | 40 | AAP34188 | 183 | 107 | 1.00E-22 | 187 | 70 | 37 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AAC25639 | 575 | 107 | 1.00E-22 | 181 | 65 | 35 | NP_420273 | 273 | 104 | 1.00E-21 | 297 | 76 | 25 |
| AAC25639 | 575 | 82 | 6.00E-15 | 162 | 56 | 34 | AAC25638 | 576 | 104 | 1.00E-21 | 181 | 64 | 35 |
| AAA25016 | 514 | 107 | 1.00E-22 | 187 | 67 | 35 | AAC25638 | 576 | 79.3 | 4.00E-14 | 121 | 44 | 36 |
| AAA25016 | 514 | 77.4 | 1.00E-13 | 121 | 47 | 38 | BAB85480 | 491 | 104 | 1.00E-21 | 181 | 63 | 34 |
| NP_222828 | 514 | 107 | 1.00E-22 | 187 | 67 | 35 | BAB85480 | 491 | 83.2 | 3.00E-15 | 174 | 55 | 31 |
| NP_222828 | 514 | 77.4 | 1.00E-13 | 121 | 47 | 38 | CAA82524 | 575 | 103 | 1.00E-21 | 182 | 69 | 37 |
| AAL86894 | 514 | 107 | 1.00E-22 | 187 | 67 | 35 | CAA82524 | 575 | 73.9 | 2.00E-12 | 107 | 40 | 37 |
| AAL86894 | 514 | 77.4 | 1.00E-13 | 121 | 47 | 38 | BAC56988 | 491 | 103 | 1.00E-21 | 184 | 63 | 34 |
| CAA82523 | 575 | 107 | 1.00E-22 | 182 | 67 | 36 | BAC56988 | 491 | 82.8 | 4.00E-15 | 174 | 59 | 33 |
| CAA82523 | 575 | 79.3 | 4.00E-14 | 107 | 43 | 40 | AAC25647 | 575 | 103 | 1.00E-21 | 171 | 62 | 36 |
| CAB46859 | 514 | 107 | 1.00E-22 | 249 | 79 | 31 | AAC25647 | 575 | 78.6 | 7.00E-14 | 107 | 43 | 40 |
| CAB46859 | 514 | 75.1 | 7.00E-13 | 148 | 50 | 33 | NP_907654 | 518 | 103 | 1.00E-21 | 192 | 63 | 32 |
| AAN74969 | 514 | 107 | 1.00E-22 | 187 | 67 | 35 | NP_907654 | 518 | 94.7 | 9.00E-19 | 333 | 85 | 25 |
| AAN74969 | 514 | 77.4 | 1.00E-13 | 121 | 47 | 38 | CAA72431 | 630 | 103 | 2.00E-21 | 181 | 64 | 35 |
| BAC56997 | 575 | 107 | 1.00E-22 | 171 | 64 | 37 | CAA72431 | 630 | 71.2 | 1.00E-11 | 105 | 38 | 36 |
| BAC56997 | 575 | 79.7 | 3.00E-14 | 121 | 44 | 36 | AAC25646 | 572 | 103 | 2.00E-21 | 181 | 67 | 37 |
| AAA17046 | 575 | 107 | 1.00E-22 | 182 | 67 | 36 | AAC25646 | 572 | 72.8 | 4.00E-12 | 132 | 45 | 34 |
| AAA17046 | 575 | 73.9 | 2.00E-12 | 107 | 40 | 37 | BAB71800 | 487 | 103 | 2.00E-21 | 183 | 63 | 34 |
| CAA40460 | | | | | | | BAB71800 | 487 | 80.1 | 2.00E-14 | 83 | 38 | 45 |
| | | | | | | | BAC56991 | 491 | 103 | 3.00E-21 | 219 | 68 | 31 |
| CAA40460 | 576 | 82 | 6.00E-15 | 162 | 56 | 34 | BAC56991 | 491 | 84 | 2.00E-15 | 171 | 56 | 32 |
| AAC25650 | 572 | 107 | 2.00E-22 | 171 | 64 | 37 | AAC35988 | 273 | 103 | 3.00E-21 | 297 | 75 | 25 |
| AAC25650 | 572 | 77.8 | 1E-13 | 132 | 48 | 36 | NP_404368 | 404 | 102 | 3.00E-21 | 223 | 67 | 30 |
| AAC25649 | 572 | 107 | 2.00E-22 | 181 | 65 | 35 | NP_670739 | 401 | 102 | 3.00E-21 | 223 | 67 | 30 |
| AAC25649 | 572 | 78.2 | 9.00E-14 | 132 | 48 | 36 | NP_670739 | 401 | 57.4 | 2.00E-07 | 84 | 28 | 33 |
| AAC25645 | 572 | 107 | 2.00E-22 | 181 | 65 | 35 | AAV35033 | 543 | 102 | 4.00E-21 | 169 | 61 | 36 |
| AAC25645 | 572 | 79.3 | 4.00E-14 | 132 | 48 | 36 | AAV35033 | 543 | 62 | 6.00E-09 | 141 | 42 | 29 |
| AAC25641 | 572 | 107 | 2.00E-22 | 181 | 65 | 35 | BAC56990 | 490 | 102 | 4.00E-21 | 219 | 68 | 31 |
| AAC25641 | 572 | 78.6 | 7.00E-14 | 83 | 37 | 44 | BAC56990 | 490 | 83.6 | 2.00E-15 | 171 | 59 | 34 |
| BAC56996 | 572 | 106 | 2.00E-22 | 184 | 61 | 33 | BAA77308 | 120 | 102 | 4.00E-21 | 119 | 55 | 46 |
| BAC56996 | 572 | 79.7 | 3.00E-14 | 124 | 46 | 37 | NP_282484 | 572 | 102 | 6.00E-21 | 181 | 66 | 36 |
| NP_282485 | 572 | 106 | 3.00E-22 | 171 | 63 | 36 | NP_282484 | 572 | 72.8 | 4.00E-12 | 132 | 45 | 34 |
| NP_282485 | 572 | 79.3 | 4.00E-14 | 132 | 48 | 36 | CAA72430 | 626 | 102 | 6.00E-21 | 183 | 65 | 35 |
| BAA77318 | 125 | 106 | 3.00E-22 | 125 | 57 | 45 | CAA72430 | 626 | 79.3 | 4.00E-14 | 148 | 50 | 33 |
| BAA77316 | 131 | 106 | 3.00E-22 | 125 | 57 | 45 | AAK73706 | 557 | 101 | 7.00E-21 | 178 | 59 | 33 |
| BAC56994 | 487 | 105 | 4.00E-22 | 183 | 64 | 34 | AAK73706 | 557 | 70.1 | 2.00E-11 | 113 | 41 | 36 |
| BAC56994 | 487 | 80.1 | 2.00E-14 | 83 | 38 | 45 | AAC25640 | 575 | 101 | 7.00E-21 | 181 | 65 | 35 |
| BAA77304 | 165 | 105 | 4.00E-22 | 165 | 68 | 41 | AAC25640 | 575 | 77.8 | 1.00E-13 | 296 | 78 | 26 |
| B39228 | 576 | 105 | 5.00E-22 | 184 | 63 | 34 | CAB46858 | 513 | 101 | 1.00E-20 | 240 | 73 | 30 |
| B39228 | 576 | 71.6 | 8.00E-12 | 83 | 33 | 39 | CAB46858 | 513 | 77.8 | 1.00E-13 | 329 | 89 | 27 |
| AAB03519 | 328 | 105 | 5.00E-22 | 308 | 87 | 28 | BAC56987 | 492 | 101 | 1.00E-20 | 174 | 61 | 35 |
| AAF25216 | 576 | 105 | 5.00E-22 | 184 | 63 | 34 | BAC56987 | 492 | 82.8 | 4.00E-15 | 175 | 58 | 33 |
| AAF25216 | 576 | 73.6 | 2.00E-12 | 83 | 34 | 40 | AAK73700 | 557 | 101 | 1.00E-20 | 178 | 59 | 33 |
| B42474 | 573 | 105 | 5E-22 | 184 | 64 | 34 | AAK73700 | 557 | 70.1 | 2.00E-11 | 113 | 41 | 36 |
| B42474 | 573 | 73.9 | 2.00E-12 | 124 | 43 | 34 | AAC25642 | 572 | 101 | 1.00E-20 | 181 | 66 | 36 |
| A35146 | 573 | 105 | 5.00E-22 | 184 | 64 | 34 | AAC25642 | 572 | 71.6 | 8.00E-12 | 132 | 45 | 34 |
| A35146 | 573 | 72.8 | 4.00E-12 | 124 | 43 | 34 | NP_214372 | 518 | 100 | 1.00E-20 | 209 | 62 | 29 |
| P18245 | 573 | 105 | 5.00E-22 | 184 | 64 | 34 | NP_214372 | 518 | 62 | 6.00E-09 | 129 | 39 | 30 |
| P18245 | 573 | 73.9 | 2.00E-12 | 124 | 43 | 34 | BAC56986 | 500 | 100 | 1.00E-20 | 153 | 61 | 39 |
| BAA77314 | 124 | 105 | 5.00E-22 | 124 | 57 | 45 | BAC56986 | 500 | 85.9 | 4.00E-16 | 316 | 82 | 25 |
| AAA23020 | 573 | 105 | 5.00E-22 | 184 | 64 | 34 | AAK73703 | 556 | 100 | 2.00E-20 | 175 | 62 | 35 |
| AAA23020 | 573 | 72.8 | 4.00E-12 | 124 | 43 | 34 | AAK73703 | 556 | 71.6 | 8.00E-12 | 287 | 73 | 25 |
| 1814303A | 556 | 105 | 5.00E-22 | 182 | 66 | 36 | AAK73702 | 558 | 100 | 2.00E-20 | 175 | 62 | 35 |
| 1814303A | 556 | 45.4 | 6.00E-04 | 75 | 24 | 32 | AAK73702 | 558 | 74.7 | 1.00E-12 | 287 | 72 | 25 |
| AAM76286 | 576 | 105 | 7.00E-22 | 184 | 62 | 33 | AAK73699 | 194 | 100 | 2.00E-20 | 175 | 62 | 35 |
| AAM76286 | 576 | 73.6 | 2.00E-12 | 83 | 34 | 40 | AAK73705 | 554 | 100 | 2.00E-20 | 175 | 61 | 34 |
| B40586 | 514 | 104 | 9.00E-22 | 189 | 63 | 33 | AAK73705 | 554 | 68.6 | 7.00E-11 | 74 | 31 | 41 |
| B40586 | 514 | 80.5 | 2.00E-14 | 123 | 48 | 39 | AAK73698 | 194 | 100 | 2.00E-20 | 175 | 61 | 34 |
| AAP78393 | 514 | 104 | 9.00E-22 | 188 | 67 | 35 | AAK73697 | 194 | 100 | 2.00E-20 | 175 | 61 | 34 |
| AAP78393 | 514 | 68.9 | 5.00E-11 | 115 | 40 | 34 | YP_061683 | 290 | 99.8 | 3.00E-20 | 308 | 85 | 27 |
| BAC56995 | 487 | 104 | 9.00E-22 | 183 | 65 | 35 | BAA77300 | 115 | 99.8 | 3.00E-20 | 115 | 58 | 50 |
| BAC56995 | 487 | 80.1 | 2.00E-14 | 83 | 38 | 45 | BAB71799 | 492 | 99.8 | 3.00E-20 | 174 | 59 | 33 |
| BAC56992 | 487 | 104 | 9.00E-22 | 183 | 65 | 35 | BAB71799 | 492 | 85.9 | 4.00E-16 | 172 | 57 | 33 |
| BAC56992 | 487 | 79 | 5.00E-14 | 83 | 37 | 44 | ZP_00313281302 | | 99.4 | 4.00E-20 | 274 | 69 | 25 |
| BAC56989 | 487 | 104 | 9.00E-22 | 183 | 65 | 35 | ZP_00100043955 | | 99.4 | 4.00E-20 | 270 | 82 | 30 |
| BAC56989 | 487 | 79 | 5.00E-14 | 83 | 37 | 44 | ZP_00100043955 | | 63.5 | 2.00E-09 | 154 | 47 | 30 |
| BAB71801 | 491 | 104 | 9.00E-22 | 180 | 63 | 35 | A44757 | 572 | 99 | 5.00E-20 | 171 | 58 | 33 |
| BAB71801 | 491 | 81.6 | 8.00E-15 | 174 | 54 | 31 | A44757 | 572 | 79.7 | 3.00E-14 | 124 | 46 | 37 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| NP_420274 | 273 | 99 | 5.00E-20 | 292 | 75 | 25 | ZP_00339045281 | 84 | 2E-15 | 296 | 75 | 25 |
| NP_419609 | 273 | 99 | 5.00E-20 | 292 | 72 | 24 | AAA85133 | 102 | 84 | 2E-15 | 87 | 43 | 49 |
| AAA23021 | 572 | 99 | 5.00E-20 | 171 | 58 | 33 | YP_080866 | 303 | 83.2 | 3E-15 | 281 | 70 | 24 |
| AAA23021 | 572 | 79.7 | 3.00E-14 | 124 | 46 | 37 | FLQL2C | 276 | 82.4 | 5E-15 | 298 | 70 | 23 |
| NP_419611 | 273 | 98.6 | 6.00E-20 | 292 | 72 | 24 | NP_773505 | 314 | 80.9 | 1E-14 | 317 | 73 | 23 |
| YP_071817 | 400 | 98.2 | 8.00E-20 | 207 | 61 | 29 | YP_148989 | 297 | 80.5 | 2E-14 | 288 | 69 | 23 |
| YP_071817 | 400 | 60.1 | 2.00E-08 | 115 | 37 | 32 | NP_353570 | 313 | 79.7 | 3.00E-14 | 313 | 75 | 23 |
| NP_865696 | 718 | 98.2 | 8.00E-20 | 284 | 88 | 30 | ZP_00339044282 | | 79.3 | 4.00E-14 | 298 | 72 | 24 |
| NP_865696 | 718 | 81.3 | 1.00E-14 | 143 | 57 | 39 | CAD11203 | 461 | 79 | 5.00E-14 | 149 | 49 | 32 |
| NP_622171 | 296 | 98.2 | 8.00E-20 | 290 | 83 | 28 | CAD11203 | 461 | 63.9 | 2.00E-09 | 109 | 39 | 35 |
| BAA77306 | 397 | 98.2 | 8.00E-20 | 188 | 67 | 35 | CAD11202 | 461 | 79 | 5.00E-14 | 149 | 49 | 32 |
| BAA77306 | 397 | 51.2 | 1.00E-05 | 91 | 27 | 29 | CAD11202 | 461 | 63.9 | 2.00E-09 | 109 | 39 | 35 |
| AAP78250 | 508 | 97.8 | 1.00E-19 | 170 | 60 | 35 | ZP_00007767281 | | 78.6 | 7.00E-14 | 302 | 70 | 23 |
| AAP78250 | 508 | 76.3 | 3.00E-13 | 297 | 74 | 24 | NP_840399 | 299 | 77.8 | 1.00E-13 | 290 | 71 | 24 |
| NP_419610 | 273 | 97.4 | 1.00E-19 | 292 | 70 | 23 | CAD11208 | 458 | 77.8 | 1.00E-13 | 136 | 45 | 33 |
| NP_866107 | 739 | 97.4 | 1.00E-19 | 257 | 76 | 29 | CAD11208 | 458 | 67.8 | 1.00E-10 | 294 | 70 | 23 |
| NP_866107 | 739 | 79.3 | 4.00E-14 | 250 | 70 | 28 | CAD11207 | 458 | 77.8 | 1.00E-13 | 136 | 45 | 33 |
| CAA43148 | 510 | 97.1 | 2.00E-19 | 170 | 57 | 33 | CAD11207 | 458 | 65.9 | 4.00E-10 | 294 | 69 | 23 |
| CAA43148 | 510 | 82.4 | 5.00E-15 | 311 | 78 | 25 | CAD11206 | 458 | 77.8 | 1.00E-13 | 136 | 45 | 33 |
| BAC56993 | 500 | 97.1 | 2.00E-19 | 222 | 73 | 32 | CAD11206 | 458 | 65.9 | 4.00E-10 | 294 | 69 | 23 |
| BAC56993 | 500 | 82.4 | 5.00E-15 | 174 | 55 | 31 | ZP_00339046273 | | 77.4 | 1.00E-13 | 280 | 73 | 26 |
| NP_223266 | 510 | 96.3 | 3.00E-19 | 170 | 57 | 33 | ZP_00338034282 | | 77.4 | 1.00E-13 | 294 | 72 | 24 |
| NP_223266 | 510 | 82.4 | 5.00E-15 | 311 | 78 | 25 | AAN08500 | 139 | 77.4 | 1.00E-13 | 74 | 38 | 51 |
| AAP72264 | 510 | 96.3 | 3.00E-19 | 170 | 57 | 33 | CAC03722 | 433 | 77.4 | 1.00E-13 | 315 | 74 | 23 |
| AAP72264 | 510 | 83.2 | 3.00E-15 | 311 | 79 | 25 | CAC03722 | 433 | 31.6 | 9.30E+00 | 199 | 49 | 24 |
| AAU21201 | 510 | 96.3 | 3.00E-19 | 170 | 57 | 33 | BAB18964 | 200 | 77.4 | 1.00E-13 | 134 | 46 | 34 |
| AAU21201 | 510 | 82 | 6.00E-15 | 311 | 78 | 25 | AAM90627 | 145 | 77 | 2.00E-13 | 158 | 53 | 33 |
| CAC03721 | 427 | 96.3 | 3.00E-19 | 251 | 76 | 30 | BAC16347 | 200 | 77 | 2.00E-13 | 134 | 46 | 34 |
| CAC03721 | 427 | 94.4 | 1.00E-18 | 271 | 74 | 27 | BAC16341 | 200 | 77 | 2.00E-13 | 134 | 46 | 34 |
| NP_404369 | 399 | 95.9 | 4.00E-19 | 295 | 76 | 25 | BAC16340 | 200 | 77 | 2.00E-13 | 134 | 46 | 34 |
| AAQ82717 | 510 | 95.9 | 4.00E-19 | 170 | 57 | 33 | ZP_00193517283 | | 76.6 | 3.00E-13 | 290 | 65 | 22 |
| AAQ82717 | 510 | 82 | 6.00E-15 | 311 | 78 | 25 | AAR98527 | 69 | 76.6 | 3E-13 | 69 | 39 | 56 |
| ZP_00299642294 | | 95.5 | 5.00E-19 | 295 | 75 | 25 | ZP_00337030282 | | 76.3 | 3.00E-13 | 299 | 69 | 23 |
| A55864 | 518 | 95.5 | 5.00E-19 | 197 | 65 | 32 | BAB19647 | 200 | 75.9 | 4.00E-13 | 134 | 45 | 33 |
| A55864 | 518 | 94.7 | 9.00E-19 | 333 | 85 | 25 | BAB18970 | 200 | 75.9 | 4.00E-13 | 134 | 45 | 33 |
| AAB95381 | 273 | 95.5 | 5.00E-19 | 292 | 70 | 23 | BAB18969 | 200 | 75.9 | 4.00E-13 | 134 | 45 | 33 |
| AAP34180 | 167 | 94.7 | 9.00E-19 | 164 | 59 | 35 | BAB18968 | 200 | 75.9 | 4.00E-13 | 134 | 45 | 33 |
| P50612 | 494 | 94.4 | 1.00E-18 | 166 | 56 | 33 | BAB18961 | 200 | 75.9 | 4.00E-13 | 134 | 45 | 33 |
| P50612 | 494 | 61.2 | 1.00E-08 | 299 | 71 | 23 | BAB18959 | 200 | 75.9 | 4.00E-13 | 134 | 45 | 33 |
| CAA81035 | 134 | 93.6 | 2.00E-18 | 154 | 59 | 38 | BAB18950 | 200 | 75.9 | 4.00E-13 | 134 | 45 | 33 |
| NP_867573 | 685 | 92.8 | 3.00E-18 | 169 | 62 | 36 | BAB18949 | 200 | 75.9 | 4.00E-13 | 134 | 45 | 33 |
| NP_867573 | 685 | 85.5 | 5.00E-16 | 126 | 55 | 43 | BAB18948 | 200 | 75.9 | 4.00E-13 | 134 | 45 | 33 |
| CAC03723 | 503 | 92.4 | 4.00E-18 | 208 | 66 | 31 | BAB18946 | 200 | 75.9 | 4.00E-13 | 134 | 45 | 33 |
| CAC03723 | 503 | 66.2 | 3.00E-10 | 252 | 61 | 24 | BAC16528 | 199 | 75.5 | 6.00E-13 | 133 | 45 | 33 |
| NP_404370 | 401 | 92 | 6.00E-18 | 309 | 79 | 25 | BAC16532 | 199 | 75.1 | 7.00E-13 | 133 | 45 | 33 |
| ZP_00329910305 | | 91.7 | 8.00E-18 | 285 | 73 | 25 | BAC16525 | 199 | 75.1 | 7.00E-13 | 133 | 45 | 33 |
| ZP_00196929279 | | 91.7 | 8.00E-18 | 288 | 79 | 27 | BAC16348 | 200 | 74.7 | 1.00E-12 | 134 | 45 | 33 |
| NP_353572 | 306 | 91.3 | 1.00E-17 | 313 | 77 | 24 | NP_907272 | 253 | 74.3 | 1.00E-12 | 278 | 65 | 23 |
| NP_693427 | 293 | 91.3 | 1.00E-17 | 293 | 75 | 25 | BAC76096 | 198 | 74.3 | 1.00E-12 | 133 | 44 | 33 |
| ZP_00098298321 | | 90.9 | 1.00E-17 | 302 | 85 | 28 | BAC76095 | 198 | 74.3 | 1.00E-12 | 133 | 44 | 33 |
| AAA88923 | 501 | 90.5 | 2.00E-17 | 200 | 57 | 28 | BAC16534 | 199 | 73.9 | 2.00E-12 | 133 | 44 | 33 |
| AAA88923 | 501 | 56.6 | 3.00E-07 | 146 | 47 | 32 | BAC16533 | 199 | 73.9 | 2.00E-12 | 133 | 44 | 33 |
| BAC98372 | 302 | 90.5 | 2.00E-17 | 301 | 81 | 26 | BAC16527 | 199 | 73.9 | 2.00E-12 | 133 | 44 | 33 |
| AAC41457 | 482 | 90.5 | 2.00E-17 | 150 | 51 | 34 | BAD18056 | 199 | 73.9 | 2.00E-12 | 133 | 44 | 33 |
| AAC41457 | 482 | 61.2 | 1.00E-08 | 299 | 71 | 23 | BAD18057 | 193 | 73.9 | 2.00E-12 | 133 | 44 | 33 |
| NP_227947 | 258 | 89.7 | 3.00E-17 | 248 | 63 | 25 | BAD18055 | 199 | 73.9 | 2.00E-12 | 133 | 44 | 33 |
| NP_954084 | 298 | 89.7 | 3.00E-17 | 290 | 75 | 25 | AAP34191 | 159 | 73.2 | 3.00E-12 | 162 | 54 | 33 |
| ZP_00289010110 | | 89.7 | 3.00E-17 | 87 | 47 | 54 | ZP_00270458289 | | 72.8 | 4.00E-12 | 302 | 69 | 22 |
| NP_700301 | 282 | 88.6 | 6.00E-17 | 298 | 76 | 25 | ZP_00289016275 | | 72 | 6.00E-12 | 275 | 64 | 23 |
| AAA85132 | 102 | 88.6 | 6.00E-17 | 87 | 45 | 51 | BAD38984 | 199 | 72 | 6.00E-12 | 133 | 43 | 32 |
| AAV35032 | 531 | 87.4 | 1.00E-16 | 142 | 52 | 36 | YP_162339 | 285 | 71.6 | 8.00E-12 | 282 | 56 | 19 |
| AAV35032 | 531 | 63.9 | 2.00E-09 | 94 | 34 | 36 | NP_353571 | 337 | 71.6 | 8.00E-12 | 324 | 75 | 23 |
| NP_391420 | 298 | 86.7 | 2.00E-16 | 288 | 80 | 27 | NP_531244 | 320 | 71.6 | 8.00E-12 | 324 | 75 | 23 |
| NP_541127 | 282 | 86.7 | 2.00E-16 | 298 | 75 | 25 | ZP_00183364320 | | 71.6 | 8.00E-12 | 321 | 74 | 23 |
| ZP_00288130268 | | 85.5 | 5.00E-16 | 295 | 76 | 25 | CAF74789 | 295 | 71.6 | 8.00E-12 | 294 | 67 | 22 |
| NP_773506 | 313 | 85.1 | 7.00E-16 | 311 | 73 | 23 | AAD41622 | 127 | 71.2 | 1.00E-11 | 100 | 41 | 41 |
| NP_104150 | 328 | 84.7 | 9E-16 | 329 | 75 | 22 | AAP34187 | 157 | 71.2 | 1.00E-11 | 160 | 53 | 33 |
| BAC98373 | 302 | 84.3 | 1E-15 | 92 | 44 | 47 | AAP34184 | 154 | 71.2 | 1.00E-11 | 160 | 53 | 33 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| AAP34192 | 155 | 69.7 | 3.00E-11 | 159 | 52 | 32 | AAA86521 | 414 | 52 | 7.00E-06 | 108 | 32 | 29 |
| CAF74790 | 283 | 69.7 | 3.00E-11 | 284 | 61 | 21 | AAQ60546 | 309 | 58.9 | 5.00E-08 | 299 | 62 | 20 |
| AAB48473 | 249 | 68.9 | 5.00E-11 | 288 | 68 | 23 | ZP_00127287 | 530 | 58.9 | 5.00E-08 | 135 | 40 | 29 |
| AAC27443 | 249 | 68.9 | 5.00E-11 | 186 | 50 | 26 | AAA23951 | 288 | 58.5 | 7.00E-08 | 46 | 28 | 60 |
| AAC27443 | 249 | 38.5 | 7.60E-02 | 49 | 20 | 40 | AAA23951 | 288 | 41.6 | 9.00E-03 | 307 | 79 | 25 |
| AAA99141 | 214 | 68.9 | 5.00E-11 | 222 | 59 | 26 | NP_772484 | 757 | 58.5 | 7.00E-08 | 273 | 72 | 26 |
| NP_281892 | 249 | 68.6 | 7.00E-11 | 288 | 66 | 22 | NP_772484 | 757 | 34.7 | 1.10E+00 | 109 | 29 | 26 |
| NP_782319 | 316 | 68.2 | 9.00E-11 | 284 | 68 | 23 | AAK58562 | 200 | 58.5 | 7.00E-08 | 205 | 50 | 24 |
| ZP_00337274 | 271 | 67.4 | 2.00E-10 | 284 | 64 | 22 | BAA77313 | 179 | 58.5 | 7.00E-08 | 69 | 29 | 42 |
| AAP34189 | 154 | 67.4 | 2.00E-10 | 158 | 52 | 32 | BAA77311 | 136 | 58.5 | 7.00E-08 | 69 | 29 | 42 |
| ZP_00335243 | 300 | 67 | 2.00E-10 | 302 | 74 | 24 | NP_637307 | 401 | 58.2 | 9.00E-08 | 134 | 38 | 28 |
| AAM90629 | 117 | 67 | 2.00E-10 | 129 | 46 | 35 | NP_637307 | 401 | 35.8 | 4.90E-01 | 119 | 31 | 26 |
| ZP_00149794 | 326 | 67 | 2.00E-10 | 322 | 67 | 20 | AAU13838 | 410 | 58.2 | 9.00E-08 | 121 | 35 | 28 |
| NP_972952 | 415 | 66.6 | 3.00E-10 | 285 | 65 | 22 | AAU13838 | 410 | 38.5 | 7.60E-02 | 260 | 55 | 21 |
| CAA24655 | 38 | 66.2 | 3.00E-10 | 37 | 34 | 91 | YP_083110 | 287 | 57.8 | 1.00E-07 | 242 | 57 | 23 |
| NP_227898 | 304 | 65.1 | 8.00E-10 | 256 | 62 | 24 | NP_978079 | 287 | 57.8 | 1.00E-07 | 241 | 60 | 24 |
| AAM90636 | 126 | 65.1 | 8.00E-10 | 130 | 41 | 31 | AAK58561 | 202 | 57.8 | 1.00E-07 | 208 | 51 | 24 |
| AAM90630 | 126 | 65.1 | 8.00E-10 | 130 | 42 | 32 | NP_772486 | 757 | 57.4 | 2.00E-07 | 255 | 72 | 28 |
| AAQ75042 | 195 | 64.7 | 1.00E-09 | 202 | 52 | 25 | NP_772486 | 757 | 34.3 | 1.40E+00 | 109 | 29 | 26 |
| YP_013346 | 291 | 64.3 | 1.00E-09 | 288 | 61 | 21 | AAS14965 | 190 | 57.4 | 2.00E-07 | 185 | 47 | 25 |
| ZP_00049388 | 242 | 63.9 | 2.00E-09 | 188 | 52 | 27 | NP_212316 | 424 | 57.4 | 2.00E-07 | 132 | 38 | 28 |
| NP_464233 | 291 | 63.9 | 2.00E-09 | 288 | 61 | 21 | NP_212316 | 424 | 35 | 8.40E-01 | 77 | 18 | 23 |
| ZP_00229464 | 291 | 63.5 | 2.00E-09 | 288 | 61 | 21 | AAB81420 | 395 | 57.4 | 2.00E-07 | 138 | 38 | 27 |
| AAO33575 | 375 | 63.5 | 2.00E-09 | 305 | 71 | 23 | AAB81420 | 395 | 50.4 | 2.00E-05 | 149 | 43 | 28 |
| AAC27442 | 254 | 63.5 | 2.00E-09 | 202 | 51 | 25 | AAG14364 | 410 | 57.4 | 2.00E-07 | 418 | 87 | 20 |
| AAC27442 | 254 | 38.5 | 7.60E-02 | 49 | 20 | 40 | NP_384775 | 394 | 57 | 2.00E-07 | 138 | 38 | 27 |
| AAC65633 | 416 | 63.2 | 3.00E-09 | 268 | 60 | 22 | NP_384775 | 394 | 50.4 | 2.00E-05 | 87 | 29 | 33 |
| AAQ75043 | 195 | 62.8 | 4.00E-09 | 202 | 51 | 25 | AAS91573 | 80 | 57 | 2.00E-07 | 60 | 27 | 45 |
| NP_384778 | 321 | 62.4 | 5.00E-09 | 321 | 68 | 21 | AAP34186 | 144 | 57 | 2.00E-07 | 149 | 47 | 31 |
| NP_642302 | 401 | 62.4 | 5.00E-09 | 134 | 40 | 29 | AAP34181 | 139 | 57 | 2.00E-07 | 135 | 41 | 30 |
| NP_642302 | 401 | 40.8 | 1.50E-02 | 118 | 31 | 26 | AAU07039 | 424 | 56.6 | 3.00E-07 | 157 | 46 | 29 |
| AAO33576 | 375 | 62.4 | 5.00E-09 | 305 | 71 | 23 | AAU07039 | 424 | 35 | 8.40E-01 | 77 | 18 | 23 |
| CAC03720 | 316 | 62.4 | 5.00E-09 | 141 | 46 | 32 | AAP08616 | 287 | 56.6 | 3.00E-07 | 243 | 57 | 23 |
| CAD11201 | 281 | 62.4 | 5.00E-09 | 108 | 38 | 35 | ZP_00128974 | 504 | 56.6 | 3.00E-07 | 113 | 32 | 28 |
| CAD11199 | 281 | 62.4 | 5.00E-09 | 108 | 38 | 35 | ZP_00128974 | 504 | 43.5 | 2.00E-03 | 238 | 50 | 21 |
| AAQ75041 | 195 | 62.4 | 5.00E-09 | 202 | 50 | 24 | A32808 | 395 | 56.2 | 4.00E-07 | 138 | 37 | 26 |
| NP_470057 | 291 | 62 | 6.00E-09 | 288 | 60 | 20 | A32808 | 395 | 50.4 | 2.00E-05 | 149 | 43 | 28 |
| AAB81422 | 321 | 62 | 6.00E-09 | 321 | 65 | 20 | NP_521913 | 316 | 56.2 | 4.00E-07 | 305 | 65 | 21 |
| AAM75948 | 452 | 61.6 | 8.00E-09 | 231 | 55 | 23 | NP_746494 | 521 | 56.2 | 4.00E-07 | 130 | 41 | 31 |
| AAQ75049 | 195 | 61.6 | 8.00E-09 | 202 | 50 | 24 | NP_746494 | 521 | 41.6 | 9.00E-03 | 149 | 37 | 24 |
| AAQ75048 | 195 | 61.6 | 8.00E-09 | 202 | 50 | 24 | AAL99374 | 205 | 56.2 | 4.00E-07 | 157 | 42 | 26 |
| AAQ75047 | 195 | 61.6 | 8.00E-09 | 202 | 50 | 24 | ZP_00173445 | 304 | 56.2 | 4.00E-07 | 301 | 68 | 22 |
| AAQ75044 | 195 | 61.6 | 8.00E-09 | 202 | 50 | 24 | AAU13837 | 400 | 55.8 | 5.00E-07 | 115 | 34 | 29 |
| AAQ75040 | 195 | 61.6 | 8.00E-09 | 202 | 50 | 24 | AAU13837 | 400 | 32.7 | 4.20E+00 | 254 | 52 | 20 |
| BAA20927 | 195 | 61.6 | 8.00E-09 | 202 | 50 | 24 | AAK15325 | 433 | 55.8 | 5.00E-07 | 132 | 36 | 27 |
| AAK58558 | 202 | 61.2 | 1.00E-08 | 208 | 52 | 25 | AAK15325 | 433 | 36.6 | 2.90E-01 | 167 | 45 | 26 |
| ZP_00237160 | 287 | 60.8 | 1.00E-08 | 243 | 62 | 25 | AAA65584 | 64 | 55.8 | 5.00E-07 | 63 | 27 | 42 |
| AAK58560 | 202 | 60.8 | 1.00E-08 | 208 | 51 | 24 | ZP_00278994 | 407 | 55.5 | 6.00E-07 | 250 | 55 | 22 |
| BAA20929 | 195 | 60.8 | 1.00E-08 | 202 | 50 | 24 | NP_718794 | 403 | 55.1 | 8.00E-07 | 136 | 36 | 26 |
| AAU13836 | 416 | 60.5 | 2.00E-08 | 124 | 36 | 29 | NP_718794 | 403 | 34.3 | 1.40E+00 | 89 | 26 | 29 |
| AAU13836 | 416 | 38.5 | 7.60E-02 | 260 | 55 | 21 | NP_791768 | 530 | 55.1 | 8.00E-07 | 130 | 36 | 27 |
| AAK58557 | 202 | 60.5 | 2.00E-08 | 208 | 50 | 24 | NP_772485 | 757 | 55.1 | 8.00E-07 | 250 | 63 | 25 |
| AAK58548 | 202 | 60.5 | 2.00E-08 | 208 | 50 | 24 | NP_772485 | 757 | 33.9 | 1.90E+00 | 109 | 29 | 26 |
| NP_348828 | 425 | 60.1 | 2.00E-08 | 289 | 65 | 22 | CAB64773 | 399 | 55.1 | 8.00E-07 | 193 | 48 | 24 |
| NP_348828 | 425 | 42.4 | 5.00E-03 | 310 | 69 | 22 | CAB64773 | 399 | 39.7 | 3.40E-02 | 72 | 22 | 30 |
| YP_126585 | 411 | 60.1 | 2.00E-08 | 147 | 39 | 26 | BAA77309 | 94 | 55.1 | 8.00E-07 | 49 | 23 | 46 |
| YP_095257 | 411 | 60.1 | 2.00E-08 | 147 | 39 | 26 | NP_880130 | 510 | 54.7 | 1.00E-06 | 136 | 43 | 31 |
| AAM90638 | 126 | 60.1 | 2.00E-08 | 124 | 41 | 33 | YP_003353 | 422 | 54.7 | 1.00E-06 | 110 | 34 | 30 |
| AAK58547 | 202 | 60.1 | 2.00E-08 | 208 | 49 | 23 | NP_992941 | 337 | 54.3 | 1.00E-06 | 310 | 73 | 23 |
| AAK58550 | 202 | 60.1 | 2.00E-08 | 208 | 49 | 23 | NP_883789 | 510 | 54.3 | 1.00E-06 | 136 | 42 | 30 |
| NP_104151 | 356 | 59.7 | 3.00E-08 | 357 | 81 | 22 | NP_405374 | 326 | 54.3 | 1.00E-06 | 310 | 73 | 23 |
| AAL99376 | 207 | 59.7 | 3.00E-08 | 162 | 42 | 25 | ZP_00212998 | 398 | 54.3 | 1.00E-06 | 111 | 29 | 26 |
| AAM90634 | 126 | 59.7 | 3.00E-08 | 138 | 44 | 31 | NP_799784 | 299 | 53.9 | 2.00E-06 | 258 | 55 | 21 |
| YP_123558 | 411 | 59.3 | 4.00E-08 | 147 | 38 | 25 | NP_772483 | 763 | 53.9 | 2.00E-06 | 186 | 47 | 25 |
| YP_123558 | 411 | 32 | 7.10E+00 | 83 | 25 | 30 | NP_772483 | 763 | 36.2 | 3.80E-01 | 109 | 29 | 26 |
| BAC75963 | 530 | 59.3 | 4.00E-08 | 130 | 38 | 29 | NP_244487 | 395 | 53.9 | 2.00E-06 | 126 | 33 | 26 |
| AAK58545 | 202 | 59.3 | 4.00E-08 | 208 | 49 | 23 | CAA75368 | 168 | 53.9 | 2.00E-06 | 159 | 39 | 24 |
| AAA86521 | 414 | 58.9 | 5.00E-08 | 270 | 64 | 23 | BAA77319 | 121 | 53.9 | 2.00E-06 | 92 | 32 | 34 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| BAA77315 | 123 | 53.9 | 2.00E-06 | 92 | 32 | 34 | YP_040849 | 10746 | 42.4 | 5.00E-03 | 340 | 71 | 20 |
| NP_353593 | 436 | 53.5 | 2.00E-06 | 256 | 59 | 23 | YP_040849 | 10746 | 36.6 | 2.90E-01 | 297 | 58 | 19 |
| NP_353593 | 436 | 46.2 | 4.00E-04 | 140 | 34 | 24 | YP_040849 | 10746 | 36.6 | 2.90E-01 | 332 | 69 | 20 |
| NP_753263 | 317 | 53.5 | 2.00E-06 | 299 | 67 | 22 | YP_040849 | 10746 | 35.8 | 4.90E-01 | 301 | 63 | 20 |
| NP_531268 | 430 | 53.5 | 2.00E-06 | 256 | 59 | 23 | YP_040849 | 10746 | 33.5 | 2.40E+00 | 279 | 55 | 19 |
| NP_531268 | 430 | 46.2 | 4.00E-04 | 140 | 34 | 24 | YP_040849 | 10746 | 33.1 | 3.20E+00 | 317 | 68 | 21 |
| AAB81421 | 395 | 53.5 | 2.00E-06 | 232 | 54 | 23 | YP_040849 | 10746 | 31.6 | 9.30E+00 | 297 | 57 | 19 |
| AAB81421 | 395 | 40 | 2.60E-02 | 87 | 24 | 27 | AAB81423 | 395 | 48.5 | 7.00E-05 | 285 | 66 | 23 |
| BAA77301 | 123 | 53.5 | 2.00E-06 | 108 | 33 | 30 | AAB81423 | 395 | 45.1 | 8.00E-04 | 146 | 38 | 26 |
| ZP_00317213 | 517 | 53.1 | 3.00E-06 | 100 | 31 | 31 | 1ORY | 55 | 48.5 | 7.00E-05 | 50 | 24 | 48 |
| ZP_00317213 | 517 | 40 | 2.60E-02 | 91 | 24 | 26 | ZP_00167907 | 404 | 48.5 | 7.00E-05 | 121 | 37 | 30 |
| ZP_00273669 | 412 | 52.8 | 4.00E-06 | 311 | 67 | 21 | ZP_00167907 | 404 | 35.4 | 6.40E-01 | 99 | 23 | 23 |
| ZP_00273669 | 412 | 35.8 | 4.90E-01 | 146 | 35 | 23 | AAB69136 | 37 | 48.5 | 7.00E-05 | 36 | 23 | 63 |
| ZP_00056435 | 521 | 52.8 | 4.00E-06 | 185 | 40 | 21 | AAG14365 | 411 | 48.1 | 1.00E-04 | 207 | 51 | 24 |
| NP_384777 | 401 | 52.8 | 4.00E-06 | 189 | 48 | 25 | AAG14365 | 411 | 42.4 | 5.00E-03 | 116 | 27 | 23 |
| NP_384777 | 401 | 40 | 2.60E-02 | 87 | 24 | 27 | NP_384776 | 394 | 47.8 | 1.00E-04 | 137 | 34 | 24 |
| AAQ63645 | 159 | 52.4 | 5.00E-06 | 150 | 40 | 26 | NP_384776 | 394 | 45.8 | 5.00E-04 | 245 | 56 | 22 |
| NP_415601 | 317 | 52 | 7.00E-06 | 305 | 70 | 22 | AAF34780 | 3381 | 47.8 | 1.00E-04 | 286 | 55 | 19 |
| AAQ62964 | 145 | 52 | 7.00E-06 | 144 | 38 | 26 | AAF34780 | 3381 | 45.1 | 8.00E-04 | 295 | 58 | 19 |
| NP_421770 | 424 | 52 | 7.00E-06 | 164 | 35 | 21 | AAF34780 | 3381 | 44.7 | 1.00E-03 | 274 | 50 | 18 |
| CAA75363 | 168 | 52 | 7.00E-06 | 159 | 38 | 23 | AAF34780 | 3381 | 42.7 | 4.00E-03 | 285 | 51 | 17 |
| AAG55829 | 317 | 51.6 | 9.00E-06 | 299 | 66 | 22 | AAF34780 | 3381 | 41.2 | 1.20E-02 | 300 | 56 | 18 |
| NP_967522 | 361 | 51.6 | 9.00E-06 | 178 | 44 | 24 | AAF34780 | 3381 | 39.7 | 3.40E-02 | 278 | 48 | 17 |
| YP_066426 | 757 | 51.6 | 9.00E-06 | 130 | 40 | 30 | BAA05156 | 24 | 47.8 | 1.00E-04 | 24 | 24 | 100 |
| AAM27194 | 181 | 51.6 | 9.00E-06 | 181 | 44 | 24 | NP_562800 | 451 | 47.4 | 2.00E-04 | 220 | 53 | 24 |
| BAA77303 | 156 | 51.6 | 9.00E-06 | 88 | 27 | 30 | NP_455677 | 317 | 47.4 | 2.00E-04 | 140 | 38 | 27 |
| B32808 | 396 | 51.2 | 1.00E-05 | 285 | 66 | 23 | NP_646141 | 9904 | 47 | 2.00E-04 | 306 | 64 | 20 |
| B32808 | 396 | 42 | 7.00E-03 | 87 | 23 | 26 | NP_646141 | 9904 | 43.1 | 3.00E-03 | 153 | 36 | 23 |
| YP_111446 | 2634 | 51.2 | 1.00E-05 | 287 | 60 | 20 | NP_646141 | 9904 | 39.7 | 3.40E-02 | 332 | 71 | 21 |
| YP_111446 | 2634 | 50.8 | 1.00E-05 | 281 | 59 | 20 | NP_646141 | 9904 | 39.3 | 4.40E-02 | 283 | 66 | 23 |
| YP_111446 | 2634 | 47 | 2.00E-04 | 296 | 63 | 21 | NP_646141 | 9904 | 38.1 | 9.90E-02 | 279 | 56 | 20 |
| YP_111446 | 2634 | 46.2 | 4.00E-04 | 291 | 60 | 20 | NP_646141 | 9904 | 35.4 | 6.40E-01 | 317 | 66 | 20 |
| YP_111446 | 2634 | 45.1 | 8.00E-04 | 292 | 58 | 19 | NP_646141 | 9904 | 33.9 | 1.90E+00 | 297 | 57 | 19 |
| YP_111446 | 2634 | 43.5 | 2.00E-03 | 284 | 58 | 20 | AAQ73340 | 142 | 47 | 2.00E-04 | 132 | 36 | 27 |
| YP_111446 | 2634 | 43.5 | 2.00E-03 | 283 | 58 | 20 | YP_012160 | 282 | 47 | 2.00E-04 | 223 | 53 | 23 |
| YP_111446 | 2634 | 43.5 | 2.00E-03 | 289 | 59 | 20 | AAB21164 | 31 | 47 | 2.00E-04 | 31 | 24 | 77 |
| YP_111446 | 2634 | 43.1 | 3.00E-03 | 292 | 59 | 20 | NP_249778 | 439 | 46.6 | 3.00E-04 | 134 | 34 | 25 |
| YP_111446 | 2634 | 42 | 7.00E-03 | 281 | 63 | 22 | NP_249778 | 439 | 32 | 7.10E+00 | 257 | 50 | 19 |
| YP_111446 | 2634 | 40 | 2.60E-02 | 295 | 59 | 20 | ZP_00138675 | 439 | 46.6 | 3.00E-04 | 134 | 34 | 25 |
| YP_111446 | 2634 | 40 | 2.60E-02 | 298 | 59 | 19 | ZP_00314296 | 822 | 46.2 | 4.00E-04 | 257 | 54 | 21 |
| YP_111446 | 2634 | 39.3 | 4.40E-02 | 302 | 59 | 19 | NP_223759 | 267 | 46.2 | 4.00E-04 | 149 | 40 | 26 |
| YP_111446 | 2634 | 38.9 | 5.80E-02 | 263 | 53 | 18 | YP_108306 | 1606 | 46.2 | 4.00E-04 | 296 | 66 | 22 |
| YP_111446 | 2634 | 37.4 | 1.70E-01 | 278 | 48 | 17 | YP_108306 | 1606 | 38.1 | 9.90E-02 | 281 | 57 | 20 |
| YP_111446 | 2634 | 35.8 | 4.90E-01 | 235 | 50 | 21 | YP_108306 | 1606 | 38.1 | 9.90E-02 | 228 | 54 | 23 |
| YP_105520 | 459 | 51.2 | 1.00E-05 | 248 | 57 | 22 | YP_108306 | 1606 | 38.1 | 9.90E-02 | 309 | 60 | 19 |
| YP_105520 | 459 | 41.6 | 9.00E-03 | 298 | 60 | 20 | YP_108306 | 1606 | 37.4 | 1.70E-01 | 256 | 68 | 22 |
| YP_027819 | 207 | 51.2 | 1.00E-05 | 115 | 30 | 26 | AAK97535 | 140 | 46.2 | 4.00E-04 | 126 | 35 | 27 |
| NP_866849 | 651 | 51.2 | 1.00E-05 | 129 | 34 | 26 | CAC84733 | 78 | 46.2 | 4.00E-04 | 71 | 25 | 35 |
| NP_947642 | 935 | 50.8 | 1.00E-05 | 284 | 70 | 24 | CAC84731 | 78 | 46.2 | 4.00E-04 | 71 | 25 | 35 |
| NP_947642 | 935 | 34.3 | 1.40E+00 | 93 | 22 | 23 | AAB69371 | 89 | 46.2 | 4.00E-04 | 78 | 21 | 26 |
| NP_949266 | 888 | 50.8 | 1.00E-05 | 284 | 69 | 24 | AAB69370 | 89 | 46.2 | 4.00E-04 | 77 | 21 | 27 |
| NP_949266 | 888 | 38.9 | 5.80E-02 | 305 | 63 | 20 | ZP_00290372 | 765 | 45.8 | 5.00E-04 | 280 | 56 | 20 |
| YP_009743 | 523 | 50.4 | 2.00E-05 | 123 | 32 | 26 | CAA75373 | 158 | 45.8 | 5.00E-04 | 139 | 33 | 23 |
| YP_009743 | 523 | 33.9 | 1.90E+00 | 171 | 36 | 21 | CAA75370 | 154 | 45.8 | 5.00E-04 | 139 | 33 | 23 |
| ZP_00129084 | 282 | 50.4 | 2.00E-05 | 285 | 68 | 23 | CAA75369 | 159 | 45.8 | 5.00E-04 | 139 | 33 | 23 |
| NP_282040 | 750 | 50.1 | 3.00E-05 | 129 | 36 | 27 | NP_267773 | 1072 | 45.4 | 6.00E-04 | 287 | 53 | 18 |
| NP_282040 | 750 | 41.6 | 9.00E-03 | 229 | 48 | 20 | NP_267773 | 1072 | 33.5 | 2.40E+00 | 91 | 21 | 23 |
| ZP_00242042 | 398 | 49.7 | 3.00E-05 | 215 | 53 | 24 | AAQ64681 | 134 | 45.4 | 6.00E-04 | 132 | 35 | 26 |
| ZP_00242042 | 398 | 39.7 | 3.40E-02 | 140 | 35 | 25 | NP_228520 | 407 | 45.4 | 6.00E-04 | 290 | 63 | 21 |
| AAS66690 | 430 | 49.3 | 4.00E-05 | 134 | 34 | 25 | ZP_00323079 | 2334 | 45.4 | 6.00E-04 | 274 | 50 | 18 |
| AAS66690 | 430 | 48.5 | 7.00E-05 | 130 | 33 | 25 | ZP_00323079 | 2334 | 39.7 | 3.40E-02 | 276 | 49 | 17 |
| BAA77305 | 78 | 48.9 | 6.00E-05 | 74 | 28 | 37 | ZP_00323079 | 2334 | 39.3 | 4.40E-02 | 293 | 54 | 18 |
| ZP_00263356 | 523 | 48.5 | 7.00E-05 | 162 | 43 | 26 | ZP_00323079 | 2334 | 38.5 | 7.60E-02 | 294 | 53 | 18 |
| ZP_00263356 | 523 | 35 | 8.40E-01 | 106 | 23 | 21 | ZP_00323079 | 2334 | 37 | 2.20E-01 | 280 | 52 | 18 |
| NP_460155 | 317 | 48.5 | 7.00E-05 | 140 | 38 | 27 | ZP_00323079 | 2334 | 34.7 | 1.10E+00 | 261 | 50 | 19 |
| YP_150904 | 317 | 48.5 | 7.00E-05 | 140 | 38 | 27 | CAA75376 | 163 | 45.4 | 6.00E-04 | 139 | 33 | 23 |
| YP_128296 | 304 | 48.5 | 7.00E-05 | 293 | 53 | 18 | CAA75374 | 155 | 45.4 | 6.00E-04 | 139 | 33 | 23 |
| YP_040849 | 10746 | 48.5 | 7.00E-05 | 303 | 63 | 20 | CAA75372 | 159 | 45.4 | 6.00E-04 | 139 | 33 | 23 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| CAA75367 | 154 | 45.4 | 6.00E-04 | 139 | 33 | 23 | ZP_00326048609 | | 43.1 | 3.00E-03 | 273 | 63 | 23 |
| CAA75365 | 157 | 45.4 | 6.00E-04 | 139 | 33 | 23 | ZP_00326048609 | | 32 | 7.10E+00 | 99 | 20 | 20 |
| CAA75364 | 159 | 45.4 | 6.00E-04 | 139 | 33 | 23 | CAA36029 | 21 | 43.1 | 3.00E-03 | 21 | 21 | 100 |
| AAD25047 | 156 | 45.4 | 6.00E-04 | 143 | 36 | 25 | ZP_00051799172 | | 43.1 | 3.00E-03 | 136 | 31 | 22 |
| BAA02072 | 24 | 45.1 | 8.00E-04 | 24 | 23 | 95 | AAP48611 | 107 | 43.1 | 3.00E-03 | 91 | 27 | 29 |
| YP_111449 | 1530 | 45.1 | 8.00E-04 | 295 | 64 | 21 | NP_207286 | 295 | 43.1 | 3.00E-03 | 150 | 42 | 28 |
| YP_111449 | 1530 | 44.7 | 1.00E-03 | 292 | 64 | 21 | NP_936893 | 989 | 43.1 | 3.00E-03 | 289 | 63 | 21 |
| YP_111449 | 1530 | 44.3 | 1.00E-03 | 278 | 59 | 21 | AAK39533 | 107 | 43.1 | 3.00E-03 | 91 | 27 | 29 |
| YP_111449 | 1530 | 42.7 | 4.00E-03 | 320 | 69 | 21 | AAQ59385 | 302 | 42.7 | 4.00E-03 | 282 | 55 | 19 |
| YP_111449 | 1530 | 41.6 | 9.00E-03 | 288 | 59 | 20 | NP_267008 | 1063 | 42.7 | 4.00E-03 | 291 | 56 | 19 |
| YP_111449 | 1530 | 41.2 | 1.20E-02 | 284 | 60 | 21 | NP_267008 | 1063 | 37 | 2.20E-01 | 231 | 42 | 18 |
| YP_111449 | 1530 | 40 | 2.60E-02 | 250 | 51 | 20 | NP_267008 | 1063 | 36.6 | 2.90E-01 | 281 | 63 | 22 |
| YP_111449 | 1530 | 37.7 | 1.30E-01 | 250 | 50 | 20 | YP_042074 | 1351 | 42.7 | 4.00E-03 | 304 | 59 | 19 |
| YP_111449 | 1530 | 37 | 2.20E-01 | 263 | 52 | 19 | CAA61527 | 436 | 42.7 | 4.00E-03 | 99 | 27 | 27 |
| YP_111449 | 1530 | 34.7 | 1.10E+00 | 257 | 55 | 21 | AAK39530 | 107 | 42.7 | 4.00E-03 | 81 | 26 | 32 |
| CAA75375 | 151 | 45.1 | 8.00E-04 | 139 | 33 | 23 | AAB69368 | 89 | 42.7 | 4.00E-03 | 77 | 20 | 25 |
| CAA61528 | 436 | 45.1 | 8.00E-04 | 105 | 29 | 27 | NP_939992 | 1254 | 42.4 | 5.00E-03 | 169 | 38 | 22 |
| AAF67137 | 159 | 45.1 | 8.00E-04 | 146 | 37 | 25 | YP_105401 | 1535 | 42.4 | 5.00E-03 | 300 | 63 | 21 |
| NP_949252 | 886 | 44.7 | 1.00E-03 | 194 | 49 | 25 | YP_105401 | 1535 | 36.2 | 3.80E-01 | 307 | 64 | 20 |
| NP_949252 | 886 | 33.9 | 1.90E+00 | 102 | 25 | 24 | YP_105401 | 1535 | 35.8 | 4.90E-01 | 217 | 46 | 21 |
| YP_155526 | 404 | 44.7 | 1.00E-03 | 130 | 35 | 26 | YP_065260 | 567 | 42.4 | 5.00E-03 | 263 | 54 | 20 |
| YP_155526 | 404 | 32 | 7.10E+00 | 196 | 41 | 20 | NP_906736 | 866 | 42.4 | 5.00E-03 | 168 | 37 | 22 |
| NP_929192 | 321 | 44.7 | 1.00E-03 | 318 | 74 | 23 | ZP_001432362005 | | 42.4 | 5.00E-03 | 256 | 59 | 23 |
| NP_647392 | 2275 | 44.7 | 1.00E-03 | 287 | 53 | 18 | AAK39535 | 107 | 42.4 | 5.00E-03 | 81 | 25 | 30 |
| NP_647392 | 2275 | 34.3 | 1.40E+00 | 216 | 42 | 19 | AAK39534 | 107 | 42.4 | 5.00E-03 | 81 | 25 | 30 |
| NP_647392 | 2275 | 34.3 | 1.40E+00 | 299 | 60 | 20 | AAB69365 | 89 | 42.4 | 5.00E-03 | 77 | 20 | 25 |
| NP_371958 | 6713 | 44.7 | 1.00E-03 | 303 | 61 | 20 | NP_523179 | 1309 | 42 | 7.00E-03 | 264 | 60 | 22 |
| NP_371958 | 6713 | 42 | 7.00E-03 | 153 | 36 | 23 | NP_523179 | 1309 | 36.2 | 3.80E-01 | 260 | 56 | 21 |
| NP_371958 | 6713 | 41.2 | 1.20E-02 | 332 | 72 | 21 | NP_523179 | 1309 | 35.8 | 4.90E-01 | 247 | 57 | 23 |
| NP_371958 | 6713 | 35.4 | 6.40E-01 | 276 | 53 | 19 | AAF95046 | 672 | 42 | 7.00E-03 | 320 | 64 | 20 |
| NP_371958 | 6713 | 33.1 | 3.20E+00 | 297 | 57 | 19 | NP_488975 | 661 | 42 | 7.00E-03 | 268 | 63 | 23 |
| AAP48612 | 107 | 44.7 | 1.00E-03 | 94 | 24 | 25 | NP_784110 | 1377 | 42 | 7.00E-03 | 285 | 64 | 22 |
| NP_374548 | 6713 | 44.7 | 1.00E-03 | 303 | 61 | 20 | AAL58470 | 2283 | 42 | 7.00E-03 | 299 | 55 | 18 |
| NP_374548 | 6713 | 42 | 7.00E-03 | 153 | 36 | 23 | AAL58470 | 2283 | 35.4 | 6.40E-01 | 269 | 58 | 21 |
| NP_374548 | 6713 | 41.2 | 1.20E-02 | 332 | 72 | 21 | AAL58470 | 2283 | 33.9 | 1.90E+00 | 285 | 52 | 18 |
| NP_374548 | 6713 | 35.4 | 6.40E-01 | 276 | 53 | 19 | AAL58470 | 2283 | 33.5 | 2.40E+00 | 270 | 44 | 16 |
| NP_374548 | 6713 | 33.1 | 3.20E+00 | 297 | 57 | 19 | AAQ97872 | 309 | 41.6 | 9.00E-03 | 306 | 71 | 23 |
| YP_106908 | 410 | 44.7 | 1.00E-03 | 124 | 28 | 22 | YP_129124 | 396 | 41.6 | 9.00E-03 | 119 | 25 | 21 |
| YP_044654 | 2275 | 44.7 | 1.00E-03 | 287 | 53 | 18 | CAC84729 | 68 | 41.6 | 9.00E-03 | 65 | 24 | 36 |
| YP_044654 | 2275 | 34.3 | 1.40E+00 | 216 | 42 | 19 | AAA27074 | 20 | 41.6 | 9.00E-03 | 20 | 20 | 100 |
| AAF67139 | 159 | 44.7 | 1.00E-03 | 146 | 37 | 25 | AAB69357 | 89 | 41.6 | 9.00E-03 | 74 | 24 | 32 |
| AAK39536 | 107 | 44.7 | 1.00E-03 | 94 | 24 | 25 | ZP_00089080401 | | 41.6 | 9.00E-03 | 122 | 36 | 29 |
| AAK39541 | 107 | 44.7 | 1.00E-03 | 94 | 24 | 25 | ZP_00089080401 | | 38.5 | 7.60E-02 | 139 | 36 | 25 |
| AAA27080 | 284 | 44.3 | 1.00E-03 | 30 | 21 | 70 | NP_465811 | 1787 | 41.2 | 1.20E-02 | 268 | 58 | 21 |
| AAA27080 | 284 | 37.4 | 1.70E-01 | 31 | 18 | 58 | ZP_002143701439 | | 41.2 | 1.20E-02 | 297 | 72 | 24 |
| YP_110805 | 1653 | 44.3 | 1.00E-03 | 269 | 58 | 22 | ZP_002143701439 | | 32.3 | 5.40E+00 | 272 | 56 | 20 |
| YP_110805 | 1653 | 40 | 2.60E-02 | 254 | 56 | 22 | AAB69377 | 89 | 41.2 | 1.20E-02 | 74 | 23 | 31 |
| YP_110805 | 1653 | 37 | 2.20E-01 | 287 | 58 | 20 | AAP07456 | 953 | 40.8 | 1.50E-02 | 263 | 49 | 18 |
| YP_110805 | 1653 | 36.2 | 3.80E-01 | 274 | 56 | 20 | CAA90950 | 20 | 40.8 | 1.50E-02 | 20 | 20 | 100 |
| YP_110805 | 1653 | 34.7 | 1.10E+00 | 265 | 52 | 19 | AAS91596 | 44 | 40.8 | 1.50E-02 | 38 | 18 | 47 |
| CAA75371 | 159 | 44.3 | 1.00E-03 | 139 | 33 | 23 | ZP_00063096901 | | 40.8 | 1.50E-02 | 241 | 60 | 24 |
| AAD21057 | 4545 | 44.3 | 1.00E-03 | 228 | 52 | 22 | NP_251152 | 5627 | 40.4 | 2.00E-02 | 329 | 67 | 20 |
| ZP_001627551140 | | 44.3 | 1.00E-03 | 295 | 62 | 21 | NP_251152 | 5627 | 34.3 | 1.40E+00 | 235 | 50 | 21 |
| T30822 | 1365 | 44.3 | 1.00E-03 | 284 | 53 | 18 | NP_251152 | 5627 | 32.7 | 4.20E+00 | 312 | 60 | 19 |
| AAF94608 | 4558 | 43.9 | 2.00E-03 | 228 | 52 | 22 | AAM90995 | 3692 | 40.4 | 2.00E-02 | 278 | 64 | 23 |
| CAA57229 | 962 | 43.9 | 2.00E-03 | 284 | 53 | 18 | AAM90995 | 3692 | 39.3 | 4.40E-02 | 321 | 76 | 23 |
| CAA57228 | 1344 | 43.9 | 2.00E-03 | 284 | 53 | 18 | AAS91595 | 44 | 40.4 | 2.00E-02 | 38 | 18 | 47 |
| CAA57228 | 1344 | 43.9 | 2.00E-03 | 284 | 53 | 18 | AAB69376 | 89 | 40.4 | 2.00E-02 | 64 | 21 | 32 |
| CAA57228 | 1344 | 43.5 | 2.00E-03 | 284 | 53 | 18 | AAB69369 | 89 | 40.4 | 2.00E-02 | 64 | 21 | 32 |
| CAA57228 | 1344 | 43.1 | 3.00E-03 | 269 | 50 | 18 | AAB69354 | 89 | 40.4 | 2.00E-02 | 64 | 21 | 32 |
| AAK39539 | 107 | 43.9 | 2.00E-03 | 94 | 24 | 25 | ZP_00288079749 | | 40 | 2.60E-02 | 236 | 51 | 21 |
| AAB69366 | 89 | 43.9 | 2.00E-03 | 77 | 21 | 27 | AAA92491 | 20 | 40 | 2.60E-02 | 20 | 18 | 90 |
| AAA81014 | 716 | 43.9 | 2.00E-03 | 284 | 53 | 18 | YP_142319 | 789 | 40 | 2.60E-02 | 302 | 64 | 21 |
| AAA81014 | 716 | 43.1 | 3.00E-03 | 269 | 50 | 18 | YP_140402 | 710 | 40 | 2.60E-02 | 302 | 64 | 21 |
| CAF74791 | 410 | 43.9 | 2.00E-03 | 224 | 46 | 21 | NP_373178 | 2271 | 40 | 2.60E-02 | 287 | 52 | 18 |
| AAP48610 | 107 | 43.5 | 2.00E-03 | 91 | 28 | 30 | NP_373178 | 2271 | 34.3 | 1.40E+00 | 216 | 42 | 19 |
| AAP48609 | 107 | 43.5 | 2.00E-03 | 91 | 28 | 30 | NP_373178 | 2271 | 32 | 7.10E+00 | 303 | 62 | 20 |
| AAB69367 | 89 | 43.5 | 2.00E-03 | 77 | 20 | 25 | AAO08483 | 623 | 40 | 2.60E-02 | 114 | 31 | 27 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| YP_114536 | 437 | 40 | 2.60E-02 | 83 | 27 | 32 | NP_419715 | 307 | 38.1 | 9.90E-02 | 73 | 21 | 28 |
| YP_034700 | 953 | 40 | 2.60E-02 | 301 | 58 | 19 | NP_207906 | 228 | 38.1 | 9.90E-02 | 110 | 32 | 29 |
| NP_936493 | 623 | 40 | 2.60E-02 | 114 | 31 | 27 | ZP_003235731130 | | 38.1 | 9.90E-02 | 292 | 65 | 22 |
| NP_764683 | 9439 | 40 | 2.60E-02 | 130 | 27 | 20 | ZP_003235731130 | | 32.3 | 5.40E+00 | 281 | 57 | 20 |
| NP_764683 | 9439 | 38.5 | 7.60E-02 | 169 | 43 | 25 | ZP_00317192676 | | 37.7 | 1.30E-01 | 169 | 35 | 20 |
| NP_764683 | 9439 | 36.2 | 3.80E-01 | 265 | 55 | 20 | CAA60556 | 61 | 37.7 | 1.30E-01 | 43 | 16 | 37 |
| NP_764683 | 9439 | 36.2 | 3.80E-01 | 288 | 61 | 21 | NP_771092 | 696 | 37.7 | 1.30E-01 | 134 | 39 | 29 |
| NP_764683 | 9439 | 36.2 | 3.80E-01 | 255 | 48 | 18 | NP_214145 | 422 | 37.7 | 1.30E-01 | 186 | 40 | 21 |
| NP_764683 | 9439 | 35.4 | 6.40E-01 | 316 | 61 | 19 | NP_765958 | 681 | 37.7 | 1.30E-01 | 176 | 45 | 25 |
| NP_764683 | 9439 | 34.7 | 1.10E+00 | 302 | 60 | 19 | ZP_003125671475 | | 37.7 | 1.30E-01 | 273 | 58 | 21 |
| NP_764683 | 9439 | 33.9 | 1.90E+00 | 314 | 65 | 20 | ZP_00240971564 | | 37.7 | 1.30E-01 | 107 | 24 | 22 |
| NP_764683 | 9439 | 33.9 | 1.90E+00 | 146 | 40 | 27 | ZP_00195263572 | | 37.7 | 1.30E-01 | 183 | 41 | 22 |
| NP_764683 | 9439 | 33.1 | 3.20E+00 | 181 | 46 | 25 | BAD13429 | 718 | 37.7 | 1.30E-01 | 89 | 18 | 20 |
| NP_764683 | 9439 | 33.1 | 3.20E+00 | 151 | 38 | 25 | AAB19816 | 20 | 37.7 | 1.30E-01 | 20 | 18 | 90 |
| NP_764683 | 9439 | 32.3 | 5.40E+00 | 329 | 68 | 20 | NP_949268 | 623 | 37.4 | 1.70E-01 | 277 | 53 | 19 |
| NP_764683 | 9439 | 31.6 | 9.30E+00 | 292 | 53 | 18 | ZP_00315446537 | | 37.4 | 1.70E-01 | 263 | 54 | 20 |
| AAN08647 | 402 | 39.7 | 3.40E-02 | 148 | 34 | 22 | ZP_0028945115245 | | 37.4 | 1.70E-01 | 272 | 65 | 23 |
| ZP_00123691638 | | 39.7 | 3.40E-02 | 352 | 74 | 21 | ZP_00273576527 | | 37.4 | 1.70E-01 | 90 | 25 | 27 |
| ZP_000642471003 | | 39.7 | 3.40E-02 | 307 | 71 | 23 | ZP_00273576527 | | 33.9 | 1.90E+00 | 83 | 22 | 26 |
| AAC09051 | 130 | 39.7 | 3.40E-02 | 97 | 26 | 26 | NP_800021 | 623 | 37.4 | 1.70E-01 | 117 | 31 | 26 |
| AAC09050 | 130 | 39.7 | 3.40E-02 | 97 | 26 | 26 | NP_772493 | 627 | 37.4 | 1.70E-01 | 229 | 49 | 21 |
| AAC09048 | 130 | 39.7 | 3.40E-02 | 97 | 26 | 26 | AAP78292 | 855 | 37.4 | 1.70E-01 | 138 | 32 | 23 |
| AAB62741 | 425 | 39.7 | 3.40E-02 | 136 | 34 | 25 | ZP_00281310507 | | 37.4 | 1.70E-01 | 119 | 31 | 26 |
| AAB62741 | 425 | 32 | 7.10E+00 | 78 | 18 | 23 | ZP_00289133779 | | 37 | 2.20E-01 | 198 | 38 | 19 |
| AAR21284 | 163 | 39.7 | 3.40E-02 | 97 | 26 | 26 | ZP_00289133779 | | 36.2 | 3.80E-01 | 89 | 26 | 29 |
| AAR21282 | 161 | 39.7 | 3.40E-02 | 97 | 26 | 26 | NP_471790 | 927 | 37 | 2.20E-01 | 281 | 59 | 20 |
| ZP_00319871233 | | 39.3 | 4.40E-02 | 139 | 37 | 26 | NP_471790 | 927 | 31.6 | 9.30E+00 | 210 | 46 | 21 |
| NP_908061 | 118 | 39.3 | 4.40E-02 | 103 | 29 | 28 | NP_522634 | 3322 | 37 | 2.20E-01 | 228 | 52 | 22 |
| ZP_002335911787 | | 39.3 | 4.40E-02 | 261 | 60 | 22 | NP_404364 | 307 | 37 | 2.20E-01 | 253 | 52 | 20 |
| AAC09046 | 130 | 39.3 | 4.40E-02 | 97 | 26 | 26 | NP_336479 | 342 | 37 | 2.20E-01 | 87 | 25 | 28 |
| 1QOY | 318 | 39.3 | 4.40E-02 | 77 | 27 | 35 | NP_248731 | 3535 | 37 | 2.20E-01 | 286 | 62 | 21 |
| NP_798012 | 3240 | 38.9 | 5.80E-02 | 269 | 58 | 21 | YP_066441 | 693 | 37 | 2.20E-01 | 120 | 30 | 25 |
| YP_015833 | 662 | 38.9 | 5.80E-02 | 167 | 43 | 25 | NP_757754 | 161 | 37 | 2.20E-01 | 77 | 23 | 29 |
| ZP_002814314726 | | 38.9 | 5.80E-02 | 310 | 62 | 20 | NP_670743 | 308 | 37 | 2.20E-01 | 253 | 52 | 20 |
| ZP_002814314726 | | 38.1 | 9.90E-02 | 308 | 61 | 19 | NP_603291 | 1724 | 37 | 2.20E-01 | 131 | 34 | 25 |
| ZP_002814314726 | | 37.4 | 1.70E-01 | 272 | 54 | 19 | ZP_00290800910 | | 37 | 2.20E-01 | 260 | 53 | 20 |
| ZP_002814314726 | | 36.6 | 2.90E-01 | 275 | 56 | 20 | ZP_00219646252 | | 37 | 2.20E-01 | 74 | 21 | 28 |
| ZP_002814314726 | | 36.6 | 2.90E-01 | 254 | 53 | 20 | ZP_00063136721 | | 37 | 2.20E-01 | 298 | 58 | 19 |
| ZP_002814314726 | | 35.4 | 6.40E-01 | 279 | 55 | 19 | NP_799785 | 346 | 36.6 | 2.90E-01 | 116 | 29 | 25 |
| ZP_002814314726 | | 35 | 8.40E-01 | 319 | 59 | 18 | NP_739300 | 290 | 36.6 | 2.90E-01 | 122 | 30 | 24 |
| ZP_002814314726 | | 34.3 | 1.40E+00 | 324 | 59 | 18 | AAP96352 | 1119 | 36.6 | 2.90E-01 | 143 | 35 | 24 |
| ZP_00211493472 | | 38.9 | 5.80E-02 | 274 | 60 | 21 | NP_359656 | 1902 | 36.6 | 2.90E-01 | 282 | 60 | 21 |
| ZP_002047941979 | | 38.9 | 5.80E-02 | 235 | 47 | 20 | NP_253231 | 1417 | 36.6 | 2.90E-01 | 201 | 49 | 24 |
| ZP_002047941979 | | 34.7 | 1.10E+00 | 235 | 50 | 21 | NP_932208 | 603 | 36.6 | 2.90E-01 | 53 | 17 | 32 |
| ZP_002047941979 | | 33.1 | 3.20E+00 | 312 | 61 | 19 | CAA60548 | 61 | 36.6 | 2.90E-01 | 43 | 15 | 34 |
| AAC43555 | 35 | 38.9 | 5.80E-02 | 34 | 21 | 61 | AAT28336 | 160 | 36.6 | 2.90E-01 | 166 | 34 | 20 |
| ZP_00208729459 | | 38.5 | 0.076 | 278 | 63 | 22 | AAT28335 | 160 | 36.6 | 2.90E-01 | 166 | 34 | 20 |
| NP_928380 | 567 | 38.5 | 0.076 | 257 | 58 | 22 | AAT28333 | 160 | 36.6 | 2.90E-01 | 166 | 34 | 20 |
| YP_115646 | 750 | 38.5 | 7.60E-02 | 144 | 32 | 22 | ZP_00218988486 | | 36.6 | 2.90E-01 | 259 | 56 | 21 |
| YP_087940 | 5399 | 38.5 | 7.60E-02 | 312 | 72 | 23 | ZP_00149774452 | | 36.6 | 2.90E-01 | 264 | 56 | 21 |
| YP_087940 | 5399 | 37.4 | 1.70E-01 | 256 | 45 | 17 | AAP34183 | 119 | 36.6 | 2.90E-01 | 115 | 31 | 26 |
| YP_087940 | 5399 | 37.4 | 1.70E-01 | 256 | 45 | 17 | ZP_00319246821 | | 36.2 | 3.80E-01 | 65 | 19 | 29 |
| YP_087940 | 5399 | 36.2 | 3.80E-01 | 273 | 58 | 21 | ZP_00284479601 | | 36.2 | 3.80E-01 | 262 | 52 | 19 |
| YP_087940 | 5399 | 36.2 | 3.80E-01 | 273 | 58 | 21 | ZP_00005278425 | | 36.2 | 3.80E-01 | 193 | 50 | 25 |
| YP_087940 | 5399 | 35.8 | 4.90E-01 | 274 | 61 | 22 | NP_522101 | 3552 | 36.2 | 3.80E-01 | 209 | 45 | 21 |
| YP_087940 | 5399 | 35 | 8.40E-01 | 294 | 58 | 19 | NP_964415 | 1096 | 36.2 | 3.80E-01 | 265 | 56 | 21 |
| YP_087940 | 5399 | 33.9 | 1.90E+00 | 289 | 57 | 19 | AAG31286 | 1363 | 36.2 | 3.80E-01 | 193 | 50 | 25 |
| YP_087940 | 5399 | 33.5 | 2.40E+00 | 289 | 57 | 19 | ZP_00313063880 | | 36.2 | 3.80E-01 | 181 | 39 | 21 |
| NP_781518 | 518 | 38.5 | 7.60E-02 | 302 | 64 | 21 | AAT28334 | 160 | 36.2 | 3.80E-01 | 166 | 34 | 20 |
| AAM46179 | 146 | 38.5 | 7.60E-02 | 95 | 25 | 26 | ZP_00182337425 | | 36.2 | 3.80E-01 | 245 | 41 | 16 |
| AAM46178 | 147 | 38.5 | 7.60E-02 | 95 | 25 | 26 | ZP_00160617717 | | 36.2 | 3.80E-01 | 289 | 62 | 21 |
| CAC51118 | 1564 | 38.5 | 7.60E-02 | 275 | 60 | 21 | ZP_00160617717 | | 31.6 | 9.30E+00 | 248 | 46 | 18 |
| ZP_00213493557 | | 38.5 | 7.60E-02 | 223 | 51 | 22 | ZP_001380311417 | | 36.2 | 3.80E-01 | 201 | 49 | 24 |
| ZP_00224552561 | | 38.5 | 7.60E-02 | 223 | 53 | 23 | AAR37720 | 394 | 36.2 | 3.80E-01 | 146 | 39 | 26 |
| ZP_00355727801 | | 38.5 | 7.60E-02 | 317 | 71 | 22 | NP_561526 | 1109 | 35.8 | 4.90E-01 | 287 | 53 | 18 |
| ZP_001404443443 | | 38.5 | 7.60E-02 | 286 | 62 | 21 | NP_561526 | 1109 | 32 | 7.10E+00 | 181 | 40 | 22 |
| AAC43560 | 36 | 38.5 | 7.60E-02 | 36 | 19 | 52 | NP_349224 | 664 | 35.8 | 4.90E-01 | 272 | 59 | 21 |
| AAB69373 | 89 | 38.5 | 7.60E-02 | 74 | 22 | 29 | AAP56614 | 499 | 35.8 | 4.90E-01 | 183 | 40 | 21 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| YP_133518 | 665 | 35.8 | 4.90E-01 | 111 | 33 | 29 | NP_695350 | 459 | 34.3 | 1.40E+00 | 271 | 54 | 19 |
| YP_071943 | 3378 | 35.8 | 4.90E-01 | 289 | 61 | 21 | NP_348729 | 570 | 34.3 | 1.40E+00 | 162 | 36 | 22 |
| YP_049813 | 317 | 35.8 | 4.90E-01 | 266 | 61 | 22 | YP_046173 | 335 | 34.3 | 1.40E+00 | 117 | 26 | 22 |
| AAT28337 | 160 | 35.8 | 4.90E-01 | 166 | 34 | 20 | NP_252997 | 632 | 34.3 | 1.40E+00 | 245 | 43 | 17 |
| AAA27141 | 17 | 35.8 | 4.90E-01 | 17 | 17 | 100 | YP_066477 | 393 | 34.3 | 1.40E+00 | 148 | 33 | 22 |
| ZP_00270453 | 727 | 35.4 | 6.40E-01 | 239 | 49 | 20 | YP_064761 | 880 | 34.3 | 1.40E+00 | 126 | 30 | 23 |
| AAQ59977 | 458 | 35.4 | 6.40E-01 | 266 | 61 | 22 | YP_064723 | 674 | 34.3 | 1.40E+00 | 248 | 48 | 19 |
| NP_773497 | 491 | 35.4 | 6.40E-01 | 121 | 28 | 23 | NP_935137 | 626 | 34.3 | 1.40E+00 | 299 | 52 | 17 |
| NP_267038 | 799 | 35.4 | 6.40E-01 | 301 | 71 | 23 | NP_866060 | 3056 | 34.3 | 1.40E+00 | 120 | 34 | 28 |
| NP_478503 | 1487 | 35.4 | 6.40E-01 | 249 | 49 | 19 | NP_866060 | 3056 | 33.1 | 3.20E+00 | 116 | 34 | 29 |
| YP_086339 | 564 | 35.4 | 6.40E-01 | 107 | 23 | 21 | ZP_00323398 | 1656 | 34.3 | 1.4 | 187 | 41 | 21 |
| NP_207948 | 1230 | 35.4 | 6.40E-01 | 292 | 62 | 21 | ZP_00308827 | 366 | 34.3 | 1.40E+00 | 138 | 35 | 25 |
| YP_039058 | 564 | 35.4 | 6.40E-01 | 107 | 23 | 21 | ZP_00137780 | 616 | 34.3 | 1.40E+00 | 245 | 43 | 17 |
| NP_864533 | 7716 | 35.4 | 6.40E-01 | 240 | 52 | 21 | ZP_00124017 | 629 | 34.3 | 1.40E+00 | 254 | 46 | 18 |
| NP_765804 | 2310 | 35.4 | 6.40E-01 | 290 | 52 | 17 | ZP_00110825 | 475 | 34.3 | 1.40E+00 | 140 | 35 | 25 |
| NP_765787 | 676 | 35.4 | 6.40E-01 | 117 | 33 | 28 | ZP_00046942 | 967 | 33.9 | 1.90E+00 | 134 | 35 | 26 |
| ZP_00323296 | 769 | 35.4 | 6.40E-01 | 148 | 35 | 23 | YP_080405 | 660 | 33.9 | 1.90E+00 | 87 | 22 | 25 |
| ZP_00288038 | 997 | 35.4 | 6.40E-01 | 294 | 56 | 19 | NP_470074 | 599 | 33.9 | 1.90E+00 | 288 | 59 | 20 |
| CAE46764 | 510 | 35.4 | 6.40E-01 | 95 | 29 | 30 | NP_927898 | 4582 | 33.9 | 1.90E+00 | 257 | 61 | 23 |
| CAE46762 | 506 | 35.4 | 6.40E-01 | 95 | 29 | 30 | NP_815456 | 533 | 33.9 | 1.90E+00 | 125 | 35 | 28 |
| T08613 | 619 | 35.4 | 6.40E-01 | 173 | 37 | 21 | NP_562046 | 933 | 33.9 | 1.90E+00 | 259 | 51 | 19 |
| AAP34195 | 125 | 35.4 | 6.40E-01 | 129 | 35 | 27 | NP_267826 | 901 | 33.9 | 1.90E+00 | 281 | 56 | 19 |
| ZP_00338261 | 589 | 35 | 8.40E-01 | 62 | 20 | 32 | YP_126425 | 657 | 33.9 | 1.90E+00 | 121 | 29 | 23 |
| NP_718836 | 667 | 35 | 8.40E-01 | 98 | 20 | 20 | YP_131301 | 638 | 33.9 | 1.90E+00 | 73 | 16 | 21 |
| YP_128297 | 361 | 35 | 8.40E-01 | 358 | 69 | 19 | YP_030040 | 660 | 33.9 | 1.90E+00 | 105 | 25 | 23 |
| YP_132326 | 529 | 35 | 8.40E-01 | 332 | 69 | 20 | NP_981473 | 564 | 33.9 | 1.90E+00 | 109 | 24 | 22 |
| NP_812240 | 868 | 35 | 8.40E-01 | 150 | 44 | 29 | NP_784971 | 983 | 33.9 | 1.9 | 299 | 58 | 19 |
| NP_964984 | 4734 | 35 | 8.40E-01 | 316 | 66 | 20 | NP_783077 | 417 | 33.9 | 1.90E+00 | 103 | 24 | 23 |
| NP_964984 | 4734 | 33.1 | 3.20E+00 | 153 | 40 | 26 | NP_965011 | 912 | 33.9 | 1.90E+00 | 214 | 49 | 22 |
| AAN33150 | 434 | 35 | 8.40E-01 | 127 | 35 | 27 | NP_964462 | 1000 | 33.9 | 1.90E+00 | 125 | 28 | 22 |
| ZP_00144637 | 646 | 35 | 8.40E-01 | 243 | 44 | 18 | AAP02960 | 599 | 33.9 | 1.90E+00 | 119 | 30 | 25 |
| ZP_00222048 | 485 | 35 | 8.40E-01 | 88 | 23 | 26 | BAB20920 | 1172 | 33.9 | 1.90E+00 | 283 | 55 | 19 |
| ZP_00220113 | 501 | 35 | 8.40E-01 | 88 | 23 | 26 | ZP_00299115 | 1200 | 33.5 | 2.4 | 61 | 17 | 27 |
| ZP_00137782 | 629 | 35 | 8.40E-01 | 245 | 43 | 17 | ZP_00056271 | 661 | 33.5 | 2.40E+00 | 278 | 54 | 19 |
| ZP_00121836 | 231 | 35 | 8.40E-01 | 165 | 39 | 23 | AAG56007 | 973 | 33.5 | 2.40E+00 | 185 | 42 | 22 |
| AAQ19127 | 2343 | 35 | 8.40E-01 | 239 | 49 | 20 | AAF81209 | 277 | 33.5 | 2.40E+00 | 199 | 45 | 22 |
| NP_946001 | 587 | 34.7 | 1.10E+00 | 121 | 36 | 29 | NP_794375 | 539 | 33.5 | 2.40E+00 | 128 | 23 | 17 |
| ZP_00319892 | 754 | 34.7 | 1.10E+00 | 284 | 62 | 21 | YP_115527 | 534 | 33.5 | 2.40E+00 | 80 | 24 | 30 |
| ZP_00319892 | 754 | 33.1 | 3.20E+00 | 261 | 51 | 19 | AAK93934 | 736 | 33.5 | 2.40E+00 | 89 | 20 | 22 |
| ZP_00311897 | 602 | 34.7 | 1.10E+00 | 269 | 56 | 20 | NP_309677 | 971 | 33.5 | 2.4 | 185 | 42 | 22 |
| YP_160437 | 862 | 34.7 | 1.10E+00 | 68 | 24 | 35 | NP_936396 | 542 | 33.5 | 2.40E+00 | 300 | 62 | 20 |
| ZP_00336629 | 824 | 34.7 | 1.10E+00 | 149 | 35 | 23 | NP_637327 | 396 | 33.5 | 2.40E+00 | 123 | 21 | 17 |
| NP_802026 | 593 | 34.7 | 1.10E+00 | 118 | 33 | 27 | NP_964159 | 982 | 33.5 | 2.40E+00 | 203 | 47 | 23 |
| NP_924800 | 1241 | 34.7 | 1.10E+00 | 73 | 24 | 32 | ZP_00217082 | 977 | 33.5 | 2.40E+00 | 109 | 32 | 29 |
| NP_463823 | 500 | 34.7 | 1.10E+00 | 233 | 47 | 20 | ZP_00106667 | 978 | 33.5 | 2.40E+00 | 112 | 29 | 25 |
| NP_645581 | 946 | 34.7 | 1.10E+00 | 219 | 44 | 20 | AAB21165 | 20 | 33.5 | 2.40E+00 | 20 | 16 | 80 |
| NP_792425 | 633 | 34.7 | 1.10E+00 | 283 | 50 | 17 | BAA23410 | 632 | 33.5 | 2.40E+00 | 229 | 43 | 18 |
| NP_561978 | 344 | 34.7 | 1.10E+00 | 232 | 49 | 21 | ZP_00290912 | 684 | 33.1 | 3.20E+00 | 130 | 24 | 18 |
| NP_350172 | 783 | 34.7 | 1.10E+00 | 129 | 29 | 22 | ZP_00290912 | 684 | 32.3 | 5.40E+00 | 188 | 35 | 18 |
| NP_349191 | 722 | 34.7 | 1.10E+00 | 143 | 36 | 25 | YP_147975 | 435 | 33.1 | 3.20E+00 | 121 | 32 | 26 |
| NP_349191 | 722 | 33.1 | 3.20E+00 | 292 | 57 | 19 | ZP_00338277 | 837 | 33.1 | 3.20E+00 | 109 | 26 | 23 |
| AAO10484 | 626 | 34.7 | 1.10E+00 | 299 | 52 | 17 | AAU01878 | 1363 | 33.1 | 3.20E+00 | 175 | 40 | 22 |
| NP_642322 | 396 | 34.7 | 1.10E+00 | 123 | 22 | 17 | NP_798538 | 678 | 33.1 | 3.20E+00 | 127 | 27 | 21 |
| YP_133410 | 577 | 34.7 | 1.10E+00 | 317 | 61 | 19 | NP_790701 | 498 | 33.1 | 3.20E+00 | 162 | 41 | 25 |
| NP_269527 | 594 | 34.7 | 1.10E+00 | 118 | 33 | 27 | NP_768559 | 816 | 33.1 | 3.20E+00 | 62 | 19 | 30 |
| YP_060520 | 593 | 34.7 | 1.10E+00 | 118 | 33 | 27 | NP_415890 | 1122 | 33.1 | 3.20E+00 | 147 | 37 | 25 |
| YP_042878 | 928 | 34.7 | 1.10E+00 | 219 | 44 | 20 | AAO08482 | 622 | 33.1 | 3.20E+00 | 120 | 30 | 25 |
| YP_012922 | 500 | 34.7 | 1.10E+00 | 233 | 47 | 20 | AAO10918 | 675 | 33.1 | 3.20E+00 | 125 | 29 | 23 |
| NP_051325 | 222 | 34.7 | 1.10E+00 | 114 | 30 | 26 | NP_889112 | 532 | 33.1 | 3.20E+00 | 250 | 48 | 19 |
| NP_782459 | 569 | 34.7 | 1.10E+00 | 305 | 61 | 20 | YP_129467 | 640 | 33.1 | 3.20E+00 | 137 | 31 | 22 |
| NP_607532 | 594 | 34.7 | 1.10E+00 | 118 | 33 | 27 | YP_133516 | 467 | 33.1 | 3.20E+00 | 127 | 26 | 20 |
| ZP_00233976 | 541 | 34.7 | 1.10E+00 | 233 | 47 | 20 | YP_132040 | 542 | 33.1 | 3.20E+00 | 107 | 27 | 25 |
| ZP_00212291 | 306 | 34.7 | 1.10E+00 | 130 | 38 | 29 | YP_076807 | 558 | 33.1 | 3.20E+00 | 118 | 30 | 25 |
| AAK84427 | 542 | 34.7 | 1.10E+00 | 233 | 47 | 20 | NP_253000 | 629 | 33.1 | 3.20E+00 | 245 | 42 | 17 |
| AAA67447 | 232 | 34.7 | 1.10E+00 | 149 | 33 | 22 | YP_063897 | 576 | 33.1 | 3.20E+00 | 263 | 46 | 17 |
| YP_162386 | 564 | 34.3 | 1.40E+00 | 242 | 55 | 22 | YP_041192 | 424 | 33.1 | 3.20E+00 | 147 | 36 | 24 |
| NP_469464 | 1788 | 34.3 | 1.40E+00 | 290 | 65 | 22 | NP_936490 | 622 | 33.1 | 3.20E+00 | 120 | 30 | 25 |
| NP_792292 | 629 | 34.3 | 1.40E+00 | 128 | 31 | 24 | NP_786249 | 1106 | 33.1 | 3.20E+00 | 330 | 64 | 19 |

Fig. 25B-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| NP_777771 | 638 | 33.1 | 3.20E+00 | 121 | 29 | 23 | YP_032604 | 1872 | 32.3 | 5.40E+00 | 118 | 31 | 26 |
| NP_764984 | 3692 | 33.1 | 3.2 | 148 | 30 | 20 | NP_782523 | 471 | 32.3 | 5.40E+00 | 107 | 20 | 18 |
| NP_764984 | 3692 | 32.3 | 5.40E+00 | 264 | 52 | 19 | NP_765908 | 300 | 32.3 | 5.40E+00 | 132 | 29 | 21 |
| NP_600104 | 441 | 33.1 | 3.20E+00 | 280 | 63 | 22 | NP_765785 | 952 | 32.3 | 5.40E+00 | 195 | 37 | 18 |
| NP_693909 | 466 | 33.1 | 3.20E+00 | 126 | 24 | 19 | NP_606940 | 628 | 32.3 | 5.40E+00 | 271 | 60 | 22 |
| NP_608047 | 400 | 33.1 | 3.20E+00 | 108 | 29 | 26 | CAF32691 | 1828 | 32.3 | 5.40E+00 | 228 | 56 | 24 |
| NP_604026 | 1193 | 33.1 | 3.20E+00 | 253 | 52 | 20 | CAD66598 | 1184 | 32.3 | 5.40E+00 | 270 | 49 | 18 |
| NP_541885 | 131 | 33.1 | 3.20E+00 | 62 | 24 | 38 | ZP_002394591038 | | 32.3 | 5.40E+00 | 243 | 52 | 21 |
| gi|42627767|tpe|CAD89361.1| TPA: SbcC exonuclease [Bradyrhizobium japonicum] | 1261 | 33.1 | 3.20E+00 | 62 | 19 | 30 | ZP_00236267289 | | 32.3 | 5.40E+00 | 156 | 31 | 19 |
| | | | | | | | ZP_002326811066 | | 32.3 | 5.40E+00 | 277 | 57 | 20 |
| CAA64859 | 624 | 33.1 | 3.20E+00 | 284 | 47 | 16 | CAB99193 | 326 | 32.3 | 5.40E+00 | 104 | 27 | 25 |
| CAA81206 | 955 | 33.1 | 3.20E+00 | 239 | 47 | 19 | AAT41983 | 427 | 32.3 | 5.40E+00 | 245 | 48 | 19 |
| BAB98269 | 413 | 33.1 | 3.20E+00 | 280 | 63 | 22 | AAF25839 | 177 | 32.3 | 5.40E+00 | 86 | 23 | 26 |
| AAD43469 | 912 | 33.1 | 3.20E+00 | 240 | 48 | 20 | AAS93940 | 693 | 32.3 | 5.40E+00 | 137 | 29 | 21 |
| ZP_00137783633 | | 33.1 | 3.20E+00 | 245 | 42 | 17 | ZP_002188313513 | | 32.3 | 5.40E+00 | 204 | 51 | 25 |
| ZP_00123950634 | | 33.1 | 3.20E+00 | 96 | 24 | 25 | ZP_00171926505 | | 32.3 | 5.40E+00 | 253 | 48 | 18 |
| ZP_00128148551 | | 33.1 | 3.20E+00 | 256 | 46 | 17 | ZP_00201727822 | | 32.3 | 5.40E+00 | 306 | 59 | 19 |
| ZP_003460801463 | | 33.1 | 3.20E+00 | 274 | 69 | 25 | P55116 | 953 | 32.3 | 5.40E+00 | 233 | 48 | 20 |
| AAG60897 | 896 | 33.1 | 3.20E+00 | 62 | 19 | 30 | ZP_00149920505 | | 32.3 | 5.40E+00 | 139 | 31 | 22 |
| PC6003 | 624 | 33.1 | 3.2 | 284 | 47 | 16 | ZP_00133930158 | | 32.3 | 5.40E+00 | 106 | 26 | 24 |
| P76072 | 1120 | 33.1 | 3.20E+00 | 147 | 37 | 25 | ZP_00098108451 | | 32.3 | 5.40E+00 | 139 | 33 | 23 |
| BAA23413 | 629 | 33.1 | 3.20E+00 | 245 | 42 | 17 | AAK27341 | 3241 | 32.3 | 5.40E+00 | 102 | 24 | 23 |
| ZP_00326431563 | | 32.7 | 4.20E+00 | 307 | 70 | 22 | ZP_00312864422 | | 32 | 7.10E+00 | 142 | 36 | 25 |
| CAA79304 | 933 | 32.7 | 4.20E+00 | 145 | 30 | 20 | ZP_00298543733 | | 32 | 7.10E+00 | 278 | 50 | 17 |
| NP_252999 | 629 | 32.7 | 4.20E+00 | 127 | 32 | 25 | ZP_003410411311 | | 32 | 7.10E+00 | 230 | 37 | 16 |
| AAM01202 | 183 | 32.7 | 4.20E+00 | 121 | 29 | 23 | ZP_00208461932 | | 32 | 7.10E+00 | 211 | 43 | 20 |
| ZP_000531851136 | | 32.7 | 4.20E+00 | 223 | 51 | 22 | ZP_00046132979 | | 32 | 7.10E+00 | 143 | 32 | 22 |
| NP_993634 | 2578 | 32.7 | 4.20E+00 | 290 | 61 | 21 | NP_464751 | 1066 | 32 | 7.10E+00 | 277 | 56 | 20 |
| YP_081346 | 561 | 32.7 | 4.20E+00 | 99 | 20 | 20 | NP_885521 | 1195 | 32 | 7.10E+00 | 65 | 18 | 27 |
| NP_471252 | 1186 | 32.7 | 4.20E+00 | 315 | 63 | 20 | AAQ60246 | 251 | 32 | 7.10E+00 | 98 | 30 | 30 |
| NP_469482 | 290 | 32.7 | 4.20E+00 | 82 | 21 | 25 | NP_768828 | 432 | 32 | 7.10E+00 | 164 | 35 | 21 |
| NP_464250 | 601 | 32.7 | 4.20E+00 | 193 | 39 | 20 | NP_699533 | 317 | 32 | 7.10E+00 | 56 | 22 | 39 |
| NP_929013 | 190 | 32.7 | 4.20E+00 | 133 | 34 | 25 | NP_346950 | 371 | 32 | 7.1 | 147 | 35 | 23 |
| NP_793014 | 6274 | 32.7 | 4.2 | 246 | 51 | 20 | NP_207534 | 493 | 32 | 7.1 | 122 | 32 | 26 |
| NP_790315 | 541 | 32.7 | 4.20E+00 | 93 | 28 | 30 | NP_249777 | 683 | 32 | 7.1 | 303 | 72 | 23 |
| NP_769573 | 564 | 32.7 | 4.20E+00 | 157 | 36 | 22 | YP_060448 | 1039 | 32 | 7.1 | 193 | 42 | 21 |
| NP_563507 | 721 | 32.7 | 4.20E+00 | 112 | 25 | 22 | YP_041227 | 2189 | 32 | 7.10E+00 | 149 | 35 | 23 |
| NP_406024 | 2535 | 32.7 | 4.20E+00 | 290 | 61 | 21 | YP_010811 | 580 | 32 | 7.10E+00 | 206 | 44 | 21 |
| NP_939703 | 888 | 32.7 | 4.20E+00 | 123 | 31 | 25 | NP_784951 | 3360 | 32 | 7.10E+00 | 76 | 21 | 27 |
| AAP56776 | 742 | 32.7 | 4.20E+00 | 186 | 40 | 21 | NP_765498 | 495 | 32 | 7.10E+00 | 74 | 16 | 21 |
| NP_882071 | 1175 | 32.7 | 4.20E+00 | 65 | 18 | 27 | NP_757771 | 1378 | 32 | 7.10E+00 | 73 | 22 | 30 |
| NP_419323 | 622 | 32.7 | 4.20E+00 | 235 | 47 | 20 | NP_688862 | 443 | 32 | 7.10E+00 | 66 | 17 | 25 |
| YP_108428 | 634 | 32.7 | 4.20E+00 | 266 | 52 | 19 | AAO19442 | 5431 | 32 | 7.10E+00 | 206 | 44 | 21 |
| NP_109825 | 228 | 32.7 | 4.20E+00 | 154 | 29 | 18 | ZP_002842243286 | | 32 | 7.10E+00 | 283 | 62 | 21 |
| YP_013363 | 601 | 32.7 | 4.20E+00 | 193 | 39 | 20 | CAA05367 | 577 | 32 | 7.10E+00 | 163 | 32 | 19 |
| NP_669014 | 2579 | 32.7 | 4.20E+00 | 290 | 61 | 21 | BAD51767 | 1173 | 32 | 7.10E+00 | 283 | 53 | 18 |
| ZP_00284267481 | | 32.7 | 4.20E+00 | 77 | 21 | 27 | BAC57543 | 289 | 32 | 7.1 | 135 | 33 | 24 |
| ZP_00280424428 | | 32.7 | 4.20E+00 | 196 | 50 | 25 | ZP_00356478659 | | 32 | 7.1 | 128 | 32 | 25 |
| AAM01201 | 183 | 32.7 | 4.20E+00 | 121 | 29 | 23 | ZP_00216525494 | | 32 | 7.1 | 118 | 25 | 21 |
| BAA23412 | 629 | 32.7 | 4.20E+00 | 127 | 32 | 25 | ZP_00215989433 | | 32 | 7.1 | 61 | 20 | 32 |
| NP_326456 | 750 | 32.3 | 5.40E+00 | 121 | 27 | 22 | ZP_00211381462 | | 32 | 7.1 | 89 | 23 | 25 |
| CAA55199 | 545 | 32.3 | 5.40E+00 | 238 | 47 | 19 | ZP_00220828371 | | 32 | 7.1 | 116 | 31 | 26 |
| NP_391003 | 662 | 32.3 | 5.40E+00 | 322 | 60 | 18 | ZP_00154800558 | | 32 | 7.1 | 139 | 31 | 22 |
| A42292 | 818 | 32.3 | 5.40E+00 | 103 | 29 | 28 | ZP_00348486544 | | 32 | 7.1 | 93 | 22 | 23 |
| BAA02196 | 777 | 32.3 | 5.40E+00 | 134 | 35 | 26 | ZP_00138674683 | | 32 | 7.1 | 303 | 72 | 23 |
| AAP08880 | 1658 | 32.3 | 5.40E+00 | 149 | 33 | 22 | ZP_00274787513 | | 31.6 | 9.3 | 247 | 48 | 19 |
| AAP08880 | 1658 | 32.3 | 5.40E+00 | 139 | 27 | 19 | NP_326524 | 1125 | 31.6 | 9.3 | 174 | 37 | 21 |
| NP_646487 | 424 | 32.3 | 5.40E+00 | 147 | 36 | 24 | CAA41384 | 1134 | 31.6 | 9.3 | 147 | 31 | 21 |
| NP_718941 | 169 | 32.3 | 5.40E+00 | 160 | 36 | 22 | AAD02406 | 269 | 31.6 | 9.3 | 81 | 21 | 25 |
| NP_716901 | 706 | 32.3 | 5.40E+00 | 273 | 59 | 21 | ZP_00054847736 | | 31.6 | 9.3 | 272 | 53 | 19 |
| NP_801002 | 542 | 32.3 | 5.40E+00 | 304 | 58 | 19 | NP_941106 | 1062 | 31.6 | 9.3 | 221 | 48 | 21 |
| AAQ60540 | 2373 | 32.3 | 5.40E+00 | 255 | 55 | 21 | NP_813981 | 522 | 31.6 | 9.3 | 137 | 33 | 24 |
| AAQ58389 | 690 | 32.3 | 5.40E+00 | 110 | 25 | 22 | NP_794891 | 647 | 31.6 | 9.3 | 119 | 27 | 22 |
| NP_770343 | 582 | 32.3 | 5.4 | 270 | 50 | 18 | NP_766736 | 691 | 31.6 | 9.3 | 101 | 30 | 29 |
| AAF96820 | 652 | 32.3 | 5.40E+00 | 120 | 31 | 25 | NP_562167 | 327 | 31.6 | 9.3 | 253 | 47 | 18 |
| AAF94794 | 596 | 32.3 | 5.40E+00 | 80 | 19 | 23 | NP_561782 | 2104 | 31.6 | 9.3 | 126 | 23 | 18 |
| NP_404241 | 3295 | 32.3 | 5.40E+00 | 289 | 61 | 21 | NP_358633 | 1091 | 31.6 | 9.3 | 137 | 31 | 22 |
| | | | | | | | NP_349987 | 570 | 31.6 | 9.3 | 300 | 64 | 21 |

Fig. 25B-Continued

| Hit_ID | Length | Bitscore | Expected | Length | #Ident | %S |
|---|---|---|---|---|---|---|
| NP_223662 | 668 | 31.6 | 9.3 | 138 | 32 | 23 |
| YP_084257 | 1041 | 31.6 | 9.3 | 243 | 51 | 20 |
| YP_130345 | 561 | 31.6 | 9.3 | 303 | 57 | 18 |
| YP_130208 | 521 | 31.6 | 9.3 | 273 | 61 | 22 |
| YP_071037 | 2550 | 31.6 | 9.3 | 290 | 61 | 21 |
| YP_070267 | 808 | 31.6 | 9.3 | 249 | 53 | 21 |
| AAK93939 | 733 | 31.6 | 9.3 | 89 | 19 | 21 |
| NP_072757 | 398 | 31.6 | 9.3 | 156 | 36 | 23 |
| YP_056420 | 529 | 31.6 | 9.3 | 94 | 25 | 26 |
| YP_030044 | 959 | 31.6 | 9.3 | 276 | 57 | 20 |
| YP_028999 | 810 | 31.6 | 9.3 | 243 | 52 | 21 |
| NP_600558 | 288 | 31.6 | 9.3 | 63 | 18 | 28 |
| NP_657914 | 598 | 31.6 | 9.3 | 276 | 57 | 20 |
| NP_656819 | 807 | 31.6 | 9.3 | 243 | 52 | 21 |
| NP_965588 | 1218 | 31.6 | 9.3 | 246 | 40 | 16 |
| ZP_00305598305 | | 31.6 | 9.3 | 69 | 21 | 30 |
| ZP_00267783642 | | 31.6 | 9.3 | 232 | 47 | 20 |
| ZP_00235052646 | | 31.6 | 9.3 | 176 | 34 | 19 |
| ZP_00233607236 | | 31.6 | 9.3 | 121 | 27 | 22 |
| BAC98831 | 1083 | 31.6 | 9.3 | 147 | 31 | 21 |
| FCSOAG | 1164 | 31.6 | 9.3 | 147 | 31 | 21 |
| CAA42442 | 1164 | 31.6 | 9.3 | 147 | 31 | 21 |
| AAT10376 | 1158 | 31.6 | 9.3 | 147 | 31 | 21 |
| AAC18948 | 269 | 31.6 | 9.3 | 81 | 21 | 25 |
| ZP_001698191318 | | 31.6 | 9.3 | 233 | 54 | 23 |
| ZP_00203712834 | | 31.6 | 9.3 | 112 | 28 | 25 |
| ZP_00125435646 | | 31.6 | 9.3 | 225 | 42 | 18 |
| ZP_00127280469 | | 31.6 | 9.3 | 275 | 54 | 19 |
| ZP_001224603554 | | 31.6 | 9.3 | 284 | 59 | 20 |
| AAK11617 | 437 | 31.6 | 9.3 | 108 | 29 | 26 |

| Hit_ID | Length | Bitscore | Expected | Length | #Ident | %S |
|---|---|---|---|---|---|---|

Fig. 25C

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| NP_929221 | 355 | 364 | 1.00E-100 | 355 | 207 | 58 | NP_642301 | 399 | 196 | 2.00E-49 | 212 | 113 | 53 |
| ZP_00169997361 | | 343 | 1.00E-93 | 361 | 201 | 55 | NP_642301 | 399 | 103 | 1.00E-21 | 307 | 87 | 28 |
| NP_992909 | 369 | 318 | 4.00E-86 | 368 | 202 | 54 | ZP_00236470278 | | 196 | 2.00E-49 | 293 | 117 | 39 |
| NP_405406 | 369 | 318 | 4.00E-86 | 368 | 202 | 54 | ZP_00236469286 | | 195 | 3.00E-49 | 292 | 118 | 40 |
| NP_288384 | 585 | 305 | 4.00E-82 | 274 | 169 | 61 | ZP_00244371402 | | 195 | 4.00E-49 | 400 | 144 | 36 |
| NP_288384 | 585 | 142 | 4.00E-33 | 115 | 74 | 64 | ZP_00313275272 | | 193 | 1.00E-48 | 292 | 118 | 40 |
| NP_310689 | 585 | 305 | 4.00E-82 | 274 | 169 | 61 | ZP_00335280609 | | 193 | 1.00E-48 | 290 | 120 | 41 |
| NP_310689 | 585 | 142 | 4.00E-33 | 115 | 74 | 64 | ZP_00335280609 | | 114 | 1.00E-24 | 159 | 67 | 42 |
| NP_754230 | 595 | 298 | 3.00E-80 | 223 | 157 | 70 | NP_637306 | 399 | 193 | 1.00E-48 | 241 | 119 | 49 |
| NP_754230 | 595 | 138 | 5.00E-32 | 255 | 106 | 41 | NP_637306 | 399 | 104 | 1.00E-21 | 319 | 93 | 29 |
| NP_707809 | 550 | 293 | 9.00E-79 | 202 | 154 | 76 | ZP_00244372404 | | 193 | 1.00E-48 | 404 | 150 | 37 |
| NP_707809 | 550 | 140 | 9.00E-33 | 116 | 71 | 61 | YP_065397 | 1128 | 192 | 3.00E-48 | 252 | 120 | 47 |
| NP_416433 | 498 | 287 | 8.00E-77 | 177 | 146 | 82 | YP_065397 | 1128 | 107 | 2.00E-22 | 254 | 79 | 31 |
| NP_416433 | 498 | 149 | 3.00E-35 | 151 | 80 | 52 | YP_001491 | 285 | 192 | 4.00E-48 | 302 | 112 | 37 |
| NP_841632 | 275 | 285 | 4.00E-76 | 297 | 159 | 53 | NP_712598 | 285 | 192 | 4.00E-48 | 302 | 112 | 37 |
| NP_456520 | 506 | 284 | 7.00E-76 | 175 | 150 | 85 | NP_231819 | 379 | 189 | 2.00E-47 | 375 | 130 | 34 |
| NP_456520 | 506 | 149 | 3.00E-35 | 91 | 76 | 83 | YP_109915 | 388 | 189 | 2.00E-47 | 385 | 136 | 35 |
| NP_461698 | 506 | 283 | 9.00E-76 | 232 | 160 | 68 | NP_831434 | 272 | 189 | 2.00E-47 | 296 | 114 | 38 |
| NP_461698 | 506 | 155 | 4.00E-37 | 100 | 81 | 81 | YP_076801 | 275 | 189 | 3.00E-47 | 296 | 114 | 38 |
| NP_460912 | 495 | 280 | 8.00E-75 | 175 | 148 | 84 | NP_967579 | 277 | 188 | 4.00E-47 | 301 | 117 | 38 |
| NP_460912 | 495 | 152 | 3.00E-36 | 98 | 79 | 80 | YP_027849 | 287 | 188 | 5.00E-47 | 292 | 112 | 38 |
| NP_883763 | 392 | 272 | 2.00E-72 | 392 | 180 | 45 | NP_972081 | 285 | 187 | 9.00E-47 | 300 | 113 | 37 |
| NP_879790 | 391 | 268 | 5.00E-71 | 391 | 182 | 46 | ZP_00236468284 | | 187 | 1.00E-46 | 295 | 111 | 37 |
| NP_889078 | 391 | 266 | 1.00E-70 | 391 | 183 | 46 | ZP_00288129272 | | 186 | 2.00E-46 | 296 | 112 | 37 |
| ZP_00091764573 | | 254 | 8.00E-67 | 262 | 144 | 54 | NP_967577 | 274 | 186 | 3.00E-46 | 292 | 115 | 39 |
| ZP_00091764573 | | 139 | 4.00E-32 | 90 | 71 | 78 | ZP_00200889296 | | 184 | 6.00E-46 | 300 | 110 | 36 |
| ZP_00173465285 | | 249 | 1.00E-65 | 297 | 145 | 48 | YP_129125 | 382 | 184 | 7.00E-46 | 382 | 130 | 34 |
| NP_903549 | 282 | 248 | 6.00E-65 | 297 | 137 | 46 | NP_219229 | 286 | 183 | 2.00E-45 | 298 | 114 | 38 |
| ZP_00288126272 | | 247 | 7.00E-65 | 296 | 145 | 48 | NP_348182 | 278 | 182 | 3.00E-45 | 292 | 115 | 39 |
| NP_903548 | 282 | 246 | 2.00E-64 | 297 | 137 | 46 | YP_010660 | 298 | 182 | 3.00E-45 | 311 | 119 | 38 |
| ZP_00289013269 | | 238 | 4.00E-62 | 292 | 133 | 45 | NP_231773 | 376 | 182 | 4.00E-45 | 375 | 133 | 35 |
| ZP_00149772273 | | 236 | 1.00E-61 | 296 | 131 | 44 | ZP_00130180299 | | 181 | 5.00E-45 | 295 | 107 | 36 |
| ZP_00289014271 | | 236 | 2.00E-61 | 296 | 133 | 44 | NP_219303 | 286 | 181 | 8.00E-45 | 304 | 107 | 35 |
| NP_718792 | 272 | 236 | 2.00E-61 | 297 | 140 | 47 | NP_219305 | 285 | 181 | 8.00E-45 | 301 | 111 | 36 |
| ZP_00274388386 | | 236 | 2.00E-61 | 167 | 122 | 73 | NP_831435 | 273 | 180 | 1.00E-44 | 298 | 115 | 38 |
| ZP_00274388386 | | 135 | 5.00E-31 | 92 | 68 | 73 | YP_123618 | 475 | 179 | 2.00E-44 | 309 | 124 | 40 |
| ZP_00289011271 | | 235 | 3.00E-61 | 296 | 133 | 44 | YP_123618 | 475 | 110 | 1.00E-23 | 200 | 77 | 38 |
| ZP_00288132271 | | 235 | 4.00E-61 | 295 | 136 | 46 | YP_035879 | 367 | 179 | 2.00E-44 | 365 | 125 | 34 |
| ZP_00288131271 | | 234 | 5.00E-61 | 295 | 136 | 46 | YP_095369 | 475 | 178 | 4.00E-44 | 309 | 125 | 40 |
| ZP_00299645314 | | 234 | 6.00E-61 | 296 | 137 | 46 | YP_095369 | 475 | 109 | 2.00E-23 | 198 | 78 | 39 |
| ZP_00288133271 | | 233 | 1.00E-60 | 295 | 135 | 45 | YP_001839 | 281 | 177 | 9.00E-44 | 300 | 107 | 35 |
| NP_718793 | 273 | 233 | 1.00E-60 | 297 | 138 | 46 | NP_971613 | 286 | 177 | 9.00E-44 | 304 | 109 | 35 |
| ZP_00288136271 | | 230 | 9.00E-60 | 296 | 132 | 44 | NP_902165 | 285 | 177 | 1.00E-43 | 299 | 104 | 34 |
| ZP_00211492272 | | 229 | 2.00E-59 | 291 | 134 | 46 | YP_066429 | 857 | 177 | 1.00E-43 | 231 | 108 | 46 |
| ZP_00289022272 | | 228 | 3.00E-59 | 296 | 136 | 45 | YP_066429 | 857 | 115 | 4.00E-25 | 227 | 81 | 35 |
| NP_954080 | 276 | 228 | 5.00E-59 | 298 | 133 | 44 | YP_011656 | 297 | 177 | 1.00E-43 | 310 | 113 | 36 |
| NP_791772 | 282 | 223 | 1.00E-57 | 297 | 129 | 43 | YP_126643 | 475 | 176 | 2.00E-43 | 309 | 122 | 39 |
| NP_622175 | 276 | 220 | 1.00E-56 | 296 | 134 | 45 | YP_126643 | 475 | 110 | 1.00E-23 | 251 | 88 | 35 |
| ZP_00302555327 | | 219 | 2.00E-56 | 329 | 133 | 40 | YP_001490 | 282 | 176 | 2.00E-43 | 300 | 107 | 35 |
| NP_871067 | 421 | 219 | 2.00E-56 | 181 | 109 | 60 | NP_970090 | 277 | 176 | 2.00E-43 | 295 | 110 | 37 |
| NP_871067 | 421 | 120 | 1.00E-26 | 345 | 109 | 31 | NP_231775 | 378 | 176 | 2.00E-43 | 377 | 134 | 35 |
| ZP_00127282271 | | 218 | 4.00E-56 | 283 | 128 | 45 | YP_072597 | 336 | 176 | 3.00E-43 | 342 | 113 | 33 |
| YP_080862 | 310 | 215 | 4.00E-55 | 313 | 135 | 43 | NP_212281 | 336 | 176 | 3.00E-43 | 342 | 113 | 33 |
| NP_244483 | 272 | 214 | 9.00E-55 | 294 | 124 | 42 | NP_712599 | 282 | 176 | 3.00E-43 | 300 | 107 | 35 |
| ZP_00263336255 | | 213 | 2.00E-54 | 269 | 125 | 46 | NP_521943 | 273 | 175 | 3.00E-43 | 297 | 109 | 36 |
| ZP_00183380275 | | 210 | 1.00E-53 | 299 | 128 | 42 | NP_231818 | 377 | 175 | 3.00E-43 | 377 | 129 | 34 |
| NP_782313 | 275 | 209 | 2.00E-53 | 296 | 125 | 42 | YP_013330 | 287 | 173 | 1.00E-42 | 296 | 107 | 36 |
| NP_693649 | 338 | 209 | 2.00E-53 | 338 | 131 | 38 | NP_470041 | 287 | 173 | 1.00E-42 | 296 | 107 | 36 |
| ZP_00289017266 | | 209 | 2.00E-53 | 285 | 125 | 43 | NP_464217 | 287 | 173 | 1.00E-42 | 296 | 107 | 36 |
| ZP_00289012373 | | 209 | 3.00E-53 | 282 | 117 | 41 | NP_797167 | 384 | 173 | 1.00E-42 | 384 | 125 | 32 |
| NP_391416 | 304 | 208 | 5.00E-53 | 306 | 130 | 42 | NP_935284 | 376 | 173 | 1.00E-42 | 375 | 121 | 32 |
| NP_801058 | 284 | 207 | 8.00E-53 | 301 | 119 | 39 | NP_969824 | 277 | 172 | 3.00E-42 | 295 | 109 | 36 |
| NP_348820 | 275 | 207 | 1.00E-52 | 295 | 122 | 41 | NP_972083 | 286 | 172 | 4.00E-42 | 304 | 106 | 34 |
| NP_798640 | 377 | 202 | 2.00E-51 | 376 | 132 | 35 | NP_760797 | 377 | 171 | 7.00E-42 | 376 | 123 | 32 |
| ZP_00313276273 | | 201 | 8.00E-51 | 295 | 120 | 40 | ZP_00346385295 | | 171 | 7.00E-42 | 292 | 98 | 33 |
| ZP_00236467307 | | 200 | 1.00E-50 | 309 | 119 | 38 | NP_348785 | 283 | 171 | 9.00E-42 | 290 | 104 | 35 |
| NP_967402 | 282 | 199 | 3.00E-50 | 295 | 124 | 42 | NP_782278 | 280 | 170 | 1.00E-41 | 294 | 105 | 35 |
| NP_967404 | 277 | 196 | 2.00E-49 | 292 | 120 | 41 | ZP_00279040381 | | 170 | 1.00E-41 | 378 | 127 | 33 |

Fig. 25C-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| NP_231774 | 377 | 169 | 2.00E-41 | 379 | 127 | 33 | NP_282485 | 572 | 106 | 3.00E-22 | 171 | 63 | 36 |
| YP_011295 | 297 | 169 | 2.00E-41 | 295 | 101 | 34 | NP_282485 | 572 | 79.3 | 3.00E-14 | 132 | 48 | 36 |
| NP_902681 | 372 | 167 | 7.00E-41 | 369 | 122 | 33 | AAP78393 | 514 | 104 | 8.00E-22 | 188 | 67 | 35 |
| NP_249783 | 488 | 167 | 9.00E-41 | 242 | 103 | 42 | AAP78393 | 514 | 68.9 | 5.00E-11 | 115 | 40 | 34 |
| NP_249783 | 488 | 113 | 2.00E-24 | 335 | 100 | 29 | NP_420273 | 273 | 104 | 1.00E-21 | 297 | 76 | 25 |
| ZP_00138680 | 488 | 167 | 9.00E-41 | 242 | 103 | 42 | NP_907654 | 518 | 103 | 2.00E-21 | 192 | 63 | 32 |
| ZP_00138680 | 488 | 113 | 2.00E-24 | 335 | 100 | 29 | NP_907654 | 518 | 94.7 | 8.00E-19 | 333 | 85 | 25 |
| ZP_00130923 | 288 | 167 | 9.00E-41 | 284 | 103 | 36 | NP_404368 | 404 | 102 | 3.00E-21 | 223 | 67 | 30 |
| NP_798637 | 376 | 167 | 1.00E-40 | 377 | 125 | 33 | NP_670739 | 401 | 102 | 3.00E-21 | 223 | 67 | 30 |
| NP_798638 | 378 | 167 | 1.00E-40 | 377 | 126 | 33 | NP_670739 | 401 | 57.4 | 1.00E-07 | 84 | 28 | 33 |
| AAP08637 | 249 | 165 | 5.00E-40 | 271 | 98 | 36 | NP_282484 | 572 | 102 | 5.00E-21 | 181 | 66 | 36 |
| ZP_00317212 | 580 | 164 | 6.00E-40 | 222 | 101 | 45 | NP_282484 | 572 | 72.8 | 3.00E-12 | 132 | 45 | 34 |
| ZP_00317212 | 580 | 99.4 | 3.00E-20 | 182 | 66 | 36 | NP_214372 | 518 | 100 | 1.00E-20 | 209 | 62 | 29 |
| NP_746492 | 687 | 164 | 8.00E-40 | 252 | 103 | 40 | NP_214372 | 518 | 62 | 6.00E-09 | 129 | 39 | 30 |
| NP_746492 | 687 | 96.3 | 3.00E-19 | 129 | 53 | 41 | ZP_00313281 | 302 | 99.4 | 3.00E-20 | 274 | 69 | 25 |
| ZP_00100062 | 385 | 163 | 1.00E-39 | 385 | 128 | 33 | ZP_00100043955 | | 99.4 | 3.00E-20 | 270 | 82 | 30 |
| ZP_00317210 | 587 | 162 | 4.00E-39 | 254 | 105 | 41 | ZP_00100043955 | | 63.5 | 2.00E-09 | 154 | 47 | 30 |
| ZP_00317210 | 587 | 95.9 | 3.00E-19 | 129 | 55 | 42 | NP_420274 | 273 | 99 | 4.00E-20 | 292 | 75 | 25 |
| NP_712200 | 283 | 162 | 4.00E-39 | 301 | 100 | 33 | NP_419609 | 273 | 99 | 4.00E-20 | 292 | 72 | 24 |
| YP_001838 | 283 | 161 | 5.00E-39 | 301 | 99 | 32 | NP_419611 | 273 | 98.6 | 5.00E-20 | 292 | 72 | 24 |
| NP_770335 | 274 | 160 | 1.00E-38 | 295 | 95 | 32 | YP_071817 | 400 | 98.2 | 7.00E-20 | 207 | 61 | 29 |
| ZP_00218989 | 614 | 156 | 2.00E-37 | 242 | 97 | 40 | YP_071817 | 400 | 60.1 | 2.00E-08 | 115 | 37 | 32 |
| ZP_00218989 | 614 | 90.1 | 2.00E-17 | 86 | 46 | 53 | NP_865696 | 718 | 98.2 | 7.00E-20 | 284 | 88 | 30 |
| ZP_00270146 | 298 | 154 | 1.00E-36 | 305 | 107 | 35 | NP_865696 | 718 | 81.3 | 9.00E-15 | 143 | 57 | 39 |
| NP_935285 | 396 | 153 | 1.00E-36 | 376 | 118 | 31 | NP_622171 | 296 | 98.2 | 7.00E-20 | 290 | 83 | 28 |
| NP_945993 | 274 | 152 | 3.00E-36 | 295 | 92 | 31 | AAP78250 | 508 | 97.8 | 9.00E-20 | 170 | 60 | 35 |
| NP_759224 | 377 | 151 | 5.00E-36 | 376 | 120 | 31 | AAP78250 | 508 | 76.3 | 3.00E-13 | 297 | 74 | 24 |
| NP_933767 | 377 | 151 | 7.00E-36 | 376 | 119 | 31 | NP_419610 | 273 | 97.4 | 1.00E-19 | 292 | 70 | 23 |
| YP_128298 | 426 | 151 | 7.00E-36 | 251 | 106 | 42 | NP_866107 | 739 | 97.4 | 1.00E-19 | 257 | 76 | 29 |
| YP_128298 | 426 | 89.4 | 3.00E-17 | 149 | 55 | 36 | NP_866107 | 739 | 79.3 | 3.00E-14 | 250 | 70 | 28 |
| ZP_00329901 | 380 | 149 | 2.00E-35 | 382 | 125 | 32 | NP_223266 | 510 | 96.3 | 3.00E-19 | 170 | 57 | 33 |
| NP_935286 | 377 | 149 | 2.00E-35 | 376 | 112 | 29 | NP_223266 | 510 | 82.4 | 4.00E-15 | 311 | 78 | 25 |
| NP_933764 | 385 | 149 | 3.00E-35 | 178 | 80 | 44 | NP_404369 | 399 | 95.9 | 3.00E-19 | 295 | 76 | 25 |
| NP_933764 | 385 | 102 | 5.00E-21 | 301 | 92 | 30 | ZP_00299642 | 294 | 95.5 | 5.00E-19 | 295 | 75 | 25 |
| ZP_00273972 | 629 | 146 | 2.00E-34 | 199 | 85 | 42 | NP_867573 | 685 | 92.8 | 3.00E-18 | 169 | 62 | 36 |
| ZP_00273972 | 629 | 104 | 8.00E-22 | 92 | 57 | 61 | NP_867573 | 685 | 85.5 | 5.00E-16 | 126 | 55 | 43 |
| YP_129126 | 393 | 145 | 4.00E-34 | 213 | 82 | 38 | NP_404370 | 401 | 92 | 5.00E-18 | 309 | 79 | 25 |
| YP_129126 | 393 | 90.5 | 1.00E-17 | 203 | 63 | 31 | ZP_00329910 | 305 | 91.7 | 7.00E-18 | 285 | 73 | 25 |
| NP_978099 | 266 | 145 | 4.00E-34 | 292 | 96 | 32 | ZP_00196929 | 279 | 91.7 | 7.00E-18 | 288 | 79 | 27 |
| ZP_00287990 | 272 | 142 | 4.00E-33 | 280 | 85 | 30 | NP_353572 | 306 | 91.3 | 9.00E-18 | 313 | 77 | 24 |
| YP_035878 | 266 | 142 | 4.00E-33 | 292 | 97 | 33 | NP_693427 | 293 | 91.3 | 9.00E-18 | 293 | 75 | 25 |
| NP_759225 | 374 | 141 | 6.00E-33 | 167 | 76 | 45 | ZP_00098298 | 321 | 90.9 | 1.00E-17 | 302 | 85 | 28 |
| NP_759225 | 374 | 102 | 5.00E-21 | 301 | 92 | 30 | NP_227947 | 258 | 89.7 | 3.00E-17 | 248 | 63 | 25 |
| NP_782289 | 268 | 141 | 6.00E-33 | 266 | 79 | 29 | NP_954084 | 298 | 89.7 | 3.00E-17 | 290 | 75 | 25 |
| ZP_00004597 | 493 | 140 | 9.00E-33 | 166 | 74 | 44 | ZP_00289010 | 110 | 89.7 | 3.00E-17 | 87 | 47 | 54 |
| ZP_00004597 | 493 | 97.1 | 2.00E-19 | 176 | 63 | 35 | NP_700301 | 282 | 88.6 | 6.00E-17 | 298 | 76 | 25 |
| YP_083129 | 266 | 140 | 9.00E-33 | 292 | 95 | 32 | NP_391420 | 298 | 86.7 | 2.00E-16 | 288 | 80 | 27 |
| AAP08634 | 266 | 140 | 1.00E-32 | 291 | 95 | 32 | NP_541127 | 282 | 86.7 | 2.00E-16 | 298 | 75 | 25 |
| NP_228567 | 387 | 140 | 2.00E-32 | 392 | 119 | 30 | ZP_00268130 | 268 | 85.5 | 5.00E-16 | 295 | 76 | 25 |
| ZP_00236466 | 266 | 138 | 5.00E-32 | 292 | 96 | 32 | NP_773506 | 313 | 85.1 | 6.00E-16 | 311 | 73 | 23 |
| YP_083130 | 460 | 137 | 8.00E-32 | 289 | 96 | 32 | NP_104150 | 328 | 84.7 | 8.00E-16 | 329 | 75 | 22 |
| YP_083130 | 460 | 80.9 | 1.00E-14 | 111 | 46 | 41 | ZP_00339045 | 281 | 84 | 1.00E-15 | 296 | 75 | 25 |
| NP_348261 | 269 | 137 | 1.00E-31 | 292 | 89 | 30 | YP_080866 | 303 | 83.2 | 2.00E-15 | 281 | 70 | 24 |
| NP_242343 | 464 | 130 | 2.00E-29 | 135 | 70 | 51 | NP_773505 | 314 | 80.9 | 1.00E-14 | 317 | 73 | 23 |
| NP_242343 | 464 | 95.9 | 3.00E-19 | 169 | 57 | 33 | NP_353570 | 313 | 79.7 | 3.00E-14 | 313 | 75 | 23 |
| NP_978100 | 465 | 126 | 2.00E-28 | 221 | 77 | 34 | ZP_00339044 | 282 | 79.3 | 3.00E-14 | 298 | 72 | 24 |
| NP_978100 | 465 | 75.1 | 6.00E-13 | 84 | 41 | 48 | ZP_00007767 | 281 | 78.6 | 6.00E-14 | 302 | 70 | 23 |
| AAO08750 | 375 | 121 | 6.00E-27 | 374 | 108 | 28 | NP_840399 | 299 | 77.8 | 1.00E-13 | 290 | 71 | 24 |
| NP_933768 | 375 | 121 | 6.00E-27 | 374 | 108 | 28 | ZP_00339046 | 273 | 77.4 | 1.00E-13 | 280 | 73 | 26 |
| NP_391395 | 160 | 116 | 2.00E-25 | 179 | 68 | 37 | ZP_00338034 | 282 | 77.4 | 1E-13 | 294 | 72 | 24 |
| NP_797170 | 374 | 109 | 2.00E-23 | 148 | 60 | 40 | ZP_00193517 | 283 | 76.6 | 2.00E-13 | 290 | 65 | 22 |
| NP_797170 | 374 | 74.3 | 1.00E-12 | 217 | 61 | 28 | ZP_00337030 | 282 | 76.3 | 3.00E-13 | 299 | 69 | 23 |
| NP_908288 | 513 | 109 | 2.00E-23 | 294 | 89 | 30 | NP_907272 | 253 | 74.3 | 1.00E-12 | 278 | 65 | 23 |
| NP_908288 | 513 | 73.2 | 2.00E-12 | 122 | 44 | 36 | ZP_00270458 | 289 | 72.8 | 3.00E-12 | 302 | 69 | 22 |
| NP_206915 | 514 | 108 | 7.00E-23 | 187 | 67 | 35 | ZP_00289016 | 275 | 72 | 5.00E-12 | 275 | 64 | 23 |
| NP_206915 | 514 | 77.4 | 1.00E-13 | 121 | 47 | 38 | NP_353571 | 337 | 71.6 | 7.00E-12 | 324 | 75 | 23 |
| NP_222828 | 514 | 107 | 1.00E-22 | 187 | 67 | 35 | NP_531244 | 320 | 71.6 | 7.00E-12 | 324 | 75 | 23 |
| NP_222828 | 514 | 77.4 | 1.00E-13 | 121 | 47 | 38 | ZP_00183364 | 320 | 71.6 | 7E-12 | 321 | 74 | 23 |

Fig. 25C-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| NP_281892 | 249 | 68.6 | 6.00E-11 | 288 | 66 | 22 | ZP_00317213517 | | 53.1 | 3.00E-06 | 100 | 31 | 31 |
| NP_782319 | 316 | 68.2 | 8.00E-11 | 284 | 68 | 23 | ZP_00317213517 | | 40 | 2.30E-02 | 91 | 24 | 26 |
| ZP_00337274271 | | 67.4 | 1.00E-10 | 284 | 64 | 22 | ZP_00273669412 | | 52.8 | 3.00E-06 | 311 | 67 | 21 |
| ZP_00335243300 | | 67 | 2.00E-10 | 302 | 74 | 24 | ZP_00273669412 | | 35.8 | 4.30E-01 | 146 | 35 | 23 |
| ZP_00149794326 | | 67 | 2.00E-10 | 322 | 67 | 20 | ZP_00056435521 | | 52.8 | 3.00E-06 | 185 | 40 | 21 |
| NP_972952 | 415 | 66.6 | 2.00E-10 | 285 | 65 | 22 | NP_384777 | 401 | 52.8 | 3.00E-06 | 189 | 48 | 25 |
| NP_227898 | 304 | 65.1 | 7.00E-10 | 256 | 62 | 24 | NP_384777 | 401 | 40 | 2.30E-02 | 87 | 24 | 27 |
| YP_013346 | 291 | 64.3 | 1.00E-09 | 288 | 61 | 21 | NP_415601 | 317 | 52 | 6.00E-06 | 305 | 70 | 22 |
| ZP_00049388242 | | 63.9 | 1.00E-09 | 188 | 52 | 27 | NP_421770 | 424 | 52 | 6.00E-06 | 164 | 35 | 21 |
| NP_464233 | 291 | 63.9 | 1.00E-09 | 288 | 61 | 21 | NP_287217 | 317 | 51.6 | 8.00E-06 | 299 | 66 | 22 |
| ZP_00229464291 | | 63.5 | 2.00E-09 | 288 | 61 | 21 | NP_967522 | 361 | 51.6 | 8.00E-06 | 178 | 44 | 24 |
| AAC65633 | 416 | 63.2 | 3.00E-09 | 268 | 60 | 22 | YP_066426 | 757 | 51.6 | 8.00E-06 | 130 | 40 | 30 |
| NP_384778 | 321 | 62.4 | 4.00E-09 | 321 | 68 | 21 | YP_111446 | 2634 | 51.2 | 1.00E-05 | 287 | 60 | 20 |
| NP_642302 | 401 | 62.4 | 4.00E-09 | 134 | 40 | 29 | YP_111446 | 2634 | 50.8 | 1.00E-05 | 281 | 59 | 20 |
| NP_642302 | 401 | 40.8 | 1.30E-02 | 118 | 31 | 26 | YP_111446 | 2634 | 47 | 2.00E-04 | 296 | 63 | 21 |
| NP_470057 | 291 | 62 | 6.00E-09 | 288 | 60 | 20 | YP_111446 | 2634 | 46.2 | 3.00E-04 | 291 | 60 | 20 |
| ZP_00237160287 | | 60.8 | 1.00E-08 | 243 | 62 | 25 | YP_111446 | 2634 | 45.1 | 7.00E-04 | 292 | 58 | 19 |
| NP_348828 | 425 | 60.1 | 2.00E-08 | 289 | 65 | 22 | YP_111446 | 2634 | 43.5 | 2.00E-03 | 284 | 58 | 20 |
| NP_348828 | 425 | 42.4 | 5.00E-03 | 310 | 69 | 22 | YP_111446 | 2634 | 43.5 | 2.00E-03 | 283 | 58 | 20 |
| YP_126585 | 411 | 60.1 | 2.00E-08 | 147 | 39 | 26 | YP_111446 | 2634 | 43.5 | 2.00E-03 | 289 | 59 | 20 |
| YP_095257 | 411 | 60.1 | 2.00E-08 | 147 | 39 | 26 | YP_111446 | 2634 | 43.1 | 3.00E-03 | 292 | 59 | 20 |
| NP_104151 | 356 | 59.7 | 3.00E-08 | 357 | 81 | 22 | YP_111446 | 2634 | 42 | 6.00E-03 | 281 | 63 | 22 |
| YP_123558 | 411 | 59.3 | 4.00E-08 | 147 | 38 | 25 | YP_111446 | 2634 | 40 | 2.30E-02 | 295 | 59 | 20 |
| YP_123558 | 411 | 32 | 6.20E+00 | 83 | 25 | 30 | YP_111446 | 2634 | 40 | 2.30E-02 | 298 | 59 | 19 |
| AAQ60546 | 309 | 58.9 | 5.00E-08 | 299 | 62 | 20 | YP_111446 | 2634 | 39.3 | 3.90E-02 | 302 | 59 | 19 |
| ZP_00127287530 | | 58.9 | 5.00E-08 | 135 | 40 | 29 | YP_111446 | 2634 | 38.9 | 5.10E-02 | 283 | 53 | 18 |
| NP_772484 | 757 | 58.5 | 6.00E-08 | 273 | 72 | 26 | YP_111446 | 2634 | 37.4 | 1.50E-01 | 278 | 48 | 17 |
| NP_772484 | 757 | 34.7 | 9.60E-01 | 109 | 29 | 26 | YP_111446 | 2634 | 35.8 | 4.30E-01 | 235 | 50 | 21 |
| NP_637307 | 401 | 58.2 | 8.00E-08 | 134 | 38 | 28 | YP_105520 | 459 | 51.2 | 1.00E-05 | 248 | 57 | 22 |
| NP_637307 | 401 | 35.8 | 4.30E-01 | 119 | 31 | 26 | YP_105520 | 459 | 41.6 | 8.00E-03 | 298 | 60 | 20 |
| YP_083110 | 287 | 57.8 | 1.00E-07 | 242 | 57 | 23 | YP_027819 | 207 | 51.2 | 1.00E-05 | 115 | 30 | 26 |
| NP_978079 | 287 | 57.8 | 1.00E-07 | 241 | 60 | 24 | NP_866849 | 651 | 51.2 | 1.00E-05 | 129 | 34 | 26 |
| NP_772486 | 757 | 57.4 | 1.00E-07 | 255 | 72 | 28 | NP_947642 | 935 | 50.8 | 1.00E-05 | 284 | 70 | 24 |
| NP_772486 | 757 | 34.3 | 1.20E+00 | 109 | 29 | 26 | NP_947642 | 935 | 34.3 | 1.20E+00 | 93 | 22 | 23 |
| NP_212316 | 424 | 57.4 | 1.00E-07 | 132 | 38 | 28 | NP_949266 | 888 | 50.8 | 1.00E-05 | 284 | 69 | 24 |
| NP_212316 | 424 | 35 | 7.30E-01 | 77 | 18 | 23 | NP_949266 | 888 | 38.9 | 5.10E-02 | 305 | 63 | 20 |
| NP_384775 | 394 | 57 | 2.00E-07 | 138 | 38 | 27 | YP_009743 | 523 | 50.4 | 2.00E-05 | 123 | 32 | 26 |
| NP_384775 | 394 | 50.4 | 2.00E-05 | 87 | 29 | 33 | YP_009743 | 523 | 33.9 | 1.60E+00 | 171 | 36 | 21 |
| YP_072631 | 424 | 56.6 | 2.00E-07 | 157 | 46 | 29 | ZP_00129084282 | | 50.4 | 2.00E-05 | 285 | 68 | 23 |
| YP_072631 | 424 | 35 | 7.30E-01 | 77 | 18 | 23 | NP_282040 | 750 | 50.1 | 2.00E-05 | 129 | 36 | 27 |
| AAP08616 | 287 | 56.6 | 2.00E-07 | 243 | 57 | 23 | NP_282040 | 750 | 41.6 | 8.00E-03 | 229 | 48 | 20 |
| ZP_00128974504 | | 56.6 | 2.00E-07 | 113 | 32 | 28 | ZP_00242042398 | | 49.7 | 3.00E-05 | 215 | 53 | 24 |
| ZP_00128974504 | | 43.5 | 2.00E-03 | 238 | 50 | 21 | ZP_00242042398 | | 39.7 | 3.00E-02 | 140 | 35 | 25 |
| NP_521913 | 316 | 56.2 | 3.00E-07 | 305 | 65 | 21 | ZP_00263356523 | | 48.5 | 6.00E-05 | 162 | 43 | 26 |
| NP_746494 | 521 | 56.2 | 3.00E-07 | 130 | 41 | 31 | ZP_00263356523 | | 35 | 7.30E-01 | 106 | 23 | 21 |
| NP_746494 | 521 | 41.6 | 8.00E-03 | 149 | 37 | 24 | NP_460155 | 317 | 48.5 | 6.00E-05 | 140 | 38 | 27 |
| ZP_00173445304 | | 56.2 | 3.00E-07 | 301 | 68 | 22 | YP_128296 | 304 | 48.5 | 6.00E-05 | 293 | 53 | 18 |
| ZP_00278994407 | | 55.5 | 5.00E-07 | 250 | 55 | 22 | YP_04084910746 | | 48.5 | 6.00E-05 | 303 | 63 | 20 |
| NP_718794 | 403 | 55.1 | 7.00E-07 | 136 | 36 | 26 | YP_04084910746 | | 42.4 | 5.00E-03 | 340 | 71 | 20 |
| NP_718794 | 403 | 34.3 | 1.20E+00 | 89 | 26 | 29 | YP_04084910746 | | 36.6 | 2.50E-01 | 297 | 58 | 19 |
| NP_791768 | 530 | 55.1 | 7.00E-07 | 130 | 36 | 27 | YP_04084910746 | | 36.6 | 2.50E-01 | 332 | 69 | 20 |
| NP_772485 | 757 | 55.1 | 7.00E-07 | 250 | 63 | 25 | YP_04084910746 | | 35.8 | 4.30E-01 | 301 | 63 | 20 |
| NP_772485 | 757 | 33.9 | 1.60E+00 | 109 | 29 | 26 | YP_04084910746 | | 33.5 | 2.10E+00 | 279 | 55 | 19 |
| NP_880130 | 510 | 54.7 | 9.00E-07 | 136 | 43 | 31 | YP_04084910746 | | 33.1 | 2.80E+00 | 317 | 68 | 21 |
| YP_003353 | 422 | 54.7 | 9.00E-07 | 110 | 34 | 30 | YP_04084910746 | | 31.6 | 8.10E+00 | 297 | 57 | 19 |
| NP_992941 | 337 | 54.3 | 1.00E-06 | 310 | 73 | 23 | ZP_00167907404 | | 48.5 | 6.00E-05 | 121 | 37 | 30 |
| NP_883789 | 510 | 54.3 | 1.00E-06 | 136 | 42 | 30 | ZP_00167907404 | | 35.4 | 5.60E-01 | 99 | 23 | 23 |
| NP_405374 | 326 | 54.3 | 1.00E-06 | 310 | 73 | 23 | NP_384776 | 394 | 47.8 | 1.00E-04 | 137 | 34 | 24 |
| ZP_00212998398 | | 54.3 | 1.00E-06 | 111 | 29 | 26 | NP_384776 | 394 | 45.8 | 4.00E-04 | 245 | 56 | 22 |
| NP_799784 | 299 | 53.9 | 2.00E-06 | 258 | 55 | 21 | NP_562800 | 451 | 47.4 | 1.00E-04 | 220 | 53 | 24 |
| NP_772483 | 763 | 53.9 | 2.00E-06 | 186 | 47 | 25 | NP_455677 | 317 | 47.4 | 1.00E-04 | 140 | 38 | 27 |
| NP_772483 | 763 | 36.2 | 3.30E-01 | 109 | 29 | 26 | NP_646141 | 9904 | 47 | 2.00E-04 | 306 | 64 | 20 |
| NP_244487 | 395 | 53.9 | 2.00E-06 | 126 | 33 | 26 | NP_646141 | 9904 | 43.1 | 3.00E-03 | 153 | 36 | 23 |
| NP_353593 | 436 | 53.5 | 2.00E-06 | 256 | 59 | 23 | NP_646141 | 9904 | 39.7 | 3.00E-02 | 332 | 71 | 21 |
| NP_353593 | 436 | 46.2 | 3.00E-04 | 140 | 34 | 24 | NP_646141 | 9904 | 39.3 | 3.90E-02 | 283 | 66 | 23 |
| NP_753263 | 317 | 53.5 | 2.00E-06 | 299 | 67 | 22 | NP_646141 | 9904 | 38.1 | 8.60E-02 | 279 | 56 | 20 |
| NP_531268 | 430 | 53.5 | 2.00E-06 | 256 | 59 | 23 | NP_646141 | 9904 | 35.4 | 5.60E-01 | 317 | 66 | 20 |
| NP_531268 | 430 | 46.2 | 3.00E-04 | 140 | 34 | 24 | NP_646141 | 9904 | 33.9 | 1.60E+00 | 297 | 57 | 19 |

Fig. 25C-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| YP_012160 | 282 | 47 | 2.00E-04 | 223 | 53 | 23 | YP_105401 | 1535 | 42.4 | 5.00E-03 | 300 | 63 | 21 |
| NP_249778 | 439 | 46.6 | 2.00E-04 | 134 | 34 | 25 | YP_105401 | 1535 | 36.2 | 3.30E-01 | 307 | 64 | 20 |
| NP_249778 | 439 | 32 | 6.20E+00 | 257 | 50 | 19 | YP_105401 | 1535 | 35.8 | 4.30E-01 | 217 | 46 | 21 |
| ZP_00138675 | 439 | 46.6 | 2.00E-04 | 134 | 34 | 25 | YP_065260 | 567 | 42.4 | 5.00E-03 | 263 | 54 | 20 |
| ZP_00314296 | 822 | 46.2 | 3.00E-04 | 257 | 54 | 21 | NP_906736 | 846 | 42.4 | 5.00E-03 | 168 | 37 | 22 |
| NP_223759 | 267 | 46.2 | 3.00E-04 | 149 | 40 | 26 | ZP_00143236 | 2005 | 42.4 | 5.00E-03 | 256 | 59 | 23 |
| YP_108306 | 1606 | 46.2 | 3.00E-04 | 296 | 66 | 22 | NP_523179 | 1309 | 42 | 6.00E-03 | 264 | 60 | 22 |
| YP_108306 | 1606 | 38.1 | 8.60E-02 | 281 | 57 | 20 | NP_523179 | 1309 | 36.2 | 3.30E-01 | 260 | 56 | 21 |
| YP_108306 | 1606 | 38.1 | 8.60E-02 | 228 | 54 | 23 | NP_523179 | 1309 | 35.8 | 4.30E-01 | 247 | 57 | 23 |
| YP_108306 | 1606 | 38.1 | 8.60E-02 | 309 | 60 | 19 | AAF95046 | 672 | 42 | 6.00E-03 | 320 | 64 | 20 |
| YP_108306 | 1606 | 37.4 | 1.50E-01 | 256 | 58 | 22 | NP_488975 | 661 | 42 | 6.00E-03 | 268 | 63 | 23 |
| ZP_00290372 | 765 | 45.8 | 4.00E-04 | 280 | 56 | 19 | NP_784110 | 1377 | 42 | 6.00E-03 | 285 | 64 | 22 |
| NP_267773 | 1072 | 45.4 | 5.00E-04 | 287 | 53 | 18 | YP_129124 | 396 | 41.6 | 8.00E-03 | 119 | 25 | 21 |
| NP_267773 | 1072 | 33.5 | 2.10E+00 | 91 | 21 | 23 | ZP_00089080 | 401 | 41.6 | 8.00E-03 | 122 | 36 | 29 |
| NP_228520 | 407 | 45.4 | 5.00E-04 | 290 | 63 | 21 | ZP_00089080 | 401 | 38.5 | 6.60E-02 | 139 | 36 | 25 |
| ZP_00323079 | 2334 | 45.4 | 5.00E-04 | 274 | 50 | 18 | NP_465811 | 1787 | 41.2 | 1.00E-02 | 268 | 58 | 21 |
| ZP_00323079 | 2334 | 39.7 | 3.00E-02 | 276 | 49 | 17 | ZP_00214370 | 1439 | 41.2 | 1.00E-02 | 297 | 72 | 24 |
| ZP_00323079 | 2334 | 39.3 | 3.90E-02 | 293 | 54 | 18 | ZP_00214370 | 1439 | 32.3 | 4.70E+00 | 272 | 56 | 20 |
| ZP_00323079 | 2334 | 38.5 | 6.60E-02 | 294 | 53 | 18 | AAP07456 | 953 | 40.8 | 1.30E-02 | 263 | 49 | 18 |
| ZP_00323079 | 2334 | 37 | 1.90E-01 | 280 | 52 | 18 | ZP_00063096 | 901 | 40.8 | 1.30E-02 | 241 | 60 | 24 |
| ZP_00323079 | 2334 | 34.7 | 9.60E-01 | 261 | 50 | 19 | ZP_00296669 | 699 | 40.4 | 1.70E-02 | 292 | 54 | 18 |
| YP_111449 | 1530 | 45.1 | 7.00E-04 | 295 | 64 | 21 | ZP_00296669 | 699 | 32 | 6.20E+00 | 133 | 26 | 19 |
| YP_111449 | 1530 | 44.7 | 1.00E-03 | 292 | 64 | 21 | NP_251152 | 5627 | 40.4 | 1.70E-02 | 329 | 67 | 20 |
| YP_111449 | 1530 | 44.3 | 1.00E-03 | 278 | 59 | 21 | NP_251152 | 5627 | 34.3 | 1.20E+00 | 235 | 50 | 21 |
| YP_111449 | 1530 | 42.7 | 4.00E-03 | 320 | 69 | 21 | NP_251152 | 5627 | 32.7 | 3.60E+00 | 312 | 60 | 19 |
| YP_111449 | 1530 | 41.6 | 8.00E-03 | 288 | 59 | 20 | ZP_00288079 | 749 | 40 | 2.30E-02 | 236 | 51 | 21 |
| YP_111449 | 1530 | 41.2 | 1.00E-02 | 284 | 60 | 21 | YP_142319 | 789 | 40 | 2.30E-02 | 302 | 64 | 21 |
| YP_111449 | 1530 | 40 | 2.30E-02 | 250 | 51 | 20 | YP_140402 | 710 | 40 | 2.30E-02 | 302 | 64 | 21 |
| YP_111449 | 1530 | 37.7 | 1.10E-01 | 250 | 50 | 20 | NP_373178 | 2271 | 40 | 2.30E-02 | 287 | 52 | 18 |
| YP_111449 | 1530 | 37 | 1.90E-01 | 263 | 52 | 19 | NP_373178 | 2271 | 34.3 | 1.20E+00 | 216 | 42 | 19 |
| YP_111449 | 1530 | 34.7 | 9.60E-01 | 257 | 55 | 21 | NP_373178 | 2271 | 32 | 6.20E+00 | 303 | 62 | 20 |
| NP_949252 | 886 | 44.7 | 1.00E-03 | 194 | 49 | 25 | AAO08483 | 623 | 40 | 2.30E-02 | 114 | 31 | 27 |
| NP_949252 | 886 | 33.9 | 1.60E+00 | 102 | 25 | 24 | YP_114536 | 437 | 40 | 2.30E-02 | 83 | 27 | 32 |
| NP_929192 | 321 | 44.7 | 1.00E-03 | 318 | 74 | 23 | YP_034700 | 953 | 40 | 2.30E-02 | 301 | 58 | 19 |
| NP_647392 | 2275 | 44.7 | 1.00E-03 | 287 | 53 | 18 | NP_936493 | 623 | 40 | 2.30E-02 | 114 | 31 | 27 |
| NP_647392 | 2275 | 34.3 | 1.20E+00 | 216 | 42 | 19 | NP_764683 | 9439 | 40 | 2.30E-02 | 130 | 27 | 20 |
| NP_647392 | 2275 | 34.3 | 1.20E+00 | 299 | 60 | 20 | NP_764683 | 9439 | 38.5 | 6.60E-02 | 169 | 43 | 25 |
| NP_371958 | 6713 | 44.7 | 1.00E-03 | 303 | 61 | 20 | NP_764683 | 9439 | 36.2 | 3.30E-01 | 265 | 55 | 20 |
| NP_371958 | 6713 | 42 | 6.00E-03 | 153 | 36 | 23 | NP_764683 | 9439 | 36.2 | 3.30E-01 | 288 | 61 | 21 |
| NP_371958 | 6713 | 41.2 | 1.00E-02 | 332 | 72 | 21 | NP_764683 | 9439 | 36.2 | 3.30E-01 | 255 | 48 | 18 |
| NP_371958 | 6713 | 35.4 | 5.60E-01 | 276 | 53 | 19 | NP_764683 | 9439 | 35.4 | 5.60E-01 | 316 | 61 | 19 |
| NP_371958 | 6713 | 33.1 | 2.80E+00 | 297 | 57 | 19 | NP_764683 | 9439 | 34.7 | 9.60E-01 | 302 | 60 | 19 |
| NP_374548 | 6713 | 44.7 | 1.00E-03 | 303 | 61 | 20 | NP_764683 | 9439 | 33.9 | 1.60E+00 | 314 | 65 | 20 |
| NP_374548 | 6713 | 42 | 6.00E-03 | 153 | 36 | 23 | NP_764683 | 9439 | 33.9 | 1.60E+00 | 146 | 40 | 27 |
| NP_374548 | 6713 | 41.2 | 1.00E-02 | 332 | 72 | 21 | NP_764683 | 9439 | 33.1 | 2.80E+00 | 181 | 46 | 25 |
| NP_374548 | 6713 | 35.4 | 5.60E-01 | 276 | 53 | 19 | NP_764683 | 9439 | 33.1 | 2.80E+00 | 151 | 38 | 25 |
| NP_374548 | 6713 | 33.1 | 2.80E+00 | 297 | 57 | 19 | NP_764683 | 9439 | 32.3 | 4.70E+00 | 329 | 68 | 20 |
| YP_106908 | 410 | 44.7 | 1.00E-03 | 124 | 28 | 22 | NP_764683 | 9439 | 31.6 | 8.10E+00 | 292 | 53 | 18 |
| YP_044654 | 2275 | 44.7 | 1.00E-03 | 287 | 53 | 18 | ZP_00123691 | 638 | 39.7 | 3.00E-02 | 352 | 74 | 21 |
| YP_044654 | 2275 | 34.3 | 1.20E+00 | 216 | 42 | 19 | ZP_00064247 | 1003 | 39.7 | 3.00E-02 | 307 | 71 | 23 |
| YP_110805 | 1653 | 44.3 | 1.00E-03 | 269 | 58 | 21 | ZP_00319871 | 233 | 39.3 | 3.90E-02 | 139 | 37 | 26 |
| YP_110805 | 1653 | 40 | 2.30E-02 | 254 | 56 | 22 | NP_908061 | 118 | 39.3 | 3.90E-02 | 103 | 29 | 28 |
| YP_110805 | 1653 | 37 | 1.90E-01 | 287 | 58 | 20 | ZP_00233591 | 1787 | 39.3 | 3.90E-02 | 261 | 60 | 22 |
| YP_110805 | 1653 | 36.2 | 3.30E-01 | 274 | 56 | 20 | NP_798012 | 3240 | 38.9 | 5.10E-02 | 269 | 58 | 21 |
| YP_110805 | 1653 | 34.7 | 9.60E-01 | 265 | 52 | 19 | YP_015833 | 662 | 38.9 | 5.10E-02 | 167 | 43 | 25 |
| ZP_00162755 | 1140 | 44.3 | 1.00E-03 | 295 | 62 | 21 | ZP_00281431 | 4726 | 38.9 | 5.10E-02 | 310 | 62 | 20 |
| AAF94608 | 4558 | 43.9 | 2.00E-03 | 228 | 52 | 22 | ZP_00281431 | 4726 | 38.1 | 8.60E-02 | 308 | 61 | 19 |
| ZP_00326048 | 609 | 43.1 | 3.00E-03 | 273 | 63 | 23 | ZP_00281431 | 4726 | 37.4 | 1.50E-01 | 272 | 54 | 19 |
| ZP_00326048 | 609 | 32 | 6.20E+00 | 99 | 20 | 19 | ZP_00281431 | 4726 | 36.6 | 2.50E-01 | 275 | 56 | 20 |
| ZP_00051799 | 172 | 43.1 | 3.00E-03 | 136 | 31 | 22 | ZP_00281431 | 4726 | 36.6 | 2.50E-01 | 254 | 53 | 20 |
| NP_207286 | 295 | 43.1 | 3.00E-03 | 150 | 42 | 28 | ZP_00281431 | 4726 | 35.4 | 5.60E-01 | 279 | 55 | 19 |
| NP_936893 | 989 | 43.1 | 3.00E-03 | 289 | 63 | 21 | ZP_00281431 | 4726 | 35 | 7.30E-01 | 319 | 59 | 18 |
| AAQ59385 | 302 | 42.7 | 4.00E-03 | 282 | 55 | 19 | ZP_00281431 | 4726 | 34.3 | 1.20E+00 | 324 | 59 | 18 |
| NP_267008 | 1063 | 42.7 | 4.00E-03 | 291 | 56 | 19 | ZP_02114934 | 72 | 38.9 | 5.10E-02 | 274 | 60 | 21 |
| NP_267008 | 1063 | 37 | 1.90E-01 | 231 | 42 | 18 | ZP_00204794 | 1979 | 38.9 | 5.10E-02 | 235 | 47 | 20 |
| NP_267008 | 1063 | 36.6 | 2.50E-01 | 281 | 63 | 22 | ZP_00204794 | 1979 | 34.7 | 9.60E-01 | 235 | 50 | 21 |
| YP_042074 | 1351 | 42.7 | 4.00E-03 | 304 | 59 | 19 | ZP_00204794 | 1979 | 33.1 | 2.8 | 312 | 61 | 19 |
| NP_939992 | 1254 | 42.4 | 5.00E-03 | 169 | 38 | 22 | ZP_00208729 | 459 | 38.5 | 6.60E-02 | 278 | 63 | 22 |

Fig. 25C-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| NP_928380 | 567 | 38.5 | 6.60E-02 | 257 | 58 | 22 | ZP_00160617717 | 31.6 | 8.10E+00 | 248 | 46 | 18 | |
| YP_115646 | 750 | 38.5 | 6.60E-02 | 144 | 32 | 22 | ZP_001380311417 | 36.2 | 3.30E-01 | 201 | 49 | 24 | |
| YP_087940 | 5399 | 38.5 | 6.60E-02 | 312 | 72 | 23 | NP_561526 | 1109 | 35.8 | 4.30E-01 | 287 | 53 | 18 |
| YP_087940 | 5399 | 37.4 | 1.50E-01 | 256 | 45 | 17 | NP_561526 | 1109 | 32 | 6.20E+00 | 181 | 40 | 22 |
| YP_087940 | 5399 | 37.4 | 1.50E-01 | 256 | 45 | 17 | NP_349224 | 664 | 35.8 | 4.30E-01 | 272 | 59 | 21 |
| YP_087940 | 5399 | 36.2 | 3.30E-01 | 273 | 58 | 21 | AAP56614 | 499 | 35.8 | 4.30E-01 | 183 | 40 | 21 |
| YP_087940 | 5399 | 36.2 | 3.30E-01 | 273 | 58 | 21 | YP_133518 | 665 | 35.8 | 4.30E-01 | 111 | 33 | 29 |
| YP_087940 | 5399 | 35.8 | 4.30E-01 | 274 | 61 | 22 | YP_071943 | 3378 | 35.8 | 4.30E-01 | 289 | 61 | 21 |
| YP_087940 | 5399 | 35 | 7.30E-01 | 294 | 58 | 19 | ZP_00270453727 | 35.4 | 5.60E-01 | 239 | 49 | 20 | |
| YP_087940 | 5399 | 33.9 | 1.60E+00 | 289 | 57 | 19 | AAQ59977 | 458 | 35.4 | 5.60E-01 | 266 | 61 | 22 |
| YP_087940 | 5399 | 33.5 | 2.10E+00 | 289 | 57 | 19 | NP_773497 | 491 | 35.4 | 5.60E-01 | 121 | 28 | 23 |
| NP_781518 | 518 | 38.5 | 6.60E-02 | 302 | 64 | 21 | NP_267038 | 799 | 35.4 | 5.60E-01 | 301 | 71 | 23 |
| ZP_00213493557 | 38.5 | 6.60E-02 | 223 | 51 | 22 | NP_478503 | 1487 | 35.4 | 5.60E-01 | 249 | 49 | 19 | |
| ZP_00224552561 | 38.5 | 6.60E-02 | 223 | 53 | 23 | YP_086339 | 564 | 35.4 | 5.60E-01 | 107 | 23 | 21 | |
| ZP_00355727801 | 38.5 | 6.60E-02 | 317 | 71 | 22 | NP_207948 | 1230 | 35.4 | 5.60E-01 | 292 | 62 | 21 | |
| ZP_001404443443 | 38.5 | 6.60E-02 | 286 | 62 | 21 | YP_039058 | 564 | 35.4 | 5.60E-01 | 107 | 23 | 21 | |
| NP_419715 | 307 | 38.1 | 8.60E-02 | 73 | 21 | 28 | NP_864533 | 7716 | 35.4 | 5.60E-01 | 240 | 52 | 21 |
| NP_207906 | 228 | 38.1 | 8.60E-02 | 110 | 32 | 29 | NP_765804 | 2310 | 35.4 | 5.60E-01 | 290 | 52 | 17 |
| ZP_003235731130 | 38.1 | 8.60E-02 | 292 | 65 | 22 | NP_765787 | 676 | 35.4 | 5.60E-01 | 117 | 33 | 28 | |
| ZP_003235731130 | 32.3 | 4.70E+00 | 281 | 57 | 20 | ZP_00323296769 | 35.4 | 5.60E-01 | 148 | 35 | 23 | | |
| ZP_00317192676 | 37.7 | 1.10E-01 | 169 | 35 | 20 | ZP_00288038997 | 35.4 | 5.60E-01 | 294 | 56 | 19 | | |
| NP_771092 | 696 | 37.7 | 1.10E-01 | 134 | 39 | 29 | ZP_00338261589 | 35 | 7.30E-01 | 62 | 20 | 32 | |
| NP_214145 | 422 | 37.7 | 1.10E-01 | 186 | 40 | 21 | NP_718836 | 667 | 35 | 7.30E-01 | 98 | 20 | 20 |
| NP_765958 | 681 | 37.7 | 1.10E-01 | 176 | 45 | 25 | YP_128297 | 361 | 35 | 7.30E-01 | 358 | 69 | 19 |
| ZP_003125671475 | 37.7 | 1.10E-01 | 273 | 58 | 21 | YP_132326 | 529 | 35 | 7.30E-01 | 332 | 69 | 20 | |
| ZP_00240971564 | 37.7 | 1.10E-01 | 107 | 24 | 22 | NP_812240 | 868 | 35 | 7.30E-01 | 150 | 44 | 29 | |
| ZP_00195263572 | 37.7 | 1.10E-01 | 183 | 41 | 22 | NP_964984 | 4734 | 35 | 7.30E-01 | 316 | 66 | 20 | |
| NP_949268 | 623 | 37.4 | 1.50E-01 | 277 | 53 | 19 | NP_964984 | 4734 | 33.1 | 2.80E+00 | 153 | 40 | 26 |
| ZP_00315446537 | 37.4 | 1.50E-01 | 263 | 54 | 20 | ZP_00144637646 | 35 | 7.30E-01 | 243 | 44 | 18 | | |
| ZP_0028945115245 | 37.4 | 1.50E-01 | 272 | 65 | 23 | ZP_00222048485 | 35 | 7.30E-01 | 88 | 23 | 26 | | |
| ZP_00273576527 | 37.4 | 1.50E-01 | 90 | 25 | 27 | ZP_00220113501 | 35 | 7.30E-01 | 88 | 23 | 26 | | |
| ZP_00273576527 | 33.9 | 1.60E+00 | 83 | 22 | 26 | ZP_00137782629 | 35 | 7.30E-01 | 245 | 43 | 17 | | |
| NP_800021 | 623 | 37.4 | 1.50E-01 | 117 | 31 | 26 | ZP_00121836231 | 35 | 7.30E-01 | 165 | 39 | 23 | |
| NP_772493 | 627 | 37.4 | 1.50E-01 | 229 | 49 | 21 | NP_946001 | 587 | 34.7 | 9.60E-01 | 121 | 36 | 29 |
| AAP78292 | 855 | 37.4 | 1.50E-01 | 138 | 32 | 23 | ZP_00319892754 | 34.7 | 9.60E-01 | 284 | 62 | 21 | |
| ZP_00281310507 | 37.4 | 1.50E-01 | 119 | 31 | 26 | ZP_00319892754 | 33.1 | 2.80E+00 | 261 | 51 | 19 | | |
| ZP_00289133779 | 37 | 1.90E-01 | 198 | 38 | 19 | ZP_00311897602 | 34.7 | 9.60E-01 | 269 | 56 | 20 | | |
| ZP_00289133779 | 36.2 | 3.30E-01 | 89 | 26 | 29 | ZP_00336629824 | 34.7 | 9.60E-01 | 149 | 35 | 23 | | |
| NP_471790 | 927 | 37 | 1.90E-01 | 281 | 59 | 20 | NP_802026 | 593 | 34.7 | 9.60E-01 | 118 | 33 | 27 |
| NP_471790 | 927 | 31.6 | 8.10E+00 | 210 | 46 | 21 | NP_924800 | 1241 | 34.7 | 9.60E-01 | 73 | 24 | 32 |
| NP_522634 | 3322 | 37 | 1.90E-01 | 228 | 52 | 22 | NP_463823 | 500 | 34.7 | 9.60E-01 | 233 | 47 | 20 |
| NP_404364 | 307 | 37 | 1.90E-01 | 253 | 52 | 20 | NP_645581 | 946 | 34.7 | 9.60E-01 | 219 | 44 | 20 |
| NP_336479 | 342 | 37 | 1.90E-01 | 87 | 25 | 28 | NP_792425 | 633 | 34.7 | 9.60E-01 | 283 | 50 | 17 |
| NP_248731 | 3535 | 37 | 1.90E-01 | 286 | 62 | 21 | NP_561978 | 344 | 34.7 | 9.60E-01 | 232 | 49 | 21 |
| YP_066441 | 693 | 37 | 1.90E-01 | 120 | 30 | 25 | NP_350172 | 783 | 34.7 | 9.60E-01 | 129 | 29 | 22 |
| NP_757754 | 161 | 37 | 1.90E-01 | 77 | 23 | 29 | NP_349191 | 722 | 34.7 | 9.60E-01 | 143 | 36 | 25 |
| NP_670743 | 308 | 37 | 1.90E-01 | 253 | 52 | 20 | NP_349191 | 722 | 33.1 | 2.80E+00 | 292 | 67 | 19 |
| NP_603291 | 1724 | 37 | 1.90E-01 | 131 | 34 | 25 | AAO10484 | 626 | 34.7 | 9.60E-01 | 299 | 52 | 17 |
| ZP_00290800910 | 37 | 1.90E-01 | 260 | 53 | 20 | NP_642322 | 396 | 34.7 | 9.60E-01 | 123 | 22 | 17 | |
| ZP_00219646252 | 37 | 1.90E-01 | 74 | 21 | 28 | YP_133410 | 577 | 34.7 | 9.60E-01 | 317 | 61 | 19 | |
| ZP_00063136721 | 37 | 1.90E-01 | 298 | 58 | 19 | NP_269527 | 594 | 34.7 | 9.60E-01 | 118 | 33 | 27 | |
| NP_799785 | 346 | 36.6 | 2.50E-01 | 116 | 29 | 25 | YP_042878 | 928 | 34.7 | 9.60E-01 | 219 | 44 | 20 |
| NP_739300 | 290 | 36.6 | 2.50E-01 | 122 | 30 | 24 | YP_012922 | 500 | 34.7 | 9.60E-01 | 233 | 47 | 20 |
| AAP96352 | 1119 | 36.6 | 2.50E-01 | 143 | 35 | 24 | NP_051325 | 222 | 34.7 | 9.60E-01 | 114 | 30 | 26 |
| NP_359656 | 1902 | 36.6 | 2.50E-01 | 282 | 60 | 21 | NP_782459 | 569 | 34.7 | 9.60E-01 | 305 | 61 | 20 |
| NP_253231 | 1417 | 36.6 | 2.50E-01 | 201 | 49 | 24 | NP_607532 | 594 | 34.7 | 9.60E-01 | 118 | 33 | 27 |
| NP_932208 | 603 | 36.6 | 2.50E-01 | 53 | 17 | 32 | ZP_00233976541 | 34.7 | 9.60E-01 | 233 | 47 | 20 | |
| ZP_00218988486 | 36.6 | 2.50E-01 | 259 | 56 | 21 | ZP_00212291306 | 34.7 | 9.60E-01 | 130 | 38 | 29 | | |
| ZP_00149774452 | 36.6 | 2.50E-01 | 264 | 56 | 21 | NP_469464 | 1788 | 34.3 | 1.20E+00 | 290 | 65 | 22 | |
| ZP_00319246821 | 36.2 | 3.30E-01 | 65 | 19 | 29 | NP_792292 | 629 | 34.3 | 1.20E+00 | 128 | 31 | 24 | |
| ZP_00284479601 | 36.2 | 3.30E-01 | 262 | 52 | 19 | NP_695350 | 459 | 34.3 | 1.20E+00 | 271 | 54 | 19 | |
| ZP_00005278425 | 36.2 | 3.30E-01 | 193 | 50 | 25 | NP_348729 | 570 | 34.3 | 1.20E+00 | 162 | 36 | 22 | |
| NP_280332 | 643 | 36.2 | 3.30E-01 | 233 | 50 | 21 | NP_252997 | 632 | 34.3 | 1.20E+00 | 245 | 43 | 17 |
| NP_522101 | 3552 | 36.2 | 3.30E-01 | 209 | 45 | 21 | YP_066477 | 393 | 34.3 | 1.20E+00 | 148 | 33 | 22 |
| NP_964415 | 1096 | 36.2 | 3.30E-01 | 265 | 56 | 21 | YP_064761 | 880 | 34.3 | 1.20E+00 | 126 | 30 | 23 |
| ZP_00313063880 | 36.2 | 3.30E-01 | 181 | 39 | 21 | YP_064723 | 674 | 34.3 | 1.20E+00 | 248 | 48 | 19 | |
| ZP_00182337425 | 36.2 | 3.30E-01 | 245 | 41 | 16 | NP_935137 | 626 | 34.3 | 1.20E+00 | 299 | 52 | 17 | |
| ZP_00160617717 | 36.2 | 3.30E-01 | 289 | 62 | 21 | NP_866060 | 3056 | 34.3 | 1.20E+00 | 120 | 34 | 28 | |

Fig. 25C-Continued

| Hit_ID | Length | Bitscore | Expected | Length | #Ident | %S | Hit_ID | Length | Bitscore | Expected | Length | #Ident | %S |
|---|---|---|---|---|---|---|---|---|---|---|---|---|---|
| NP_866060 | 3056 | 33.1 | 2.80E+00 | 116 | 34 | 29 | ZP_00147410749 | | 33.1 | 2.80E+00 | 131 | 34 | 25 |
| NP_616105 | 1074 | 34.3 | 1.20E+00 | 257 | 49 | 19 | ZP_00137783633 | | 33.1 | 2.80E+00 | 245 | 42 | 17 |
| ZP_003233981656 | | 34.3 | 1.20E+00 | 187 | 41 | 21 | ZP_00123950634 | | 33.1 | 2.80E+00 | 96 | 24 | 25 |
| ZP_00308827366 | | 34.3 | 1.20E+00 | 138 | 35 | 25 | ZP_00128148551 | | 33.1 | 2.80E+00 | 256 | 46 | 17 |
| ZP_00137780616 | | 34.3 | 1.20E+00 | 245 | 43 | 17 | ZP_003460801463 | | 33.1 | 2.80E+00 | 274 | 69 | 25 |
| ZP_00124017629 | | 34.3 | 1.20E+00 | 254 | 46 | 18 | ZP_00326431563 | | 32.7 | 3.60E+00 | 307 | 70 | 22 |
| ZP_00110825475 | | 34.3 | 1.20E+00 | 140 | 35 | 25 | NP_252999 | 629 | 32.7 | 3.60E+00 | 127 | 32 | 25 |
| ZP_00046942967 | | 33.9 | 1.60E+00 | 134 | 35 | 26 | ZP_000531851136 | | 32.7 | 3.60E+00 | 223 | 51 | 22 |
| YP_080405 | 660 | 33.9 | 1.60E+00 | 87 | 22 | 25 | NP_993634 | 2578 | 32.7 | 3.60E+00 | 290 | 61 | 21 |
| NP_470074 | 599 | 33.9 | 1.60E+00 | 288 | 59 | 20 | YP_081346 | 561 | 32.7 | 3.60E+00 | 99 | 20 | 20 |
| NP_927898 | 4582 | 33.9 | 1.60E+00 | 257 | 61 | 23 | NP_471252 | 1186 | 32.7 | 3.60E+00 | 315 | 63 | 20 |
| NP_815456 | 533 | 33.9 | 1.60E+00 | 125 | 35 | 28 | NP_469482 | 290 | 32.7 | 3.60E+00 | 82 | 21 | 25 |
| NP_562046 | 933 | 33.9 | 1.60E+00 | 259 | 51 | 19 | NP_464250 | 601 | 32.7 | 3.60E+00 | 193 | 39 | 20 |
| NP_267826 | 901 | 33.9 | 1.60E+00 | 281 | 56 | 19 | NP_929013 | 190 | 32.7 | 3.60E+00 | 133 | 34 | 25 |
| YP_135620 | 471 | 33.9 | 1.60E+00 | 121 | 30 | 24 | NP_793014 | 6274 | 32.7 | 3.60E+00 | 246 | 51 | 20 |
| YP_126425 | 657 | 33.9 | 1.60E+00 | 121 | 29 | 23 | NP_790315 | 541 | 32.7 | 3.60E+00 | 93 | 28 | 30 |
| YP_131301 | 638 | 33.9 | 1.60E+00 | 73 | 16 | 21 | NP_769573 | 564 | 32.7 | 3.60E+00 | 157 | 36 | 22 |
| NP_987908 | 720 | 33.9 | 1.60E+00 | 95 | 27 | 28 | NP_563507 | 721 | 32.7 | 3.60E+00 | 112 | 25 | 22 |
| YP_030040 | 660 | 33.9 | 1.60E+00 | 105 | 25 | 23 | NP_406024 | 2535 | 32.7 | 3.60E+00 | 290 | 61 | 21 |
| NP_981473 | 564 | 33.9 | 1.60E+00 | 109 | 24 | 22 | NP_939703 | 888 | 32.7 | 3.60E+00 | 123 | 31 | 25 |
| NP_784971 | 983 | 33.9 | 1.60E+00 | 299 | 58 | 19 | AAP56776 | 742 | 32.7 | 3.60E+00 | 186 | 40 | 21 |
| NP_783077 | 417 | 33.9 | 1.60E+00 | 103 | 24 | 23 | NP_882071 | 1175 | 32.7 | 3.60E+00 | 65 | 18 | 27 |
| NP_965011 | 912 | 33.9 | 1.60E+00 | 214 | 49 | 22 | NP_419323 | 622 | 32.7 | 3.60E+00 | 235 | 47 | 20 |
| NP_964462 | 1000 | 33.9 | 1.60E+00 | 125 | 28 | 22 | YP_134634 | 596 | 32.7 | 3.60E+00 | 63 | 14 | 22 |
| ZP_002991151200 | | 33.5 | 2.10E+00 | 61 | 17 | 27 | YP_108428 | 634 | 32.7 | 3.60E+00 | 266 | 52 | 19 |
| ZP_00056271661 | | 33.5 | 2.10E+00 | 278 | 54 | 19 | NP_109825 | 228 | 32.7 | 3.60E+00 | 154 | 29 | 18 |
| NP_287395 | 973 | 33.5 | 2.10E+00 | 185 | 42 | 22 | YP_013363 | 601 | 32.7 | 3.60E+00 | 193 | 39 | 20 |
| NP_794375 | 539 | 33.5 | 2.10E+00 | 128 | 23 | 17 | NP_669014 | 2579 | 32.7 | 3.60E+00 | 290 | 61 | 21 |
| YP_137657 | 727 | 33.5 | 2.10E+00 | 86 | 25 | 29 | ZP_00284267481 | | 32.7 | 3.60E+00 | 77 | 21 | 27 |
| YP_115527 | 534 | 33.5 | 2.10E+00 | 80 | 24 | 30 | ZP_00280424428 | | 32.7 | 3.60E+00 | 196 | 50 | 25 |
| NP_309677 | 971 | 33.5 | 2.10E+00 | 185 | 42 | 22 | NP_326456 | 750 | 32.3 | 4.70E+00 | 121 | 27 | 22 |
| NP_936396 | 542 | 33.5 | 2.10E+00 | 300 | 62 | 20 | NP_391003 | 662 | 32.3 | 4.70E+00 | 322 | 60 | 18 |
| NP_637327 | 396 | 33.5 | 2.10E+00 | 123 | 21 | 17 | NP_852542 | 1658 | 32.3 | 4.70E+00 | 149 | 33 | 22 |
| NP_616912 | 1052 | 33.5 | 2.10E+00 | 132 | 36 | 27 | NP_852542 | 1658 | 32.3 | 4.70E+00 | 139 | 27 | 19 |
| NP_964159 | 982 | 33.5 | 2.10E+00 | 203 | 47 | 23 | NP_646487 | 424 | 32.3 | 4.70E+00 | 147 | 36 | 24 |
| ZP_00296785641 | | 33.5 | 2.10E+00 | 275 | 60 | 21 | NP_718941 | 169 | 32.3 | 4.70E+00 | 160 | 36 | 22 |
| ZP_00217082977 | | 33.5 | 2.10E+00 | 109 | 32 | 29 | NP_716901 | 706 | 32.3 | 4.70E+00 | 273 | 59 | 21 |
| ZP_00106667978 | | 33.5 | 2.10E+00 | 112 | 29 | 25 | NP_801002 | 542 | 32.3 | 4.70E+00 | 304 | 58 | 19 |
| ZP_00290912684 | | 33.1 | 2.80E+00 | 130 | 24 | 18 | AAQ60540 | 2373 | 32.3 | 4.70E+00 | 255 | 55 | 21 |
| ZP_00290912684 | | 32.3 | 4.70E+00 | 188 | 35 | 18 | AAQ58389 | 690 | 32.3 | 4.70E+00 | 110 | 25 | 22 |
| ZP_00338277837 | | 33.1 | 2.80E+00 | 109 | 26 | 23 | NP_770343 | 582 | 32.3 | 4.70E+00 | 270 | 50 | 18 |
| NP_798538 | 678 | 33.1 | 2.80E+00 | 127 | 27 | 21 | AAF96820 | 652 | 32.3 | 4.70E+00 | 120 | 31 | 25 |
| NP_790701 | 498 | 33.1 | 2.80E+00 | 162 | 41 | 25 | AAF94794 | 596 | 32.3 | 4.70E+00 | 80 | 19 | 23 |
| NP_768559 | 816 | 33.1 | 2.80E+00 | 62 | 19 | 30 | NP_404241 | 3295 | 32.3 | 4.70E+00 | 289 | 61 | 21 |
| NP_415890 | 1122 | 33.1 | 2.80E+00 | 147 | 37 | 25 | YP_137110 | 536 | 32.3 | 4.70E+00 | 199 | 47 | 23 |
| AAO08482 | 622 | 33.1 | 2.80E+00 | 120 | 30 | 25 | YP_032604 | 1872 | 32.3 | 4.70E+00 | 118 | 31 | 26 |
| AAO10918 | 675 | 33.1 | 2.80E+00 | 125 | 29 | 23 | NP_782523 | 471 | 32.3 | 4.70E+00 | 107 | 20 | 18 |
| NP_889112 | 532 | 33.1 | 2.80E+00 | 250 | 48 | 19 | NP_765908 | 300 | 32.3 | 4.70E+00 | 132 | 29 | 21 |
| YP_129467 | 640 | 33.1 | 2.80E+00 | 137 | 31 | 22 | NP_765785 | 952 | 32.3 | 4.70E+00 | 195 | 37 | 18 |
| YP_133516 | 467 | 33.1 | 2.80E+00 | 127 | 26 | 20 | NP_606940 | 628 | 32.3 | 4.70E+00 | 271 | 60 | 22 |
| YP_132040 | 542 | 33.1 | 2.80E+00 | 107 | 27 | 25 | ZP_002394591038 | | 32.3 | 4.70E+00 | 243 | 52 | 21 |
| YP_076807 | 558 | 33.1 | 2.80E+00 | 118 | 30 | 25 | ZP_00236267289 | | 32.3 | 4.70E+00 | 156 | 31 | 19 |
| NP_987607 | 729 | 33.1 | 2.80E+00 | 95 | 26 | 27 | ZP_002326811066 | | 32.3 | 4.70E+00 | 277 | 57 | 20 |
| NP_378194 | 467 | 33.1 | 2.80E+00 | 53 | 17 | 32 | ZP_002188313513 | | 32.3 | 4.70E+00 | 204 | 61 | 25 |
| NP_253000 | 629 | 33.1 | 2.80E+00 | 245 | 42 | 17 | ZP_00171925505 | | 32.3 | 4.70E+00 | 253 | 48 | 18 |
| YP_063897 | 576 | 33.1 | 2.80E+00 | 263 | 46 | 17 | ZP_00201727822 | | 32.3 | 4.70E+00 | 306 | 59 | 19 |
| YP_041192 | 424 | 33.1 | 2.80E+00 | 147 | 36 | 24 | ZP_00149920505 | | 32.3 | 4.70E+00 | 139 | 31 | 22 |
| NP_936490 | 622 | 33.1 | 2.80E+00 | 120 | 30 | 25 | ZP_00133930158 | | 32.3 | 4.70E+00 | 106 | 26 | 24 |
| NP_786249 | 1106 | 33.1 | 2.80E+00 | 330 | 64 | 19 | ZP_00098108451 | | 32.3 | 4.70E+00 | 139 | 33 | 23 |
| NP_777771 | 638 | 33.1 | 2.80E+00 | 121 | 29 | 23 | ZP_00312864422 | | 32 | 6.20E+00 | 142 | 36 | 25 |
| NP_764984 | 3692 | 33.1 | 2.80E+00 | 148 | 30 | 20 | ZP_00298543733 | | 32 | 6.20E+00 | 278 | 50 | 17 |
| NP_764984 | 3692 | 32.3 | 4.70E+00 | 264 | 52 | 19 | ZP_003410411311 | | 32 | 6.20E+00 | 230 | 37 | 16 |
| NP_600104 | 441 | 33.1 | 2.80E+00 | 280 | 63 | 22 | ZP_00208461932 | | 32 | 6.20E+00 | 211 | 43 | 20 |
| NP_693909 | 466 | 33.1 | 2.80E+00 | 126 | 24 | 19 | ZP_00046132979 | | 32 | 6.20E+00 | 143 | 32 | 22 |
| NP_608047 | 400 | 33.1 | 2.80E+00 | 108 | 29 | 26 | NP_279901 | 636 | 32 | 6.20E+00 | 244 | 53 | 21 |
| NP_604026 | 1193 | 33.1 | 2.80E+00 | 253 | 52 | 20 | NP_464751 | 1066 | 32 | 6.20E+00 | 277 | 56 | 20 |
| NP_559170 | 396 | 33.1 | 2.80E+00 | 119 | 29 | 24 | NP_885521 | 1195 | 32 | 6.20E+00 | 65 | 18 | 27 |
| NP_541885 | 131 | 33.1 | 2.80E+00 | 62 | 24 | 38 | AAQ60246 | 251 | 32 | 6.20E+00 | 98 | 30 | 30 |

Fig. 25C-Continued

| Hit_ID | Length | Bitscore | Expected | Length | #Ident | %S |
|---|---|---|---|---|---|---|
| NP_768828 | 432 | 32 | 6.20E+00 | 164 | 35 | 21 |
| NP_699533 | 317 | 32 | 6.20E+00 | 56 | 22 | 39 |
| NP_346950 | 371 | 32 | 6.20E+00 | 147 | 35 | 23 |
| NP_207534 | 493 | 32 | 6.20E+00 | 122 | 32 | 26 |
| NP_249777 | 683 | 32 | 6.20E+00 | 303 | 72 | 23 |
| YP_041227 | 2189 | 32 | 6.20E+00 | 149 | 35 | 23 |
| YP_010811 | 580 | 32 | 6.20E+00 | 206 | 44 | 21 |
| NP_784951 | 3360 | 32 | 6.20E+00 | 76 | 21 | 27 |
| NP_765498 | 495 | 32 | 6.20E+00 | 74 | 16 | 21 |
| NP_757771 | 1378 | 32 | 6.20E+00 | 73 | 22 | 30 |
| NP_688862 | 443 | 32 | 6.20E+00 | 66 | 17 | 25 |
| ZP_00284224 | 3286 | 32 | 6.20E+00 | 283 | 62 | 21 |
| ZP_00356478 | 659 | 32 | 6.20E+00 | 128 | 32 | 25 |
| ZP_00216525 | 494 | 32 | 6.20E+00 | 118 | 25 | 21 |
| ZP_00215989 | 433 | 32 | 6.20E+00 | 61 | 20 | 32 |
| ZP_00211381 | 462 | 32 | 6.20E+00 | 89 | 23 | 25 |
| ZP_00220828 | 371 | 32 | 6.20E+00 | 116 | 31 | 26 |
| ZP_00154800 | 558 | 32 | 6.20E+00 | 139 | 31 | 22 |
| ZP_00348486 | 544 | 32 | 6.20E+00 | 93 | 22 | 23 |
| ZP_00138674 | 683 | 32 | 6.20E+00 | 303 | 72 | 23 |
| ZP_00274787 | 513 | 31.6 | 8.10E+00 | 247 | 48 | 19 |
| NP_326524 | 1125 | 31.6 | 8.10E+00 | 174 | 37 | 21 |
| ZP_00054847 | 736 | 31.6 | 8.10E+00 | 272 | 53 | 19 |
| NP_813981 | 522 | 31.6 | 8.10E+00 | 137 | 33 | 24 |
| NP_794891 | 647 | 31.6 | 8.10E+00 | 119 | 27 | 22 |
| NP_766736 | 691 | 31.6 | 8.10E+00 | 101 | 30 | 29 |
| NP_562167 | 327 | 31.6 | 8.10E+00 | 253 | 47 | 18 |
| NP_561782 | 2104 | 31.6 | 8.10E+00 | 126 | 23 | 18 |
| NP_358633 | 1091 | 31.6 | 8.10E+00 | 137 | 31 | 22 |
| NP_349987 | 570 | 31.6 | 8.10E+00 | 300 | 64 | 21 |
| YP_138060 | 1562 | 31.6 | 8.10E+00 | 103 | 23 | 22 |
| NP_223662 | 668 | 31.6 | 8.10E+00 | 138 | 32 | 23 |
| YP_084257 | 1041 | 31.6 | 8.10E+00 | 243 | 51 | 20 |
| YP_130345 | 561 | 31.6 | 8.10E+00 | 303 | 57 | 18 |
| YP_130208 | 521 | 31.6 | 8.10E+00 | 273 | 61 | 22 |
| YP_071037 | 2550 | 31.6 | 8.10E+00 | 290 | 61 | 21 |
| YP_070267 | 808 | 31.6 | 8.10E+00 | 249 | 53 | 21 |
| NP_072757 | 398 | 31.6 | 8.10E+00 | 156 | 36 | 23 |
| YP_056420 | 529 | 31.6 | 8.10E+00 | 94 | 25 | 26 |
| YP_030044 | 959 | 31.6 | 8.10E+00 | 276 | 57 | 20 |
| YP_028999 | 810 | 31.6 | 8.10E+00 | 243 | 52 | 21 |
| NP_600558 | 288 | 31.6 | 8.10E+00 | 63 | 18 | 28 |
| NP_657914 | 598 | 31.6 | 8.10E+00 | 276 | 57 | 20 |
| NP_656819 | 807 | 31.6 | 8.10E+00 | 243 | 52 | 21 |
| NP_965588 | 1218 | 31.6 | 8.10E+00 | 246 | 40 | 16 |
| ZP_00305598 | 305 | 31.6 | 8.10E+00 | 69 | 21 | 30 |
| ZP_00267783 | 642 | 31.6 | 8.10E+00 | 232 | 47 | 20 |
| ZP_00235052 | 646 | 31.6 | 8.10E+00 | 176 | 34 | 19 |
| ZP_00233607 | 236 | 31.6 | 8.10E+00 | 121 | 27 | 22 |
| ZP_00169819 | 1318 | 31.6 | 8.10E+00 | 233 | 54 | 23 |
| ZP_00203712 | 834 | 31.6 | 8.10E+00 | 112 | 28 | 25 |
| ZP_00125435 | 646 | 31.6 | 8.10E+00 | 225 | 42 | 18 |
| ZP_00127280 | 469 | 31.6 | 8.10E+00 | 275 | 54 | 19 |
| ZP_00122460 | 3554 | 31.6 | 8.10E+00 | 284 | 59 | 20 |

Fig. 25D

| Hit_ID | Expected | Length | #Ident | %S | Hit_ID | Expected | Length | #Ident | %S |
|---|---|---|---|---|---|---|---|---|---|
| AADY01000001 | 1.00E-100 | 373 | 213 | 57 | spara_B_SPA.0.22632 | 4.00E-74 | 175 | 147 | 84 |
| NZ_AADY01000001 | 1.00E-100 | 373 | 213 | 57 | spara_B_SPA.0.22632 | 2.00E-37 | 100 | 82 | 82 |
| NC_005126 | 1.00E-100 | 355 | 207 | 58 | NC_002928 | 3.00E-72 | 392 | 180 | 45 |
| Yersinia | 7.00E-89 | 364 | 202 | 55 | NC_002928 | 1.00E-06 | 136 | 42 | 30 |
| Yersinia | 9.00E-89 | 367 | 200 | 54 | NC_002929 | 6.00E-71 | 391 | 182 | 46 |
| Yersinia | 7.00E-59 | 308 | 149 | 48 | NC_002929 | 1.00E-06 | 136 | 43 | 31 |
| Yersinia | 2.00E-31 | 294 | 107 | 36 | NC_002927 | 2.00E-70 | 391 | 183 | 46 |
| NC_005810 | 5.00E-86 | 368 | 202 | 54 | NC_002927 | 1.00E-06 | 136 | 42 | 30 |
| NC_005810 | 3.00E-21 | 223 | 67 | 30 | NZ_AAAI02000003 | 1.00E-67 | 179 | 134 | 74 |
| NC_005810 | 1.00E-04 | 66 | 22 | 33 | NZ_AAAI02000003 | 6.00E-31 | 92 | 68 | 73 |
| NC_003143 | 5.00E-86 | 368 | 202 | 54 | AAAI02000003 | 1.00E-67 | 179 | 134 | 74 |
| NC_003143 | 3.00E-21 | 223 | 67 | 30 | AAAI02000003 | 6.00E-31 | 92 | 68 | 73 |
| NC_003143 | 4.00E-19 | 295 | 76 | 25 | NZ_AAAU02000002 | 9.00E-67 | 262 | 144 | 54 |
| NC_003143 | 6.00E-18 | 309 | 79 | 25 | NZ_AAAU02000002 | 4.00E-32 | 90 | 71 | 78 |
| NC_006155 | 5.00E-86 | 368 | 202 | 54 | AAAU02000002 | 9.00E-67 | 262 | 144 | 54 |
| NC_006155 | 9.00E-20 | 207 | 61 | 29 | AAAU02000002 | 4.00E-32 | 90 | 71 | 78 |
| NC_006155 | 3.00E-08 | 115 | 37 | 32 | AADX01000003 | 2.00E-65 | 297 | 145 | 48 |
| NC_004088 | 5.00E-86 | 368 | 202 | 54 | NZ_AADX01000003 | 2.00E-65 | 297 | 145 | 48 |
| NC_004088 | 3.00E-21 | 223 | 67 | 30 | NC_005085 | 7.00E-65 | 297 | 137 | 46 |
| NC_004088 | 2.00E-07 | 84 | 28 | 33 | NC_005085 | 3.00E-64 | 297 | 137 | 46 |
| NC_002655 | 5.00E-82 | 274 | 169 | 61 | NC_005085 | 1.00E-43 | 299 | 104 | 34 |
| NC_002655 | 5.00E-33 | 115 | 74 | 64 | NC_005085 | 9.00E-41 | 369 | 122 | 33 |
| NC_002655 | 9.00E-06 | 299 | 66 | 22 | NC_005085 | 6.00E-08 | 299 | 62 | 20 |
| NC_002655 | 2.60E+00 | 185 | 42 | 22 | NC_005085 | 6.80E-01 | 266 | 61 | 22 |
| NC_002695 | 5.00E-82 | 274 | 169 | 61 | NZ_AAAN02000069 | 9.00E-65 | 296 | 145 | 48 |
| NC_002695 | 5.00E-33 | 115 | 74 | 64 | NZ_AAAN02000069 | 5.00E-61 | 295 | 136 | 46 |
| NC_002695 | 9.00E-06 | 299 | 66 | 22 | NZ_AAAN02000069 | 6.00E-61 | 295 | 136 | 46 |
| NC_002695 | 2.60E+00 | 185 | 42 | 22 | NZ_AAAN02000069 | 1.00E-60 | 295 | 135 | 45 |
| senteritdis_716_10.21 | 5.00E-82 | 161 | 160 | 99 | NZ_AAAN02000069 | 1.00E-59 | 296 | 132 | 44 |
| shig277d06.q1k | 5.00E-82 | 299 | 183 | 61 | NZ_AAAN02000069 | 1.00E-59 | 296 | 132 | 44 |
| shig277d06.q1k | 6.00E-35 | 92 | 76 | 82 | NZ_AAAN02000069 | 2.00E-46 | 296 | 112 | 37 |
| Epath054a03.p1k | 1.00E-80 | 266 | 171 | 64 | AAAN02000069 | 9.00E-65 | 296 | 145 | 48 |
| Epath054a03.p1k | 1.00E-32 | 102 | 69 | 67 | AAAN02000069 | 5.00E-61 | 295 | 136 | 46 |
| NC_004431 | 3.00E-80 | 223 | 157 | 70 | AAAN02000069 | 6.00E-61 | 295 | 136 | 46 |
| NC_004431 | 6.00E-32 | 255 | 106 | 41 | AAAN02000069 | 1.00E-60 | 295 | 135 | 45 |
| Eagg66e09.q1k | 2.00E-79 | 237 | 161 | 67 | AAAN02000069 | 1.00E-59 | 296 | 132 | 44 |
| Eagg66e09.q1k | 9.00E-33 | 295 | 105 | 35 | AAAN02000069 | 1.00E-59 | 296 | 132 | 44 |
| NC_004337 | 1.00E-78 | 202 | 154 | 76 | AAAN02000069 | 2.00E-46 | 296 | 112 | 37 |
| NC_004337 | 1.00E-32 | 116 | 71 | 61 | NZ_AAAN02000032 | 1.00E-62 | 296 | 134 | 45 |
| NC_004741 | 1.00E-78 | 202 | 154 | 76 | NZ_AAAN02000032 | 3.00E-61 | 296 | 133 | 44 |
| NC_004741 | 1.00E-32 | 116 | 71 | 61 | NZ_AAAN02000032 | 3.00E-61 | 296 | 133 | 44 |
| dys055h06.q1k | 2.00E-78 | 237 | 159 | 67 | NZ_AAAN02000032 | 4.00E-59 | 296 | 136 | 45 |
| dys055h06.q1k | 2.00E-31 | 100 | 67 | 67 | NZ_AAAN02000032 | 7.00E-56 | 295 | 130 | 44 |
| NC_000913 | 1.00E-76 | 177 | 146 | 82 | NZ_AAAN02000032 | 3.00E-53 | 282 | 117 | 41 |
| NC_000913 | 4.00E-35 | 151 | 80 | 52 | NZ_AAAN02000032 | 3.00E-17 | 87 | 47 | 54 |
| NC_004757 | 5.00E-76 | 297 | 159 | 53 | NZ_AAAN02000032 | 7.00E-12 | 275 | 64 | 23 |
| NC_003198 | 8.00E-76 | 175 | 150 | 85 | AAAN02000032 | 1.00E-62 | 296 | 134 | 45 |
| NC_003198 | 4.00E-35 | 91 | 76 | 83 | AAAN02000032 | 3.00E-61 | 296 | 133 | 44 |
| NC_004631 | 8.00E-76 | 175 | 150 | 85 | AAAN02000032 | 3.00E-61 | 296 | 133 | 44 |
| NC_004631 | 4.00E-35 | 91 | 76 | 83 | AAAN02000032 | 4.00E-59 | 296 | 136 | 45 |
| NC_006511 | 1.00E-75 | 279 | 165 | 59 | AAAN02000032 | 7.00E-56 | 295 | 130 | 44 |
| NC_006511 | 4.00E-74 | 175 | 147 | 84 | AAAN02000032 | 3.00E-53 | 282 | 117 | 41 |
| NC_006511 | 2.00E-37 | 100 | 82 | 82 | AAAN02000032 | 3.00E-17 | 87 | 47 | 54 |
| NC_006511 | 5.00E-37 | 100 | 81 | 81 | AAAN02000032 | 7.00E-12 | 275 | 64 | 23 |
| NC_003197 | 1.00E-75 | 232 | 160 | 68 | AAAT03000008 | 4.00E-62 | 297 | 138 | 46 |
| NC_003197 | 9.00E-75 | 175 | 148 | 84 | NZ_AAAT03000008 | 4.00E-62 | 297 | 138 | 46 |
| NC_003197 | 5.00E-37 | 100 | 81 | 81 | AADF01000011 | 2.00E-61 | 296 | 131 | 44 |
| NC_003197 | 4.00E-36 | 98 | 79 | 80 | AADF01000011 | 2.00E-10 | 322 | 67 | 20 |
| spara_B_SPA.0.15635 | 1.00E-75 | 279 | 165 | 59 | AADF01000011 | 3.10E-01 | 264 | 56 | 21 |
| spara_B_SPA.0.15635 | 1.00E-31 | 74 | 65 | 87 | NZ_AADF01000011 | 2.00E-61 | 296 | 131 | 44 |
| spara_B_SPA.0.15635 | 1.00E-31 | 26 | 16 | 61 | NZ_AADF01000011 | 2.00E-10 | 322 | 67 | 20 |
| salt7-76a12.p1k | 1.00E-75 | 232 | 160 | 68 | NZ_AADF01000011 | 3.10E-01 | 264 | 56 | 21 |
| salt7-76a12.p1k | 5.00E-37 | 100 | 81 | 81 | NC_004347 | 3.00E-61 | 297 | 140 | 47 |
| NC_003916 | 3.00E-75 | 296 | 167 | 56 | NC_004347 | 2.00E-60 | 297 | 138 | 46 |
| salt11-469e08.p1k | 9.00E-75 | 175 | 148 | 84 | NC_004347 | 8.00E-07 | 136 | 36 | 26 |
| salt11-469e08.p1k | 4.00E-36 | 98 | 79 | 80 | NC_004347 | 1.50E+00 | 89 | 26 | 29 |
| bong465h05.q1k | 3.00E-74 | 175 | 147 | 84 | NZ_AAAS02000027 | 8.00E-61 | 296 | 137 | 46 |
| bong465h05.q1k | 2.00E-36 | 100 | 80 | 80 | AAAS02000027 | 8.00E-61 | 296 | 137 | 46 |

Fig. 25D-Continued

| Hit_ID | Expected | Length | #Ident | %S | Hit_ID | Expected | Length | #Ident | %S |
|---|---|---|---|---|---|---|---|---|---|
| NC_006510 | 8.00E-61 | 307 | 134 | 43 | J10154Af04.p1k | 1.00E-51 | 300 | 115 | 38 |
| NC_006510 | 4.00E-33 | 269 | 96 | 35 | NC_004603 | 6.00E-51 | 376 | 131 | 34 |
| NC_006510 | 3.00E-21 | 179 | 62 | 34 | NC_004603 | 2.00E-42 | 384 | 125 | 32 |
| NC_006510 | 2.00E-14 | 288 | 69 | 23 | NC_004603 | 2.00E-40 | 377 | 125 | 33 |
| contig:3337:p_fluorescens | 7.00E-60 | 300 | 134 | 44 | NC_004603 | 2.00E-40 | 377 | 126 | 33 |
| contig:3337:p_fluorescens | 5.00E-06 | 130 | 37 | 28 | NC_004603 | 2.00E-40 | 377 | 126 | 33 |
| NZ_AABP02000008 | 1.00E-59 | 297 | 135 | 45 | NC_004603 | 3.00E-23 | 148 | 60 | 40 |
| NZ_AABP02000008 | 4.00E-08 | 138 | 41 | 29 | NC_004603 | 1.00E-12 | 217 | 61 | 28 |
| AABP02000008 | 1.00E-59 | 297 | 135 | 45 | NZ_AABG03000012 | 9.00E-51 | 295 | 120 | 40 |
| AABP02000008 | 4.00E-08 | 138 | 41 | 29 | NZ_AABG03000012 | 2.00E-48 | 292 | 118 | 40 |
| AAEI01000040 | 2.00E-59 | 291 | 134 | 46 | NZ_AABG03000012 | 4.00E-20 | 274 | 69 | 25 |
| NZ_AAEI01000040 | 2.00E-59 | 291 | 134 | 46 | AABG03000012 | 9.00E-51 | 295 | 120 | 40 |
| bstearo.fasta.screen.Contig | 4.00E-59 | 292 | 131 | 44 | AABG03000012 | 2.00E-48 | 292 | 118 | 40 |
| bstearo.fasta.screen.Contig | 1.00E-54 | 327 | 133 | 40 | AABG03000012 | 4.00E-20 | 274 | 69 | 25 |
| bstearo.fasta.screen.Contig | 1.00E-14 | 291 | 68 | 23 | NZ_AAEK01000005 | 1.00E-50 | 309 | 119 | 38 |
| NC_002939 | 6.00E-59 | 298 | 133 | 44 | NZ_AAEK01000005 | 3.00E-49 | 293 | 117 | 39 |
| NC_002939 | 2.00E-17 | 293 | 76 | 25 | NZ_AAEK01000005 | 4.00E-49 | 292 | 118 | 40 |
| contig:4013:c_hydrogenoform | 2.00E-58 | 298 | 133 | 44 | NZ_AAEK01000005 | 1.00E-46 | 295 | 111 | 37 |
| contig:4013:c_hydrogenoform | 6.00E-21 | 288 | 81 | 28 | NZ_AAEK01000005 | 6.00E-32 | 292 | 96 | 32 |
| NC_004578 | 1.00E-57 | 297 | 129 | 43 | AAEK01000005 | 1.00E-50 | 309 | 119 | 38 |
| NC_004578 | 1.50E+00 | 128 | 31 | 24 | AAEK01000005 | 3.00E-49 | 293 | 117 | 39 |
| NC_003869 | 1.00E-56 | 298 | 134 | 44 | AAEK01000005 | 4.00E-49 | 292 | 118 | 40 |
| NC_003869 | 9.00E-20 | 290 | 83 | 28 | AAEK01000005 | 1.00E-46 | 295 | 111 | 37 |
| NZ_AAAV02000005 | 3.00E-56 | 329 | 133 | 40 | AAEK01000005 | 6.00E-32 | 292 | 96 | 32 |
| AAAV02000005 | 3.00E-56 | 329 | 133 | 40 | NC_005363 | 4.00E-50 | 295 | 124 | 42 |
| NC_004344 | 3.00E-56 | 181 | 109 | 60 | NC_005363 | 3.00E-49 | 292 | 120 | 41 |
| NC_004344 | 2.00E-26 | 345 | 109 | 31 | NC_005363 | 5.00E-47 | 301 | 117 | 38 |
| NC_006270 | 5.00E-55 | 313 | 135 | 43 | NC_005363 | 3.00E-46 | 292 | 115 | 39 |
| NC_006270 | 2.00E+00 | 87 | 22 | 25 | NC_005363 | 2.00E-43 | 295 | 110 | 37 |
| NC_006322 | 5.00E-55 | 313 | 135 | 43 | NC_005363 | 4.00E-42 | 296 | 109 | 37 |
| NC_006322 | 2.00E+00 | 87 | 22 | 25 | AAEM01000002 | 8.00E-50 | 404 | 146 | 36 |
| Cbot440b12.q1c | 6.00E-55 | 298 | 127 | 42 | AAEM01000002 | 2.00E-48 | 404 | 150 | 37 |
| Cbot440b12.q1c | 1.00E-54 | 298 | 127 | 42 | NZ_AAEM01000002 | 8.00E-50 | 404 | 146 | 36 |
| Cbot440b12.q1c | 4.00E-40 | 304 | 103 | 33 | NZ_AAEM01000002 | 2.00E-48 | 404 | 150 | 37 |
| Cbot440b12.q1c | 2.00E-37 | 280 | 84 | 30 | NC_003919 | 3.00E-49 | 212 | 113 | 53 |
| Cbot440b12.q1c | 3.00E-11 | 305 | 63 | 20 | NC_003919 | 2.00E-21 | 307 | 87 | 28 |
| NC_002570 | 1.00E-54 | 294 | 124 | 42 | NC_003919 | 5.00E-09 | 134 | 40 | 29 |
| NC_002570 | 2.00E-29 | 135 | 70 | 51 | contig:492:b_thailandensis | 7.00E-49 | 380 | 136 | 35 |
| NC_002570 | 4.00E-19 | 169 | 57 | 33 | contig:492:b_thailandensis | 8.90E-01 | 49 | 18 | 36 |
| Cd183h6.p1t | 5.00E-54 | 300 | 125 | 41 | sdublin_Contig2945_12.23 | 9.00E-49 | 106 | 104 | 98 |
| Cd183h6.p1t | 3.00E-08 | 293 | 62 | 21 | senteritdis_1988_10.21 | 9.00E-49 | 106 | 104 | 98 |
| Cd183h6.p1t | 1.50E+00 | 309 | 55 | 17 | NZ_AAFH01000001 | 2.00E-48 | 290 | 120 | 41 |
| Cd183h6.p1t | 2.00E+00 | 113 | 24 | 21 | NZ_AAFH01000001 | 2.00E-24 | 159 | 67 | 42 |
| AADW01000019 | 1.00E-53 | 299 | 128 | 42 | AAFH01000001 | 2.00E-48 | 290 | 120 | 41 |
| AADW01000019 | 7.00E-46 | 300 | 110 | 36 | AAFH01000001 | 2.00E-24 | 159 | 67 | 42 |
| AADW01000019 | 9.00E-12 | 321 | 74 | 23 | NC_003902 | 2.00E-48 | 241 | 119 | 49 |
| NZ_AADW01000019 | 1.00E-53 | 299 | 128 | 42 | NC_003902 | 1.00E-21 | 319 | 93 | 29 |
| NZ_AADW01000019 | 7.00E-46 | 300 | 110 | 36 | NC_003902 | 1.00E-07 | 134 | 38 | 28 |
| NZ_AADW01000019 | 9.00E-12 | 321 | 74 | 23 | NC_006138 | 3.00E-48 | 252 | 120 | 47 |
| NC_004557 | 2.00E-53 | 296 | 125 | 42 | NC_006138 | 1.00E-43 | 231 | 108 | 46 |
| NC_004557 | 1.00E-41 | 294 | 105 | 35 | NC_006138 | 5.00E-25 | 227 | 81 | 35 |
| NC_004557 | 3.00E-33 | 270 | 80 | 29 | NC_006138 | 2.00E-22 | 254 | 79 | 31 |
| NC_004557 | 1.00E-10 | 284 | 68 | 23 | NC_006138 | 9.00E-06 | 130 | 40 | 30 |
| NC_004557 | 2.00E+00 | 103 | 24 | 23 | NC_006138 | 1.50E+00 | 148 | 33 | 22 |
| NC_004193 | 2.00E-53 | 338 | 131 | 38 | NC_005823 | 1.00E-47 | 302 | 111 | 36 |
| NC_004193 | 1.00E-17 | 293 | 75 | 25 | NC_005823 | 1.00E-43 | 300 | 107 | 35 |
| BC10B5Le10.q1ka | 2.00E-53 | 381 | 141 | 37 | NC_005823 | 2.00E-43 | 300 | 107 | 35 |
| BC10B5Le10.q1ka | 4.00E-07 | 183 | 45 | 24 | NC_005823 | 6.00E-39 | 301 | 99 | 32 |
| NC_000964 | 6.00E-53 | 306 | 130 | 42 | NC_005823 | 1.00E-06 | 110 | 34 | 30 |
| NC_000964 | 1.00E-30 | 206 | 81 | 39 | NC_005823 | 2 | 59 | 18 | 30 |
| NC_004605 | 1.00E-52 | 301 | 119 | 39 | NC_004342 | 1.00E-47 | 302 | 111 | 36 |
| NC_004605 | 3.10E-01 | 116 | 29 | 25 | NC_004342 | 1.00E-43 | 300 | 107 | 35 |
| NC_003030 | 1.00E-52 | 295 | 122 | 41 | NC_004342 | 3.00E-43 | 300 | 107 | 35 |
| NC_003030 | 3.00E-45 | 292 | 115 | 39 | NC_004342 | 5.00E-39 | 301 | 100 | 33 |
| NC_003030 | 1.00E-41 | 290 | 104 | 35 | NC_004342 | 1.00E-06 | 110 | 34 | 30 |
| NC_003030 | 1.00E-31 | 292 | 89 | 30 | NC_004342 | 2.00E+00 | 59 | 18 | 30 |
| NC_003030 | 3.00E-08 | 289 | 65 | 22 | NC_002505 | 2.00E-47 | 375 | 130 | 34 |
| NC_003030 | 6.00E-03 | 310 | 69 | 22 | NC_002505 | 5E-45 | 375 | 133 | 35 |

Fig. 25D-Continued

| Hit_ID | Expected | Length | #Ident | %S | Hit_ID | Expected | Length | #Ident | %S |
|---|---|---|---|---|---|---|---|---|---|
| NC_002505 | 2.00E-43 | 377 | 134 | 35 | NC_003296 | 4.00E-01 | 260 | 56 | 21 |
| NC_002505 | 4.00E-43 | 377 | 129 | 34 | NC_003296 | 5.20E-01 | 247 | 57 | 23 |
| NC_002505 | 2.00E-41 | 379 | 127 | 33 | NZ_AABN02000015 | 9.00E-43 | 300 | 108 | 36 |
| NC_002505 | 2.00E-03 | 228 | 52 | 22 | NZ_AABN02000015 | 2.00E-42 | 295 | 99 | 33 |
| NC_006348 | 2.00E-47 | 385 | 136 | 35 | AABN02000015 | 9.00E-43 | 300 | 108 | 36 |
| NC_006348 | 1.50E+00 | 76 | 24 | 31 | AABN02000015 | 2.00E-42 | 295 | 99 | 33 |
| Burkholderia | 2.00E-47 | 385 | 136 | 35 | NZ_AADQ01000005 | 2.00E-42 | 296 | 107 | 36 |
| Burkholderia | 2.80E-02 | 335 | 74 | 22 | NZ_AADR01000002 | 2.00E-42 | 296 | 107 | 36 |
| Burkholderia | 1.50E+00 | 76 | 24 | 31 | AADR01000002 | 2.00E-42 | 296 | 107 | 36 |
| NC_004722 | 3.00E-47 | 296 | 114 | 38 | AADQ01000005 | 2.00E-42 | 296 | 107 | 36 |
| NC_004722 | 2.00E-44 | 298 | 115 | 38 | NC_003212 | 2.00E-42 | 296 | 107 | 36 |
| NC_004722 | 6.00E-40 | 271 | 98 | 36 | NC_003212 | 6.20E-02 | 261 | 57 | 21 |
| NC_004722 | 2.00E-32 | 291 | 95 | 32 | NC_003212 | 1.40E-01 | 292 | 64 | 21 |
| NC_004722 | 3.00E-07 | 243 | 57 | 23 | NC_003210 | 2.00E-42 | 296 | 107 | 36 |
| NC_006177 | 4.00E-47 | 296 | 114 | 38 | NC_003210 | 6.00E-03 | 273 | 58 | 21 |
| NZ_AAER01000023 | 6.00E-47 | 292 | 112 | 38 | NC_002973 | 2.00E-42 | 296 | 107 | 36 |
| NZ_AAES01000034 | 6.00E-47 | 292 | 112 | 38 | NC_005139 | 2.00E-42 | 375 | 121 | 32 |
| NZ_AAEO01000025 | 6.00E-47 | 292 | 112 | 38 | NC_005139 | 2.00E-36 | 376 | 118 | 31 |
| NZ_AAEN01000011 | 6.00E-47 | 292 | 112 | 38 | NC_005139 | 9.00E-36 | 376 | 119 | 31 |
| NZ_AAEP01000035 | 6.00E-47 | 292 | 112 | 38 | NC_005139 | 4.00E-35 | 178 | 80 | 44 |
| NZ_AAEQ01000029 | 6.00E-47 | 292 | 112 | 38 | NC_005139 | 7.00E-35 | 376 | 111 | 29 |
| AAES01000034 | 6.00E-47 | 292 | 112 | 38 | NC_005139 | 7.00E-27 | 374 | 108 | 28 |
| AAER01000023 | 6.00E-47 | 292 | 112 | 38 | NC_005139 | 6.00E-21 | 301 | 92 | 30 |
| AAEQ01000029 | 6.00E-47 | 292 | 112 | 38 | NC_004459 | 2.00E-42 | 375 | 121 | 32 |
| AAEP01000035 | 6.00E-47 | 292 | 112 | 38 | NC_004459 | 2.00E-41 | 376 | 122 | 32 |
| AAEO01000025 | 6.00E-47 | 292 | 112 | 38 | NC_004459 | 7.00E-36 | 376 | 120 | 31 |
| AAEN01000011 | 6.00E-47 | 292 | 112 | 38 | NC_004459 | 9.00E-36 | 376 | 119 | 31 |
| NC_005945 | 6.00E-47 | 292 | 112 | 38 | NC_004459 | 4.00E-35 | 178 | 80 | 44 |
| NC_007530 | 6.00E-47 | 292 | 112 | 38 | NC_004459 | 7.00E-27 | 374 | 108 | 28 |
| NC_003997 | 6.00E-47 | 292 | 112 | 38 | NC_004459 | 6.00E-21 | 301 | 92 | 30 |
| NC_003995 | 6.00E-47 | 292 | 112 | 38 | NC_006087 | 4.00E-42 | 299 | 105 | 35 |
| NC_002967 | 1.00E-46 | 300 | 113 | 37 | NC_006087 | 3.00E-20 | 308 | 85 | 27 |
| NC_002967 | 1.00E-43 | 304 | 109 | 35 | NC_006513 | 6.00E-42 | 151 | 89 | 58 |
| NC_002967 | 5.00E-42 | 304 | 106 | 34 | Eagg631c06.q1k | 8.00E-42 | 310 | 107 | 34 |
| NC_002967 | 3.00E-10 | 285 | 65 | 22 | Eagg631c06.q1k | 8.00E-08 | 309 | 62 | 20 |
| NC_006370 | 9.00E-46 | 382 | 130 | 34 | NZ_AAAJ03000013 | 1.00E-41 | 378 | 127 | 33 |
| NC_006370 | 9.00E-36 | 251 | 106 | 42 | AAAJ03000013 | 1.00E-41 | 378 | 127 | 33 |
| NC_006370 | 5.00E-34 | 213 | 82 | 38 | NZ_AABQ07000002 | 1.00E-40 | 242 | 103 | 42 |
| NC_006370 | 2.00E-17 | 203 | 63 | 31 | NZ_AABQ07000002 | 3.00E-24 | 335 | 100 | 29 |
| NC_006370 | 4.00E-17 | 149 | 55 | 36 | NZ_AABQ07000002 | 3.00E-04 | 134 | 34 | 25 |
| NC_006370 | 2.00E+00 | 73 | 16 | 22 | AABQ07000002 | 1.00E-40 | 242 | 103 | 42 |
| NC_000919 | 2.00E-45 | 298 | 114 | 38 | AABQ07000002 | 3.00E-24 | 335 | 100 | 29 |
| NC_000919 | 1.00E-44 | 301 | 111 | 36 | AABQ07000002 | 3.00E-04 | 134 | 34 | 25 |
| NC_000919 | 1.00E-44 | 304 | 107 | 35 | NC_002516 | 1.00E-40 | 242 | 103 | 42 |
| NC_000919 | 3.00E-09 | 268 | 60 | 22 | NC_002516 | 3.00E-24 | 335 | 100 | 29 |
| NC_002937 | 3.00E-45 | 311 | 119 | 38 | NC_002516 | 3.00E-04 | 134 | 34 | 25 |
| NC_002937 | 1.00E-43 | 310 | 113 | 36 | NC_002516 | 3.10E-01 | 201 | 49 | 24 |
| NC_002937 | 2.00E-41 | 295 | 101 | 34 | AABI03000002 | 7.00E-40 | 222 | 101 | 45 |
| NC_002937 | 2.00E+00 | 171 | 36 | 21 | AABI03000002 | 5.00E-39 | 254 | 105 | 41 |
| NZ_AABN02000006 | 6.00E-45 | 295 | 107 | 36 | AABI03000002 | 4.00E-20 | 182 | 66 | 36 |
| NZ_AABN02000006 | 3.00E-03 | 46 | 21 | 45 | AABI03000002 | 4.00E-19 | 129 | 55 | 42 |
| AABN02000006 | 6.00E-45 | 295 | 107 | 36 | AABI03000002 | 1.00E-06 | 128 | 33 | 25 |
| AABN02000006 | 3.00E-03 | 46 | 21 | 45 | AABI03000002 | 2.80E-02 | 91 | 24 | 26 |
| sdublin_Contig1652_12.23 | 1.00E-44 | 97 | 97 | 100 | AABI03000002 | 1.40E-01 | 169 | 35 | 20 |
| NC_006368 | 2.00E-44 | 309 | 124 | 40 | NZ_AABI03000002 | 7.00E-40 | 222 | 101 | 45 |
| NC_006368 | 1.00E-23 | 200 | 77 | 38 | NZ_AABI03000002 | 5.00E-39 | 254 | 105 | 41 |
| NC_005957 | 3.00E-44 | 365 | 125 | 34 | NZ_AABI03000002 | 4.00E-20 | 182 | 66 | 36 |
| NC_005957 | 5.00E-33 | 292 | 97 | 33 | NZ_AABI03000002 | 4.00E-19 | 129 | 55 | 42 |
| NC_002942 | 5.00E-44 | 309 | 125 | 40 | NZ_AABI03000002 | 1.00E-06 | 128 | 33 | 25 |
| NC_002942 | 3.00E-23 | 198 | 78 | 39 | NZ_AABI03000002 | 2.80E-02 | 91 | 24 | 26 |
| NC_006369 | 2.00E-43 | 309 | 122 | 39 | NZ_AABI03000002 | 1.40E-01 | 169 | 35 | 20 |
| NC_006369 | 2.00E-23 | 251 | 88 | 35 | contig:1731:c_psychroerythr | 7.00E-40 | 259 | 108 | 41 |
| NC_006156 | 3.00E-43 | 342 | 113 | 33 | contig:1731:c_psychroerythr | 6.00E-39 | 259 | 108 | 41 |
| NC_006156 | 8.90E-01 | 77 | 18 | 23 | contig:1731:c_psychroerythr | 6.00E-24 | 263 | 82 | 31 |
| NC_001318 | 3.00E-43 | 342 | 113 | 33 | contig:1731:c_psychroerythr | 1.00E-21 | 263 | 78 | 29 |
| NC_001318 | 8.90E-01 | 77 | 18 | 23 | contig:1731:c_psychroerythr | 8.00E-07 | 135 | 32 | 23 |
| NC_003296 | 4.00E-43 | 297 | 109 | 36 | NC_002947 | 1.00E-39 | 252 | 103 | 40 |
| NC_003296 | 7.00E-03 | 264 | 60 | 22 | NC_002947 | 3.00E-19 | 129 | 53 | 41 |

Fig. 25D-Continued

| Hit_ID | Expected | Length | #Ident | %S | Hit_ID | Expected | Length | #Ident | %S |
|---|---|---|---|---|---|---|---|---|---|
| NC_002947 | 4.00E-07 | 130 | 41 | 31 | NC_000853 | 8.00E-10 | 256 | 62 | 24 |
| AAAW02000007 | 2.00E-39 | 385 | 128 | 33 | pputldprs_GPPBG16TR | 7.00E-28 | 123 | 66 | 53 |
| AAAW02000007 | 8.00E-23 | 298 | 89 | 29 | stdt25b06.p1k | 9.00E-25 | 77 | 58 | 75 |
| AAAW02000007 | 2.00E-09 | 154 | 47 | 30 | AAEF01000080 | 3.00E-24 | 245 | 76 | 31 |
| NZ_AAAW02000007 | 2.00E-39 | 385 | 128 | 33 | AAEF01000080 | 7.00E-20 | 195 | 65 | 33 |
| NZ_AAAW02000007 | 8.00E-23 | 298 | 89 | 29 | AAEF01000080 | 3.00E-13 | 301 | 76 | 25 |
| NZ_AAAW02000007 | 2.00E-09 | 154 | 47 | 30 | NZ_AAEF01000080 | 3.00E-24 | 245 | 76 | 31 |
| NC_004463 | 1.00E-38 | 295 | 95 | 32 | NZ_AAEF01000080 | 7.00E-20 | 195 | 65 | 33 |
| NC_004463 | 8.00E-16 | 311 | 73 | 23 | NZ_AAEF01000080 | 3.00E-13 | 301 | 76 | 25 |
| NC_004463 | 1.00E-14 | 317 | 74 | 23 | NC_005090 | 3.00E-23 | 294 | 89 | 30 |
| NC_004463 | 8.00E-08 | 273 | 72 | 26 | NC_005090 | 2.00E-21 | 192 | 63 | 32 |
| NC_004463 | 2.00E-07 | 255 | 72 | 28 | NC_005090 | 9.00E-19 | 333 | 85 | 25 |
| NC_004463 | 8.00E-07 | 250 | 63 | 25 | NC_005090 | 1.00E-12 | 278 | 65 | 23 |
| NC_004463 | 2.00E-06 | 186 | 47 | 25 | NC_005090 | 3.00E-12 | 122 | 44 | 36 |
| NC_004463 | 8.10E-02 | 233 | 50 | 21 | NC_005090 | 6.00E-03 | 168 | 37 | 22 |
| NC_004463 | 1.40E-01 | 134 | 39 | 29 | contig:521:c_jejuni | 3.00E-23 | 161 | 66 | 36 |
| NC_004463 | 4.00E-01 | 109 | 29 | 26 | contig:521:c_jejuni | 1.00E-21 | 181 | 66 | 36 |
| NC_004463 | 6.80E-01 | 121 | 28 | 23 | contig:521:c_jejuni | 2.00E-14 | 156 | 53 | 33 |
| NC_004463 | 1.20E+00 | 109 | 29 | 26 | contig:521:c_jejuni | 2.00E-12 | 156 | 50 | 32 |
| NC_004463 | 1.50E+00 | 109 | 29 | 26 | contig:521:c_jejuni | 6.00E-11 | 288 | 68 | 23 |
| NC_004463 | 2.00E+00 | 109 | 29 | 26 | NC_000915 | 8.00E-23 | 187 | 67 | 35 |
| Pflu019c02.p1c | 2.00E-38 | 230 | 97 | 42 | NC_000915 | 3.00E-19 | 170 | 57 | 33 |
| Pflu019c02.p1c | 2.00E-17 | 330 | 81 | 24 | NC_000915 | 5.00E-15 | 311 | 78 | 25 |
| contig:491:b_thailandensis | 3.00E-38 | 305 | 107 | 35 | NC_000915 | 2.00E-13 | 121 | 47 | 38 |
| AAEH01000086 | 2.00E-37 | 242 | 97 | 40 | NC_000921 | 1.00E-22 | 187 | 67 | 35 |
| AAEH01000086 | 2.00E-17 | 86 | 46 | 53 | NC_000921 | 3.00E-19 | 170 | 57 | 33 |
| NZ_AAEH01000086 | 2.00E-37 | 242 | 97 | 40 | NC_000921 | 5.00E-15 | 311 | 78 | 25 |
| NZ_AAEH01000086 | 2.00E-17 | 86 | 46 | 53 | NC_000921 | 2.00E-13 | 121 | 47 | 38 |
| AAAG02000001 | 1.00E-36 | 305 | 107 | 35 | NC_000921 | 4.00E-04 | 149 | 40 | 26 |
| AAAG02000001 | 4.00E-12 | 302 | 69 | 22 | NC_002163 | 3.00E-22 | 171 | 63 | 36 |
| AAAG02000001 | 6.80E-01 | 239 | 49 | 20 | NC_002163 | 6.00E-21 | 181 | 66 | 36 |
| NZ_AAAG02000001 | 1.00E-36 | 305 | 107 | 35 | NC_002163 | 4.00E-14 | 132 | 48 | 36 |
| NZ_AAAG02000001 | 4.00E-12 | 302 | 69 | 22 | NC_002163 | 4.00E-12 | 132 | 45 | 34 |
| NZ_AAAG02000001 | 6.80E-01 | 239 | 49 | 20 | NC_002163 | 7.00E-11 | 288 | 66 | 22 |
| NC_005296 | 4.00E-36 | 295 | 92 | 31 | NC_004917 | 9.00E-22 | 188 | 67 | 35 |
| NC_005296 | 2.00E-05 | 284 | 70 | 24 | NC_004917 | 1.00E-19 | 170 | 60 | 35 |
| NC_005296 | 2.00E-05 | 284 | 69 | 24 | NC_004917 | 1.00E-19 | 170 | 60 | 35 |
| NC_005296 | 1.00E-03 | 194 | 49 | 25 | NC_004917 | 3.00E-13 | 297 | 74 | 24 |
| NC_005296 | 8.90E-01 | 261 | 58 | 22 | NC_004917 | 3.00E-13 | 297 | 74 | 24 |
| sdublin_Contig993_12.23 | 4.00E-36 | 81 | 81 | 100 | NC_004917 | 6.00E-11 | 115 | 40 | 34 |
| stdt38a03.p1k | 4.00E-36 | 98 | 79 | 80 | NC_002696 | 1.00E-21 | 297 | 76 | 25 |
| stdt23f04.p1k | 4.00E-36 | 98 | 79 | 80 | NC_002696 | 4.00E-20 | 298 | 76 | 25 |
| NZ_AADT02000011 | 2.00E-35 | 382 | 125 | 32 | NC_002696 | 5.00E-20 | 292 | 75 | 25 |
| NZ_AADT02000011 | 8.00E-18 | 285 | 73 | 25 | NC_002696 | 5.00E-20 | 292 | 72 | 24 |
| AADT02000011 | 2.00E-35 | 382 | 125 | 32 | NC_002696 | 7.00E-20 | 292 | 72 | 24 |
| AADT02000011 | 8.00E-18 | 285 | 73 | 25 | NC_002696 | 1.00E-19 | 292 | 70 | 23 |
| NC_006512 | 6.00E-35 | 170 | 82 | 48 | NC_002696 | 1.10E-01 | 73 | 21 | 28 |
| NC_006512 | 4.00E-20 | 267 | 77 | 28 | NC_000918 | 1.00E-20 | 209 | 62 | 29 |
| NC_006512 | 1.00E-03 | 130 | 35 | 26 | NC_000918 | 7.00E-09 | 129 | 39 | 30 |
| NZ_AAAI02000004 | 3.00E-34 | 199 | 85 | 42 | contig:4798:g_obscuriglobus | 7.00E-20 | 139 | 57 | 41 |
| NZ_AAAI02000004 | 9.00E-22 | 92 | 57 | 61 | contig:4798:g_obscuriglobus | 3.00E-12 | 157 | 52 | 33 |
| AAAI02000004 | 3.00E-34 | 199 | 85 | 42 | AAED01000008 | 9.00E-20 | 294 | 80 | 27 |
| AAAI02000004 | 9.00E-22 | 92 | 57 | 61 | AAED01000008 | 8.00E-15 | 297 | 68 | 22 |
| NC_003909 | 5.00E-34 | 292 | 96 | 32 | NZ_AAED01000008 | 9.00E-20 | 294 | 80 | 27 |
| NC_003909 | 2.00E-28 | 221 | 77 | 34 | NZ_AAED01000008 | 8.00E-15 | 297 | 68 | 22 |
| NC_003909 | 8.00E-13 | 84 | 41 | 48 | NC_005027 | 9.00E-20 | 284 | 88 | 30 |
| NZ_AAAN02000082 | 5.00E-33 | 280 | 85 | 30 | NC_005027 | 1.00E-19 | 257 | 76 | 29 |
| AAAN02000082 | 5.00E-33 | 280 | 85 | 30 | NC_005027 | 4.00E-18 | 169 | 62 | 36 |
| NZ_AAAE01000066 | 1.00E-32 | 166 | 74 | 44 | NC_005027 | 6.00E-16 | 126 | 55 | 43 |
| NZ_AAAE01000066 | 2.00E-19 | 176 | 63 | 35 | NC_005027 | 1.00E-14 | 143 | 57 | 39 |
| AAAE01000066 | 1.00E-32 | 166 | 74 | 44 | NC_005027 | 4.00E-14 | 250 | 70 | 28 |
| AAAE01000066 | 2.00E-19 | 176 | 63 | 35 | NC_005027 | 6.80E-01 | 240 | 52 | 21 |
| NC_006274 | 1.00E-32 | 292 | 95 | 32 | NC_005027 | 1.50E+00 | 120 | 34 | 28 |
| NC_006274 | 1.00E-31 | 289 | 96 | 33 | rhiz573a05.p1n | 2.00E-19 | 303 | 84 | 27 |
| NC_006274 | 1.00E-14 | 111 | 46 | 41 | AAAW02000158 | 2.00E-18 | 314 | 89 | 28 |
| NC_006274 | 1.00E-07 | 242 | 57 | 23 | NZ_AAAW02000158 | 2.00E-18 | 314 | 89 | 28 |
| NC_000853 | 2.00E-32 | 392 | 119 | 30 | NC_003062 | 1E-17 | 313 | 77 | 24 |
| NC_000853 | 3.00E-17 | 248 | 63 | 25 | NC_003062 | 3.00E-14 | 313 | 75 | 23 |

Fig. 25D-Continued

| Hit_ID | Expected | Length | #Ident | %S | Hit_ID | Expected | Length | #Ident | %S |
|---|---|---|---|---|---|---|---|---|---|
| NC_003062 | 9.00E-12 | 324 | 75 | 23 | AAEA01000001 | 1.00E-03 | 295 | 62 | 21 |
| NC_003062 | 2.00E-06 | 256 | 60 | 23 | NZ_AAEA01000001 | 1.00E-03 | 295 | 62 | 21 |
| NC_003062 | 4.00E-04 | 140 | 34 | 24 | NC_002662 | 1.00E-03 | 287 | 50 | 17 |
| NC_003304 | 1.00E-17 | 313 | 77 | 24 | Pflu552a01.p1kz | 3.00E-03 | 277 | 69 | 24 |
| NC_003304 | 3.00E-14 | 313 | 75 | 23 | AABK03000008 | 3.00E-03 | 273 | 63 | 23 |
| NC_003304 | 9.00E-12 | 324 | 75 | 23 | NZ_AABK03000008 | 3.00E-03 | 273 | 63 | 23 |
| NC_003304 | 2.00E-06 | 256 | 60 | 23 | AAEH01000003 | 3.00E-03 | 284 | 62 | 21 |
| NC_003304 | 4.00E-04 | 140 | 34 | 24 | AAEH01000003 | 2.10E-02 | 282 | 56 | 19 |
| NC_004311 | 7.00E-17 | 298 | 76 | 25 | AAEH01000003 | 2.80E-02 | 287 | 60 | 20 |
| NC_003318 | 3.00E-16 | 298 | 75 | 25 | AAEH01000003 | 2.80E-02 | 295 | 59 | 20 |
| sdublin_Contig1019_12.23 | 3.00E-16 | 80 | 49 | 61 | AAEH01000003 | 3.60E-02 | 285 | 61 | 21 |
| rhiz606c07.p1n | 4.00E-16 | 303 | 78 | 25 | AAEH01000003 | 4.70E-02 | 285 | 61 | 21 |
| rhiz606c07.p1n | 5.00E-15 | 304 | 76 | 25 | AAEH01000003 | 8.10E-02 | 285 | 59 | 20 |
| rhiz606c07.p1n | 1.00E-05 | 317 | 66 | 20 | AAEH01000003 | 1.10E-01 | 285 | 60 | 21 |
| NC_002678 | 1.00E-15 | 329 | 75 | 22 | AAEH01000003 | 1.10E-01 | 322 | 67 | 20 |
| NC_002678 | 3.00E-08 | 356 | 80 | 22 | NZ_AAEH01000003 | 3.00E-03 | 284 | 62 | 21 |
| NZ_AAFG01000002 | 2.00E-15 | 296 | 75 | 25 | NZ_AAEH01000003 | 2.10E-02 | 282 | 56 | 19 |
| NZ_AAFG01000002 | 4.00E-14 | 298 | 72 | 24 | NZ_AAEH01000003 | 2.80E-02 | 287 | 60 | 20 |
| AAFG01000002 | 2.00E-15 | 296 | 75 | 25 | NZ_AAEH01000003 | 2.80E-02 | 295 | 59 | 20 |
| AAFG01000002 | 4.00E-14 | 298 | 72 | 24 | NZ_AAEH01000003 | 3.60E-02 | 285 | 61 | 21 |
| rhiz24d12.p1k | 3.00E-14 | 310 | 77 | 24 | NZ_AAEH01000003 | 4.70E-02 | 285 | 61 | 21 |
| NZ_AAAE01000155 | 7.00E-14 | 302 | 70 | 23 | NZ_AAEH01000003 | 8.10E-02 | 285 | 59 | 20 |
| AAAE01000155 | 7.00E-14 | 302 | 70 | 23 | NZ_AAEH01000003 | 1.10E-01 | 285 | 60 | 21 |
| NZ_AAFG01000004 | 2.00E-13 | 294 | 72 | 24 | NZ_AAEH01000003 | 1.10E-01 | 322 | 67 | 20 |
| AAFG01000004 | 2.00E-13 | 294 | 72 | 24 | NC_005140 | 3.00E-03 | 289 | 63 | 21 |
| NZ_AAFG01000007 | 3.00E-13 | 299 | 69 | 23 | NZ_AADQ01000014 | 4.00E-03 | 258 | 56 | 21 |
| AAFG01000007 | 3.00E-13 | 299 | 69 | 23 | AADQ01000014 | 4.00E-03 | 258 | 56 | 21 |
| contig:519:c_jejuni | 6.00E-11 | 288 | 68 | 23 | AAEI01000009 | 4.00E-03 | 304 | 61 | 20 |
| NZ_AAAP01001822 | 1.00E-10 | 276 | 72 | 26 | AAEI01000009 | 4.00E-03 | 298 | 64 | 21 |
| AAAP01001822 | 1.00E-10 | 276 | 72 | 26 | AAEI01000009 | 8.10E-02 | 292 | 62 | 21 |
| Cbot389c10.p2c412 | 1.00E-10 | 257 | 63 | 24 | AAEI01000009 | 1.80E-01 | 278 | 57 | 20 |
| NC_003047 | 5.00E-09 | 321 | 68 | 21 | NZ_AAEI01000009 | 4.00E-03 | 304 | 61 | 20 |
| NC_003047 | 2.00E-05 | 87 | 29 | 33 | NZ_AAEI01000009 | 4.00E-03 | 298 | 64 | 21 |
| NC_003047 | 5.00E-04 | 245 | 56 | 22 | NZ_AAEI01000009 | 8.10E-02 | 292 | 62 | 21 |
| NC_003047 | 2.80E-02 | 87 | 24 | 27 | NZ_AAEI01000009 | 1.80E-01 | 278 | 57 | 20 |
| NZ_AAEK01000008 | 2.00E-08 | 243 | 62 | 25 | NC_002935 | 6.00E-03 | 169 | 38 | 22 |
| AAEK01000008 | 2.00E-08 | 243 | 62 | 25 | NC_004567 | 7.00E-03 | 285 | 64 | 22 |
| NZ_AABN02000001 | 3.00E-07 | 113 | 32 | 28 | NC_004567 | 2.00E+00 | 299 | 58 | 19 |
| NZ_AABN02000001 | 3.00E-03 | 238 | 50 | 21 | NZ_AAAU02000026 | 1.00E-02 | 122 | 36 | 29 |
| AABN02000001 | 3.00E-07 | 113 | 32 | 28 | AAAU02000026 | 1.00E-02 | 122 | 36 | 29 |
| AABN02000001 | 3.00E-03 | 238 | 50 | 21 | AAEI01000011 | 1.20E-02 | 297 | 72 | 24 |
| contig:2663:s_pomeroyi | 4.00E-07 | 278 | 64 | 23 | NZ_AAEI01000011 | 1.20E-02 | 297 | 72 | 24 |
| contig:2663:s_pomeroyi | 4.00E-03 | 180 | 36 | 20 | NC_002758 | 1.20E-02 | 332 | 72 | 21 |
| contig:1062:h_neptunium | 6.00E-07 | 153 | 39 | 25 | NC_002745 | 1.20E-02 | 332 | 72 | 21 |
| NZ_AAAI02000005 | 3.00E-06 | 326 | 70 | 21 | NZ_AABH02000009 | 1.60E-02 | 241 | 60 | 24 |
| NZ_AAAI02000005 | 2.00E+00 | 93 | 28 | 30 | AABH02000009 | 1.60E-02 | 241 | 60 | 24 |
| AAAI02000005 | 3.00E-06 | 326 | 70 | 21 | NZ_AAAR02000005 | 2.10E-02 | 292 | 54 | 18 |
| AAAI02000005 | 2.00E+00 | 93 | 28 | 30 | AAAR02000005 | 2.10E-02 | 292 | 54 | 18 |
| Bcep1110a03.q2kb4087 | 3.00E-05 | 298 | 66 | 22 | NC_006449 | 2.80E-02 | 302 | 64 | 21 |
| Bcep1110a03.q2kb4087 | 5.00E-05 | 299 | 67 | 22 | NC_006448 | 2.80E-02 | 302 | 64 | 21 |
| Bcep1110a03.q2kb4087 | 3.00E-04 | 286 | 66 | 23 | sdublin_Contig4745_12.23 | 2.80E-02 | 19 | 18 | 94 |
| Bcep1110a03.q2kb4087 | 4.00E-01 | 226 | 52 | 23 | sdublin_Contig3450_12.23 | 2.80E-02 | 19 | 18 | 94 |
| AADY01000003 | 8.00E-05 | 121 | 37 | 30 | mar499b01.q1k | 3.60E-02 | 87 | 25 | 28 |
| NZ_AADY01000003 | 8.00E-05 | 121 | 37 | 30 | NZ_AAAM01000127 | 4.70E-02 | 57 | 21 | 36 |
| NZ_AABG03000053 | 2.00E-04 | 83 | 28 | 33 | NZ_AACK01000006 | 4.70E-02 | 146 | 38 | 26 |
| AAEI01000016 | 2.00E-04 | 291 | 67 | 23 | AACK01000006 | 4.70E-02 | 146 | 38 | 26 |
| AAEI01000016 | 9.00E-04 | 289 | 59 | 20 | AAAM01000127 | 4.70E-02 | 57 | 21 | 36 |
| AABG03000053 | 2.00E-04 | 83 | 28 | 33 | NC_003923 | 4.70E-02 | 283 | 66 | 23 |
| NZ_AAEI01000016 | 2.00E-04 | 291 | 67 | 23 | NC_003923 | 1.50E+00 | 299 | 60 | 20 |
| NZ_AAEI01000016 | 9.00E-04 | 289 | 59 | 20 | NC_002953 | 4.70E-02 | 283 | 66 | 23 |
| NZ_AABG03000001 | 4.00E-04 | 257 | 54 | 21 | ap5.fasta.screen.Contig207 | 4.70E-02 | 146 | 38 | 26 |
| AABG03000001 | 4.00E-04 | 257 | 54 | 21 | NZ_AAAN02000006 | 6.20E-02 | 294 | 57 | 19 |
| contig:313:m_arthritidis | 4.00E-04 | 263 | 60 | 22 | NZ_AAAJ03000006 | 6.20E-02 | 310 | 62 | 20 |
| contig:313:m_arthritidis | 1.40E-01 | 127 | 32 | 25 | NZ_AAAJ03000006 | 1.10E-01 | 308 | 61 | 19 |
| contig:313:m_arthritidis | 1.80E-01 | 124 | 33 | 26 | NZ_AAAJ03000006 | 1.80E-01 | 272 | 54 | 19 |
| contig:313:m_arthritidis | 1.50E+00 | 137 | 32 | 23 | NZ_AAAJ03000006 | 3.10E-01 | 275 | 56 | 20 |
| Bcep825a04.p2n33 | 4.00E-04 | 255 | 58 | 22 | NZ_AAAJ03000006 | 3.10E-01 | 254 | 53 | 20 |
| contig:510:v_spinosum | 7.00E-04 | 262 | 66 | 25 | NZ_AAAJ03000006 | 6.80E-01 | 279 | 55 | 19 |

Fig. 25D-Continued

| Hit_ID | Expected | Length | #Ident | %S |
|---|---|---|---|---|
| NZ_AAAJ03000006 | 8.90E-01 | 319 | 59 | 18 |
| NZ_AAAJ03000006 | 1.50E+00 | 324 | 59 | 18 |
| AAAN02000006 | 6.20E-02 | 294 | 57 | 19 |
| AAAJ03000006 | 6.20E-02 | 310 | 62 | 20 |
| AAAJ03000006 | 1.10E-01 | 308 | 61 | 19 |
| AAAJ03000006 | 1.80E-01 | 272 | 54 | 19 |
| AAAJ03000006 | 3.10E-01 | 275 | 56 | 20 |
| AAAJ03000006 | 3.10E-01 | 254 | 53 | 20 |
| AAAJ03000006 | 6.80E-01 | 279 | 55 | 19 |
| AAAJ03000006 | 8.90E-01 | 319 | 59 | 18 |
| AAAJ03000006 | 1.50E+00 | 324 | 59 | 18 |
| NZ_AAAP01003482 | 8.10E-02 | 278 | 63 | 22 |
| AAAP01003482 | 8.10E-02 | 278 | 63 | 22 |
| AADW01000010 | 8.10E-02 | 317 | 71 | 22 |
| NZ_AADW01000010 | 8.10E-02 | 317 | 71 | 22 |
| NC_004461 | 8.10E-02 | 169 | 43 | 25 |
| NC_004461 | 1.20E+00 | 302 | 60 | 19 |
| contig:370:s_epidermidis | 8.10E-02 | 169 | 43 | 25 |
| contig:370:s_epidermidis | 1.20E+00 | 302 | 60 | 19 |
| AAED01000003 | 1.40E-01 | 183 | 41 | 22 |
| NZ_AAED01000003 | 1.40E-01 | 183 | 41 | 22 |
| NZ_AAAN02000003 | 2.30E-01 | 260 | 53 | 20 |
| AAAN02000003 | 2.30E-01 | 260 | 53 | 20 |
| AADW01000069 | 2.30E-01 | 285 | 51 | 17 |
| NZ_AADW01000069 | 2.30E-01 | 285 | 51 | 17 |
| NZ_AABH02000010 | 2.30E-01 | 298 | 58 | 19 |
| AABH02000010 | 2.30E-01 | 298 | 58 | 19 |
| Bcep1157h02.p1c | 3.10E-01 | 300 | 58 | 19 |
| NZ_AABG03000015 | 4.00E-01 | 181 | 39 | 21 |
| NZ_AAAN02000029 | 4.00E-01 | 89 | 26 | 29 |
| AAAN02000029 | 4.00E-01 | 89 | 26 | 29 |
| AABG03000015 | 4.00E-01 | 181 | 39 | 21 |
| NZ_AABQ07000001 | 4.00E-01 | 201 | 49 | 24 |
| AABQ07000001 | 4.00E-01 | 201 | 49 | 24 |
| NC_006300 | 4.00E-01 | 273 | 58 | 21 |
| NC_006300 | 4.00E-01 | 273 | 58 | 21 |
| NC_006300 | 5.20E-01 | 274 | 61 | 22 |
| NC_003272 | 5.20E-01 | 286 | 59 | 20 |
| NC_004829 | 5.20E-01 | 183 | 40 | 21 |
| NZ_AAAN02000076 | 6.80E-01 | 294 | 56 | 19 |
| AAAN02000076 | 6.80E-01 | 294 | 56 | 19 |
| NZ_AAFG01000003 | 8.90E-01 | 62 | 20 | 32 |
| AAFG01000003 | 8.90E-01 | 62 | 20 | 32 |
| NZ_AABM02000032 | 8.90E-01 | 165 | 39 | 23 |
| AABM02000032 | 8.90E-01 | 165 | 39 | 23 |
| NC_004663 | 8.90E-01 | 150 | 44 | 29 |
| contig:3563:m_smegmatis | 8.90E-01 | 102 | 30 | 29 |
| AAEI01000026 | 1.20E+00 | 130 | 38 | 29 |
| NZ_AAEI01000026 | 1.20E+00 | 130 | 38 | 29 |
| NC_005125 | 1.20E+00 | 73 | 24 | 32 |
| NC_003366 | 1.20E+00 | 232 | 49 | 21 |
| NC_000951 | 1.20E+00 | 114 | 30 | 26 |
| Bcep1115d11.q1k | 1.20E+00 | 130 | 37 | 28 |
| contig:4304:c_perfringens | 1.20E+00 | 232 | 49 | 21 |
| NZ_AAEV01000005 | 1.50E+00 | 187 | 41 | 21 |
| AAEV01000005 | 1.50E+00 | 187 | 41 | 21 |
| NZ_AABP02000001 | 1.50E+00 | 254 | 46 | 18 |
| AABP02000001 | 1.50E+00 | 254 | 46 | 18 |
| NC_003552 | 1.50E+00 | 257 | 49 | 19 |
| NC_005362 | 2.00E+00 | 125 | 28 | 22 |
| AAAY02000105 | 2.60E+00 | 112 | 29 | 25 |
| AAEH01000017 | 2.60E+00 | 238 | 54 | 22 |
| NZ_AAEH01000017 | 2.60E+00 | 238 | 54 | 22 |
| NZ_AAAY02000105 | 2.60E+00 | 112 | 29 | 25 |
| Eagg385b08.q1ka | 2.60E+00 | 185 | 42 | 22 |

Fig. 26

| Accession | Source | Amino % Identity | Carboxy % Identity | Length |
|---|---|---|---|---|
| Q53970 | Phase-1 flagellin [fliC1] [Salmonella dublin] | 100 | 100 | 505 |
| P72151 | B-type flagellin [fliC] [Pseudomonas aeruginosa] | 50 | 58 | 488 |
| Q5X5M6 | Flagelline [flaA] [Legionella pneumophila str. Paris] | 46 | 61 | 475 |
| Q6VMV6 | Flagellin [fliC] [Escherichia coli] | 74 | 84 | 488 |
| P13713 | Flagellin [fliC] [Serratia marcescens] | 65 | 75 | 351 |
| Q93RK8 | Flagellin [hag] [Bacillus subtilis] | 50 | 49 | 333 |
| Q02551 | Flagellin [flaA] [Listeria monocytogenes] | 39 | 38 | 287 |
| Q09012 | Flagellin [fliC-SS(a)] [Shigella sonnei] | 72 | 84 | 524 |
| Q8GNT8 | Flagellin [Edwardsiella tarda] | 65 | 77 | 416 |
| Q9FAE7 | Flagellin [H8301-fla1] [Acidovorax avenae subsp. avenae] | 61 | 56 | 492 |
| Q8ZF76 | Thermoregulated motility protein (Putative flagellin) [fliC] [Yersinia pestis] | 82 | 80 | 369 |
| Q7N5J4 | Flagellin [fliC] [Photorhabdus luminescens (subsp. laumondii)] | 63 | 77 | 355 |
| O33578 | Flagellar filament protein [fliC] [Rhodobacter sphaeroides (Rhodopseudomonas sphaeroides)] | 46 | 55 | 493 |
| Q56826 | Flagellin [fliC] [Xenorhabdus nematophilus] | 76 | 75 | 313 |
| P42273 | Flagellin 2 [fliC2] [Proteus mirabilis] | 63 | 78 | 367 |
| O31059 | Flagellin A protein [flaA] [Butyrivibrio fibrisolvens] | 53 | 56 | 472 |
| Q7VZC2 | Flagellin [flaA] [Bordetella pertussis] | 74 | 77 | 391 |
| Q9F4A4 | Flagellin protein FliA(C) [fliC] [Clostridium chauvoei] | 51 | 48 | 413 |
| Q8P9C4 | Flagellar protein [fliC] [Xanthomonas campestris (pv. campestris)] | 48 | 55 | 399 |
| Q82UA3 | Hag; flagellin [hag] [Nitrosomonas europaea] | 58 | 57 | 275 |
| Q84IC5 | Flagellin (Fragment) [flaA] [Campylobacter lari] | 32 | 45 | 490 |

Fig. 38

AA'
Nucleotide sequence (990 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGG*CACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTGATGTGAAAAGC
CTTGGCCTTGATGGGTTCAATGTTAATTCCCCGGGAATTTCCGGTGGTGGTGGTGGAATT
CTAGACTCCATGGGTACATTAATCAATGAAGACGCTGCCGCAGCCAAGAAAAGTACCGCT
AACCCACTGGCTTCAATTGATTCTGCATTGTCAAAAGTGGACGCAGTTCGTTCTTCTCTG
GGGGCAATTCAAAACCGTTTTGATTCAGCCATTACCAACCTTGGCAATACGGTAACCAAT
CTGAACTCCGCGCGTAGCCGTATCGAAGATGCTGACTATGCAACGGAAGTTTCTAATATG
TCTAAAGCGCAGATTCTGCAGCAGGCTGGTACTTCCGTTCTGGCGCAGGCTAACCAGGTT
CCGCAAAACGTCCTCTCTTTACTGCGTTAG
Protein sequence (329 AA):
*MRGSHHHHHHGMASMTGGQQMGRDLYDDDDKDPM*AQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLDGFNVNSPGISGGGGGILDSMGTLINEDAAAAKKSTANPLASIDSALSKVDAVRSSLGAIQNRFD
SAITNLGNTVTNLNSARSRIEDADYATEVSNMSKAQILQQAGTSVLAQANQVPQNVLSLLR AB'
Nucleotide sequence (825 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGG*CACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTGATGTGAAAAGC
CTTGGCCTTGATGGGTTCAATGTTAATTCCCCGGGAATTTCCGGTGGTGGTGGTGGAATT
CTAGACTCCATGGGTACATTAATCAATGAAGACGCTGCCGCAGCCAAGAAAAGTACCGCT
AACCCACTGGCTTCAATTGATTCTGCATTGTCAAAAGTGGACGCAGTTCGTTCTTCTCTG
GGGGCAATTCAAAACCGTTTTGATTCAGCCATTACCAACCTTTAG
Protein sequence (274 AA):
*MRGSHHHHHHGMASMTGGQQMGRDLYDDDDKDPM*AQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLDGFNVNSPGISGGGGGILDSMGTLINEDAAAAKKSTANPLASIDSALSKVDAVRSSLGAIQNRFD
SAITNL Fig. 38 - Continued BA'
Nucleotide sequence (831 bp):
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTCTCTCAG
GACAACCAGATGAAAATCCAGGTTGGTGCTAACGATGGTGAAACCATTACCATCGATCTG
CAAAAAATTGATGTGAAAAGCCTTGGCCTTGATGGGTTCAATGTTAATTCCCCGGGAATT
TCCGGTGGTGGTGGTGGAATTCTAGACTCCATGGGTACATTAATCAATGAAGACGCTGCC
GCAGCCAAGAAAAGTACCGCTAACCCACTGGCTTCAATTGATTCTGCATTGTCAAAAGTG
GACGCAGTTCGTTCTTCTCTGGGGGCAATTCAAAACCGTTTTGATTCAGCCATTACCAAC
CTTGGCAATACGGTAACCAATCTGAACTCCGCGCGTAGCCGTATCGAAGATGCTCACTAT
GCAACGGAAGTTTCTAATATGTCTAAAGCGCAGATTCTGCAGCAGGCTGGTACTTCCGTT
CTGGCGCAGGCTAACCAGGTTCCGCAAAACGTCCTCTCTTTACTGCGTTAG
Protein sequence (276 AA):
MRGSHHHHHHGMASMTGGQQMGRDLYDDDDKDPFTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLDGFNVNSPGISGGGGGILDSMGTLINEDAAAAKKSTANPLASIDSALSKVD
AVRSSLGAIQNRFDSAITNLGNTVTNLNSARSRIEDADYATEVSNMSKAQILQQAGTSVLAQANQVP
QNVLSLLR BB'
Nucleotide sequence (666 bp):
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTCTCTCAG
GACAACCAGATGAAAATCCAGGTTGGTGCTAACGATGGTGAAACCATTACCATCGATCTG
CAAAAAATTGATGTGAAAAGCCTTGGCCTTGATGGGTTCAATGTTAATTCCCCGGGAATT
TCCGGTGGTGGTGGTGGAATTCTAGACTCCATGGGTACATTAATCAATGAAGACGCTGCC
GCAGCCAAGAAAAGTACCGCTAACCCACTGGCTTCAATTGATTCTGCATTGTCAAAAGTG
GACGCAGTTCGTTCTTCTCTGGGGGCAATTCAAAACCGTTTTGATTCAGCCATTACCAAC
CTTTAG
Protein sequence (221 AA):
MRGSHHHHHHGMASMTGGQQMGRDLYDDDDKDPFTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLDGFNVNSPGISGGGGGILDSMGTLINEDAAAAKKSTANPLASIDSALSKVD
AVRSSLGAIQNRFDSAITNL CA'
Nucleotide sequence (603 bp):
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGC
CTGACTCAGGCTTCCCGTAACGCTAACGACGGCATTTCTATTGCGCAGACCACTGAAGGT Fig. 38 - Continued GCGCTGAATGAAATCAACAACAACCTGCAGCGTGTGCGTGAGTTGTCTGTTCAGGCCACT
TCCCCGGGAATTTCCGGTGGTGGTGGTGGAATTCTAGACTCCATGGGTACATTAATCAAT
GAAGACGCTGCCGCAGCCAAGAAAAGTACCGCTAACCCACTGGCTTCAATTGATTCTGCA
TTGTCAAAAGTGGACGCAGTTCGTTCTTCTCTGGGGGCAATTCAAAACCGTTTTGATTCA
GCCATTACCAACCTTGGCAATACGGTAACCAATCTGAACTCCGCGCGTAGCCGTATCGAA
GATGCTGACTATGCAACGGAAGTTTCTAATATGTCTAAAGCGCAGATTCTGCAGCAGGCT
GGTACTTCCGTTCTGGCGCAGGCTAACCAGGTTCCGCAAAACGTCCTCTCTTTACTGCGT
TAG Protein sequence (200 AA):
*MRGSHHHHHHGMASMTGGQQMGRDLYDDDDKDPFTSNIKGLTQASRNANDGISIAQTTEGALNEINN*
*NLQRVRELSVQATSPGISGGGGGILDSMGTLINEDAAAAKKSTANPLASIDSALSKVDAVRSSLGAI*
*QNRFDSAITNLGNTVTNLNSARSRIEDADYATEVSNMSKAQILQQAGTSVLAQANQVPQNVLSLLR*

CB'
Nucleotide sequence (438 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGTTCACTTCTAATATCAAAGGC*
*CTGACTCAGGCTTCCCGTAACGCTAACGACGGCATTTCTATTGCGCAGACCACTGAAGGT*
*GCGCTGAATGAAATCAACAACAACCTGCAGCGTGTGCGTGAGTTGTCTGTTCAGGCCACT*
TCCCCGGGAATTTCCGGTGGTGGTGGTGGAATTCTAGACTCCATGGGTACATTAATCAAT
GAAGACGCTGCCGCAGCCAAGAAAAGTACCGCTAACCCACTGGCTTCAATTGATTCTGCA
TTGTCAAAAGTGGACGCAGTTCGTTCTTCTCTGGGGGCAATTCAAAACCGTTTTGATTCA
GCCATTACCAACCTTTAG Protein sequence (145 AA):
*MRGSHHHHHHGMASMTGGQQMGRDLYDDDDKDPFTSNIKGLTQASRNANDGISIAQTTEGALNEINN*
*NLQRVRELSVQATSPGISGGGGGILDSMGTLINEDAAAAKKSTANPLASIDSALSKVDAVRSSLGAI*
*QNRFDSAITNL*

A
Nucleotide sequence (639 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGGCACAAGTCATTAATACA*
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAGGGTCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTGTCTCAGGACAACCAGATGAAAATCCAG
GTTGGTGCTAACGATGGTGAAACCATTACCATCGATCTGCAAAAAATTGATGTGAAAAGC
CTTGGCCTTGATGGGTTCAATGTTAATTCCCCGGGATGA Protein sequence (212 AA), last three amino acids are derived from primer and pRSETb polylinker:
*MRGSHHHHHHGMASMTGGQQMGRDLYDDDDKDPMAQVINTNSLSLLTQNNLNKSQSSLSSAIERLSS*
*GLRINSAKDDAAGQAIANRFTSNIKGLTQASRNANDGISIAQTTEGALNEINNNLQRVRELSVQATN*
*GTNSDSDLKSIQDEIQQRLEEIDRVSNQTQFNGVKVLSQDNQMKIQVGANDGETITIDLQKIDVKSL*
*GLDGFNVNSPG*

Fig. 38 - Continued

B
Nucleotide sequence (480 bp):
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGT
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTGTCTCAG
GACAACCAGATGAAAATCCAGGTTGGTGCTAACGATGGTGAAACCATTACCATCGATCTG
CAAAAAATTGATGTGAAAAGCCTTGGCCTTGATGGGTTCAATGTTAATTCCCCGGGATGA Protein sequence (159 AA), last three amino acids are derived from primer and pRSETb polylinker:
MRGSHHHHHHGMASMTGGQQMGRDLYDDDDKDPFTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLDGFNVNSPG C
Nucleotide sequence (252 bp):
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGT
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
TCCCCGGGATGA Protein sequence (83 AA), last three amino acids are derived from primer and pRSETb polylinker:
MRGSHHHHHHGMASMTGGQQMGRDLYDDDDKDPFTSNIKGLTQASRNANDGISIAQTTEGALNEINN
NLQRVRELSVQATSPG GST-A'
Nucleotide sequence (1038 bp), GST highlighted:

ATGTCCCCTATACTAGGTTATTGGAAAATTAAGGGCCTTGTGCAACCCACTCGACTTCTT
TTGGAATATCTTGAAGAAAAATATGAAGAGCATTTGTATGAGCGCGATGAAGGTGATAAA
TGGCGAAACAAAAAGTTTGAATTGGGTTTGGAGTTTCCCAATCTTCCTTATTATATTGAT
GGTGATGTTAAATTAACACAGTCTATGGCCATCATACGTTATATAGCTGACAAGCACAAC
ATGTTGGGTGGTTGTCCAAAAGAGCGTGCAGAGATTTCAATGCTTGAAGGAGCGGTTTTG
GATATTAGATACGGTGTTTCGAGAATTGCATATATGTAAAGACTTTGAAACTCTCAAAGTT
GATTTTCTTAGCAAGCTACCTGAAATGCTGAAAATGTTCGAAGATCGTTTATGTCATAAA
ACATATTTAAATGGTGATCATGTAACCCATCCTGACTTCATGTTGTATGACGCTCTTGAT
GTTGTTTTATACATGGACCCAATGTGCCTGGATGCGTTCCCAAAATTAGTTTGTTTTAAA
AAACGTATTGAAGCTATCCCACAAATTGATAAGTACTTGAAATCCAGCAAGTATATAGCA
TGGCCTTTGCAGGGCTGGCAAGCCACGTTTGGTGGTGGCGACCATCCTCAAAATCGGAT
CTGGTTCCGCGTGGATCCCCGGGAATTTCCGGTGGTGGTGGTGGAATTCTAGACTCCATG
GGTACATTAATCAATGAAGACGCTGCCGCAGCCAAGAAAAGTACCGCTAACCCACTGGCT
TCAATTGATTCTGCATTGTCAAAAGTGGACGCAGTTCGTTCTTCTCTGGGGGCAATTCAA
AACCGTTTTGATTCAGCCATTACCAACCTTGGCAATACGGTAACCAATCTGAACTCCGCG
CGTAGCCGTATCGAAGATGCTGACTATGCAACGGAAGTTTCTAATATGTCTAAAGCGCAG
ATTCTGCAGCAGGCTGGTACTTCCGTTCTGGCGCAGGCTAACCAGGTTCCGCAAAACGTC
CTCTCTTTACTGCGTTAG

Protein sequence (345 AA):

Fig. 38 - Continued

MSPILGYWKIKGLVQPTRLLLEYLEEKYEEHLYERDEGDKWRNKKFELGLEFPNLPYYIDGDVKLTQ
SMAIIRYIADKHNMLGGCPKERAEISMLEGAVLDIRYGVSRIAYSKDFETLKVDFLSKLPEMLKMFE
DRLCHKTYLNGDHVTHPDFMLYDALDVVLYMDPMCLDAFPKLVCFKKRIEAIPQIDKYLKSSKYIAW
PLQGWQATFGGGDHPPKSDLVPRGSPGISGGGGGILDSMGTLINEDAAAAKKSTANPLASIDSALSK
VDAVRSSLGAIQNRFDSAITNLGNTVTNLNSARSRIEDADYATEVSNMSKAQILQQAGTSVLAQANQ
VPQNVLSLLR

GST-B'
Nucleotide sequence (873 bp), GST highlighted:
ATGTCCCCTATACTAGGTTATTGGAAAATTAAGGGCCTTGTGCAACCCACTCGACTTCTT
TTGGAATATCTTGAAGAAAAATATGAAGAGCATTTGTATGAGCGCGATGAAGGTGATAAA
TGGCGAAACAAAAAGTTTGAATTGGGTTTGGAGTTTCCCAATCTTCCTTATTATATTGAT
GGTGATGTTAAATTAACACAGTCTATGGCCATCATACGTTATATAGCTGACAAGCACAAC
ATGTTGGGTGGTTGTCCAAAAGAGCGTGCAGAGATTTCAATGCTTGAAGGAGCGGTTTTG
GATATTAGATACGGTGTTTCGAGAATTGCATATAGTAAAGACTTTGAAACTCTCAAAGTT
GATTTTCTTAGCAAGCTACCTGAAATGCTGAAAATGTTCGAAGATCGTTTATGTCATAAA
ACATATTTAAATGGTGATCATGTAACCCATCCTGACTTCATGTTGTATGACGCTCTTGAT
GTTGTTTTATACATGGACCCAATGTGCCTGGATGCGTTCCCAAAATTAGTTTGTTTTAAA
AAACGTATTGAAGCTATCCCACAAATTGATAAGTACTTGAAATCCAGCAAGTATATAGCA
TGGCCTTTGCAGGGCTGGCAAGCCACGTTTGGTGGTGGCGACCATCCTCCAAAATCGGAT
CTGGTTCCGCGTGGATCCCCGGGAATTTCCGGTGGTGGTGGTGGAATTCTAGACTCCATG
GGTACATTAATCAATGAAGACGCTGCCGCAGCCAAGAAAAGTACCGCTAACCCACTGGCT
TCAATTGATTCTGCATTGTCAAAAGTGGACGCAGTTCGTTCTTCTCTGGGGGCAATTCAA
AACCGTTTTGATTCAGCCATTACCAACCTTTAG Protein sequence (290 AA):
MSPILGYWKIKGLVQPTRLLLEYLEEKYEEHLYERDEGDKWRNKKFELGLEFPNLPYYIDGDVKLTQ
SMAIIRYIADKHNMLGGCPKERAEISMLEGAVLDIRYGVSRIAYSKDFETLKVDFLSKLPEMLKMFE
DRLCHKTYLNGDHVTHPDFMLYDALDVVLYMDPMCLDAFPKLVCFKKRIEAIPQIDKYLKSSKYIAW
PLQGWQATFGGGDHPPKSDLVPRGSPGISGGGGGILDSMGTLINEDAAAAKKSTANPLASIDSALSK
VDAVRSSLGAIQNRFDSAITNL AA'n1-170
Nucleotide sequence (972 bp):
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTGATGTGAAAAGC
CTTGGCCTTATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGGCAATTCAAAACCGT
TTTGATTCAGCCATTACCAACCTTGGCAATACGGTAACCAATCTGAACTCCGCGCGTAGC
CGTATCGAAGATGCTGACTATGCAACGGAAGTTTCTAATATGTCTAAAGCGCAGATTCTG
CAGCAGGCTGGTACTTCCGTTCTGGCGCAGGCTAACCAGGTTCCGCAAAACGTCCTCTCT Fig. 38 - Continued

```
TTACTGCGTTAG
```
Protein sequence (323 AA):
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLIPGISGGGGGILDSMGTLINEDAAAAKKSTANPLASIDSALSKVDAVRSSLGAIQNRFDSAITNL
GNTVTNLNSARSRIEDADYATEVSNMSKAQILQQAGTSVLAQANQVPQNVLSLLR AA'n1-163
Nucleotide sequence (951 bp):
```
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTATCCCGGGAATT
TCCGGTGGTGGTGGTGGAATTCTAGACTCCATGGGTACATTAATCAATGAAGACGCTGCC
GCAGCCAAGAAAAGTACCGCTAACCCACTGGCTTCAATTGATTCTGCATTGTCAAAAGTG
GACGCAGTTCGTTCTTCTCTGGGGGCAATTCAAAACCGTTTTGATTCAGCCATTACCAAC
CTTGGCAATACGGTAACCAATCTGAACTCCGCGCGTAGCCGTATCGAAGATGCTGACTAT
GCAACGGAAGTTTCTAATATGTCTAAAGCGCAGATTCTGCAGCAGGCTGGTACTTCCGTT
CTGGCGCAGGCTAACCAGGTTCCGCAAAACGTCCTCTCTTTACTGCGTTAG
```
Protein sequence (316 AA):
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIIPGIS
GGGGGILDSMGTLINEDAAAAKKSTANPLASIDSALSKVDAVRSSLGAIQNRFDSAITNLGNTVTNL
NSARSRIEDADYATEVSNMSKAQILQQAGTSVLAQANQVPQNVLSLLR AA'n54-170
Nucleotide sequence (813 bp):
```
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTCTCTCAG
GACAACCAGATGAAAATCCAGGTTGGTGCTAACGATGGTGAAACCATTACCATCGATCTG
CAAAAAATTGATGTGAAAAGCCTTGGCCTTATCCCGGGAATTTCCGGTGGTGGTGGTGGA
ATTCTAGACTCCATGGGTACATTAATCAATGAAGACGCTGCCGCAGCCAAGAAAAGTACC
GCTAACCCACTGGCTTCAATTGATTCTGCATTGTCAAAAGTGGACGCAGTTCGTTCTTCT
CTGGGGGCAATTCAAAACCGTTTTGATTCAGCCATTACCAACCTTGGCAATACGGTAACC
AATCTGAACTCCGCGCGTAGCCGTATCGAAGATGCTGACTATGCAACGGAAGTTTCTAAT
ATGTCTAAAGCGCAGATTCTGCAGCAGGCTGGTACTTCCGTTCTGGCGCAGGCTAACCAG
GTTCCGCAAAACGTCCTCTCTTTACTGCGTTAG
```

Fig. 38 - Continued

Protein sequence (270 AA):
*MRGSHHHHHHGMASMTGGQQMGRDLYDDDDKDPFT*SNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLIPGISGGGGGILDSMGTLINEDAAAAKKSTANPLASIDSALSKVDAVRSSL
GAIQNRFDSAITNLGNTVTNLNSARSRIEDADYATEVSNMSKAQILQQAGTSVLAQANQVPQNVLSL
LR AA'n54-163
Nucleotide sequence (792 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGTT*CACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTCTCTCAG
GACAACCAGATGAAAATCCAGGTTGGTGCTAACGATGGTGAAACCATTACCATCGATCTG
CAAAAAATTATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGCAATTCAAAACCGT
TTTGATTCAGCCATTACCAACCTTGGCAATACGGTAACCAATCTGAACTCCGCGCGTAGC
CGTATCGAAGATGCTGACTATGCAACGGAAGTTTCTAATATGTCTAAAGCGCAGATTCTG
CAGCAGGCTGGTACTTCCGTTCTGGCGCAGGCTAACCAGGTTCCGCAAAACGTCCTCTCT
TTACTGCGTTAG*
Protein sequence (263 AA):
*MRGSHHHHHHGMASMTGGQQMGRDLYDDDDKDP*FTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIIPGISGGGGGILDSMGTLINEDAAAAKKSTANPLASIDSALSKVDAVRSSLGAIQNRF
DSAITNLGNTVTNLNSARSRIEDADYATEVSNMSKAQILQQAGTSVLAQANQVPQNVLSLLR AB'n1-170 (or AA'n1-170c402-450)
Nucleotide sequence (807 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGGCACAAGTCATTAATACA*
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTGATGTGAAAAGC
CTTGGCCTTATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGCAATTCAAAACCGT
TTTGATTCAGCCATTACCAACCTTTAG
Protein sequence (268 AA):
*MRGSHHHHHHGMASMTGGQQMGRDLYDDDDKDP*MAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN Fig. 38 - Continued GTNSDSDLKSIQDEIQQRLEEIDRVSNQTQFNGVKVLSQDNQMKIQVGANDGETITIDLQKIDVKSL
GLIPGISGGGGGILDSMGTLINEDAAAAKKSTANPLASIDSALSKVDAVRSSLGAIQNRFDSAITNL AB'n1-163 (or AA'n1-163c402-450)
Nucleotide sequence (786 bp):
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTATCCCGGGAATT
TCCGGTGGTGGTGGTGGAATTCTAGACTCCATGGGTACATTAATCAATGAAGACGCTGCC
GCAGCCAAGAAAAGTACCGCTAACCCACTGGCTTCAATTGATTCTGCATTGTCAAAAGTG
GACGCAGTTCGTTCTTCTCTGGGGGCAATTCAAAACCGTTTTGATTCAGCCATTACCAAC
CTTTAG
Protein sequence (261 AA):
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIIPGIS
GGGGGILDSMGTLINEDAAAAKKSTANPLASIDSALSKVDAVRSSLGAIQNRFDSAITNL AA'n1-129
Nucleotide sequence (849 bp):
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGATCCCGGGAATTTCCGGTGGTGGTGGTGGAATTCTAGACTCCATGGGTACATTA
ATCAATGAAGACGCTGCCGCAGCCAAGAAAAGTACCGCTAACCCACTGGCTTCAATTGAT
TCTGCATTGTCAAAAGTGGACGCAGTTCGTTCTTCTCTGGGGGCAATTCAAAACCGTTTT
GATTCAGCCATTACCAACCTTGGCAATACGGTAACCAATCTGAACTCCGCGCGTAGCCGT
ATCGAAGATGCTGACTATGCAACGGAAGTTTCTAATATGTCTAAAGCGCAGATTCTGCAG
CAGGCTGGTACTTCCGTTCTGGCGCAGGCTAACCAGGTTCCGCAAAACGTCCTCTCTTTA
CTGCGTTAG
Protein sequence (282 AA):
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQIPGISGGGGGILDSMGTLINEDAAAAKKSTANPLASIDS
ALSKVDAVRSSLGAIQNRFDSAITNLGNTVTNLNSARSRIEDADYATEVSNMSKAQILQQAGTSVLA
QANQVPQNVLSLLR Fig. 38 - Continued AA'n54-129
Nucleotide sequence (690 bp):
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGATCCCGGGAATTTCCGGTGGTGGTGGTGGAATT
CTAGACTCCATGGGTACATTAATCAATGAAGACGCTGCCGCAGCCAAGAAAAGTACCGCT
AACCCACTGGCTTCAATTGATTCTGCATTGTCAAAAGTGGACGCAGTTCGTTCTTCTCTG
GGGGCAATTCAAAACCGTTTTGATTCAGCCATTACCAACCTTGGCAATACGGTAACCAAT
CTGAACTCCGCGCGTAGCCGTATCGAAGATGCTGACTATGCAACGGAAGTTTCTAATATG
TCTAAAGCGCAGATTCTGCAGCAGGCTGGTACTTCCGTTCTGGCGCAGGCTAACCAGGTT
CCGCAAAACGTCCTCTCTTTACTGCGTTAG
Protein sequence (229 AA):
MRGSHHHHHHGMASMTGGQQMGRDLYDDDDKDPFTSNIKGLTQASRNANDGISIAQTTEGALNEINN
NLQRVRELSVQATNGTNSDSDLKSIQDEIQQRLEEIDRVSNQIPGISGGGGGILDSMGTLINEDAAA
AKKSTANPLASIDSALSKVDAVRSSLGAIQNRFDSAITNLGNTVTNLNSARSRIEDADYATEVSNMS
KAQILQQAGTSVLAQANQVPQNVLSLLR AB'n1-129
Nucleotide sequence (684 bp):
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGATCCCGGGAATTTCCGGTGGTGGTGGTGGAATTCTAGACTCCATGGGTACATTA
ATCAATGAAGACGCTGCCGCAGCCAAGAAAAGTACCGCTAACCCACTGGCTTCAATTGAT
TCTGCATTGTCAAAAGTGGACGCAGTTCGTTCTTCTCTGGGGGCAATTCAAAACCGTTTT
GATTCAGCCATTACCAACCTTTAG
Protein sequence (227 AA):
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQIPGISGGGGGILDSMGTLINEDAAAAKKSTANPLASIDS
ALSKVDAVRSSLGAIQNRFDSAITNL AB'n54-129
Nucleotide sequence (525 bp):
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT Fig. 38 - Continued

```
AACGGGACTAACTCTGATTCCGATCTGAAATCTATCCAGGATGAAATTCAGCAACGTCTG
GAAGAAATCGATCGCGTTTCTAATCAGATCCCGGGAATTTCCGGTGGTGGTGGTGGAATT
CTAGACTCCATGGGTACATTAATCAATGAAGACGCTGCCGCAGCCAAGAAAAGTACCGCT
AACCCACTGGCTTCAATTGATTCTGCATTGTCAAAAGTGGACGCAGTTCGTTCTTCTCTG
GGGGCAATTCAAAACCGTTTTGATTCAGCCATTACCAACCTTTAG
```
Protein sequence (174 AA):
*MRGSHHHHHHGMASMTGGQQMGRDLYDDDDKDPFTSNIKGLTQASRNANDGISIAQTTEGALNEINN
NLQRVRELSVQATNGTNSDSDLKSIQDEIQQRLEEIDRVSNQIPGISGGGGGILDSMGTLINEDAAA
AKKSTANPLASIDSALSKVDAVRSSLGAIQNRFDSAITNL*

AA'n1-100
Nucleotide sequence (762 bp):
```
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTCACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTATCCCGGGAATTTCCGGTGGT
GGTGGTGGAATTCTAGACTCCATGGGTACATTAATCAATGAAGACGCTGCCGCAGCCAAG
AAAAGTACCGCTAACCCACTGGCTTCAATTGATTCTGCATTGTCAAAAGTGGACGCAGTT
CGTTCTTCTCTGGGGGCAATTCAAAACCGTTTTGATTCAGCCATTACCAACCTTGGCAAT
ACGGTAACCAATCTGAACTCCGCGCGTAGCCGTATCGAAGATGCTGACTATGCAACGGAA
GTTTCTAATATGTCTAAAGCGCAGATTCTGCAGCAGGCTGGTACTTCCGTTCTGGCGCAG
GCTAACCAGGTTCCGCAAAACGTCCTCTCTTTACTGCGTTAG
```
Protein sequence (253 AA):
*MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATI
PGISGGGGILDSMGTLINEDAAAAKKSTANPLASIDSALSKVDAVRSSLGAIQNRFDSAITNLGNT
VTNLNSARSRIEDADYATEVSNMSKAQILQQAGTSVLAQANQVPQNVLSLLR*

AB'n1-100
Nucleotide sequence (597 bp):
```
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTATCCCGGGAATTTCCGGTGGT
GGTGGTGGAATTCTAGACTCCATGGGTACATTAATCAATGAAGACGCTGCCGCAGCCAAG
AAAAGTACCGCTAACCCACTGGCTTCAATTGATTCTGCATTGTCAAAAGTGGACGCAGTT
CGTTCTTCTCTGGGGGCAATTCAAAACCGTTTTGATTCAGCCATTACCAACCTTTAG
```
Protein sequence (198 AA):
*MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATI
PGISGGGGILDSMGTLINEDAAAAKKSTANPLASIDSALSKVDAVRSSLGAIQNRFDSAITNL*

Fig. 38 - Continued

AA'n1-70
Nucleotide sequence (672 bp):
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGGCAATTCAAAACCGT
TTTGATTCAGCCATTACCAACCTTGGCAATACGGTAACCAATCTGAACTCCGCGCGTAGC
CGTATCGAAGATGCTGACTATGCAACGGAAGTTTCTAATATGTCTAAAGCGCAGATTCTG
CAGCAGGCTGGTACTTCCGTTCTGGCGCAGGCTAACCAGGTTCCGCAAAACGTCCTCTCT
TTACTGCGTTAG
Protein sequence (223 AA):
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDIPGISGGGGGILDSMGTLINEDAAAAKKSTA
NPLASIDSALSKVDAVRSSLGAIQNRFDSAITNLGNTVTNLNSARSRIEDADYATEVSNMSKAQILQ
QAGTSVLAQANQVPQNVLSLLR AB'n1-70
Nucleotide sequence (507 bp):
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGGCAATTCAAAACCGT
TTTGATTCAGCCATTACCAACCTTTAG
Protein sequence (168 AA):
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDIPGISGGGGGILDSMGTLINEDAAAAKKSTA
NPLASIDSALSKVDAVRSSLGAIQNRFDSAITNL

FLAGELLIN RELATED POLYPEPTIDES AND USES THEREOF

CROSS REFERENCE TO RELATED APPLICATIONS

This application is the National Stage of International Application Number PCT/US2005/046485, filed Dec. 22, 2005, which claims the benefit of U.S. Provisional Application No. 60/639,826, filed Dec. 22, 2004, which is incorporated herein by reference.

FIELD OF THE INVENTION

This invention relates to the use of flagellin related polypeptides to protect mammals from the effects of apoptosis. More specifically, this invention relates to the use of flagellin related polypeptides to protect mammals from exposure to stress, such as radiation and cancer treatments.

REFERENCE TO THE SEQUENCE LISTING

Reference is made to the sequence listing submitted via EFS-Web, which consists of a file named, "Sequence.txt" (134 KB), created on Jul. 1, 2010, the contents of which are incorporated herein by reference.

BACKGROUND OF THE INVENTION

The progression from normal cells to tumor cells involves a loss of negative mechanisms of growth regulation, including resistance to growth inhibitory stimuli and a lack of dependence on growth factors and hormones. Traditional cancer treatments that are based on radiation or cytotoxic drugs rely on the differences in growth control of normal and malignant cells. Traditional cancer treatments subject cells to severe genotoxic stress. Under these conditions, the majority of normal cells become arrested and therefore saved, while tumor cells continue to divide and die.

However, the nature of conventional cancer treatment strategy is such that normal rapidly dividing or apoptosis-prone tissues are at risk. Damage to these normal rapidly dividing cells causes the well-known side effects of cancer treatment (sensitive tissues: hematopoiesis, small intestine, hair follicles). The natural sensitivity of such tissues is complicated by the fact that cancer cells frequently acquire defects in suicidal (apoptotic) machinery and those therapeutic procedures that cause death in normal sensitive tissues may not be that damaging to cancer cells. Conventional attempts to minimize the side effects of cancer therapies are based on (a) making tumor cells more susceptible to treatment, (b) making cancer therapies more specific for tumor cells, or (c) promoting regeneration of normal tissue after treatment (e.g., erythropoietin, GM-CSF, and KGF).

There continues to be a need for therapeutic agents to mitigate the side effects associated with chemotherapy and radiation therapy in the treatment of cancer. This invention fulfills these needs and provides other related advantages.

SUMMARY OF THE INVENTION

A method of protecting a mammal from one or more treatments or conditions that trigger apoptosis comprising administering to said patient a composition comprising a pharmaceutically effective amount of flagellin. The flagellin may comprise SEQ ID NO: 1 or a fragment, variant, analog, homolog, derivative of SEQ ID NO: 1, or combination thereof. The flagellin may induce TLR-5 mediated activity.

The flagellin may be at least 30% identical to amino acids 1-174 and 418-505 of SEQ ID NO: 1. The flagellin may comprise at least 10 conserved amino acids at positions selected from the group consisting of 89, 90, 91, 95, 98, 101, 115, 422, 423, 426, 431, 436 and 452. The flagellin may comprise the sequence of SEQ ID NOS: 1, 8, 10, 12, 30, 32, 34, 36, 38, 40, 42, 44, 46, 48, 50 and 52.

The flagellin may be used to treat a mammal undergoing cancer treatment, which may be chemotherapy or radiation therapy. The flagellin may be used to treat a mammal exposed to radiation. The flagellin may be administered in combination with a radioprotectant. The flagellin may be used to treat a mammal from wounding, poisoning, bacterial infection, viral infection and temperature shock. The flagellin may be used to protect from apoptosis in tissues including the GI tract, lungs, kidneys, liver, cardiovascular system, blood vessel endothelium, central and peripheral neural system, hematopoietic progenitor cells, immune system, and hair follicles. The flagellin may also be used to prevent sepsis in the mammal.

This invention also relates to a method of treating a mammal suffering from a constitutively active NF-κB cancer comprising administering to the mammal a composition comprising a pharmaceutically acceptable amount of an agent which induces NF-κB. The agent may be flagellin. The agent may be administered prior to, together with, or after a treatment for the cancer. The treatment may be chemotherapy or radiation therapy.

This invention also relates to a method of treating a mammal suffering from damage to normal tissue attributable to treatment of a cancer comprising administering to the mammal a composition comprising a pharmaceutically acceptable amount of an agent which induces NF-κB. The agent may be flagellin. The agent may be administered prior to, together with, or after a treatment for the cancer. The treatment may be chemotherapy or radiation therapy.

This invention also relates to a method of treating a mammal suffering from damage to normal tissue attributable to stress, comprising administering to the mammal a composition comprising a pharmaceutically acceptable amount of an agent which induces NF-κB. The agent may be flagellin. The agent may be administered prior to, together with, or after a treatment for a disease suffered by the mammal.

This invention also relates to a method of modulating cell aging in a mammal, comprising administering to the mammal a composition comprising a pharmaceutically acceptable amount of an agent which induces NF-κB. The agent may be flagellin. The agent may be administered prior to, together with, or after a treatment for a disease suffered by the mammal.

This invention also relates to a pharmaceutical composition comprising an agent which induces NF-κB activity, a chemotherapeutic drug, and optionally a pharmaceutically acceptable adjuvant, diluent, or carrier. The agent may be flagellin.

This invention also relates to a method of screening for an inducer of NF-κB comprising adding a suspected inducer to an NF-κB activated expression system, and separately adding a control to an NF-κB activated expression system, whereby an inducer of NF-κB is identified by the ability to increase the level of NF-κB activated expression.

This invention also relates to a method of protecting a mammal from the effects of radiation comprising administering to said mammal a composition comprising a pharmaceutically effective amount of an agent which induces NF-κB.

The agent may be flagellin, which may be derived from a species of *Salmonella*. The composition may be administered in combination with a radioprotectant. The radioprotectant may be an antioxidant, which may be amifostine or vitamin E. The radioprotectant may also be a cytokine, which may be stem cell factor.

This invention relates to a method of protecting a patient from one or more treatments or conditions that trigger apoptosis comprising administering to said patient a composition comprising a pharmaceutically effective amount of an agent which induces NF-κB. The agent may be flagellin, which may be derived from a species of *Salmonella*. The treatment may be a cancer treatment, which may be chemotherapy or radiation therapy. The condition may be a stress, which may be radiation, wounding, poisoning, infection and temperature shock.

This invention also relates to a method of screening for a modulator of apoptosis comprising adding a suspected modulator to a cell-based apoptosis system, and separately adding a control to a cell-based apoptosis system, whereby a modulator of apoptosis is identified by the ability to alter the rate of apoptosis, wherein the suspected modulator is derived from a mammalian parasite or symbiont.

This invention also relates to a method of screening for a modulator of NF-κB comprising adding a suspected modulator to an NF-κB activated expression system, and separately adding a control to an NF-κB activated expression system, whereby a modulator of NF-κB is identified by the ability to alter the rate of NF-κB activated expression, wherein the suspected modulator is derived from a mammalian parasite. The parasite may be of a species including, but not limited to, *Salmonella, Mycoplasma*, and *Chlamydia*.

This invention also relates to a modulator identified by any of the screening methods described herein. This invention also relates to a composition comprising a modulator described herein. The composition may be a pharmaceutical composition comprising a pharmaceutically acceptable amount of a modulator described herein.

This invention also relates to a method of treating cancer comprising administering to a subject in need of such treatment a pharmaceutical composition comprising a modulator that enhances apoptosis.

This invention also relates to a method of protecting a patient from one or more treatments that trigger apoptosis comprising administering to said patient a pharmaceutical composition comprising a modulator that inhibits apoptosis. The one or more treatments may be a cancer treatment. The cancer treatment may be chemotherapy or radiation therapy.

BRIEF DESCRIPTION OF THE DRAWINGS

FIG. 5 shows histological sections (HE stained) of small intestinal epithelium of mice that were treated with 15 Gy of gamma radiation with or without i.v. injection of 0.25 mg/kg of flagellin. Complete destruction of crypts and villi in control mouse contrasts with close to normal morphology of tissue from flagellin-treated animal.

FIG. 7 shows the effect of flagellin injected i.v. at indicated times before irradiation on mouse sensitivity to 13 Gy (left) and 10 Gy (right) of total body gamma radiation.

FIGS. 24A and 24B show a comparison of amino acid sequences of the conserved amino (FIG. 24A) and carboxy (FIG. 24B) terminus from 21 species of bacteria. The 13 conserved amino acids important for TLR5 activity are shown with shading. The amino acid sequences are identified by their accession numbers from TrEMBL (first letter=Q) or Swiss-Prot (first letter=P). The amino terminus sequences have SEQ ID NOs: 1-21, respectively, for each of the 21 bacterial species, and the carboxy terminus sequences have SEQ ID NOs: 22-42, respectively.

FIG. 25 shows results of a BLAST search using SEQ ID NO: 1 as the query sequence. The parameters used in all searches was as follows: expected value cutoff=10, matrix=BLOSUM62, gap penalties of existence=11 and extension=1, filtering=none. FIG. 25A: NR_Bacteria (Protein-Protein); FIG. 25B: NR_Bacteria (Protein-DNA); FIG. 25C: Bacterial Genomes (Protein-Protein); FIG. 25D: Bacterial Genomes (Protein-DNA).

FIG. 26 shows the percentage identities of the amino- and carboxy-terminus of the homologs shown in FIG. 24 compared to SEQ ID NO: 1, as shown in BLAST results using the same search parameters as listed for FIG. 25.

2000 January; 278(1):G1-5). Red channel of the image is shown (positive signal is bright white on the dark background).

Figure 33:
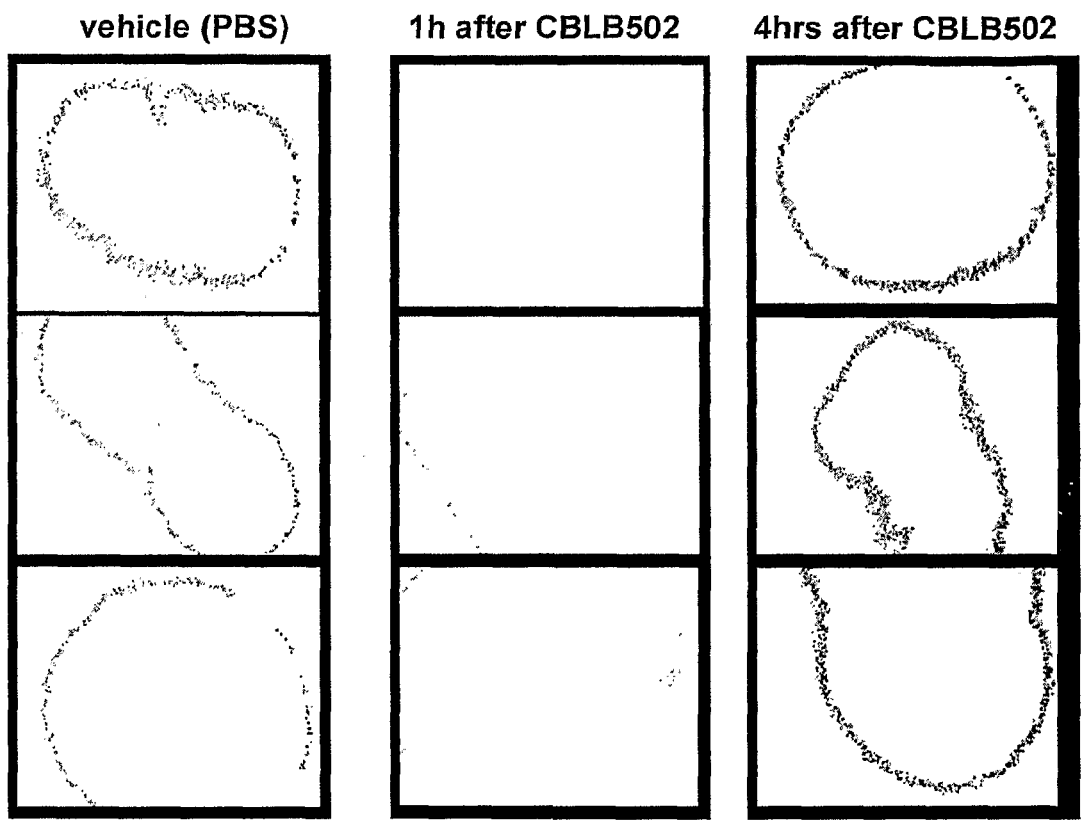

FIG. 33 demonstrates the duration of AA'-mediated growth arrest and reduced BrdU incorporation in small intestine of mice. BrdU (50 mg/kg) was injected in Balb/c mice i.p., 1 or 4 hrs after CBLB502 (AA') injection. Samples of small intestine were obtained 1.5 hrs after BrdU injection. Immunostaining was done as previously described (Watson A J & Pritchard D M., *Am J Physiol Gastrointest Liver Physiol.* 2000 January; 278(1):G1-5). Inverted image is shown (positive signal is dark on the light background).

Figure 34:
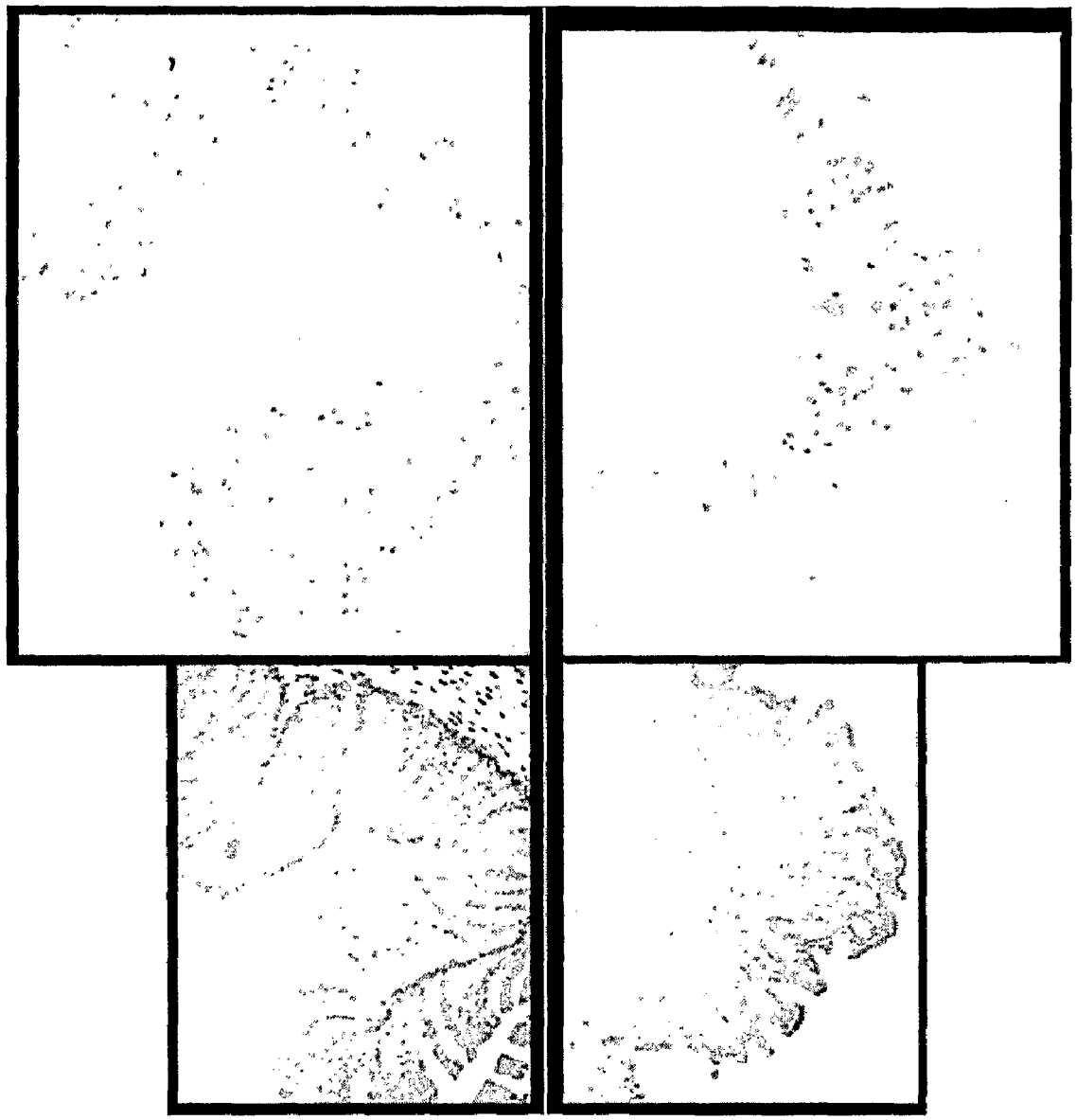

FIG. 34 demonstrates the influence of AA' on BrdU incorporation in colonic crypts of NIH-Swiss mice. BrdU (50 mg/kg) was injected in NIH-Swiss mice i.p., 1 hr after CBLB502 (AA') injection, Samples of colon were obtained 1.5 hrs after BrdU injection. Immunostaining was done as previously described (Watson A J & Pritchard D M., *Am J Physiol Gastroinitest Liver Physiol.* 2000 January; 278(1): G1-5). Inverted image is shown (positive signal is dark on the light background). Bottom panel shows smaller magnification/larger area of the sample.

Figure 35:
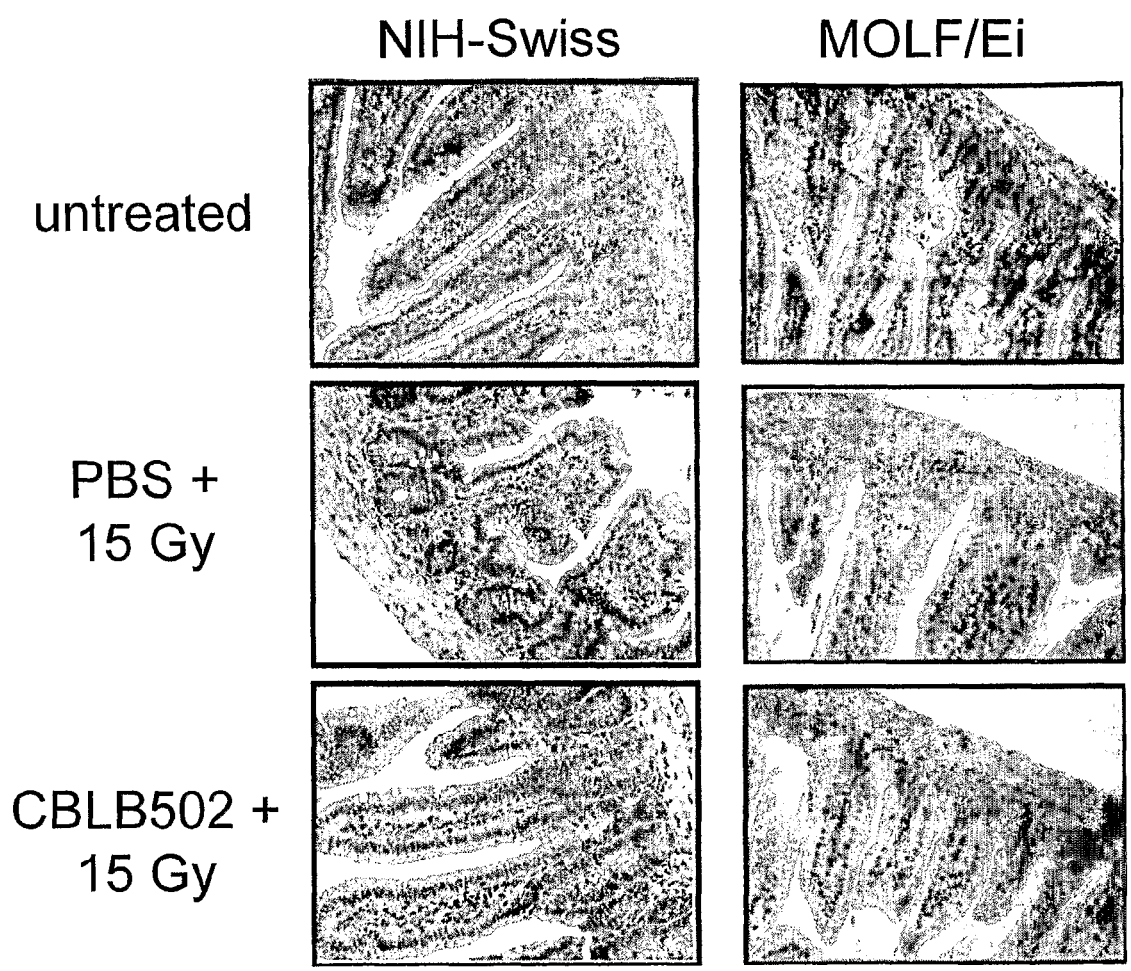

FIG. 35 demonstrates the morphology of small intestine in TLR5 deficient MOLF/Ei and TLR5 wt NIH-Swiss mice after treatment with AA'.

Figure 36:
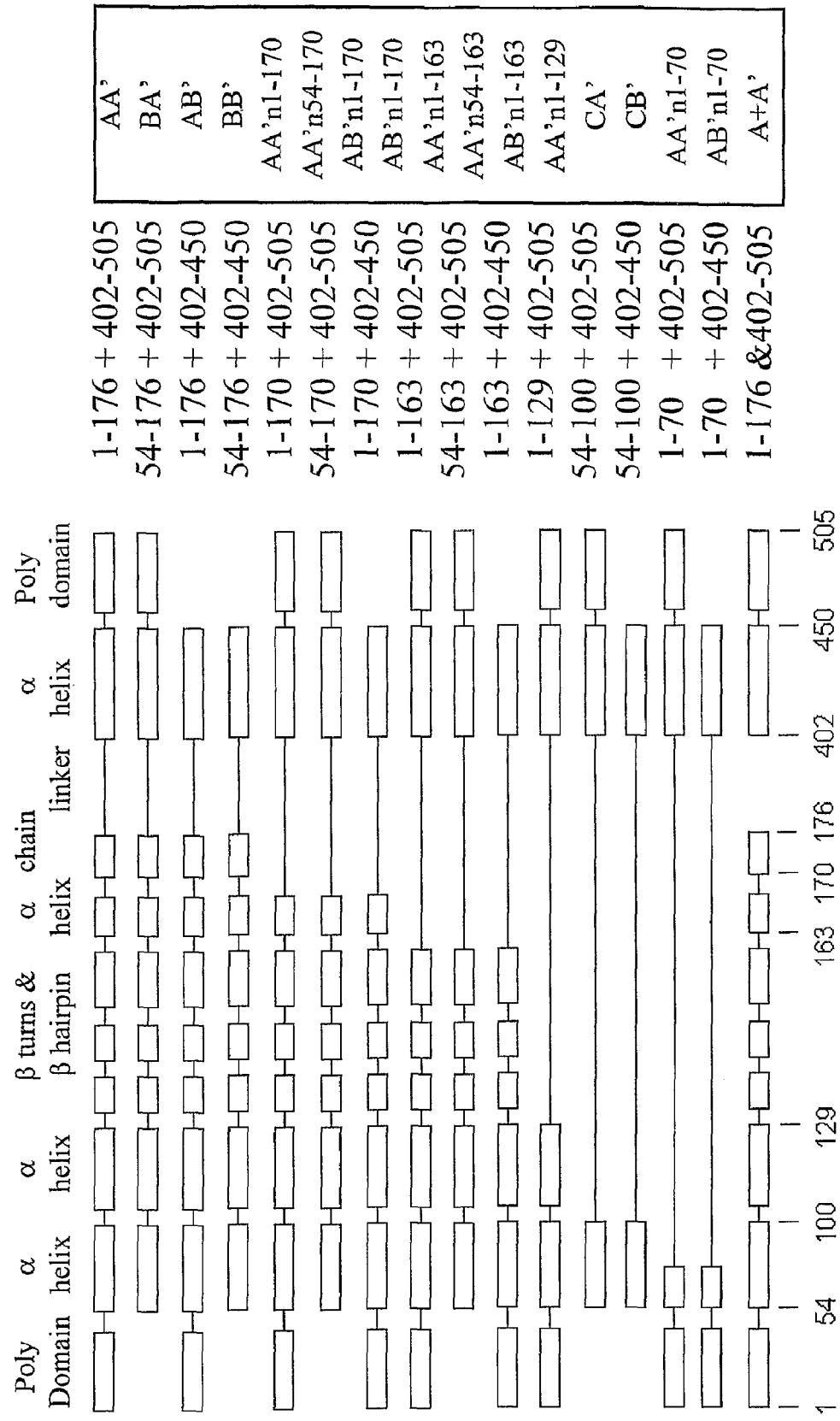

FIG. 36 depicts flagellin derivatives. The domain structure and approximate boundaries (amino acid coordinates) of selected flagellin derivatives (listed on the right). FliC flagellin of *Salmonella dublin* is encoded within 505 amino acids (aa).

Figure 37:
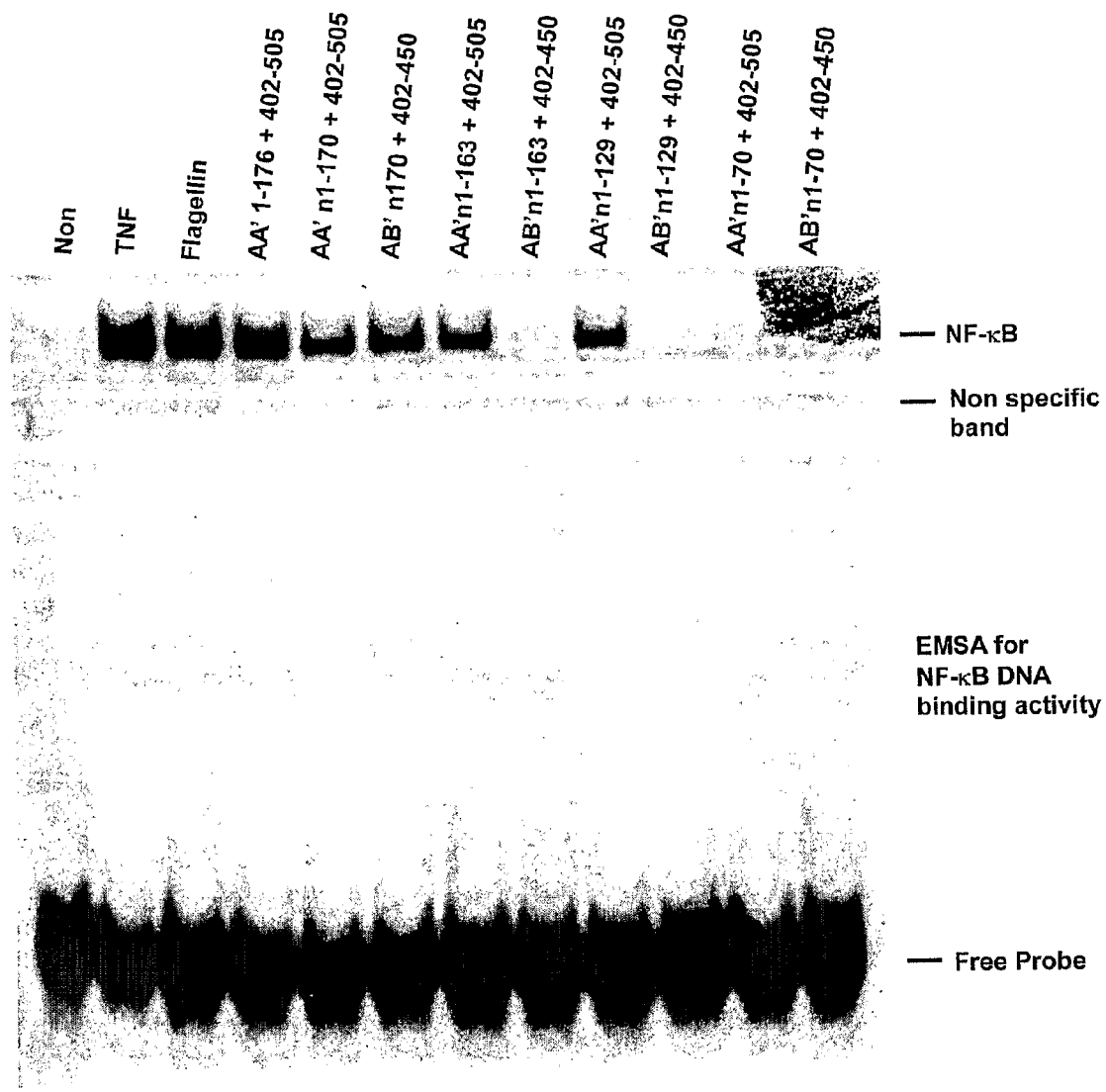

FIG. 37 shows the testing of additional flagellin derivatives tested for NF-κB stimulating activity.

FIG. 38 shows the nucleotide and amino acid sequence for the following flagellin variants: AA' (SEQ ID NO: 7-8), AB' (SEQ ID NO: 9-10), BA'(SEQ ID NO: 11-12), BB' (SEQ ID NO: 13-14), CA'(SEQ ID NO: 15-16), CB'(SEQ ID NO: 17-18), A (SEQ ID NO: 19-20), B (SEQ ID NO: 21-22), C (SEQ ID NO: 23-24), GST-A' (SEQ ID NO: 25-26), GST-B' (SEQ ID NO: 27-28), AA'n1-170 (SEQ ID NO: 29-30), AA'n1-163 (SEQ ID NO: 33-34), AA'n54-170 (SEQ ID NO: 31-32), AA'n54-163 (SEQ ID NO: 335-36), AB'n1-170 (SEQ ID NO: 37-38), AB'n1-163 (SEQ ID NO: 39-40), AA'n1-129 (SEQ ID NO: 41-42), AA'n54-129 (SEQ ID NO: 43-44), AB'n1-129 (SEQ ID NO: 45-46), AB'n54-129 (SEQ ID NO: 47-48), AA'n1-100 (SEQ ID NO: 49-50), AB'n1-100 (SEQ ID NO: 51-52), AA'n1-70 (SEQ ID NO: 53-54) and AB'n1-70 (SEQ ID NO: 55-56). The pRSETb leader sequence is shown in Italic (leader includes Met, which is also amino acid 1 of FliC). The N terminal constant domain is underlined. The amino acid linker sequence is in Bold. The C terminal constant domain is underlined. GST, if present, is highlighted.

DETAILED DESCRIPTION

This invention is related to protecting normal cells and tissues from apoptosis caused by stresses including, but not limited to, chemotherapy, radiation therapy and radiation. There are two major mechanisms controlling apoptosis in the cell: the p53 pathway (pro-apoptotic) and the NF-κB pathway (anti-apoptotic). Both pathways are frequently deregulated in tumors: p53 is usually lost, while NF-κB becomes constitutively active. Hence, inhibition of p53 and activation of NF-κB in normal cells may protect them from death caused by stresses, such as cancer treatment, but would not make tumor cells more resistant to treatment because they have these control mechanisms deregulated. This contradicts the conventional view on p53 and NF-κB, which are considered as targets for activation and repression, respectively.

This invention relates to inducing NF-κB activity to protect normal cells from apoptosis. By inducing NF-κB activity in a mammal, normal cells may be protected from apoptosis attributable to cellular stress, which occurs in cancer treatments and hyperthermia; exposure to harmful doses of radiation, for example, workers in nuclear power plants, the defense industry or radiopharmaceutical production, and soldiers; and cell aging. Since NF-κB is constitutively active in many tumor cells, the induction of NF-κB activity may protect normal cells from apoptosis without providing a beneficial effect to tumor cells. Once the normal cells are repaired, NF-κB activity may be restored to normal levels. NF-κB activity may be induced to protect such radiation- and chemotherapy-sensitive tissues as the hematopoietic system (including immune system), the epithelium of the gut, and hair follicles.

Inducers of NF-κB activity may also be used for several other applications. Pathological consequences and death caused by exposure of mammals to a variety of severe conditions including, but not limited to, radiation, wounding, poisoning, infection, aging, and temperature shock, may result from the activity of normal physiological mechanisms of stress response, such as induction of programmed cell death (apoptosis) or release of bioactive proteins, cytokines.

Apoptosis normally functions to "clean" tissues from wounded and genetically damaged cells, while cytokines serve to mobilize the defense system of the organism against the pathogen. However, under conditions of severe injury both stress response mechanisms can by themselves act as causes of death. For example, lethality from radiation may result from massive p53-mediated apoptosis occurring in hematopoietic, immune and digestive systems. Rational pharmacological regulation of NF-κB may increase survival under conditions of severe stress. Control over these factors may allow control of both inflammatory response and the life-death decision of cells from the injured organs. Tissues that may be protected from apoptosis by administering NF-κB inducers include, but are not limited to, the GI tract, lungs, kidneys, liver, cardiovascular system, blood vessel endothelium, central and peripheral neural system, hematopoietic progenitor cells, immune system, and hair follicles.

The protective role of NF-κB is mediated by transcriptional activation of multiple genes coding for: a) anti-apoptotic proteins that block both major apoptotic pathways, b) cytokines and growth factors that induce proliferation and survival of BP and other stem cells, and c) potent ROS-scavenging antioxidant proteins, such as MnSOD (SOD-2). Thus, by temporal activation of NF-κB for radioprotection, it may be possible to achieve not only suppression of apoptosis in cancer patients, but also the ability to reduce the rate of secondary cancer incidence because of simultaneous immunostimulatory effect, which may be achieved if activation of NF-κB is reached via activation of Toll-like receptors.

Another attractive property of the NF-κB pathway as a target is its activation by numerous natural factors that can be considered as candidate radioprotectants. Among these, are multiple pathogen-associated molecular patterns (PAMPs). PAMPs are molecules that are not found in the host organism, are characteristic for large groups of pathogens, and cannot be easily mutated. They are recognized by Toll-like receptors (TLRs), the key sensor elements of innate immunity. TLRs act as a first warning mechanism of immune system by inducing migration and activation of immune cells directly or through cytokine release. TLRs are type I membrane proteins, known to work as homo- and heterodimers. Upon ligand binding, TLRs recruit MyD88 protein, an indispensable signaling adaptor for most TLRs. The signaling cascade that follows leads to effects including (i) activation of NF-κB pathway, and (ii) activation of MAPKs, including Jun N-terminal kinease (JNK). The activation of the NF-κB pathway by Toll-like receptor ligands makes the ligands attractive as potential radioprotectors. Unlike cytokines, many PAMPs have little effect besides activating TLRs and thus are unlikely to produce side effects. Moreover, many PAMPs are present in humans.

Consistently with their function of immunocyte activation, all TLRs are expressed in spleen and peripheral blood leukocytes, with more TLR-specific patterns of expression in other lymphoid organs and subsets of leukocytes. However, TLRs are also expressed in other tissues and organs of the body, e.g., TLR1 is expressed ubiquitously, TLR5 is also found in GI epithelium and endothelium, while TLRs 2, 6, 7 and 8 are known to be expressed in lung.

1. DEFINITIONS

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

As used herein, the terms "administer" when used to describe the dosage of an agent that induces NF-κB activity, means a single dose or multiple doses of the agent.

As used herein, the term "analog", when used in the context of a peptide or polypeptide, means a peptide or polypeptide comprising one or more non-standard amino acids or other structural variations from the conventional set of amino acids.

As used herein, the term "antibody" means an antibody of classes IgG, IgM, IgA, IgD or IgE, or fragments, fragments or derivatives thereof, including Fab, F(ab')$_2$, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety.

As used herein, "apoptosis" refers to a form of cell death that includes progressive contraction of cell volume with the preservation of the integrity of cytoplasmic organelles; condensation of chromatin (i.e., nuclear condensation), as viewed by light or electron microscopy; and/or DNA cleavage into nucleosome-sized fragments, as determined by centrifuged sedimentation assays. Cell death occurs when the membrane integrity of the cell is lost (e.g., membrane blebbing) with engulfment of intact cell fragments ("apoptotic bodies") by phagocytic cells.

As used herein, the term "cancer" means any malignant growth or tumor caused by abnormal and uncontrolled cell division; it may spread to other parts of the body through the lymphatic system or the blood stream.

As used herein, the term "cancer treatment" means any treatment for cancer known in the art including, but not limited to, chemotherapy and radiation therapy.

As used herein, the term "combination with" when used to describe administration of an agent that induces NF-κB activity and an additional treatment means that the agent may be administered prior to, together with, after, or metronomically with the additional treatment. The term "together with," "simultaneous" or "simultaneously" as used herein, means that the additional treatment and the agent of this invention are administered within 48 hours, preferably 24 hours, more preferably 12 hours, yet more preferably 6 hours, and most preferably 3 hours or less, of each other. The term "metronomically" as used herein means the administration of the agent at times different from the additional treatment and at certain frequency relative to repeat administration and/or the additional treatment.

The agent may be administered at any point prior to the additional treatment including, but not limited to, about 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, or 1 hr prior to the additional treatment. The agent may be administered at any point after the additional treatment including, but not limited to, about 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, or 48 hr after exposure.

As used herein, the term "derivative", when used in the context of a peptide or polypeptide, means a peptide or polypeptide different other than in primary structure (amino acids and amino acid analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the invention. Other derivatives include, but are not limited to, fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

As used herein, the term "fragment", when used in the context of a peptide or polypeptide, means a portion of a reference peptide or polypeptide.

As used herein, the term "homolog", when used in the context of a peptide or polypeptide, means a peptide or polypeptide sharing a common evolutionary ancestor.

As used herein, the term "treat" or "treating" when referring to protection of a mammal from a condition, means preventing, suppressing, repressing, or eliminating the condition. Preventing the condition involves administering a composition of this invention to a mammal prior to onset of the condition. Suppressing the condition involves administering a composition of this invention to a mammal after induction of the condition but before its clinical appearance. Repressing the condition involves administering a composition of this invention to a mammal after clinical appearance of the condition such that the condition is reduced or maintained. Elimination the condition involves administering a composition of this invention to a mammal after clinical appearance of the condition such that the mammal no longer suffers the condition.

As used herein, the term "tumor cell" means any cell associated with a cancer.

As used herein, the term "variant", when used in the context of a peptide or polypeptide, means a peptide or polypeptide that differs in amino acid sequence by the insertion, deletion, or conservative substitution of amino acids, but retain at least one biological activity. Representative examples of "biological activity" include, but are not limited to, the ability to bind to TLR5 and to be bound by a specific antibody. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated herein by reference. Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. METHODS OF TREATMENT a. Constitutively Active NF-κB Tumor

This invention relates to a method of treating a mammal suffering from a constitutively active NF-κB cancer comprising administering to the mammal a composition comprising a therapeutically effective amount of an agent that induces NF-κB activity. The agent that induces NF-κB activity may be administered in combination with a cancer treatment, such as chemotherapy and radiation therapy.

The cancer treatment may comprise administration of a cytotoxic agent or cytostatic agent, or combination thereof. Cytotoxic agents prevent cancer cells from multiplying by: (1) interfering with the cell's ability to replicate DNA and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include, but are not limited to, the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxycoformycin, mitomycin-c, l-asparaginase, interferons (preferably IFN-α), etoposide, and teniposide. Other proliferative cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; and Panda (1996) J. Biol. Chem. 271:29807-29812.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used include, but are not limited to, hormones and steroids (including synthetic analogs): 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminoglutethimide, estramustine, medroxyprogesteroneacetate, leuprolide, flutamide, toremifene, zoladex.

Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

A variety of cancers may be treated according to this invention including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; and other tumors including melanoma, xenoderma pigmentosum, keratoactanthoma, seminoma, thyroid follicular cancer, teratocarcinoma, and cancers of the gastrointestinal tract or the abdominopelvic cavity.

b. Treatment of Side Effects from Cancer Treatment

This invention also relates to a method of treating a mammal suffering from damage to normal tissue attributable to treatment of a constitutively active NF-κB cancer, comprising administering to the mammal a composition comprising a therapeutically effective amount of an agent that induces NF-κB activity. The agent that induces NF-κB activity may be administered in combination with a cancer treatment described above.

c. Modulation of Cell Aging

This invention also relates to a method of modulating cell aging in a mammal, comprising administering to the mammal a therapeutically effective amount of an agent that induces NF-κB activity. The agent that induces NF-κB activity may be administered in combination with other treatments.

d. Treatment of Stress

This invention also relates to a method of treating a mammal suffering from damage to normal tissue attributable to stress, comprising administering to the mammal a composition comprising a therapeutically effective amount of an agent that induces NF-κB activity. The agent that induces NF-κB activity may be administered in combination with other treatments. The stress may be attributable to any source including, but not limited to, radiation, wounding, poisoning, infection, and temperature shock.

e. Radiation

This invention is also related to the protection of cells from the effects of exposure to radiation. Injury and death of normal cells from ionizing radiation is a combination of direct radiation-induced damage to the exposed cells and an active genetically programmed cell reaction to radiation-induced stress resulting in suicidal death or apoptosis. Apoptosis plays a key role in massive cell loss occurring in several radiosensitive organs (i.e., hematopoietic and immune systems, epithelium of digestive tract, etc.), the failure of which determines general radiosensitivity of the organism.

Exposure to ionizing radiation (IR) may be short- or long-term, it may be applied as a single or multiple doses, to the whole body or locally. Thus, nuclear accidents or military attacks may involve exposure to a single high dose of whole body irradiation (sometimes followed by a long-term poisoning with radioactive isotopes). The same is true (with strict control of the applied dose) for pretreatment of patients for bone marrow transplantation when it is necessary to prepare hematopoietic organs for donor's bone marrow by "cleaning" them from the host blood precursors. Cancer treatment may involve multiple doses of local irradiation that greatly exceeds lethal dose if it were applied as a total body irradiation. Poisoning or treatment with radioactive isotopes results in a long-term local exposure to radiation of targeted organs (e.g., thyroid gland in the case of inhalation of 125I). Finally, there are many physical forms of ionizing radiation differing significantly in the severity of biological effects.

At the molecular and cellular level, radiation particles are able to produce breakage and cross-linking in the DNA, proteins, cell membranes and other macromolecular structures. Ionizing radiation also induces the secondary damage to the cellular components by giving rise to the free radicals and reactive oxygen species (ROS). Multiple repair systems counteract this damage, such as several DNA repair pathways that restore the integrity and fidelity of the DNA, and antioxidant chemicals and enzymes that scavenge the free radicals and ROS and reduce the oxidized proteins and lipids. Cellular checkpoint systems detect the DNA defects and delay cell cycle progression until damage is repaired or decision to commit cell to growth arrest or programmed cell death (apoptosis) is reached Radiation can cause damage to mammalian organism ranging from mild mutagenic and carcinogenic effects of low doses to almost instant killing by high doses. Overall radiosensitivity of the organism is determined by pathological alterations developed in several sensitive tissues that include hematopoietic system, reproductive system and different epithelia with high rate of cell turnover.

The acute pathological outcome of gamma irradiation leading to death is different for different doses and is determined by the failure of certain organs that define the threshold of the organism's sensitivity to each particular dose. Thus, lethality at lower doses occurs from bone marrow aplasia, while moderate doses kill faster by inducing gastrointestinal (GI) syndrome. Very high doses of radiation can cause almost instant death eliciting neuronal degeneration.

Organisms that survive a period of acute toxicity of radiation can suffer from long-term remote consequences that include radiation-induced carcinogenesis and fibrosis developing in exposed organs (e.g., kidney, liver or lungs) months and years after irradiation.

Cellular DNA is the major target of IR causing a variety of types of DNA damage (genotoxic stress) by direct and indirect (free radical-based) mechanisms. All organisms maintain DNA repair system capable of effective recovery of radiation-damaged DNA; however, errors in the DNA repair process may lead to mutations.

Tumors are generally more sensitive to gamma radiation and can be treated with multiple local doses that cause relatively low damage to normal tissue. Nevertheless, in some instances, damage of normal tissues is a limiting factor in application of gamma radiation for cancer treatment. The use of gamma-irradiation during cancer therapy by conventional, three-dimensional conformal or even more focused Beam-Cath delivery has also dose-limiting toxicities caused by cumulative effect of irradiation and inducing the damage of the stem cells of rapidly renewing normal tissues, such as bone marrow and gastrointestinal (GI) tract.

At high doses, radiation-induced lethality is associated with so-called hematopoietic and gastrointestinal radiation syndromes. Hematopoietic syndrome is characterized by loss of hematopoietic cells and their progenitors making it impossible to regenerate blood and lymphoid system. The death usually occurs as a consequence of infection (result of immunosuppression), hemorrhage and/or anemia. GI syndrome is caused by massive cell death in the intestinal epithelium, predominantly in the small intestine, followed by disintegration of intestinal wall and death from bacteriemia and sepsis.

Hematopoietic syndrome usually prevails at the lower doses of radiation and leads to a more delayed death than GI syndrome.

In the past, radioprotectants were typically antioxidants—both synthetic and natural. More recently, cytokines and growth factors have been added to the list of radioprotectants. The mechanism of their radioprotection is considered to be a result of a facilitating effect on regeneration of sensitive tissues. There is no clear functional distinction between both groups of radioprotectants, however, since some cytokines induce the expression of cellular antioxidant proteins, such as manganese superoxide dismutase (MnSOD) and metallothionein.

The measure of protection for a particular agent is expressed by dose modification factor (DMF or DRF). DMF is determined by irradiating the radioprotector treated subject and untreated control subjects with a range of radiation doses and then comparing the survival or some other endpoints. DMF is commonly calculated for 30-day survival (LD50/30 drug-treated divided by LD50/30 vehicle-treated) and quantifies the protection of the hematopoietic system. In order to estimate gastrointestinal system protection, LD50 and DMF are calculated for 6- or 7-day survival. DMF values provided herein are 30-day unless indicated otherwise.

As shown below, inducers of NF-κB possess strong pro-survival activity at the cellular level and on the organism as a whole. In response to super-lethal doses of radiation, inducers of NF-κB inhibit both gastrointestinal and hematopoietic syndromes, which are the major causes of death from acute radiation exposure. As a result of these properties, inducers of NF-κB may be used to treat the effects of natural radiation events and nuclear accidents. Moreover, since inducers of NF-κB acts through mechanisms different from all presently known radioprotectants, they can be used in combination with other radioprotectants, thereby, dramatically increasing the scale of protection from ionizing radiation.

As opposed to conventional radioprotective agents (e.g., scavengers of free radicals), inducers of NF-κB activity may not reduce primary radiation-mediated damage but may act against secondary events involving active cell reaction to primary damage, therefore complementing the existing lines of defense. Pifithrin-alpha, a pharmacological inhibitor of p53 (a key mediator of radiation response in mammalian cells), is an example of this new class of radioprotectants. However, the activity of p53 inhibitors is limited to protection of the hematopoietic system and has no protective effect in digestive tract (gastrointestinal syndrome), therefore, reducing therapeutic value of these compounds. Anti-apoptotic pharmaceuticals with broader range of activity are desperately needed.

Inducers of NF-κB may be used as a radioprotective agent to extend the range of tolerable radiation doses by increasing radioresistance beyond the levels achievable by currently available measures (shielding and application of existing bio-protective agents) and drastically increase the chances of survival, for example, in case of onboard nuclear accidents or large-scale solar particle events during the spaceflight. With an approximate DMF (30-day survival) greater than 1.5, the NF-κB inducer flagellin is more effective than any currently reported natural compound.

Inducers of NF-κB may be also useful for treating irreplaceable cell loss caused by low-dose irradiation, for example, in the central nervous system and reproductive organs. Inducers of NF-κB may also be used during cancer chemotherapy to treat the side effects associated with chemotherapy, including alopecia.

In one embodiment, a mammal is treated for exposure to radiation, comprising administering to the mammal a composition comprising a therapeutically effective amount of a composition comprising an inducer of NF-κB. The composition comprising an inducer of NF-κB may be administered in combination with one or more radioprotectants. The one or more radioprotectants may be any agent that treats the effects of radiation exposure including, but not limited to, antioxidants, free radical scavengers and cytokines.

Inducers of NF-κB may inhibit radiation-induced programmed cell death in response to damage in DNA and other cellular structures; however, inducers of NF-κB may not deal with damage at the cellular level and may not prevent mutations. Free radicals and reactive oxygen species (ROS) are the major cause of mutations and other intracellular damage. Antioxidants and free radical scavengers are effective at preventing damage by free radicals. The combination of an inducer of NF-κB and an antioxidant or free radical scavenger may result in less extensive injury, higher survival, and improved health for exposure. Antioxidants and free radical scavengers that may be used in the practice of the invention include, but are not limited to, thiols, such as cysteine, cysteamine, glutathione and bilirubin; amifostine (WR-2721); vitamin A; vitamin C; vitamin E; and flavonoids such as orientin and vicenin derived from Indian holy basil (*Ocimum sanctum*).

Inducers of NF-κB may also be administered in combination with a number of cytokines and growth factors that confer radioprotection by replenishing and/or protecting the radiosensitive stem cell populations. Radioprotection with minimal side effects may be achieved by the use of stem cell factor (SCF, c-kit ligand), Flt-3 ligand, and interleukin-1 fragment IL-1b-rd. Protection may be achieved through induction of proliferation of stem cells (all mentioned cytokines), and prevention of their apoptosis (SCF). The treatment allows accumulation of leukocytes and their precursors prior to irradiation thus enabling quicker reconstitution of the immune system after irradiation. SCF efficiently rescues lethally irradiated mice with DMF in the range of 1.3-1.35 and is also effective against gastrointestinal syndrome. Flt-3 ligand also provides strong protection in mice (70-80% 30-day survival at LD100/30, equivalent to DMF>1.2) and rabbits.

In addition, combinations of cytokines may provide enhanced radioprotection, such as: TPO combined with interleukin 4 (IL-4) and/or interleukin 11 (IL-11); GM-CSF combined with IL-3; G-CSF combined with Flt-3 ligand; 4F combination: SCF, Flt-3 ligand, TPO and IL-3; and 5F combination: 4F with addition of SDF-1.

In addition, gastrointestinal radioprotectors may be used, including transforming growth factor beta3 (TGFb3), interleukin 11 (IL-11), and mentioned keratinocyte growth factor (KGF). While these radioprotectors also protect the intestine, they are likely to synergize with flagellin or flagellin related polypeptides since the results below show that flagellin and flagellin related polypeptides protect endothelium, while these gastrointestinal radioprotectors protect epithelium of GI tract.

Several factors, while not cytokines by nature, stimulate the proliferation of immunocytes and may be used in combination with inducers of NF-κB. For example, 5-AED (5-androstenediol) is a steroid that stimulates the expression of cytokines and increases resistance to bacterial and viral infections. A subcutaneous injection of 5-AED in mice 24 h before irradiation improved survival with DMF=1.26. Synthetic compounds, such as ammonium tri-chloro(dioxoethylene-O, O'-) tellurate (AS-101), may also be used to induce secretion of numerous cytokines and for combination with inducers of NF-κB. Additional radioprotectors include, growth hormone (GH), thrombopoietin (TPO), interleukin 3 (IL-3), granulocyte-macrophage colony-stimulating factor (GM-CSF), granulocyte colony-stimulating factor (G-CSF), and stromal derived factor-1 (SDF-1).

Growth factors and cytokines may also be used to provide protection against gastrointestinal syndrome. Keratinocyte growth factor (KGF) promotes proliferation and differentiation in the intestinal mucosa, and increases the post-irradiation cell survival in the intestinal crypts. Hematopoietic cytokine and radioprotectant SCF may also increase intestinal stem cell survival and associated short-term organism survival.

Inducers of NF-κB may offer protection against both gastrointestinal (GI) and hematopoietic syndromes. Since mice exposed to 15 Gy of whole-body lethal irradiation die mostly from GI syndrome, a composition comprising an inducer of NF-κB and one or more inhibitors of GI syndrome may be more effective. Inhibitors of GI syndrome that may be used in the practice of the invention include, but are not limited to, cytokines such as SCF and KGF.

The composition comprising an inducer of NF-κB may be administered at any point prior to exposure to radiation including, but not limited to, about 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, or 1 hr prior to exposure. The composition comprising an inducer of NF-κB may be administered at any point after exposure to radiation including, but not limited to, about 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, or 48 hr after exposure to radiation.

f. Sepsis

This invention also relates to a method of preventing sepsis in a mammal comprising administering to the mammal a composition comprising a therapeutically effective amount of an agent that induces NF-κB activity. The agent that induces NF-κB activity may be administered in combination with other treatments.

Viral or bacterial infections may stimulate the innate immune system through Toll-like receptor (TLR) ligands. Macrophages may be protected and/or stimulated by flagellin and flagellin related polypeptides due to the presence of TLR5 on their surface. For example, a crucial step in the development of an anthrax infection is death of macrophages killed from within by *B. anthracis*. Protection of intestinal endothelium against various stresses using flagellin and flagellin related polypeptides may prevent GI cell death and also may prevent penetration of the GI wall by infectious agent, thereby preventing GI bleeding caused by infections such as Ebola. Other hemorrhagic viral infections may also be prevented by rescue of endothelium and gastrointestinal epithelium.

3. AGENT

This invention also relates to an agent that induces NF-κB activity. The agent may be an artificially synthesized compound or a naturally occurring compound. The agent may be a low molecular weight compound, polypeptide or peptide, or a fragment, analog, homolog, variant or derivative thereof.

The agent may also be an NF-κB inducing cytokine including, but not limited to, IL2, IL6, TNF and TGFβ. The agent may also be a prostaglandin. The agent may also be a growth factor including, but not limited to, KGF and PDGF. The agent may also be an antibody that induces NF-κB activity.

a. Flagellin

In one embodiment, the agent that induces NF-κB activity is flagellin. As shown in the Examples below, flagellin and flagellin related polypeptides possess strong pro-survival activity at the cellular level and for the organism as a whole. Interestingly, flagellin also stimulates natural killer (NK) cells and T-lymphocytes, which are the major components of anti-tumor immunity (Tsujimoto H, et. al., *J Leukoc Biol*. 2005 October; 78(4):888-97; Caron G., et. al., *J Immunol*. 2005 Aug. 1; 175(3):1551-7; Honko A N & Mizel S B, *Immunol Res*. 2005; 33(1):83-101). As a result, flagellin may be used as a radioprotectant in cancer treatments.

The present invention is also related to flagellin related polypeptides, such as those polypeptides described herein. As used herein, the term "flagellin" is intended to mean a flagellin or flagellin-related polypeptide from any source, including a variety of Gram-positive and Gram-negative bacterial species. The amino acid sequences of flagellin from 23 bacterial species are depicted in FIG. 7 of U.S. Patent Publication No. 2003/0044429, the contents of which are incorporated herein by reference. The nucleotide sequences encoding the flagellin polypeptides listed in FIG. 7 of U.S. 2003/0044429 are publicly available at sources including the NCBI Genbank database.

Figure 9:
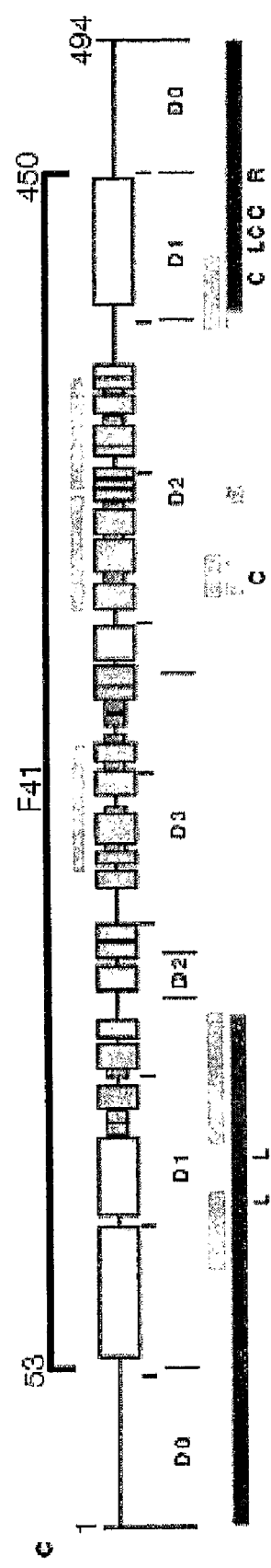
FIG. 9 shows the domain structure of bacterial flagellin. The Ca backbone trace, hydrophobic core distribution and structural information of F41. Four distinct hydrophobic cores that define domains D1, D2a, D2b and D3. All the hydrophobic side-chain atoms are displayed with the Ca backbone. Side-chain atoms are color coded: Ala, yellow; Leu, Ile or Val, orange; Phe and Tyr, purple (carbon atoms) and red (oxygen atoms). c, Position and region of various structural features in the amino-acid sequence of flagellin. Shown are, from top to bottom: the F41 fragment in blue; three b-folium folds in brown; the secondary structure distribution with a-helix in yellow, b-structure in green, and b-turn in purple; tic mark at every 50th residue in blue; domains D0, D1, D2 and D3; the axial subunit contact region within the proto-element in cyan; the well-conserved amino-acid sequence in red and variable region in violet; point mutations in F41 that produce the elements of different supercoils. Letters at the bottom indicate the morphology of mutant elements: L (D107E, R124A, R124S, G426A), L-type straight; R (A449V), R-type straight; C (D313Y, A414V, A427V, N433D), curly33.

Flagellin is the major component of bacterial flagellum. Flagellin is composed of three domains (FIG. 9). Domain 1 (D1) and domain 2 (D2) are discontinuous and are formed when residues in the amino terminus and carboxy terminus are juxtaposed by the formation of a hairpin structure. The amino and carboxy terminus comprising the D1 and D2 domains is most conserved, whereas the middle hypervariable domain (D3) is highly variable. Studies with a recombinant protein containing the amino D1 and D2 and carboxyl D1 and D2 separated by an *Escherichia coli* hinge (ND1-2/ECH/CD2) indicate that D1 and D2 are bioactive when coupled to an ECH element. This chimera, but not the hinge alone, induced $I_\kappa B_\alpha$ degradation, NF-κB activation, and NO and IL-8 production in two intestinal epithelial cell lines. The non-conserved D3 domain is on the surface of the flagellar filament and contains the major antigenic epitopes. The potent proinflammatory activity of flagellin may reside in the highly conserved N and C D1 and D2 regions.

Flagellin induces NF-κB activity by binding to Toll-like receptor 5 (TLR5). The TLR family is composed of at least 10 members and is essential in innate immune defense against pathogens. The innate immune system recognizes pathogen-associated molecular patterns (PAMPs) that are conserved on microbial pathogens. TLR may recognize a conserved structure that is particular to bacterial flagellin. The conserved structure may be comprised of a large group of residues that are somewhat permissive to variation in amino acid content. Smith et al., Nat. Immunol. 4:1247-53 (2003) have identified 13 conserved amino acids in flagellin that are part of the conserved structure recognized by TLR5. The 13 conserved amino acids of flagellin important for TLR5 activity are shown in FIG. 24.

In a preferred embodiment, the flagellin is from a species of *Salmonlella*, a representative example of which is *S. dublin* (encoded by GenBank Accession Number M84972) (SEQ ID NO: 1). In another preferred embodiment, the flagellin related-polypeptide is a fragment, variant, analog, homolog, or derivative of SEQ ID NO: 1, or combination thereof, that binds to TLR5 and induces TLR5-mediated activity, such as activation of NF-κB activity. A fragment, variant, analog, homolog, or derivative of flagellin may be obtained by rational-based design based on the domain structure of Flagellin and the conserved structure recognized by TLR5.

In a more preferred embodiment, the fragment, variant, analog, homolog, or derivative of SEQ ID NO: 1, or combination thereof, comprises at least 10, 11, 12, or 13 of the 13 conserved amino acids shown in FIG. 24 (positions 89, 90, 91, 95, 98, 101, 115, 422, 423, 426, 431, 436 and 452). In another more preferred embodiment, the amino- and carboxy-terminus of the fragment, variant, analog, homolog, or derivative of SEQ ID NO: 1, or combination thereof, is at least 30%, 35%, 40%, 45%, 50%, 55%, 60%, 65%, 70%, 75%, 80%, 85%, 90%, 95%, 97%, 98%, or 99% identical to amino acids 1-174 and 418-505 of SEQ ID NO: 1. FIG. 26 lists the percentage identity of the amino- and carboxy-terminus of flagellin with known TLR-5 stimulating activity, as compared to SEQ ID NO: 1.

Flagellin homologs may be a flagellin polypeptide from any Gram-positive or Gram-negative bacterial species including, but not limited to, the flagellin polypeptides disclosed in U.S. Pat. Pub. 2003/000044429, the contents of which are incorporated herein, and the flagellin peptides corresponding to the Accession numbers listed in the BLAST results shown in FIG. 25. Also contemplated, are fragments, variants, analogs and derivatives of flagellin homologs.

Flagellin fragments may be portions of a flagellin polypeptide that stimulate TLR5 activity. Numerous deletional mutants of flagellin have been made that retain at least some TLR5 stimulating activity. In addition to the deletional mutants disclosed in the Examples herein, representative deletional mutants include translation of GenBank Accession number D13689 missing amino acids 185-306 or 444-492, and translation of GenBank Accession number M84973 missing amino acids 179-415. Also contemplated, are homologs, variants, analogs and derivatives of flagellin fragments.

Flagellin variants include flagellin polypeptides with transposon insertions and changes to the variable D3 domain. The D3 domain may be substituted in part, or in whole, with a hinge or linker polypeptide that allows the D1 and D2 domains to properly fold such that the variant stimulates TLR5 activity. Representative examples of variant hinge elements may be found in the *E. coli* MukB protein and SEQ ID NOS: 3 and 4. Also contemplated, are fragments, homologs, analogs and derivatives of flagellin variants.

4. COMPOSITION

This invention also relates to a composition comprising a therapeutically effective amount of an inducer of NF-κB. The composition may be a pharmaceutical composition, which may be produced using methods well known in the art. As described above, the composition comprising an inducer of NF-κB may be administered to a mammal for the treatment of conditions associated with apoptosis including, but not limited to, exposure to radiation, side effect from cancer treatments, stress and cell aging. The composition may also comprise additional agents including, but not limited to, a radioprotectant or a chemotherapeutic drug.

a. Administration

Compositions of this invention may be administered in any manner including, but not limited to, orally, parenterally, sublingually, transdermally, rectally, transmucosally, topically, via inhalation, via buccal administration, intrapleurally, or combinations thereof. Parenteral administration includes, but is not limited to, intravenous, intraarterial, intraperitoneal, subcutaneous, intramuscular, intrathecal, and intraarticular. Transmucosally administration includes, but is not limited to intranasal. For veterinary use, the composition may be administered as a suitably acceptable formulation in accordance with normal veterinary practice. The veterinarian can readily determine the dosing regimen and route of administration that is most appropriate for a particular animal.

The composition may be administered prior to, after or simultaneously with a stress that triggers apoptosis, or a combination thereof. The composition may be administered from about 1 hour to about 48 hours prior to or after exposure to a stress that triggers apoptosis.

b. Formulation

Compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

Compositions of this invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or nonaqueous vehicles including, but not limited to, creams, ointments, lotions, pastes, medicated plaster, patch, or membrane.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

c. Dosage

A therapeutically effective amount of the agent required for use in therapy varies with the nature of the condition being treated, the length of time that induction of NF-κB activity is desired, and the age and the condition of the patient, and is ultimately determined by the attendant physician. In general, however, doses employed for adult human treatment typically are in the range of 0.001 mg/kg to about 200 mg/kg per day. The dose may be about 1 μg/kg to about 100 μg/kg per day. The desired dose may be conveniently administered in a single dose, or as multiple doses administered at appropriate intervals, for example as two, three, four or more subdoses per day. Multiple doses often are desired, or required, because NF-κB activity in normal cells may be decreased once the agent is no longer administered.

The dosage of an inducer of NF-κB may be at any dosage including, but not limited to, about 1 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg or 1 mg/kg.

This invention has multiple aspects, illustrated by the following non-limiting examples.

EXAMPLE 1

P53 Deficiency Accelerated Development of GI Syndrome in Mice

Figure 1:
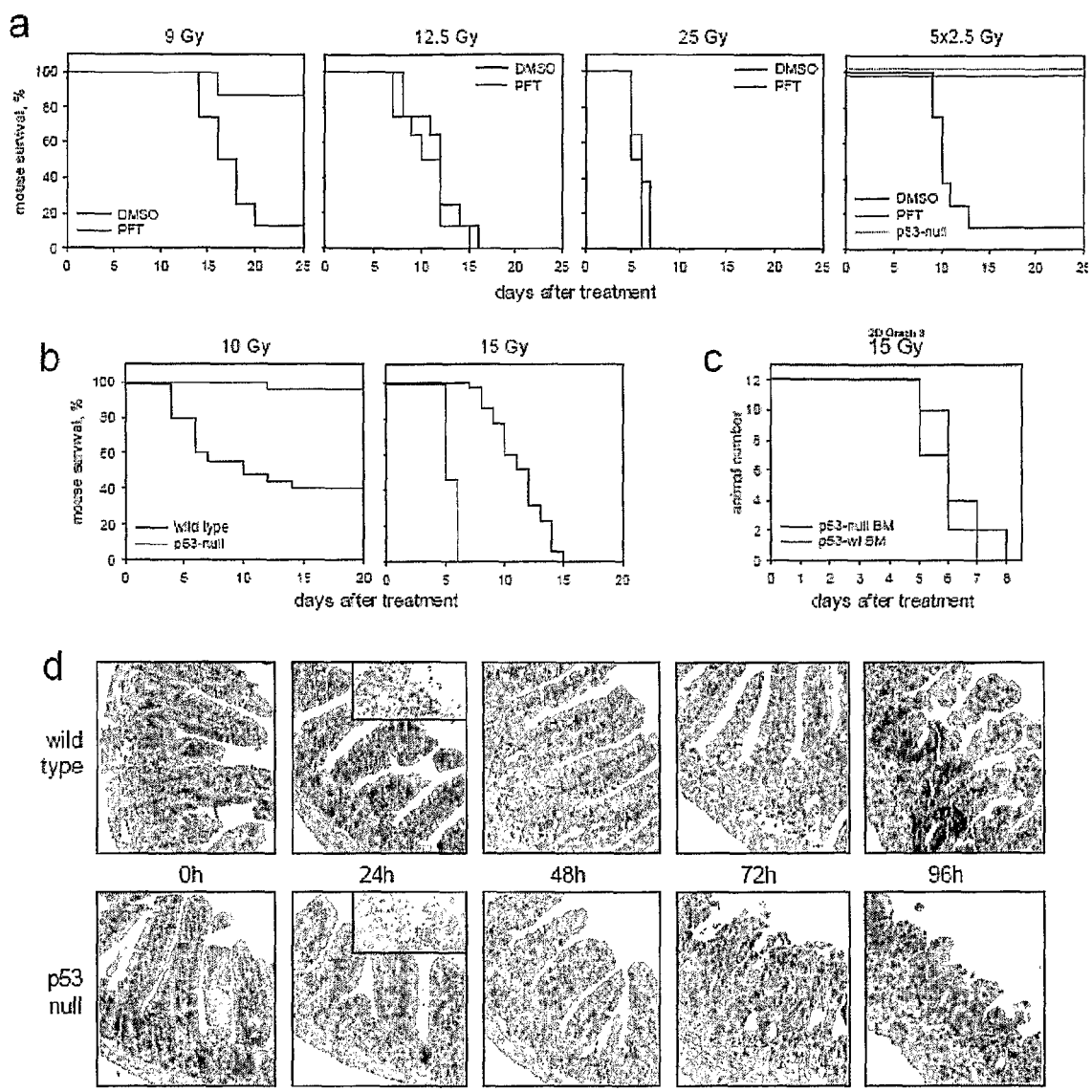
FIG. 1 demonstrates that p53 deficiency accelerated development of GI syndrome in mice. Panel A: I.P. injection of PFTα (10 mg/kg) protects C57Bl/6J mice (if not indicated otherwise, here and below 6-8 weeks old males were used) from a single 9 Gy dose of gamma radiation and a fractioned cumulative radiation dose 12.5 Gy (5×2.5 Gy). PFTα has no effect on survival of mice treated with single 12.5 and 25 Gy doses of IR: (results of representative experiments are shown; Shepherd 4000 Ci Cesium 137 source at a dose rate of 4 Gy per minute was used). Panel B: Wild-type and p53-null C57Bl/6J mice differ in their relative sensitivity to low (10 Gy) and high (15 Gy) doses of gamma radiation: wild-type mice were more sensitive to 10 Gy but more resistant to 15 Gy as compared to p53-null mice. Panel C: Mice treated with 11 Gy of total body gamma irradiation were injected 12 h later with 1.5×10$^7$ bone marrow cells from wild type or p53-null syngeneic C57Bl/6J mice. (This dose causes 100% lethality in nonreconstituted controls group of mice). Two months later, after complete recovery of hematopoiesis, animals were treated with 15 Gy of total body gamma radiation and showed no difference in death rates between the two groups differing in the p53 status of their bone marrow. Panel D: Comparison of dynamics of injury to small intestines of wild-type and p53-null mice at the indicated time points after 15 Gy of gamma radiation indicates accelerated damage in p53-null mice (haematoxylin-eosin stained paraffin sections; magnification ×125). 24 h panels include images of TUNEL staining if sections of crypts: massive apoptosis is evident in wild type but not in p53-deficient epithelium.
Figure 2:
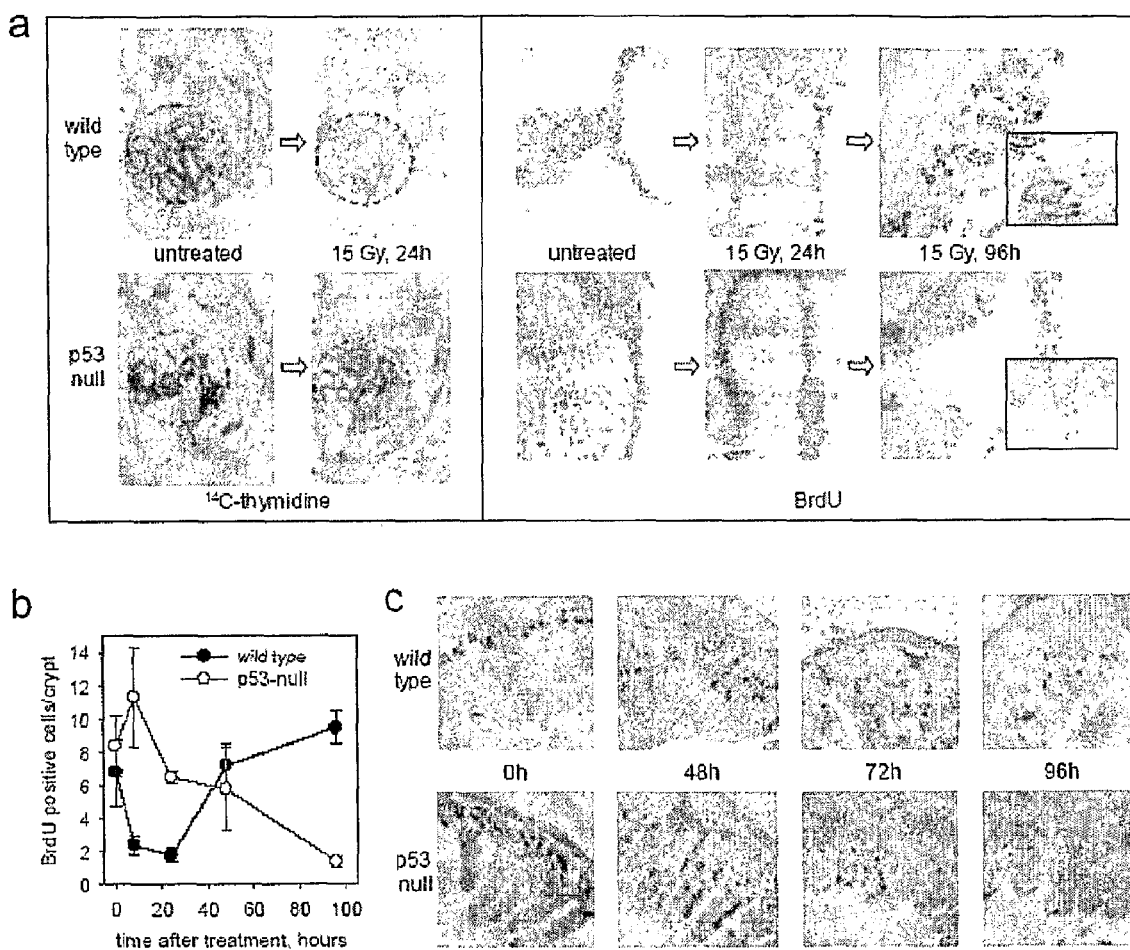
FIG. 2 demonstrates the dynamics of cell proliferation and survival in small intestine of wild type and p53-null mice. Panel A: Comparison of proliferation rates in intestines of wild-type and p53 null mice after treatment with IR. (Left) Autoradiographs of whole-body sections (1.7× magnification) of 4-week-old wild-type and p53 null mice injected intraperitoneally with $^{14}$C-thymidine (10 μCi per animal) treated or untreated with 15 Gy of gamma radiation. Arrows point at intestines. (Right) Comparison of BrdU incorporation in small intestine of wild-type and p53-null mice at different time points after 15 Gy of gamma radiation. BrdU (50 mg/kg) was injected 2 h before sacrificing mice followed by immunostaining. Fragments of 96 h panels are shown at higher magnification (×400). Panel B: Comparison of the number of BrdU positive cells/crypt in small intestine of wild-type and p53-null mice at different time points after 15 Gy of gamma radiation. Three animals were analyzed for each time point, five ileum cross sections were prepared from each animal and analyzed microscopically to estimate the number of crypts and villi. Numbers of BrdU-positive cells in the crypts were counted in 5 random fields under 200× magnification (100-30 crypts) and the average number of BrdU-positive cells was plotted. Panel C: Tracing the number and position of BrdU-labeled cells in small intestine of wild type and p53-null mice during different time points after 15 Gy of gamma radiation. BrdU was injected 30 min. before irradiation and mice were sacrificed at the indicated time points. Accelerated migration from crypts to villi followed by rapid elimination of labeled cells was observed in p53-null mice.
Figure 3:
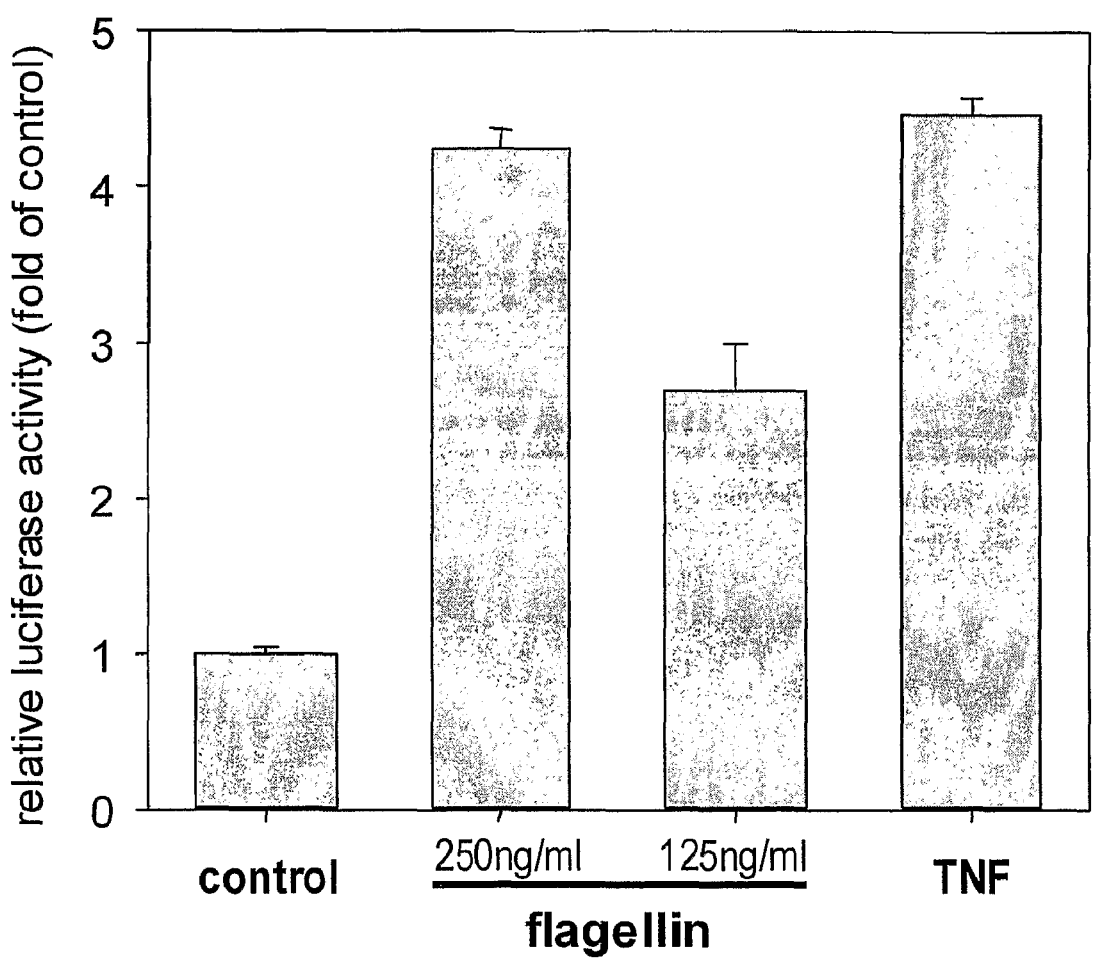
FIG. 3 demonstrates that recombinant flagellin is capable of NF-κB activation.

The primary cause of death from ionizing radiation (IR) of mammals depends on the radiation dose. At doses of up to 9-10 Gy, mice die 12-20 days later, primarily from lethal bone marrow depletion-hematopoietic (HP) syndrome. At this dose, irradiated mice can be rescued from lethality by bone marrow transplantation. Animals that receive >15 Gy die between 7-12 days after treatment (before hematopoietic syndrome can kill them) from complications of damage to the small intestine-gastrointestinal (G1) syndrome. In both cases of HP and GI syndromes, lethal damage of tissues starts from massive p53-dependent apoptosis. This observation allowed us earlier to suggest that p53 could be a determinant of radiation-induced death. Consistently, p53-deficient mice were resistant to doses of radiation that kill through HP syndrome, and lethality of wild type animals receiving 6-11 Gy of gamma radiation could be reduced by temporary pharmacological inhibition of p53 by the small molecule p53 inhibitor pifithrin-alpha (PFT) (Komarov et al 1999). Identification of p53 as a factor sensitizing tissues to genotoxic stress was further strengthened by demonstrating the p53 dependence of hair loss (alopecia) occurring as a result of experimental chemotherapy or radiation. Hence, based on previous observations, one would expect that p53 continues to play an important role in development of lethal GI syndrome after higher doses of IR. Surprisingly, p53-deficiency sensitizes mice to higher doses of IR causing lethal gastro-intestinal syndrome (FIG. 1). Continuous cell proliferation in the crypts of p53-deficient epithelium after IR correlates with accelerated death of damaged cells of crypt and rapid destruction of villi. p53 prolongs survival by inducing growth arrest in the crypts of small intestine thereby preserving integrity of the guts (FIG. 2). Thus, proapoptotic function of p53 promotes hematopoietic syndrome while its growth arrest function delays development of gastro-intestinal syndrome.

The dynamics of cell population in the small intestine have been analyzed in great detail. Cell proliferation in the epithelia of the gut is limited to the crypts where stem cells and early proliferating progenitors are located. After a couple of cell divisions, already differentiated descendants of crypt stem cells move up the villi to be shed at the villar tip. In the small intestine of the mouse, the entire "trip" of the cell (the proliferative compartment to the tip of the villus) normally takes between 3 and 5 days. Although reaction of the small intestine to gamma radiation has been well examined at a pathomorphological level, it still remains unclear what is the exact cause of GI lethality, including the primary event. Death may occur as a direct consequence of the damage of epithelial crypt cells and followed denudation of villi leading to fluid and electrolyte imbalance, bacteremia and endotoxemia. Besides inflammation and stromal responses, endothelial dysfunctions seem to be the important factors contributing to lethality. In summary, pharmacological suppression of p53 that was shown to be so effective as a method of protection from IR-induced HP syndrome, is useless (if not detrimental) against GI syndrome. Therefore, it is necessary to develop alternative approaches to radioprotection of epithelium of small intestine that will rely on another mechanism, such as, for example, activation of NF-κB and subsequent inhibition of cell death.

EXAMPLE 2

Flagellin Delays Mouse Death Caused by IR-Induced GI Syndrome

Figure 4:
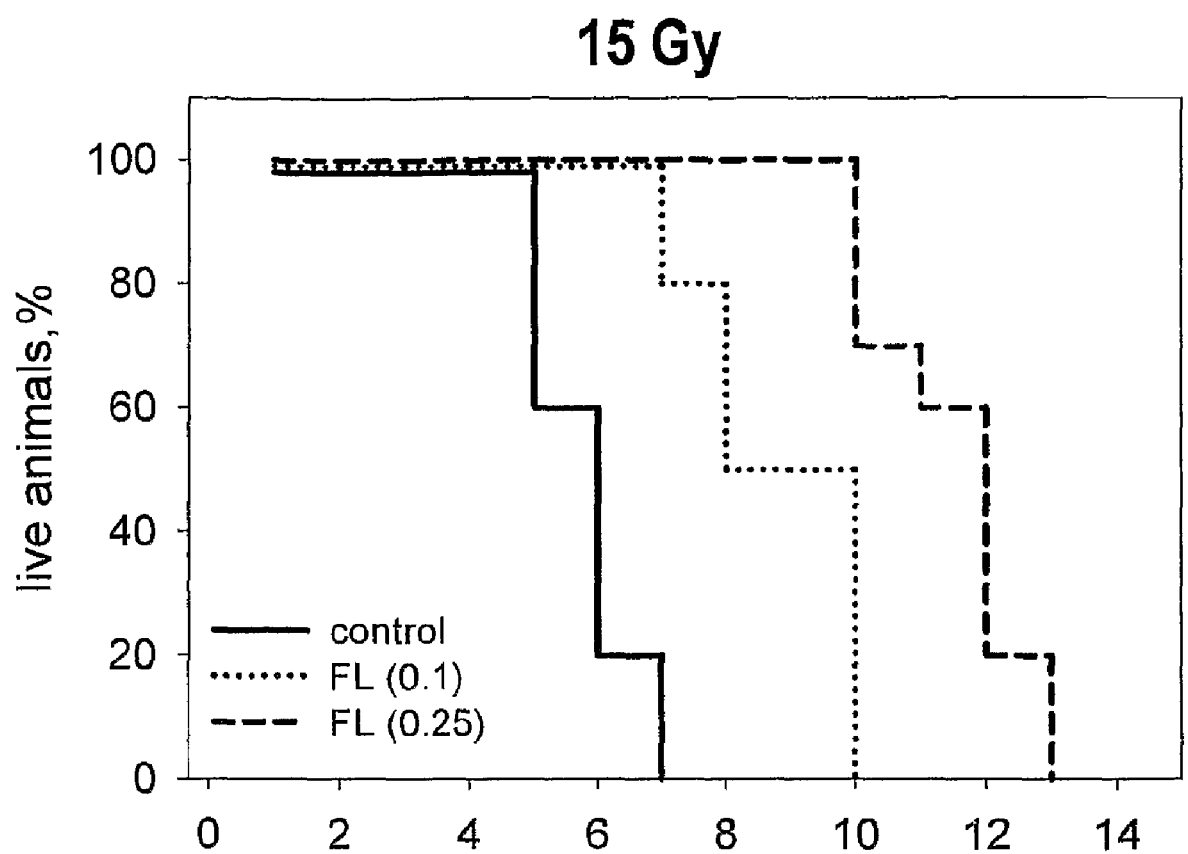
FIG. 4 shows a representative experiment testing the ability of flagellin to protect mice from radiation. C56BL6 mice (6 week old males, 10 animals per group) were injected i.v. with 2.0 μg (0.1 mg/kg) or 5 μg (0.25 mg/kg) of flagellin in PBS. Four hours later, mice were irradiated with 15 Gy and mouse survival was monitored daily.

Whole body irradiation of mice with 15 Gy gamma radiation caused death within 8 days from GI syndrome providing a conventional model of radiation induced damage of GI tract. To test whether flagellin was capable of protecting GI epithelium from IR, we tested the effect of i.v.-injected flagellin on the dynamics of mouse lethality after 15 Gy of radiation. We used a range of flagellin doses, all of which were significantly lower than the highest tolerable dose known from literature (300 μg/mouse). Irradiation was done 4 hours post treatment. The results of a representative experiment are shown in FIG. 4. As expected, control irradiated mice (that received PBS i.v.) died between 5 and 8 days post-treatment. Animals that received flagellin lived significantly longer; the extension of animal survival correlated with the dose of flagellin. Pathomorphological analysis of the small intestine on day 7 after irradiation revealed dramatic differences between flagellin-treated and control groups (FIG. 5). Intravenous, intraperitoneal and subcutaneous delivery of 0.2 mg/kg of flagellin followed by 13 Gy irradiation afforded similar degree of protection, leading to 85-90% 30-day survival of mice (data not shown). While not being bound by theory, flagellin may be a radioprotectant due to its activation of NF-κB, which presumably acts as an inhibitor of apoptotic death.

EXAMPLE 3

Flagellin Rescues Mice From Lethal IR-Induced Hematopoietic Syndrome

Figure 6:
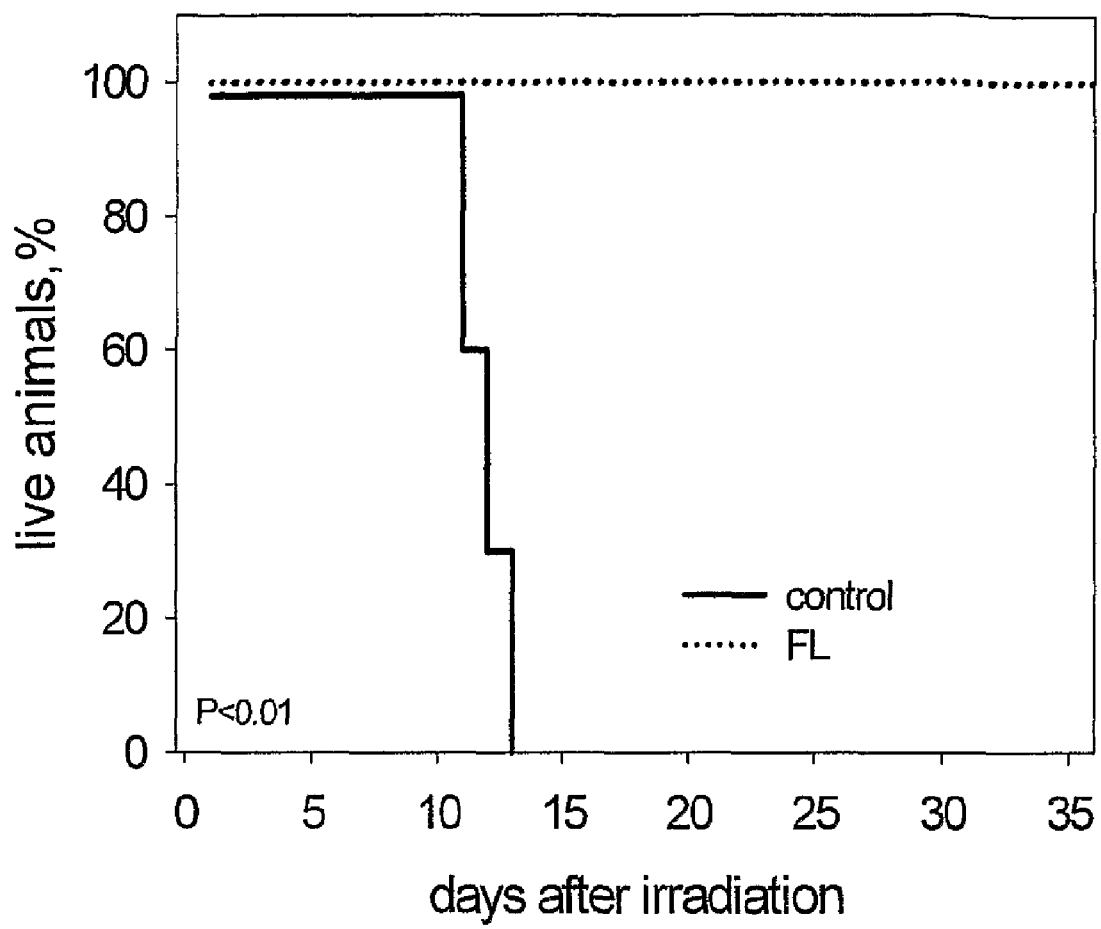
FIG. 6 shows the effect of flagellin on mouse sensitivity to 10 Gy of total body gamma radiation.

We next tested whether flagellin had an effect on mouse IR-induced death from BP syndrome that was experimentally induced by lower radiation doses (usually up to 11 Gy) that are incapable of causing lethal GI toxicity. The experiments were done similarly to the above-described ones (FIGS. 14 and 15), however, instead of 15Gy, mice received 10Gy, the dose that caused 100% killing in control group by day 13 (FIG. 6). Flagellin-treated group (5 μg/mouse) showed complete protection from this dose of IR surprisingly indicating that flagellin-mediated radioprotection acts not only against GI but also against HP IR-induced syndromes.

EXAMPLE 4

Time Dependence on the Protective Effect of Flagellin

Mice were next administered flagellin at different times prior to 13Gy of gamma irradiation. The results of one of such experiments is shown in FIG. 7. The obtained results show that flagellin is effective as a radioprotectant from 13Gy if injected 1-4 h before treatment.

In order to further estimate the dependence of radioprotective activity of flagellin on the time of treatment, mice were injected at several time points relative to the moment of gamma-irradiation. Experiments were performed essentially as explained above, using intraperitoneal injection of 5 μg/mouse (0.2 mg/kg) of full-length flagellin or, for control mice, 5 μg/mouse (0.2 mg/kg) of bacterial RNA polymerase. The experiments were performed using the NIH-Swiss mouse strain. The results show that flagellin provides ~90% survival after 13 Gy irradiation if injected at 1 or 2 hours before treatment (FIG. 7). Only −1 h graph is shown for clarity, however, both timepoints (−1 and −2 h) provide similar degree and dynamics of survival. The 4 h timepoint shows somewhat lower protection. Flagellin injected 24 hours before irradiation had no protective effect against 13 Gy induced death.

Interestingly, administration of flagellin 24 hours before 10 Gy gamma-irradiation provided 100% protection. While 13 Gy irradiation in mice primarily induces death from GI syndrome, 10 Gy-induced death is mostly mediated by hematopoietic syndrome. Accordingly, such long-term protection from 10 Gy irradiation may be mediated by enhanced proliferation or survival of hematopoietic stem cell induced by flagellin and/or long-living secondary cytokines.

EXAMPLE 5

Determination of $LD_{50/30}$, $LD_{50/7}$ and DMF for Flagellin

We next obtained an estimate of radiation dose-dependent protection for flagellin. As shown above (FIG. 7), treatment with flagellin was sufficient for 100% protection against 10 Gy gamma-irradiation (this dose causes death from hematopoietic syndrome) and 90% 30-day survival at 13 Gy (both hematopoietic and GI syndromes). Experiments were performed as described above, using flagellin 5 μg/mouse (0.2 mg/kg), intraperitoneally injected 1 h before irradiation.

Figure 8:
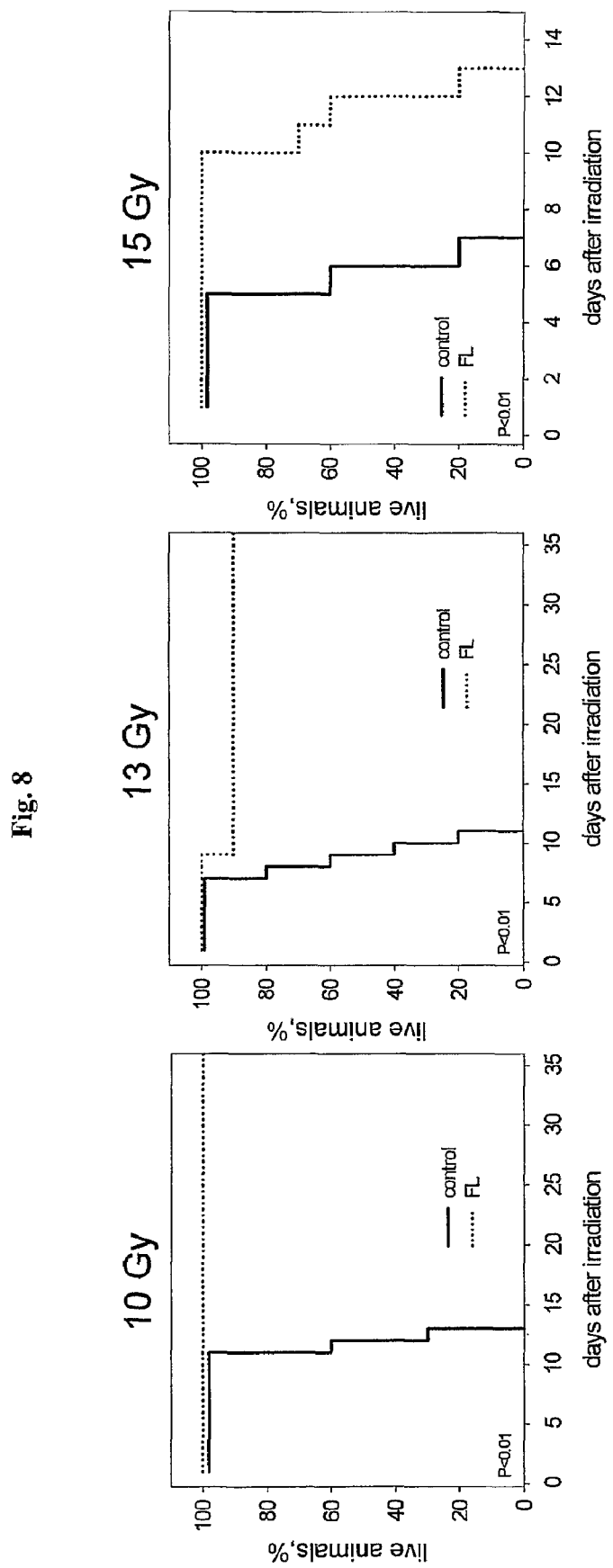
FIG. 8 shows the effect of flagellin on mouse sensitivity to 10, 13 and 15 Gy of total body gamma radiation.

At 15 Gy, however, 100% 7-day survival was followed by delayed death after 13 days (0% 30-day survival), while control group had fully succumbed to GI syndrome by day 7 (FIG. 8). The kinetics of the flagellin-treated group mortality after 15 Gy irradiation is reminiscent of such of control group at 10 Gy, hinting at death caused by hematopoietic syndrome. The results provide an estimate of flagellin $LD_{50/30}$ around 13.5-14 Gy and $DMF_{30}$ of about 1.75-1.8. This degree of radioprotection is significantly higher than any reported for a natural compound.

EXAMPLE 6

Rational Design and Cloning of Flagellin Fragments

Figure 10:
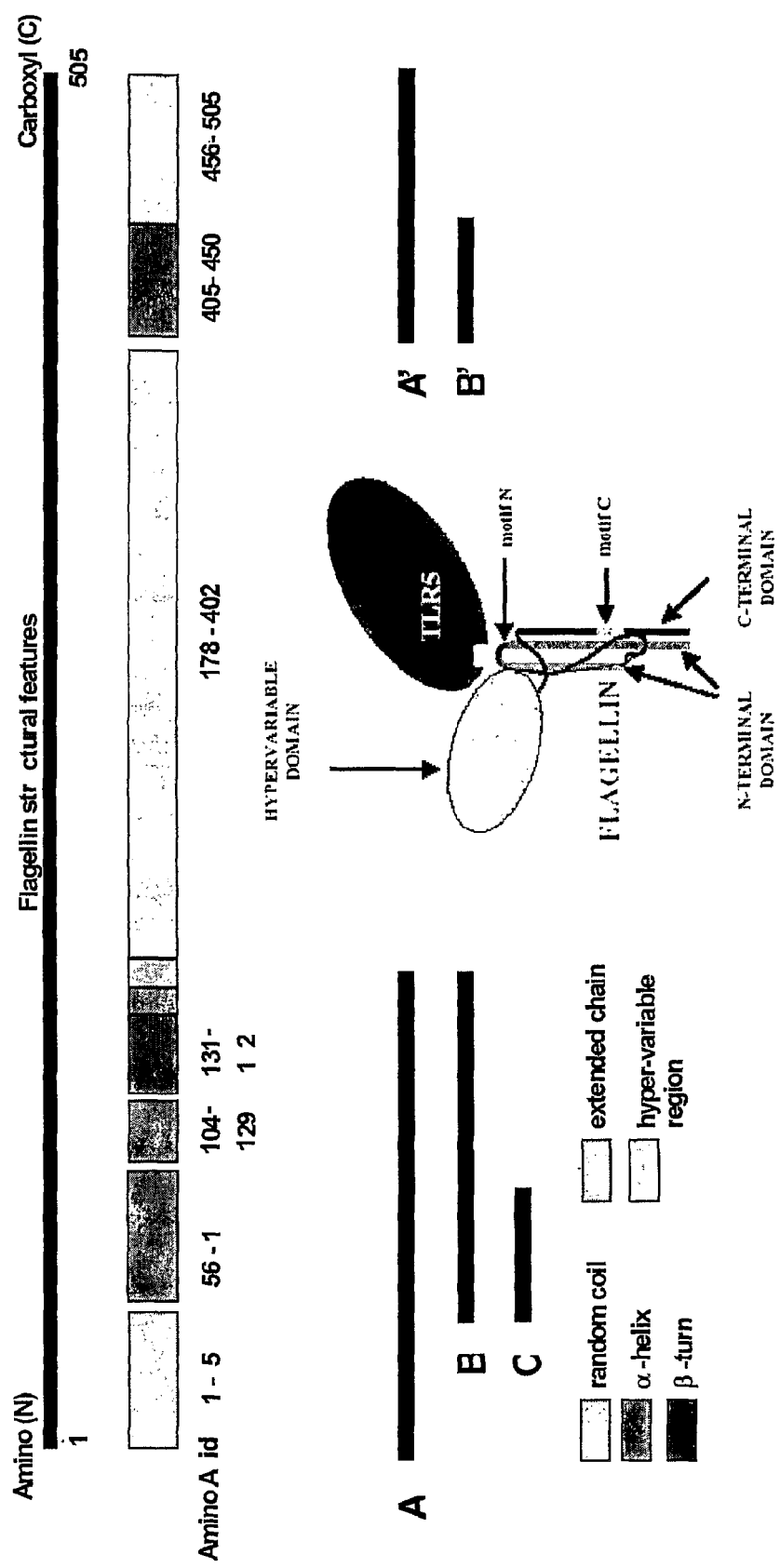
FIG. 10 shows a schematic of *Salmonella* flagellin domains, its fragments, and its interaction with TLR5. Dark bars denote regions of the flagellin gene used to construct fragments comprising A, B, C, A' and B'.

*Salmonella* flagellin, encoded by the FliC gene (SEQ ID NO: 2), is a strong activator of pro-survival NF-κB pathway. This is the most likely mechanism of its radioprotective action. Previous studies have shown that binding of flagellin to Toll-like receptor 5 (TLR5) on the cell surface is a necessary step that triggers activation of NF-κB. The domain structure of *Salmonella* flagellin is described in sufficient detail in the literature (FIG. 9). Moreover, previous structural studies of flagellin-TLR5 complex (FIG. 10) provide the ability to distinguish between domains that are essential or dispensable for binding and thus NF-κB activation. Protein minimization may provide reduced immune response after repeated administration of flagellin-related polypeptides. This may be achieved, in part, due to lower immunogenicity of low molecular weight proteins and smaller number of immunogenic epitopes available.

The domains needed for TLR5 binding may be located exclusively in the evolutionary conserved N- and C-terminal domains of bacterial flagellins. The hypervariable domain (amino acids 178-402) does not come into close contact with TLR5. As was demonstrated previously, replacement of this domain with a flexible linker peptide did not disrupt binding to TLR5. In addition, N-terminal and C-terminal coiled-coil polymerization domains (amino acids 1-55, 456-505) do not bind to TLR5 and likely are dispensable (see modified N and C termini B and B', respectively, as shown herein). Also, another fragment N-terminus lacking all domains but major N-terminal α-helix that actually binds TLR5 (amino acids 56-100) may be sufficient for binding.

Figure 11:
FIG. 11 shows soluble flagellin (FliC), and two fragments (AA' and BB") after fractionation by SDS-PAGE, with molecular weight markers listed to the left.

Accordingly, three types of N-termini (A, B, C) and two types of C-termini (A',B'), connected with a flexible linker (SEQ ID NOS: 3 and 4) taken from pGEX-KG cloning vector (SEQ ID NOS: 5 and 6) were combined into expression constructs to produce several possible flagellin fragments (Table 1). In addition, constructs representing separate N-termini (A, B, C) and glutathione-S-transferase (GST)-fusions of C-termini (GST-A', GST-B') were prepared. All constructs were cloned in the pRSETb bacterial expression vector and 6×His-tagged proteins were produced and purified for further experiments (FIG. 11).

TABLE 1

| Name | Structure | DNA | Protein |
|---|---|---|---|
| AA' | (1-177)-Linker-(402-505) | SEQ ID NO: 7 | SEQ ID NO: 8 |
| AB' | (1-177)-Linker-(402-450) | SEQ ID NO: 9 | SEQ ID NO: 10 |
| BA' | (56-177)-Linker-(402-505) | SEQ ID NO: 11 | SEQ ID NO: 12 |
| BB' | (56-177)-Linker-(402-450) | SEQ ID NO: 13 | SEQ ID NO: 14 |
| CA' | (56-100)-Linker-(402-505) | SEQ ID NO: 15 | SEQ ID NO: 16 |
| CB' | (56-100)-Linker-(402-450) | SEQ ID NO: 17 | SEQ ID NO: 18 |
| A | (1-177) | SEQ ID NO: 19 | SEQ ID NO: 20 |
| B | (56-177) | SEQ ID NO: 21 | SEQ ID NO: 22 |
| C | (56-100) | SEQ ID NO: 23 | SEQ ID NO: 24 |
| GST-A' | GST-Linker-(402-505) | SEQ ID NO: 25 | SEQ ID NO: 26 |
| GST-B' | GST-Linker-(402-450) | SEQ ID NO: 27 | SEQ ID NO: 28 |

EXAMPLE 7

Selection of Biologically Active Flagellin Fragments

Since the radioprotective activities of flagellin appear to be NF-κB dependent, we tested the ability of the flagellin fragments to induce NF-κB translocation to the nucleus and binding to its target sites in DNA. This was tested by electrophoretic mobility shift assay (EMSA) using nuclear extracts from flagellin- and fragment-treated A549 lung cancer cells and labeled synthetic NF-κB binding κB oligonucleotide.

Figure 12:
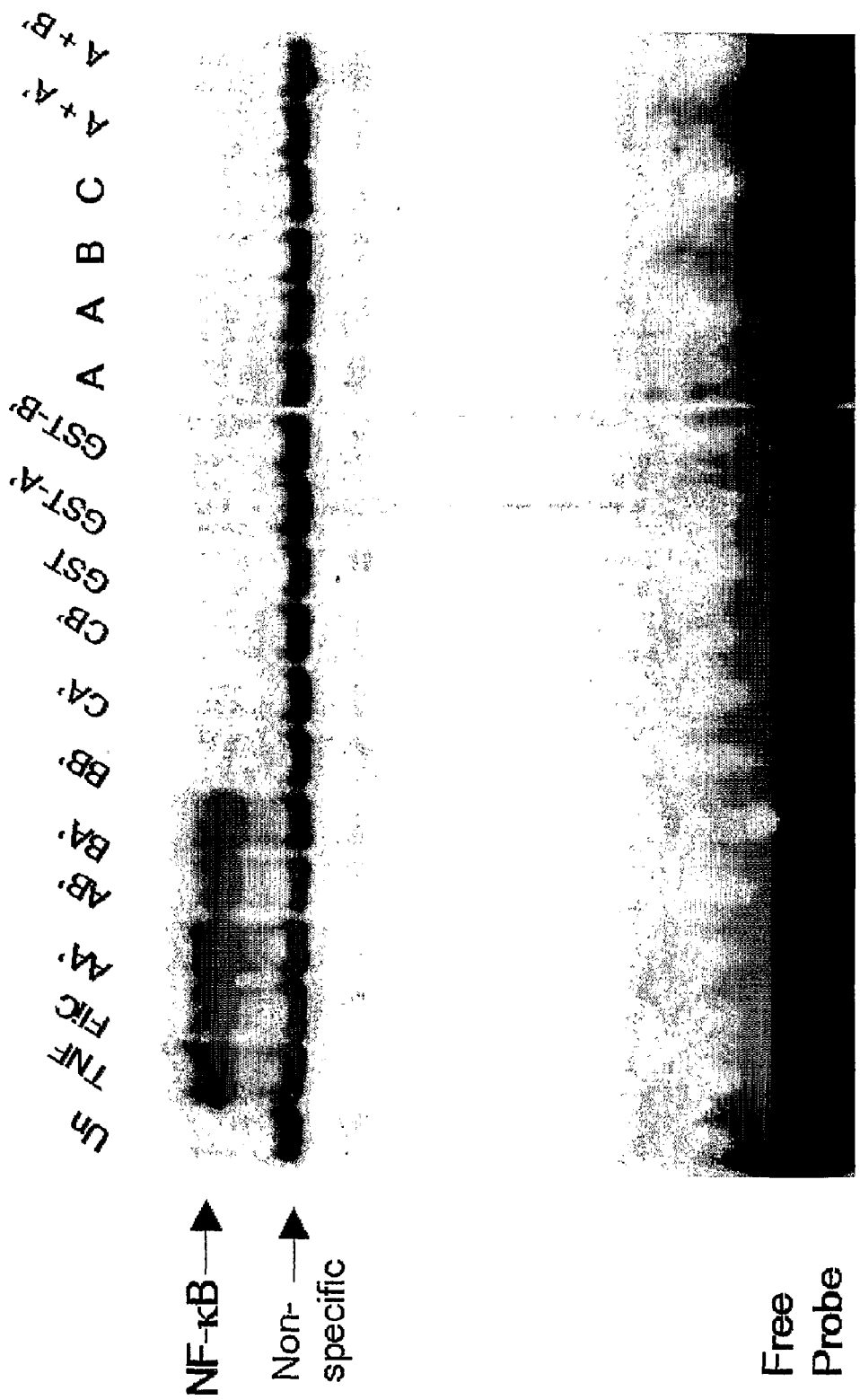
FIG. 12 shows induction of NF-κB nuclear translocation by *Salmonella* flagellin (FliC) and flagellin fragments.

Only flagellin itself and fragments AA', AB', and BA' were capable of inducing NF-κB translocation (FIG. 12). The level of translocation is comparable for flagellin and fragments AA', AB', and BA'. The hypervariable domain does not appear to be necessary for NF-κB translocation, while the presence of at least one polymerization domain, N- or C-terminal, is required. Mixtures of the N- and C-terminal fragments (A+A', A+B') were inactive.

Figure 13:
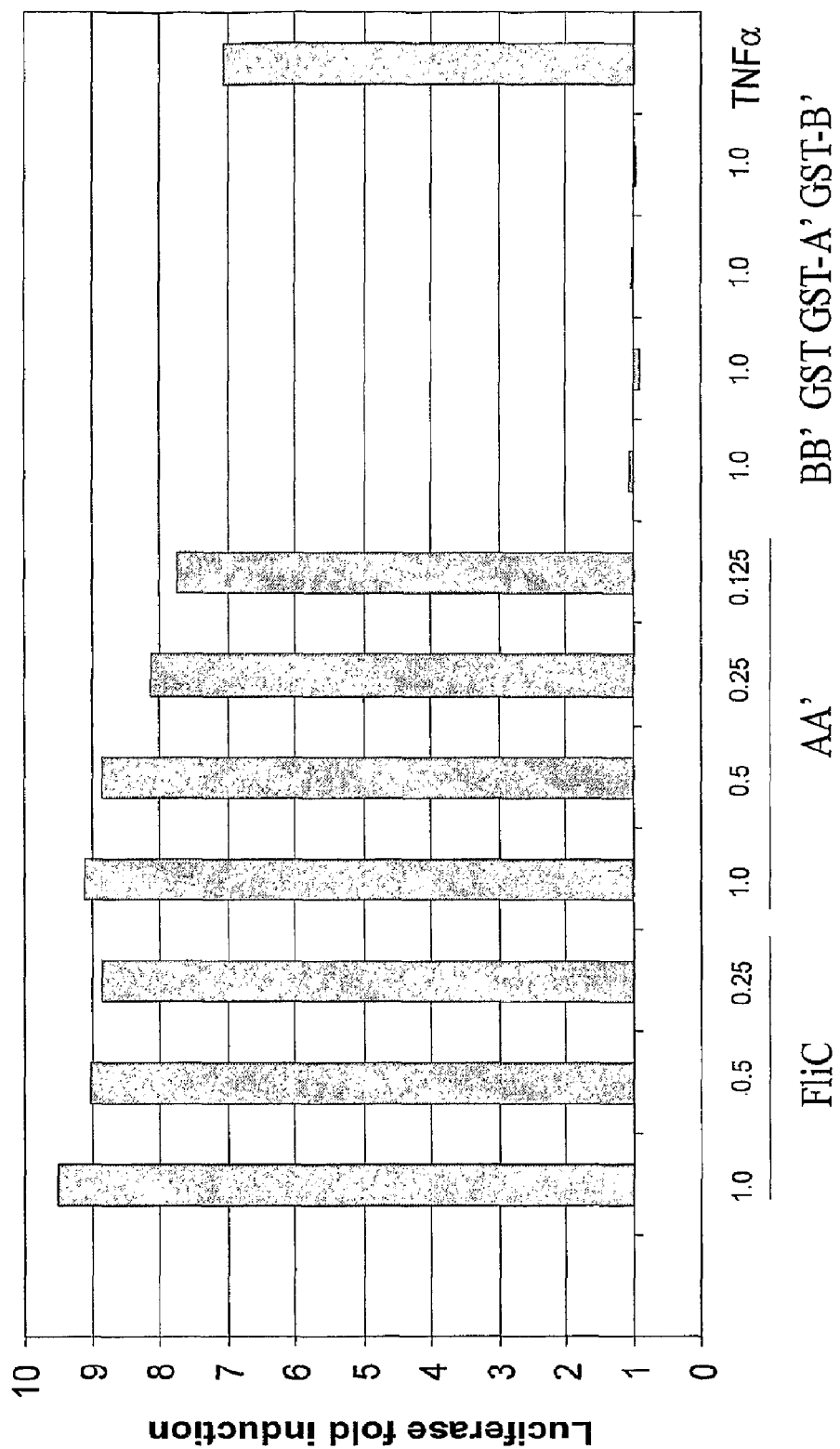
FIG. 13 shows activation of NF-κB-regulated luciferase reporter construct by flagellin and flagellin fragments in H116 cells. Concentrations of proteins are given in μg/ml.

While translocation of NF-κB to the nucleus is a crucial step in induction of NF-κB-regulated inhibitors of apoptosis, it is not sufficient in itself. To directly test the ability of selected fragments to induce expression of NF-κB-regulated genes, we performed reporter assay experiments. Flagellin and the AA', BB', A' and B' fragments were used for treatment of H116 human colon cancer cells carrying luciferase gene under a NF-κB-responsive promoter. The reporter construct contained three NF-κB-binding sites from the E-selectin promoter combined with a Hsp70 minimal promoter that is routinely used for the detection of NF-κB status of cells. Luciferase activity was measured in cell lysates six hours after addition of flagellin or its truncated fragments into the medium. TNF was used as positive control. The results of a representative experiment are shown in FIG. 13 and indicates that flagellin and fragment AA' are capable of NF-κB activation, whereas fragments BB', GST-A' and GST-B' are not.

EXAMPLE 8

Further Optimization of Flagellin Fragments

Figure 14:
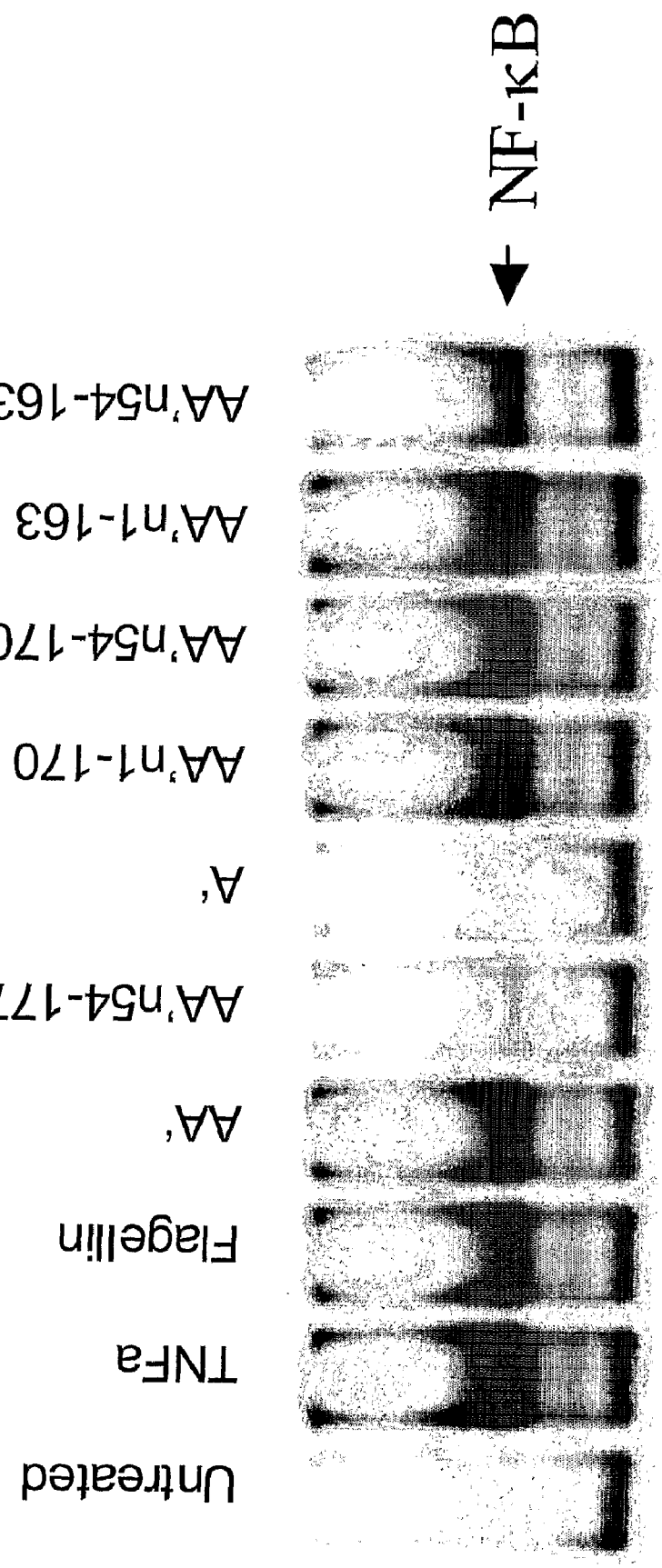
FIG. 14 shows NF-κB DNA binding in HT29 human colon cancer cells induced by flagellin and flagellin fragments.

We further minimized the AA' flagellin fragment by producing additional fragments through stepwise removal of peptide fragments from its N-terminal half (Table 2). Electrophoretic mobility shift assays were performed as described above using nuclear extracts from flagellin- and fragment-treated HT29 human colon cancer cells and labeled synthetic NF-κB binding KB oligonucleotide. NF-κB binding activity in HT29 cells was stimulated with TNFa (10 ng/ml), or flagellin fragments (1 mg/ml) for 15 min. As shown in FIG. 14, fragments AA'n1-170, AA'n54-170, AA'n1-163 and AA'n54-163 each induce NF-κB translocation, with levels comparable to that of flagellin for AA'n1-170, AA'n54-170 and AA'n1-163.

TABLE 2

| Name | Structure | DNA | Protein |
| --- | --- | --- | --- |
| AA'n54-177 | (54-177)-Linker-(402-505) | SEQ ID NO: 11 | SEQ ID NO: 12 |
| AA'n1-170 | (1-170)-Linker-(402-505) | SEQ ID NO: 29 | SEQ ID NO: 30 |
| AA'n54-170 | (54-170)-Linker-(402-505) | SEQ ID NO: 31 | SEQ ID NO: 32 |
| AA'n1-163 | (1-163)-Linker-(402-505) | SEQ ID NO: 33 | SEQ ID NO: 34 |
| AA'n54-163 | (54-163)-Linker-(402-505) | SEQ ID NO: 35 | SEQ ID NO: 36 |

Figure 15:
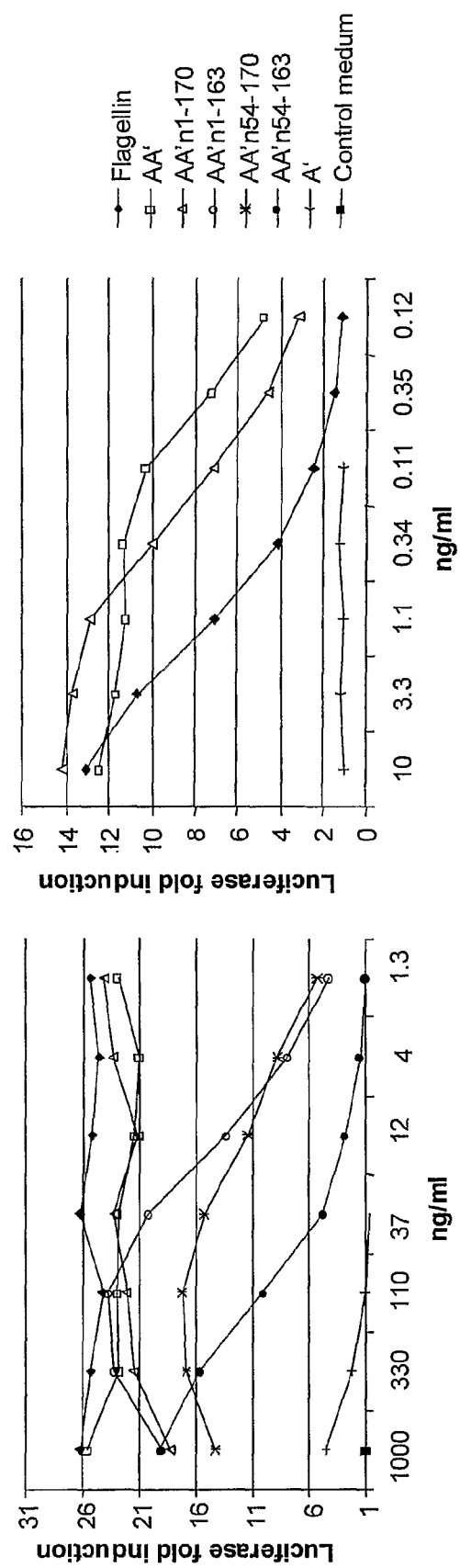
FIG. 15 shows the activation of a NF-κB reporter in HCT116 reporter cells by full-length flagellin and flagellin fragments.

In order to study the ability of the AA' fragments to directly activate NF-κB-regulated transcription, we performed reporter assay experiments as described above for a wide range of concentrations of flagellin, original AA' and AA'-derived fragments. As shown above, AA' and AA'n1-170 induce NF-κB-regulated transcription at the level comparable to such of flagellin over the studied range of concentrations (FIG. 15, left). AA' and AA'n1-170 are more active than flagellin in the very low concentration range (FIG. 15, right), possibly due to their reduced molecular weight. The results with fragment AA'n1-170 show that AA'-derived flagellin fragments may be made with a portion of the N-terminal domain removed without significant loss of activity and may be used as effective radioprotectors.

The above experiments (EMSA and reporter activation assay) were repeated with flagellin and AA' fragments subjected to 30 minutes boiling and renaturation before being applied to cells. The results were comparable to those obtained without boiling (data not shown). This shows that the observed differences in flagellin fragment activity may not be caused by changes in protein stability.

EXAMPLE 9

In Vivo Comparison of Radioprotective Properties of Flagellin and Flagellin Fragments As shown above, full-length flagellin provides protection from both hematopoietic and gastrointestinal syndromes. The radioprotective potential of flagellin fragments was similarly tested after gamma-irradiation with 11 Gy (dose that induces hematopoietic syndrome-associated mortality in mice) or 14 Gy (dose that causes death from GI syndrome). Mice (10 animals per group) were injected subcutaneously with 5.0 µg/mouse (0.2 mg/kg) of flagellin or its fragments, AA' or BB', and gamma-irradiated 1 hour later.

Figure 16:
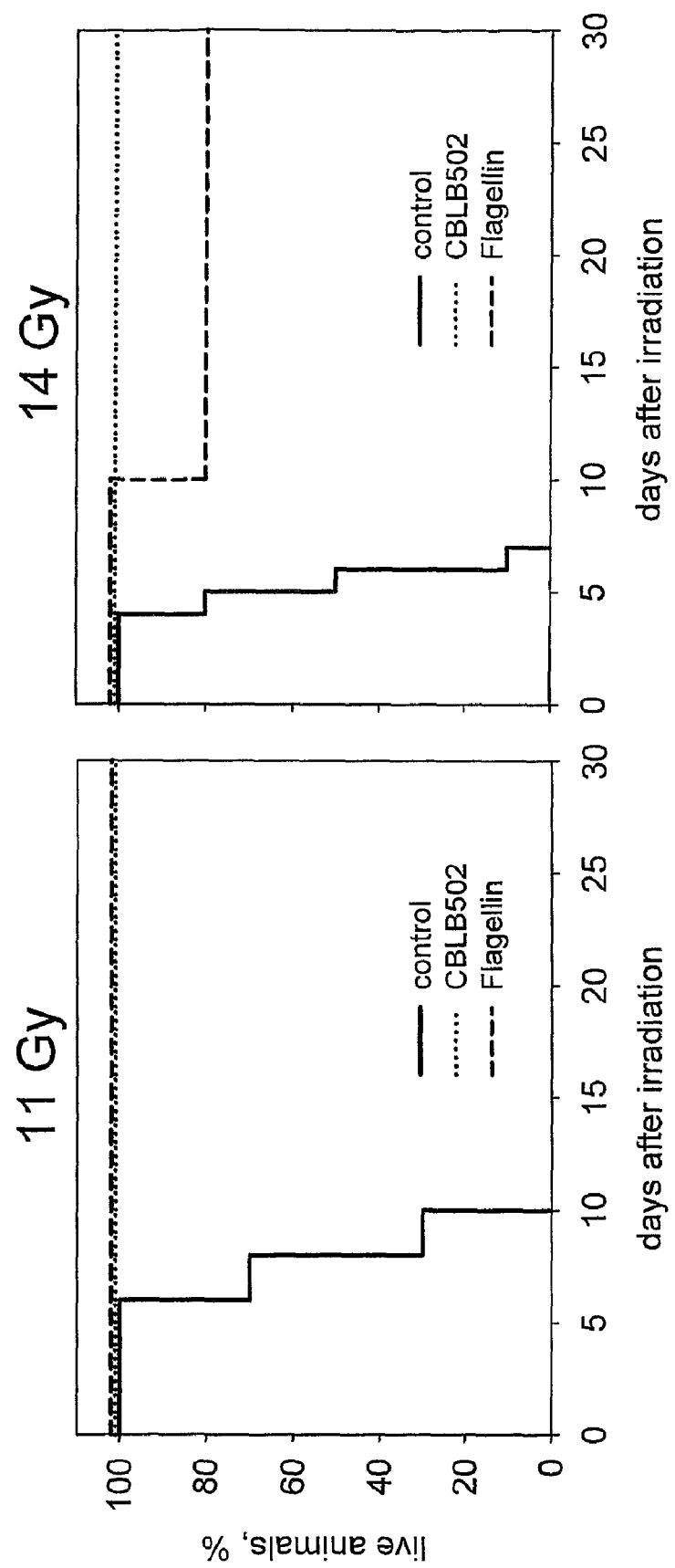
FIG. 16 shows a comparison of the radioprotective properties of flagellin (FliC) and fragments AA' and BB'.

The degree of radioprotection displayed by the AA' fragment is at least comparable to full-length flagellin (FIG. 16). Both the AA' fragment and full-length flagellin showed 100% 30-day survival for mice irradiated with 11 Gy and 14 Gy. Meanwhile, 0% of mice injected with the BB' fragment survived to 30 days. This is expected since the BB' fragment is incapable of inducing NF-κB in vitro. These results show that significant reduction in the size of flagellin (about 40% removed) may be achieved without a decrease in the degree of radioprotection. In addition, the ability to predict radioprotective potential from results of in vitro NF-κB activation is confirmed.

EXAMPLE 10

Identification of Cellular Targets of Flagellin-Mediated Radioprotection

Figure 17:
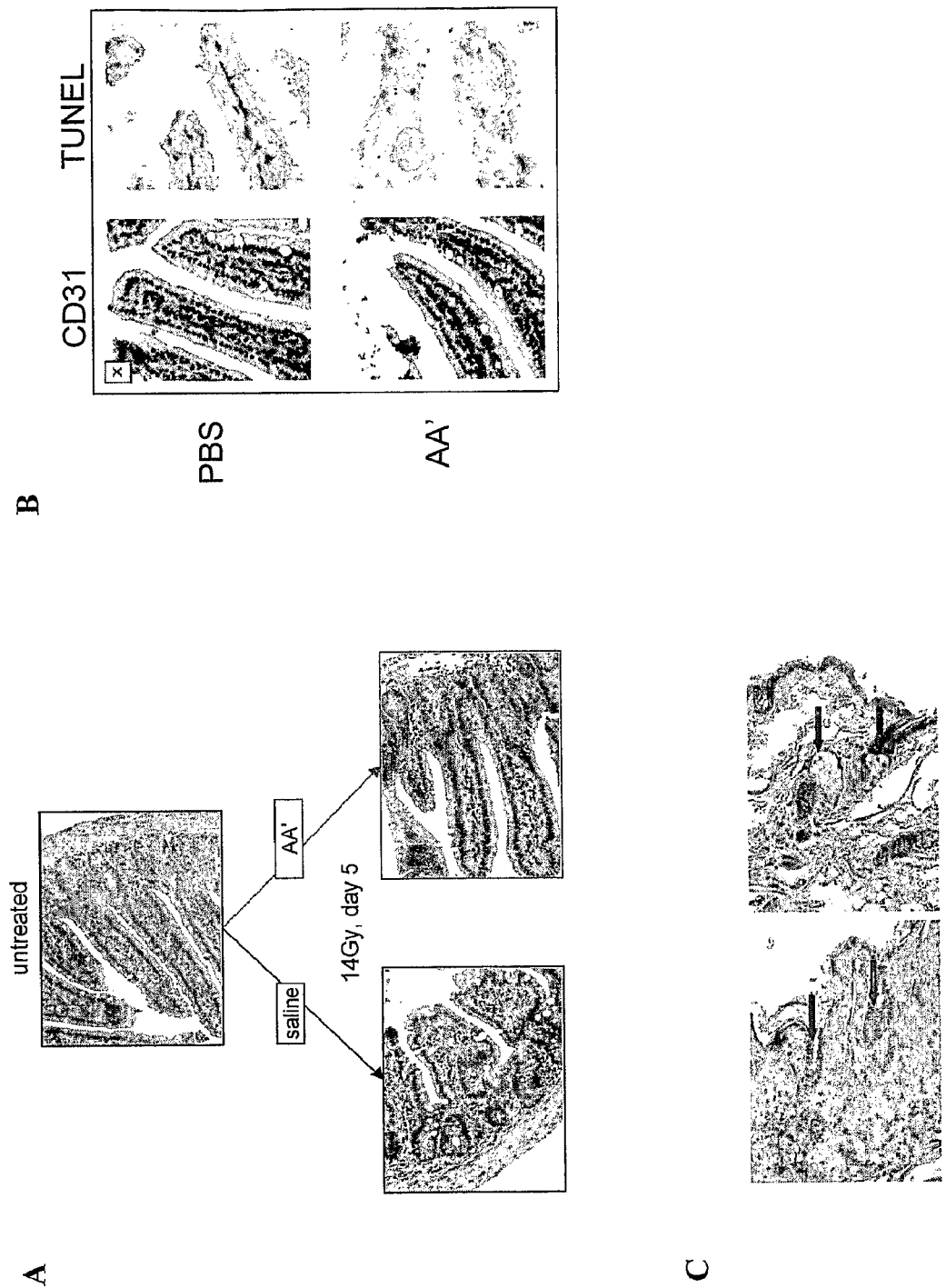
FIG. 17 shows that the AA' fragment protects intestinal epithelium from degeneration caused by radiation. A: Histological sections (hematoxylin and eosin-stained) of small intestinal epithelium of mice 5 days after 14 Gy irradiation are shown. B: Treatment with the AA' fragment prevents apoptosis ongoing 5 hours after irradiation in endothelial cells of villi (detected by immunostaining for endothelial marker CD31 and marked by arrows), as determined by TUNEL assay. C: Histological sections of skin of mice 5 days after 14Gy of gamma irradiation demonstrate the protective effect of the AA' fragment for sebaceous glands (red arrows).

Tissue samples of intestinal mucosa were taken 5 days after 14 Gy irradiation from mice pretreated with flagellin and control mice. Control animals were treated with 5.0 µg/mouse (0.2 mg/kg) bacterial RNA-polymerase. Pathomorphological analysis of the small intestine reveals reduction of the size of crypts and villi and a number of the cells with condensed apoptotic nuclei in control mouse and near-normal morphology in the treated mouse (data not shown). Tissue samples (small intestine and skin from the back) were also obtained from mice treated with the AA' fragment. The results shown in FIG. 17 are areas of typical morphology observed over a set of at least 3 mice. After treatment with flagellin and the AA' fragment, mice demonstrated near-normal intestinal morphology with preservation of the villi/crypt structure (FIG. 17A).

In addition to purely histological observation of cell death and survival, we performed more specialized tests of apoptotic cell death in intestinal tissue using a TUNEL assay, which detects apoptosis-associated DNA fragmentation.

These experiments allowed us to define with a high degree of probability cellular populations that are depleted by radiation and rescued by flagellin fragment treatment. The earliest radiation-induced alterations detectable in the small intestine after treatment with IR is apoptosis occurring in vascular endothelial cells of villi, which is seen as early as 5 hours post treatment (FIG. 17B). This apoptosis, which is believed to be critical for radiosensitivity of the small intestine, was almost completely blocked in the mice pretreated with the AA' fragment (FIG. 17B, bottom panel). Degeneration of villi and crypts, occurring within the next several days post treatment and greatly suppressed in AA' fragment-treated animals, comes as a consequence of injury of blood vessels. Effective protection of endothelial cells of the small intestine by the flagellin fragment may be due to expression of TLR5 in these cells.

Remarkably, the AA' fragment and flagellin also prevented the radiation-induced disappearance of sebaceous glands located at the base of skin hair follicles (FIG. 27C). These results further confirm the suitability of AA' fragment for radioprotection and for the prevention of radiation-induced hair loss.

EXAMPLE 11

Protection from Supralethal Radiation

In order to explore the limits of radioprotection provided by the AA' fragment, we irradiated mice with 17 Gy and 20 Gy single doses of total body gamma-radiation. The experiment was performed as described above using inactive flagellin fragment (CB) as a negative control.

Figure 18:
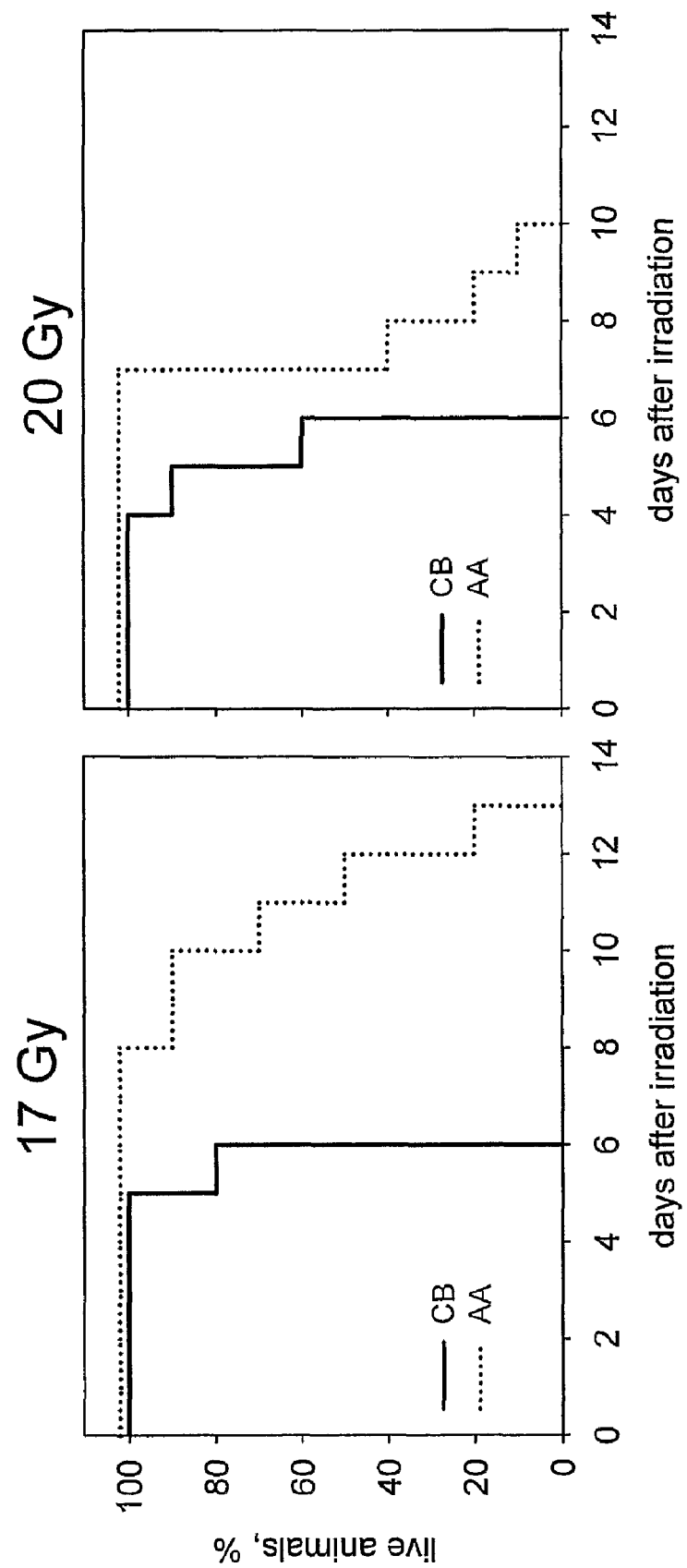
FIG. 18 shows that the AA' fragment provides partial protection and delays death of mice after supralethal irradiation with 17 and 20 Gy total-body gamma radiation.

As expected, we observed a 100% mortality in both groups at 17 and 20 Gy (FIG. 18). However, death was significantly delayed in both cases by administration of the AA' fragment. Most remarkably, the kinetics of death at 17 Gy in control mice conform to GI syndrome (6-7 day mortality), while death of mice treated with the AA' fragment appear to be mediated by hematopoietic syndrome (10-15 day mortality). This shows that flagellin and flagellin fragments may protect against the GI syndrome at doses as high as 17 Gy. In addition, this shows that even further radioprotection may be obtained by flagellin and flagellin fragments combined with hematopoietic radioprotectors.

EXAMPLE 12

Immunogenicity and Repetitive Administration Studies

Overall immunogenicity of a protein may determines its suitability for repeated use. Antibodies generated by immune system are capable of reducing the therapeutic activity of the protein and also may induce anaphylactic reaction upon second exposure if IgE antibodies are produced against the protein. Thus, any reduction in the amount and variety of antibodies compared to full-length flagellin is an improvement. Accordingly, after repeated introduction of flagellin or its fragments we monitored; a) efficiency of radioprotection afforded at second exposure; b) local and general allergic reactions; and c) antibody titer.

We tested the ability of AA' to protect mice that were exposed to it. A group of 20 NIH-Swiss mice were subcutaneously injected with 5 µg/mouse (0.2 mg/kg) of AA'. A second injection of a equal dose of AA' was administered after 21 (10 mice) and 28 days (another 10 mice), with the time elapsed being sufficient for formation of antibodies. The second injection of AA' was followed by 13 Gy of whole-body gamma irradiation (1 h post-injection). 100% 30-day survival was observed in both groups, as it was observed with mice that had no previous exposure to AA' (data not shown). These results show that activity of AA' is not diminished over long-term repeated administration and reaffirm its potential for multiple-use applications. Also, no local allergic reaction or anaphylaxis was observed either with flagellin or AA'.

Figure 19:
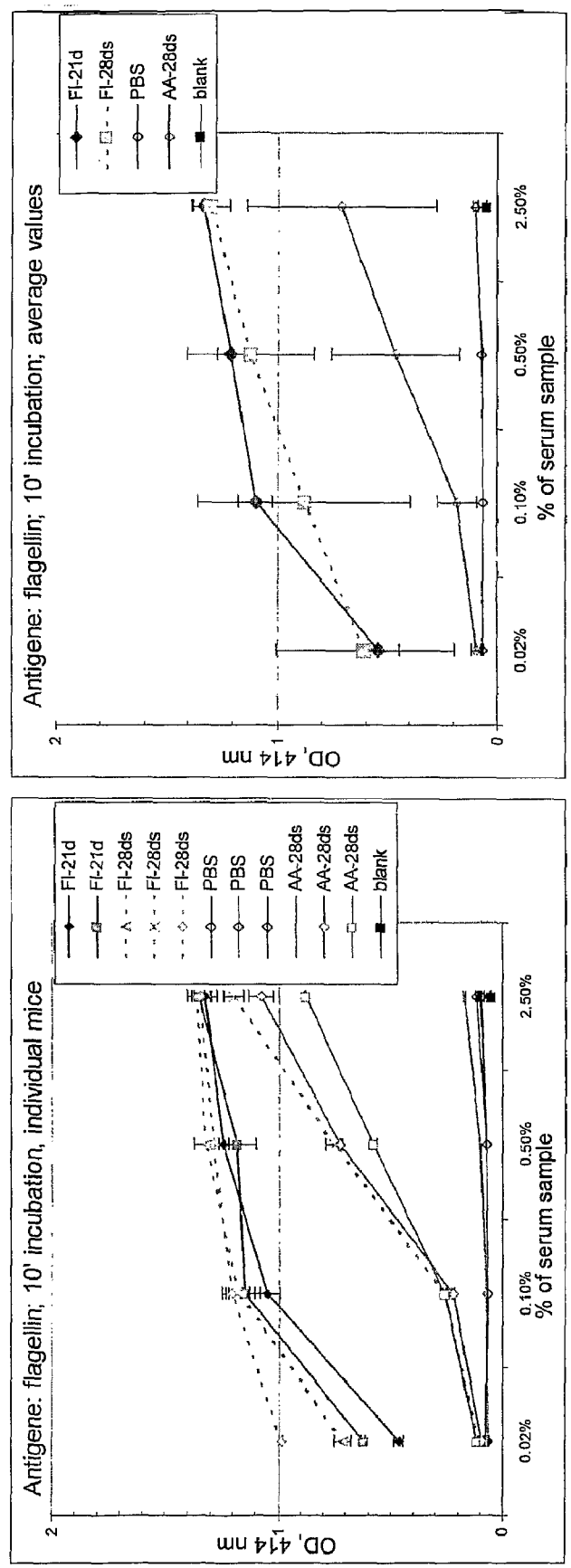
FIG. 19 shows anti-flagellin antibody titers induced in mice after 21 and 28 days by flagellin and AA'. For individual mice, the averages of two measurements are shown. Mice were injected with: Fl: flagellin; or AA'. 21d and 28ds—mice injected with first dose 21 and 28 days before second, respectively. PBS: saline buffer (no serum) control; blank: empty well reading control.
Figure 20:
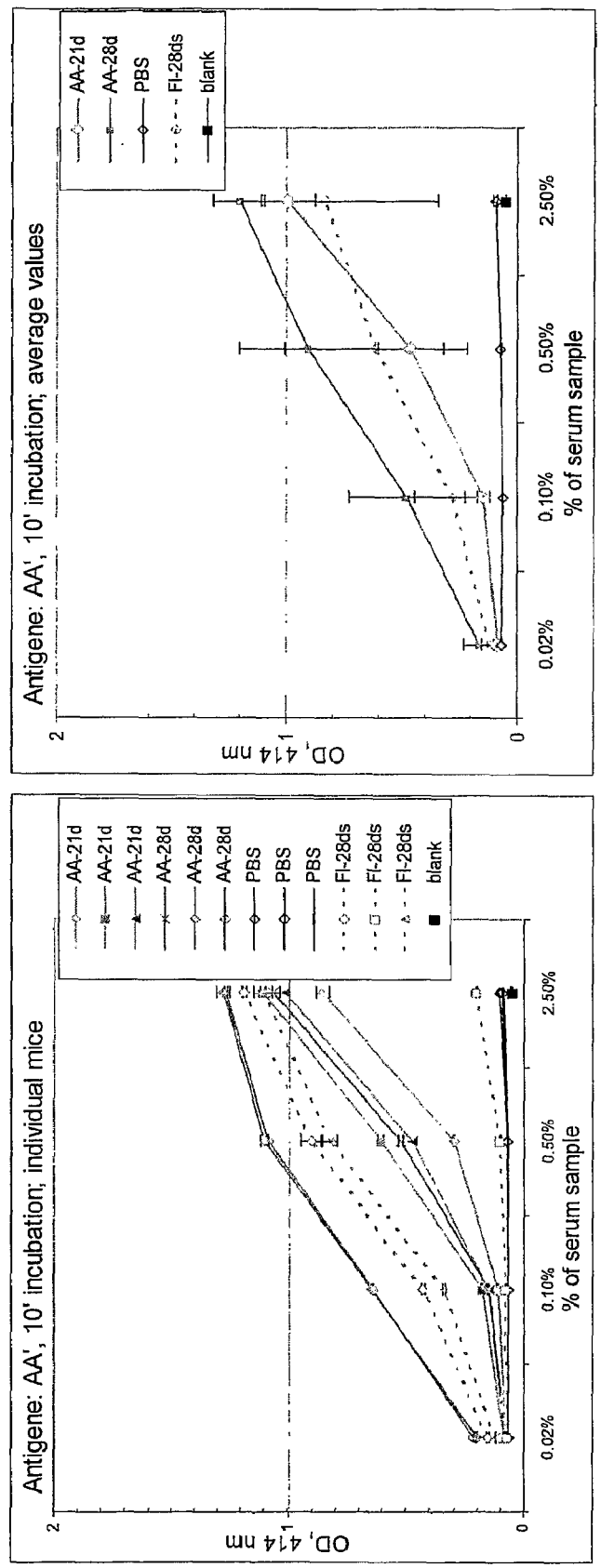
FIG. 20 shows anti-flagellin antibody titers induced in mice after 21 and 28 days by flagellin and AA'. For individual mice, the averages of two measurements are shown. Mice were injected with: Fl: flagellin; or AA'. 21d and 28ds—mice injected with first dose 21 and 28 days before second, respectively. PBS: saline buffer (no serum) control; blank: empty well reading control.

We also performed an ELISA determination of antibody titers in order to quantify the effect that AA' has on the immune status of the organism. 96-well plates were coated with flagellin or AA', 20 mg/ml, 50 ml/well, and incubated overnight at +4° C. Blood serum samples collected from mice were added to the wells in several dilutions and incubated overnight followed by 6 hrs reaction with secondary goat anti-mouse IgG HPO-conjugate antibodies. Measurements were performed using a spectrophotometer with a 414 nm filter. The antibody titers determined for individual mice and average titers are shown in FIG. 19 and FIG. 20.

AA' induces far lower antibody levels in mice (FIG. 19), on the order of 0.8 mg/ml serum at 21 day and about 10% more at 28 days. Flagellin, on another hand (FIG. 20), induces a high titer of antibodies, around 20 mg/ml, at both 21 and 28 days. Overall, this shows that removal of the hypervariable domain sharply reduces the immunogenicity of AA' compared to the original protein (approximately 25×). FIG. 19 also shows that the majority of AA'-specific antibodies are capable of recognizing flagellin. This confirms that the rational design of AA' does not produce a sizable number of new immunogenic epitopes while removing >95% of the immunogenicity of the original protein.

EXAMPLE 13

Acute Toxicity Studies of Flagellin and AA'

The lethal dose of *Salmonella* flagellin is between 1 mg/kg (systemic inflammation) and 10 mg/kg (100% lethality). We subcutaneously administered increasing doses of AA' to mice (4 mice per dose group) at 0.5, 1, 2, 4 and 8 mg/kg. Due to the lower (~60%) molecular weight, 8 mg/kg of AA' correspond to a molar-equivalent dose of 13.3 mg/kg of flagellin. Several days after administration at all doses, no visible detrimental effects were observed, such as mortality, morbidity or signs of systemic inflammation such as reduced activity and fever. This shows that the pro-inflammatory effect of AA' is negligible compared to full-length flagellin, especially considering that AA' provides an efficient radioprotection at 0.2 mg/kg. The reduced toxicity may be sue to the absence of the central pro-inflammatory domain in the AA' fragment.

EXAMPLE 14

Protection from Fractioned Irradiation by AA'

Repetitive irradiation within a short period of time may be common, for example, in space radiation events and in clinical radiotherapy regimens. We tested the ability of the AA' flagellin fragment to protect mice from sub-lethal (4 treatments of 3 Gy) and 100% lethal (4 treatments of 4 Gy) regimens of fractionated gamma-irradiation. Fragment AA' or saline buffer was given to NIH-Swiss female mice before every irradiation (once a day for 4 days). AA' was administered as described above for single-dose irradiation (5 µg/mouse, given subcutaneously 1 h before irradiation).

Figure 21:
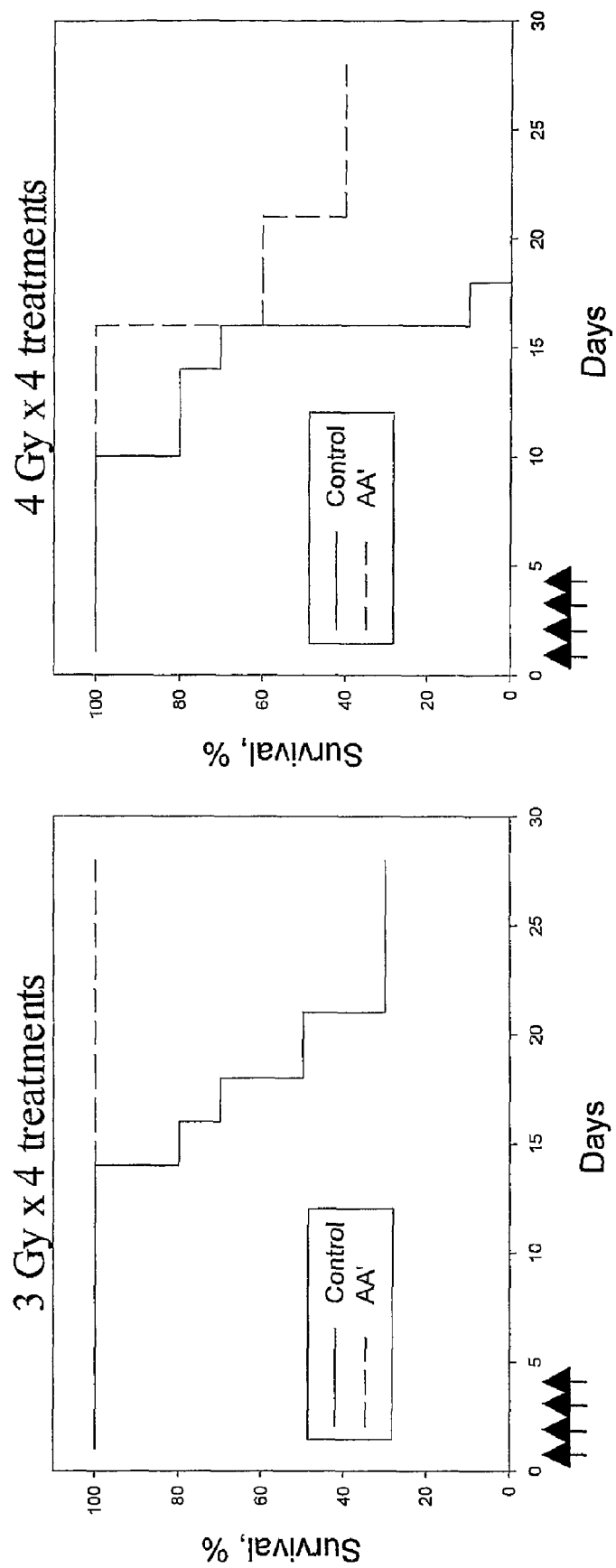
FIG. 21 shows that flagellin fragment AA' protects mice from multiple successive doses of gamma-irradiation. Arrows denote radiation treatments (days 1-4).
Figure 22:
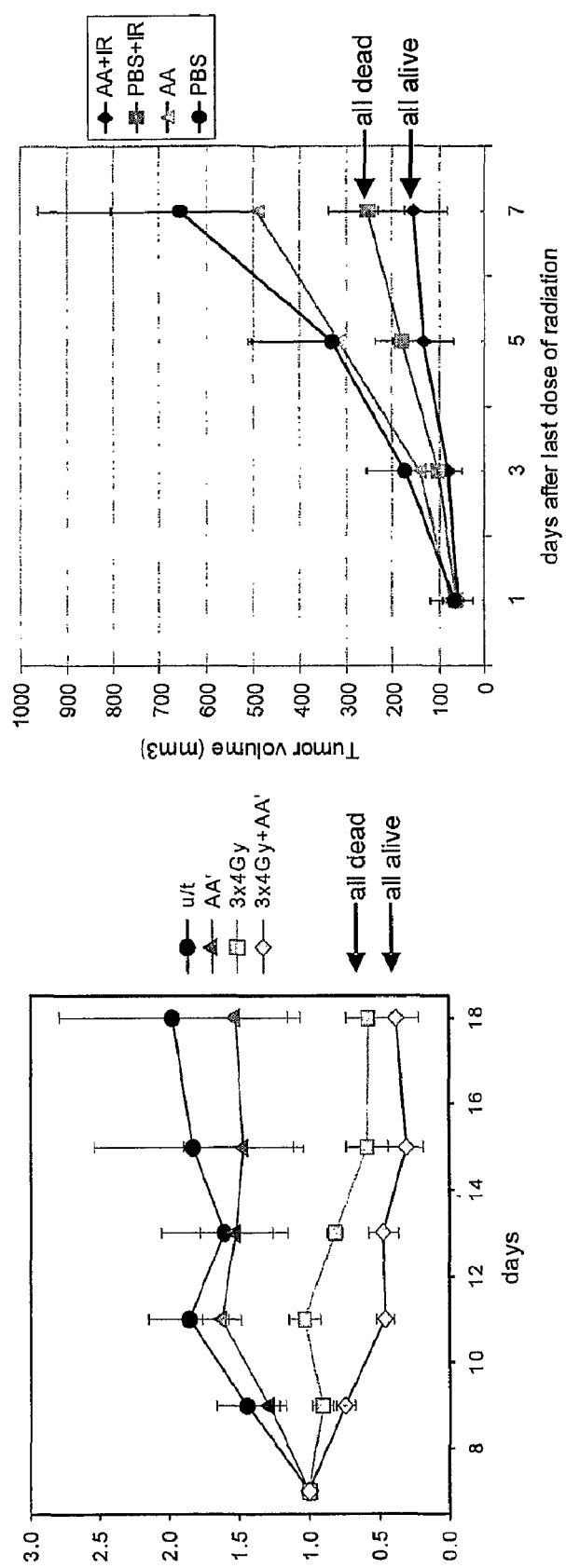
FIG. 22 shows the effect of AA' on tumor sensitivity to radiation treatment. Left Panel: NIH3T3-derived sarcoma cells were injected s.c. in NIII-Swiss mice. When tumors reached 7-10 mm in diameter, mice received three 4.3 Gy doses of total body irradiation, with or without pretreatment with AA'. The dynamics of tumor growth after radiation treatment is displayed. U/t: untreated; AA': AA' with no irradiation; 3×4Gy: irradiation only; 3×4Gy+AA': AA' and irradiation. (The shape of curves reflects slow growth of tumors that is a characteristic of this model). Results are displayed as relative tumor volumes normalized to tumor volume measured at day 7 after last irradiation. Right Panel: The experiment was done in the same way with another syngeneic mouse tumor model: B16 melanoma (C57BL6 background). Treatment was applied when tumors reached 4-5 mm in diameter and involved three subsequent 4 Gy doses of total body gamma radiation applied with or without pretreatment with AA' (30 min. before irradiation, 5 μg/mouse).
Figure 23:
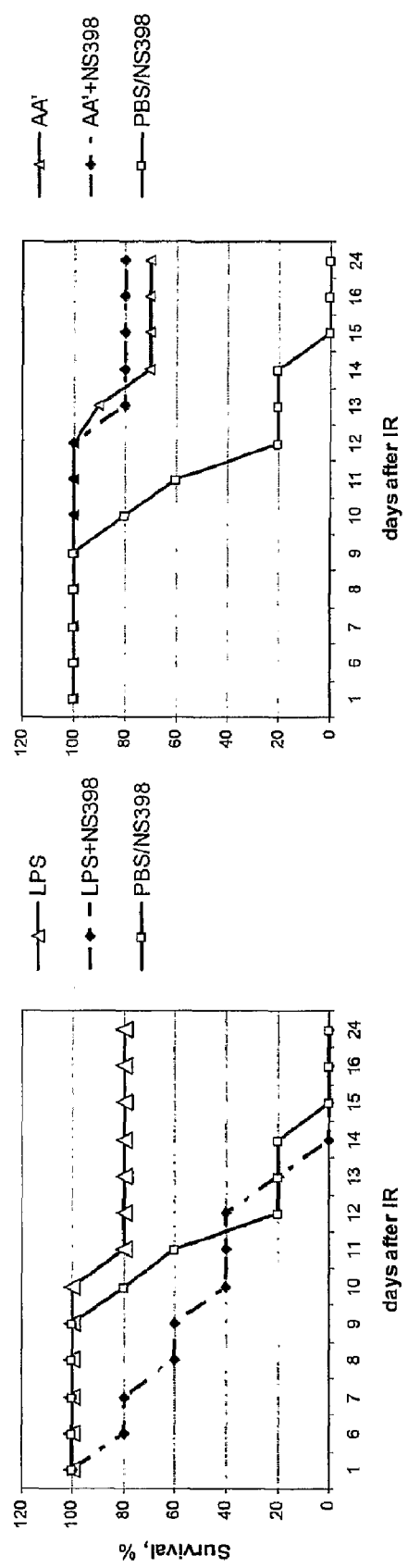
FIG. 23 shows the influence of NS398 on the radioprotection of LPS and AA' in mice after 13 Gy of total-body gamma irradiation.

The results in FIG. 21 show that AA' provides significant protection against repetitive doses of radiation received within a short timeframe. The cumulative dose of fractionated radiation that is still compatible with 100% 30-day survival after AA' treatment is comparable to such obtained in single-dose irradiation scenarios.

EXAMPLE 15

AA' Protects Normal Tissues Without Compromising the Anti-Tumor Therapeutic Effect of Radiation The ultimate test of a potential radioprotective agent in cancer treatment is tumor selectivity, its ability to protect normal tissues while providing no or little protection to the tumor. We injected 10 NIH-Swiss mice subcutaneously, in both flanks (20 tumors total), with $2 \times 10^6$ cells of syngeneic sarcoma cell line model (NIH3T3-derived and spontaneously transformed sarcoma with p53 inactivated by dominant negative inhibitor GSE56). When tumors reached the size of 5-7 mm in diameter (day 5), the mice were injected subcutaneously with 0.2 mg/kg of AA' or saline vehicle and irradiated 1 hours later with 4 Gy of total-body γ-irradiation ($3 \times 4.3$ Gy=12.9 Gy total dose). Injections and irradiations were done at days 5, 6 and 7.

As the results show in FIG. 11, AA' enhanced the radiation-induced shrinkage of tumors. By day 18, all the irradiated tumor-bearing mice died from acute radiation toxicity whereas 100% of mice that obtained both radiotherapy and AA' were both cured and survived the treatment. Similar result was obtained with another syngeneic tumor model—B 16 melanoma cells (FIG. 11, right panel). Surprisingly, even in unirradiated mice, AA' administration caused a decrease in the growth rate of tumors. This may be due to AA'-induced immunostimulating, which is known to be caused by other ligands of Toll-like receptors. These results indicate that AA' increases the tolerance of mice to radiation with no effect on the radiosensitivity of two types of tumors, thus opening the possibility of combining radiotherapy with AA' to improve treatment outcome.

EXAMPLE 16

Radioprotective Mechanisms of AA' and LPS are Different

Lipopolysaccharide of gram-negative bacteria (LPS) is a ligand of another Toll-like receptor, TLR4. LPS is a strong inducer of NF-κB and a subsequent cascade of cytokines. LPS is known as a radioprotective compound, but its high toxicity makes its use unfeasible (radioprotective dose is very close to the lethal dose). One of the major mechanisms underlying the radioprotection by LPS is the activation of cyclooxygenase 2 (COX-2) that, in turn, drives the synthesis of G1-protective prostaglandins. The possibility that radio-protection by TLR5 also relies on COX-2 activity was tested by administering s.c. LPS (2 mg/kg), AA' (0.2 mg/kg') or vehicle 1 hr before irradiation of NHI-Swiss mice in combination with i.p injection of 1 mg/kg of NS398, a synthetic COX-2 inhibitor, or the corresponding vehicle. The mice were then treated with 13 Gy of total-body γ-irradiation. NS398 completely abolished LPS-mediated radioprotection but not the radioprotection of AA' (FIG. 12). This result shows that AA' does not significantly rely on COX-2 for its activity and induces radioprotection by a mechanism different from the mechanism of LPS-mediated protection.

EXAMPLE 17

AA' Protects Multiple Mouse Strains

We have extensively confirmed that AA' protects NIH-Swiss and ICR mice from radiation. To confirm that the radioprotection activity of AA' is not confined to a few mouse strains, several additional strains of mice with dissimilar origins were tested for protection by AA':129/Sv, DBA/2 (relatively radioresistant), Balb/c (relatively radiosensitive) and Balb/c×DBA/2 F1 hybrid CD2F1. Experimental groups were injected with 0.2 mg/kg AA' 30 minutes before irradiation, while control groups were injected with vehicle (PBS).

Figure 27:
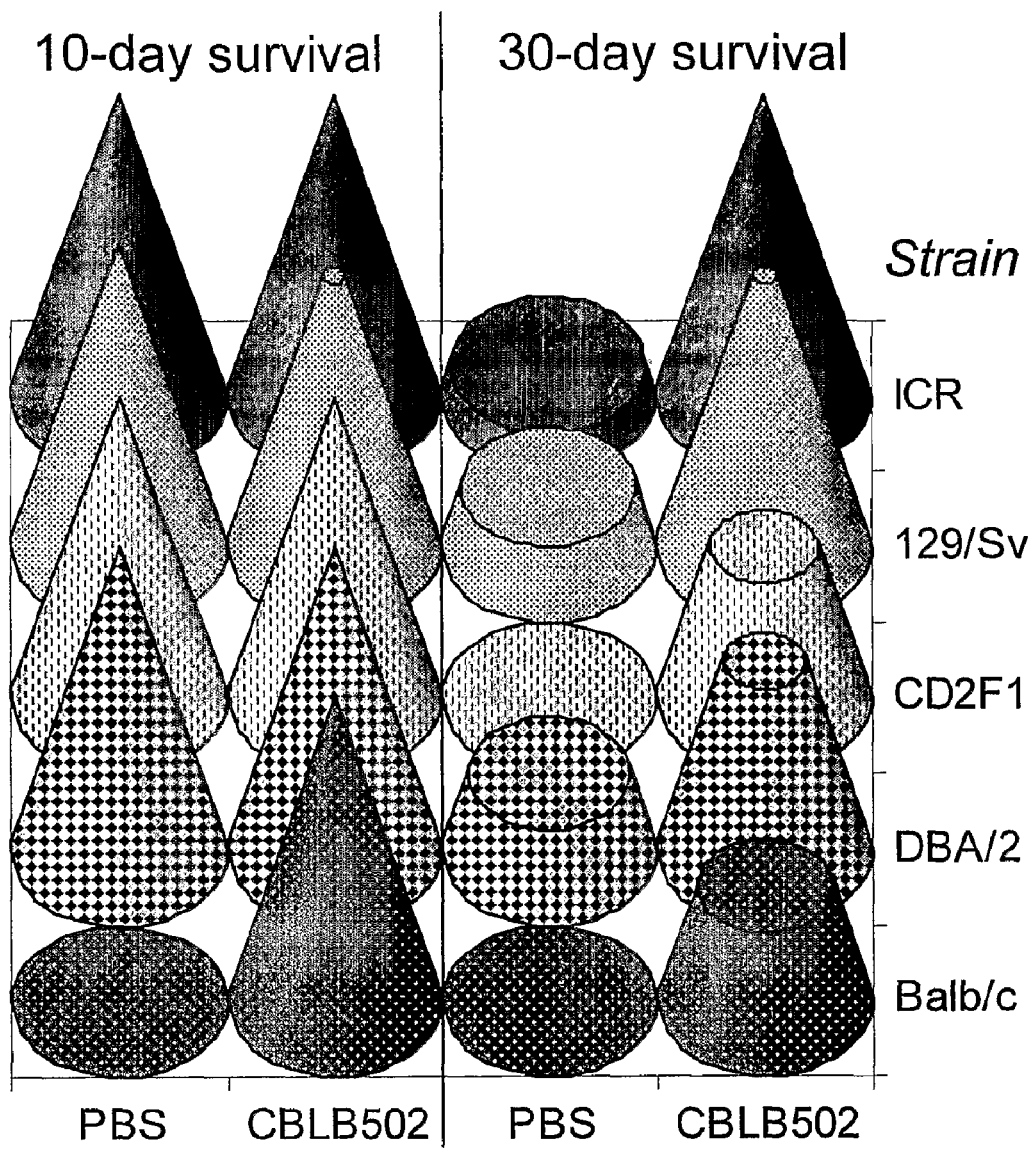
FIG. 27 demonstrates that AA' mediates rescue of multiple mouse strains after 10 Gy total-body γ-IR. Cone heights represent fractions of survivors.

All groups of mice (8-10 mice each, 8-12 week old females) were exposed to 10 Gy of single-dose, whole-body gamma-irradiation. Survival of mice at days 10 and 30 is shown. The results are shown in FIG. 27 as a cone graph. At 10 days, only Balb/c mice display mortality, which is drastically reduced by AA' administration (0% vs. 100% survival). At day 30, all tested strains display improved survival (0-25% vs. 50-100%) after AA' administration.

EXAMPLE 18

Pharmacokinetics of AA'

Figure 28:
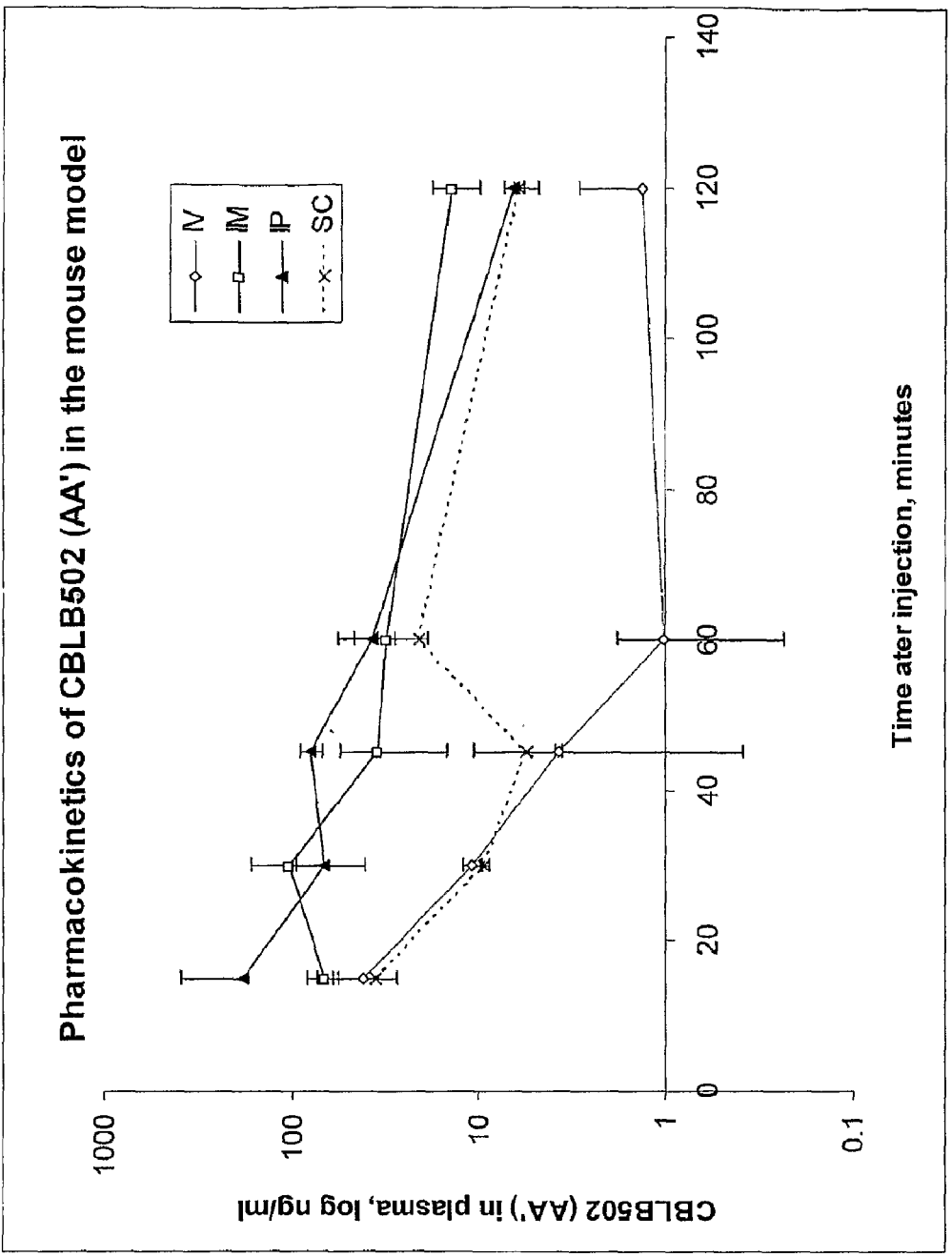
FIG. 28 demonstrates the pharmacokinetics of AA' after intravenous (i.v.), subcutaneous (s.c.), intraperitoneal (i.p.) or intramuscular (i.m.) injection.
Figure 29:
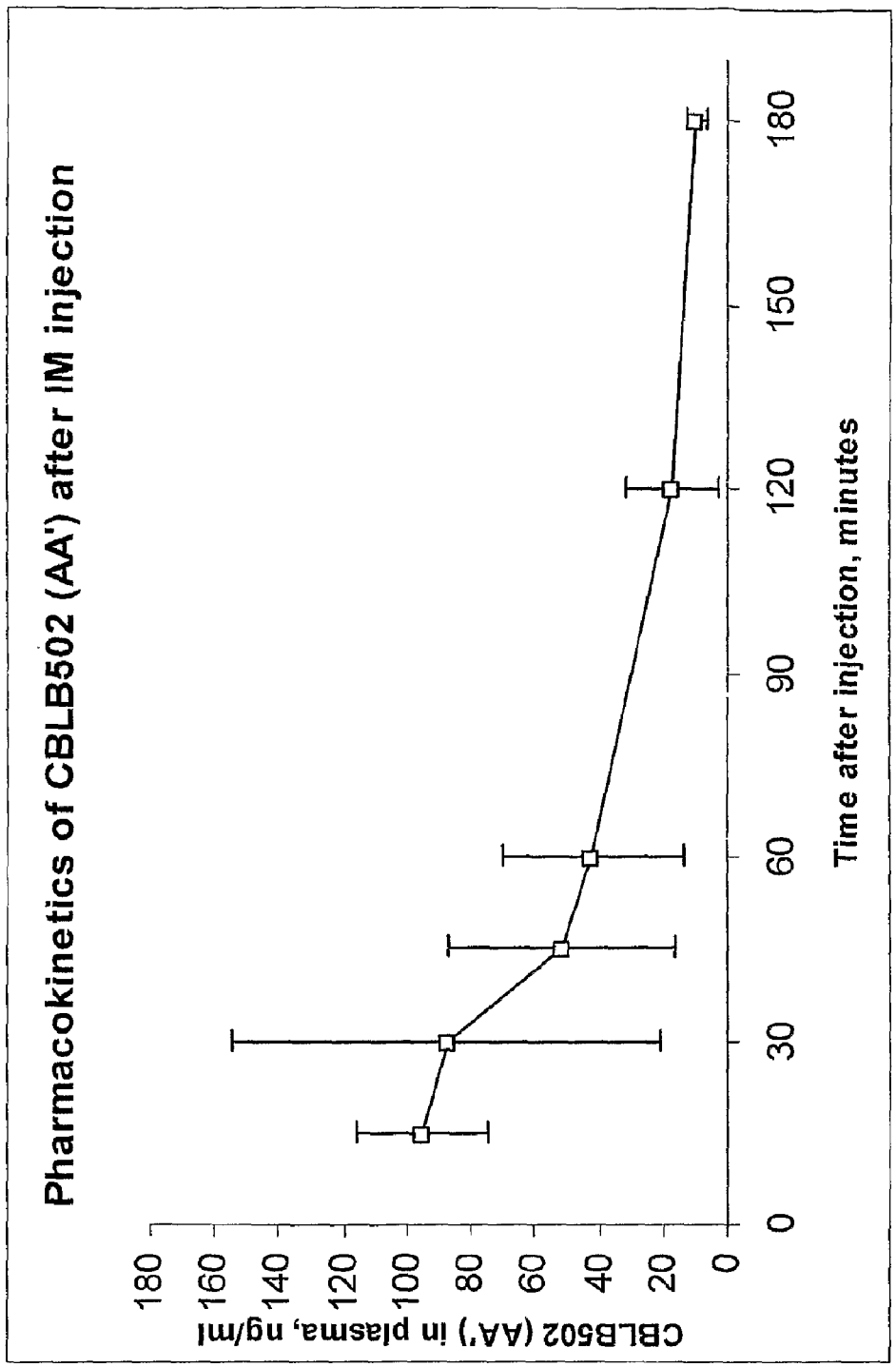
FIG. 29 demonstrates the extended pharmacokinetics of AA' after intramuscular (i.m.) injection.

Pharmacokinetic parameters (effective concentration and the duration of drug the presence in the organism) may be important for route, dose and time of drug administration. The pharmacokinetics of CBLB502 (AA') were thus tested for four common routes of injection: intravenous (i.v.), subcutaneous (s.c.), intraperitoneal (i.p.) or intramuscular (i.m.). A radioprotective dose of CBLB502 (AA'), 0.2 mg/kg, was injected in 12-15 week old ICR mice and plasma samples were collected at the specified times after injection (at least 3 mice/point). The levels of CBLB502 in plasma were measured by sandwich ELISA using known concentrations of CBLB502 spiked in the control ICR plasma for calibration. The results are shown in FIG. 28 and FIG. 29.

The results show that the highest levels and longest persistence of CBLB502 in plasma are provided by intramuscular or intraperitoneal injection. After intramuscular injection, significant (>5 ng/ml) levels of CBLB502 are observed in mouse plasma >3 hours. Intravenous injection leads to a more rapid disappearance of CBLB502 from the bloodstream.

EXAMPLE 19

Influence of AA' on Gamma-Irradiation Induced Cell Death and Growth Inhibition in A549 Cells The A549 human lung adenocarcinoma cell line is reported to respond to flagellin by activation of NF-κB DNA-binding activity (Tallant T., et. al., *BMC Microbiol.* 2004 Aug. 23; 4:33). We decided to check whether this activation translates in the protection of cells from γ-IR in cell growth inhibition assay.

Figure 30:
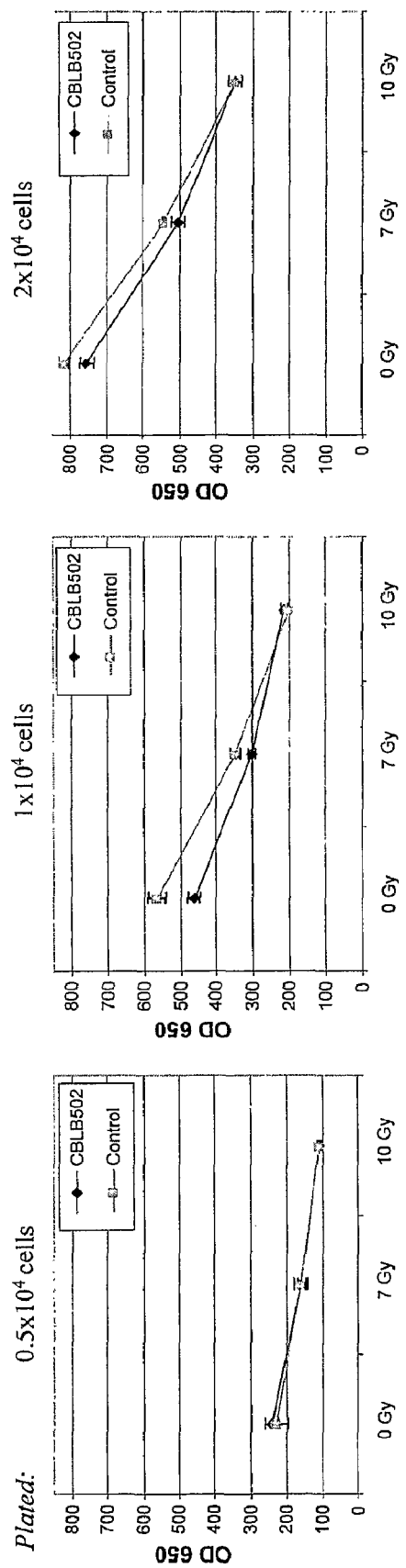
FIG. 30 demonstrates the influence of AA' on gamma-irradiation induced cell death and growth inhibition in A549 cells.

Tumor cells were seeded in wells of three 96-well plates in 3 different densities ($0.5 \times 10^4$, $1 \times 10^4$ and $2 \times 10^4$ cells/well, producing single-cell, spare or semi-contact layer). After cells had attached to plastic, CBLB502 (2 μg/ml) was added to the wells of non-irradiated cells, or 15 min prior to 7 Gy or 10 Gy of gamma-irradiation. Control wells received equal volume of vehicle (PBS). All points were done in quadruplicate. 72 hours after irradiation, medium was replaced with methylene blue in 50%-methanol and the relative numbers of viable cells in wells were measured using spectrophotometer at 650 nm. The results are shown in FIG. 30. This experiment was also repeated with fixed dose of 1×10⁴ A549 cells/well, CBLB502 was added 1 hour before 5, 10 or 15 Gy of gamma-irradiation (data not shown). We observed a similar effect of flagellin in all tested experiment conditions.

Gamma-irradiation induced a dose-dependent reduction in the number of A549 cells plated at all three densities (up to 60% as compared to non-irradiated control wells). CBLB502 had no or slight effect on cell numbers, with or without gamma-irradiation. This indicates that tumor cells are not significantly protected by CBLB502 (AA') from radiation. This effect may be due to tumor cells having constitutively active NF-κB pathway or some other mechanism.

EXAMPLE 20

Figure 31:
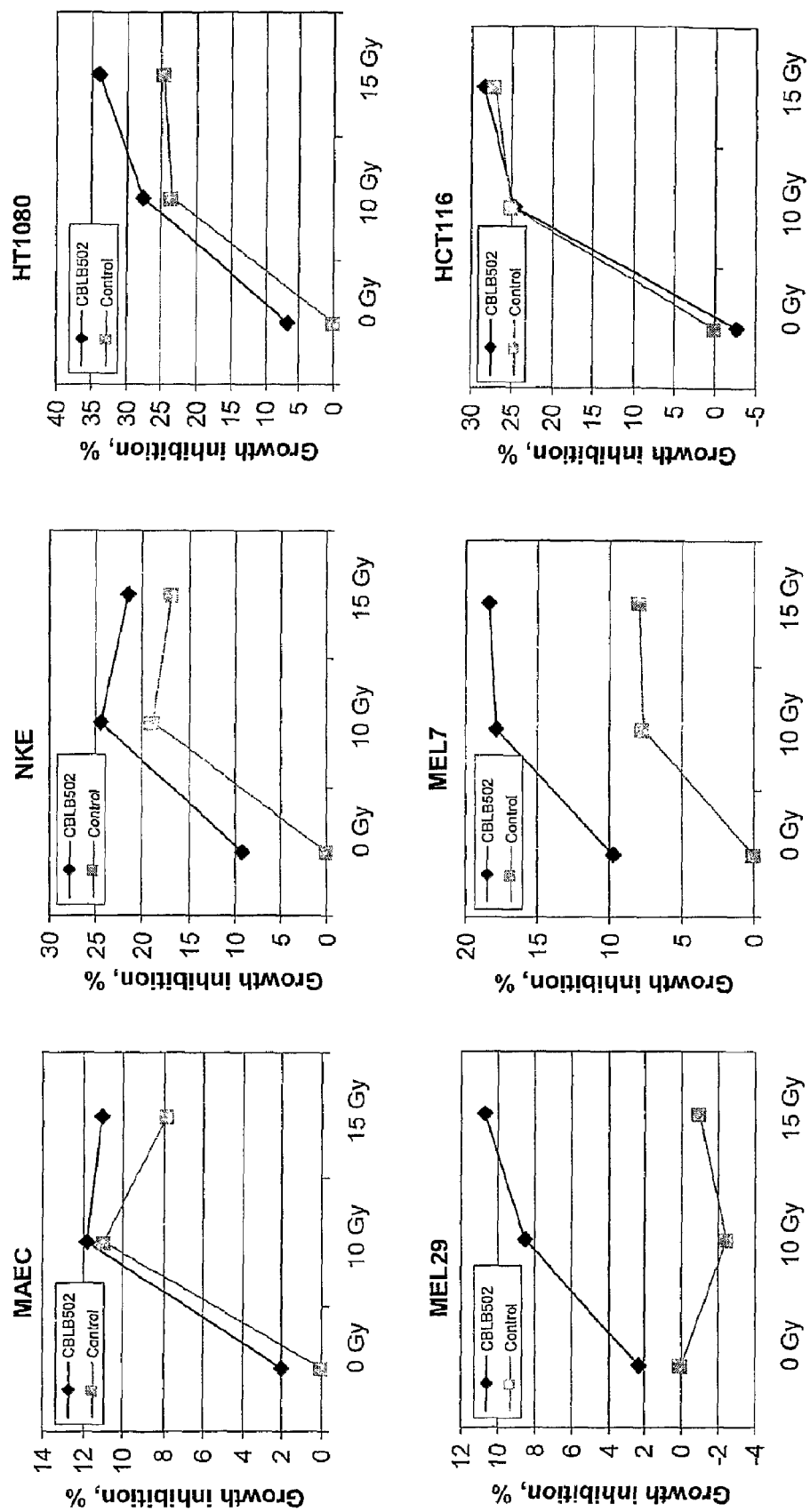
FIG. 31 demonstrates the influence of AA' on gamma-irradiation induced cell death and growth inhibition in multiple cell lines.

Influence of AA' on Gamma-Irradiation Induced Cell Death and Growth Inhibition in Multiple Cell Lines Based on the results using A549 cells, several additional tumor cell lines (human melanoma MeI-7 and MeI-29, colon cancer HCT116, lung cancer HT1080), immortalized kidney epithelial cells (NKE) and normal mouse aortal endothelial cells (MAEC)) were tested in growth inhibition assay after 10 and 15 Gy of gamma-irradiation, as compared with intact control, with or without pretreatment with CBLB502. Cells were seeded in 96-well plates night before the treatments. CBLB502 (2 µg/ml) was added to the wells 4 hrs, 1 hr or 10 min before irradiation (all points were done in quadruplicate). 48 hours later, methylene blue staining was performed to determine the relative amount of the viable cells in the wells. All three time-points had shown the same effect (results for CBLB502 added 1 hr before irradiation are shown in FIG. 31). The percent of growth inhibition was calculated from the OD650 in control non-irradiated wells, taken as 0% inhibition.

Both human melanoma cell lines and MAEC cells were rather resistant to gamma-irradiation and showed only slight (<20%) growth inhibition after both 10 and 15 Gy comparing with intact cells (0 Gy). NKE, HT1080 and HCT116 cells showed up to 40% of growth inhibition after gamma-irradiation. Remarkably, CBLB502 had no or only a slight inhibitory effect on tumor cell growth, irradiated or not. The experiment was repeated twice. In addition, similar results were obtained on tested lung adenocarcinoma H1299 and prostate cancer CW22 (data not shown). This indicates that there is no significant protection provided by CBLB502 to the tumor cell lines against radiation-induced cell death.

EXAMPLE 21

Figure 32:
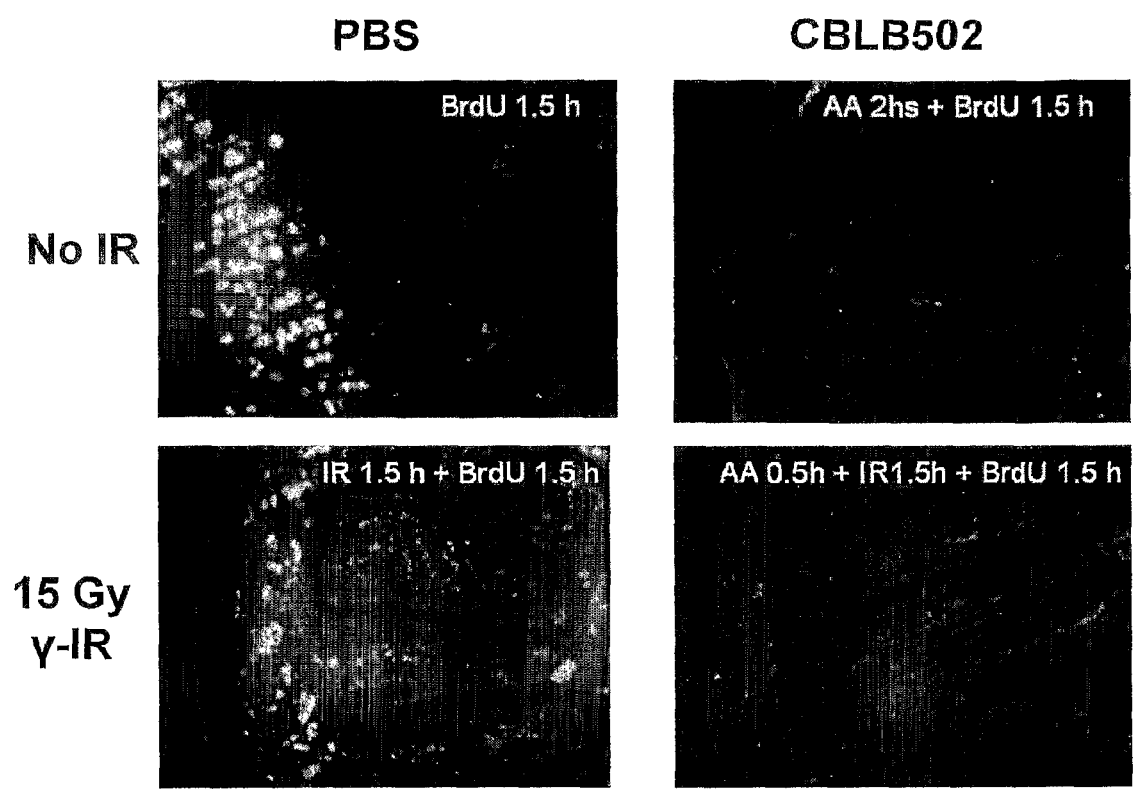
FIG. 32 demonstrates the influence of irradiation and AA' on BrdU incorporation in small intestinal crypts of NIH-Swiss mice. A comparison of BrdU incorporation in small intestine of control and AA' treated NIH-Swiss mice, with and without 15 Gy of gamma radiation is shown. BrdU (50 mg/kg) was injected 1.5 h before sacrificing mice and immunostaining was done as previously described (Watson A J & Pritchard D M., *Am J Physiol Gastrointest Liver Physiol*.

Influence of Irradiation and AA' on BrdU Incorporation in Small Intestinal Crypts Besides a direct inhibition of apoptosis, temporary halt of proliferation followed by repair may be an alternative mechanism of radioprotection, and has been described for other radioprotectors such as TGF-β3 (Booth D., et. al., *Int J. Cancer.* 2000 Apr. 1; 86(1):53-9). Accordingly, we decided to examine the possible influence of CBLB502 (AA') on the proliferative activity of the cells in small intestine (with and without irradiation) during the first hours after its administration (FIG. 32). CBLB502 or PBS was injected i.p. in mice, followed after 30 min by 15 Gy irradiation (if used). 2 hr after injection (1.5 hr after irradiation if it was applied), BrdU was injected intraperitoneally. Samples of small intestine were obtained after additional 1.5 hours.

Without irradiation, BrdU was incorporated at high levels in the nuclei of cells in the intestinal crypts of untreated NIH-Swiss mice (FIG. 32, top left), whereas DNA synthesis (as measured by BrdU incorporation) was nearly undetectable in the crypts of CBLB502-treated mice (FIG. 32, top right). In vehicle-treated irradiated mice, the incorporation of BrdU was lower than in control mice. Importantly, the level of BrdU incorporation was strongly reduced by CBLB502, possibly indicating quick (S phase) growth arrest, as opposed to later (G2 phase) irradiation-induced growth arrest. Therefore, cytostatic activity of CBLB502 or flagellin may be an additional mechanism of radioprotection of small intestine.

EXAMPLE 22

Duration of AA'-Mediated Growth Arrest and Reduced BrdU Incorporation

We next determined the duration of the CBLB502-induced growth arrest in small intestine. CBLB502 or PBS was injected i.p. in mice, BrdU was injected 1 or 4 hours later and samples of small intestine were obtained after additional 1.5 hours from several mice (samples from three mice are shown) (FIG. 33).

Incorporation of BrdU in intestine was reduced as compared to control if BrdU was injected after 1 hour (as it was shown in the previous experiment where BrdU was injected after 2 hr). NIH-Swiss, ICR and Balb/c mice displayed a similar degree of CBLB502-mediated block of BrdU incorporation (Balb/c samples are shown in FIG. 33). If BrdU was injected 4 hr after injection of CBLB502, the levels of incorporation/DNA synthesis were even higher than in control. This indicates that inhibition of intestinal stem cell proliferation by CBLB502 may be temporary and may be quickly resolved (by 4 hours), followed by a period of increased proliferation (possibly due to the partial synchronization of cells).

EXAMPLE 23

Influence of AA' on BrdU Incorporation in Colonic Crypts

The colon is much less radiosensitive than small intestine. To further examine the relationship between reduced proliferation in the small intestine and radioprotection, we determined the effect of CBLB502 on BrdU incorporation in the colon. CBLB502 or PBS was injected i.p. in mice, BrdU was injected 1 hour later and samples of small intestine were obtained after additional 1.5 hours (FIG. 34).

Unlike in the small intestine, CBLB502 has no effect on BrdU incorporation in colon. This is surprising since TLR5 is plentiful in both organs. The difference in effects may be due to the higher amount of symbiotic bacteria in the colon, which may mask the effect of additional TLR5 signaling induced by CBLB502.

EXAMPLE 24

Comparison of Radioprotective Potential by Route of Administration

We next tested radioprotection provided by FliC flagellin administered via several routes: intravenous (i.v.), intraperitoneal (i.p.), intramuscular (i.m.), subcutaneous (s.c.) and gavage. For parenteral (non-gavage) routes, mice were injected with 0.2 mg/kg of FliC flagellin dissolved in PBS or vehicle, followed 1 hr later by 13 Gy irradiation. In gavage delivery experiment; 5 mice were given to swallow an increased dose (50 µg) of FliC in 50 µl of PBS 1 h before 13 Gy gamma-irradiation. Both experiments were done in 8-10 week old female NIH-Swiss mice, 5-10 mice/group.

All tested routes besides gavage afforded similar degree of protection, leading to 85-90% 30-day survival of mice (data not shown). No protection against radiation was provided by gavage delivery, which may be due to digestion of the protein by the gastrointestinal environment. In addition, flagellin receptor, TLR5, is absent on the luminal side of intestinal epithelium that is exposed to intestinal contents (Gewirtz A T., et. al., *J Immunol.* 2001 Aug. 15; 167(4):1882-5)

EXAMPLE 25

Effect of AA' on the Morphology of Small Intestine

Flagellin (and CBLB502) may induce NF-κB activity via binding to TLR5. Accordingly, CBLB502-mediated radioprotection may be dependent on the presence and activity of TLR5. MOLF/Ei mice are a known natural model of TLR5 deficiency (Sebastiani G., et. al., *Genomics.* 2000 Mar. 15; 64(3):230-40). To verify that CBLB502-mediated radioprotection is indeed TLR5-dependent, we tested the protection of small intestine from radiation by CBLB502 in MOLF/Ei and NIH-Swiss mice (FIG. 35). Both strains of mice were given 0.2 mg/kg CBLB502 (AA') or PBS 0.5 hr before 15 Gy of gamma-irradiation. The samples of small intestine were obtained 4 days after irradiation, stained by hematoxylin-eosin and subjected to pathomorphological analysis.

In NIH-Swiss (TLR5 wild type) mice, CBLB502 pretreatment led to preservation of intestinal morphology (long villae, normal crypts) as compared to short villae and disappearance of normal crypt structure in PBS-treated mice. Meanwhile, in TLR5-deficient MOLF/Ei mice the administration of CBLB502 had no improving effect on intestinal morphology after 15 Gy of gamma-irradiation: short villae and destruction of the normal crypt structure was observed, with or without CBLB502. This indicates that the presence of TLR5 may be necessary for CBLB502-mediated radioprotection in the small intestine.

EXAMPLE 26

Flagellin Derivatives

Additional flagellin variants were produced based on the domain structure shown in FIG. 36. The flagellin variants were then tested along with some of the variants discussed above for NF-κB stimulating activity (Table 3). A549 cells were left unstimulated or stimulated with TNF (10 ng/ml) as indicated or 1 µg/ml of purified flagellin or the various indicated flagellin derivatives for 45 min and whole cell extracts prepared as described in Example 7. EMSA assays were preformed and the NF-κB DNA-protein complex detected as described in Example 7.

TABLE 3

| Name | N-terminal | C-terminal | DNA | Protein | NF-κB Stimulation |
|---|---|---|---|---|---|
| AA' | 1-176 | 402-505 | SEQ ID NO: 7 | SEQ ID NO: 8 | Yes |
| AB' | 1-176 | 402-450 | SEQ ID NO: 9 | SEQ ID NO: 10 | Yes |
| BA' | 54-176 | 402-505 | SEQ ID NO: 11 | SEQ ID NO: 12 | Yes |
| BB' | 54-176 | 402-450 | SEQ ID NO: 13 | SEQ ID NO: 14 | No |
| CA' | 54-100 | 402-505 | SEQ ID NO: 15 | SEQ ID NO: 16 | No |
| CB' | 54-100 | 402-450 | SEQ ID NO: 17 | SEQ ID NO: 18 | No |
| AA'n1-170 | 1-170 | 402-505 | SEQ ID NO: 29 | SEQ ID NO: 30 | Yes |
| AA'n54-170 | 54-170 | 402-505 | SEQ ID NO: 31 | SEQ ID NO: 32 | Yes |
| AB'n1-170 | 1-170 | 402-450 | SEQ ID NO: 37 | SEQ ID NO: 38 | Yes |
| AA'n1-163 | 1-163 | 402-505 | SEQ ID NO: 33 | SEQ ID NO: 34 | Yes |
| AA'n54-163 | 54-163 | 402-505 | SEQ ID NO: 35 | SEQ ID NO: 36 | Yes |
| AB'n1-163 | 1-163 | 402-450 | SEQ ID NO: 39 | SEQ ID NO: 40 | Yes |
| AA'n1-129 | 1-129 | 402-505 | SEQ ID NO: 41 | SEQ ID NO: 42 | Yes |
| AA'n54-129 | 54-129 | 402-505 | SEQ ID NO: 43 | SEQ ID NO: 44 | Yes |
| AB'n1-129 | 1-129 | 402-450 | SEQ ID NO: 45 | SEQ ID NO: 46 | untested |
| AB'n54-129 | 54-129 | 402-450 | SEQ ID NO: 47 | SEQ ID NO: 48 | Untested |
| AA'n1-100 | 1-100 | 402-505 | SEQ ID NO: 49 | SEQ ID NO: 50 | untested |
| AB'n1-100 | 1-100 | 402-450 | SEQ ID NO: 51 | SEQ ID NO: 52 | untested |
| AA'n1-70 | 1-70 | 402-505 | SEQ ID NO: 53 | SEQ ID NO: 54 | No |
| AB'n1-70 | 1-70 | 402-450 | SEQ ID NO: 55 | SEQ ID NO: 56 | No |
| A | 1-176 | | SEQ ID NO: 19 | SEQ ID NO: 20 | No |
| B | 54-176 | | SEQ ID NO: 21 | SEQ ID NO: 22 | No |
| C | 54-100 | | SEQ ID NO: 23 | SEQ ID NO: 24 | No |
| GST-A' | | 402-505 | SEQ ID NO: 25 | SEQ ID NO: 26 | No |
| GST-B' | | 402-450 | SEQ ID NO: 27 | SEQ ID NO: 28 | No |

The results in Table 3 indicate that flagellin variants with at least one polymerization domain (aa 1-50 or aa 450-505) that linked to domains contained within the amino-terminal region (aa 1-176) and those of the carboxy terminus (aa 402-505) are capable of stimulating NF-κB and would thus be expected to be radioprotectors. Physical linkage of the recognition domains may be required for activity as domains supplied unlinked in trans fail to activate NF-κB. As an alternative to the linking of the domains in a single polypeptide, the domains may be linked using a linker, which is a molecule that is used to join two molecules. The linker may be capable of forming covalent bonds or high-affinity non-covalent bonds to both molecules. Suitable linkers are well known to those of ordinary skill in the art and include, but are not limited to, straight or branched-chain carbon linkers, heterocyclic carbon linkers, or peptide linkers. The linkers may be joined to the constituent amino acids through their side groups (e.g., through a disulfide linkage to cysteine).

The region between amino acids 163 and 176 may be required for activity when the carboxyl polymerization domain (aa 450-505) is absent. Since this region is dispensable for activity when the carboxyl polymerization domain is present it may be involved in stabilizing the derivative. The region between amino acids 70 and 129 may be important for activation and may be involved in derivative recognition. The region between amino acids 402 and 450 may also be required for activity. The domains identified above are located within three large α-helices (located within amino acids 54-129 and 402-450) and, to produce an active derivative, may need to form a ring-like structure (with or without polymerization domain).

The invention claimed is:

1. A method of protecting a mammal from gastrointestinal and hematopoietic radiation syndromes comprising administering to a mammal in need thereof a composition comprising a flagellin polypeptide, wherein the polypeptide comprises the amino acid sequence of SEQ ID NO: 8.

2. The method of claim 1, wherein the composition is administered prior to, together with, or after said radiation.

3. The method of claim 1, wherein the composition is administered in combination with a radioprotectant.

* * * * *

SEQUENCE LISTING

```
<160> NUMBER OF SEQ ID NOS: 98

<210> SEQ ID NO 1
<211> LENGTH: 505
<212> TYPE: PRT
<213> ORGANISM: Salmonella dublin

<400> SEQUENCE: 1

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

Val Thr Gly Tyr Asp Thr Tyr Ala Ala Gly Ala Asp Lys Tyr Arg Val
        195                 200                 205

Asp Ile Asn Ser Gly Ala Val Val Thr Asp Ala Ala Ala Pro Asp Lys
    210                 215                 220

Val Tyr Val Asn Ala Ala Asn Gly Gln Leu Thr Thr Asp Asp Ala Glu
225                 230                 235                 240

Asn Asn Thr Ala Val Asp Leu Phe Lys Thr Thr Lys Ser Thr Ala Gly
                245                 250                 255

Thr Ala Glu Ala Lys Ala Ile Ala Gly Ala Ile Lys Gly Gly Lys Glu
            260                 265                 270

Gly Asp Thr Phe Asp Tyr Lys Gly Val Thr Phe Thr Ile Asp Thr Lys
        275                 280                 285

Thr Gly Asp Asp Gly Asn Gly Lys Val Ser Thr Thr Ile Asn Gly Glu
    290                 295                 300

Lys Val Thr Leu Thr Val Ala Asp Ile Ala Thr Gly Ala Ala Asp Val
305                 310                 315                 320
```

```
Asn Ala Ala Thr Leu Gln Ser Lys Asn Val Tyr Thr Ser Val Val
                325                 330                 335

Asn Gly Gln Phe Thr Phe Asp Asp Lys Thr Lys Asn Glu Ser Ala Lys
            340                 345                 350

Leu Ser Asp Leu Glu Ala Asn Asn Ala Val Lys Gly Glu Ser Lys Ile
        355                 360                 365

Thr Val Asn Gly Ala Glu Tyr Thr Ala Asn Ala Thr Gly Asp Lys Ile
    370                 375                 380

Thr Leu Ala Gly Lys Thr Met Phe Ile Asp Lys Thr Ala Ser Gly Val
385                 390                 395                 400

Ser Thr Leu Ile Asn Glu Asp Ala Ala Ala Lys Lys Ser Thr Ala
                405                 410                 415

Asn Pro Leu Ala Ser Ile Asp Ser Ala Leu Ser Lys Val Asp Ala Val
            420                 425                 430

Arg Ser Ser Leu Gly Ala Ile Gln Asn Arg Phe Asp Ser Ala Ile Thr
        435                 440                 445

Asn Leu Gly Asn Thr Val Thr Asn Leu Asn Ser Ala Arg Ser Arg Ile
    450                 455                 460

Glu Asp Ala Asp Tyr Ala Thr Glu Val Ser Asn Met Ser Lys Ala Gln
465                 470                 475                 480

Ile Leu Gln Gln Ala Gly Thr Ser Val Leu Ala Gln Ala Asn Gln Val
                485                 490                 495

Pro Gln Asn Val Leu Ser Leu Leu Arg
            500                 505

<210> SEQ ID NO 2
<211> LENGTH: 1518
<212> TYPE: DNA
<213> ORGANISM: Salmonella dublin

<400> SEQUENCE: 2
atggcacaag tcattaatac aaacagcctg tcgctgttga cccagaataa cctgaacaaa      60
tctcagtcct cactgagttc cgctattgag cgtctgtcct ctggtctgcg tatcaacagc     120
gcgaaagacg atgcggcagg ccaggcgatt gctaaccgct tcacttctaa tatcaaaggc     180
ctgactcagg cttcccgtaa cgctaacgac ggcatttcta ttgcgcagac cactgaaggt     240
gcgctgaatg aaatcaacaa caacctgcag cgtgtgcgtg agttgtctgt tcaggccact     300
aacgggacta actctgattc cgatctgaaa tctatccagg atgaaattca gcaacgtctg     360
gaagaaatcg atcgcgtttc taatcagact caatttaacg tgttaaagt cctctctcag     420 gacaaccaga tgaaaatcca ggttggtgct aacgatggtg aaaccattac catcgatctg     480
caaaaaattg atgtgaaaag ccttggcctt gatgggttca atgttaatgg ccaaaagaa     540 gcgacagtgg gtgatctgaa atccagcttc aagaatgtta cgggttacga cacctatgca     600
gcgggtgccg ataaatatcg tgtagatatt aattccggtg ctgtagtgac tgatgcagca     660
gcaccggata agtatatgt aaatgcagca acggtcagt aacaactga cgatgcggaa     720 aataacactg cggttgatct ctttaagacc actaaatcta ctgctggtac cgctgaagcc     780
aaagcgatag ctggtgccat taaggtggt aaggaaggag ataccttga ttataaaggc     840 gtgacttta ctattgatac aaaaactggt gatgacggta atggtaaggt ttctactacc     900
atcaatggtg aaaaagttac gttaactgtc gctgatattg ccactggcgc ggcggatgtt     960
aatgctgcta cctttacaatc aagcaaaaat gtttatacat ctgtagtgaa cggtcagttt    1020
acttttgatg ataaaaccaa aaacgagagt gcgaaacttt ctgatttgga agcaaacaat    1080
```

-continued

```
gctgttaagg gcgaaagtaa aattacagta aatggggctg aatatactgc taacgccacg    1140
ggtgataaga tcaccttagc tggcaaaacc atgtttattg ataaaacagc ttctggcgta    1200
agtacattaa tcaatgaaga cgctgccgca gccaagaaaa gtaccgctaa cccactggct    1260
tcaattgatt ctgcattgtc aaaagtggac gcagttcgtt cttctctggg ggcaattcaa    1320
aaccgttttg attcagccat taccaacctt ggcaatacgg taaccaatct gaactccgcg    1380
cgtagccgta tcgaagatgc tgactatgca acggaagttt ctaatatgtc taaagcgcag    1440
attctgcagc aggctggtac ttccgttctg gcgcaggcta accaggttcc gcaaaacgtc    1500
ctctctttac tgcgttaa                                                  1518
```

<210> SEQ ID NO 3
<211> LENGTH: 16
<212> TYPE: PRT
<213> ORGANISM: Artificial
<220> FEATURE:
<223> OTHER INFORMATION: peptide linker

<400> SEQUENCE: 3

Ser Pro Gly Ile Ser Gly Gly Gly Gly Gly Ile Leu Asp Ser Met Gly
1               5                   10                  15

<210> SEQ ID NO 4
<211> LENGTH: 16
<212> TYPE: PRT
<213> ORGANISM: Artificial
<220> FEATURE:
<223> OTHER INFORMATION: peptide linker

<400> SEQUENCE: 4

Ile Pro Gly Ile Ser Gly Gly Gly Gly Gly Ile Leu Asp Ser Met Gly
1               5                   10                  15

<210> SEQ ID NO 5
<211> LENGTH: 46
<212> TYPE: DNA
<213> ORGANISM: Artificial
<220> FEATURE:
<223> OTHER INFORMATION: peptide linker

<400> SEQUENCE: 5

```
tccccgggaa tttccggtgg tggtggtgga attctagact ccatgg                    46
```

<210> SEQ ID NO 6
<211> LENGTH: 46
<212> TYPE: DNA
<213> ORGANISM: Artificial
<220> FEATURE:
<223> OTHER INFORMATION: peptide linker

<400> SEQUENCE: 6

```
atcccgggaa tttccggtgg tggtggtgga attctagact ccatgg                    46
```

<210> SEQ ID NO 7
<211> LENGTH: 990
<212> TYPE: DNA
<213> ORGANISM: Salmonella dublin

<400> SEQUENCE: 7

```
atgcggggtt ctcatcatca tcatcatcat ggtatggcta gcatgactgg tggacagcaa     60
atgggtcggg atctgtacga cgatgacgat aaggatccga tggcacaagt cattaataca    120
aacagcctgt cgctgttgac ccagaataac ctgaacaaat ctcagtcctc actgagttcc    180
```

```
gctattgagc gtctgtcctc tggtctgcgt atcaacagcg cgaaagacga tgcggcaggc   240
caggcgattg ctaaccgctt cacttctaat atcaaaggcc tgactcaggc ttcccgtaac   300
gctaacgacg gcatttctat tgcgcagacc actgaaggtg cgctgaatga aatcaacaac   360
aacctgcagc gtgtgcgtga gttgtctgtt caggccacta acgggactaa ctctgattcc   420
gatctgaaat ctatccagga tgaaattcag caacgtctgg aagaaatcga tcgcgtttct   480
aatcagactc aatttaacgg tgttaaagtc ctctctcagg acaaccagat gaaaatccag   540
gttggtgcta acgatggtga accattacc atcgatctgc aaaaaattga tgtgaaaagc   600
cttggccttg atgggttcaa tgttaattcc ccgggaattt ccggtggtgg tggtggaatt   660
ctagactcca tgggtacatt aatcaatgaa gacgctgccg cagccaagaa aagtaccgct   720
aacccactgg cttcaattga ttctgcattg tcaaaagtgg acgcagttcg ttcttctctg   780
ggggcaattc aaaaccgttt tgattcagcc attaccaacc ttggcaatac ggtaaccaat   840
ctgaactccg cgcgtagccg tatcgaagat gctgactatg caacgaagt ttctaatatg   900 tctaaagcgc agattctgca gcaggctggt acttccgttc tggcgcaggc taaccaggtt   960
ccgcaaaacg tcctctcttt actgcgttag                                    990
```

`<210>` SEQ ID NO 8
`<211>` LENGTH: 329
`<212>` TYPE: PRT
`<213>` ORGANISM: Salmonella dublin

`<400>` SEQUENCE: 8

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
        50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
            115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
            195                 200                 205

Asn Ser Pro Gly Ile Ser Gly Gly Gly Gly Ile Leu Asp Ser Met
    210                 215                 220

Gly Thr Leu Ile Asn Glu Asp Ala Ala Ala Lys Lys Ser Thr Ala
225                 230                 235                 240
```

Asn Pro Leu Ala Ser Ile Asp Ser Ala Leu Ser Lys Val Asp Ala Val
            245                 250                 255

Arg Ser Ser Leu Gly Ala Ile Gln Asn Arg Phe Asp Ser Ala Ile Thr
            260                 265                 270

Asn Leu Gly Asn Thr Val Thr Asn Leu Asn Ser Ala Arg Ser Arg Ile
            275                 280                 285

Glu Asp Ala Asp Tyr Ala Thr Glu Val Ser Asn Met Ser Lys Ala Gln
            290                 295                 300

Ile Leu Gln Gln Ala Gly Thr Ser Val Leu Ala Gln Ala Asn Gln Val
305             310                 315                 320

Pro Gln Asn Val Leu Ser Leu Leu Arg
            325

<210> SEQ ID NO 9
<211> LENGTH: 825
<212> TYPE: DNA
<213> ORGANISM: Salmonella dublin

<400> SEQUENCE: 9
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga aatcaacaac     360
aacctgcagc gtgtgcgtga gttgtctgtt caggccacta cgggactaa ctctgattcc     420
gatctgaaat ctatccagga tgaaattcag caacgtctgg aagaaatcga tcgcgtttct     480
aatcagactc aatttaacgg tgttaaagtc ctctctcagg acaaccagat gaaaatccag     540
gttggtgcta cgatggtga aaccattacc atcgatctgc aaaaaattga tgtgaaaagc     600
cttggccttg atgggttcaa tgttaattcc ccgggaattt ccgtggtgg tggtggaatt     660
ctagactcca tgggtacatt aatcaatgaa gacgctgccg cagccaagaa aagtaccgct     720
aaccccactgg cttcaattga ttctgcattg tcaaaagtgg acgcagttcg ttcttctctg     780
ggggcaattc aaaaccgttt tgattcagcc attaccaacc tttag                    825

<210> SEQ ID NO 10
<211> LENGTH: 274
<212> TYPE: PRT
<213> ORGANISM: Salmonella dublin

<400> SEQUENCE: 10

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
        50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Gly Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Ile Leu Asp Ser Met
    210                 215                 220

Gly Thr Leu Ile Asn Glu Asp Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Gln Asn Arg Phe Asp Ser Ala Ile Thr
            260                 265                 270

Asn Leu

<210> SEQ ID NO 11
<211> LENGTH: 831
<212> TYPE: DNA
<213> ORGANISM: Salmonella dublin

<400> SEQUENCE: 11

```
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta ctctgattcc gatctgaaa tctatccagg atgaaattca gcaacgtctg      300
gaagaaatcg atcgcgtttc taatcagact caatttaacg gtgttaaagt cctctctcag     360
gacaaccaga tgaaaatcca ggttggtgct aacgatggtg aaaccattac catcgatctg     420
caaaaaattg atgtgaaaag ccttggcctt gatgggttca atgttaattc cccgggaatt     480
tccggtggtg gtggtggaat tctagactcc atgggtacat taatcaatga agacgctgcc     540
gcagccaaga aaagtaccgc taacccactg gcttcaattg attctgcatt gtcaaaagtg     600
gacgcagttc gttcttctct gggggcaatt caaaaccgtt ttgattcagc cattaccaac     660
cttgcaata cggtaaccaa tctgaactcc gcgcgtagcc gtatcgaaga tgctgactat     720
gcaacggaag tttctaatat gtctaaagcg cagattctgc agcaggctgg tacttccgtt     780
ctggcgcagg ctaaccaggt tccgcaaaac gtcctctctt tactgcgtta g             831
```

<210> SEQ ID NO 12
<211> LENGTH: 276
<212> TYPE: PRT
<213> ORGANISM: Salmonella dublin

<400> SEQUENCE: 12

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
            35                  40                  45

Asn Asp Gly Ile Ser Ile Ala Gln Thr Thr Glu Gly Ala Leu Asn Glu
            50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
            115                 120                 125

Gly Ala Asn Asp Gly Glu Thr Ile Thr Ile Asp Leu Gln Lys Ile Asp
            130                 135                 140

Val Lys Ser Leu Gly Leu Asp Gly Phe Asn Val Asn Ser Pro Gly Ile
145                 150                 155                 160

Ser Gly Gly Gly Gly Ile Leu Asp Ser Met Gly Thr Leu Ile Asn
                165                 170                 175

Glu Asp Ala Ala Ala Ala Lys Lys Ser Thr Ala Asn Pro Leu Ala Ser
            180                 185                 190

Ile Asp Ser Ala Leu Ser Lys Val Asp Ala Val Arg Ser Ser Leu Gly
            195                 200                 205

Ala Ile Gln Asn Arg Phe Asp Ser Ala Ile Thr Asn Leu Gly Asn Thr
            210                 215                 220

Val Thr Asn Leu Asn Ser Ala Arg Ser Arg Ile Glu Asp Ala Asp Tyr
225                 230                 235                 240

Ala Thr Glu Val Ser Asn Met Ser Lys Ala Gln Ile Leu Gln Gln Ala
            245                 250                 255

Gly Thr Ser Val Leu Ala Gln Ala Asn Gln Val Pro Gln Asn Val Leu
            260                 265                 270

Ser Leu Leu Arg
            275

<210> SEQ ID NO 13
<211> LENGTH: 666
<212> TYPE: DNA
<213> ORGANISM: Salmonella dublin

<400> SEQUENCE: 13
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta actctgattc cgatctgaaa tctatccagg atgaaattca gcaacgtctg     300
gaagaaatcg atcgcgtttc taatcagact caatttaacg gtgttaaagt cctctctcag     360
gacaaccaga tgaaaatcca ggttggtgct aacgatggtg aaaccattac catcgatctg     420
caaaaaattg atgtgaaaag ccttggcctt gatgggttca atgttaattc cccgggaatt     480
tccggtggtg gtggtggaat tctagactcc atgggtacat taatcaatga agacgctgcc     540
```

```
gcagccaaga aaagtaccgc taacccactg gcttcaattg attctgcatt gtcaaaagtg      600
gacgcagttc gttcttctct gggggcaatt caaaaccgtt ttgattcagc cattaccaac      660
ctttag                                                                 666
```

<210> SEQ ID NO 14
<211> LENGTH: 221
<212> TYPE: PRT
<213> ORGANISM: Salmonella dublin

<400> SEQUENCE: 14

```
Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
             20                  25                  30

Pro Phe Thr Ser Asn Ile Lys Gly Leu Thr Gln Ala Ser Arg Asn Ala
         35                  40                  45

Asn Asp Gly Ile Ser Ile Ala Gln Thr Thr Glu Gly Ala Leu Asn Glu
     50                  55                  60

Ile Asn Asn Asn Leu Gln Arg Val Arg Glu Leu Ser Val Gln Ala Thr
 65                  70                  75                  80

Asn Gly Thr Asn Ser Asp Ser Asp Leu Lys Ser Ile Gln Asp Glu Ile
                 85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Asp Gly Phe Asn Val Asn Ser Pro Gly Ile
145                 150                 155                 160

Ser Gly Gly Gly Gly Ile Leu Asp Ser Met Gly Thr Leu Ile Asn
                165                 170                 175

Glu Asp Ala Ala Ala Ala Lys Lys Ser Thr Ala Asn Pro Leu Ala Ser
            180                 185                 190

Ile Asp Ser Ala Leu Ser Lys Val Asp Ala Val Arg Ser Ser Leu Gly
        195                 200                 205

Ala Ile Gln Asn Arg Phe Asp Ser Ala Ile Thr Asn Leu
    210                 215                 220
```

<210> SEQ ID NO 15
<211> LENGTH: 603
<212> TYPE: DNA
<213> ORGANISM: Salmonella dublin

<400> SEQUENCE: 15

```
atgcggggtt ctcatcatca tcatcatcat ggtatggcta gcatgactgg tggacagcaa       60
atgggtcggg atctgtacga cgatgacgat aaggatccgt tcacttctaa tatcaaaggc      120
ctgactcagg cttcccgtaa cgctaacgac ggcatttcta ttgcgcagac cactgaaggt      180
gcgctgaatg aaatcaacaa caacctgcag cgtgtgcgtg agttgtctgt tcaggccact      240
tccccgggaa tttccggtgg tggtggtgga attctagact ccatgggtac attaatcaat      300
gaagacgctg ccgcagccaa gaaaagtacc gctaacccac tggcttcaat tgattctgca      360
ttgtcaaaag tggacgcagt tcgttcttct ctggggggaa ttcaaaaccg ttttgattca      420
gccattacca accttggcaa tacggtaacc aatctgaact ccgcgcgtag ccgtatcgaa      480
```

```
gatgctgact atgcaacgga agtttctaat atgtctaaag cgcagattct gcagcaggct      540
ggtacttccg ttctggcgca ggctaaccag gttccgcaaa cgtcctctc tttactgcgt      600 tag                                                                    603
```

<210> SEQ ID NO 16
<211> LENGTH: 200
<212> TYPE: PRT
<213> ORGANISM: Salmonella dublin

<400> SEQUENCE: 16

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Phe Thr Ser Asn Ile Lys Gly Leu Thr Gln Ala Ser Arg Asn Ala
                35                  40                  45

Asn Asp Gly Ile Ser Ile Ala Gln Thr Thr Glu Gly Ala Leu Asn Glu
            50                  55                  60

Ile Asn Asn Asn Leu Gln Arg Val Arg Glu Leu Ser Val Gln Ala Thr
65                  70                  75                  80

Ser Pro Gly Ile Ser Gly Gly Gly Gly Ile Leu Asp Ser Met Gly
                85                  90                  95

Thr Leu Ile Asn Glu Asp Ala Ala Ala Lys Lys Ser Thr Ala Asn
                100                 105                 110

Pro Leu Ala Ser Ile Asp Ser Ala Leu Ser Lys Val Asp Ala Val Arg
            115                 120                 125

Ser Ser Leu Gly Ala Ile Gln Asn Arg Phe Asp Ser Ala Ile Thr Asn
130                 135                 140

Leu Gly Asn Thr Val Thr Asn Leu Asn Ser Ala Arg Ser Arg Ile Glu
145                 150                 155                 160

Asp Ala Asp Tyr Ala Thr Glu Val Ser Asn Met Ser Lys Ala Gln Ile
                165                 170                 175

Leu Gln Gln Ala Gly Thr Ser Val Leu Ala Gln Ala Asn Gln Val Pro
            180                 185                 190

Gln Asn Val Leu Ser Leu Leu Arg
        195                 200
```

<210> SEQ ID NO 17
<211> LENGTH: 438
<212> TYPE: DNA
<213> ORGANISM: Salmonella dublin

<400> SEQUENCE: 17

```
atgcggggtt ctcatcatca tcatcatcat ggtatggcta gcatgactgg tggacagcaa       60
atgggtcggg atctgtacga cgatgacgat aaggatccgt tcacttctaa tatcaaaggc      120
ctgactcagg cttcccgtaa cgctaacgac ggcatttcta ttgcgcagac cactgaaggt      180
gcgctgaatg aaatcaacaa caacctgcag cgtgtgcgtg agttgtctgt tcaggccact      240
tccccgggaa tttccggtgg tggtggtgga attctagact ccatgggtac attaatcaat      300
gaagacgctg ccgcagccaa gaaaagtacc gctaacccac tggcttcaat tgattctgca      360
ttgtcaaaag tggacgcagt tcgttcttct ctgggggcaa ttcaaaaccg ttttgattca      420
gccattacca acctttag                                                    438
```

<210> SEQ ID NO 18
<211> LENGTH: 145

<212> TYPE: PRT
<213> ORGANISM: Salmonella dublin

<400> SEQUENCE: 18

```
Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Phe Thr Ser Asn Ile Lys Gly Leu Thr Gln Ala Ser Arg Asn Ala
        35                  40                  45
Asn Asp Gly Ile Ser Ile Ala Gln Thr Thr Glu Gly Ala Leu Asn Glu
    50                  55                  60
Ile Asn Asn Asn Leu Gln Arg Val Arg Glu Leu Ser Val Gln Ala Thr
65                  70                  75                  80
Ser Pro Gly Ile Ser Gly Gly Gly Gly Ile Leu Asp Ser Met Gly
                85                  90                  95
Thr Leu Ile Asn Glu Asp Ala Ala Ala Lys Lys Ser Thr Ala Asn
            100                 105                 110
Pro Leu Ala Ser Ile Asp Ser Ala Leu Ser Lys Val Asp Ala Val Arg
        115                 120                 125
Ser Ser Leu Gly Ala Ile Gln Asn Arg Phe Asp Ser Ala Ile Thr Asn
    130                 135                 140
Leu
145
```

<210> SEQ ID NO 19
<211> LENGTH: 639
<212> TYPE: DNA
<213> ORGANISM: Salmonella dublin

<400> SEQUENCE: 19

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggtc tgactcaggc ttcccgtaac   300
gctaacgacg gcatttctat tgcgcagacc actgaaggtg cgctgaatga aatcaacaac   360
aacctgcagc gtgtgcgtga gttgtctgtt caggccacta cgggactaa ctctgattcc   420
gatctgaaat ctatccagga tgaaattcag caacgtctgg aagaaatcga tcgcgtttct   480
aatcagactc aatttaacgg tgttaaagtc ctgtctcagg acaaccagat gaaaatccag   540
gttggtgcta cgatggtga aaccattacc atcgatctgc aaaaaattga tgtgaaaagc   600
cttggccttg atgggttcaa tgttaattcc ccgggatga                          639
```

<210> SEQ ID NO 20
<211> LENGTH: 212
<212> TYPE: PRT
<213> ORGANISM: Salmonella dublin

<400> SEQUENCE: 20

```
Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Met Ala Gln Val Ile Asn Thr Asn Ser Leu Ser Leu Leu Thr Gln
```

```
                  35                  40                  45
Asn Asn Leu Asn Lys Ser Gln Ser Ser Leu Ser Ser Ala Ile Glu Arg
 50                  55                  60

Leu Ser Ser Gly Leu Arg Ile Asn Ser Ala Lys Asp Asp Ala Ala Gly
 65                  70                  75                  80

Gln Ala Ile Ala Asn Arg Phe Thr Ser Asn Ile Lys Gly Leu Thr Gln
                 85                  90                  95

Ala Ser Arg Asn Ala Asn Asp Gly Ile Ser Ile Ala Gln Thr Thr Glu
                100                 105                 110

Gly Ala Leu Asn Glu Ile Asn Asn Asn Leu Gln Arg Val Arg Glu Leu
                115                 120                 125

Ser Val Gln Ala Thr Asn Gly Thr Asn Ser Asp Ser Asp Leu Lys Ser
130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
                180                 185                 190

Leu Gln Lys Ile Asp Val Lys Ser Leu Gly Leu Asp Gly Phe Asn Val
                195                 200                 205

Asn Ser Pro Gly
    210

<210> SEQ ID NO 21
<211> LENGTH: 480
<212> TYPE: DNA
<213> ORGANISM: Salmonella dublin

<400> SEQUENCE: 21
atgcggggtt ctcatcatca tcatcatcat ggtatggcta gcatgactgg tggacagcaa      60
atgggtcggg atctgtacga cgatgacgat aaggatccgt tcacttctaa tatcaaaggt     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta actctgattc cgatctgaaa tctatccagg atgaaattca gcaacgtctg     300
gaagaaatcg atcgcgtttc taatcagact caatttaacg gtgttaaagt cctgtctcag     360
gacaaccaga tgaaaatcca ggttggtgct aacgatggtg aaaccattac catcgatctg     420
caaaaaattg atgtgaaaag ccttggcctt gatgggttca tgttaattc cccgggatga     480

<210> SEQ ID NO 22
<211> LENGTH: 159
<212> TYPE: PRT
<213> ORGANISM: Salmonella dublin

<400> SEQUENCE: 22

Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
             20                  25                  30

Pro Phe Thr Ser Asn Ile Lys Gly Leu Thr Gln Ala Ser Arg Asn Ala
            35                  40                  45

Asn Asp Gly Ile Ser Ile Ala Gln Thr Thr Glu Gly Ala Leu Asn Glu
 50                  55                  60

Ile Asn Asn Asn Leu Gln Arg Val Arg Glu Leu Ser Val Gln Ala Thr
```

```
                65                  70                  75                  80
Asn Gly Thr Asn Ser Asp Ser Asp Leu Lys Ser Ile Gln Asp Glu Ile
                    85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Asp Gly Phe Asn Val Asn Ser Pro Gly
145                 150                 155

<210> SEQ ID NO 23
<211> LENGTH: 252
<212> TYPE: DNA
<213> ORGANISM: Salmonella dublin

<400> SEQUENCE: 23
atgcggggtt ctcatcatca tcatcatcat ggtatggcta gcatgactgg tggacagcaa      60
atgggtcggg atctgtacga cgatgacgat aaggatccgt tcacttctaa tatcaaaggt     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
tccccgggat ga                                                         252

<210> SEQ ID NO 24
<211> LENGTH: 83
<212> TYPE: PRT
<213> ORGANISM: Salmonella dublin

<400> SEQUENCE: 24

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Ser Pro Gly

<210> SEQ ID NO 25
<211> LENGTH: 1038
<212> TYPE: DNA
<213> ORGANISM: Salmonella dublin

<400> SEQUENCE: 25
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca atagtaaag actttgaaac tctcaaagtt     360
```

```
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca     600
tggcctttgc agggctggca agccacgttt ggtggtggcg accatcctcc aaaatcggat    660
ctggttccgc gtggatcccc gggaattccc ggtggtggtg gtggaattct agactccatg    720
ggtacattaa tcaatgaaga cgctgccgca gccaagaaaa gtaccgctaa cccactggct    780
tcaattgatt ctgcattgtc aaagtggac gcagttcgtt cttctctggg ggcaattcaa     840
aaccgttttg attcagccat taccaacctt ggcaatacgg taaccaatct gaactccgcg    900
cgtagccgta tcgaagatgc tgactatgca acggaagttt ctaatatgtc taaagcgcag    960
attctgcagc aggctggtac ttccgttctg gcgcaggcta accaggttcc gcaaaacgtc   1020
ctctctttac tgcgttag                                                  1038

<210> SEQ ID NO 26
<211> LENGTH: 345
<212> TYPE: PRT
<213> ORGANISM: Salmonella dublin

<400> SEQUENCE: 26

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Ser Gly Gly Gly Gly Ile Leu Asp Ser Met
225                 230                 235                 240

Gly Thr Leu Ile Asn Glu Asp Ala Ala Ala Lys Lys Ser Thr Ala
                245                 250                 255
```

```
Asn Pro Leu Ala Ser Ile Asp Ser Ala Leu Ser Lys Val Asp Ala Val
            260                 265                 270

Arg Ser Ser Leu Gly Ala Ile Gln Asn Arg Phe Asp Ser Ala Ile Thr
        275                 280                 285

Asn Leu Gly Asn Thr Val Thr Asn Leu Asn Ser Ala Arg Ser Arg Ile
    290                 295                 300

Glu Asp Ala Asp Tyr Ala Thr Glu Val Ser Asn Met Ser Lys Ala Gln
305                 310                 315                 320

Ile Leu Gln Gln Ala Gly Thr Ser Val Leu Ala Gln Ala Asn Gln Val
                325                 330                 335

Pro Gln Asn Val Leu Ser Leu Leu Arg
            340                 345
```

<210> SEQ ID NO 27
<211> LENGTH: 873
<212> TYPE: DNA
<213> ORGANISM: Salmonella dublin

<400> SEQUENCE: 27

```
atgtcccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagattcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa gtatatagca   600
tggcctttgc agggctggca agccacgttt ggtggtggcg accatcctcc aaaatcggat   660
ctggttccgc gtggatcccc gggaatttcc ggtggtggtg gtggaattct agactccatg   720
ggtacattaa tcaatgaaga cgctgccgca gccaagaaaa gtaccgctaa cccactggct   780
tcaattgatt ctgcattgtc aaaagtggac gcagttcgtt cttctctggg ggcaattcaa   840
aaccgttttg attcagccat taccaacctt tag                                873
```

<210> SEQ ID NO 28
<211> LENGTH: 290
<212> TYPE: PRT
<213> ORGANISM: Salmonella dublin

<400> SEQUENCE: 28

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
```

```
                85                  90                  95
Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
            210                 215                 220

Gly Ser Pro Gly Ile Ser Gly Gly Gly Gly Ile Leu Asp Ser Met
225                 230                 235                 240

Gly Thr Leu Ile Asn Glu Asp Ala Ala Ala Lys Lys Ser Thr Ala
                245                 250                 255

Asn Pro Leu Ala Ser Ile Asp Ser Leu Ser Lys Val Asp Ala Val
            260                 265                 270

Arg Ser Ser Leu Gly Ala Ile Gln Asn Arg Phe Asp Ser Ala Ile Thr
            275                 280                 285

Asn Leu
    290

<210> SEQ ID NO 29
<211> LENGTH: 972
<212> TYPE: DNA
<213> ORGANISM: Salmonella dublin

<400> SEQUENCE: 29
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga atcaacaac      360 aacctgcagc gtgtgcgtga gttgtctgtt caggccacta cgggactaa ctctgattcc      420 gatctgaaat ctatccagga tgaaattcag caacgtctgg aagaaatcga tcgcgtttct     480
aatcagactc aatttaacgg tgttaaagtc ctctctcagg acaaccagat gaaaatccag     540
gttggtgcta cgatggtga aaccattacc atcgatctgc aaaaaattga tgtgaaaagc      600
cttggcctta tcccgggaat tccggtggt ggtggtggaa ttctagactc catgggtaca      660
ttaatcaatg aagacgctgc cgcagccaag aaaagtaccg ctaacccact ggcttcaatt     720
gattctgcat tgtcaaaagt ggacgcagtt cgttcttctc tgggggcaat tcaaaaccgt     780
tttgattcag ccattaccaa ccttggcaat acggtaacca atctgaactc cgcgcgtagc     840
cgtatcgaag atgctgacta tgcaacggaa gtttctaata tgtctaaagc gcagattctg     900
cagcaggctg gtacttccgt tctggcgcag gctaaccagg ttccgcaaaa cgtcctctct     960
```
ttactgcgtt ag                                                         972

<210> SEQ ID NO 30
<211> LENGTH: 323
<212> TYPE: PRT
<213> ORGANISM: Salmonella dublin

<400> SEQUENCE: 30

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
        50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
            115                 120                 125

Ser Val Gln Ala Thr Asn Gly Thr Asn Ser Asp Ser Asp Leu Lys Ser
130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Ile Pro Gly Ile Ser
            195                 200                 205

Gly Gly Gly Gly Ile Leu Asp Ser Met Gly Thr Leu Ile Asn Glu
        210                 215                 220

Asp Ala Ala Ala Lys Lys Ser Thr Ala Asn Pro Leu Ala Ser Ile
225                 230                 235                 240

Asp Ser Ala Leu Ser Lys Val Asp Ala Val Arg Ser Ser Leu Gly Ala
                245                 250                 255

Ile Gln Asn Arg Phe Asp Ser Ala Ile Thr Asn Leu Gly Asn Thr Val
            260                 265                 270

Thr Asn Leu Asn Ser Ala Arg Ser Arg Ile Glu Asp Ala Asp Tyr Ala
        275                 280                 285

Thr Glu Val Ser Asn Met Ser Lys Ala Gln Ile Leu Gln Gln Ala Gly
        290                 295                 300

Thr Ser Val Leu Ala Gln Ala Asn Gln Val Pro Gln Asn Val Leu Ser
305                 310                 315                 320

Leu Leu Arg

<210> SEQ ID NO 31
<211> LENGTH: 813
<212> TYPE: DNA
<213> ORGANISM: Salmonella dublin

<400> SEQUENCE: 31

```
atgcggggtt ctcatcatca tcatcatcat ggtatggcta gcatgactgg tggacagcaa    60
atgggtcggg atctgtacga cgatgacgat aaggatccgt tcacttctaa tatcaaaggc   120
ctgactcagg cttcccgtaa cgctaacgac ggcatttcta ttgcgcagac cactgaaggt   180
gcgctgaatg aaatcaacaa caacctgcag cgtgtgcgtg agttgtctgt tcaggccact   240
aacgggacta actctgattc cgatctgaaa tctatccagg atgaaattca gcaacgtctg   300
gaagaaatcg atcgcgtttc taatcagact caatttaacg gtgttaaagt cctctctcag   360
gacaaccaga tgaaaatcca ggttggtgct aacgatggtg aaaccattac catcgatctg   420
caaaaaattg atgtgaaaag ccttggcctt atcccgggaa tttccggtgg tggtggtgga   480
attctagact ccatgggtac attaatcaat gaagacgctg ccgcagccaa gaaaagtacc   540
gctaacccac tggcttcaat tgattctgca ttgtcaaaag tggacgcagt tcgttcttct   600
ctggggggcaa ttcaaaaccg ttttgattca gccattacca accttggcaa tacggtaacc   660
aatctgaact ccgcgcgtag ccgtatcgaa gatgctgact atgcaacgga agtttctaat   720
atgtctaaag cgcagattct gcagcaggct ggtacttccg ttctggcgca ggctaaccag   780
gttccgcaaa acgtcctctc tttactgcgt tag                                813
```

<210> SEQ ID NO 32
<211> LENGTH: 270
<212> TYPE: PRT
<213> ORGANISM: Salmonella dublin

<400> SEQUENCE: 32

```
Met Arg Gly Ser His His His His His Gly Met Ala Ser Met Thr
 1               5                  10                  15

Gly Gly Gln Gln Met Gly Arg Asp Leu Tyr Asp Asp Asp Lys Asp
                20                  25                  30

Pro Phe Thr Ser Asn Ile Lys Gly Leu Thr Gln Ala Ser Arg Asn Ala
                35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Ile Pro Gly Ile Ser Gly Gly Gly Gly Gly
145                 150                 155                 160

Ile Leu Asp Ser Met Gly Thr Leu Ile Asn Glu Asp Ala Ala Ala Ala
                165                 170                 175

Lys Lys Ser Thr Ala Asn Pro Leu Ala Ser Ile Asp Ser Ala Leu Ser
            180                 185                 190

Lys Val Asp Ala Val Arg Ser Ser Leu Gly Ala Ile Gln Asn Arg Phe
        195                 200                 205

Asp Ser Ala Ile Thr Asn Leu Gly Asn Thr Val Thr Asn Leu Asn Ser
    210                 215                 220

Ala Arg Ser Arg Ile Glu Asp Ala Asp Tyr Ala Thr Glu Val Ser Asn
```

```
                225                 230                 235                 240
Met Ser Lys Ala Gln Ile Leu Gln Gln Ala Gly Thr Ser Val Leu Ala
                245                 250                 255
Gln Ala Asn Gln Val Pro Gln Asn Val Leu Ser Leu Leu Arg
            260                 265                 270

<210> SEQ ID NO 33
<211> LENGTH: 951
<212> TYPE: DNA
<213> ORGANISM: Salmonella dublin

<400> SEQUENCE: 33
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggcc tgactcaggc ttcccgtaac   300
gctaacgacg gcatttctat tgcgcagacc actgaaggtg cgctgaatga aatcaacaac   360
aacctgcagc gtgtgcgtga gttgtctgtt caggccacta cgggactaaa ctctgattcc   420
gatctgaaat ctatccagga tgaaattcag caacgtctgg aagaaatcga tcgcgtttct   480
aatcagactc aatttaacgg tgttaaagtc ctctctcagg acaaccagat gaaaatccag   540
gttggtgcta cgatggtga aaccattacc atcgatctgc aaaaaattat cccgggaatt   600
tccggtggtg gtggtggaat tctagactcc atgggtacat taatcaatga agacgctgcc   660
gcagccaaga aaagtaccgc taacccactg gcttcaattg attctgcatt gtcaaaagtg   720
gacgcagttc gttcttctct gggggcaatt caaaaccgtt ttgattcagc cattaccaac   780
cttggcaata cggtaaccaa tctgaactcc gcgcgtagcc gtatcgaaga tgctgactat   840
gcaacggaag tttctaatat gtctaaagcg cagattctgc agcaggctgg tacttccgtt   900
ctggcgcagg ctaaccaggt tccgcaaaac gtcctctctt tactgcgtta g            951

<210> SEQ ID NO 34
<211> LENGTH: 316
<212> TYPE: PRT
<213> ORGANISM: Salmonella dublin

<400> SEQUENCE: 34

Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Met Ala Gln Val Ile Asn Thr Asn Ser Leu Ser Leu Leu Thr Gln
        35                  40                  45
Asn Asn Leu Asn Lys Ser Gln Ser Ser Leu Ser Ser Ala Ile Glu Arg
    50                  55                  60
Leu Ser Ser Gly Leu Arg Ile Asn Ser Ala Lys Asp Asp Ala Ala Gly
65                  70                  75                  80
Gln Ala Ile Ala Asn Arg Phe Thr Ser Asn Ile Lys Gly Leu Thr Gln
                85                  90                  95
Ala Ser Arg Asn Ala Asn Asp Gly Ile Ser Ile Ala Gln Thr Thr Glu
            100                 105                 110
Gly Ala Leu Asn Glu Ile Asn Asn Asn Leu Gln Arg Val Arg Glu Leu
        115                 120                 125
```

Ser Val Gln Ala Thr Asn Gly Thr Asn Ser Asp Ser Asp Leu Lys Ser
130                 135                 140

Ile Gln Asp Glu Ile Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
                180                 185                 190

Leu Gln Lys Ile Ile Pro Gly Ile Ser Gly Gly Gly Gly Ile Leu
        195                 200                 205

Asp Ser Met Gly Thr Leu Ile Asn Glu Asp Ala Ala Ala Lys Lys
210                 215                 220

Ser Thr Ala Asn Pro Leu Ala Ser Ile Asp Ser Ala Leu Ser Lys Val
225                 230                 235                 240

Asp Ala Val Arg Ser Ser Leu Gly Ala Ile Gln Asn Arg Phe Asp Ser
                245                 250                 255

Ala Ile Thr Asn Leu Gly Asn Thr Val Thr Asn Leu Asn Ser Ala Arg
                260                 265                 270

Ser Arg Ile Glu Asp Ala Asp Tyr Ala Thr Glu Val Ser Asn Met Ser
                275                 280                 285

Lys Ala Gln Ile Leu Gln Gln Ala Gly Thr Ser Val Leu Ala Gln Ala
                290                 295                 300

Asn Gln Val Pro Gln Asn Val Leu Ser Leu Leu Arg
305                 310                 315

<210> SEQ ID NO 35
<211> LENGTH: 792
<212> TYPE: DNA
<213> ORGANISM: Salmonella dublin

<400> SEQUENCE: 35
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta ctctgattc cgatctgaaa tctatccagg atgaaattca gcaacgtctg     300
gaagaaatcg atcgcgtttc taatcagact caatttaacg gtgttaaagt cctctctcag     360
gacaaccaga tgaaaatcca ggttggtgct aacgatggtg aaaccattac catcgatctg     420
caaaaaatta tcccgggaat tccggtggt ggtggtggaa ttctagactc catgggtaca     480
ttaatcaatg aagacgctgc cgcagccaag aaaagtaccg ctaacccact ggcttcaatt     540
gattctgcat tgtcaaagt ggacgcagtt cgttcttctc tgggggcaat tcaaaaccgt     600
tttgattcag ccattaccaa ccttggcaat acggtaacca atctgaactc cgcgcgtagc     660
cgtatcgaag atgctgacta tgcaacggaa gtttctaata tgtctaaagc gcagattctg     720
cagcaggctg gtacttccgt tctggcgcag gctaaccagg ttccgcaaaa cgtcctctct     780
ttactgcgtt ag                                                         792

<210> SEQ ID NO 36
<211> LENGTH: 263
<212> TYPE: PRT
<213> ORGANISM: Salmonella dublin

<400> SEQUENCE: 36

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
            35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
            115                 120                 125

Gly Ala Asn Asp Gly Glu Thr Ile Thr Ile Asp Leu Gln Lys Ile Ile
        130                 135                 140

Pro Gly Ile Ser Gly Gly Gly Gly Ile Leu Asp Ser Met Gly Thr
145                 150                 155                 160

Leu Ile Asn Glu Asp Ala Ala Ala Lys Lys Ser Thr Ala Asn Pro
            165                 170                 175

Leu Ala Ser Ile Asp Ser Ala Leu Ser Lys Val Asp Ala Val Arg Ser
            180                 185                 190

Ser Leu Gly Ala Ile Gln Asn Arg Phe Asp Ser Ala Ile Thr Asn Leu
            195                 200                 205

Gly Asn Thr Val Thr Asn Leu Asn Ser Ala Arg Ser Arg Ile Glu Asp
    210                 215                 220

Ala Asp Tyr Ala Thr Glu Val Ser Asn Met Ser Lys Ala Gln Ile Leu
225                 230                 235                 240

Gln Gln Ala Gly Thr Ser Val Leu Ala Gln Ala Asn Gln Val Pro Gln
            245                 250                 255

Asn Val Leu Ser Leu Leu Arg
            260

<210> SEQ ID NO 37
<211> LENGTH: 807
<212> TYPE: DNA
<213> ORGANISM: Salmonella dublin

<400> SEQUENCE: 37
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga atcaacaac      360 aacctgcagc gtgtgcgtga gttgtctgtt caggccacta acgggactaa ctctgattcc     420
gatctgaaat ctatccagga tgaaattcag caacgtctgg aagaaatcga tcgcgtttct     480
aatcagactc aatttaacgg tgttaaagtc ctctctcagg acaaccagat gaaaatccag     540
gttggtgcta acgatggtga aaccattacc atcgatctgc aaaaaattga tgtgaaaagc     600
cttggcctta tcccgggaat tccggtggt ggtggtggaa ttctagactc catgggtaca      660
```

```
ttaatcaatg aagacgctgc cgcagccaag aaaagtaccg ctaacccact ggcttcaatt    720
gattctgcat tgtcaaaagt ggacgcagtt cgttcttctc tgggggcaat tcaaaaccgt    780
tttgattcag ccattaccaa cctttag                                        807
```

<210> SEQ ID NO 38
<211> LENGTH: 268
<212> TYPE: PRT
<213> ORGANISM: Salmonella dublin

<400> SEQUENCE: 38

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Ala Gln Val Ile Asn Thr Asn Ser Leu Ser Leu Thr Gln
                35                  40                  45

Asn Asn Leu Asn Lys Ser Gln Ser Ser Leu Ser Ser Ala Ile Glu Arg
50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
                100                 105                 110

Gly Ala Leu Asn Glu Ile Asn Asn Asn Leu Gln Arg Val Arg Glu Leu
                115                 120                 125

Ser Val Gln Ala Thr Asn Gly Thr Asn Ser Asp Ser Asp Leu Lys Ser
130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
                180                 185                 190

Leu Gln Lys Ile Asp Val Lys Ser Leu Gly Leu Ile Pro Gly Ile Ser
                195                 200                 205

Gly Gly Gly Gly Gly Ile Leu Asp Ser Met Gly Thr Leu Ile Asn Glu
                210                 215                 220

Asp Ala Ala Ala Ala Lys Lys Ser Thr Ala Asn Pro Leu Ala Ser Ile
225                 230                 235                 240

Asp Ser Ala Leu Ser Lys Val Asp Ala Val Arg Ser Ser Leu Gly Ala
                245                 250                 255

Ile Gln Asn Arg Phe Asp Ser Ala Ile Thr Asn Leu
                260                 265
```

<210> SEQ ID NO 39
<211> LENGTH: 786
<212> TYPE: DNA
<213> ORGANISM: Salmonella dublin

<400> SEQUENCE: 39

```
atgcggggtt ctcatcatca tcatcatcat ggtatggcta gcatgactgg tggacagcaa     60
atgggtcggg atctgtacga cgatgacgat aaggatccga tggcacaagt cattaataca    120
aacagcctgt cgctgttgac ccagaataac ctgaacaaat ctcagtcctc actgagttcc    180
```

```
gctattgagc gtctgtcctc tggtctgcgt atcaacagcg cgaaagacga tgcggcaggc    240
caggcgattg ctaaccgctt cacttctaat atcaaaggcc tgactcaggc ttcccgtaac    300
gctaacgacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagactc aatttaacgg tgttaaagtc ctctctcagg acaaccagat gaaaatccag    540
gttggtgcta acgatggtga aaccattacc atcgatctgc aaaaaattat cccgggaatt    600
tccggtggtg gtggtggaat tctagactcc atgggtacat taatcaatga agacgctgcc    660
gcagccaaga aaagtaccgc taacccactg gcttcaattg attctgcatt gtcaaaagtg    720
gacgcagttc gttcttctct gggggcaatt caaaaccgtt ttgattcagc cattaccaac    780
ctttag                                                              786

<210> SEQ ID NO 40
<211> LENGTH: 261
<212> TYPE: PRT
<213> ORGANISM: Salmonella dublin

<400> SEQUENCE: 40

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Ile Pro Gly Ile Ser Gly Gly Gly Gly Ile Leu
        195                 200                 205

Asp Ser Met Gly Thr Leu Ile Asn Glu Asp Ala Ala Ala Ala Lys Lys
210                 215                 220

Ser Thr Ala Asn Pro Leu Ala Ser Ile Asp Ser Ala Leu Ser Lys Val
225                 230                 235                 240

Asp Ala Val Arg Ser Ser Leu Gly Ala Ile Gln Asn Arg Phe Asp Ser
                245                 250                 255

Ala Ile Thr Asn Leu
            260
```

<210> SEQ ID NO 41
<211> LENGTH: 849
<212> TYPE: DNA
<213> ORGANISM: Salmonella dublin

<400> SEQUENCE: 41

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtcgtcctc tggtctgcgt atcaacagcg cgaaagacga tgcggcaggc   240
caggcgattg ctaaccgctt cacttctaat atcaaaggcc tgactcaggc ttcccgtaac   300
gctaacgacg gcatttctat tgcgcagacc actgaaggtg cgctgaatga atcaacaac   360
aacctgcagc gtgtgcgtga gttgtctgtt caggccacta acgggactaa ctctgattcc   420
gatctgaaat ctatccagga tgaaattcag caacgtctgg aagaaatcga tcgcgtttct   480
aatcagatcc cgggaatttc cggtggtggt ggtggaattc tagactccat gggtacatta   540
atcaatgaag acgctgccgc agccaagaaa agtaccgcta cccactggc ttcaattgat   600
tctgcattgt caaaagtgga cgcagttcgt tcttctctgg gggcaattca aaaccgtttt   660
gattcagcca ttaccaacct tggcaatacg gtaaccaatc tgaactccgc gcgtagccgt   720
atcgaagatg ctgactatgc aacggaagtt tctaatatgt ctaaagcgca gattctgcag   780
caggctggta cttccgttct ggcgcaggct aaccaggttc gcaaaacgt cctctcttta   840
ctgcgttag                                                           849
```

<210> SEQ ID NO 42
<211> LENGTH: 282
<212> TYPE: PRT
<213> ORGANISM: Salmonella dublin

<400> SEQUENCE: 42

```
Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Met Ala Gln Val Ile Asn Thr Asn Ser Leu Ser Leu Leu Thr Gln
        35                  40                  45
Asn Asn Leu Asn Lys Ser Gln Ser Ser Leu Ser Ser Ala Ile Glu Arg
    50                  55                  60
Leu Ser Ser Gly Leu Arg Ile Asn Ser Ala Lys Asp Asp Ala Ala Gly
65                  70                  75                  80
Gln Ala Ile Ala Asn Arg Phe Thr Ser Asn Ile Lys Gly Leu Thr Gln
                85                  90                  95
Ala Ser Arg Asn Ala Asn Asp Gly Ile Ser Ile Ala Gln Thr Thr Glu
            100                 105                 110
Gly Ala Leu Asn Glu Ile Asn Asn Leu Gln Arg Val Arg Glu Leu
        115                 120                 125
Ser Val Gln Ala Thr Asn Gly Thr Asn Ser Asp Ser Asp Leu Lys Ser
    130                 135                 140
Ile Gln Asp Glu Ile Gln Gln Arg Leu Glu Glu Ile Asp Arg Val Ser
145                 150                 155                 160
Asn Gln Ile Pro Gly Ile Ser Gly Gly Gly Gly Ile Leu Asp Ser
                165                 170                 175
```

```
Met Gly Thr Leu Ile Asn Glu Asp Ala Ala Ala Lys Lys Ser Thr
            180                 185                 190

Ala Asn Pro Leu Ala Ser Ile Asp Ser Ala Leu Ser Lys Val Asp Ala
        195                 200                 205

Val Arg Ser Ser Leu Gly Ala Ile Gln Asn Arg Phe Asp Ser Ala Ile
    210                 215                 220

Thr Asn Leu Gly Asn Thr Val Thr Asn Leu Asn Ser Ala Arg Ser Arg
225                 230                 235                 240

Ile Glu Asp Ala Asp Tyr Ala Thr Glu Val Ser Asn Met Ser Lys Ala
                245                 250                 255

Gln Ile Leu Gln Gln Ala Gly Thr Ser Val Leu Ala Gln Ala Asn Gln
            260                 265                 270

Val Pro Gln Asn Val Leu Ser Leu Leu Arg
        275                 280

<210> SEQ ID NO 43
<211> LENGTH: 690
<212> TYPE: DNA
<213> ORGANISM: Salmonella dublin

<400> SEQUENCE: 43
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta actctgattc cgatctgaaa tctatccagg atgaaattca gcaacgtctg     300
gaagaaatcg atcgcgtttc taatcagatc ccgggaattt ccgtggtgg tggtggaattt     360
ctagactcca tgggtacatt aatcaatgaa gacgctgccg cagccaagaa aagtaccgct     420
aaccccactgg cttcaattga ttctgcattg tcaaaagtgg acgcagttcg ttcttctctg     480
ggggcaattc aaaaccgttt tgattcagcc attaccaacc ttggcaatac ggtaaccaat     540
ctgaactccg cgcgtagccg tatcgaagat gctgactatg caacggaagt ttctaatatg     600
tctaaagcgc agattctgca gcaggctggt acttccgttc tggcgcaggc taaccaggtt     660
ccgcaaaacg tcctctcttt actgcgttag                                      690

<210> SEQ ID NO 44
<211> LENGTH: 229
<212> TYPE: PRT
<213> ORGANISM: Salmonella dublin

<400> SEQUENCE: 44

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Ile Pro Gly
```

| | | | | | | | | | | | |
|---|---|---|---|---|---|---|---|---|---|---|---|
| | | | | 100 | | | | 105 | | | 110 |
| Ile | Ser | Gly | Gly | Gly | Gly | Ile | Leu | Asp | Ser | Met | Gly | Thr | Leu | Ile |
| | | 115 | | | | 120 | | | | 125 | |

Ile Ser Gly Gly Gly Gly Ile Leu Asp Ser Met Gly Thr Leu Ile
            115                    120                    125

Asn Glu Asp Ala Ala Ala Ala Lys Lys Ser Thr Ala Asn Pro Leu Ala
130                    135                    140

Ser Ile Asp Ser Ala Leu Ser Lys Val Asp Ala Val Arg Ser Ser Leu
145                    150                    155                    160

Gly Ala Ile Gln Asn Arg Phe Asp Ser Ala Ile Thr Asn Leu Gly Asn
                    165                    170                    175

Thr Val Thr Asn Leu Asn Ser Ala Arg Ser Arg Ile Glu Asp Ala Asp
        180                    185                    190

Tyr Ala Thr Glu Val Ser Asn Met Ser Lys Ala Gln Ile Leu Gln Gln
            195                    200                    205

Ala Gly Thr Ser Val Leu Ala Gln Ala Asn Gln Val Pro Gln Asn Val
210                    215                    220

Leu Ser Leu Leu Arg
225

<210> SEQ ID NO 45
<211> LENGTH: 684
<212> TYPE: DNA
<213> ORGANISM: Salmonella dublin

<400> SEQUENCE: 45

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggcc tgactcaggc ttcccgtaac   300
gctaacgacg gcatttctat tgcgcagacc actgaaggtg cgctgaatga aatcaacaac   360
aacctgcagc gtgtgcgtga gttgtctgtt caggccacta acgggactaa ctctgattcc   420
gatctgaaat ctatccagga tgaaattcag caacgtctgg aagaaatcga tcgcgtttct   480
aatcagatcc cgggaatttc cggtggtggt ggtggaattc tagactccat gggtacatta   540
atcaatgaag acgctgccgc agccaagaaa agtaccgcta acccactggc ttcaattgat   600
tctgcattgt caaaagtgga cgcagttcgt tcttctctgg ggcaattca aaaccgtttt   660
gattcagcca ttaccaacct ttag                                          684
```

<210> SEQ ID NO 46
<211> LENGTH: 227
<212> TYPE: PRT
<213> ORGANISM: Salmonella dublin

<400> SEQUENCE: 46

Met Arg Gly Ser His His His His His His Gly Met Ala Ser Met Thr
1                  5                    10                    15

Gly Gly Gln Gln Met Gly Arg Asp Leu Tyr Asp Asp Asp Lys Asp
                    20                    25                    30

Pro Met Ala Gln Val Ile Asn Thr Asn Ser Leu Ser Leu Thr Gln
              35                    40                    45

Asn Asn Leu Asn Lys Ser Gln Ser Ser Leu Ser Ala Ile Glu Arg
    50                    55                    60

Leu Ser Ser Gly Leu Arg Ile Asn Ser Ala Lys Asp Asp Ala Ala Gly
65                    70                    75                    80

```
Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Ile Pro Gly Ile Ser Gly Gly Gly Gly Ile Leu Asp Ser
            165                 170                 175

Met Gly Thr Leu Ile Asn Glu Asp Ala Ala Ala Lys Lys Ser Thr
        180                 185                 190

Ala Asn Pro Leu Ala Ser Ile Asp Ser Ala Leu Ser Lys Val Asp Ala
            195                 200                 205

Val Arg Ser Ser Leu Gly Ala Ile Gln Asn Arg Phe Asp Ser Ala Ile
    210                 215                 220

Thr Asn Leu
225

<210> SEQ ID NO 47
<211> LENGTH: 525
<212> TYPE: DNA
<213> ORGANISM: Salmonella dublin

<400> SEQUENCE: 47
atgcggggtt ctcatcatca tcatcatcat ggtatggcta gcatgactgg tggacagcaa     60
atgggtcggg atctgtacga cgatgacgat aaggatccgt tcacttctaa tatcaaaggc    120
ctgactcagg cttcccgtaa cgctaacgac ggcatttcta ttgcgcagac cactgaaggt    180
gcgctgaatg aaatcaacaa caacctgcag cgtgtgcgtg agttgtctgt tcaggccact    240
aacgggacta actctgattc cgatctgaaa tctatccagg atgaaattca gcaacgtctg    300
gaagaaatcg atcgcgtttc taatcagatc ccgggaattt ccggtggtgg tggtggaatt    360
ctagactcca tgggtacatt aatcaatgaa gacgctgccg cagccaagaa aagtaccgct    420
aacccactgg cttcaattga ttctgcattg tcaaaagtgg acgcagttcg ttcttctctg    480
ggggcaattc aaaaccgttt tgattcagcc attaccaacc tttag               525

<210> SEQ ID NO 48
<211> LENGTH: 174
<212> TYPE: PRT
<213> ORGANISM: Salmonella dublin

<400> SEQUENCE: 48

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80
```

```
Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Ile Pro Gly
            100                 105                 110

Ile Ser Gly Gly Gly Gly Gly Ile Leu Asp Ser Met Gly Thr Leu Ile
        115                 120                 125

Asn Glu Asp Ala Ala Ala Ala Lys Lys Ser Thr Ala Asn Pro Leu Ala
    130                 135                 140

Ser Ile Asp Ser Ala Leu Ser Lys Val Asp Ala Val Arg Ser Ser Leu
145                 150                 155                 160

Gly Ala Ile Gln Asn Arg Phe Asp Ser Ala Ile Thr Asn Leu
                165                 170
```

<210> SEQ ID NO 49
<211> LENGTH: 762
<212> TYPE: DNA
<213> ORGANISM: Salmonella dublin

<400> SEQUENCE: 49

```
atgcggggtt ctcatcatca tcatcatcat ggtatggcta gcatgactgg tggacagcaa     60
atgggtcggg atctgtacga cgatgacgat aaggatccga tggcacaagt cattaataca    120
aacagcctgt cgctgttgac ccagaataac ctgaacaaat ctcagtcctc actgagttcc    180
gctattgagc gtctgtcctc tggtctgcgt atcaacagcg cgaaagacga tgcggcaggc    240
caggcgattg ctaaccgctt cacttctaat atcaaaggcc tgactcaggc ttcccgtaac    300
gctaacgacg gcatttctat tgcgcagacc actgaaggtg cgctgaatga atcaacaac     360
aacctgcagc gtgtgcgtga gttgtctgtt caggccacta cccgggaat tccggtggt     420
ggtggtggaa ttctagactc catgggtaca ttaatcaatg aagacgctgc cgcagccaag    480
aaaagtaccg ctaacccact ggcttcaatt gattctgcat tgtcaaaagt ggacgcagtt    540
cgttcttctc tggggggcaat tcaaaaccgt tttgattcag ccattaccaa ccttggcaat    600
acggtaacca atctgaactc cgcgcgtagc cgtatcgaag atgctgacta tgcaacggaa    660
gtttctaata tgtctaaagc gcagattctg cagcaggctg gtacttccgt tctggcgcag    720
gctaaccagg ttccgcaaaa cgtcctctct ttactgcgtt ag                       762
```

<210> SEQ ID NO 50
<211> LENGTH: 253
<212> TYPE: PRT
<213> ORGANISM: Salmonella dublin

<400> SEQUENCE: 50

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110
```

```
Gly Ala Leu Asn Glu Ile Asn Asn Leu Gln Arg Val Arg Glu Leu
            115                 120                 125

Ser Val Gln Ala Thr Ile Pro Gly Ile Ser Gly Gly Gly Gly Ile
            130                 135                 140

Leu Asp Ser Met Gly Thr Leu Ile Asn Glu Asp Ala Ala Ala Lys
145                 150                 155                 160

Lys Ser Thr Ala Asn Pro Leu Ala Ser Ile Asp Ser Ala Leu Ser Lys
                165                 170                 175

Val Asp Ala Val Arg Ser Ser Leu Gly Ala Ile Gln Asn Arg Phe Asp
                180                 185                 190

Ser Ala Ile Thr Asn Leu Gly Asn Thr Val Thr Asn Leu Asn Ser Ala
                195                 200                 205

Arg Ser Arg Ile Glu Asp Ala Asp Tyr Ala Thr Glu Val Ser Asn Met
            210                 215                 220

Ser Lys Ala Gln Ile Leu Gln Gln Ala Gly Thr Ser Val Leu Ala Gln
225                 230                 235                 240

Ala Asn Gln Val Pro Gln Asn Val Leu Ser Leu Leu Arg
                245                 250
```

<210> SEQ ID NO 51
<211> LENGTH: 597
<212> TYPE: DNA
<213> ORGANISM: Salmonella dublin

<400> SEQUENCE: 51

```
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga atcaacaac      360
aacctgcagc gtgtgcgtga gttgtctgtt caggccacta tcccgggaat ttccggtggt     420
ggtggtggaa ttctagactc catgggtaca ttaatcaatg aagacgctgc cgcagccaag     480
aaaagtaccg ctaaccccact ggcttcaatt gattctgcat tgtcaaaagt ggacgcagtt    540
cgttcttctc tggggcaat tcaaaaccgt tttgattcag ccattaccaa cctttag        597
```

<210> SEQ ID NO 52
<211> LENGTH: 198
<212> TYPE: PRT
<213> ORGANISM: Salmonella dublin

<400> SEQUENCE: 52

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
        50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
```

```
                        85                  90                  95
Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
            115                 120                 125

Ser Val Gln Ala Thr Ile Pro Gly Ile Ser Gly Gly Gly Gly Ile
        130                 135                 140

Leu Asp Ser Met Gly Thr Leu Ile Asn Glu Asp Ala Ala Ala Lys
145                 150                 155                 160

Lys Ser Thr Ala Asn Pro Leu Ala Ser Ile Asp Ser Ala Leu Ser Lys
                165                 170                 175

Val Asp Ala Val Arg Ser Ser Leu Gly Ala Ile Gln Asn Arg Phe Asp
            180                 185                 190

Ser Ala Ile Thr Asn Leu
            195

<210> SEQ ID NO 53
<211> LENGTH: 672
<212> TYPE: DNA
<213> ORGANISM: Salmonella dublin

<400> SEQUENCE: 53
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgaca tcccgggaat tccggtggt ggtggtggaa ttctagactc catgggtaca     360
ttaatcaatg aagacgctgc cgcagccaag aaaagtaccg ctaacccact ggcttcaatt     420
gattctgcat tgtcaaaagt ggacgcagtt cgttcttctc tgggggcaat tcaaaaccgt     480
tttgattcag ccattaccaa ccttggcaat acggtaacca atctgaactc cgcgcgtagc     540
cgtatcgaag atgctgacta tgcaacggaa gtttctaata tgtctaaagc gcagattctg     600
cagcaggctg gtacttccgt tctggcgcag gctaaccagg ttccgcaaaa cgtcctctct     660
ttactgcgtt ag                                                         672

<210> SEQ ID NO 54
<211> LENGTH: 223
<212> TYPE: PRT
<213> ORGANISM: Salmonella dublin

<400> SEQUENCE: 54

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
            85                  90                  95
```

```
Ala Ser Arg Asn Ala Asn Asp Ile Pro Gly Ile Ser Gly Gly Gly Gly
            100                 105                 110

Gly Ile Leu Asp Ser Met Gly Thr Leu Ile Asn Glu Asp Ala Ala Ala
        115                 120                 125

Ala Lys Lys Ser Thr Ala Asn Pro Leu Ala Ser Ile Asp Ser Ala Leu
    130                 135                 140

Ser Lys Val Asp Ala Val Arg Ser Ser Leu Gly Ala Ile Gln Asn Arg
145                 150                 155                 160

Phe Asp Ser Ala Ile Thr Asn Leu Gly Asn Thr Val Thr Asn Leu Asn
                165                 170                 175

Ser Ala Arg Ser Arg Ile Glu Asp Ala Asp Tyr Ala Thr Glu Val Ser
            180                 185                 190

Asn Met Ser Lys Ala Gln Ile Leu Gln Gln Ala Gly Thr Ser Val Leu
        195                 200                 205

Ala Gln Ala Asn Gln Val Pro Gln Asn Val Leu Ser Leu Leu Arg
    210                 215                 220
```

<210> SEQ ID NO 55
<211> LENGTH: 507
<212> TYPE: DNA
<213> ORGANISM: Salmonella dublin

<400> SEQUENCE: 55

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggcc tgactcaggc ttcccgtaac   300
gctaacgaca tcccgggaat tccggtggt ggtggtggaa ttctagactc catgggtaca    360
ttaatcaatg aagacgctgc cgcagccaag aaaagtaccg ctaacccact ggcttcaatt   420
gattctgcat tgtcaaaagt ggacgcagtt cgttcttctc tggggcaatt caaaaccgt    480
tttgattcag ccattaccaa cctttag                                       507
```

<210> SEQ ID NO 56
<211> LENGTH: 168
<212> TYPE: PRT
<213> ORGANISM: Salmonella dublin

<400> SEQUENCE: 56

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
    35                  40                  45

Asn Asn Leu Asn Lys Ser Gln Ser Ser Leu Ser Ser Ala Ile Glu Arg
50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Ile Pro Gly Ile Ser Gly Gly Gly Gly
            100                 105                 110
```

Gly Ile Leu Asp Ser Met Gly Thr Leu Ile Asn Glu Asp Ala Ala Ala
                115                 120                 125

Ala Lys Lys Ser Thr Ala Asn Pro Leu Ala Ser Ile Asp Ser Ala Leu
    130                 135                 140

Ser Lys Val Asp Ala Val Arg Ser Ser Leu Gly Ala Ile Gln Asn Arg
145                 150                 155                 160

Phe Asp Ser Ala Ile Thr Asn Leu
                165

<210> SEQ ID NO 57
<211> LENGTH: 174
<212> TYPE: PRT
<213> ORGANISM: Salmonella enterica

<400> SEQUENCE: 57

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn
                165                 170

<210> SEQ ID NO 58
<211> LENGTH: 189
<212> TYPE: PRT
<213> ORGANISM: Pseudomonas aeruginosa

<400> SEQUENCE: 58

Met Ala Leu Thr Val Asn Thr Asn Ile Ala Ser Leu Asn Thr Gln Arg
1               5                   10                  15

Asn Leu Asn Ala Ser Ser Asn Asp Leu Asn Thr Ser Leu Gln Arg Leu
                20                  25                  30

Thr Thr Gly Tyr Arg Ile Asn Ser Ala Lys Asp Asp Ala Ala Gly Leu
            35                  40                  45

Gln Ile Ser Asn Arg Leu Ser Asn Gln Ile Ser Gly Leu Asn Val Ala
    50                  55                  60

Thr Arg Asn Ala Asn Asp Gly Ile Ser Leu Ala Gln Thr Ala Glu Gly
65                  70                  75                  80

Ala Leu Gln Gln Ser Thr Asn Ile Leu Gln Arg Ile Arg Asp Leu Ala
                85                  90                  95

Leu Gln Ser Ala Asn Gly Ser Asn Ser Asp Ala Asp Arg Ala Ala Leu

```
                       100                 105                 110
Gln Lys Glu Val Ala Ala Gln Gln Ala Glu Leu Thr Arg Ile Ser Asp
            115                 120                 125

Thr Thr Thr Phe Gly Gly Arg Lys Leu Leu Asp Gly Ser Phe Gly Thr
        130                 135                 140

Thr Ser Phe Gln Val Gly Ser Asn Ala Tyr Glu Thr Ile Asp Ile Ser
145                 150                 155                 160

Leu Gln Asn Ala Ser Ala Ser Ala Ile Gly Ser Tyr Gln Val Gly Ser
                165                 170                 175

Asn Gly Ala Gly Thr Val Ala Ser Val Ala Gly Thr Ala
                180                 185

<210> SEQ ID NO 59
<211> LENGTH: 179
<212> TYPE: PRT
<213> ORGANISM: Legionella pneumophila

<400

```
Ser Arg Asn Ala Asn Asp Gly Ile Ser Val Ala Gln Thr Thr Glu Gly
 65                  70                  75                  80

Ala Leu Asn Glu Ile Asn Asn Leu Gln Arg Val Arg Glu Leu Thr
                 85                  90                  95

Val Gln Ala Thr Asn Gly Thr Asn Ser Asp Ser Asp Leu Ser Ser Ile
            100                 105                 110

Gln Ala Glu Ile Thr Gln Arg Leu Glu Glu Ile Asp Arg Val Ser Glu
        115                 120                 125

Gln Thr Gln Phe Asn Gly Val Lys Val Leu Ala Glu Asn Asn Glu Met
    130                 135                 140

Lys Ile Gln Val Gly Ala Asn Asp Gly Glu Thr Ile Thr Ile Asn Leu
145                 150                 155                 160

Ala Lys Ile Asp Ala Lys Thr Leu Gly Leu Asp Gly Phe Asn
                165                 170
```

<210> SEQ ID NO 61
<211> LENGTH: 173
<212> TYPE: PRT
<213> ORGANISM: Serratia marcescens

<400> SEQUENCE: 61

```
Met Ala Gln Val Ile Asn Thr Asn Ser Leu Ser Leu Met Ala Gln Asn
 1               5                  10                  15

Asn Leu Asn Lys Ser Gln Ser Ser Leu Gly Thr Ala Ile Glu Arg Leu
                 20                  25                  30

Ser Ser Gly Leu Arg Ile Asn Ser Ala Lys Asp Asp Ala Ala Gly Gln
            35                  40                  45

Ala Ile Ser Asn Arg Phe Thr Ala Asn Ile Lys Gly Leu Thr Gln Ala
         50                  55                  60

Ser Arg Asn Ala Asn Asp Gly Ile Ser Leu Ala Gln Thr Thr Glu Gly
 65                  70                  75                  80

Ala Leu Asn Glu Val Asn Asp Asn Leu Gln Asn Ile Arg Arg Leu Thr
                 85                  90                  95

Val Gln Ala Gln Asn Gly Ser Asn Ser Thr Ser Asp Leu Lys Ser Ile
            100                 105                 110

Gln Asp Glu Ile Thr Gln Arg Leu Ser Glu Ile Asn Arg Ile Ser Glu
        115                 120                 125

Gln Thr Asp Phe Asn Gly Val Lys Val Leu Ser Ser Asp Gln Lys Leu
    130                 135                 140

Thr Ile Gln Val Gly Ala Asn Asp Gly Glu Thr Thr Asp Ile Asp Leu
145                 150                 155                 160

Lys Lys Ile Asp Ala Lys Gln Leu Gly Met Asp Thr Phe
                165                 170
```

<210> SEQ ID NO 62
<211> LENGTH: 168
<212> TYPE: PRT
<213> ORGANISM: Bacillus subtilis

<400> SEQUENCE: 62

```
Met Arg Ile Asn His Asn Ile Ala Ala Leu Asn Thr Ser Arg Gln Leu
 1               5                  10                  15

Asn Ala Gly Ser Asn Ser Ala Ala Lys Asn Met Glu Lys Leu Ser Ser
                 20                  25                  30

Gly Leu Arg Ile Asn Arg Ala Gly Asp Asp Ala Ala Gly Leu Ala Ile
            35                  40                  45

Ser Glu Lys Met Arg Ser Gln Ile Arg Gly Leu Asp Met Ala Ser Lys
```

-continued

```
                    50                  55                  60
Asn Ala Gln Asp Gly Ile Ser Leu Ile Gln Thr Ser Glu Gly Ala Leu
 65                  70                  75                  80

Asn Glu Thr His Ser Ile Leu Gln Arg Met Ser Glu Leu Ala Thr Gln
                     85                  90                  95

Ala Ala Asn Asp Thr Asn Thr Asp Ser Asp Arg Ser Glu Leu Gln Lys
                    100                 105                 110

Glu Met Asp Gln Leu Ala Ser Glu Val Thr Arg Ile Ser Thr Asp Thr
                115                 120                 125

Glu Phe Asn Thr Lys Lys Leu Leu Asp Gly Thr Ala Gln Asn Leu Thr
                130                 135                 140

Phe Gln Ile Gly Ala Asn Glu Gly Gln Thr Met Ser Leu Ser Ile Asn
145                 150                 155                 160

Lys Met Asp Ser Glu Ser Leu Lys
                165

<210> SEQ ID NO 63
<211> LENGTH: 192
<212> TYPE: PRT
<213> ORGANISM: Listeria monocytogenes

<400> SEQUENCE: 63

Met Lys Val Asn Thr Asn Ile Ile Ser Leu Lys Thr Gln Glu Tyr Leu
 1               5                  10                  15

Arg Lys Asn Asn Glu Gly Met Thr Gln Ala Gln Glu Arg Leu Ala Ser
                 20                  25                  30

Gly Lys Arg Ile Asn Ser Ser Leu Asp Asp Ala Ala Gly Leu Ala Val
             35                  40                  45

Val Thr Arg Met Asn Val Lys Ser Thr Gly Leu Asp Ala Ala Ser Lys
 50                  55                  60

Asn Ser Ser Met Gly Ile Asp Leu Leu Gln Thr Ala Asp Ser Ala Leu
 65                  70                  75                  80

Ser Ser Met Ser Ser Ile Leu Gln Arg Met Arg Gln Leu Ala Val Gln
                     85                  90                  95

Ser Ser Asn Gly Ser Phe Ser Asp Glu Asp Arg Lys Gln Tyr Thr Ala
                    100                 105                 110

Glu Phe Gly Ser Leu Ile Lys Glu Leu Asp His Val Ala Asp Thr Thr
                115                 120                 125

Asn Tyr Asn Asn Ile Lys Leu Leu Asp Gln Thr Ala Thr Gly Ala Ala
                130                 135                 140

Thr Gln Val Ser Ile Gln Ala Ser Asp Lys Ala Asn Asp Leu Ile Asn
145                 150                 155                 160

Ile Asp Leu Phe Asn Ala Lys Gly Leu Ser Ala Gly Thr Ile Thr Leu
                    165                 170                 175

Gly Ser Gly Ser Thr Val Ala Gly Tyr Ser Ala Leu Ser Val Ala Asp
                180                 185                 190

<210> SEQ ID NO 64
<211> LENGTH: 174
<212> TYPE: PRT
<213> ORGANISM: Shigella sonnei

<400> SEQUENCE: 64

Met Ala Gln Val Ile Asn Thr Asn Ser Leu Ser Leu Leu Thr Gln Asn
 1               5                  10                  15

Asn Leu Asn Lys Ser Gln Ser Ser Leu Ser Ser Ala Ile Glu Arg Leu
                 20                  25                  30
```

```
Ser Ser Gly Leu Arg Ile Asn Ser Ala Lys Asp Asp Ala Ala Gly Gln
            35                  40                  45

Ala Ile Ala Asn Arg Phe Thr Ala Asn Ile Lys Gly Leu Thr Gln Ala
 50                  55                  60

Ser Arg Asn Ala Asn Asp Gly Ile Ser Val Ala Gln Thr Thr Glu Gly
 65                  70                  75                  80

Ala Leu Ser Glu Ile Asn Asn Asn Leu Gln Arg Ile Arg Glu Leu Ser
                 85                  90                  95

Val Gln Ala Thr Asn Gly Thr Asn Ser Asp Ser Asp Leu Asn Ser Ile
                100                 105                 110

Gln Asp Glu Ile Thr Gln Arg Leu Ser Glu Ile Asp Arg Val Ser Asn
                115                 120                 125

Gln Thr Gln Phe Asn Gly Val Lys Val Leu Ala Ser Asp Gln Thr Met
            130                 135                 140

Lys Ile Gln Val Gly Ala Asn Asp Gly Glu Thr Ile Glu Ile Ala Leu
145                 150                 155                 160

Asp Lys Ile Asp Ala Lys Thr Leu Gly Leu Asp Asn Phe Ser
                165                 170

<210> SEQ ID NO 65
<211> LENGTH: 174
<212> TYPE: PRT
<213> ORGANISM: Edwardsiella tarda

<400> SEQUENCE: 65

Met Ala Gln Val Ile Asn Thr Asn Ser Leu Ser Leu Met Ala Gln Asn
 1               5                  10                  15

Asn Leu Asn Lys Ser Gln Ser Ala Leu Gly Thr Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ser Asn Arg Phe Thr Ala Asn Ile Asn Gly Leu Thr Gln Ala
 50                  55                  60

Ser Arg Asn Ala Asn Asp Gly Ile Ser Leu Ala Gln Thr Thr Glu Gly
 65                  70                  75                  80

Ala Leu Asn Glu Val Asn Asp Asn Leu Gln Asn Ile Arg Arg Leu Thr
                 85                  90                  95

Val Gln Ala Gln Asn Gly Ser Asn Ser Ser Asp Leu Gln Ser Ile
                100                 105                 110

Gln Asp Glu Ile Thr Gln Arg Leu Ser Glu Ile Asp Arg Ile Ser Gln
                115                 120                 125

Gln Thr Asp Phe Asn Gly Val Lys Val Leu Ser Lys Asp Gln Lys Leu
            130                 135                 140

Thr Ile Gln Val Gly Ala Asn Asp Gly Glu Thr Ile Asp Ile Asp Leu
145                 150                 155                 160

Lys Asn Ile Asn Ala Gln Ser Leu Gly Leu Asp Lys Phe Asn
                165                 170

<210> SEQ ID NO 66
<211> LENGTH: 186
<212> TYPE: PRT
<213> ORGANISM: Acidovorax avenae

<400> SEQUENCE: 66

Met Ala Ser Thr Ile Asn Thr Asn Val Ser Ser Leu Thr Ala Gln Arg
 1               5                  10                  15
```

```
Asn Leu Ser Leu Ser Gln Ser Ser Leu Asn Thr Ser Ile Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Phe Thr Ser Gln Ile Arg Gly Leu Asn Gln Ala
    50                  55                  60

Val Arg Asn Ala Asn Asp Gly Ile Ser Leu Ala Gln Thr Ala Glu Gly
65                  70                  75                  80

Ala Leu Lys Ser Thr Gly Asp Ile Leu Gln Arg Val Arg Glu Leu Ala
                85                  90                  95

Val Gln Ser Ala Asn Ala Thr Asn Ser Ser Gly Asp Arg Lys Ala Ile
            100                 105                 110

Gln Ala Glu Val Gly Gln Leu Leu Ser Glu Met Asp Arg Ile Ala Gly
        115                 120                 125

Asn Thr Glu Phe Asn Gly Gln Lys Leu Leu Asp Gly Ser Phe Gly Ser
    130                 135                 140

Ala Thr Phe Gln Val Gly Ala Asn Ala Asn Gln Thr Ile Thr Ala Thr
145                 150                 155                 160

Thr Gly Asn Phe Arg Thr Asn Asn Tyr Gly Ala Gln Leu Thr Ala Ser
                165                 170                 175

Ala Ser Gly Ala Ala Thr Ser Gly Ala Ser
            180                 185
```

<210> SEQ ID NO 67
<211> LENGTH: 173
<212> TYPE: PRT
<213> ORGANISM: Yersinia pestis

<400> SEQUENCE: 67

```
Met Ala Val Ile Asn Thr Asn Ser Leu Ser Leu Leu Thr Gln Asn Asn
1               5                   10                  15

Leu Asn Lys Ser Gln Ser Ser Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ser Asn Ile Lys Gly Leu Thr Gln Ala Ala
    50                  55                  60

Arg Asn Ala Asn Asp Gly Ile Ser Ile Ala Gln Thr Thr Glu Gly Ser
65                  70                  75                  80

Leu Asn Glu Ile Asn Asn Asn Leu Gln Arg Val Arg Glu Leu Thr Val
                85                  90                  95

Gln Ala Gln Asn Gly Ser Asn Ser Ser Ser Asp Leu Asp Ser Ile Gln
            100                 105                 110

Asp Glu Ile Ser Leu Arg Leu Ala Glu Ile Asp Arg Val Ser Asp Gln
        115                 120                 125

Thr Gln Phe Asn Gly Lys Lys Val Leu Ala Glu Asn Thr Thr Met Ser
    130                 135                 140

Ile Gln Val Gly Ala Asn Asp Gly Glu Thr Ile Asp Ile Asn Leu Gln
145                 150                 155                 160

Lys Ile Asp Ser Lys Ser Leu Gly Leu Gly Ser Tyr Ser
                165                 170
```

<210> SEQ ID NO 68
<211> LENGTH: 174
<212> TYPE: PRT
<213> ORGANISM: Photorhabdus luminescens

<400> SEQUENCE: 68

```
Met Ala Gln Val Ile Asn Thr Asn Ser Leu Ser Leu Leu Thr Gln Asn
1               5                   10                  15

Asn Leu Asn Arg Ser Gln Gly Thr Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Arg Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Thr Asn Leu Gln Arg Ile Arg Glu Leu Thr
                85                  90                  95

Val Gln Ser Gln Asn Gly Ser Asn Ser Glu Ser Asp Ile Lys Ser Ile
            100                 105                 110

Gln Glu Glu Val Thr Gln Arg Leu Lys Glu Ile Asp Arg Ile Ser Glu
        115                 120                 125

Gln Thr Gln Phe Asn Gly Val Arg Val Leu Arg Glu Asp Ser Lys Met
    130                 135                 140

Thr Ile Gln Val Gly Ala Asn Asp Asn Glu Val Ile Asp Ile Asp Leu
145                 150                 155                 160

Lys Lys Ile Asp Lys Glu Ala Leu Asn Leu Gly Lys Phe Thr
                165                 170
```

<210> SEQ ID NO 69
<211> LENGTH: 189
<212> TYPE: PRT
<213> ORGANISM: Rhodobacter sphaeroides

<400> SEQUENCE: 69

```
Met Thr Thr Ile Asn Thr Asn Ile Gly Ala Ile Ala Ala Gln Ala Asn
1               5                   10                  15

Met Thr Lys Val Asn Asp Gln Phe Asn Thr Ala Met Thr Arg Leu Ser
            20                  25                  30

Thr Gly Leu Arg Ile Asn Ala Ala Lys Asp Asp Ala Ala Gly Met Ala
        35                  40                  45

Ile Gly Glu Lys Met Thr Ala Gln Val Met Gly Leu Asn Gln Ala Ile
    50                  55                  60

Arg Asn Ala Gln Asp Gly Lys Asn Leu Val Asp Thr Thr Glu Gly Ala
65                  70                  75                  80

His Val Glu Val Ser Ser Met Leu Gln Arg Leu Arg Glu Leu Ala Val
                85                  90                  95

Gln Ser Ser Asn Asp Thr Asn Thr Ala Ala Asp Arg Gly Ser Leu Ala
            100                 105                 110

Ala Glu Gly Lys Gln Leu Ile Ala Glu Ile Asn Arg Val Ala Glu Ser
        115                 120                 125

Thr Thr Phe Asn Gly Met Lys Val Leu Asp Gly Ser Phe Thr Gly Lys
    130                 135                 140

Gln Leu Gln Ile Gly Ala Asp Ser Gly Gln Thr Met Ala Ile Asn Val
145                 150                 155                 160

Asp Ser Ala Ala Ala Thr Asp Ile Gly Ala His Lys Ile Ser Ser Ala
                165                 170                 175

Ser Thr Val Val Ala Asp Ala Ala Leu Thr Asp Thr Thr
            180                 185
```

```
<210> SEQ ID NO 70
<211> LENGTH: 175
<212> TYPE: PRT
<213> ORGANISM: Xenorhabdus nematophila

<400> SEQUENCE: 70

Met Ala Ser Val Ile Asn Thr Asn Asp Ser Ala Leu Leu Ala Gln Asn
1               5                   10                  15

Asn Leu Thr Lys Ser Lys Gly Ile Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ser Glu Asn Gly Ser Asn Ser Lys Ser Asp Leu Asp Ser Ile
            100                 105                 110

Gln Lys Glu Val Thr Gln Arg Leu Glu Glu Ile Asp Arg Ile Ser Thr
        115                 120                 125

Gln Thr Gln Phe Asn Gly Ile Lys Val Leu Asn Gly Asp Val Thr Glu
    130                 135                 140

Met Lys Ile Gln Val Gly Ala Asn Asp Asn Glu Thr Ile Gly Ile Lys
145                 150                 155                 160

Leu Gly Lys Ile Asn Ser Glu Lys Leu Asn Leu Lys Glu Phe Ser
                165                 170                 175

<210> SEQ ID NO 71
<211> LENGTH: 175
<212> TYPE: PRT
<213> ORGANISM: Proteus mirabilis

<400> SEQUENCE: 71

Met Ala Gln Val Ile Asn Thr Asn Tyr Leu Ser Leu Val Thr Gln Asn
1               5                   10                  15

Asn Leu Asn Arg Ser Gln Ser Ala Leu Gly Asn Ala Ile Glu Arg Leu
            20                  25                  30

Ser Ser Gly Met Arg Ile Asn Ser Ala Lys Asp Asp Ala Ala Gly Gln
        35                  40                  45

Ala Ile Ala Asn Arg Phe Thr Ser Asn Ile Asn Gly Leu Thr Gln Ala
    50                  55                  60

Ser Arg Asn Ala Asn Asp Gly Ile Ser Val Ser Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ala Lys Asn Gly Thr Asn Ser Asn Ser Asp Ile Asn Ser Ile
            100                 105                 110

Gln Asn Glu Val Asn Gln Arg Leu Asp Glu Ile Asn Arg Val Ser Glu
        115                 120                 125

Gln Thr Gln Phe Asn Gly Val Lys Val Leu Ser Gly Glu Lys Ser Lys
    130                 135                 140

Met Thr Ile Gln Val Gly Thr Asn Asp Asn Glu Val Ile Glu Phe Asn
145                 150                 155                 160

Leu Asp Lys Ile Asp Asn Asp Thr Leu Gly Val Ala Ser Asp Lys
                165                 170                 175
```

<210> SEQ ID NO 72
<211> LENGTH: 200
<212> TYPE: PRT
<213> ORGANISM: Butyrivibrio fibrisolvens

<400> SEQUENCE: 72

Met Val Val Gln His Asn Met Gln Ala Ala Asn Ala Ser Arg Met Leu
1               5                   10                  15

Gly Ile Thr Thr Gly Asp Gln Ser Lys Ser Thr Glu Lys Leu Ser Ser
            20                  25                  30

Gly Phe Lys Ile Asn Arg Ala Ala Asp Ala Ala Gly Leu Ser Ile
        35                  40                  45

Ser Glu Lys Met Arg Lys Gln Ile Arg Gly Leu Asp Gln Ala Ser Thr
50                  55                  60

Asn Ala Ser Asp Gly Ile Ser Ala Val Gln Thr Ala Glu Gly Ala Leu
65                  70                  75                  80

Thr Glu Val His Ser Met Leu Gln Arg Met Asn Glu Leu Ala Val Gln
                85                  90                  95

Ala Ala Asn Gly Thr Asn Ser Glu Ser Asp Arg Ser Ser Ile Gln Asp
            100                 105                 110

Glu Ile Asn Gln Leu Thr Thr Glu Ile Asp Arg Val Ala Glu Thr Thr
        115                 120                 125

Lys Phe Asn Glu Thr Tyr Leu Leu Lys Gly Gly Asn Gly Asp Arg Thr
130                 135                 140

Val Arg Val Tyr Ala His Asp Ala Gly Leu Val Gly Ser Leu Ser Gln
145                 150                 155                 160

Asn Thr Thr Lys Ala Thr Phe Gln Met Arg Lys Leu Glu Ile Gly Asp
                165                 170                 175

Ser Tyr Thr Ile Gly Gly Thr Thr Tyr Lys Ile Gly Ala Glu Thr Val
            180                 185                 190

Lys Glu Ala Met Thr Ala Leu Lys
        195                 200

<210> SEQ ID NO 73
<211> LENGTH: 177
<212> TYPE: PRT
<213> ORGANISM: Bordetella pertussis

<400> SEQUENCE: 73

```
Met Ala Ala Val Ile Asn Thr Asn Tyr Leu Ser Leu Val Ala Gln Asn
1               5                   10                  15

Asn Leu Asn Lys Ser Gln Ser Ala Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ala Ser Asn Gly Thr Asn Ser Ala Ser Asp Ile Asp Ser Ile
            100                 105                 110

Gln Gln Glu Val Asn Gln Arg Leu Glu Glu Ile Asn Arg Ile Ala Glu
        115                 120                 125
```

```
Gln Thr Asp Phe Asn Gly Ile Lys Val Leu Lys Ser Asn Ala Thr Asp
    130                 135                 140

Met Thr Leu Ser Ile Gln Val Gly Ala Lys Asp Asn Glu Thr Ile Asp
145                 150                 155                 160

Ile Lys Ile Asp Arg Asn Ser Asn Trp Asn Leu Tyr Asp Ala Val Gly
                165                 170                 175

Thr
```

```
<210> SEQ ID NO 74
<211> LENGTH: 167
<212> TYPE: PRT
<213> ORGANISM: Clostridium chauvoei

<400> SEQUENCE: 74

Met Ile Ile Asn His Asn Met Asn Ala Leu Asn Ala His Arg Asn Met
1               5                   10                  15

Met Gly Asn Ile Ala Thr Ala Gly Lys Ser Met Glu Lys Leu Ser Ser
            20                  25                  30

Gly Leu Arg Ile Asn Arg Ala Gly Asp Asp Ala Ala Gly Leu Ala Ile
        35                  40                  45

Ser Glu Lys Met Arg Gly Gln Ile Arg Gly Leu Asp Gln Ala Ser Arg
50                  55                  60

Asn Ala Gln Asp Gly Ile Ser Leu Ile Gln Thr Ala Glu Gly Ala Leu
65                  70                  75                  80

Ala Glu Thr His Ser Ile Leu Gln Arg Met Arg Glu Leu Ser Val Gln
                85                  90                  95

Ser Ala Asn Asp Thr Asn Val Ala Val Asp Arg Thr Ala Ile Gln Asp
            100                 105                 110

Glu Ile Asn Ser Leu Thr Glu Glu Ile Asn Arg Ile Ser Gly Asp Thr
        115                 120                 125

Glu Phe Asn Thr Gln Lys Leu Leu Asp Gly Gly Phe Lys Gly Glu Phe
130                 135                 140

Gln Ile Gly Ala Asn Ser Asn Gln Thr Val Lys Leu Asp Ile Gly Asn
145                 150                 155                 160

Met Ser Ala Ala Ser Leu Gly
                165
```

```
<210> SEQ ID NO 75
<211> LENGTH: 178
<212> TYPE: PRT
<213> ORGANISM: Xanthomonas campestris

<400> SEQUENCE: 75

Met Ala Gln Val Ile Asn Thr Asn Val Met Ser Leu Asn Ala Gln Arg
1               5                   10                  15

Asn Leu Asn Thr Asn Ser Ser Ser Met Ala Leu Ser Ile Gln Gln Leu
            20                  25                  30

Ser Ser Gly Lys Arg Ile Thr Ser Ala Ser Val Asp Ala Ala Gly Leu
        35                  40                  45

Ala Ile Ser Glu Arg Phe Thr Thr Gln Ile Arg Gly Leu Asp Val Ala
    50                  55                  60

Ser Arg Asn Ala Asn Asp Gly Ile Ser Leu Ala Gln Thr Ala Glu Gly
65                  70                  75                  80

Ala Met Val Glu Ile Gly Asn Asn Leu Gln Arg Ile Arg Glu Leu Ser
                85                  90                  95

Val Gln Ser Ala Asn Ala Thr Asn Ser Ala Thr Asp Arg Glu Ala Leu
            100                 105                 110
```

```
Asn Ser Glu Val Lys Gln Leu Thr Ser Glu Ile Asp Arg Val Ala Asn
        115                 120                 125

Gln Thr Ser Phe Asn Gly Thr Lys Leu Leu Asn Gly Asp Phe Ser Gly
    130                 135                 140

Ala Leu Phe Gln Val Gly Ala Asp Ala Gly Gln Thr Ile Gly Ile Asn
145                 150                 155                 160

Ser Ile Val Asp Ala Asn Val Asp Ser Leu Gly Lys Ala Asn Phe Ala
                165                 170                 175

Ala Ser
```

<210> SEQ ID NO 76
<211> LENGTH: 161
<212> TYPE: PRT
<213> ORGANISM: Nitrosomonas europaea

<400> SEQUENCE: 76

```
Met Pro Gln Val Ile Asn Thr Asn Ile Ala Ser Leu Asn Ala Gln Arg
1               5                   10                  15

Asn Leu Asn Val Ser Gln Asn Ser Leu Ser Thr Ala Leu Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Met Thr Ser Gln Ile Arg Gly Met Asn Gln Ala
 50                 55                  60

Ala Arg Asn Ala Asn Asp Gly Ile Ser Leu Ala Gln Thr Ala Glu Gly
65                  70                  75                  80

Ala Leu Val Glu Ile Gly Asn Asn Leu Gln Arg Ile Arg Glu Leu Ala
                85                  90                  95

Val Gln Ser Ala Asn Ala Thr Asn Ser Glu Asp Asp Arg Glu Ala Leu
            100                 105                 110

Gln Lys Glu Val Thr Gln Leu Ile Asp Glu Ile Gln Arg Val Gly Glu
        115                 120                 125

Gln Thr Ser Phe Asn Gly Thr Lys Leu Leu Asp Gly Ser Phe Ala Ser
    130                 135                 140

Gln Ile Phe Gln Val Gly Ala Asn Glu Gly Glu Thr Ile Asp Phe Thr
145                 150                 155                 160

Asp
```

<210> SEQ ID NO 77
<211> LENGTH: 178
<212> TYPE: PRT
<213> ORGANISM: Campylobacter lari

<400> SEQUENCE: 77

```
Gly Phe Arg Ile Asn Thr Asn Gly Ala Ser Leu Asn Ala Gln Val Asn
1               5                   10                  15

Ala Gly Leu Asn Ser Arg Asn Leu Asp Ser Ser Leu Ala Arg Leu Ser
            20                  25                  30

Ser Gly Leu Arg Ile Asn Ser Ala Ala Asp Ala Ala Ser Gly Leu Ala
        35                  40                  45

Ile Ala Asp Ser Leu Lys Thr Gln Ala Asn Ser Leu Gly Gln Ala Ile
 50                 55                  60

Asn Asn Ala Asn Asp Ala Asn Ser Met Leu Gln Ile Ala Asp Lys Ala
65                  70                  75                  80

Met Asp Glu Gln Leu Lys Ile Leu Asp Thr Ile Lys Val Lys Ala Thr
                85                  90                  95
```

```
Gln Ala Ala Gln Asp Gly Gln Thr Ala Lys Thr Arg Ala Met Ile Gln
                100                 105                 110
Gly Glu Ile Asn Lys Leu Met Glu Glu Leu Asp Asn Ile Ala Asn Thr
            115                 120                 125
Thr Thr Tyr Asn Gly Lys Gln Leu Leu Ser Gly Phe Ser Asn Ala
    130                 135                 140
Gln Phe Gln Ile Gly Asp Lys Ala Asn Gln Thr Val Asn Ala Thr Ile
145                 150                 155                 160
Gly Ser Thr Asn Ser Ala Lys Val Gly Gln Thr Arg Phe Glu Thr Gly
                165                 170                 175
Ala Val
```

<210> SEQ ID NO 78
<211> LENGTH: 88
<212> TYPE: PRT
<213> ORGANISM: Salmonella enterica

<400> SEQUENCE: 78

```
Pro Leu Ala Ser Ile Asp Ser Ala Leu Ser Lys Val Asp Ala Val Arg
1               5                   10                  15
Ser Ser Leu Gly Ala Ile Gln Asn Arg Phe Asp Ser Ala Ile Thr Asn
            20                  25                  30
Leu Gly Asn Thr Val Thr Asn Leu Asn Ser Ala Arg Ser Arg Ile Glu
        35                  40                  45
Asp Ala Asp Tyr Ala Thr Glu Val Ser Asn Met Ser Lys Ala Gln Ile
    50                  55                  60
Leu Gln Gln Ala Gly Thr Ser Val Leu Ala Gln Ala Asn Gln Val Pro
65                  70                  75                  80
Gln Asn Val Leu Ser Leu Leu Arg
                85
```

<210> SEQ ID NO 79
<211> LENGTH: 88
<212> TYPE: PRT
<213> ORGANISM: Pseudomonas aeruginosa

<400> SEQUENCE: 79

```
Ala Ile Ala Val Val Asp Asn Ala Leu Ala Ile Asp Ala Gln Arg
1               5                   10                  15
Ala Asp Leu Gly Ala Val Gln Asn Arg Phe Lys Asn Thr Ile Asp Asn
            20                  25                  30
Leu Thr Asn Ile Ser Glu Asn Ala Thr Asn Ala Arg Ser Arg Ile Lys
        35                  40                  45
Asp Thr Asp Phe Ala Ala Glu Thr Ala Ala Leu Ser Lys Asn Gln Val
    50                  55                  60
Leu Gln Gln Ala Gly Thr Ala Ile Leu Ala Gln Ala Asn Gln Leu Pro
65                  70                  75                  80
Gln Ala Val Leu Ser Leu Leu Arg
                85
```

<210> SEQ ID NO 80
<211> LENGTH: 89
<212> TYPE: PRT
<213> ORGANISM: Legionella pneumophila

<400> SEQUENCE: 80

```
Ala Ile Lys Arg Ile Asp Ala Ala Leu Asn Ser Val Asn Ser Asn Arg
1               5                   10                  15
```

```
Ala Asn Met Gly Ala Leu Gln Asn Arg Phe Glu Ser Thr Ile Ala Asn
            20                  25                  30

Leu Gln Asn Val Ser Asp Asn Leu Ser Ala Ala Arg Ser Arg Ile Gln
        35                  40                  45

Asp Ala Asp Tyr Ala Ala Glu Met Ala Ser Leu Thr Lys Asn Gln Ile
    50                  55                  60

Leu Gln Gln Ala Gly Thr Ala Met Leu Ala Gln Ala Asn Ser Leu Pro
65                  70                  75                  80

Gln Ser Val Leu Ser Leu Leu Gly Arg
                85
```

<210> SEQ ID NO 81
<211> LENGTH: 89
<212> TYPE: PRT
<213> ORGANISM: Escherichia coli

<400> SEQUENCE: 81

```
Pro Leu Glu Thr Ile Asp Lys Ala Leu Ala Lys Val Asp Asn Leu Arg
1               5                   10                  15

Ser Asp Leu Gly Ala Val Gln Asn Arg Phe Asp Ser Ala Ile Thr Asn
            20                  25                  30

Leu Gly Asn Thr Val Asn Asn Leu Ser Ser Ala Arg Ser Arg Ile Glu
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Thr Thr
65                  70                  75                  80

Gln Asn Val Leu Ser Leu Leu Gln Gly
                85
```

<210> SEQ ID NO 82
<211> LENGTH: 88
<212> TYPE: PRT
<213> ORGANISM: Serratia marcescens

<400> SEQUENCE: 82

```
Pro Leu Ala Thr Leu Asp Lys Ala Leu Ala Gln Val Asp Gly Leu Arg
1               5                   10                  15

Ser Ser Leu Gly Ala Val Gln Asn Arg Phe Asp Ser Val Ile Asn Asn
            20                  25                  30

Leu Asn Ser Thr Val Asn Asn Leu Ser Ala Ser Gln Ser Arg Ile Gln
        35                  40                  45

Asp Ala Asp Tyr Ala Thr Glu Val Ser Asn Met Ser Arg Ala Asn Ile
    50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
                85
```

<210> SEQ ID NO 83
<211> LENGTH: 89
<212> TYPE: PRT
<213> ORGANISM: Bacillus subtilis

<400> SEQUENCE: 83

```
Ala Leu Thr Thr Ile Lys Thr Ala Ile Asp Thr Val Ser Ser Glu Arg
1               5                   10                  15

Ala Lys Leu Gly Ala Val Gln Asn Arg Leu Glu His Thr Ile Asn Asn
```

-continued

```
                20                  25                  30
Leu Gly Thr Ser Ser Glu Asn Leu Thr Ser Ala Glu Ser Arg Ile Arg
            35                  40                  45

Asp Val Asp Met Ala Ser Glu Met Met Glu Tyr Thr Lys Asn Asn Ile
         50                  55                  60

Leu Thr Gln Ala Ser Gln Ala Met Leu Ala Gln Ala Asn Gln Gln Pro
 65                  70                  75                  80

Gln Gln Val Leu Gln Leu Leu Lys Gly
                 85

<210> SEQ ID NO 84
<211> LENGTH: 90
<212> TYPE: PRT
<213> ORGANISM: Leptospira interrogans

<400> SEQUENCE: 84

Val Ile Gly Leu Ala Asp Ala Leu Thr Lys Ile Met Lys Gln Arg
 1               5                  10                  15

Ala Asp Met Gly Ala Tyr Tyr Asn Arg Leu Glu Tyr Thr Ala Lys Gly
                20                  25                  30

Leu Met Gly Ala Tyr Glu Asn Met Gln Ala Ser Glu Ser Arg Ile Arg
            35                  40                  45

Asp Ala Asp Met Ala Glu Glu Val Val Ser Leu Thr Thr Lys Gln Ile
         50                  55                  60

Leu Val Gln Ser Gly Thr Ala Met Leu Ala Gln Ala Asn Met Lys Pro
 65                  70                  75                  80

Asn Ser Val Leu Lys Leu Leu Gln Gln Ile
                 85                  90

<210> SEQ ID NO 85
<211> LENGTH: 88
<212> TYPE: PRT
<213> ORGANISM: Shigella sonnei

<400> SEQUENCE: 85

Pro Leu Ser Lys Leu Asp Glu Ala Leu Ala Lys Val Asp Lys Leu Arg
 1               5                  10                  15

Ser Ser Leu Gly Ala Val Gln Asn Arg Phe Asp Ser Ala Ile Thr Asn
                20                  25                  30

Leu Gly Asn Thr Val Asn Asp Leu Ser Ser Ala Arg Ser Arg Ile Glu
            35                  40                  45

Asp Ala Asp Tyr Ala Thr Glu Val Ser Asn Met Ser Arg Ala Gln Ile
         50                  55                  60

Leu Gln Gln Ala Gly Thr Ser Val Leu Ala Gln Ala Asn Gln Thr Thr
 65                  70                  75                  80

Gln Asn Val Leu Ser Leu Leu Arg
                 85

<210> SEQ ID NO 86
<211> LENGTH: 88
<212> TYPE: PRT
<213> ORGANISM: Edwardsiella tarda

<400> SEQUENCE: 86

Pro Leu Ala Thr Leu Asp Lys Ala Leu Ser Gln Val Asp Asp Leu Arg
 1               5                  10                  15

Ser Gly Leu Gly Ala Val Gln Asn Arg Phe Asp Ser Val Ile Asn Asn
                20                  25                  30
```

```
Leu Asn Ser Thr Val Asn Asn Leu Ser Ala Ser Arg Ser Arg Ile Gln
            35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
                85

<210> SEQ ID NO 87
<211> LENGTH: 88
<212> TYPE: PRT
<213> ORGANISM: Acidovorax avenae

<400> SEQUENCE: 87

Ala Leu Lys Ile Ile Asp Ala Ala Leu Ser Ala Val Asn Gly Gln Arg
1               5                   10                  15

Ala Ser Phe Gly Ala Leu Gln Ser Arg Phe Glu Thr Thr Val Asn Asn
            20                  25                  30

Leu Gln Ser Thr Ser Glu Asn Met Ser Ala Ser Arg Ser Arg Ile Gln
            35                  40                  45

Asp Ala Asp Phe Ala Ala Glu Thr Ala Asn Leu Ser Arg Ser Gln Ile
    50                  55                  60

Leu Gln Gln Ala Gly Thr Ala Met Val Ala Gln Ala Asn Gln Leu Pro
65                  70                  75                  80

Gln Gly Val Leu Ser Leu Leu Lys
                85

<210> SEQ ID NO 88
<211> LENGTH: 88
<212> TYPE: PRT
<213> ORGANISM: Yersinia pestis

<400> SEQUENCE: 88

```
Asp Ala Asp Tyr Ala Thr Glu Val Ser Asn Met Ser Arg Gly Gln Ile
    50                  55                  60

Leu Gln Gln Ala Gly Thr Ala Val Leu Ala Gln Ala Asn Gln Val Pro
65                  70                  75                  80

Gln Asn Val Met Ser Leu Leu Arg
                85

<210> SEQ ID NO 90
<211> LENGTH: 89
<212> TYPE: PRT
<213> ORGANISM: Rhodobacter sphaeroides

<400> SEQUENCE: 90

Ala Ile Gly Val Ile Asp Val Ala Leu Ser Lys Ile Ser Gln Ser Arg
1               5                   10                  15

Ser Glu Leu Gly Ala Val Ser Asn Arg Leu Asp Ser Thr Ile Ser Asn
                20                  25                  30

Leu Thr Asn Ile Ser Thr Ser Val Gln Ala Ala Lys Ser Gln Val Met
            35                  40                  45

Asp Ala Asp Phe Ala Ala Glu Ser Thr Asn Leu Ala Arg Ser Gln Ile
    50                  55                  60

Leu Ser Gln Ala Ser Thr Ala Met Leu Ala Gln Ala Asn Ser Ser Lys
65                  70                  75                  80

Gln Asn Val Leu Ser Leu Leu Arg Gly
                85

<210> SEQ ID NO 91
<211> LENGTH: 88
<212> TYPE: PRT
<213> ORGANISM: Xenorhabdus nematophila

<400> SEQUENCE: 91

Pro Leu Asp Thr Leu Asp Lys Ala Leu Ala Gln Val Asp Met Arg
1               5                   10                  15

Ser Ser Leu Gly Ala Val Gln Asn Arg Leu Glu Ser Thr Val Asn Asn
                20                  25                  30

Leu Asn Asn Thr Val Asn Asn Leu Ser Ala Ala Arg Ser Arg Ile Glu
            35                  40                  45

Asp Ala Asp Tyr Ala Val Glu Val Ser Asn Met Ser Arg Gly Gln Ile
    50                  55                  60

Leu Gln Gln Ala Gly Thr Ser Val Leu Ala Gln Ala Asn Gln Val Pro
65                  70                  75                  80

Gln Thr Val Leu Ser Leu Leu Arg
                85

<210> SEQ ID NO 92
<211> LENGTH: 88
<212> TYPE: PRT
<213> ORGANISM: Proteus mirabilis

<400> SEQUENCE: 92

Ala Leu Ala Thr Leu Asp Asn Ala Ile Ser Lys Val Asp Glu Ser Arg
1               5                   10                  15

Ser Lys Leu Gly Ala Ile Gln Asn Arg Phe Gln Ser Thr Ile Asn Asn
                20                  25                  30

Leu Asn Asn Thr Val Asn Asn Leu Ser Ala Ser Arg Ser Arg Ile Leu
            35                  40                  45

Asp Ala Asp Tyr Ala Thr Glu Val Ser Asn Met Ser Lys Asn Gln Ile
```

```
                50                  55                  60
Leu Gln Gln Ala Gly Thr Ala Val Leu Ala Gln Ala Asn Gln Val Pro
 65                  70                  75                  80

Gln Thr Val Leu Ser Leu Leu Arg
                 85

<210> SEQ ID NO 93
<211> LENGTH: 88
<212> TYPE: PRT
<213> ORGANISM: Butyrivibrio fibrisolvens

<400> SEQUENCE: 93

Ala Ile Asp Ala Ile Ser Asp Ala Leu Ala Lys Val Ser Ala Gln Arg
  1               5                  10                  15

Ser Ala Leu Gly Ser Ile Gln Asn Arg Leu Glu His Ser Ile Ala Asn
                 20                  25                  30

Leu Asp Asn Val Val Glu Asn Thr Asn Ala Ala Glu Ser Arg Ile Arg
             35                  40                  45

Asp Thr Asp Met Ala Asp Glu Met Val Thr Tyr Ser Lys Asn Asn Ile
         50                  55                  60

Leu Met Gln Ala Gly Gln Ser Met Leu Ala Gln Ala Asn Gln Ala Thr
 65                  70                  75                  80

Gln Gly Val Leu Ser Ile Leu Gln
                 85

<210> SEQ ID NO 94
<211> LENGTH: 88
<212> TYPE: PRT
<213> ORGANISM: Bordetella pertussis

<400> SEQUENCE: 94

Ala Leu Ser Lys Leu Asp Asp Ala Met Lys Ala Val Asp Glu Gln Arg
  1               5                  10                  15

Ser Ser Leu Gly Ala Ile Gln Asn Arg Phe Glu Ser Thr Val Ala Asn
                 20                  25                  30

Leu Asn Asn Thr Ile Thr Asn Leu Ser Ala Ala Arg Ser Arg Ile Glu
             35                  40                  45

Asp Ser Asp Tyr Ala Thr Glu Val Ser Asn Met Thr Lys Asn Gln Ile
         50                  55                  60

Leu Gln Gln Ala Gly Thr Ser Val Leu Ala Gln Ala Asn Gln Val Pro
 65                  70                  75                  80

Gln Asn Val Leu Ser Leu Leu Arg
                 85

<210> SEQ ID NO 95
<211> LENGTH: 88
<212> TYPE: PRT
<213> ORGANISM: Clostridium chauvoei

<400> SEQUENCE: 95

Ser Ile Lys Thr Ile Asn Ser Ala Ile Glu Gln Val Ser Thr Gln Arg
  1               5                  10                  15

Ser Lys Leu Gly Ala Val Gln Asn Arg Leu Glu His Thr Ile Asn Asn
                 20                  25                  30

Leu Asn Thr Ser Ser Glu Asn Leu Thr Ala Ala Glu Ser Arg Val Arg
             35                  40                  45

Asp Val Asp Met Ala Lys Glu Met Met Ala Phe Ser Lys Asn Asn Ile
         50                  55                  60
```

```
Leu Ser Gln Ala Ala Gln Ala Met Leu Gly Gln Ala Asn Gln Gln Pro
 65                  70                  75                  80

Gln Gly Val Leu Gln Leu Leu Arg
                85

<210> SEQ ID NO 96
<211> LENGTH: 88
<212> TYPE: PRT
<213> ORGANISM: Xanthomonas campestris

<400> SEQUENCE: 96

Ala Leu Glu Ile Val Asp Lys Ala Leu Thr Ser Val Asn Ser Ser Arg
  1               5                  10                  15

Ala Asp Met Gly Ala Val Gln Asn Arg Phe Thr Ser Thr Ile Ala Asn
                 20                  25                  30

Leu Ala Ala Thr Ser Glu Asn Leu Thr Ala Ser Arg Ser Arg Ile Ala
             35                  40                  45

Asp Thr Asp Tyr Ala Lys Thr Thr Ala Glu Leu Thr Arg Thr Gln Ile
 50                  55                  60

Leu Gln Gln Ala Gly Thr Ala Met Leu Ala Gln Ala Lys Ser Val Pro
 65                  70                  75                  80

Gln Asn Val Leu Ser Leu Leu Gln
                85

<210> SEQ ID NO 97
<211> LENGTH: 84
<212> TYPE: PRT
<213> ORGANISM: Nitrosomonas europaea

<400> SEQUENCE: 97

Ile Asp Asp Ala Leu Lys Ile Val Asn Ser Thr Arg Ala Asp Leu Gly
  1               5                  10                  15

Ala Ile Gln Asn Arg Phe Ser Ser Ala Ile Ala Asn Leu Gln Thr Ser
                 20                  25                  30

Ala Glu Asn Leu Ser Ala Ser Arg Ser Arg Ile Gln Asp Ala Asp Phe
             35                  40                  45

Ala Ala Glu Thr Ala Ala Leu Thr Arg Ala Gln Ile Leu Gln Gln Ala
 50                  55                  60

Gly Val Ala Met Leu Ser Gln Ala Asn Ala Leu Pro Asn Asn Val Leu
 65                  70                  75                  80

Ser Leu Leu Arg

<210> SEQ ID NO 98
<211> LENGTH: 88
<212> TYPE: PRT
<213> ORGANISM: Campylobacter lari

<400> SEQUENCE: 98

Val Met Asp Ile Ala Asp Thr Ala Ile Ala Asn Leu Asp Thr Ile Arg
  1               5                  10                  15

Ala Asn Ile Gly Ala Thr Gln Asn Gln Ile Thr Ser Thr Ile Asn Asn
                 20                  25                  30

Ile Ser Val Thr Gln Val Asn Val Lys Ala Ala Glu Ser Gln Ile Arg
             35                  40                  45

Asp Val Asp Phe Ala Ser Glu Ser Ala Asn Tyr Ser Lys Ala Asn Ile
 50                  55                  60
```

```
Leu Ala Gln Ser Gly Ser Tyr Ala Met Ala Gln Ala Asn Ala Ala Ser
65                  70                  75                  80

Gln Asn Val Leu Arg Leu Leu Gln
                85
```